US011059795B2

(12) United States Patent
Zhou et al.

(10) Patent No.: US 11,059,795 B2
(45) Date of Patent: Jul. 13, 2021

(54) ANDROGEN RECEPTOR MODULATORS AND METHODS FOR THEIR USE

(71) Applicants: ESSA Pharma, Inc., Vancouver (CA); The University of British Columbia, Vancouver (CA); Provincial Health Services Authority, Vancouver (CA)

(72) Inventors: Han-Jie Zhou, Foster City, CA (US); Peter Virsik, Portola Valley, CA (US); Raymond John Andersen, Vancouver (CA); Marianne Dorothy Sadar, West Vancouver (CA)

(73) Assignees: ESSA Pharma, Inc., Vancouver (CA); The University of British Columbia, Vancouver (CA); Provincial Health Services Authority, Vancouver (CA)

( * ) Notice: Subject to any disclaimer, the term of this patent is extended or adjusted under 35 U.S.C. 154(b) by 0 days.

(21) Appl. No.: 16/852,810

(22) Filed: Apr. 20, 2020

(65) Prior Publication Data
US 2020/0247763 A1 Aug. 6, 2020

Related U.S. Application Data

(63) Continuation of application No. 16/657,625, filed on Oct. 18, 2019.

(60) Provisional application No. 62/747,209, filed on Oct. 18, 2018, provisional application No. 62/803,516, filed on Feb. 10, 2019, provisional application No. 62/857,516, filed on Jun. 5, 2019.

(51) Int. Cl.
| C07D 263/46 | (2006.01) |
| A61P 35/00 | (2006.01) |
| C07D 271/113 | (2006.01) |
| C07D 261/08 | (2006.01) |
| C07D 263/48 | (2006.01) |
| C07D 231/38 | (2006.01) |
| C07D 239/42 | (2006.01) |
| C07D 233/74 | (2006.01) |
| C07D 277/36 | (2006.01) |
| C07D 277/42 | (2006.01) |
| C07D 277/56 | (2006.01) |
| C07D 307/64 | (2006.01) |
| C07D 241/20 | (2006.01) |
| C07D 263/38 | (2006.01) |
| C07D 233/84 | (2006.01) |
| C07D 233/88 | (2006.01) |
| C07D 233/80 | (2006.01) |
| C07D 233/76 | (2006.01) |

(52) U.S. Cl.
CPC .......... *C07D 263/46* (2013.01); *A61P 35/00* (2018.01); *C07D 231/38* (2013.01); *C07D 233/74* (2013.01); *C07D 233/76* (2013.01); *C07D 233/80* (2013.01); *C07D 233/84* (2013.01); *C07D 233/88* (2013.01); *C07D 239/42* (2013.01); *C07D 241/20* (2013.01); *C07D 261/08* (2013.01); *C07D 263/38* (2013.01); *C07D 263/48* (2013.01); *C07D 271/113* (2013.01); *C07D 277/36* (2013.01); *C07D 277/42* (2013.01); *C07D 277/56* (2013.01); *C07D 307/64* (2013.01)

(58) Field of Classification Search
CPC .................................................. C07D 263/46
See application file for complete search history.

(56) References Cited

U.S. PATENT DOCUMENTS

| 2,571,217 | A | 10/1951 | Davis et al. |
| 2,890,189 | A | 6/1959 | Greenlee |
| 3,074,974 | A | 1/1963 | Gebura |
| 3,162,615 | A | 12/1964 | Bremmer |
| 4,284,574 | A | 8/1981 | Bagga |
| 4,369,298 | A | 1/1983 | Kida et al. |
| 4,855,184 | A | 8/1989 | Klun et al. |
| 4,904,760 | A | 2/1990 | Gaku et al. |
| 5,043,375 | A | 8/1991 | Henning et al. |
| 5,155,196 | A | 10/1992 | Kolb et al. |
| 5,362,615 | A | 11/1994 | Hagemann et al. |
| 5,403,697 | A | 4/1995 | Doessel et al. |
| 5,753,730 | A | 5/1998 | Nagata et al. |
| 5,807,899 | A | 9/1998 | Rolf et al. |
| 5,998,674 | A | 12/1999 | Taketani et al. |
| 6,218,430 | B1 | 4/2001 | Allegretto et al. |
| 6,245,117 | B1 | 6/2001 | Nishikawa et al. |
| 7,183,323 | B2 | 2/2007 | Chinn et al. |
| 7,273,867 | B2 | 9/2007 | Dorsch et al. |
| 7,595,345 | B2 | 9/2009 | Bunel et al. |

(Continued)

FOREIGN PATENT DOCUMENTS

| CA | 2206422 A1 | 6/1996 |
| CA | 2226469 A1 | 1/1997 |

(Continued)

OTHER PUBLICATIONS

Wolff, M.E., "Burger's Medicinal Chemistry", pp. 975-977 (1997)
Banker et al., "Modern Pharmaceuticals", p. 596 (1997).*

(Continued)

*Primary Examiner* — Paul V Ward
(74) *Attorney, Agent, or Firm* — Cooley LLP

(57) ABSTRACT

The present invention relates to compounds of formula (I)-(VI) and/or (A)-(H-I), or any subgenera thereof, or a pharmaceutically acceptable salt, tautomer or stereoisomer. The compounds of the present disclosure are useful in modulating androgen receptor activity and for treating cancer including prostate cancer.

25 Claims, 8 Drawing Sheets

(56) References Cited

U.S. PATENT DOCUMENTS

| | | |
|---|---|---|
| 7,674,795 B2 | 3/2010 | Mailliet et al. |
| 8,048,888 B2 | 11/2011 | Wosikowski-Buters et al. |
| 8,455,477 B2 | 6/2013 | Katz |
| 8,686,050 B2 | 4/2014 | Sadar et al. |
| 9,173,939 B2 | 11/2015 | Andersen et al. |
| 9,365,510 B2 | 6/2016 | Andersen et al. |
| 9,375,496 B2 | 6/2016 | Andersen et al. |
| 9,388,112 B2 | 7/2016 | Sadar et al. |
| 9,862,667 B2 | 1/2018 | Sadar et al. |
| 10,654,811 B2 | 5/2020 | Andersen et al. |
| 2003/0092724 A1 | 5/2003 | Kao et al. |
| 2003/0105268 A1 | 6/2003 | Boriack et al. |
| 2004/0049004 A1 | 3/2004 | Boriack et al. |
| 2004/0243316 A1 | 12/2004 | Weinmann et al. |
| 2008/0153837 A1 | 6/2008 | Mailliet et al. |
| 2008/0193380 A1 | 8/2008 | Dalton et al. |
| 2008/0255395 A1 | 10/2008 | Dai et al. |
| 2009/0105349 A1 | 4/2009 | Barvian et al. |
| 2009/0246158 A1 | 10/2009 | Rudolph et al. |
| 2011/0230556 A1 | 9/2011 | Sadar et al. |
| 2013/0045204 A1 | 2/2013 | Sadar et al. |
| 2013/0109758 A1 | 5/2013 | Sadar et al. |
| 2013/0131167 A1 | 5/2013 | Sadar et al. |
| 2013/0245129 A1 | 9/2013 | Sadar et al. |
| 2013/0336962 A1 | 12/2013 | Andersen et al. |
| 2014/0248263 A1 | 9/2014 | Andersen et al. |
| 2014/0335080 A1 | 11/2014 | Andersen et al. |
| 2015/0010469 A1 | 1/2015 | Andersen et al. |
| 2015/0125389 A1 | 5/2015 | Andersen et al. |
| 2016/0068466 A1 | 3/2016 | Andersen et al. |
| 2016/0367707 A1 | 12/2016 | Andersen et al. |
| 2017/0056336 A1 | 3/2017 | Sadar et al. |
| 2017/0121261 A1 | 5/2017 | Sadar et al. |
| 2017/0298033 A1 | 10/2017 | Andersen et al. |
| 2018/0064657 A1 | 3/2018 | Andersen et al. |
| 2018/0235925 A1 | 8/2018 | Andersen et al. |
| 2018/0327368 A1 | 11/2018 | Andersen et al. |
| 2020/0123117 A1 | 4/2020 | Zhou et al. |

FOREIGN PATENT DOCUMENTS

| | | | |
|---|---|---|---|
| CA | 2339775 A1 | | 3/2000 |
| CA | 2606262 A1 | | 11/2006 |
| CA | 2728219 A1 | | 1/2010 |
| CA | 2786319 A1 | | 7/2011 |
| CN | 102083780 A | | 6/2011 |
| CN | 103342892 A | | 10/2013 |
| EP | 0056175 A1 | | 7/1982 |
| EP | 0155238 A2 | | 9/1985 |
| EP | 0293768 A1 | | 12/1988 |
| EP | 0515128 A1 | | 11/1992 |
| FR | 1389005 | | 2/1965 |
| JP | B-S45-008432 | | 3/1970 |
| JP | S56-5472 A | | 1/1981 |
| JP | 63-196675 | | 8/1988 |
| JP | S63-317539 A | | 12/1988 |
| JP | H01-503541 | | 11/1989 |
| JP | H02-4815 | | 1/1990 |
| JP | 6-049473 A2 | | 2/1994 |
| JP | 7-117349 A | | 5/1995 |
| JP | 09-176240 A | | 7/1997 |
| JP | H10133427 A | | 5/1998 |
| JP | A-H10-316803 | | 12/1998 |
| JP | 11-166087 A2 | | 6/1999 |
| JP | 2000-072705 A2 | | 3/2000 |
| JP | 2001-511170 A | | 8/2001 |
| JP | 2005-325301 A | | 11/2005 |
| JP | 2006-208607 A | | 8/2006 |
| JP | 2006-265351 A2 | | 10/2006 |
| JP | 2007-513089 A | | 5/2007 |
| JP | 2007-290980 | | 11/2007 |
| KR | 10-2011-0044216 A | | 4/2011 |
| PL | 141793 B1 | | 8/1987 |
| RU | 2454394 | * | 6/2012 |
| RU | 2454394 C2 | | 6/2012 |
| SU | 638596 | | 12/1978 |
| SU | 929630 | | 5/1982 |
| WO | WO 1988/009782 A1 | | 12/1988 |
| WO | WO 1996/16646 A1 | | 6/1996 |
| WO | WO 1998/034930 A1 | | 8/1998 |
| WO | WO 2000/001813 A2 | | 1/2000 |
| WO | WO 2000/010958 A1 | | 3/2000 |
| WO | WO 2001/088013 A2 | | 11/2001 |
| WO | WO 2002/005813 A2 | | 1/2002 |
| WO | WO 2003/004481 A1 | | 1/2003 |
| WO | WO 2005/042464 A1 | | 5/2005 |
| WO | WO 2005/077967 A1 | | 8/2005 |
| WO | WO 2008/101806 A2 | | 8/2008 |
| WO | WO 2010/000066 A1 | | 1/2010 |
| WO | WO 2011/082487 A1 | | 7/2011 |
| WO | WO 2011/082488 A1 | | 7/2011 |
| WO | WO 2012/139039 A2 | | 10/2012 |
| WO | WO 2012/145328 A1 | | 10/2012 |
| WO | WO 2012/145330 A1 | | 10/2012 |
| WO | WO 2013/028572 A1 | | 2/2013 |
| WO | WO 2013/028791 A1 | | 2/2013 |
| WO | WO 2014/179867 A1 | | 11/2014 |
| WO | WO 2015/031984 A1 | | 3/2015 |
| WO | WO 2016/058080 A1 | | 4/2016 |
| WO | WO 2016/058082 A1 | | 4/2016 |
| WO | WO 2016/112455 A1 | | 7/2016 |
| WO | WO 2016/141458 A1 | | 9/2016 |
| WO | WO 2017/177307 A1 | | 10/2017 |
| WO | WO 2017/210771 A1 | | 12/2017 |
| WO | WO 2018/045450 A1 | | 3/2018 |

OTHER PUBLICATIONS

Vippagunta et al. (2001).*
Alabi et al., J. of Chrom., (2014).*
Yonekubo, J. Agric. Food Chem., (2008).*
Alvarez, C. et al., "Conformational and Experimental Studies on the Dipole Moments of Models of Comblike Polymers", Macromolecules, 30(20): 6369-6375 (1997).
Anderson, R. et al., "Regression of Castrate-Recurrent Prostate Cancer by a Small-Molecule Inhibitor of the Amino-Terminus Domain of the Androgen Receptor", Cancer Cell, 17:535-546 (2010).
Anton, R. et al., Opinion of the scientific panel on food additives, flavourings, processing aids and materials in contact with food (AFC) on a request from the commission related to 2,2-bis(4-hydroxyphenyl)propane bis(2,3-epoxypropyl)ether (bisphenol A diglycidyl ether, BADGE), Ref. No. 13510 and 39700 (EFSA-Q-2003-178), The EFSA Journal, 86:1-40 (2004).
Antonarakis et al., "Androgen receptor variant-driven prostate cancer: clinical implications and therapeutic targeting," Prostate Cancer and Prostatic Diseases (2016), 1-11.
Antonarakis et al., "Targeting the N-Terminal Domain of the Androgen Receptor: A New Approach for the Treatment of Advanced Prostate Cancer," The Oncologist 2016;21:1-9.
Auzou et al., European Journal of Medicinal Chemistry, 9(5):548-554 (1974) (with English Abstract).
Balbay, M.D. et al., "Highly Metastatic Human Prostate Cancer Growing within the Prostate of Athymic Mice Overexpresses Vascular Endothelial Growth Factor", Clinical Cancer Research, 5:783-789 (1999).
Banuelos et al., "Sintokamide A is a novel antagonist of androgen receptor that uniquely binds activation function-1 in its amino-terminal domain," The Journal of Biological Chemistry, vol. 291, No. 42, pp. 22231-22243, Oct. 14, 2016.
Bao, B. et al., "Androgen signaling is required for the vitamin D-mediated growth inhibition in human prostate cancer cells", Oncogene, 23:3350-3360 (2004).
Berge, S.M. et al., "Pharmaceutical Salts", Pharmaceutical Sciences, 66(1):1-19 (1977).
Berger, U. et al., "Identification of Derivatives of Bisphenol A Diglycidyl Ether and Novolac Glycidyl Ether in Can Coatings by Liquid Chromatography/Ion Trap Mass Spectrometry," Journal of AOAC International, Food Chemical Contaminants, 83(6):1367-1376 (2000).

(56) References Cited

OTHER PUBLICATIONS

Biles, J.E. et al., "Determination of the Diglycidyl Ether of Bisphenol A and its Derivatives in Canned Foods", J. Agric. Food Chem., 47:1965-1969 (1999).
Bisson, W.H. et al., "Discovery of antiandrogen activity of nonsteroidal scaffolds of marketed drugs", PNAS, 104(29):11927-11932 (2007).
Blaszczyk, N. et al., "Osteoblast-Derived factors Induce Androgen-Independent Proliferation and Expression of Prostate-Specific Antigen in Human Prostate Cancer Cells", Clin. Cancer Res., 10:1860-1869 (2004).
Bodei, et al., "Radionuclide Therapy with Iodine-125 and Other Auger-Electron-Emitting Radionuclides: Experimental Models and Clinical Applications." Cancer Biother. & Radiopharm. (2003); 18(6): 861-877.
Bohler, Paul et al., "Identification of Migrants from Coatings of Food Cans and Tubes: Reaction Products of Bisphenol-A-Diglycidyl Ether (BADGE) with Phenols and Solvents", Mitt. Gebiete Lebensm. Hyg., 89:529-547 (1998).
Brand et al., "EPI-001 is a selective peroxisome proliferator-activated receptor-gamma modulator with inhibitory effects on androgen receptor expression and activity in prostate cancer." Oncotarget (2015); 6(6): 3811-3824.
Brzozowski, Z. et al., "Precursors for bisphenolic resins", CAPLUS Database Accession No. 1990:36690, Document No. 112:33690, (1987), 1 page (Abstract).
Bruckheimer, E.M. et al., "Apoptosis in prostate carcinogenesis a growth regulator and a therapeutic target", Cell Tissue Res, 301:153-162 (2000).
Cascini, et al., "Iodine: A Longer-Life Positron Emitter Isotope—New Opportunities in Molecular Imaging." Hindawi Publishing Corp. Biomed. Res. Int. (2014); vol. 2014, Article ID 672094, 7 pages.
Chang, C. et al., "Development of Peptide Antagonists for the Androgen Receptor Using Combinatorial Peptide Phage Display", Molecular Endocrinology, 19(10):2478-2490 (2005).
Choi, K. M. et al., "New Families of Photocurable Oligomeric Fluoromonomers for Use in Dental Composites", Chemistry of Materials, 8(12):2704-2707 (1996).
Clinton, G.M. et al., "Estrogen action in human ovarian cancer", Critical Reviews in Oncology/Hematology, 25:1-9 (1997).
Crivello, J. V. et al., "Synthesis and photopolymerization of multifunctional propenyl ether monomers," Database CAPLUS [online], Chemical Abstracts Service, Columbus, Ohio, US, XP002729292, retrieved from STN CA Caesar Accession No. 1994-606067 (1994), 3 pages.
Crivello, J. V. et al., "Synthesis and photopolymerization of multifunctional propenyl ether monomers", Journal of Macromolecular Science, Pure and Applied Chemistry, A31(9):1105-1119 (1994).
Cook, W. D., "Fracture and Structure of Highly Crosslinked Polymer Composites", Journal of Applied Polymer Science, 42:1259-1269 (1991).
Culig, Zoran et al., "Androgen Receptor Activation in Prostatic Tumor Cell Lines by Insulin-like Growth Factor-I, Keratinocyte Growth Factor, and Epidermal Growth Factor", Cancer Research, 54:5474-5478 (1994).
Danquah, M. et al., "Micellar Delivery of Bicalutamide and Embelin for Treating Prostate Cancer", Pharmaceutical Research, 26:2081-2092 (2009).
Das, Debasish et al., "Sulfonic acid functionalized mesoporous MCM-41 silica as a convenient catalyst for Bisphenol-A synthesis", Chemical Communications, pp. 2178-2179 (2001).
De Mol et al., "EPI-001, a compound active against castration-resistant prostate cancer, targets transactivation unit 5 of the androgen receptor," ACS Chem. Biol., 2016, 11, 9, 2499-2505.
Dehm, S. et al., "Ligand-independent Androgen Receptor Activity is Activation Function-2-independent and Resistant to Antiandrogens in Androgen Refractory Prostate Cancer Cells", The Journal of Biological Chemistry, 281(38):27882-27893 (2006).
Dehm, S. et al., "Splicing of a Novel Androgen Receptor Exon Generates a Constitutively Active Androgen Receptor that Mediates Prostate Cancer Therapy Resistance", Cancer Research, 68:5469-5477 (2008).
Edmondson, R.J., et al., "The human ovarian surface epithelium is an androgen responsive tissue", British Journal of Cancer, 86:879-885 (2002).
Estebanez-Perpiñá, E. et al., "A surface on the androgen receptor that allosterically regulates coactivator binding," PNAS, 104(41):16074-16079 (2007).
Estebanez-Perpiñá, E. et al., "The Molecular Mechanisms of Coactivator Utilization in Ligand-dependent Transactivation by the Androgen Receptor," The Journal of Biological Chemistry, 280(9):8060-8068 (2005).
Fehlberg S. et al., "Bisphenol A diglycidyl ether induces apoptosis in tumor cells independently of peroxisome proliferator-activated receptor-γ, in caspase-dependent and -independent manners," Biochem. J., 362:573-578 (2002).
Gallart-Ayala, H. et al., "The analysis of bisphenol A-diglycidyl ether (BADGE), bisphenol F-diglycidyl ether (BFDGE) and their derivatives in canned food and beverages by LC-MS/MS", Thermo Fisher Scientific Inc., 4 pages (2011).
Garuti, L., et al., "Irreversible Protein Kinase Inhibitors", Current Medicinal Chemistry, 18:2981-2994 (2011).
Garcia et al., "Determination of compounds from epoxy resins in food simulants by HPLC-fluorescence." Chromatographia, 58(5-6): 337-342 (2003).
Gleave, Martin et al., "Acceleration of Human Prostate Cancer Growth in Vivo by Factors Produced by Prostate and Bone Fibroblasts", Cancer Research, 51:3753-3761 (1991).
Gregory, Christopher et al., "Epidermal Growth Factor Increases Coactivation of the Androgen Receptor in Recurrent Prostate Cancer", The Journal of Biological Chemistry, 279(8):7119-7130 (2004).
Guinan, P.D. et al., "Impotence Therapy and Cancer of the Prostate", The American Journal of Surgery, 131:599-600 (1976).
Guo, Zhiyong et al., "A Novel Androgen Receptor Splice Variant Is Up-regulated during Prostate Cancer Progression and Promotes Androgen Depletion-Resistant Growth", Cancer Research, 69:2305-13 (2009).
Haggstrom, Stina et al., "Testosterone Induces Vascular Endothelial Growth Factor Synthesis in the Ventral Prostate in Castrated Rats", The Journal of Urology, 161:1620-1625 (1999).
Harper et al., "Expression of Androgen Receptor and Growth Factors in Premalignant Lesions of the Prostate", Journal of Pathology, 186:169-177 (1998).
He, B. et al., "Activation Function 2 in the Human Androgen Receptor Ligand Binding Domain Mediates Interdomain Communication with the $NH_2$-terminal Domain", The Journal of Biological Chemistry, 274(52):37219-37225 (1999).
He, B. et al., "Structural Basis for Androgen Receptor Interdomain and Coactivator Interactions Suggests a Transition in Nuclear Receptor Activation Function Dominance", Molecular Cell, 16:425-438 (2004).
Henke, H., "Selektive präparative gelchromatographische Trennung niedermolekularer Verbindungen an Sephadex LH-20", Journal of Chromatography, 254: 296-308 (1983).
Heinlein, Cynthia A., et al., "Androgen Receptor in Prostate Cancer", Endocrine Reviews, 25(2):276-308 (2004).
Helzlsouer, Kathy J., et al., "Serum Gonadotropins and Steroid Hormones and the Development of Ovarian Cancer", JAMA, 274(24):1926-1930 (1995).
Horoszewicz, J.S. et al., "LNCaP Model of Human Prostatic Carcinoma", Cancer Research, 43:1809-1818 (1983).
Hu, R. et al., "Ligand-Independent Androgen Receptor Variants Derived from Splicing of Cryptic Exons Signify Hormone-Refractory Prostate Cancer", Cancer Research, 69:16-22 (2009).
Huber, P.R. et al., "Prostate Specific Antigen. Experimental and Clinical Observations", Scand. J. Urol Nephrol., 104:33-39 (1987).
Hur, E. et al., "Recognition and Accommodation at the Androgen Receptor Coactivator Binding Interface", PLoS Biology, 2(9)(e274):1303-1312 (2004).

(56) References Cited

OTHER PUBLICATIONS

Imamura et al., "An imaging agent to detect androgen receptor and its active splice variants in prostate cancer," JCI Insight. 2016;1(11):e87850 15 pages.
Imamura et al., "Androgen receptor targeted therapies in castration-resistant prostate cancer: Bench to clinic," International Journal of Urology (2016), 23(8):654-65.
Isaacs, J.T., et al., "New Biochemical Methods to Determine Androgen Sensitivity of Prostatic Cancer: The Relative Enzymatic Index (REI)", Prostate Cancer and Hormone Receptors, pp. 133-144 (1979).
Isaacs, J.T., "Antagonistic Effect of Androgen on Prostatic Cell Death", The Prostate, 5:545-557 (1984).
Jackson, J. A. et al., "Prostatic Complications of Testosterone Replacement Therapy", Arch Intern Med., 149:2365-2366 (1989).
Japanese Patent Application No. 2016-512175, Notice of Reasons for Rejection dated Jun. 21, 2016 (and English translation), 12 pages.
Jenster, G. et al., "Domains of the Human Androgen Receptor Involved in Steroid Binding, Transcriptional Activation, and Subcellular Localization", Molecular Endocrinology, 5:1396-1404 (1991).
Jenster, G., et al. "Identification of two transcription activation units in the N-terminal domain of the human androgen receptor." Journal of Biological Chemistry (1995); 270.13: 7341-7346.
Jia, L. et al., "Androgen Receptor Signaling: Mechanism of Interleukin-6 Inhibition", Cancer Research, 64:2619-2626 (2004).
Jia, L. et al., "Androgen Receptor-Dependent PSA Expression in Androgen-Independent Prostate Cancer Cells Does Not Involve Androgen Receptor Occupancy of the PSA Locus", Cancer Research, 65:8003-8008 (2005).
Kaighn, M.E. et al., "Prostate Carcinoma: Tissue Culture Cell Lines", National Cancer Institute Monograph No. 49, pp. 17-21 (1978).
Kato, M. et al., "Cotargeting androgen receptor splice variants and mTOR signaling pathway for the treatment of castration-resistant prostate cancer," Clin Cancer Res, Jun. 2016, vol. 22, pp. 2744-2754.
Kemppainen, J. A. et al., "Distinguishing Androgen Receptor Agonists and Antagonists: Distinct Mechanisms of Activation by Medroxyprogesterone Acetate and Dihydrotestosterone", Mol. Endocrinol., 13:440-454 (1999).
Kim, D. et al., "Androgen Receptor Expression and Cellular Proliferation During Transition from Androgen-Dependent to Recurrent Growth after Castration in the CWR22 Prostate Cancer Xenograft", American Journal of Pathology, 160(1):219-226 (2002).
Kolbel, M. et al., "Design of Liquid Crystalline Block Molecules with Nonconventional Mesophase Morphologies: Calamitic Bolaamphiphiles with Lateral Alkyl Chains", J. Am. Chem. Soc.,123:6809-6818 (2001).
Kumar, S. et al., "Synthesis of new crown analogs derived from bisphenol," Indian Journal Chemistry, 36B:656-661 (1997).
L'Heureux, A. et al., "Aminodifluorosulfinium Salts: Selective Fluorination Reagents with Enhanced Thermal Stability and Ease of Handling", J. Org. Chem, 75:3401-3411 (2010).
Langley, E. et al., "Evidence for an Anti-parallel Orientation of the Ligand-activated Human Androgen Receptor Dimer", The Journal of Biological Chemistry, 270(50):29983-29990 (1995).
Lannoye, G.S. et al., "N-Fluoroalkylated and N-alkylated analogs of the dopaminergic D-2 receptor antagonist raclopride", J. Med. Chem., 33(9):2430-2437 (1990).
Leepipatpiboon, N. et al., "Simultaneous determination of bisphenol-A-diglycidyl ether, bisphenol-F-diglycidyl ether, and their derivatives in oil-in-water and aqueous-based canned foods by high-performance liquid chromatography with fluorescence detection." Journal of Chromatography A (2005); 1073.1: 331-339.
Levoin et al., "Determination of the binding mode and interacting amino-acids for dibasic H3 receptor antagonists", Bioorganic & Medicinal Chemistry, 21 (2013) 4526-4529 and Levoin et al., "Supporting Information—Determination of the binding mode and interacting amino-acids for dibasic H3 receptor agonists", Bioorganic & Medicinal Chemistry, vol. 21, Jan. 2013, pp. S1-S3.
Loren, J.C. et al., "Synthesis of achiral and racemic catenanes based on terpyridine and a directionalized terpyridine mimic, pyndyl-phenanthroline", Org. Biomol. Chem., 3(17):3105-3116 (2005).
Louie, M.C. et al., "Androgen-induced recruitment of RNA polymerase II to a nuclear receptor-p160 coactivator complex", PNAS, 100(5):2226-2230 (2003).
Makary, P., "Principles of salt formation." UK Journal of Pharmaceutical and Biosciences (2014); 2(4): 01-04.
Marriott et al., "Pharmaceutical Compounding and Dispensing," Second Edition, Pharmaceutical Press, 305 pages (2005).
Martin, S.J. et al., "A new precursor for the radiosynthesis of [$^{18}$F]FLT", Nuclear Medicine and Biology, 29:263-273 (2002).
Martin, S.K. et al., "N-terminal targeting of androgen receptor variant enhances response of castration resistant prostate cancer to taxane chemotherapy," Molecular Oncology, 2015, vol. 9, pp. 628-639.
Masiello, D. et al., "Bicalutamide Functions as an Androgen Receptor Antagonist by Assembly of a Transcriptionally Inactive Receptor", The Journal of Biological Chemistry, 277(29):26321-26326 (2002).
Mawji et al., "Preparation of ester derivatives of bisphenol-related compounds as androgen receptor modulators", CAPLUS Database Accession No. 2014:1909735, Document No. 161:737220, Entered on Jan. 6, 2015, 7 pages (Abstract).
Melnyk, O. et al., "Neutralizing Anti-Vascular Endothelial Growth Factor Antibody Inhibits Further Growth of Established Prostate Cancer and Metastases in a Pre-Clinical Model", The Journal of Urology, 161:960-963 (1999).
Miller, J.I. et al., "The Clinical Usefulness of Serum Prostate Specific Antigen After Hormonal Therapy of Metastatic Prostate Cancer", The Journal of Urology, 147:956-961 (1992).
Mitsiades, C.S. et al., "Molecular biology and cellular physiology of refractoriness to androgen ablation therapy in advanced prostate cancer", Expert Opin. Investig. Drugs,10(6):1099-1115 (2001).
Lima, Lidia M., and Barreiro, Eliezer J. "Bioisosterism: a useful strategy for molecular modification and drug design." Current Medicinal Chemistry (2005); 12.1: 23-49.
Myung, J-K et al., "An androgen receptor N-terminal domain antagonist for treating prostate cancer", The Journal of Clinical Investigation, 123(7):2948-2960 (2013).
Nakazawa, H. et al., "In vitro assay of hydrolysis and chlorohydroxy derivatives of bisphenol A diglycidyl ether for estrogenic activity", Food and Chemical Toxicology, 40:1827-1832 (2002).
Nazareth, L.V. et al, "Activation of the Human Androgen Receptor through a Protein Kinase A Signaling Pathway", The Journal of Biological Chemistry, 271(33):19900-19907 (1996).
Nedolya, N. A. et al., Zhurnal Organicheskoi Khimii, 30(8):1163-1166 (1994) (non English document).
Nishikawa et al., "Epichlorohydrin derivative-based modifier of cellulose fibers and modification method of cellulose fibers," Accession No. 2000:98153 CAPLUS (2009).
Noble, R. L., "The development of prostatic adenocarcinoma in Nb Rats following prolonged sex hormone administration", Cancer Research, 37:1929-1933 (1977).
Noble, R. L., "Sex steroids as a cause of adenocarcinoma of the dorsal prostate in Nb Rats, and their Influence on the growth of transplants", Oncology, 34:138-141 (1977).
Ogawa, Y. et al., "Estrogenic activities of chemicals related to food contact plastics and rubbers tested by the yeast two-hybrid assay," Food Additives and Contaminants, 23:4, 422-430 (2006).
Paris, F. et al., "Phenylphenols, biphenols, bisphenol-A and 4-tert-octyphenol exhibit α and β estrogen activities and antiandrogen activity in reporter cell lines," Molecular and Cellular Endocrinology, 193:43-49 (2002).
Patani and LaVoie, "Bioisosterism: A Rational Approach in Drug Design", Chem. Rev., 96: 3147-3176 (1996).
Penczek, P. et al., "Synthesis and cyclotrimerization of dipropargyl derivatives of diepoxides," Database CAPLUS [Online] Chemical Abstracts Service, Columbus, Ohio, retrieved from STN CA Caesar Accession No. 1995:741510 (1995), 2 pages.

(56) References Cited

OTHER PUBLICATIONS

Penczek, P. et al., "Synthesis and cyclotrimerization of dipropargyl derivatives of diepoxides," Polimery, (Warsaw), 40(5):274-277 (1995).
Petersen, H. et al., "Determination of bisphenol A diglycidyl ether (BADGE) and its derivatives in food: identification and quantification by internal Standard", Eur. Food Res. Technol., 216:355-364 (2003).
Poouthree, K. et al., "Comparison of resolution in microemulsion EKC and MEKC employing suppressed electroosmosis: Application to bisphenol-A-diglycidyl ether and its derivatives", Electrophoresis, 28(20):3705-3711 (2007).
Poustka, J. et al., "Determination and occurrence of bisphenol A, bisphenol A diglycidyl ether, and bisphenol F diglycidyl ether, including their derivatives, in canned foodstuffs' from the Czech retail market," Czech J. Food Sci., 25(4):221-229 (2006).
Poustková et al., "Stability of bisphenol A diglycidyl ether and bisphenol F diglycidyl ether in water-based food simulants." European Food Research and Technology, 219(5): 534-539 (2004).
PubChem Compound Summary for CID 15305867, '4-Acetyl-4'-ethylbiphenyl', U.S. National Library of Medicine, Feb. 9, 2007, pp. 1-17; retrieved from https://pubchem.ncbi.nlm.nih.gov/compound/15305867.
PubChem Compound Summary for CID 18533308, '2-[4-[[4-(Aminomethoxy)phenyl]methyl]-2-methylphenoxy]acetic acid', U.S. National Library of Medicine, Dec. 4, 2007, pp. 1-15 retrieved from https://pubchem.ncbi.nlm.nih.gov/compound/18533308.
Quayle, S. et al., "Androgen receptor decoy molecules block the growth of prostate cancer", PNAS, 104(4):1331-1336 (2007).
Rao, B.R. et al., "Endocrine Factors in Common Epithelial Ovarian Cancer", Endocrine Reviews, 12(1):14-26 (1991).
Reader, C. E. L., "Epoxy Resin Derivatives for Stoving Systems", Surface Coatings Australia, 25(10):6-9 (1988).
Reid, J. et al., "Conformational Analysis of the Androgen Receptor Amino-terminal Domain Involved in Transactivation," The Journal of Biological Chemistry, 277:20079-20086 (2002).
Risch, H.A., "Hormonal Etiology of Epithelial Ovarian Cancer, With a Hypothesis Concerning the Role of Androgens and Progesterone", Journal of the National Cancer Institute, 90(23):1774-1786 (1998).
Riu, A. et al., "Characterization of Novel Ligands of ERα, Erβ, and PPARγ: The Case of Halogenated Bisphenol A and Their Conjugated Metabolites", Toxicology Sciences, 122(2): 372-382 (2011).
Roberts, J. T. et al., "Adenocarcinoma of Prostate in 40-Year-Old Body-Builder", Lancet, 2:742 (1986).
Roberts et al., "Emerging drugs for hepatocellular carcinoma," Expert Opin Emerg Drugs, 11(3):469-487 (2006).
Rokicki, G. et al., "Reactions of 4-chloromethyl-1,3-dioxolan-2-one with phenols as a new route to polyols and cyclic carbonates", Journal f. prakt. Chemie., 327:718-722 (1985).
Ross, R.K. et al., "Androgen Metabolism and Prostate Cancer: Establishing a Model of Genetic Susceptibility", European Urology, 35:355-361 (1999).
Roulin et al., "Targeting renal cell carcinoma with NVP-BEZ235, a dual PI3K/mTOR inhibitor, in combination with sorafenib," Mol Cancer, 10:90 (2011).
Rusu, E. et al.: "Photosensitive compounds with chloromethyl groups", Revue Roumaine de Chimie, 45(5):451-456 (2000).
Sadar, M., "Androgen-independent Induction of Prostate-specific Antigen Gene Expression via Cross-talk between the Androgen Receptor and Protein Kinase A signal Transduction Pathways," The Journal of Biological Chemistry, 274(12):7777-7783 (1999).
Sadar, M. et al., "Prostate cancer: molecular biology of early progression to androgen independence", Endocrine-Related Cancer, 6:487-502 (1999).
Sadar, M.D. et al., "Characterization of a New in Vivo Hollow Fiber Model for the Study of Progression of Prostate Cancer to Androgen Independence", Molecular Cancer Therapeutics, 1:629-637 (2002).
Sato, N. et al., "Intermittent Androgen Suppression Delays Progression to Androgen-independent Regulation of Prostate-specific Antigen Gene in the LNCaP Prostate Tumour Model", J. Steroid Biochem. Mol. Biol., 58:139-146 (1996).
Sato, N. et al., "A Metastatic and Androgen-sensitive Human Prostate Cancer Model Using Intraprostatic Inoculation of LNCaP Cells in SCID Mice", Cancer Research, 57:1584-1589 (1997).
Satoh, K. et al., "Study on Anti-Androgenic Effects of Bisphenol A Diglycidyl Ether (BADGE), Bisphenol F Diglycidyl Ether (BFDGE) and Their Derivatives Using Cells Stably Transfected with Human Androgen Receptor, AR—EcoScreen", Food and Chemical Toxicology, 42:983-993 (2004).
Schaefer, A. et al, "Migration from can coatings: Part 3. Synthesis, identification and quantification of migrating epoxy-based substances below 1000 Da", Food Additives and Contaminants, 21(4):390-405 (2004).
Schellhammer, "An evaluation of bicalutamide in the treatment of prostate cancer." Expert Opinion on Pharmacotherapy, 3(9): 1313-1328 (2002).
Sharp et al., "Targeting Androgen Receptor Aberrations in Castration-Resistant Prostate Cancer," Clin Cancer Res., Sep. 1, 2016;22(17):4280-4282.
Silverman, R. B., The Organic Chemistry of Drug Design and Drug Action, Academic Press, Inc., Harcourt Brace Jovanovich, pp. 15-20, 9 pages (1992).
Snoek, R. et al., "Induction of Cell-free, In Vitro Transcription by Recombinant Androgen Receptor Peptides", J. Steroid Biochem. Mol. Biol., 59:243-250 (1996).
Stanciuc et al., "Reaction of Pyrylium Salts with Nucleophiles. 23: Triarylethene Derivatives Containing an Oxyalkyleneamino or Oxyalkylene-N-pyridinium Side Chain", Journal of Pharmaceutical Sciences, vol. 82, No. 9, Sep. 1993, pp. 927-933.
Still, W. C. et al., "Rapid Chromatographic Technique for Preparative Separations with Moderate Resolution", J. Org. Chem., 43(14):2923-2925 (1978).
STN Structure Search, dated Oct. 30, 2014 citing PL 135932, 3 pages.
Strub and McKim, "Dimethyl Sulfoxide USP, PhEur in Approved Pharmaceutical Products and Medical Devices", PharmaTech.com, 6 pages (2008). http://www.pharmtech.com/print/224268?page=full&rel=canonical.
Sun, S. et al., "Castration resistance in human prostate cancer is conferred by a frequently occurring androgen receptor splice variant", The Journal of Clinical Investigation, 120(8):2715-30 (2010).
Tanji, N. et al., "Growth Factors: Roles in Andrology", Archives of Andrology, 47:1-7 (2001).
Taplin, M.E. et al., "Selection for Androgen Receptor Mutations in Prostate cancers Treated with Androgen Antagonist", Cancer Research, 59:2511-2515 (1999).
Taskeen, A. et al., "Analysis of bisphenol A in canned food: A mini review", Asian Journal of Chemistry, 22(5):4133-4135 (2010).
Thomson, A.A., "Role of androgens and fibroblast growth factors in prostatic development", Reproduction, 121:187-195 (2001).
Ueda, T. et al., "Activation of the Androgen Receptor N-terminal Domain by Interleukin-6 via MAPK and STAT3 Signal Transduction Pathways", The Journal of Biological Chemistry, 277(9):7076-7085 (2002).
Ueda, T. et al., "Ligand-independent Activation of the Androgen Receptor by Interleukin-6 and the Role of Steroid Receptor Coactivator-1 in Prostate cancer Cells", The Journal of Biological Chemistry, 277(41): 38087-38094 (2002).
Uematsu, Y. et al., "Chlorohydrins of bisphenol A diglycidyl ether (BADGE) and bisphenol F diglycidyl ether (BFDGE) in canned foods and ready-to-drink coffees from the Japanese market", Food Additives and Contaminants, 18(2):177-185 (2001).
Van Der Kwast, T.H. et al., "Androgen Receptors in Endocrine-Therapy-Resistant Human Prostate Cancer", Inter. J. Cancer, 48:189-193 (1991).
Van Scherpenzeel, M. et al., "Nanomolar affinity, iminosugar-based chemical probes for specific labeling of lysosomal glucocerebrosidase", Bioorganic & Medicinal Chemistry, 18:267-273 (2010).
Venkatesh, Srini, and Lipper, Robert A. "Role of the development scientist in compound lead selection and optimization." Journal of Pharmaceutical Sciences (2000); 89.2: 145-154.

(56) References Cited

OTHER PUBLICATIONS

Walfried et al., "Bisphenol F-Diglycidylether (BFDGE) und Folgeprodukte in Konservenfüllgütern: Synthese und Analytik," Deutsche Lebensmittel-Rundschau, vol. 96, No. 11, 2000, pp. 417-422 (with English abstract).
Wang, G. et al., "Identification of genes targeted by the androgen and PKA signaling pathways in prostate cancer cells", Oncogene, 25:7311-7323 (2006).
Wang, Q. et al., "Spatial and Temporal Recruitment of Androgen Receptor and Its Coactivators Involves Chromosomal Looping and Polymerase Tracking", Molecular Cell, 19:631-642 (2005).
Wetherill, Y. B. et al., "In vitro molecular mechanisms of bisphenol A action," Reproductive Toxicology, 24:178-198 (2007).
Wiedmann and Naqwi, "Pharmaceutical salts: Theory, use in solid dosage forms and in situ preparation in an aerosol." Asian Journal of Pharmaceutical Sciences (2016); 11(6): 722-734.
Wilcox and Cowart, "New Approaches to Synthetic Receptors. Synthesis and Host Properties of a Water Soluble Macrocyclic Analog of Troger's Base", Tetrahedron Letters, 27(46): 5563-5566 (1986).
Wilding, G., "The Importance of Steroid Hormones in Prostate Cancer", Cancer Surveys, 14:113-130 (1992).
Wilson, J.D. et al., "Long-Term Consequences of Castration in Men: Lessons from the Skoptzy and the Eunuchs of the Chinese and Ottoman Courts", The Journal of Clinical Endocrinology & Metabolism, 84:4324-4331 (1999).
Wong, C. et al., "Steroid Requirement for Androgen Receptor Dimerization and DNA Binding", J. Bioi. Chem., 268(25):19004-19012 (1993).
Xu, X. et al, "Synthesis and Stability Study of Dental Monomers Containing Methacrylamidoethyl Phosphonic Acids", Journal of Polymer Science: Part A Polymer Chemistry, 45:99-110 (2007).
Yang et al., "Targeting Androgen Receptor Activation Function-1 with EPI to Overcome Resistance Mechanisms in Castration-Resistant Prostate Cancer," Clin Cancer Res; 22(17) Sep. 1, 2016, 4466-4477.
Ye, Deyong, "An Introduction to Computer-Aided Drug Design", 3 pages, Jan. 31, 2004 (non-English document).
Yong, Eu Leong, et al. "Molecular basis of androgen receptor diseases." Annals of Medicine (2000); 32.1: 15-22.
Zuhayra, M. et al., "New approach for the synthesis of [$^{18}$F]fluoroethyltyrosine for cancer imaging: Simple, fast, and high yielding automated synthesis", Bioorganic & Medicinal Chemistry, 17:7441-7448 (2009).
Extended European Search Report in Application No. EP 12768410.8 dated Sep. 22, 2014, 10 pages.
Extended European Search Report in Application No. EP 14793978.9 dated Sep. 1, 2016, 8 pages.
Supplementary European Search Report in EP Application No. 09771876.1 dated Jun. 20, 2011, 5 pages.
Supplementary European Search Report in EP Application No. 11731645.5 dated Jun. 20, 2013, 11 pages.
Extended European Search Report in Application No. EP 14843037.4 dated Mar. 8, 2017, 5 pages.
Extended European Search Report in Application No. EP 17177010.0 dated Oct. 20, 2017, 10 pages.
Extended European Search Report in Application No. 16736999.0 dated May 24, 2018, 14 pages.
Extended European Search Report for European Application No. 17781660.0 dated Oct. 31, 2019, 8 pages.
Decision of Refusal for Japanese Application No. 2011-515039, dated Dec. 2, 2014, 18 pages (English translation).
International Search Report for International Application No. PCT/CA2009/000902 dated Sep. 1, 2009, 4 pages.
Written Opinion for International Application No. PCT/CA2009/000902 dated Sep. 1, 2009, 6 pages.
International Preliminary Report on Patentability for International Application No. PCT/CA2009/000902 dated Jan. 5, 2011, 7 pages.
International Search Report for International Application No. PCT/US2012/032584 dated Jul. 31, 2012, 3 pages.
Written Opinion for International Application No. PCT/US2012/032584 dated Jul. 31, 2012, 5 pages.
International Preliminary Report on Patentability for PCT/US2012/032584 dated Oct. 8, 2013, 6 pages.
International Search Report for International Application No. PCT/US2012/033959 dated Jul. 18, 2012, 3 pages.
Written Opinion for International Application No. PCT/US2012/033959 dated Jul. 18, 2012, 7 pages.
International Preliminary Report on Patentability for International Application No. PCT/US2012/033959 dated Oct. 22, 2013, 8 pages.
International Search Report for International Application No. PCT/US2012/033957 dated Jul. 18, 2012, 3 pages.
Written Opinion for International Application No. PCT/US2012/033957 dated Jul. 18, 2012, 5 pages.
International Preliminary Report on Patentability for International Application No. PCT/US2012/033957 dated Oct. 22, 2013, 6 pages.
International Search Report for International Application No. PCT/CA2011/000019 dated Mar. 21, 2011, 7 pages.
Written Opinion for International Application No. PCT/CA2011/000019 dated Mar. 21, 2011, 7 pages.
International Preliminary Report on Patentability for International Application No. PCT/CA2011/000019 dated Jul. 10, 2012, 8 pages.
International Search Report for International Application No. PCT/CA2011/000021 dated Apr. 18, 2011, 8 pages.
Written Opinion for International Application No. PCT/CA2011/000021 dated Apr. 18, 2011, 7 pages.
International Preliminary Report on Patentability for International Application No. PCT/CA2011/000021 dated Jul. 10, 2012, 8 pages.
International Search Report for International Application No. PCT/US2012/051481 dated Nov. 26, 2012, 4 pages.
Written Opinion for International Application No. PCT/US2012/051481 dated Nov. 26, 2012, 7 pages.
International Preliminary Report on Patentability for International Application No. PCT/US2012/051481 dated Feb. 25, 2014, 8 pages.
International Search Report for International Application No. PCT/US2012/051923 dated Jan. 28, 2013, 4 pages.
Written Opinion for International Application No. PCT/US2012/051923 dated Jan. 28, 2013, 8 pages.
International Preliminary Report on Patentability for International Application No. PCT/US2012/051923 dated Feb. 25, 2014, 9 pages.
International Search Report and Written Opinion for International Application No. PCT/CA2014/000414 dated Aug. 5, 2014, 6 pages.
International Preliminary Report on Patentability for International Application No. PCT/CA2014/000414 dated Nov. 10, 2015, 7 pages.
International Search Report and Written Opinion for International Application No. PCT/CA2014/000685 dated Dec. 4, 2014, 13 pages.
International Preliminary Report on Patentability for International Application No. PCT/CA2014/000685 dated Mar. 15, 2016, 7 pages.
International Search Report and Written Opinion for International Application No. PCT/CA2015/000533 dated Dec. 18, 2015, 11 pages.
International Preliminary Report on Patentability for International Application No. PCT/CA2015/000533 dated Apr. 18, 2017, 7 pages.
International Search Report and Written Opinion for International Application No. PCT/CA2015/000535 dated Dec. 23, 2015, 9 pages.
International Preliminary Report on Patentability for International Application No. PCT/CA2015/000535 dated Apr. 18, 2017, 6 pages.
International Search Report and Written Opinion for International Application No. PCT/CA2016/000008 dated Mar. 15, 2016, 13 pages.
International Preliminary Report on Patentability for International Application No. PCT/CA2016/000008 dated Jul. 18, 2017, 7 pages.
International Search Report and Written Opinion for International Application No. PCT/CA2016/000070 dated Jun. 2, 2016, 10 pages.
International Search Report and Written Opinion for International Application No. PCT/CA2017/000083 dated Aug. 3, 2017, 14 pages.

(56) References Cited

OTHER PUBLICATIONS

International Preliminary Report on Patentability for International Application No. PCT/CA2016/000070 dated Sep. 12, 2017, 6 pages.
International Search Report and Written Opinion for International Application No. PCT/CA2017/000141 dated Sep. 1, 2017, 11 pages.
International Search Report and Written Opinion for International Application No. PCT/CA2017/000201 dated Dec. 8, 2017, 9 pages.
International Search Report and Written Opinion for International Application No. PCT/US2019/057034 dated Feb. 6, 2020, 10 pages.
Alabi, A. et al., "Quick and simple sample treatment for multiresidue analysis of bisphenols, bisphenol diglycidyl ethers and their derivatives in canned food prior to liquid chromatography and fluorescence detection," J. of Chromatography A, 2014, 1336, 23-33.
Yonekubo, J. et al., "Concentrations of Bisphenol A, Bisphenol A Diglycidyl Ether, and Their Derivatives in Canned Foods in Japanese Markets," J. Agric. Food Chem., 2008, 56, 2041-2047.

* cited by examiner

ANDROGEN RECEPTOR MODULATORS AND METHODS FOR THEIR USE

CROSS-REFERENCE TO RELATED APPLICATIONS

This application is a continuation application of U.S. application Ser. No. 16/657,625, filed Oct. 18, 2019, which claims priority to U.S. Provisional Application No. 62/747,209, filed Oct. 18, 2018, U.S. Provisional Application No. 62/803,516, filed Feb. 10, 2019, and U.S. Provisional Application No. 62/857,516, filed Jun. 5, 2019, the disclosures of which are herein incorporated by reference in their entirety for all purposes.

FIELD OF THE INVENTION

The present disclosure generally relates to tricyclic compounds and their use for treatment of various indications. In particular the disclosure relates to tricyclic compounds and their use for treatment of various cancers, for example prostate cancer, including but not limited to, primary/localized prostate cancer (newly diagnosed), locally advanced prostate cancer, recurrent prostate cancer, non-metastatic castration-resistant prostate cancer, metastatic prostate cancer, metastatic castration-resistant prostate cancer (CRPC), and hormone-sensitive prostate cancer. This invention also relates to tricyclic compounds and their use for modulating androgen receptor (AR) activity, including truncated AR.

BACKGROUND OF THE INVENTION

Androgens mediate their effects through the androgen receptor (AR). Androgens play a role in a wide range of developmental and physiological responses and are involved in male sexual differentiation, maintenance of spermatogenesis, and male gonadotropin regulation (R. K. Ross, G. A. Coetzee, C. L. Pearce, J. K. Reichardt, P. Bretsky, L. N. Kolonel, B. E. Henderson, E. Lander, D. Altshuler & G. Daley, Eur Urol 35, 355-361 (1999); A. A. Thomson, Reproduction 121, 187-195 (2001); N. Tanji, K. Aoki & M. Yokoyama, Arch Androl 47, 1-7 (2001)). Several lines of evidence show that androgens are associated with the development of prostate carcinogenesis. Firstly, androgens induce prostatic carcinogenesis in rodent models (R. L. Noble, Cancer Res 37, 1929-1933 (1977); R. L. Noble, Oncology 34, 138-141 (1977)) and men receiving androgens in the form of anabolic steroids have a higher incidence of prostate cancer (J. T. Roberts & D. M. Essenhigh, Lancet 2, 742 (1986); J. A. Jackson, J. Waxman & A. M. Spiekerman, Arch Intern Med 149, 2365-2366 (1989); P. D. Guinan, W. Sadoughi, H. Alsheik, R. J. Ablin, D. Alrenga & I. M. Bush, Am J Surg 131, 599-600 (1976)). Secondly, prostate cancer does not develop if humans or dogs are castrated before puberty (J. D. Wilson & C. Roehrborn, J Clin Endocrinol Metab 84, 4324-4331 (1999); G. Wilding, Cancer Surv 14, 113-130 (1992)). Castration of adult males causes involution of the prostate and apoptosis of prostatic epithelium while eliciting no effect on other male external genitalia (E. M. Bruckheimer & N. Kyprianou, Cell Tissue Res 301, 153-162 (2000); J. T. Isaacs, Prostate 5, 545-557 (1984)). This dependency on androgens provides the underlying rationale for treating prostate cancer with chemical or surgical castration (androgen ablation), also known as androgen ablation therapy (ABT) or androgen depravation therapy (ADT).

Androgens also play a role in female diseases such as polycystic ovary syndrome as well as cancers. One example is ovarian cancer where elevated levels of androgens are associated with an increased risk of developing ovarian cancer (K. J. Helzlsouer, A. J. Alberg, G. B. Gordon, C. Longcope, T. L. Bush, S. C. Hoffman & G. W. Comstock, JAMA 274, 1926-1930 (1995); R. J. Edmondson, J. M. Monaghan & B. R. Davies, Br J Cancer 86, 879-885 (2002)). The AR has been detected in a majority of ovarian cancers (H. A. Risch, J Natl Cancer Inst 90, 1774-1786 (1998); B. R. Rao & B. J. Slotman, Endocr Rev 12, 14-26 (1991); G. M. Clinton & W. Hua, Crit Rev Oncol Hematol 25, 1-9 (1997)), whereas estrogen receptor-alpha (ERa) and the progesterone receptor are detected in less than 50% of ovarian tumors.

The only effective treatment available for advanced prostate cancer is the withdrawal of androgens which are essential for the survival of prostate luminal cells. Androgen ablation therapy causes a temporary reduction in tumor burden concomitant with a decrease in serum prostate-specific antigen (PSA). Unfortunately prostate cancer can eventually grow again in the absence of testicular androgens (castration-resistant disease) (Huber et al 1987 Scand J. Urol Nephrol. 104, 33-39). Castration-resistant prostate cancer that is still driven by AR is biochemically characterized before the onset of symptoms by a rising titre of serum PSA (Miller et al 1992 J. Urol. 147, 956-961). Once the disease becomes castration-resistant most patients succumb to their disease within two years.

The AR has distinct functional domains that include the carboxy-terminal ligand-binding domain (LBD), a DNA-binding domain (DBD) comprising two zinc finger motifs, and an N-terminus domain (NTD) that contains two transcriptional activation units (tau1 and tau5) within activation function-1 (AF-1). Binding of androgen (ligand) to the LBD of the AR results in its activation such that the receptor can effectively bind to its specific DNA consensus site, termed the androgen response element (ARE), on the promoter and enhancer regions of "normally" androgen regulated genes, such as PSA, to initiate transcription. The AR can be activated in the absence of androgen by stimulation of the cAMP-dependent protein kinase (PKA) pathway, with interleukin-6 (IL-6) and by various growth factors (Culig et al 1994 Cancer Res. 54, 5474-5478; Nazareth et al 1996 J. Biol. Chem. 271, 19900-19907; Sadar 1999 J. Biol. Chem. 274, 7777-7783; Ueda et al 2002 A J. Biol. Chem. 277, 7076-7085; and Ueda et al 2002 B J. Biol. Chem. 277, 38087-38094). The mechanism of ligand-independent transformation of the AR has been shown to involve: 1) increased nuclear AR protein suggesting nuclear translocation; 2) increased AR/ARE complex formation; and 3) the AR-NTD (Sadar 1999 J. Biol. Chem. 274, 7777-7783; Ueda et al 2002 A J Biol. Chem. 277, 7076-7085; and Ueda et al 2002 B J. Biol. Chem. 277, 38087-38094). The AR can be activated in the absence of testicular androgens by alternative signal transduction pathways in castration-resistant disease, which is consistent with the finding that nuclear AR protein is present in secondary prostate cancer tumors (Kim et al 2002 Am. J. Pathol. 160, 219-226; and van der Kwast et al 1991 Inter. J. Cancer 48, 189-193).

Clinically available inhibitors of the AR include non-steroidal antiandrogens such as apalutamide, darolutamide, bicalutamide (Casodex™), nilutamide, flutamide, and enzalutamide. There is also a class of steroidal antiandrogens, such as cyproterone acetate and spironolactone. Both steroidal and non-steroidal antiandrogens target the LBD of the AR and predominantly fail presumably due to poor affinity and mutations that lead to activation of the AR by these same antiandrogens (Taplin, M. E., Bubley, G. J., Kom Y. J., Small E. J., Uptonm M., Rajeshkumarm B., Balkm S. P., *Cancer Res.*, 59, 2511-2515 (1999)), and constitutively active AR splice variants. Antiandrogens have no effect on the constitutively active AR splice variants that lack the ligand-binding domain (LBD) and are associated with castration-recurrent prostate cancer (Dehm S M, Schmidt L J, Heemers H V, Vessella R L, Tindall D J., *Cancer Res* 68, 5469-77, 2008; Guo Z, Yang X, Sun F, Jiang R, Linn D E, Chen H, Chen H, Kong X, Melamed J, Tepper C G, Kung H J, Brodie A M, Edwards J, Qiu Y., *Cancer Res.* 69, 2305-13, 2009; Hu et al 2009 *Cancer Res.* 69, 16-22; Sun et al 2010 *J Clin Invest.* 2010 120, 2715-30) and resistant to abiraterone and enzalutamide (Antonarakis et al., *N Engl J Med.* 2014, 371, 1028-38; Scher et al *JAMA Oncol.* 2016 doi: 10.1001). Conventional therapy has concentrated on androgen-dependent activation of the AR through its C-terminal domain.

Other relevant AR antagonists previously reported (see, WO 2010/000066, WO 2011/082487; WO 2011/082488; WO 2012/145330; WO 2015/031984; WO 2016/058080; and WO 2016/058082) that bind to full-length AR and/or truncated AR splice variants that have been recently developed or are currently being developed include: AR degraders such as niclosamide (Liu C et al 2014), galeterone (Njar et al 2015; Yu Z at al 2014), and ARV-330/Androgen receptor PROTAC (Neklesa et al 2016 *J Clin Oncol* 34 suppl 2S; abstr 267); AR DBD inhibitor VPC-14449 (Dalal K et al 2014 *J Biol Chem.* 289(38):26417-29; Li H et al 2014 *J Med Chem.* 57(15):6458-67); antiandrogens apalutamide (Clegg N J et al 2012), ODM-201 (Moilanen A M et al 2015), ODM-204 (Kallio et al *J Clin Oncol* 2016 vol. 34 no. 2_suppl 230), TAS3681 (Minamiguchi et al 2015 *J Clin Oncol* 33, suppl 7; abstr 266); and AR NTD inhibitors 3E10-AR441bsAb (Goicochea N L et al 2015), and sintokamide (Sadar et al 2008; Banuelos et al 2016).

The AR-NTD is also a target for drug development (e.g. WO 2000/001813; Myung et al. *J. Clin. Invest* 2013, 123, 2948), since the NTD contains Activation-Function-1 (AF-1) which is the essential region required for AR transcriptional activity (Jenster et al 1991. *Mol Endocrinol.* 5, 1396-404). The AR-NTD importantly plays a role in activation of the AR in the absence of androgens (Sadar, M. D. 1999 *J Biol. Chem.* 274, 7777-7783; Sadar M D et al 1999 *Endocr Relat Cancer.* 6, 487-502; Ueda et al 2002 *J. Biol. Chem.* 277, 7076-7085; Ueda 2002 *J. Biol. Chem.* 277, 38087-38094; Blaszczyk et al 2004 *Clin Cancer Res.* 10, 1860-9; Dehm et al 2006 *J Biol Chem.* 28, 27882-93; Gregory et al 2004 *J Biol Chem.* 279, 7119-30). The AR-NTD is important in hormonal progression of prostate cancer as shown by application of decoy molecules (Quayle et al 2007, *Proc Natl Acad Sci USA.* 104, 1331-1336).

While the crystal structure has been resolved for the AR C-terminus LBD, this has not been the case for the NTD due to its high flexibility and intrinsic disorder in solution (Reid et al 2002 *J. Biol. Chem.* 277, 20079-20086) thereby hampering virtual docking drug discovery approaches. Compounds that modulate AR, potentially through interaction with NTD domain, include the bisphenol compounds disclosed in published PCT Nos: WO 2010/000066, WO 2011/ 082487; WO 2011/082488; WO 2012/145330; WO 2012/ 139039; WO 2012/145328; WO 2013/028572; WO 2013/ 028791; WO 2014/179867; WO 2015/031984; WO 2016/ 058080; WO 2016/058082; WO 2016/112455; WO 2016/ 141458; WO 2017/177307; WO 2017/210771; and WO 2018/045450, and which are hereby incorporated by reference in their entireties.

Transcriptionally active androgen receptor plays a major role in CRPC in spite of reduced blood levels of androgen (Karantanos, T. et al *Oncogene* 2013, 32, 5501-5511; Harris, W. P. et al *Nature Clinical Practice Urology,* 2009, 6, 76-85). AR mechanisms of resistance to ADT include: overexpression of AR (Visakorpi, T. et al *Nature Genetics* 1995, 9, 401-406; Koivisto, P. et al *Scandinavian Journal of Clinical and Laboratory Investigation Supplementum* 1996, 226, 57-63); gain-of-function mutations in the AR LBD (Culig Z. et al *Molecular Endocrinology* 1993, 7, 1541-1550); intratumoral androgen synthesis (Cai, C. et al *Cancer Research* 2011, 71, 6503-6513); altered expression and function of AR coactivators (Ueda, T. et al *The Journal of Biological Chemistry* 2002, 277, 38087-38094; Xu J. et al *Nature Reviews Cancer* 2009, 9, 615-630); aberrant post-translational modifications of AR (Gioeli D. et al *Molecular and Cellular Endocrinology* 2012, 352, 70-78; van der Steen T. et al *International Journal of Molecular Sciences* 2013, 14, 14833-14859); and expression of AR splice variants (AR-Vs) which lack the ligand-binding domain (LBD) (Karantanos, T. et al *Oncogene* 2013, 32, 5501-5511; Andersen R. J. et al *Cancer Cell* 2010, 17, 535-546; Myung J. K. et al *The Journal of Clinical Investigation* 2013, 123, 2948-2960; Sun S. et al *The Journal of Clinical Investigation* 2010, 120, 2715-2730). Anti-androgens such as bicalutamide and enzalutamide target AR LBD, but have no effect on truncated constitutively active AR-Vs such as AR-V7 (Li Y. et al *Cancer Research* 2013, 73, 483-489). Expression of AR-V7 is associated with resistance to current hormone therapies (Li Y. et al *Cancer Research* 2013, 73, 483-489; Antonarakis E. S. et al *The New England Journal of Medicine* 2014, 371, 1028-1038).

While significant advances have been made in this field, there remains a need for improved treatment for AR-mediated disorders including prostate cancer, especially metastatic castration-resistant prostate cancer. Development of compounds, via unique interactions with AR NTD, would provide patients alternative options and new hope.

SUMMARY OF THE INVENTION

The compounds of the present disclosure are androgen receptor modulators which may be useful in treating various diseases and conditions as disclosed herein. In one embodiment, the present disclosure provides compounds comprising the structure of formula (IIIA):

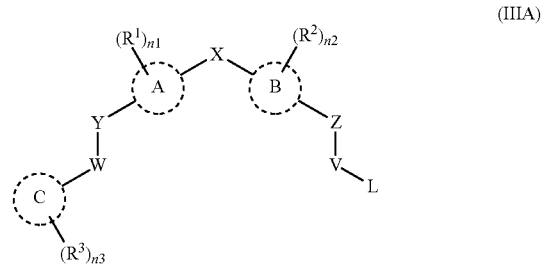

or a pharmaceutically acceptable salt, tautomer, stereoisomer or prodrug thereof, wherein:
A and B are each independently selected from phenyl, pyridyl, pyrimidyl, or thiophene;
C is a 3- to 10-membered ring;
X is a bond, —$(CR^5R^6)_t$—, or —$NR^7$;

Y is a bond, —(CR$^8$R$^9$)$_m$—, —O—, —S—, —S(=O)—, —SO$_2$—, —NR$^7$—, or —N(COCH$_3$)—;
W is a bond, —(CR$^{8a}$R$^{9a}$)$_m$—, —C(=O)—, —N(R$^7$)CO—, —CONR$^7$—, or —NSO$_2$R$^7$—;
Z is a bond, —CH$_2$—, —C(CH$_3$)H—, —O—, —S—, —NH—, —NCH$_3$—, or —N(COCH$_3$)—;
V is —CH$_2$— and L is halogen, —NH$_2$, —CHCl$_2$, —CCl$_3$, or —CF$_3$; or
V is —CH$_2$CH$_2$— and L is halogen or —NH$_2$;
R$^1$ and R$^2$ are each independently hydrogen, halogen, —CN, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{13}$R$^{14}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$ or optionally substituted —(C$_1$-C$_6$ alkyl)-SO$_2$R$^{16}$;
R$^3$ is selected from halogen, oxo, =S, =NR$^{16}$, —CN, —CF$_3$, —OH, —S(C$_1$-C$_3$ alkyl), C$_1$-C$_3$ alkyl, C$_2$-C$_3$ alkenyl, C$_2$-C$_3$ alkynyl, C$_1$-C$_3$ alkoxy, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl)NR$^{14}$SO$_2$R$^{16}$, —NR$^{14}$COR$^{16}$, —(C$_1$-C$_6$ alkyl)-NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO$_2$(C$_1$-C$_3$ alkyl), or —(C$_1$-C$_6$ alkyl)-SO$_2$(C$_1$-C$_3$ alkyl);
R$^5$ and R$^6$ are each independently hydrogen, halogen, —OH, C$_1$-C$_3$ alkyl, C$_2$-C$_3$ alkenyl, C$_2$-C$_3$ alkynyl, or C$_1$-C$_3$ alkoxy; or R$^5$ and R$^6$ taken together form an optionally substituted 3- to 6-membered carbocyclyl or heterocyclyl;
R$^7$ is hydrogen, C$_1$-C$_6$ alkyl, C$_2$-C$_6$ alkenyl, or C$_2$-C$_6$ alkynyl;
R$^8$ and R$^9$ are each independently hydrogen, halogen, or C$_1$-C$_3$ alkyl;
R$^{8a}$ and R$^{9a}$ are each independently hydrogen, —OH, halogen, C$_1$-C$_3$ alkyl, C$_2$-C$_3$ alkenyl, C$_2$-C$_3$ alkynyl, C$_1$-C$_3$ alkoxy, —NR$^{13}$R$^{14}$, —(C$_1$-C$_3$ alkyl)NR$^{13}$R$^{14}$, —NR$^{14}$COR$^{16}$, —(C$_1$-C$_3$ alkyl)-NR$^{14}$COR$^{16}$, —CONR$^{14}$R$^{15}$, or —(C$_1$-C$_3$ alkyl)-CONR$^{14}$R$^{15}$; or R$^{8a}$ and R$^{8b}$ taken together form an optionally substituted 3- to 6-membered carbocyclyl or heterocyclyl;
R$^{13}$, R$^{14}$ and R$^{15}$ are each independently hydrogen, C$_1$-C$_3$ alkyl, C$_2$-C$_3$ alkenyl, or C$_2$-C$_3$ alkynyl; or R$^{14}$ and R$^{15}$ taken together form a 3- to 6-membered heterocyclyl;
R$^{16}$ is hydrogen, optionally substituted C$_1$-C$_3$ alkyl, optionally substituted C$_2$-C$_3$ alkenyl, optionally substituted C$_2$-C$_3$ alkynyl, C$_3$-C$_6$ cycloalky, or phenyl;
each m is independently 0, 1, or 2;
n1 and n2 are each independently 0, 1, or 2;
R$^{13}$, R$^{14}$ and R$^{15}$ are each independently hydrogen, C$_1$-C$_3$ alkyl, C$_2$-C$_3$ alkenyl, or C$_2$-C$_3$ alkynyl; or R$^{14}$ and R$^{15}$ taken together form a 3- to 6-membered heterocyclyl;
R$^{16}$ is hydrogen, optionally substituted C$_1$-C$_3$ alkyl, optionally substituted C$_2$-C$_3$ alkenyl, optionally substituted C$_2$-C$_3$ alkynyl, C$_3$-C$_6$ cycloalky, or phenyl;
each m is independently 0, 1, or 2;
n1 and n2 are each independently 0, 1, or 2;
n3 is 1, 2, 3, 4 or 5; and
t is 0, 1 or 2.
In one embodiment, the present disclosure provides compounds comprising the structure of formula (IVA):

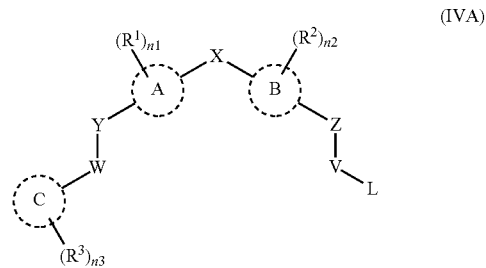

(IVA)

or a pharmaceutically acceptable salt, tautomer, stereoisomer or prodrug thereof, wherein:
A and B are each independently selected from phenyl, pyridyl, pyrimidyl, or thiophene;
C is a 3- to 10-membered ring;
X is a bond, —(CR$^5$R$^6$)$_t$—, or —NR$^7$—;
Y and Z are each independently a bond, —CH$_2$—, —C(CH$_3$)H—, —O—, —S—, —NH—, —NCH$_3$—, or —N(COCH$_3$)—;
W is a bond, —CH$_2$—, —C(CH$_3$)H—, —C(=O)—, —N(R$^7$)CO—, or —CONR$^7$—;
V is —CH$_2$— and L is halogen, —NH$_2$, or —CF$_3$; or
V is —CH$_2$CH$_2$— and L is halogen or —NH$_2$;
R$^1$ and R$^2$ are each independently hydrogen, halogen, —CN, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{13}$R$^{14}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$ or optionally substituted —(C$_1$-C$_6$ alkyl)-SO$_2$R$^{16}$;
R$^3$ is selected from halogen, oxo, =S, =NR$^{16}$, —CN, —CF$_3$, —OH, —S(C$_1$-C$_3$ alkyl), C$_1$-C$_3$ alkyl, C$_2$-C$_3$ alkenyl, C$_2$-C$_3$ alkynyl, C$_1$-C$_3$ alkoxy, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl)NR$^{14}$SO$_2$R$^{16}$, —NR$^{14}$COR$^{16}$, —(C$_1$-C$_6$ alkyl)-NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO$_2$(C$_1$-C$_3$ alkyl), or —(C$_1$-C$_6$ alkyl)-SO$_2$(C$_1$-C$_3$ alkyl);
R$^5$ and R$^6$ are each independently hydrogen, halogen, —OH, C$_1$-C$_3$ alkyl, C$_2$-C$_3$ alkenyl, C$_2$-C$_3$ alkynyl, or C$_1$-C$_3$ alkoxy; or R$^5$ and R$^6$ taken together form an optionally substituted 3- to 6-membered carbocyclyl or heterocyclyl;
R$^7$ is H or C$_1$-C$_6$ alkyl;
R$^{13}$, R$^{14}$ and R$^{15}$ are each independently hydrogen, C$_1$-C$_3$ alkyl, C$_2$-C$_3$ alkenyl, or C$_2$-C$_3$ alkynyl; or R$^{14}$ and R$^{15}$ taken together form a 3- to 6-membered heterocyclyl;
R$^{16}$ is hydrogen, C$_1$-C$_3$ alkyl, C$_2$-C$_3$ alkenyl, or C$_2$-C$_3$ alkynyl;
n1 and n2 are each independently 0, 1, or 2;
n3 is 1, 2, 3, 4 or 5; and
t is 0, 1 or 2.
In one embodiment of the compound of formula (IVA), C is 5- to 10-membered heteroaryl or aryl. In some embodiments, C is 5- to 7-membered heteroaryl comprising 1, 2, or 3 heteroatoms selected from O, S, or N as a ring member. In some embodiments, C, which is substituted with (R$^3$)n3, is pyrazole, imidazole, oxazole, oxadiazole, oxazolone, isoxazole, thiazole, pyridyl, pyrazine, furan or pyrimidyl. In some embodiments, C, which is substituted with $(R^3)n3$, is selected from
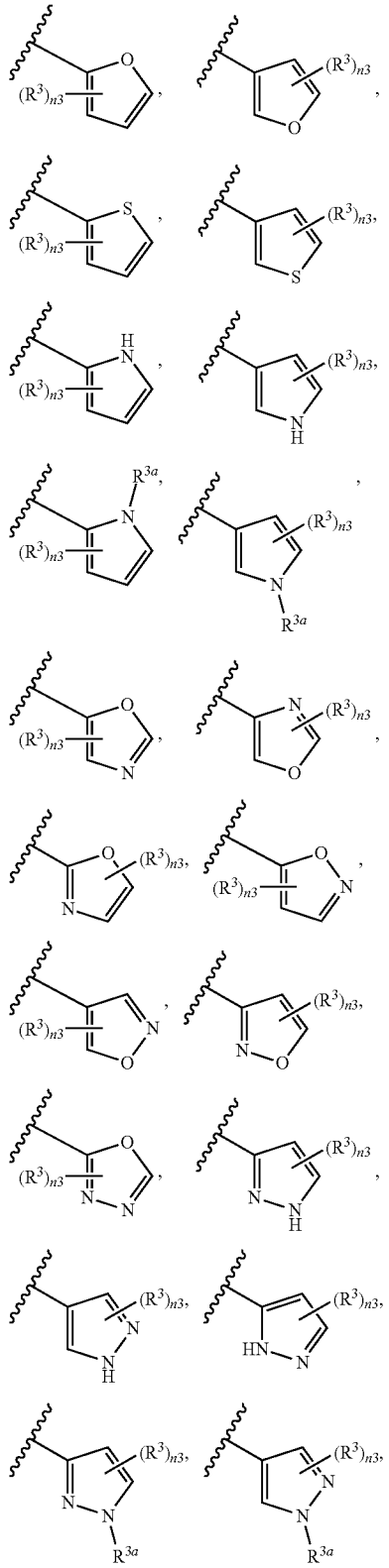
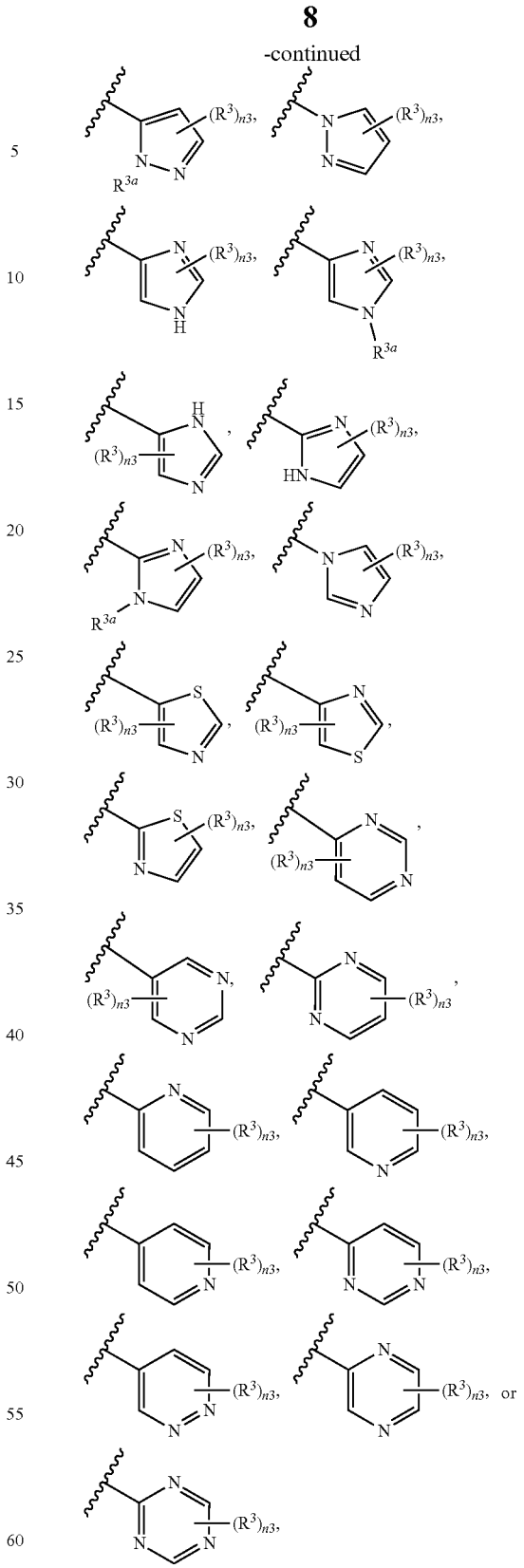
wherein $R^{3a}$ is $C_1$-$C_3$ alkyl.
In one embodiment of the compound of formula (IVA), $R^1$ and $R^2$ are each independently Cl, —CN, —CF$_3$, —OH, methyl, methoxy, or —CONH$_2$.

In one embodiment of the compound of formula (IVA),
A and B are phenyl;
X is —(CR$^5$R$^6$)$_t$—;
Y and Z are each —O—;
V is —CH$_2$— or —CH$_2$CH$_2$—;
L is halogen;
R$^1$ and R$^2$ are each independently hydrogen, halogen, —CN, —CF$_3$, —OH, or optionally substituted C$_1$-C$_6$ alkyl;
R$^5$ and R$^6$ are each independently hydrogen, halogen, —OH, or C$_1$-C$_3$ alkyl; and
R$^{16}$ is hydrogen, C$_1$-C$_3$ alkyl, C$_2$-C$_3$ alkenyl, or C$_2$-C$_3$ alkynyl. [68] In one embodiment of the compound of formula (IVA),
A and B are phenyl;
X is —(CR$^5$R$^6$)$_t$—;
W is —CH$_2$— or —C(CH$_3$)H—;
Y and Z are each —O—;
V is —CH$_2$CH$_2$—;
L is halogen;
R$^1$ and R$^2$ are each independently hydrogen, halogen, or —CN;
R$^5$ and R$^6$ are each independently hydrogen, or C$_1$-C$_3$ alkyl; and
R$^{16}$ is hydrogen, C$_1$-C$_3$ alkyl, C$_2$-C$_3$ alkenyl, or C$_2$-C$_3$ alkynyl.

In one embodiment, the present disclosure provides compounds comprising the structure of formula (A-I):

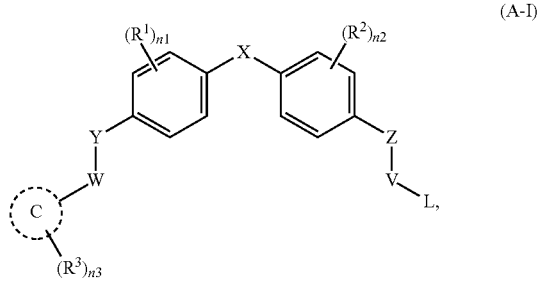

(A-I)

or a pharmaceutically acceptable salt, tautomer, stereoisomer or prodrug thereof, wherein:
C is a phenyl or a 5- to 7-membered monocyclic heteroaryl comprising 1, 2, or 3 heteroatoms selected from O, S, or N as a ring member;
X is a bond, —(CR$^5$R$^6$)$_t$—, or —NR$^7$—;
Y is a bond, —CH$_2$—, —C(CH$_3$)H—, —O—, —S—, —NH—, —NCH$_3$—, or —N(COCH$_3$)—;
Z is a bond, —CH$_2$—, —O—, or —NH—;
W is a bond, —CH$_2$—, —C(CH$_3$)H—, —C(=O)—, —N(R$^7$)CO—, or —CONR$^7$—;
V is —CH$_2$— and L is halogen, —NH$_2$, or —CF$_3$; or
V is —CH$_2$CH$_2$— and L is halogen or —NH$_2$;
R$^1$ and R$^2$ are each independently hydrogen, halogen, —CN, —CF$_3$, methyl, or —CONH$_2$;
R$^3$ is selected from from —CN, C$_1$-C$_3$ alkoxy, —CF$_3$, C$_1$-C$_3$ alkyl, C$_2$-C$_3$ alkenyl, C$_2$-C$_3$ alkynyl, —S(C$_1$-C$_3$ alkyl), —SO$_2$(C$_1$-C$_3$ alkyl), —NH$_2$, —(C$_1$-C$_3$ alkyl)NH$_2$, —NHSO$_2$CH$_3$, —NHSO$_2$CF$_3$, —N(CH$_3$)SO$_2$CH$_3$, —NHSO$_2$CH$_2$CH$_3$, —N(CH$_3$)SO$_2$CH$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), —N(CH$_3$)COO(C$_1$-C$_3$ alkyl), —NHCO(C$_1$-C$_3$ alkyl), or —N(CH$_3$)COO(C$_1$-C$_3$ alkyl);
R$^5$ and R$^6$ are each independently hydrogen, halogen, —OH, or C$_1$-C$_3$ alkyl;
R$^7$ is H or C$_1$-C$_6$ alkyl;
n1 and n2 are each independently 0, 1, or 2;
n3 is 1, 2, 3, 4 or 5; and
t is 0, 1 or 2.

In one embodiment of the compound of formula (IVA),
In one embodiment of the compound of formula (A-I), at least one R$^3$ is selected from —CN, C$_1$-C$_3$ alkoxy, —CONH$_2$, —NHSO$_2$CH$_3$, —N(CH$_3$)SO$_2$CH$_3$, —NHSO$_2$CH$_2$CH$_3$, —N(CH$_3$)SO$_2$CH$_2$CH$_3$, or —SO$_2$CH$_3$ and the other R$^3$, if present, is selected from —CN, —CF$_3$, C$_1$-C$_3$ alkyl, C$_2$-C$_3$ alkenyl, C$_2$-C$_3$ alkynyl, C$_1$-C$_3$ alkoxy, —S(C$_1$-C$_3$ alkyl), —SO$_2$(C$_1$-C$_3$ alkyl), —NH$_2$, —(C$_1$-C$_3$ alkyl)NH$_2$, —NHSO$_2$CH$_3$, —NHSO$_2$CF$_3$, —N(CH$_3$)SO$_2$CH$_3$, —NHSO$_2$CH$_2$CH$_3$, —N(CH$_3$)SO$_2$CH$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), —N(CH$_3$)COO(C$_1$-C$_3$ alkyl), —NHCO(C$_1$-C$_3$ alkyl), or —N(CH$_3$)COO(C$_1$-C$_3$ alkyl).

In one embodiment of the compound of formula (A-I),
X is a bond or —(CR$^5$R$^6$)$_t$;
W is a bond, —CH$_2$—, or —C(CH$_3$)H—;
Y is —O—;
Z is —O—;
V is —CH$_2$— or —CH$_2$CH$_2$—; and
L is halogen In one embodiment, the present disclosure provides compounds comprising the structure of formula (G-II):

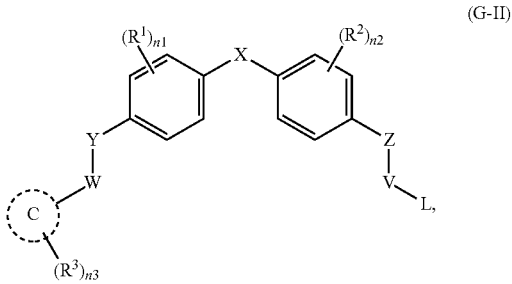

(G-II)

or a pharmaceutically acceptable salt, tautomer, stereoisomer or prodrug thereof, wherein:
C is

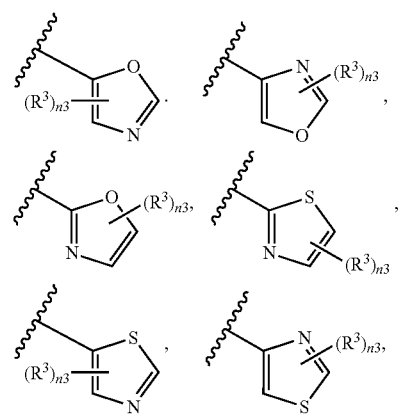

-continued

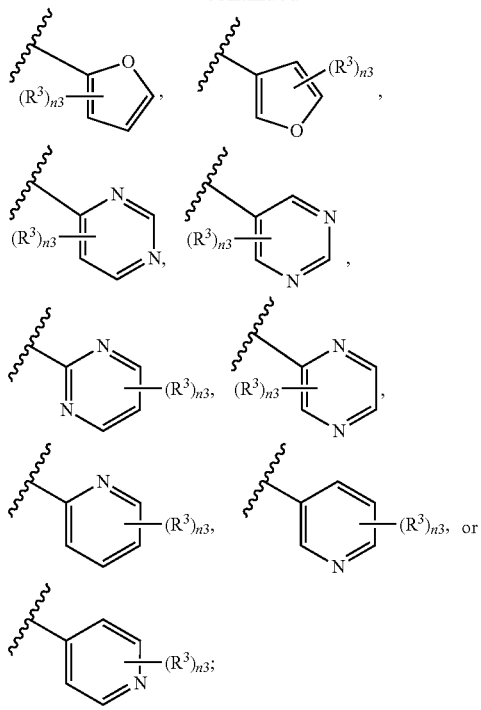

X is —(CR⁵R⁶)$_t$—;
Y is —O—;
Z is —O—;
W is —CH$_2$— or —C(CH$_3$)H—;
V is —CH$_2$CH$_2$—;
L is halogen;
$R^1$ and $R^2$ are each independently Cl or —CN;
at least one $R^3$ is selected from —CN, $C_1$-$C_3$ alkoxy, —CONH$_2$, —NHSO$_2$CH$_3$, —N(CH$_3$)SO$_2$CH$_3$, —NHSO$_2$CH$_2$CH$_3$, —N(CH$_3$)SO$_2$CH$_2$CH$_3$, or —SO$_2$CH$_3$ and the other $R^3$, if present, is selected from —CN, —CF$_3$, $C_1$-$C_3$ alkyl, $C_2$-$C_3$ alkenyl, $C_2$-$C_3$ alkynyl, $C_1$-$C_3$ alkoxy, —S($C_1$-$C_3$ alkyl), —SO$_2$($C_1$-$C_3$ alkyl), —NH$_2$, —($C_1$-$C_3$ alkyl)NH$_2$, —NHSO$_2$CH$_3$, —NHSO$_2$CF$_3$, —N(CH$_3$)SO$_2$CH$_3$, —NHSO$_2$CH$_2$CH$_3$, —N(CH$_3$)SO$_2$CH$_2$CH$_3$, —CH$_2$NHSO$_2$CH$_3$, —CH$_2$N(CH$_3$)SO$_2$CH$_3$, —SO$_2$NH$_2$, —CONH$_2$, —CON($C_1$-$C_3$ alkyl)$_2$, —CONH($C_1$-$C_3$ alkyl), —NHCO($C_1$-$C_3$ alkyl), —N(CH$_3$)COO($C_1$-$C_3$ alkyl), —NHCO($C_1$-$C_3$ alkyl), or —N(CH$_3$)COO($C_1$-$C_3$ alkyl);
$R^5$ and $R^6$ are each independently hydrogen or methyl;
n1 and n2 are each independently 0, 1, or 2;
n3 is 1 or 2; and
t is 1.

In one embodiment of the compound of formula (G-II), at least one $R^3$ is selected from —NHSO$_2$CH$_3$, —NHSO$_2$CH$_2$CH$_3$, or —SO$_2$CH$_3$ and the other $R^3$, if present, is selected from —CN, $C_1$-$C_3$ alkyl, $C_1$-$C_3$ alkoxy, —SO$_2$($C_1$-$C_3$ alkyl), —NH$_2$, —($C_1$-$C_3$ alkyl)NH$_2$, —NHSO$_2$CH$_3$, —N(CH$_3$)SO$_2$CH$_3$, —NHSO$_2$CH$_2$CH$_3$, —N(CH$_3$)SO$_2$CH$_2$CH$_3$, —SO$_2$NH$_2$, —CONH$_2$, —CON($C_1$-$C_3$ alkyl)$_2$, —CONH($C_1$-$C_3$ alkyl), —NHCO($C_1$-$C_3$ alkyl), —N(CH$_3$)COO($C_1$-$C_3$ alkyl), —NHCO($C_1$-$C_3$ alkyl), or —N(CH$_3$)COO($C_1$-$C_3$ alkyl).

In one embodiment, the present disclosure provides Compounds A1-A96, A98-A116, A118-A159, A161-A175, and A177-A234, or a pharmaceutically acceptable salt, tautomer, stereoisomer or prodrug thereof. In one embodiment, the present disclosure provides Compounds A13, A57, A74, A93, A109, A112, A122, A126, A131, A134, A136, A137, A164, A168, A169, A170, A171, A172, A184, A185, A195, and/or A204, or a pharmaceutically acceptable salt, tautomer, stereoisomer or prodrug thereof.

In one embodiment, the present disclosure provides a pharmaceutical composition comprising any one of the compound of formula (IIIA), or a pharmaceutically acceptable salt, tautomer, stereoisomer or prodrug thereof, and a pharmaceutically acceptable carrier. In one embodiment, the present disclosure provides a pharmaceutical composition comprising any one of the compound of formula (IVA), or a pharmaceutically acceptable salt, tautomer, stereoisomer or prodrug thereof, and a pharmaceutically acceptable carrier. In one embodiment, the present disclosure provides a pharmaceutical composition comprising any one of the compound of formula (A-I), or a pharmaceutically acceptable salt, tautomer, stereoisomer or prodrug thereof, and a pharmaceutically acceptable carrier. In one embodiment, the present disclosure provides a pharmaceutical composition comprising any one of the compound of formula (G-II), or a pharmaceutically acceptable salt, tautomer, stereoisomer or prodrug thereof, and a pharmaceutically acceptable carrier.

In one embodiment, the present disclosure provides a pharmaceutical composition comprising any one of Compounds A1-A96, A98-A116, A118-A159, A161-A175, and A177-A234, or a pharmaceutically acceptable salt, tautomer, stereoisomer or prodrug thereof, and a pharmaceutically acceptable carrier. In one embodiment, the present disclosure provides a pharmaceutical composition comprising any one of Compounds A13, A57, A74, A93, A109, A112, A122, A126, A131, A134, A136, A137, A164, A168, A169, A170, A171, A172, A184, A185, A195, and A204, or a pharmaceutically acceptable salt, tautomer, stereoisomer or prodrug thereof, and a pharmaceutically acceptable carrier.

In one embodiment, the present disclosure provides a method for treating cancer, comprising administering any one of the compound of formula (IIIA), (IVA), (A-I), or (G-II), and Compounds A1-A96, A98-A116, A118-A159, A161-A175, or A177-A234, or a pharmaceutically acceptable salt, tautomer, stereoisomer or prodrug thereof, to a subject in need thereof. In one embodiment, the cancer is prostate cancer. In one embodiment, the prostate cancer is metastatic castration-resistant prostate cancer. In other embodiments, the prostate cancer expresses full-length androgen receptor or truncated androgen receptor splice variant.

In one embodiment, the present disclosure provides a method for treating cancer, comprising administering any one of Compounds A13, A57, A74, A93, A109, A112, A122, A126, A131, A134, A136, A137, A164, A168, A169, A170, A171, A172, A184, A185, A195, and A204, or a pharmaceutically acceptable salt, tautomer, stereoisomer or prodrug thereof.

DETAILED DESCRIPTION

Figure 1:
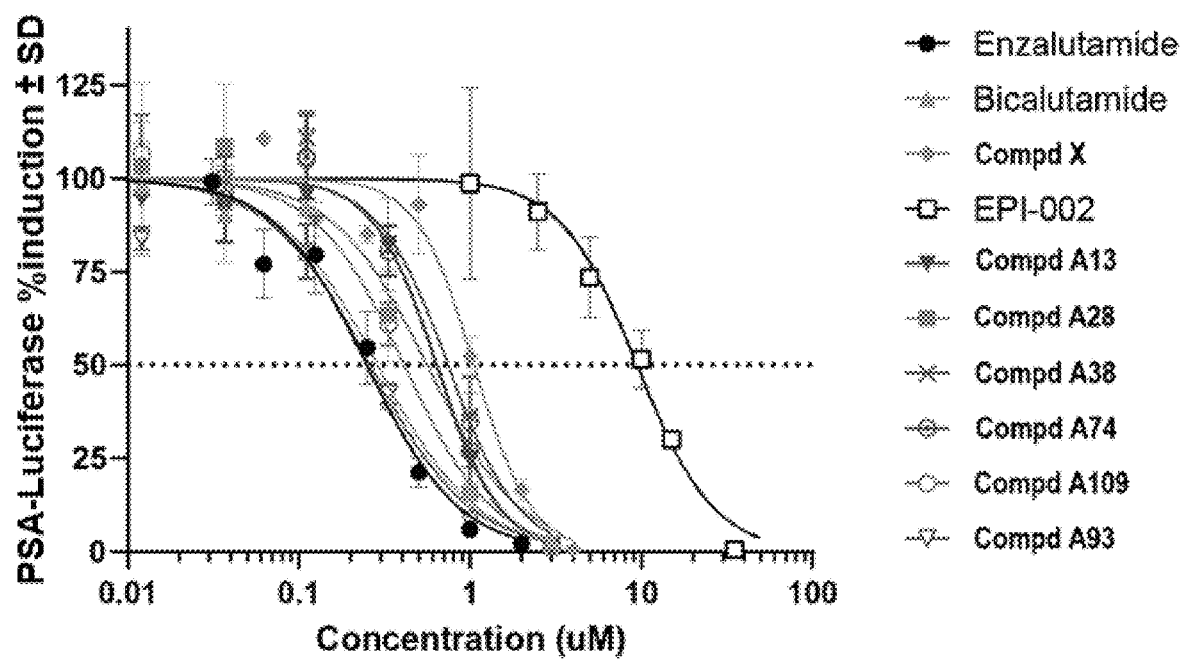
FIG. 1 shows a dose-dependent curve of PSA-luciferase activities in response to representative compounds in transiently transfected LNCaP cells treated with synthetic androgen (R1881).

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

Definitions

While the following terms are believed to be well understood by one of ordinary skill in the art, the following definitions are set forth to facilitate explanation of the presently disclosed subject matter.

Throughout the present specification, the terms "about" and/or "approximately" may be used in conjunction with numerical values and/or ranges. The term "about" is understood to mean those values near to a recited value. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "a" or "an" refers to one or more of that entity; for example, "a androgen receptor modulator" refers to one or more androgen receptor modulators or at least one androgen receptor modulator. As such, the terms "a" (or "an"), "one or more" and "at least one" are used interchangeably herein. In addition, reference to "an inhibitor" by the indefinite article "a" or "an" does not exclude the possibility that more than one of the inhibitors is present, unless the context clearly requires that there is one and only one of the inhibitors.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "pharmaceutically acceptable salts" includes both acid and base addition salts. Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

The term "treating" means one or more of relieving, alleviating, delaying, reducing, improving, or managing at least one symptom of a condition in a subject. The term "treating" may also mean one or more of arresting, delaying the onset (i.e., the period prior to clinical manifestation of the condition) or reducing the risk of developing or worsening a condition.

The compounds of the invention, or their pharmaceutically acceptable salts can contain one or more asymmetric centers and can thus give rise to enantiomers, diastereomers, and other stereoisomeric forms that can be defined, in terms of absolute stereochemistry, as (R)- or (S)- or, as (D)- or (L)- for amino acids. The present disclosure is meant to include all such possible isomers, as well as their racemic and optically pure forms whether or not they are specifically depicted herein. Optically active (+) and (−), (R)- and (S)-, or (D)- and (L)-isomers can be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present disclosure includes tautomers of any said compounds.

A "prodrug" refers to a derivative of a compound of the present disclosure that will be converted to the compound in vivo. In one embodiment of the present disclosure, a prodrug includes a compound of formula (I), (IA), (IB), (IC), (II), (IIA), (IIIA), (IIB), (III), (IV), (V), (VA), (VI), (A), (A-I), (B)-(D), (E), (E-I)-(E-VII), (F), (G), (G-I), (G-II), (H), and (H-I), having a free hydroxyl group (—OH) that is acetylated (—OCOMe) at one or more positions.

An "effective amount" means the amount of a formulation according to the invention that, when administered to a patient for treating a state, disorder or condition is sufficient to effect such treatment. The "effective amount" will vary depending on the active ingredient, the state, disorder, or condition to be treated and its severity, and the age, weight, physical condition and responsiveness of the mammal to be treated.

The term "therapeutically effective" applied to dose or amount refers to that quantity of a compound or pharmaceutical formulation that is sufficient to result in a desired clinical benefit after administration to a patient in need thereof.

As used herein, a "subject" can be a human, non-human primate, mammal, rat, mouse, cow, horse, pig, sheep, goat, dog, cat and the like. The subject can be suspected of having or at risk for having a cancer, such as prostate cancer, breast cancer, ovarian cancer, salivary gland carcinoma, or endometrial cancer, or suspected of having or at risk for having acne, hirsutism, alopecia, benign prostatic hyperplasia, ovarian cysts, polycystic ovary disease, precocious puberty, spinal and bulbar muscular atrophy, or age-related macular degeneration. Diagnostic methods for various cancers, such as prostate cancer, breast cancer, ovarian cancer, bladder cancer, pancreatic cancer, hepatocellular cancer, salivary gland carcinoma, or endometrial cancer, and diagnostic methods for acne, hirsutism, alopecia, benign prostatic hyperplasia, ovarian cysts, polycystic ovary disease, precocious puberty, spinal and bulbar muscular atrophy, or age-related macular degeneration and the clinical delineation of cancer, such as prostate cancer, breast cancer, ovarian cancer, bladder cancer, pancreatic cancer, hepatocellular cancer, salivary gland carcinoma, or endometrial cancer, diagnoses and the clinical delineation of acne, hirsutism, alopecia, benign prostatic hyperplasia, ovarian cysts, polycystic ovary disease, precocious puberty, spinal and bulbar muscular atrophy, or age-related macular degeneration are known to those of ordinary skill in the art.

"Mammal" includes humans and both domestic animals such as laboratory animals (e.g., mice, rats, monkeys, dogs, etc.) and household pets (e.g., cats, dogs, swine, cattle, sheep, goats, horses, rabbits), and non-domestic animals such as wildlife and the like.

All weight percentages (i.e., "% by weight" and "wt. %" and w/w) referenced herein, unless otherwise indicated, are measured relative to the total weight of the pharmaceutical composition.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" other active agents would either completely lack other active agents, or so nearly completely lack other active agents that the effect would be the same as if it completely lacked other active agents. In other words, a composition that is "substantially free of" an ingredient or element or another active agent may still contain such an item as long as there is no measurable effect thereof.

The terms below, as used herein, have the following meanings, unless indicated otherwise:

"Amino" refers to the —$NH_2$ radical.

"Cyano" refers to the —CN radical.

"Halo" or "halogen" refers to bromo, chloro, fluoro or iodo radical, including their radioisotopes. "$^{123}$I" refers to the radioactive isotope of iodine having atomic mass 123. The compounds of Formula I can comprise at least one $^{123}$I moiety. Throughout the present application, where structures depict a $^{123}$I moiety at a certain position it is meant that the I moiety at this position is enriched for $^{123}$I. In other words, the compounds contain more than the natural abundance of $^{123}$I at the indicated position(s). It is not required that the compounds comprise 100% $^{123}$I at the indicated positions, provided $^{123}$I is present in more than the natural abundance. Typically the $^{123}$I isotope is enriched to greater than 50%, greater than 60%, greater than 70%, greater than, 80% or greater than 90%, relative to $^{127}$I. "$^{18}$F" refers to the radioactive isotope of fluorine having atomic mass 18. "F" or "$^{19}$F" refers to the abundant, non-radioactive fluorine isotope having atomic mass 19. The compounds of Formula I can comprise at least one $^{18}$F moiety. Throughout the present application, where structures depict a $^{18}$F moiety at a certain position it is meant that the F moiety at this position is enriched for $^{18}$F. In other words, the compounds contain more than the natural abundance of $^{18}$F at the indicated position(s). It is not required that the compounds comprise 100% $^{18}$F at the indicated positions, provided $^{18}$F is present in more than the natural abundance. Typically the $^{18}$F isotope is enriched to greater than 50%, greater than 60%, greater than 70%, greater than 80% or greater than 90%, relative to $^{19}$F.

"Hydroxy" or "hydroxyl" refers to the —OH radical.

"Imino" refers to the =NH substituent.

"Nitro" refers to the —$NO_2$ radical.

"Oxo" refers to the =O substituent.

"Thioxo" refers to the =S substituent.

"Alkyl" or "alkyl group" refers to a fully saturated, straight or branched hydrocarbon chain radical having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula —$OR_a$ where $R_a$ is an alkyl, alkenyl or alknyl radical as defined above containing one to twelve carbon atoms. Unless stated otherwise specifically in the specification, an alkoxy group can be optionally substituted.

"Alkylamino" refers to a radical of the formula —$NHR_a$ or —$NR_aR_a$ where each $R_a$ is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the —C(=O)$R_a$ moiety, wherein $R_a$ is an alkyl, alkenyl or alkynyl radical as defined above. A non-limiting example of an alkyl carbonyl is the methyl carbonyl ("acetal") moiety. Alkylcarbonyl groups can also be referred to as "Cw-Cz acyl" where w and z depicts the range of the number of carbon in $R_a$, as defined above. For example, "C1-$C_{10}$ acyl" refers to alkylcarbonyl group as defined above, where $R_a$ is $C_1$-$C_{10}$ alkyl, $C_1$-$C_{10}$ alkenyl, or $C_1$-$C_{10}$ alkynyl radical as defined above. Unless stated otherwise specifically in the specification, an alkyl carbonyl group can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aralkyl" or "arylalkyl" refers to a radical of the formula —$R_b$—$R_c$ where $R_b$ is an alkylene group as defined above and $R_c$ is one or more aryl radicals as defined above, for example, benzyl, diphenylmethyl and the like. Unless stated otherwise specifically in the specification, an aralkyl group can be optionally substituted.

"Aralkenyl" or "arylalkenyl" refers to a radical of the formula —$R_b$—$R_c$ where $R_b$ is an alkenylene o group as defined above and $R_c$ is one or more aryl radicals as defined above. Unless stated otherwise specifically in the specification, an aralkenyl group can be optionally substituted.

"Aralkynyl" or "arylalkynyl" refers to a radical of the formula —$R_b$—$R_c$ where $R_b$ is an alkynylene group as defined above and $R_c$ is one or more aryl radicals as defined above. Unless stated otherwise specifically in the specification, an aralkynyl group can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include aryls and cycloalkyl. cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Cycloalkylalkyl" refers to a radical of the formula —$R_b$—$R_d$ where $R_b$ is an alkylene, alkenylene, or alkynylene group as defined above and $R_d$ is a cycloalkyl, cycloalkenyl, cycloalkynyl radical as defined above. Unless stated otherwise specifically in the specification, a cycloalkylalkyl group can be optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl radical, as defined above, that is substituted by one or more halo radicals, as defined above, e.g., 1-fluoropropenyl, 1,1-difluorobutenyl, and the like. Unless stated otherwise specifically in the specification, a haloalkenyl group can be optionally substituted.

"Haloalkynyl" refers to an alkynyl radical, as defined above, that is substituted by one or more halo radicals, as defined above, e.g., 1-fluoropropynyl, 1-fluorobutynyl, and the like. Unless stated otherwise specifically in the specification, a haloalkenyl group can be optionally substituted.

"Heterocyclyl," "heterocyclic ring" or "heterocycle" refers to a stable 3- to 20-membered non-aromatic, partially aromatic, or aromatic ring radical which consists of two to twelve carbon atoms and from one to six heteroatoms selected from the group consisting of nitrogen, oxygen and sulfur. Heterocyclycl or heterocyclic rings include heteroaryls as defined below. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group can be optionally substituted.

"Heterocyclylalkyl" refers to a radical of the formula —$R_b$—$R_e$ where $R_b$ is an alkylene group as defined above and $R_e$ is a heterocyclyl radical as defined above. Unless stated otherwise specifically in the specification, a heterocycloalkylalkyl group can be optionally substituted.

"Heterocyclylalkenyl" refers to a radical of the formula —$R_b$—$R_e$ where $R_b$ is an alkenylene group as defined above and $R_e$ is a heterocyclyl radical as defined above. Unless stated otherwise specifically in the specification, a heterocycloalkylalkenyl group can be optionally substituted.

"Heterocyclylalkynyl" refers to a radical of the formula —$R_b$—$R_e$ where $R_b$ is an alkynylene group as defined above and $R_e$ is a heterocyclyl radical as defined above. Unless stated otherwise specifically in the specification, a heterocycloalkylalkynyl group can be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group can be optionally substituted.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophene), benzotriazolyl, benzo[4,6]imidazo[1,2-a]pyridinyl, carbazolyl, cinnolinyl, dibenzofuranyl, dibenzothiophene, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophene (i.e. thienyl). Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" refers to a radical of the formula —$R_b$—$R_f$ where $R_b$ is an alkylene chain as defined above and $R_f$ is a heteroaryl radical as defined above. Unless stated otherwise specifically in the specification, a heteroarylalkyl group can be optionally substituted.

"Heteroarylalkenyl" refers to a radical of the formula —$R_b$—$R_f$ where $R_b$ is an alkenylene, chain as defined above and $R_f$ is a heteroaryl radical as defined above. Unless stated otherwise specifically in the specification, a heteroarylalkenyl group can be optionally substituted.

"Heteroarylalkynyl" refers to a radical of the formula —$R_b$—$R_f$ where $R_b$ is an alkynylene chain as defined above and $R_f$ is a heteroaryl radical as defined above. Unless stated otherwise specifically in the specification, a heteroarylalkynyl group can be optionally substituted.

"Ring" refers to a cyclic group which can be fully saturated, partially saturated, or fully unsaturated. A ring can be monocyclic, bicyclic, tricyclic, or tetracyclic. Unless stated otherwise specifically in the specification, a ring can be optionally substituted.

"Thioalkyl" refers to a radical of the formula —$SR_a$ where $R_a$ is an alkyl, alkenyl, or alkynyl radical as defined above containing one to twelve carbon atoms. Unless stated otherwise specifically in the specification, a thioalkyl group can be optionally substituted.

The term "substituted" used herein means any of the above groups (i.e., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atom such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups.

"Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol

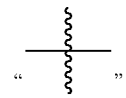

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

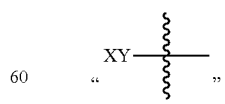

indicates that the chemical entity "XY" is bonded to another chemical entity via the point of attachment bond. Furthermore, the specific point of attachment to the non-depicted chemical entity can be specified by inference. For example, the compound $CH_3$—$R^3$, wherein $R^3$ is H or

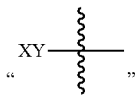
" "

infers that when R³ is "XY", the point of attachment bond is the same bond as the bond by which R³ is depicted as being bonded to CH₃.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring can be replaced with a nitrogen atom.

The following description includes information that may be useful in understanding the present invention. It is not an admission that any of the information provided herein is prior art or relevant to the presently claimed inventions, or that any publication specifically or implicitly referenced is prior art.

Compounds of the Present Disclosure

The compound of the present disclosure can be useful for modulating androgen receptor (AR). Further, the compound of the present disclosure can be useful for treating various diseases and conditions including, but not limited to, cancer. In some embodiments, the cancer is prostate cancer or breast cancer.

In one embodiment, the present disclosure provides compounds comprising the structure of formula (I):

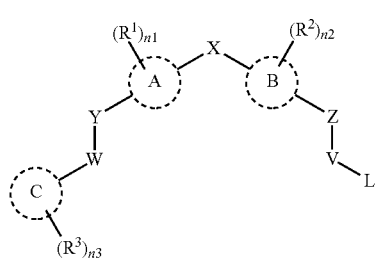
(I)

or a pharmaceutically acceptable salt, tautomer, stereoisomer or prodrug thereof, wherein:

A and B are each independently aryl or heteroaryl;

C is a 3- to 10-membered ring;

X is a bond, $-(CR^5R^6)_t-$, $-O-$, $-C(=O)-$, $-S-$, $-S(=O)-$, $-SO_2-$, $-NR^7-$, $-N(R^7)CO-$, $-CON(R^7)-$, or $-NSO_2R^7-$;

Y and Z are each independently a bond, $-(CR^8R^9)_m-$, $-O-$, $-C(=O)-$, $-S-$, $-S(=O)-$, $-SO_2-$, or $-NR^7-$;

W and V are each independently a bond, $-(CR^{8a}R^{9a})_m-$, $-C(=O)-$, $-N(R^7)CO-$, $-CONR^7-$, or $-NSO_2R^7-$;

L is hydrogen, halogen, $-CF_2R^{10}$, $-CF_3$, $-CN$, $-OR^{10}$; $-NR^{11}R^{12}$, or $-CONR^{11}R^{12}$;

R¹ and R² are each independently hydrogen, halogen, $-CN$, $-CF_3$, $-OH$, optionally substituted $C_1-C_6$ alkyl, optionally substituted $C_1-C_6$ alkoxy, optionally substituted $-(C_1-C_6$ alkyl)-$(C_1-C_6$ alkoxy), optionally substituted $-(C_1-C_6$ alkyl)-OH, $-NR^{13}R^{14}$, optionally substituted $-(C_1-C_6$ alkyl)-$NR^{13}R^{14}$, $-NR^{14}SO_2R^{16}$, optionally substituted $-(C_1-C_6$ alkyl)$NR^{14}SO_2R^{16}$, $-NR^{14}COR^{16}$, optionally substituted $-(C_1-C_6$ alkyl)-$NR^{14}COR^{16}$, $-CONR^{14}R^{15}$, optionally substituted $-(C_1-C_6$ alkyl)-$CONR^{14}R^{15}$, $-SO_2NR^{14}R^{15}$, optionally substituted $-(C_1-C_6$ alkyl)-$SO_2NR^{14}R^{15}$, optionally substituted $-SO_2R^{16}$, optionally substituted $-(C_1-C_6$ alkyl)-$SO_2R^{16}$, optionally substituted carbocyclyl, optionally substituted heterocyclyl, optionally substituted aryl, or optionally substituted heteroaryl;

R³ is hydrogen, halogen, oxo, =S, =NR¹⁶, $-CN$, $-CF_3$, $-OH$, $-SR^{16}$, optionally substituted $C_1-C_6$ alkyl, optionally substituted $C_2-C_6$ alkenyl, optionally substituted $C_2-C_6$ alkynyl, optionally substituted $C_1-C_6$ alkoxy, optionally substituted $-(C_1-C_6$ alkyl)-$(C_1-C_6$ alkoxy), optionally substituted $-(C_1-C_6$ alkyl)-OH, $-NR^{13}R^{14}$, optionally substituted $-(C_1-C_6$ alkyl)-$NR^{13}R^{14}$, $-NR^{14}SO_2R^{16}$, optionally substituted $-(C_1-C_6$ alkyl)$NR^{14}SO_2R^{16}$, $-NR^{14}COR^{16}$, optionally substituted $-(C_1-C_6$ alkyl)-$NR^{14}COR^{16}$, $-CONR^{14}R^{15}$, optionally substituted $-(C_1-C_6$ alkyl)-$CONR^{14}R^{15}$, $-SO_2NR^{14}R^{15}$, optionally substituted $-(C_1-C_6$ alkyl)-$SO_2NR^{14}R^{15}$, optionally substituted $-SO_2R^{16}$, optionally substituted $-(C_1-C_6$ alkyl)-$SO_2R^{16}$ optionally substituted carbocyclyl, optionally substituted heterocyclyl, optionally substituted aryl, or optionally substituted heteroaryl;

R⁵ and R⁶ are each independently hydrogen, halogen, $-OH$, optionally substituted $C_1-C_6$ alkyl, optionally substituted $C_2-C_6$ alkenyl, optionally substituted $C_2-C_6$ alkynyl, optionally substituted $C_1-C_6$ alkoxy, $-NR^{13}R^{14}$, optionally substituted $-(C_1-C_6$ alkyl)-$NR^{13}R^{14}$, $-NR^{14}COR^{16}$, optionally substituted $-(C_1-C_6$ alkyl)-$NR^{14}COR^{16}$, $-CONR^{14}R^{15}$, optionally substituted $-(C_1-C_6$ alkyl)-$CONR^{14}R^{15}$, optionally substituted carbocyclyl, optionally substituted heterocyclyl, optionally substituted aryl, or optionally substituted heteroaryl; or R⁵ and R⁶ taken together form an optionally substituted carbocyclyl or optionally substituted heterocyclyl;

R⁸ and R⁹ are each independently hydrogen, halogen, or $C_1-C_3$ alkyl;

$R^{8a}$ and $R^{9a}$ are each independently hydrogen, $-OH$, halogen, optionally substituted $C_1-C_6$ alkyl, optionally substituted $C_2-C_6$ alkenyl, optionally substituted $C_2-C_6$ alkynyl, optionally substituted $C_1-C_6$ alkoxy, optionally substituted $-OCO(C_1-C_6$ alkyl), $-NR^{13}R^{14}$, optionally substituted $-(C_1-C_6$ alkyl)-$NR^{13}R^{14}$, $-NR^{14}COR^{16}$, optionally substituted $-(C_1-C_6$ alkyl)-$NR^{14}COR^{16}$, $-CONR^{14}R^{15}$, optionally substituted $-(C_1-C_6$ alkyl)-$CONR^{14}R^{15}$, optionally substituted carbocyclyl, optionally substituted heterocyclyl, optionally substituted aryl, or optionally substituted heteroaryl; or $R^{8a}$ and $R^{8b}$ taken together form an optionally substituted carbocyclyl or optionally substituted heterocyclyl;

R⁷, R¹⁰ and R¹⁶ are each independently hydrogen, optionally substituted $C_1-C_6$ alkyl, optionally substituted $C_2-C_6$ alkenyl, optionally substituted $C_2-C_6$ alkynyl, optionally substituted carbocyclyl, optionally substituted heterocyclyl, optionally substituted aryl, or optionally substituted heteroaryl; or R⁷ and $R^{8a}$ taken together form an optionally substituted heterocyclyl;

R¹¹, R¹², R¹³, R¹⁴ and R¹⁵ are each independently hydrogen, optionally substituted $C_1-C_6$ alkyl, optionally substituted $C_2-C_6$ alkenyl, optionally substituted $C_2-C_6$ alkynyl, optionally substituted carbocyclyl, optionally substituted heterocyclyl, optionally substituted aryl, or optionally substituted heteroaryl; or ($R^{11}$ and $R^{12}$) or ($R^{14}$ and $R^{15}$) taken together form an optionally substituted heterocyclyl;

each m is independently 0, 1 or 2;

n1 and n2 are each independently 0, 1, 2, 3, or 4;

n3 is 0, 1, 2, 3, 4 or 5; and each t is independently 0, 1 or 2.

In one embodiment the present disclosure provides compounds comprising the structure of formula (IA):

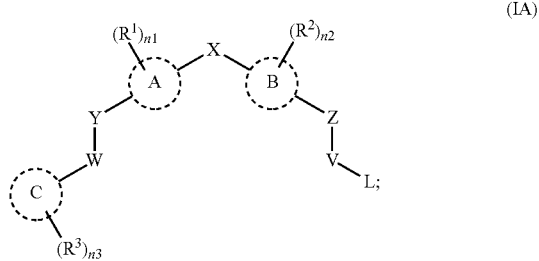

(IA)

or a pharmaceutically acceptable salt, tautomer, stereoisomer or prodrug thereof, wherein:

A and B are each independently aryl or heteroaryl;

C is a 3- to 10-membered ring;

X is a bond, —$(CR^5R^6)_t$—, —O—, —C(=O)—, —S—, —S(=O)—, —SO$_2$—, —$NR^7$—, —$N(R^7)CO$—, —$CON(R^7)$—, or —$NSO_2R^7$—;

Y and Z are each independently a bond, —$(CR^8R^9)_m$—, —O—, —C(=O)—, —S—, —S(=O)—, —SO$_2$—, or —$NR^7$—;

W and V are each independently a bond, —$(CR^{8a}R^{9a})_m$—, —C(=O)—, —$N(R^7)CO$—, —$CONR^7$—, or —$NSO_2R^7$—;

L is hydrogen, halogen, —$CF_2R^{10}$, —$CF_3$, —CN, —$OR^{10}$, —$NR^{11}R^{12}$, or —$CONR^{11}R^{12}$;

$R^1$ and $R^2$ are each independently hydrogen, halogen, —CN, —$CF_3$, —OH, optionally substituted $C_1$-$C_6$ alkyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —$NR^{13}R^{14}$, optionally substituted —($C_1$-$C_6$ alkyl)-$NR^{13}R^{14}$, —$NR^{14}SO_2R^{16}$, optionally substituted —($C_1$-$C_6$ alkyl)$NR^{14}SO_2R^{16}$, —$NR^{14}COR^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, —$SO_2NR^{14}R^{15}$, optionally substituted —($C_1$-$C_6$ alkyl)-$SO_2NR^{14}R^{15}$, optionally substituted —$SO_2R^{16}$, optionally substituted —($C_1$-$C_6$ alkyl)-$SO_2R^{16}$, optionally substituted carbocyclyl, optionally substituted heterocyclyl, optionally substituted aryl, or optionally substituted heteroaryl;

$R^3$ is hydrogen, halogen, oxo, =S, =$NR^{16}$, —CN, —$CF_3$, —OH, —$SR^{16}$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —$NR^{13}R^{14}$, optionally substituted —($C_1$-$C_6$ alkyl)-$NR^{13}R^{14}$, —$NR^{14}SO_2R^{16}$, optionally substituted —($C_1$-$C_6$ alkyl)$NR^{14}SO_2R^{16}$, —$NR^{14}COOR^{16}$, —$NR^{14}COR^{16}$, —$NR^{14}CONR^{14}R^{15}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, —$SO_2NR^{14}R^{15}$, optionally substituted —($C_1$-$C_6$ alkyl)-$SO_2NR^{14}R^{15}$, optionally substituted —$SO_2R^{16}$, optionally substituted —($C_1$-$C_6$ alkyl)-$SO_2R^{16}$, optionally substituted carbocyclyl, optionally substituted heterocyclyl, optionally substituted aryl, or optionally substituted heteroaryl;

$R^5$ and $R^6$ are each independently hydrogen, halogen, —OH, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, —$NR^{13}R^{14}$, optionally substituted —($C_1$-$C_6$ alkyl)-$NR^{13}R^{14}$, —$NR^{14}COR^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, optionally substituted carbocyclyl, optionally substituted heterocyclyl, optionally substituted aryl, or optionally substituted heteroaryl; or $R^5$ and $R^6$ taken together form an optionally substituted carbocyclyl or optionally substituted heterocyclyl;

$R^8$ and $R^9$ are each independently hydrogen, halogen, or $C_1$-$C_3$ alkyl;

$R^{8a}$ and $R^{9a}$ are each independently hydrogen, —OH, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted —OCO($C_1$-$C_6$ alkyl), —$NR^{13}R^{14}$, optionally substituted —($C_1$-$C_6$ alkyl)-$NR^{13}R^{14}$, —$NR^{14}COR^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, optionally substituted carbocyclyl, optionally substituted heterocyclyl, optionally substituted aryl, or optionally substituted heteroaryl; or $R^{8a}$ and $R^{8b}$ taken together form an optionally substituted carbocyclyl or optionally substituted heterocyclyl;

$R^7$, $R^{10}$ and $R^{16}$ are each independently hydrogen, optionally substituted $C_1$-$C_6$ alkyl, optionally substituted $C_2$-$C_6$ alkenyl, optionally substituted $C_2$-$C_6$ alkynyl, $C_1$-$C_6$ haloalkyl, $C_2$-$C_6$ haloalkenyl, $C_2$-$C_6$ haloalkynyl, optionally substituted carbocyclyl, optionally substituted —CO($C_1$-$C_6$ alkyl), —CO(optionally substituted heterocyclyl), optionally substituted heterocyclyl, optionally substituted aryl, or optionally substituted heteroaryl; or $R^7$ and $R^{8a}$ taken together form an optionally substituted heterocyclyl;

$R^{11}$, $R^{12}$, $R^{13}$, $R^{14}$ and $R^{15}$ are each independently hydrogen, optionally substituted $C_1$-$C_6$ alkyl, optionally substituted $C_2$-$C_6$ alkenyl, optionally substituted $C_2$-$C_6$ alkynyl, optionally substituted —COO($C_1$-$C_6$ alkyl), optionally substituted carbocyclyl, optionally substituted heterocyclyl, optionally substituted aryl, or optionally substituted heteroaryl; or ($R^{11}$ and $R^{12}$) or ($R^{14}$ and $R^{15}$) taken together form an optionally substituted heterocyclyl;

each m is independently 0, 1 or 2;

n1 and n2 are each independently 0, 1, 2, 3, or 4;

n3 is 0, 1, 2, 3, 4 or 5; and each t is independently 0, 1 or 2.

In one embodiment the present disclosure provides compounds comprising the structure of formula (IB):

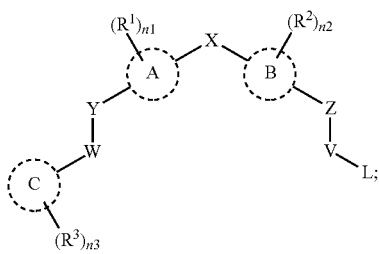

(IB)

or a pharmaceutically acceptable salt, tautomer, stereoisomer or prodrug thereof, wherein:

A and B are each independently aryl or heteroaryl;

C is a 3- to 10-membered ring;

X is a bond, —(CR$^5$R$^6$)$_t$—, —O—, —C(=O)—, —S—, —S(=O)—, —SO$_2$—, —NR$^7$—, —N(R$^7$)CO—, —CON(R$^7$)—, or —NSO$_2$R$^7$—;

Y is a bond, —(CR$^8$R$^9$)$_m$—, —O—, —S—, —S(=O)—, —SO$_2$—, or —NR$^7$—;

W is a bond, —(CR$^{8a}$R$^{9a}$)$_m$—, —N(R$^7$)CO—, —CONR$^7$—, or —NSO$_2$R$^7$—;

Z is a bond, —CH$_2$—, —C(CH$_3$)H—, —O—, —S—, —NH—, —NCH$_3$—, or —N(COCH$_3$)—;

V is —CH$_2$—, —CH$_2$CH$_2$—, —CH(CH$_3$)CH$_2$—, —CH$_2$CH(CH$_3$)—, or —CH$_2$CH$_2$CH$_2$—;

L is hydrogen, halogen, —CF$_2$R$^{10}$, —CF$_3$, —CN, —OR$^{10}$; —NR$^{11}$R$^{12}$, or —CONR$^{11}$R$^{12}$;

R$^1$ and R$^2$ are each independently hydrogen, deuterium, halogen, —CN, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$, optionally substituted —(C$_1$-C$_6$ alkyl)-SO$_2$R$^{16}$, optionally substituted carbocyclyl, optionally substituted heterocyclyl, optionally substituted aryl, or optionally substituted heteroaryl;

R$^3$ is hydrogen, halogen, oxo, =S, =NR$^{16}$, —CN, —CF$_3$, —OH, —SR$^{16}$, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, NR$^{14}$COOR$^{16}$, —NR$^{14}$COR$^{16}$, —NR$^{14}$CONR$^{14}$R$^{15}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$, optionally substituted —(C$_1$-C$_6$ alkyl)-SO$_2$R$^{16}$, optionally substituted carbocyclyl, optionally substituted heterocyclyl, optionally substituted aryl, or optionally substituted heteroaryl;

R$^5$ and R$^6$ are each independently hydrogen, halogen, —OH, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, —NR$^{13}$R$^{14}$, optionally substituted —(C$_1$-C$_6$ alkyl)-NR$^{13}$R$^{14}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, optionally substituted carbocyclyl, optionally substituted heterocyclyl, optionally substituted aryl, or optionally substituted heteroaryl; or R$^5$ and R$^6$ taken together form an optionally substituted carbocyclyl or optionally substituted heterocyclyl;

R$^8$ and R$^9$ are each independently hydrogen, halogen, or C$_1$-C$_3$ alkyl;

R$^{8a}$ and R$^{9a}$ are each independently hydrogen, halogen, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, —NR$^{13}$R$^{14}$, optionally substituted —(C$_1$-C$_6$ alkyl)-NR$^{13}$R$^{14}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, optionally substituted carbocyclyl, optionally substituted heterocyclyl, optionally substituted aryl, or optionally substituted heteroaryl; or R$^{8a}$ and R$^{8b}$ taken together form an optionally substituted carbocyclyl or optionally substituted heterocyclyl;

R$^7$, R$^{10}$ and R$^{16}$ are each independently hydrogen, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkyl-NH$_2$, C$_1$-C$_6$ haloalkyl, C$_2$-C$_6$ haloalkenyl, C$_2$-C$_6$ haloalkynyl, optionally substituted carbocyclyl, optionally substituted —CO(C$_1$-C$_6$ alkyl), —CO(optionally substituted heterocyclyl), optionally substituted heterocyclyl, optionally substituted aryl, or optionally substituted heteroaryl; or R$^7$ and R$^{8a}$ taken together form an optionally substituted heterocyclyl;

R$^{11}$, R$^{12}$, R$^{13}$, R$^{14}$ and R$^{15}$ are each independently hydrogen, optionally substituted C$_1$-C$_6$ alkyl, optionally substituted C$_2$-C$_6$ alkenyl, optionally substituted C$_2$-C$_6$ alkynyl, optionally substituted —COO(C$_1$-C$_6$ alkyl), optionally substituted carbocyclyl, optionally substituted heterocyclyl, optionally substituted aryl, or optionally substituted heteroaryl; or (R$^{11}$ and R$^{12}$) or (R$^{14}$ and R$^{15}$) or (R$^{14}$ and R$^{16}$) taken together form an optionally substituted heterocyclyl;

each m is independently 0, 1 or 2;

n1 and n2 are each independently 0, 1, 2, 3, or 4;

n3 is 0, 1, 2, 3, 4 or 5; and each t is independently 0, 1 or 2.

In one embodiment the present disclosure provides compounds comprising the structure of formula (IC)

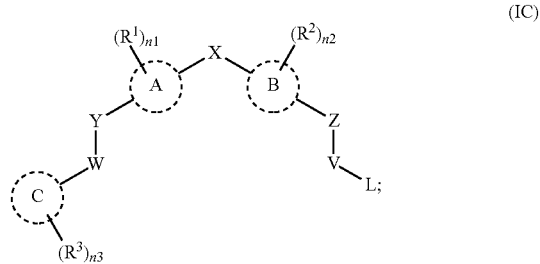

(IC)

or a pharmaceutically acceptable salt, tautomer, stereoisomer or prodrug thereof, wherein:

A and B are each independently aryl or heteroaryl;

C is a 3- to 10-membered ring;

X is a bond, $-(CR^5R^6)_t-$, $-O-$, $-C(=O)-$, $-S-$, $-S(=O)-$, $-SO_2-$, $-NR^7-$, $-N(R^7)CO-$, $-CON(R^7)-$, or $-NSO_2R^7-$;

Y is a bond, $-(CR^8R^9)_m-$, $-O-$, $-S-$, $-S(=O)-$, $-SO_2-$, or $-NR^7-$;

W is a bond, $-(CR^{8a}R^{9a})_m-$, $-C(=O)-$, $N(R^7)CO-$, $-CONR^7-$, or $-NSO_2R^7-$;

Z is a bond, $-(CR^8R^9)_m-$, $-O-$, $-S-$, $-S(=O)-$, $-SO_2-$, or $-NR^7-$;

V is $-CH_2-$, $-CH_2CH_2-$, $-CH(CH_3)CH_2-$, $-CH_2CH(CH_3)-$, or $-CH_2CH_2CH_2-$;

L is hydrogen, halogen, $-CF_2R^{10}$, $-CF_3$, $-CCl_2R^{10}$, $-CCl_3$, $-CN$, $-OR^{10}$; $-NR^{11}R^{12}$ or $-CONR^{11}R^{12}$;

$R^1$ and $R^2$ are each independently hydrogen, deuterium, halogen, $-CN$, $-CF_3$, $-OH$, optionally substituted $C_1$-$C_6$ alkyl, optionally substituted $C_1$-$C_6$ alkoxy, optionally substituted $-(C_1$-$C_6$ alkyl)-$(C_1$-$C_6$ alkoxy), optionally substituted $-(C_1$-$C_6$ alkyl)-OH, $-NR^{13}R^{14}$, optionally substituted $-(C_1$-$C_6$ alkyl)-$NR^{13}R^{14}$, $-NR^{14}SO_2R^{16}$, optionally substituted $-(C_1$-$C_6$ alkyl)$NR^{14}SO_2R^{16}$, $-NR^{14}COR^{16}$, optionally substituted $-(C_1$-$C_6$ alkyl)-$NR^{14}COR^{16}$, $-CONR^{14}R^{15}$, optionally substituted $-(C_1$-$C_6$ alkyl)-$CONR^{14}R^{15}$, $-SO_2NR^{14}R^{15}$, optionally substituted $-(C_1$-$C_6$ alkyl)-$SO_2NR^{14}R^{15}$, optionally substituted $-SO_2R^{16}$, optionally substituted $-(C_1$-$C_6$ alkyl)-$SO_2R^{16}$, optionally substituted carbocyclyl, optionally substituted heterocyclyl, optionally substituted aryl, or optionally substituted heteroaryl;

$R^3$ is hydrogen, halogen, oxo, $=S$, $=NR^{16}$, $-CN$, $-CF_3$, $-OH$, $-SR^{16}$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted $-(C_1$-$C_6$ alkyl)-$(C_1$-$C_6$ alkoxy), optionally substituted $-(C_1$-$C_6$ alkyl)-OH, $-NR^{13}R^{14}$, optionally substituted $-(C_1$-$C_6$ alkyl)-$NR^{13}R^{14}$, $-NR^{14}SO_2R^{16}$, optionally substituted $-(C_1$-$C_6$ alkyl)$NR^{14}SO_2R^{16}$, $NR^{14}COOR^{16}$, $-NR^{14}COR^{16}$, $-NR^{14}CONR^{14}R^{15}$, optionally substituted $-(C_1$-$C_6$ alkyl)-$NR^{14}COR^{16}$, $-CONR^{14}R^{15}$, optionally substituted $-(C_1$-$C_6$ alkyl)-$CONR^{14}R^{15}$, $-SO_2NR^{14}R^{15}$, optionally substituted $-(C_1$-$C_6$ alkyl)-$SO_2NR^{14}R^{15}$, optionally substituted $-SO_2R^{16}$, optionally substituted $-(C_1$-$C_6$ alkyl)-$SO_2R^{16}$, optionally substituted carbocyclyl, optionally substituted heterocyclyl, optionally substituted aryl, or optionally substituted heteroaryl;

$R^5$ and $R^6$ are each independently hydrogen, halogen, $-OH$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, $-NR^{13}R^{14}$, optionally substituted $-(C_1$-$C_6$ alkyl)-$NR^{13}R^{14}$, $-NR^{14}COR^{16}$, optionally substituted $-(C_1$-$C_6$ alkyl)-$NR^{14}COR^{16}$, $-CONR^{13}R^{14}$, $-CONR^{14}R^{15}$, optionally substituted $-(C_1$-$C_6$ alkyl)-$CONR^{14}R^{15}$, optionally substituted carbocyclyl, optionally substituted heterocyclyl, optionally substituted aryl, or optionally substituted heteroaryl; or $R^5$ and $R^6$ taken together form an optionally substituted carbocyclyl or optionally substituted heterocyclyl;

$R^8$ and $R^9$ are each independently hydrogen, halogen, or $C_1$-$C_3$ alkyl;

$R^{8a}$ and $R^{9a}$ are each independently hydrogen, $-OH$, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, $-NR^{13}R^{14}$, optionally substituted $-(C_1$-$C_6$ alkyl)-$NR^{13}R^{14}$, $-NR^{14}COR^{16}$, optionally substituted $-(C_1$-$C_6$ alkyl)-$NR^{14}COR^{16}$, $-CONR^{14}R^{15}$, optionally substituted $-(C_1$-$C_6$ alkyl)-$CONR^{14}R^{15}$, optionally substituted carbocyclyl, optionally substituted heterocyclyl, optionally substituted aryl, or optionally substituted heteroaryl; or $R^{8a}$ and $R^{8b}$ taken together form an optionally substituted carbocyclyl or optionally substituted heterocyclyl;

$R^7$, $R^{10}$ and $R^{16}$ are each independently hydrogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkyl-$NH_2$, $C_1$-$C_6$ haloalkyl, $C_2$-$C_6$ haloalkenyl, $C_2$-$C_6$ haloalkynyl, optionally substituted carbocyclyl, optionally substituted $-CO(C_1$-$C_6$ alkyl), $-CO$(optionally substituted heterocyclyl), optionally substituted heterocyclyl, optionally substituted aryl, or optionally substituted heteroaryl; or $R^7$ and $R^{8a}$ taken together form an optionally substituted heterocyclyl;

$R^{11}$, $R^{12}$, $R^{13}$, $R^{14}$ and $R^{15}$ are each independently hydrogen, optionally substituted $C_1$-$C_6$ alkyl, optionally substituted $C_2$-$C_6$ alkenyl, optionally substituted $C_2$-$C_6$ alkynyl, optionally substituted $-COO(C_1$-$C_6$ alkyl), optionally substituted carbocyclyl, optionally substituted heterocyclyl, optionally substituted aryl, or optionally substituted heteroaryl; or ($R^{11}$ and $R^{12}$) or ($R^{14}$ and $R^{15}$) or ($R^{14}$ and $R^{16}$) taken together form an optionally substituted heterocyclyl;

each m is independently 0, 1 or 2;

n1 and n2 are each independently 0, 1, 2, 3, or 4;

n3 is 0, 1, 2, 3, 4 or 5; and each t is independently 0, 1 or 2.

In one embodiment, the present disclosure provides compounds comprising the structure of formula (II):

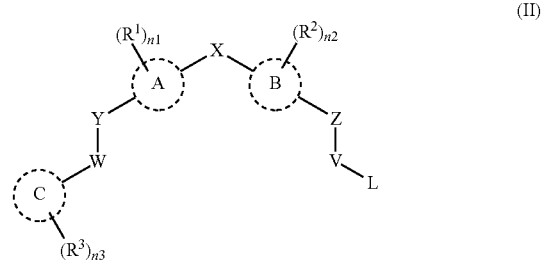

or a pharmaceutically acceptable salt, tautomer, stereoisomer or prodrug thereof, wherein:

A and B are each independently selected from phenyl, pyridyl, pyrimidyl, or thiophene;

C is a 3- to 10-membered ring;

X is a bond, $-(CR^5R^6)_t-$, or $-NR^7-$;

Y is a bond, $-CH_2-$, $-C(CH_3)H-$, $-O-$, $-S-$, $-NH-$, $-NCH_3-$, or $-N(COCH_3)-$;

Z is a bond, $-(CR^8R^9)_m-$, $-O-$, $-S-$, $-S(=O)-$, $-SO_2-$, or $-NR^7-$;

W is a bond, $-CH_2-$, $-C(CH_3)H-$, $-C(=O)-$, $-NHCO-$, $-N(C_1$-$C_3$ alkyl)CO-$, or $-CONH-$, or $-CON(C_1$-$C_3$ alkyl)-$;

V is a bond, $-(CR^{8a}R^{9a})_m-$, $-C(=O)-$, $-N(R^7)CO-$, $-CONR^7-$, or $-NSO_2R^7-$;

L is hydrogen, halogen, $-CF_2R^1$, $-CF_3$, $-CN$, $-OR^{10}$; $-NR^{11}R^{12}$, or $-CONR^{11}R^{12}$;

$R^1$ and $R^2$ are each independently hydrogen, halogen, —CN, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{13}$R$^{14}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$ or optionally substituted —(C$_1$-C$_6$ alkyl)-SO$_2$R$^{16}$;

$R^3$ is selected from hydrogen, halogen, oxo, =S, =NR$^{16}$, —CN, —CF$_3$, —OH, —S(C$_1$-C$_3$ alkyl), C$_1$-C$_3$ alkyl, C$_2$-C$_3$ alkenyl, C$_2$-C$_3$ alkynyl, C$_1$-C$_3$ alkoxy, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl)NR$^{14}$SO$_2$R$^{16}$, —NR$^{14}$COR$^{16}$, —(C$_1$-C$_6$ alkyl)- NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO$_2$(C$_1$-C$_3$ alkyl), or —(C$_1$-C$_6$ alkyl)-SO$_2$(C$_1$-C$_3$ alkyl);

$R^5$ and $R^6$ are each independently hydrogen, halogen, —OH, C$_1$-C$_3$ alkyl, C$_2$-C$_3$ alkenyl, C$_2$-C$_3$ alkynyl, or C$_1$-C$_3$ alkoxy; or $R^5$ and $R^6$ taken together form an optionally substituted 3- to 6-membered carbocyclyl or heterocyclyl;

$R^8$ and $R^9$ are each independently hydrogen, halogen, or C$_1$-C$_3$ alkyl;

$R^{8a}$ and $R^{9a}$ are each independently hydrogen, —OH, halogen, C$_1$-C$_3$ alkyl, C$_2$-C$_3$ alkenyl, C$_2$-C$_3$ alkynyl, C$_1$-C$_3$ alkoxy, —NR$^{13}$R$^{14}$, —(C$_1$-C$_3$ alkyl)-NR$^{13}$R$^{14}$, —NR$^{14}$COR$^{16}$, —(C$_1$-C$_3$ alkyl)-NR$^{14}$COR$^{16}$, —CONR$^{14}$R$^{15}$, or —(C$_1$-C$_3$ alkyl)-CONR$^{14}$R$^{15}$; or $R^{8a}$ and $R^{8b}$ taken together form an optionally substituted 3- to 6-membered carbocyclyl or heterocyclyl;

$R^{11}$, $R^{12}$, $R^{13}$, $R^{14}$ and $R^{15}$ are each independently hydrogen, C$_1$-C$_3$ alkyl, C$_2$-C$_3$ alkenyl, or C$_2$-C$_3$ alkynyl; or $R^{14}$ and $R^{15}$ taken together form a 3- to 6-membered heterocyclyl;

$R^7$, $R^{10}$ and $R^{16}$ are each independently hydrogen, C$_1$-C$_6$ alkyl, C$_2$-C$_6$ alkenyl, or C$_2$-C$_6$ alkynyl;

each m is independently 0, 1 or 2;

n1 and n2 are each independently 0, 1, or 2;

n3 is 0, 1, 2, 3, 4 or 5; and t is 0, 1 or 2.

In one embodiment, the present disclosure provides compounds comprising the structure of formula (IIA):

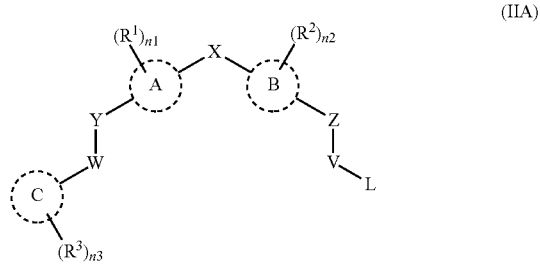

(IIA)

or a pharmaceutically acceptable salt, tautomer, stereoisomer or prodrug thereof, wherein:

A and B are each independently selected from phenyl, pyridyl, pyrimidyl, or thiophene;

C is a 3- to 10-membered ring;

X is a bond, —(CR$^5$R$^6$)$_t$—, or —NR$^7$—;

Y is a bond, —CH$_2$—, —C(CH$_3$)H—, —O—, —S—, —NH—, —NCH$_3$—, or —N(COCH$_3$)—;

Z is a bond, —(CR$^8$R$^9$)$_m$—, —O—, —S—, —S(=O)—, —SO$_2$—, or —NR$^7$—;

W is a bond, —CH$_2$—, —C(CH$_3$)H—, —NHCO—, —N(C$_1$-C$_3$ alkyl)CO—, or —CONH—, or —CON(C$_1$-C$_3$ alkyl)-;

V is —CH$_2$—, —CH$_2$CH$_2$—, —CH(CH$_3$)CH$_2$—, —CH$_2$CH(CH$_3$)—, or —CH$_2$CH$_2$CH$_2$—;

L is hydrogen, halogen, —CF$_2$R$^{10}$, —CF$_3$, —CN, —OR$^{10}$; —NR$^{11}$R$^{12}$, or —CONR$^{11}$R$^{12}$;

$R^1$ and $R^2$ are each independently hydrogen, deuterium, halogen, —CN, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{13}$R$^{14}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$ or optionally substituted —(C$_1$-C$_6$ alkyl)-SO$_2$R$^{16}$;

$R^3$ is selected from hydrogen, halogen, oxo, =S, =NR$^{16}$, —CN, —CF$_3$, —OH, —S(C$_1$-C$_3$ alkyl), C$_1$-C$_3$ alkyl, C$_2$-C$_3$ alkenyl, C$_2$-C$_3$ alkynyl, C$_1$-C$_3$ alkoxy, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl)NR$^{14}$SO$_2$R$^{16}$, —NR$^{14}$COR$^{16}$, —(C$_1$-C$_6$ alkyl)- NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO$_2$(C$_1$-C$_3$ alkyl), or —(C$_1$-C$_6$ alkyl)-SO$_2$(C$_1$-C$_3$ alkyl);

$R^5$ and $R^6$ are each independently hydrogen, halogen, —OH, C$_1$-C$_3$ alkyl, C$_2$-C$_3$ alkenyl, C$_2$-C$_3$ alkynyl, or C$_1$-C$_3$ alkoxy; or $R^5$ and $R^6$ taken together form an optionally substituted 3- to 6-membered carbocyclyl or heterocyclyl;

$R^8$ and $R^9$ are each independently hydrogen, halogen, or C$_1$-C$_3$ alkyl;

$R^{11}$, $R^{12}$, $R^{13}$, $R^{14}$ and $R^{15}$ are each independently hydrogen, C$_1$-C$_3$ alkyl, C$_2$-C$_3$ alkenyl, or C$_2$-C$_3$ alkynyl; or $R^{14}$ and $R^{15}$ taken together form a 3- to 6-membered heterocyclyl;

$R^7$, $R^{10}$ and $R^{16}$ are each independently hydrogen, C$_1$-C$_6$ alkyl, C$_2$-C$_6$ alkenyl, C$_2$-C$_6$ alkynyl or C$_1$-C$_6$ alkyl-NH$_2$; or $R^{14}$ and $R^{16}$ taken together form a 3- to 6-membered heterocyclyl;

each m is independently 0, 1 or 2;

n1 and n2 are each independently 0, 1, or 2;

n3 is 0, 1, 2, 3, 4 or 5; and t is 0, 1 or 2.

In one embodiment, the present disclosure provides compounds comprising the structure of formula (IIB):

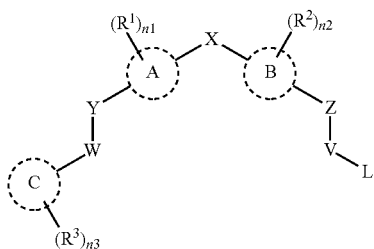

(IIB)

or a pharmaceutically acceptable salt, tautomer, stereoisomer or prodrug thereof, wherein:

A and B are each independently selected from phenyl, pyridyl, pyrimidyl, or thiophene;

C is a 3- to 10-membered ring;

X is a bond, $-(CR^5R^6)_t-$, or $-NR^7-$;

Y is a bond, $-CH_2-$, $-C(CH_3)H-$, $-O-$, $-S-$, $-NH-$, $-NCH_3-$, or $-N(COCH_3)-$;

Z is a bond, $-(CR^8R^9)_m-$, $-O-$, $-S-$, $-S(=O)-$, $-SO_2-$, or $-NR^7-$;

W is a bond, $-CH_2-$, or $-C(CH_3)H-$;

V is a bond, $-(CR^{8a}R^{9a})_m-$, $-C(=O)-$, $-N(R^7)CO-$, $-CONR^7-$, or $-NSO_2R^7-$;

L is hydrogen, halogen, $-CF_2R^{10}$, $-CF_3$, $-CN$, $-OR^{10}$; $-NR^{11}R^{12}$, or $-CONR^{11}R^{12}$;

$R^1$ and $R^2$ are each independently hydrogen, deuterium, halogen, $-CN$, $-CF_3$, $-OH$, optionally substituted $C_1$-$C_6$ alkyl, optionally substituted $C_1$-$C_6$ alkoxy, optionally substituted $-(C_1$-$C_6$ alkyl)-$(C_1$-$C_6$ alkoxy), optionally substituted $-(C_1$-$C_6$ alkyl)-OH, $-NR^{13}R^{14}$, optionally substituted $-(C_1$-$C_6$ alkyl)-$NR^{13}R^{14}$, $-NR^{14}SO_2R^{16}$, optionally substituted $-(C_1$-$C_6$ alkyl)$NR^{14}SO_2R^{16}$, $-NR^{14}COR^{16}$, optionally substituted $-(C_1$-$C_6$ alkyl)-$NR^{14}COR^{16}$, $-CONR^{13}R^{14}$, optionally substituted $-(C_1$-$C_6$ alkyl)-$CONR^{14}R^{15}$, $-SO_2NR^{14}R^{15}$, optionally substituted $-(C_1$-$C_6$ alkyl)-$SO_2NR^{14}R^{15}$, optionally substituted $-SO_2R^{16}$ or optionally substituted $-(C_1$-$C_6$ alkyl)-$SO_2R^{16}$;

$R^3$ is selected from hydrogen, halogen, oxo, $=S$, $=NR^{16}$, $-CN$, $-CF_3$, $-OH$, $-S(C_1$-$C_3$ alkyl), $C_1$-$C_3$ alkyl, $C_2$-$C_3$ alkenyl, $C_2$-$C_3$ alkynyl, $C_1$-$C_3$ alkoxy, $-NR^{13}R^{14}$, $-(C_1$-$C_3$ alkyl)-$NR^{13}R^{14}$, $-NR^{14}SO_2R^{16}$, $-(C_1$-$C_3$ alkyl)$NR^{14}SO_2R^{16}$, $-NR^{14}COR^{16}$, $-(C_1$-$C_6$ alkyl)- $NR^{14}COR^{16}$, $-CONR^{14}R^{15}$, $-(C_1$-$C_3$ alkyl)-$CONR^{14}R^{15}$, $-SO_2NR^{14}R^{15}$, $-(C_1$-$C_3$ alkyl)-$SO_2NR^{14}R^{15}$, $-SO_2(C_1$-$C_3$ alkyl), or $-(C_1$-$C_6$ alkyl)-$SO_2(C_1$-$C_3$ alkyl);

$R^5$ and $R^6$ are each independently hydrogen, halogen, $-OH$, $C_1$-$C_3$ alkyl, $C_2$-$C_3$ alkenyl, $C_2$-$C_3$ alkynyl, or $C_1$-$C_3$ alkoxy; or $R^5$ and $R^6$ taken together form an optionally substituted 3- to 6-membered carbocyclyl or heterocyclyl;

$R^8$ and $R^9$ are each independently hydrogen, halogen, or $C_1$-$C_3$ alkyl;

$R^{8a}$ and $R^{9a}$ are each independently hydrogen, $-OH$, halogen, $C_1$-$C_3$ alkyl, $C_2$-$C_3$ alkenyl, $C_2$-$C_3$ alkynyl, $C_1$-$C_3$ alkoxy, $-NR^{13}R^{14}$, $-(C_1$-$C_3$ alkyl)-$NR^{13}R^{14}$, $-NR^{14}COR^{16}$, $-(C_1$-$C_3$ alkyl)-$NR^{14}COR^{16}$, $-CONR^{14}R^{15}$, or $-(C_1$-$C_3$ alkyl)-$CONR^{14}R^{15}$; or $R^{8a}$ and $R^{8b}$ taken together form an optionally substituted 3- to 6-membered carbocyclyl or heterocyclyl;

$R^{11}$, $R^{12}$, $R^{13}$, $R^{14}$ and $R^{15}$ are each independently hydrogen, $C_1$-$C_3$ alkyl, $C_2$-$C_3$ alkenyl, or $C_2$-$C_3$ alkynyl; or $R^{14}$ and $R^{15}$ taken together form a 3- to 6-membered heterocyclyl;

$R^7$, $R^{10}$ and $R^{16}$ are each independently hydrogen, $C_1$-$C_6$ alkyl, $C_2$-$C_6$ alkenyl, $C_2$-$C_6$ alkynyl or $C_1$-$C_6$ alkyl-$NH_2$; or $R^{14}$ and $R^{16}$ taken together form a 3- to 6-membered heterocyclyl;

each m is independently 0, 1 or 2;

n1 and n2 are each independently 0, 1, or 2;

n3 is 1, 2, 3, 4 or 5; and t is 0, 1 or 2.

In one embodiment, the present disclosure provides compounds comprising the structure of formula (III):

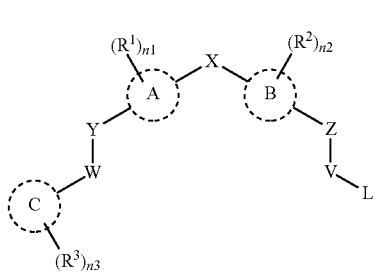

(III)

or a pharmaceutically acceptable salt, tautomer, stereoisomer or prodrug thereof, wherein:

A and B are each independently selected from phenyl, pyridyl, pyrimidyl, or thiophene;

C is a 3- to 10-membered ring;

X is a bond, $-(CR^5R^6)_t-$, or $-NR^7-$;

Y is a bond, $-(CR^8R^9)_m-$, $-O-$, $-S-$, $-S(=O)-$, $-SO_2-$, or $-NR^7-$;

W is a bond, $-(CR^{8a}R^{9a})_m-$, $-C(=O)-$, $-N(R^7)CO-$, $-CONR^7-$, or $-NSO_2R^7-$;

Z is a bond, $-CH_2-$, $-C(CH_3)H-$, $-O-$, $-S-$, $-NH-$, $-NCH_3-$, or $-N(COCH_3)-$;

V is $-CH_2-$, $-CH_2CH_2-$, or $-CH_2CH_2CH_2-$;

L is halogen, $-NH_2$, or $-CF_3$;

$R^1$ and $R^2$ are each independently hydrogen, halogen, $-CN$, $-CF_3$, $-OH$, optionally substituted $C_1$-$C_6$ alkyl, optionally substituted $C_1$-$C_6$ alkoxy, optionally substituted $-(C_1$-$C_6$ alkyl)-$(C_1$-$C_6$ alkoxy), optionally substituted $-(C_1$-$C_6$ alkyl)-OH, $-NR^{13}R^{14}$, optionally substituted $-(C_1$-$C_6$ alkyl)-$NR^{13}R^{14}$, $-NR^{14}SO_2R^{16}$, optionally substituted $-(C_1$-$C_6$ alkyl)$NR^{14}SO_2R^{16}$, $-NR^{14}COR^{16}$, optionally substituted $-(C_1$-$C_6$ alkyl)-$NR^{14}COR^{16}$, $-CONR^{13}R^{14}$, optionally substituted $-(C_1$-$C_6$ alkyl)-$CONR^{14}R^{15}$, $-SO_2NR^{14}R^{15}$, optionally substituted $-(C_1$-$C_6$ alkyl)-$SO_2NR^{14}R^{15}$, optionally substituted $-SO_2R^{16}$ or optionally substituted $-(C_1$-$C_6$ alkyl)-$SO_2R^{16}$;

$R^3$ is selected from hydrogen, halogen, oxo, $=S$, $=NR^{16}$, $-CN$, $-CF_3$, $-OH$, $-S(C_1$-$C_3$ alkyl), $C_1$-$C_3$ alkyl, $C_2$-$C_3$ alkenyl, $C_2$-$C_3$ alkynyl, $C_1$-$C_3$ alkoxy, $-NR^{13}R^{14}$, $-(C_1$-$C_3$ alkyl)-$NR^{13}R^{14}$, $-NR^{14}SO_2R^{16}$, $-(C_1$-$C_3$ alkyl)$NR^{14}SO_2R^{16}$, $-NR^{14}COR^{16}$, $-(C_1$-$C_6$ alkyl)- $NR^{14}COR^{16}$, $-CONR^{14}R^{15}$, $-(C_1$-$C_3$ alkyl)-$CONR^{14}R^{15}$, $-SO_2NR^{14}R^{15}$, $-(C_1$-$C_3$ alkyl)-$SO_2NR^{14}R^{15}$, $-SO_2(C_1$-$C_3$ alkyl), or $-(C_1$-$C_6$ alkyl)-$SO_2(C_1$-$C_3$ alkyl);

$R^5$ and $R^6$ are each independently hydrogen, halogen, $-OH$, $C_1$-$C_3$ alkyl, $C_2$-$C_3$ alkenyl, $C_2$-$C_3$ alkynyl, or $C_1$-$C_3$ alkoxy; or $R^5$ and $R^6$ taken together form an optionally substituted 3- to 6-membered carbocyclyl or heterocyclyl;

$R^7$ is hydrogen, $C_1$-$C_6$ alkyl, $C_2$-$C_6$ alkenyl, or $C_2$-$C_6$ alkynyl;

$R^8$ and $R^9$ are each independently hydrogen, halogen, or $C_1$-$C_3$ alkyl;

$R^{8a}$ and $R^{9a}$ are each independently hydrogen, —OH, halogen, $C_1$-$C_3$ alkyl, $C_2$-$C_3$ alkenyl, $C_2$-$C_3$ alkynyl, $C_1$-$C_3$ alkoxy, —$NR^{13}R^{14}$, —($C_1$-$C_3$ alkyl)-$NR^{13}R^{14}$, —$NR^{14}COR^{16}$, —($C_1$-$C_3$ alkyl)-$NR^{14}COR^{16}$, —$CONR^{14}R^{15}$, or —($C_1$-$C_3$ alkyl)-$CONR^{14}R^{15}$; or $R^{8a}$ and $R^{8b}$ taken together form an optionally substituted 3- to 6-membered carbocyclyl or heterocyclyl;

$R^{13}$, $R^{14}$ and $R^{15}$ are each independently hydrogen, $C_1$-$C_3$ alkyl, $C_2$-$C_3$ alkenyl, or $C_2$-$C_3$ alkynyl; or $R^{14}$ and $R^{15}$ taken together form a 3- to 6-membered heterocyclyl;

$R^{16}$ is hydrogen, $C_1$-$C_3$ alkyl, $C_2$-$C_3$ alkenyl, or $C_2$-$C_3$ alkynyl;

each m is independently 0, 1 or 2;

n1 and n2 are each independently 0, 1, or 2;

n3 is 0, 1, 2, 3, 4 or 5; and t is 0, 1 or 2.

In one embodiment, the present disclosure provides compounds comprising the structure of formula (IIIA):

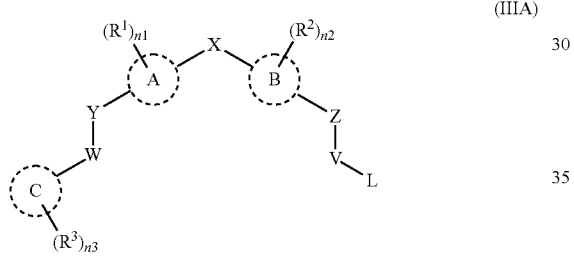

(IIIA)

or a pharmaceutically acceptable salt, tautomer, stereoisomer or prodrug thereof, wherein:

A and B are each independently selected from phenyl, pyridyl, pyrimidyl, or thiophene;

C is a 3- to 10-membered ring;

X is a bond, —$(CR^5R^6)_t$—, or —$NR^7$;

Y is a bond, —$(CR^8R^9)_m$—, —O—, —S—, —S(=O)—, —$SO_2$—, —$NR^7$— or —$N(COCH_3)$—;

W is a bond, —$(CR^{8a}R^{9a})_m$—, —C(=O)—, —$N(R^7)$CO—, —$CONR^7$—, or —$NSO_2R^7$—;

Z is a bond, —$CH_2$—, —$C(CH_3)H$—, —O—, —S—, —NH—, —$NCH_3$—, or —$N(COCH_3)$—;

V is —$CH_2$— and L is halogen, —$NH_2$, —$CHCl_2$, —$CCl_3$, or —$CF_3$; or

V is —$CH_2CH_2$— and L is halogen or —$NH_2$;

$R^1$ and $R^2$ are each independently hydrogen, halogen, —CN, —$CF_3$, —OH, optionally substituted $C_1$-$C_6$ alkyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —$NR^{13}R^{14}$, optionally substituted —($C_1$-$C_6$ alkyl)-$NR^{13}R^{14}$, —$NR^{14}SO_2R^{16}$, optionally substituted —($C_1$-$C_6$ alkyl) $NR^{14}SO_2R^{16}$, —$NR^{14}COR^{16}$, optionally substituted —($C_1$-$C_6$ alkyl)-$NR^{14}COR^{16}$, —$CONR^{13}R^{14}$, optionally substituted —($C_1$-$C_6$ alkyl)-$CONR^{14}R^{15}$, —$SO_2NR^{14}R^{15}$, optionally substituted —($C_1$-$C_6$ alkyl)-$SO_2NR^{14}R^{15}$, optionally substituted —$SO_2R^{16}$ or optionally substituted —($C_1$-$C_6$ alkyl)-$SO_2R^{16}$;

$R^3$ is selected from halogen, oxo, =S, =$NR^{16}$, —CN, —$CF_3$, —OH, —$S(C_1$-$C_3$ alkyl), $C_1$-$C_3$ alkyl, $C_2$-$C_3$ alkenyl, $C_2$-$C_3$ alkynyl, $C_1$-$C_3$ alkoxy, —$NR^{13}R^{14}$, —($C_1$-$C_3$ alkyl)-$NR^{13}R^{14}$, —$NR^{14}SO_2R^{16}$, —($C_1$-$C_3$ alkyl)$NR^{14}SO_2R^{16}$, —$NR^{14}COR^{16}$, —($C_1$-$C_6$ alkyl)-$NR^{14}COR^{16}$, —$CONR^{14}R^{15}$, —($C_1$-$C_3$ alkyl)-$CONR^{14}R^{15}$, —$SO_2NR^{14}R^{15}$, —($C_1$-$C_3$ alkyl)-$SO_2NR^{14}R^{15}$, —$SO_2(C_1$-$C_3$ alkyl), or —($C_1$-$C_6$ alkyl)-$SO_2(C_1$-$C_3$ alkyl);

$R^5$ and $R^6$ are each independently hydrogen, halogen, —OH, $C_1$-$C_3$ alkyl, $C_2$-$C_3$ alkenyl, $C_2$-$C_3$ alkynyl, or $C_1$-$C_3$ alkoxy; or $R^5$ and $R^6$ taken together form an optionally substituted 3- to 6-membered carbocyclyl or heterocyclyl;

$R^7$ is hydrogen, $C_1$-$C_6$ alkyl, $C_2$-$C_6$ alkenyl, or $C_2$-$C_6$ alkynyl;

$R^8$ and $R^9$ are each independently hydrogen, halogen, or $C_1$-$C_3$ alkyl;

$R^{8a}$ and $R^{9a}$ are each independently hydrogen, —OH, halogen, $C_1$-$C_3$ alkyl, $C_2$-$C_3$ alkenyl, $C_2$-$C_3$ alkynyl, $C_1$-$C_3$ alkoxy, —$NR^{13}R^{14}$, —($C_1$-$C_3$ alkyl)$NR^{13}R^{14}$, —$NR^{14}COR^{16}$, —($C_1$-$C_3$ alkyl)-$NR^{14}COR^{16}$, —$CONR^{14}R^{15}$, or —($C_1$-$C_3$ alkyl)-$CONR^{14}R^{15}$; or $R^{8a}$ and $R^{8b}$ taken together form an optionally substituted 3- to 6-membered carbocyclyl or heterocyclyl;

$R^{13}$, $R^{14}$ and $R^{15}$ are each independently hydrogen, $C_1$-$C_3$ alkyl, $C_2$-$C_3$ alkenyl, or $C_2$-$C_3$ alkynyl; or $R^{14}$ and $R^{15}$ taken together form a 3- to 6-membered heterocyclyl;

$R^{16}$ is hydrogen, optionally substituted $C_1$-$C_3$ alkyl, optionally substituted $C_2$-$C_3$ alkenyl, optionally substituted $C_2$-$C_3$ alkynyl, $C_3$-$C_6$ cycloalkyl, or phenyl;

each m is independently 0, 1 or 2;

n1 and n2 are each independently 0, 1, or 2;

n3 is 1, 2, 3, 4 or 5; and t is 0, 1 or 2.

In one embodiment, the present disclosure provides compounds comprising the structure of formula (IV):

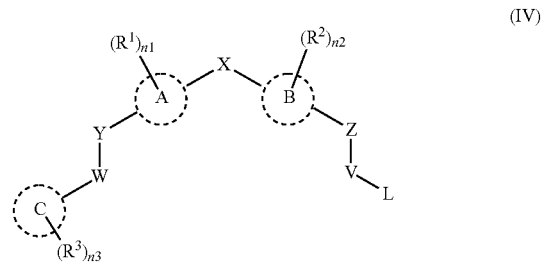

(IV)

or a pharmaceutically acceptable salt, tautomer, stereoisomer or prodrug thereof, wherein:

A and B are each independently selected from phenyl, pyridyl, pyrimidyl, or thiophene;

C is a 3- to 10-membered ring;

X is a bond, —$(CR^5R^6)_t$—, or —$NR^7$—;

Y and Z are each independently a bond, —$CH_2$—, —$C(CH_3)H$—, —O—, —S—, —NH—, —$NCH_3$—, or —$N(COCH_3)$—;

W is a bond, —$CH_2$—, —$C(CH_3)H$—, —C(=O)—, —$N(R^7)CO$—, or —$CONR^7$—;

V is —$CH_2$—, —$CH_2CH_2$—, or —$CH_2CH_2CH_2$—;

L is halogen, —$NH_2$, or —$CF_3$;

$R^1$ and $R^2$ are each independently hydrogen, halogen, —CN, —$CF_3$, —OH, optionally substituted $C_1$-$C_6$ alkyl, optionally substituted $C_1$-$C_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{13}$R$^{14}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$ or optionally substituted —(C$_1$-C$_6$ alkyl)-SO$_2$R$^{16}$;

R$^3$ is selected from hydrogen, halogen, oxo, =S, =NR$^{16}$, —CN, —CF$_3$, —OH, —S(C$_1$-C$_3$ alkyl), C$_1$-C$_3$ alkyl, C$_2$-C$_3$ alkenyl, C$_2$-C$_3$ alkynyl, C$_1$-C$_3$ alkoxy, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl)NR$^{14}$SO$_2$R$^{16}$, —NR$^{14}$COR$^{16}$, —(C$_1$-C$_6$ alkyl)- NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO$_2$(C$_1$-C$_3$ alkyl), or —(C$_1$-C$_6$ alkyl)-SO$_2$(C$_1$-C$_3$ alkyl);

R$^5$ and R$^6$ are each independently hydrogen, halogen, —OH, C$_1$-C$_3$ alkyl, C$_2$-C$_3$ alkenyl, C$_2$-C$_3$ alkynyl, or C$_1$-C$_3$ alkoxy; or R$^5$ and R$^6$ taken together form an optionally substituted 3- to 6-membered carbocyclyl or heterocyclyl;

R$^7$ is H or C$_1$-C$_6$ alkyl;

R$^{13}$, R$^{14}$ and R$^{15}$ are each independently hydrogen, C$_1$-C$_3$ alkyl, C$_2$-C$_3$ alkenyl, or C$_2$-C$_3$ alkynyl; or R$^{14}$ and R$^{15}$ taken together form a 3- to 6-membered heterocyclyl;

R$^{16}$ is hydrogen, C$_1$-C$_3$ alkyl, C$_2$-C$_3$ alkenyl, or C$_2$-C$_3$ alkynyl;

n1 and n2 are each independently 0, 1, or 2;

n3 is 0, 1, 2, 3, 4 or 5; and t is 0, 1 or 2.

In one embodiment, the present disclosure provides compounds comprising the structure of formula (V):

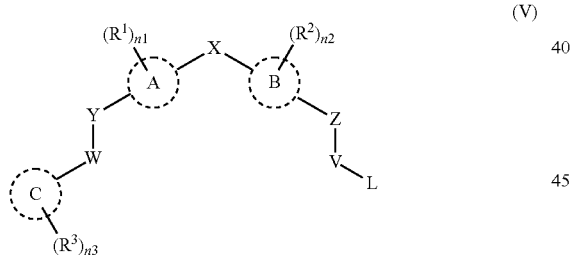

(V)

or a pharmaceutically acceptable salt, tautomer, stereoisomer or prodrug thereof, wherein:

A and B are each independently selected from phenyl, pyridyl, pyrimidyl, or thiophene;

C is a 5- to 10-membered heteroaryl or aryl;

X is a bond, —(CR$^5$R$^6$)$_t$—, or —NR$^7$—;

Y is a bond, —CH$_2$—, —C(CH$_3$)H—, —O—, —S—, —NH—, —NCH$_3$—, or —N(COCH$_3$)—;

Z is a bond, —CH$_2$—, —C(CH$_3$)H—, —O—, —S—, —NH—, —NCH$_3$—, or —N(COCH$_3$)—;

W is a bond, —CH$_2$—, —C(CH$_3$)H—, —C(=O)—, —N(R$^7$)CO—, or —CONR$^7$—;

V is —CH$_2$—, —CH$_2$CH$_2$—, or —CH$_2$CH$_2$CH$_2$—;

L is halogen, —NH$_2$, or —CF$_3$;

R$^1$ and R$^2$ are each independently hydrogen, halogen, —CN, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{13}$R$^{14}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$ or optionally substituted —(C$_1$-C$_6$ alkyl)-SO$_2$R$^{16}$;

R$^3$ is selected from hydrogen, halogen, oxo, =S, —CN, —CF$_3$, —OH, —S(C$_1$-C$_3$ alkyl), C$_1$-C$_3$ alkyl, C$_2$-C$_3$ alkenyl, C$_2$-C$_3$ alkynyl, C$_1$-C$_3$ alkoxy, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl)NR$^{14}$SO$_2$R$^{16}$, —NR$^{14}$COR$^{16}$, —(C$_1$-C$_6$ alkyl)-NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO$_2$(C$_1$-C$_3$ alkyl), or —(C$_1$-C$_6$ alkyl)-SO$_2$(C$_1$-C$_3$ alkyl);

R$^5$ and R$^6$ are each independently hydrogen, halogen, —OH, C$_1$-C$_3$ alkyl, C$_2$-C$_3$ alkenyl, C$_2$-C$_3$ alkynyl, C$_1$-C$_3$ alkoxy; or R$^5$ and R$^6$ taken together form an optionally substituted 3- to 6-membered carbocyclyl or heterocyclyl;

R$^7$ is H or C$_1$-C$_6$ alkyl;

R$^{13}$, R$^{14}$ and R$^{15}$ are each independently hydrogen, C$_1$-C$_3$ alkyl, C$_2$-C$_3$ alkenyl, C$_2$-C$_3$ alkynyl; or R$^{14}$ and R$^{15}$ taken together form a 3- to 6-membered heterocyclyl;

R$^{16}$ is hydrogen, C$_1$-C$_3$ alkyl, C$_2$-C$_3$ alkenyl, or C$_2$-C$_3$ alkynyl;

n1 and n2 are each independently 0, 1, or 2;

n3 is 0, 1, 2, 3, 4 or 5; and t is 0, 1 or 2.

In one embodiment the present disclosure provides compounds comprising the structure of formula (VA):

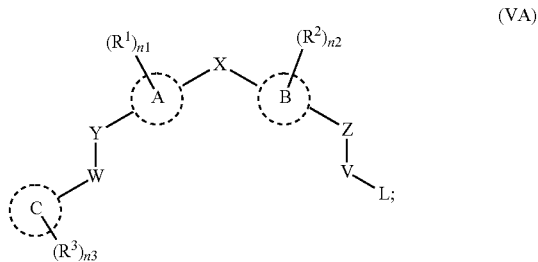

(VA)

or a pharmaceutically acceptable salt, tautomer, stereoisomer or prodrug thereof, wherein:

A and B are each independently selected from phenyl, pyridyl, pyrimidyl, or thiophene;

C is a 5- to 10-membered heteroaryl or aryl;

X is a bond, —(CR$^5$R$^6$)$_t$—, or —NR$^7$;

Y is a bond, —CH$_2$—, —C(CH$_3$)H—, —O—, —S—, —NH—, —NCH$_3$—, or —N(COCH$_3$)—;

Z is a bond, —CH$_2$—, —C(CH$_3$)H—, —O—, —S—, —NH—, —NCH$_3$—, or —N(COCH$_3$)—;

W is a bond, —CH$_2$—, —C(CH$_3$)H—, —C(=O)—, —N(R$^7$)CO—, or —CONR$^7$—;

V is —CH$_2$—, —CH$_2$CH$_2$—, —CH(CH$_3$)CH$_2$—, —CH$_2$CH(CH$_3$)—, or —CH$_2$CH$_2$CH$_2$—;

L is hydrogen, halogen, —OH, —NH$_2$, or —CF$_3$;

R$^1$ and R$^2$ are each independently hydrogen, halogen, —CN, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C₁-C₆ alkyl)-OH, —NR¹³R¹⁴, optionally substituted —(C₁-C₆ alkyl)-NR¹³R¹⁴, —NR¹⁴SO₂R¹⁶, optionally substituted —(C₁-C₆ alkyl)NR¹⁴SO₂R¹⁶, —NR¹⁴COR¹⁶, optionally substituted —(C₁-C₆ alkyl)-NR¹⁴COR¹⁶, —CONR¹³R¹⁴, optionally substituted —(C₁-C₆ alkyl)-CONR¹⁴R¹⁵, —SO₂NR¹⁴R¹⁵, optionally substituted —(C₁-C₆ alkyl)-SO₂NR¹⁴R¹⁵, optionally substituted —SO₂R¹⁶ or optionally substituted —(C₁-C₆ alkyl)-SO₂R¹⁶;

R³ is selected from hydrogen, halogen, oxo, =S, —CN, —CF₃, —OH, —S(C₁-C₃ alkyl), C₁-C₃ alkyl, C₂-C₃ alkenyl, C₂-C₃ alkynyl, C₁-C₃ alkoxy, —NR¹³R¹⁴, —(C₁-C₃ alkyl)-NR¹³R¹⁴, —NR¹⁴SO₂R¹⁶, —(C₁-C₃ alkyl)NR¹⁴SO₂R¹⁶, —NR¹⁴COR¹⁶, —NR¹⁴COOR¹⁶, —NR¹⁴CONR¹⁴R¹⁵, —(C₁-C₆ alkyl)-NR¹⁴COR¹⁶, —CONR¹⁴R¹⁵, —(C₁-C₃ alkyl)-CONR¹⁴R¹⁵, —SO₂NR¹⁴R¹⁵, —(C₁-C₃ alkyl)-SO₂NR¹⁴R¹⁵, —SO₂(C₁-C₃ alkyl), or —(C₁-C₆ alkyl)-SO₂(C₁-C₃ alkyl);

R⁵ and R⁶ are each independently hydrogen, halogen, —OH, —NH₂, C₁-C₃ alkyl, C₂-C₃ alkenyl, C₂-C₃ alkynyl, or C₁-C₃ alkoxy; or R⁵ and R⁶ taken together form an optionally substituted 3- to 6-membered carbocyclyl or heterocyclyl;

R⁷ is H, C₁-C₆ alkyl, —CO(C₁-C₆ alkyl);

R¹³, R¹⁴ and R¹⁵ are each independently hydrogen, C₁-C₃ alkyl, C₂-C₃ alkenyl, C₂-C₃ alkynyl, or —COO(C₁-C₆ alkyl); or R¹⁴ and R¹⁵ taken together form a 3- to 6-membered heterocyclyl;

R¹⁶ is hydrogen, C₁-C₃ alkyl, C₁-C₃ haloalkyl, C₂-C₃ alkenyl, or C₂-C₃ alkynyl;

n1 and n2 are each independently 0, 1, or 2;

n3 is 0, 1, 2, 3, 4 or 5; and t is 0, 1 or 2.

In one embodiment, the present disclosure provides compounds comprising the structure of formula (VI):

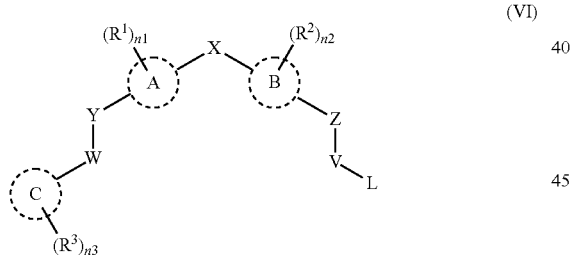

(VI)

or a pharmaceutically acceptable salt, tautomer, stereoisomer or prodrug thereof, wherein:

A and B are each independently selected from phenyl, pyridyl, pyrimidyl, or thiophene;

C is a 5- to 10-membered heterocyclyl;

X is a bond, —(CR⁵R⁶)ₜ—, or —NR⁷—;

Y is a bond, —CH₂—, —C(CH₃)H—, —O—, —S—, —NH—, —NCH₃—, or —N(COCH₃)—;

Z is a bond, —CH₂—, —C(CH₃)H—, —O—, —S—, —NH—, —NCH₃—, or —N(COCH₃)—;

W is a bond, —CH₂—, —C(CH₃)H—, —C(=O)—, —N(R⁷)CO—, or —CONR⁷—;

V is —CH₂—, —CH₂CH₂—, or —CH₂CH₂CH₂—;

L is halogen, —NH₂, or —CF₃;

R¹ and R² are each independently hydrogen, halogen, —CN, —CF₃, —OH, optionally substituted C₁-C₆ alkyl, optionally substituted C₁-C₆ alkoxy, optionally substituted —(C₁-C₆ alkyl)-(C₁-C₆ alkoxy), optionally substituted —(C₁-C₆ alkyl)-OH, —NR¹³R¹⁴, optionally substituted —(C₁-C₆ alkyl)-NR¹³R¹⁴, —NR¹⁴SO₂R¹⁶, optionally substituted —(C₁-C₆ alkyl)NR¹⁴SO₂R¹⁶, —NR¹⁴COR¹⁶, optionally substituted —(C₁-C₆ alkyl)-NR¹⁴COR¹⁶, —CONR¹³R¹⁴, optionally substituted —(C₁-C₆ alkyl)-CONR¹⁴R¹⁵, —SO₂NR¹⁴R¹⁵, optionally substituted —(C₁-C₆ alkyl)-SO₂NR¹⁴R¹⁵, optionally substituted —SO₂R¹⁶ or optionally substituted —(C₁-C₆ alkyl)-SO₂R¹⁶;

R³ is selected from hydrogen, halogen, oxo, =S, =NR¹⁶, —CN, —CF₃, —OH, —S(C₁-C₃ alkyl), C₁-C₃ alkyl, C₂-C₃ alkenyl, C₂-C₃ alkynyl, C₁-C₃ alkoxy, —NR¹³R¹⁴, —(C₁-C₃ alkyl)-NR¹³R¹⁴, —NR¹⁴SO₂R¹⁶, —(C₁-C₃ alkyl)NR¹⁴SO₂R¹⁶, —NR¹⁴COR¹⁶, —(C₁-C₆ alkyl)- NR¹⁴COR¹⁶, —CONR¹⁴R¹⁵, —(C₁-C₃ alkyl)-CONR¹⁴R¹⁵, —SO₂NR¹⁴R¹⁵, —(C₁-C₃ alkyl)-SO₂NR¹⁴R¹⁵, —SO₂(C₁-C₃ alkyl), or —(C₁-C₆ alkyl)-SO₂(C₁-C₃ alkyl);

R⁵ and R⁶ are each independently hydrogen, halogen, —OH, C₁-C₃ alkyl, C₂-C₃ alkenyl, C₂-C₃ alkynyl, or C₁-C₃ alkoxy; or R⁵ and R⁶ taken together form an optionally substituted 3- to 6-membered carbocyclyl or heterocyclyl;

R⁷ is H or C₁-C₆ alkyl;

R¹³, R¹⁴ and R¹⁵ are each independently hydrogen, C₁-C₃ alkyl, C₂-C₃ alkenyl, or C₂-C₃ alkynyl; or R¹⁴ and R¹⁵ taken together form a 3- to 6-membered heterocyclyl;

R¹⁶ is hydrogen, C₁-C₃ alkyl, C₂-C₃ alkenyl, or C₂-C₃ alkynyl;

n1 and n2 are each independently 0, 1, or 2;

n3 is 0, 1, 2, 3, 4 or 5; and t is 0, 1 or 2.

In one embodiment, the present disclosure provides compounds comprising the structure of formula (A):

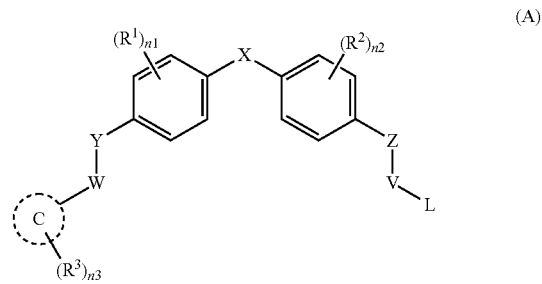

(A)

or a pharmaceutically acceptable salt, tautomer, stereoisomer or prodrug thereof, wherein:

C is a phenyl or a 5- to 7-membered monocyclic heteroaryl comprising 1, 2, or 3 heteroatoms selected from O, S, or N as a ring member;

X is a bond, —(CR⁵R⁶)ₜ—, or —NR⁷—;

Y is a bond, —CH₂—, —C(CH₃)H—, —O—, —S—, —NH—, —NCH₃—, or —N(COCH₃)—;

Z is a bond, —CH₂—, —O—, or —NH—;

W is a bond, —CH₂—, —C(CH₃)H—, —C(=O)—, —N(R⁷)CO—, or —CONR⁷—;

V is —CH₂—, —CH₂CH₂—, or —CH₂CH₂CH₂—;

L is halogen, —NH₂, or —CF₃;

R¹ and R² are each independently hydrogen, halogen, —CN, —CF₃, methyl, or —CONH₂;

R³ is selected from hydrogen, F, Cl, Br, I, oxo, —CN, —CF₃, —OH, C₁-C₃ alkyl, C₂-C₃ alkenyl, C₂-C₃ alkynyl, —S(C₁-C₃ alkyl), —SO₂(C₁-C₃ alkyl), —NHSO$_2$CH$_3$, —N(CH$_3$)SO$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), or —N(CH$_3$)CO(C$_1$-C$_3$ alkyl);

R$^5$ and R$^6$ are each independently hydrogen, halogen, —OH, or C$_1$-C$_3$ alkyl;

R$^7$ is H or C$_1$-C$_6$ alkyl;

n1 and n2 are each independently 0, 1, or 2;

n3 is 0, 1, 2, 3, 4 or 5; and t is 0, 1 or 2.

In one embodiment, the present disclosure provides compounds comprising the structure of formula (B)

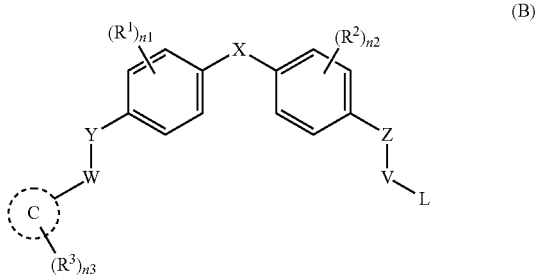

(B)

or a pharmaceutically acceptable salt, tautomer, stereoisomer or prodrug thereof, wherein:

C is a 5- to 7-membered saturated or partially saturated monocyclic heterocycle comprising 1, 2, or 3 heteroatoms selected from O, S, or N as a ring member;

X is a bond, —(CR$^5$R$^6$)$_t$—, or —NR$^7$—;

Y is a bond, —CH$_2$—, —C(CH$_3$)H—, —O—, —S—, —NH—, —NCH$_3$—, or —N(COCH$_3$)—;

Z is a bond, —CH$_2$—, —O—, or —NH—;

W is a bond, —CH$_2$—, —C(CH$_3$)H—, —C(=O)—, —N(R$^7$)CO—, or —CONR$^7$—;

V is —CH$_2$—, —CH$_2$CH$_2$—, or —CH$_2$CH$_2$CH$_2$—;

L is halogen, —NH$_2$, or —CF$_3$;

R$^1$ and R$^2$ are each independently hydrogen, halogen, —CN, —CF$_3$, methyl, or —CONH$_2$;

R$^3$ is selected from hydrogen, F, Cl, Br, I, oxo, =S, =NR$^{16}$, —CN, —CF$_3$, —OH, C$_1$-C$_3$ alkyl, C$_2$-C$_3$ alkenyl, C$_2$-C$_3$ alkynyl, —S(C$_1$-C$_3$ alkyl), —SO$_2$(C$_1$-C$_3$ alkyl), —NHSO$_2$CH$_3$, —N(CH$_3$)SO$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), or —N(CH$_3$)CO(C$_1$-C$_3$ alkyl);

R$^5$ and R$^6$ are each independently hydrogen, halogen, —OH, or C$_1$-C$_3$ alkyl;

R$^7$ is H or C$_1$-C$_6$ alkyl;

R$^{16}$ is hydrogen or C$_1$-C$_3$ alkyl;

n1 and n2 are each independently 0, 1, or 2;

n3 is 0, 1, 2, 3, 4 or 5; and t is 0, 1 or 2.

In one embodiment of the compounds of formula (I), (IC), (II), (III), (IIIA), (IV), (V), (VI), (A), or (B), —V-L is —CH$_2$CH$_2$Cl, —CH$_2$CH$_2$CH$_2$Cl, —CH$_2$CH$_2$NH$_2$, or —CH$_2$CH$_2$CH$_2$NH$_2$.

In one embodiment of the compounds of formula (I), (IC), (II), (III), (IIIA), (IV), (V), (VI), (A), or (B), —Y—W— is a bond, —OCH$_2$—, —OCH$_2$CH$_2$—, —OCH(CH$_3$)—, —NH—, —NHCH$_2$—, —NHC(=O)—, or —C(=O)NH—.

In one embodiment of the compounds of formula (I), (IC), (II), (III), (IIIA), (IV), (V), (VI), (A), or (B), X is a bond, —CH$_2$—, —C(CH$_3$)H—, —C(CH$_3$)$_2$—, or —CH$_2$CH$_2$—.

In one embodiment, the present disclosure provides compounds comprising the structure of formula (C):

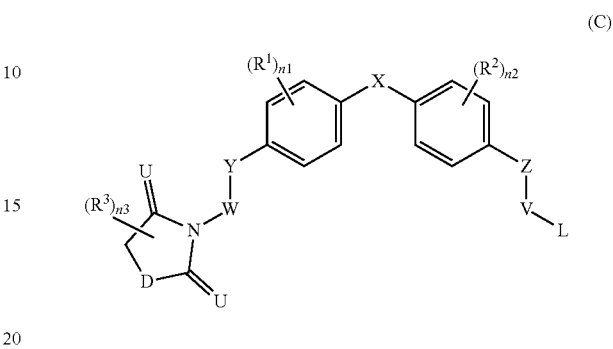

(C)

or a pharmaceutically acceptable salt, tautomer, stereoisomer or prodrug thereof, wherein:

A and B are each independently selected from phenyl, pyridyl, pyrimidyl, or thiophene;

X is a bond, (CR$^5$R$^6$)$_t$—, or —NR$^7$—;

Y is a bond, —CH$_2$—, —C(CH$_3$)H—, —O—, —S—, —NH—, —NCH$_3$—, or —N(COCH$_3$)—;

Z is a bond, —CH$_2$—, —C(CH$_3$)H—, —O—, —S—, —NH—, —NCH$_3$—, or —N(COCH$_3$)—;

W is a bond, —CH$_2$—, —C(CH$_3$)H—, —C(=O)—, —N(R$^7$)CO—, or —CONR$^7$—;

V is —CH$_2$—, —CH$_2$CH$_2$—, or —CH$_2$CH$_2$CH$_2$—;

L is halogen, —NH$_2$, or —CF$_3$;

D is —NH or —NR$^3$;

U is each independently O, S, or NR$^{16}$;

R$^1$ and R$^2$ are each independently hydrogen, halogen, —CN, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl) NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{13}$R$^{14}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$ or optionally substituted —(C$_1$-C$_6$ alkyl)-SO$_2$R$^{16}$;

R$^3$ is selected from hydrogen, halogen, —CN, —CF$_3$, —OH, —S(C$_1$-C$_3$ alkyl), C$_1$-C$_3$ alkyl, C$_2$-C$_3$ alkenyl, C$_2$-C$_3$ alkynyl, C$_1$-C$_3$ alkoxy, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl) NR$^{14}$SO$_2$R$^{16}$, —NR$^{14}$COR$^{16}$, —(C$_1$-C$_6$ alkyl)-NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO$_2$(C$_1$-C$_3$ alkyl), or —(C$_1$-C$_6$ alkyl)-SO$_2$(C$_1$-C$_3$ alkyl);

R$^5$ and R$^6$ are each independently hydrogen, halogen, —OH, C$_1$-C$_3$ alkyl, C$_2$-C$_3$ alkenyl, C$_2$-C$_3$ alkynyl, or C$_1$-C$_3$ alkoxy; or R$^5$ and R$^6$ taken together form an optionally substituted 3- to 6-membered carbocyclyl or heterocyclyl;

R$^7$ is H or C$_1$-C$_6$ alkyl;

R$^{13}$, R$^{14}$ and R$^{15}$ are each independently hydrogen, C$_1$-C$_3$ alkyl, C$_2$-C$_3$ alkenyl, or C$_2$-C$_3$ alkynyl; or R$^{14}$ and R$^{15}$ taken together form a 3- to 6-membered heterocyclyl;

$R^{16}$ is hydrogen, $C_1$-$C_3$ alkyl, $C_2$-$C_3$ alkenyl, or $C_2$-$C_3$ alkynyl;

n1 and n2 are each independently 0, 1, or 2;

n3 is 0, 1, 2, or 3; and t is 0, 1 or 2.

In one embodiment, the present disclosure provides compounds comprising the structure of formula (D):

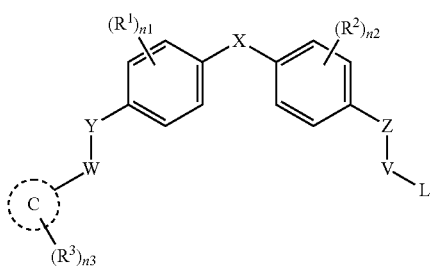

(D)

or a pharmaceutically acceptable salt, tautomer, stereoisomer or prodrug thereof, wherein:

C is a 5- or 6-membered heteroaryl comprising 1 or 2 heteroatoms selected from O, S, or N as a ring member;

X is —$(CR^5R^6)_t$— or —$NR^7$—;

Y is a bond, —$CH_2$—, —O—, or —NH—;

Z is a bond, —$CH_2$—, —O—, or —NH—;

W is a bond, —$CH_2$—, or —$C(CH_3)H$—;

V is —$CH_2$—, —$CH_2CH_2$—, or —$CH_2CH_2CH_2$—;

L is hydrogen, halogen, —$NH_2$, or —$CF_3$;

$R^1$ and $R^2$ are each independently hydrogen, halogen, —CN, —$CF_3$, methyl, or —$CONH_2$;

$R^3$ is selected from hydrogen, F, Cl, Br, I, oxo, —CN, —$CF_3$, —OH, $C_1$-$C_3$ alkyl, $C_2$-$C_3$ alkenyl, $C_2$-$C_3$ alkynyl, —$S(C_1$-$C_3$ alkyl), —$SO_2(C_1$-$C_3$ alkyl), —$NHSO_2CH_3$, —$N(CH_3)SO_2CH_3$, —$CH_2NHSO_2CH_3$, —$CH_2N(CH_3)SO_2CH_3$, —$SO_2NH_2$, —$CONH_2$, —$CON(C_1$-$C_3$ alkyl)$_2$, —$CONH(C_1$-$C_3$ alkyl), —$NHCO(C_1$-$C_3$ alkyl), or —$N(CH_3)CO(C_1$-$C_3$ alkyl);

$R^5$ and $R^6$ are each independently hydrogen, halogen, —OH, or $C_1$-$C_3$ alkyl;

$R^7$ is H or $C_1$-$C_6$ alkyl;

n1 and n2 are each independently 0, 1, or 2;

n3 is 0, 1, 2, 3, 4 or 5; and t is 0, 1 or 2.

In one embodiment, the present disclosure provides compounds comprising the structure of formula (E):

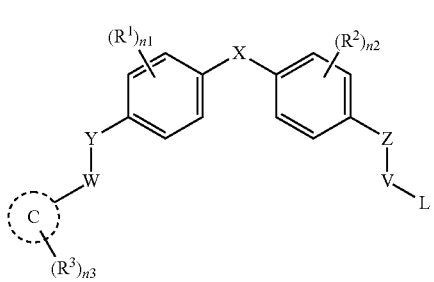

(E)

or a pharmaceutically acceptable salt, tautomer, stereoisomer or prodrug thereof, wherein:

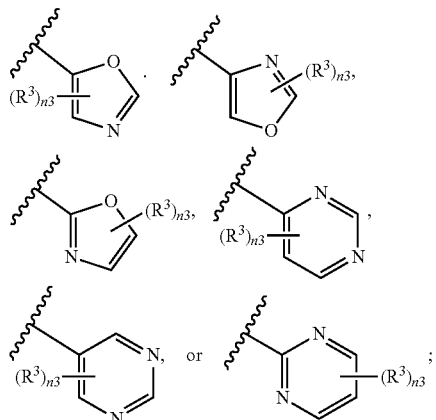

X is —$(CR^5R^6)_t$— or —$NR^7$—;

Y is a bond, —$CH_2$—, —O—, or —NH—;

Z is a bond, —$CH_2$—, —O—, or —NH—;

W is a bond, —$CH_2$—, or —$C(CH_3)H$—;

V is —$CH_2$—, —$CH_2CH_2$—, or —$CH_2CH_2CH_2$—;

L is hydrogen or halogen;

$R^1$ and $R^2$ are each independently hydrogen, halogen, —CN, —$CF_3$, methyl, or —$CONH_2$;

$R^3$ is selected from hydrogen, F, Cl, Br, I, oxo, —CN, —$CF_3$, —OH, $C_1$-$C_3$ alkyl, $C_2$-$C_3$ alkenyl, $C_2$-$C_3$ alkynyl, —$S(C_1$-$C_3$ alkyl), —$SO_2(C_1$-$C_3$ alkyl), —$NHSO_2CH_3$, —$N(CH_3)SO_2CH_3$, —$CH_2NHSO_2CH_3$, —$CH_2N(CH_3)SO_2CH_3$, —$SO_2NH_2$, —$CONH_2$, —$CON(C_1$-$C_3$ alkyl)$_2$, —$CONH(C_1$-$C_3$ alkyl), —$NHCO(C_1$-$C_3$ alkyl), or —$N(CH_3)CO(C_1$-$C_3$ alkyl);

$R^5$ and $R^6$ are each independently hydrogen or $C_1$-$C_3$ alkyl;

$R^7$ is H or $C_1$-$C_6$ alkyl;

n1 and n2 are each independently 0, 1, or 2;

n3 is 0, 1, or 2; and t is 1 or 2.

In one embodiment the present disclosure provides compounds comprising the structure of formula (E-I):

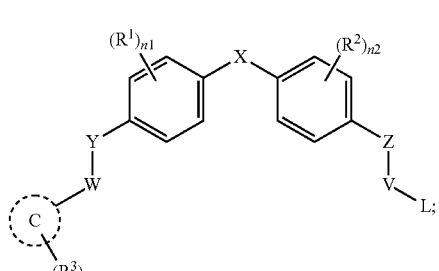

(E-I)

or a pharmaceutically acceptable salt, tautomer, stereoisomer or prodrug thereof, wherein:

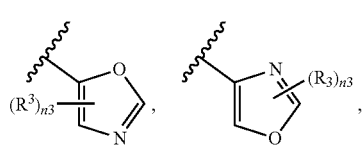

-continued

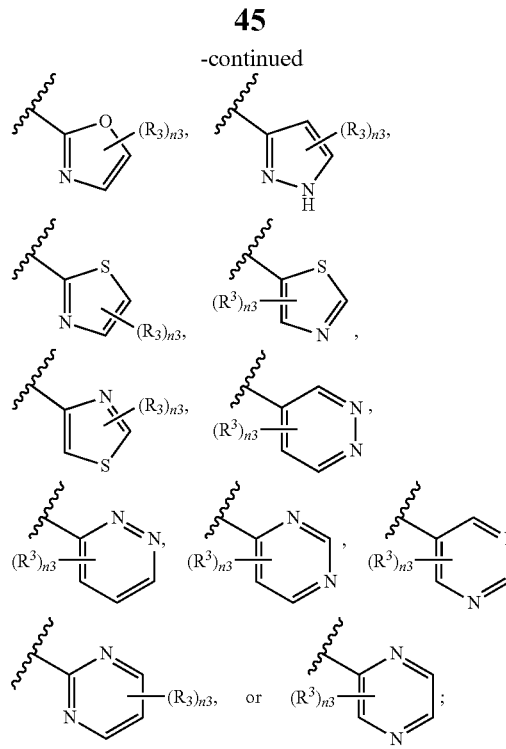

X is —(CR⁵R⁶)$_t$— or —NR⁷—;
Y is a bond, —CH$_2$—, —O—, or —NH—;
Z is a bond, —CH$_2$—, —O—, or —NH—;
W is a bond, —CH$_2$—, or —C(CH$_3$)H—;
V is —CH$_2$—, —CH$_2$CH$_2$—, —CH$_2$CH$_2$CH$_2$—, or —CH$_2$CHClCH$_2$—;
L is hydrogen, —OH, or halogen;
R¹ and R² are each independently hydrogen, halogen, —CN, —CF$_3$, methyl, or —CONH$_2$;
R³ is selected from hydrogen, F, Cl, Br, I, oxo, —CN, —CF$_3$, —OH, C$_1$-C$_3$ alkyl, C$_2$-C$_3$ alkenyl, C$_2$-C$_3$ alkynyl, C$_1$-C$_3$ alkoxy, —S(C$_1$-C$_3$ alkyl), —SO$_2$(C$_1$-C$_3$ alkyl), —NH$_2$, —NHSO$_2$CH$_3$, —NHSO$_2$CF$_3$, —N(CH$_3$)SO$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), —N(CH$_3$)COO(C$_1$-C$_3$ alkyl), —NHCO(C$_1$-C$_3$ alkyl), or —N(CH$_3$)COO(C$_1$-C$_3$ alkyl);
R⁵ and R⁶ are each independently hydrogen or C$_1$-C$_3$ alkyl;
R⁷ is H or C$_1$-C$_6$ alkyl;
n1 and n2 are each independently 0, 1, or 2;
n3 is 0, 1, or 2; and
t is 1 or 2.

In one embodiment of the compounds of formula (A)-(C) or (E-1), R³ is selected from hydrogen, F, Cl, Br, I, —CN, —CF$_3$, —OH, methyl, methoxy, —S(C$_1$-C$_3$ alkyl), —SO$_2$(C$_1$-C$_3$ alkyl), —NH$_2$, —NHSO$_2$CH$_3$, —NHSO$_2$CF$_3$, —N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), or —NHCO(C$_1$-C$_3$ alkyl).

In one embodiment, the present disclosure provides compounds comprising the structure of formula (F):

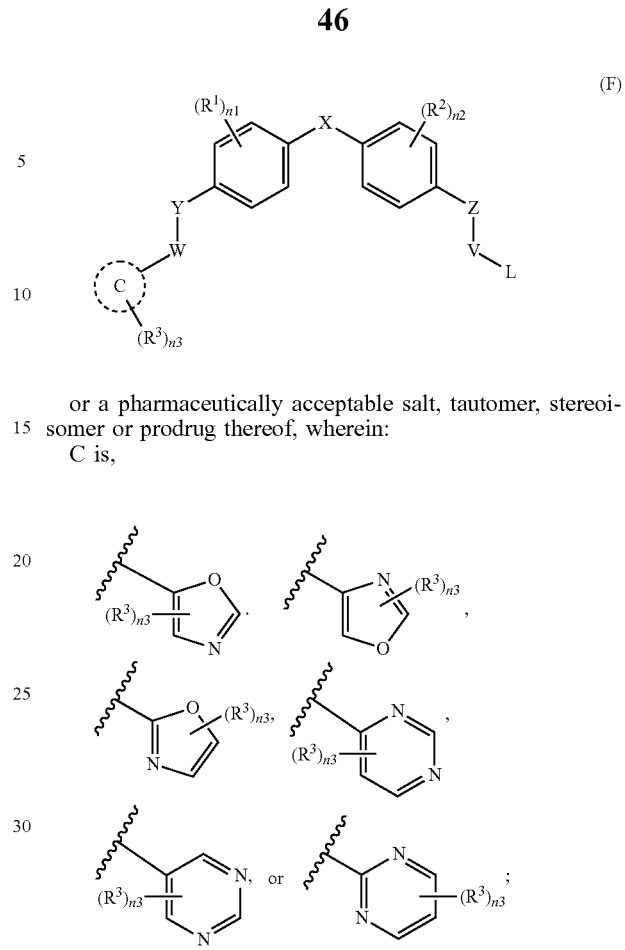

or a pharmaceutically acceptable salt, tautomer, stereoisomer or prodrug thereof, wherein:
C is, X is —(CR⁵R⁶)$_t$— or —NR⁷—;
Y is —O—;
Z is —O—;
W is —CH$_2$— or —C(CH$_3$)H—;
V is —CH$_2$—, —CH$_2$CH$_2$—, or —CH$_2$CH$_2$CH$_2$—;
L is hydrogen or halogen;
R¹ and R² are each independently halogen or —CN;
R³ is selected from —NHSO$_2$CH$_3$, —N(CH$_3$)SO$_2$CH$_3$, or —SO$_2$CH$_3$;
R⁵ and R⁶ are each independently hydrogen or C$_1$-C$_3$ alkyl;
R⁷ is H or C$_1$-C$_6$ alkyl;
n1 and n2 are each independently 0, 1, or 2;
n3 is 0, 1, or 2; and
t is 1 or 2

In one embodiment, the present disclosure provides compounds comprising the structure of formula (G):

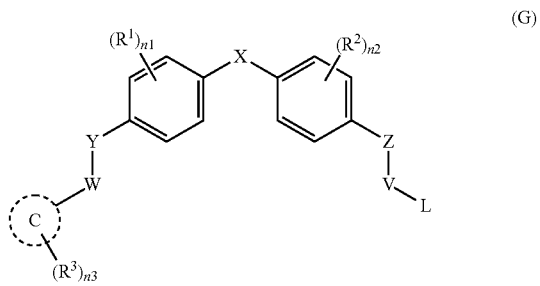

or a pharmaceutically acceptable salt, tautomer, stereoisomer or prodrug thereof, wherein:

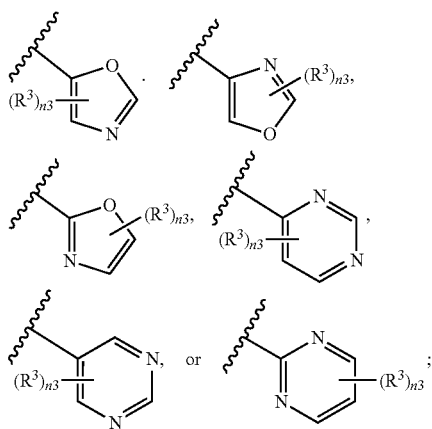

X is —(CR⁵R⁶)_t— or —NR⁷—;
Y is —O—;
Z is —O—;
W is —CH₂— or —C(CH₃)H—;
V is —CH₂— and L is hydrogen;
or alternatively, V is —CH₂CH₂— or —CH₂CH₂CH₂—, and L is halogen;
R¹ and R² are each independently C or —CN;
R³ is selected from —NHSO₂CH₃, —N(CH₃)SO₂CH₃, or —SO₂CH₃;
R⁵ and R⁶ are each independently hydrogen or methyl;
R⁷ is H or C₁-C₆ alkyl;
n1 and n2 are each independently 0, 1, or 2;
n3 is 1, or 2; and
t is 1.

In one embodiment the present disclosure provides compounds comprising the structure of (G-I)

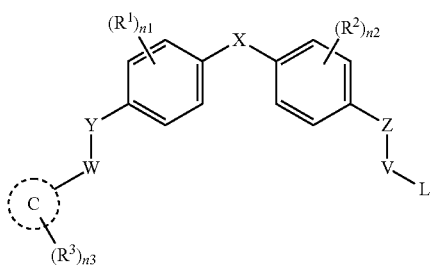

or a pharmaceutically acceptable salt, tautomer, stereoisomer or prodrug thereof, wherein:

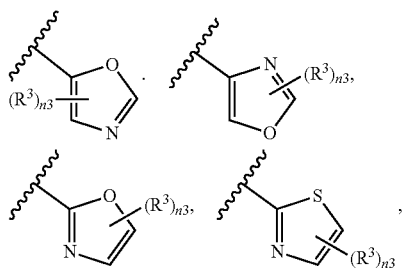

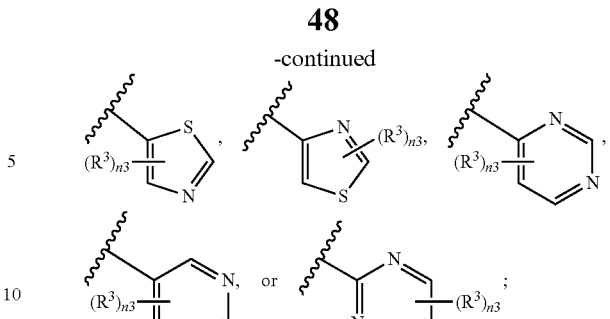

X is —(CR⁵R⁶)_t—;
Y is —O—;
Z is —O—;
W is —CH₂— or —C(CH₃)H—;
V is —CH₂CH₂— or —CH₂CH₂CH₂—;
L is halogen;
R¹ and R² are each independently Cl or —CN;
R³ is selected from —NHSO₂CH₃, —N(CH₃)SO₂CH₃, or —SO₂CH₃;
R⁵ and R⁶ are each independently hydrogen or methyl;
n1 and n2 are each independently 0, 1, or 2;
n3 is 1 or 2; and
t is 1.

In one embodiment, the present disclosure provides compounds comprising the structure of formula (G-II)

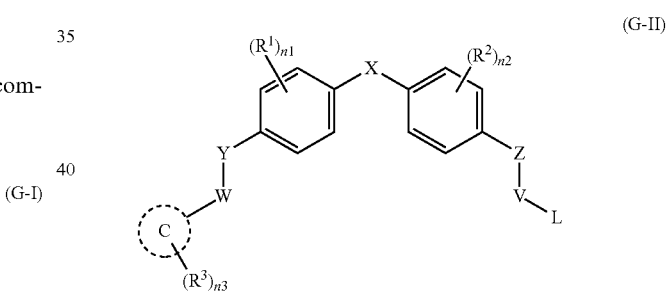

or a pharmaceutically acceptable salt, tautomer, stereoisomer or prodrug thereof, wherein:
C is

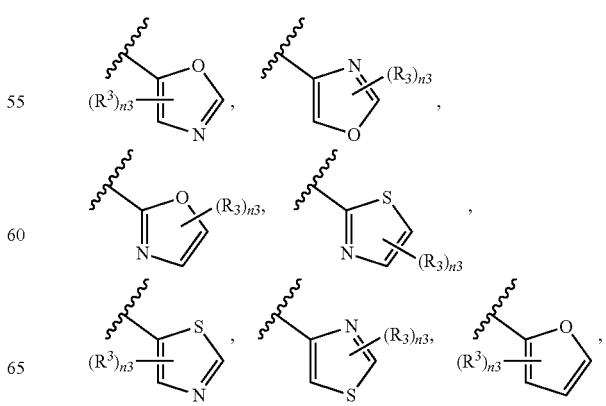

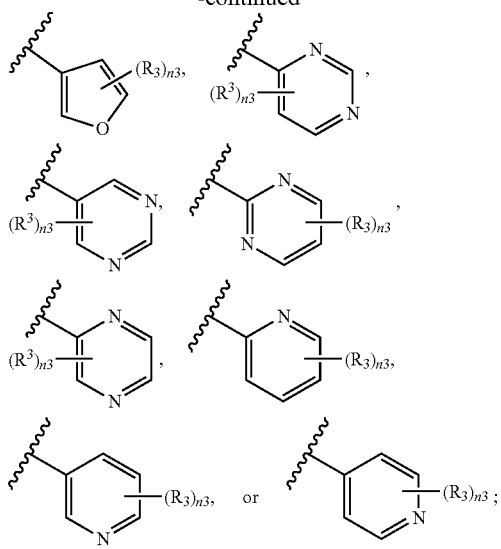

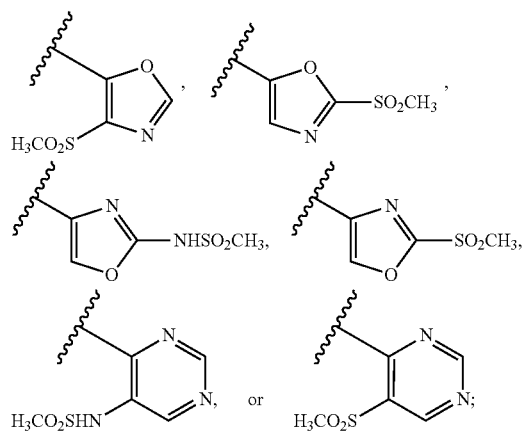

C-I is

X is —(CR$^5$R$^6$)$_t$—;
Y is —O—;
Z is —O—;
W is —CH$_2$— or —C(CH$_3$)H—;
V is —CH$_2$—, —CH$_2$CH$_2$— or —CH$_2$CH$_2$CH$_2$—;
L is halogen;
R$^1$ and R$^2$ are each independently Cl or —CN;
R$^5$ and R$^6$ are each independently hydrogen or methyl;
R$^7$ is H or C$_1$-C$_6$ alkyl;
n1 and n2 are each independently 0, 1, or 2; and
t is 1.

In one embodiment the present disclosure provides compounds comprising the structure of formula (H-I):

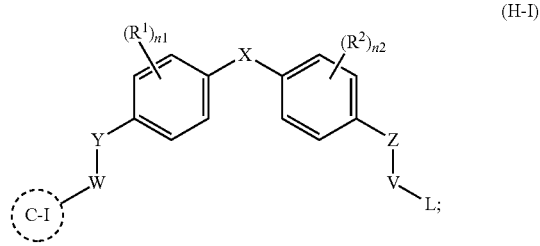

or a pharmaceutically acceptable salt, tautomer, stereoisomer or prodrug thereof, wherein:

C-I is

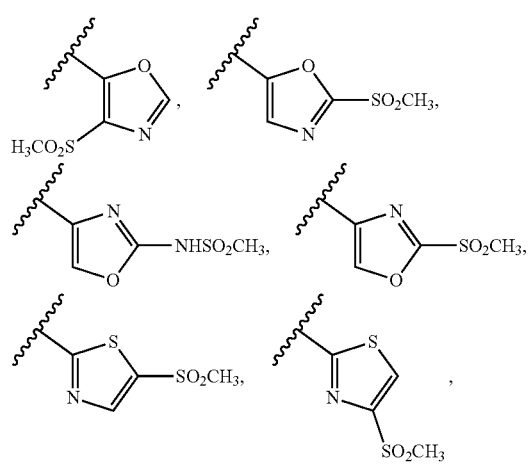

X is —(CR$^5$R$^6$)$_t$—;
Y is —O—;
Z is —O—;
W is —CH$_2$— or —C(CH$_3$)H—;
V is —CH$_2$CH$_2$—;
L is halogen;
R$^1$ and R$^2$ are each independently Cl or —CN;
at least one R$^3$ is selected from —CN, C$_1$-C$_3$ alkoxy, —CONH$_2$, —NHSO$_2$CH$_3$, —N(CH$_3$)SO$_2$CH$_3$, —NHSO$_2$CH$_2$CH$_3$, —N(CH$_3$)SO$_2$CH$_2$CH$_3$, or —SO$_2$CH$_3$ and the other R$^3$, if present, is selected from —CN, —CF$_3$, C$_1$-C$_3$ alkyl, C$_2$-C$_3$ alkenyl, C$_2$-C$_3$ alkynyl, C$_1$-C$_3$ alkoxy, —S(C$_1$-C$_3$ alkyl), —SO$_2$(C$_1$-C$_3$ alkyl), —NH$_2$, —(C$_1$-C$_3$ alkyl)NH$_2$, —NHSO$_2$CH$_3$, —NHSO$_2$CF$_3$, —N(CH$_3$)SO$_2$CH$_3$, —NHSO$_2$CH$_2$CH$_3$, —N(CH$_3$)SO$_2$CH$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), —N(CH$_3$)COO(C$_1$-C$_3$ alkyl), —NHCO(C$_1$-C$_3$ alkyl), or —N(CH$_3$)COO(C$_1$-C$_3$ alkyl);
R$^5$ and R$^6$ are each independently hydrogen or methyl;
n1 and n2 are each independently 0, 1, or 2;
n3 is 1 or 2; and
t is 1.

In one embodiment, the present disclosure provides compounds comprising the structure of formula (H):

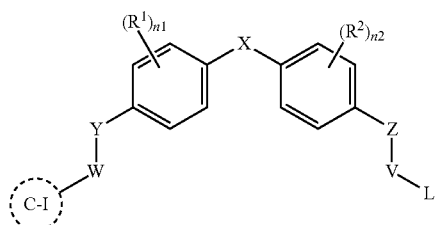

or a pharmaceutically acceptable salt, tautomer, stereoisomer or prodrug thereof, wherein:

-continued

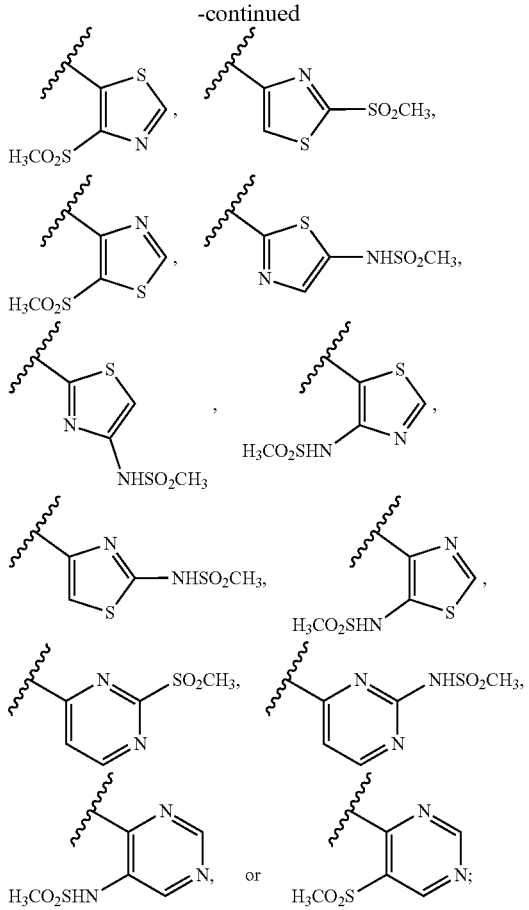

X is —(CR⁵R⁶)ₜ—;
Y is —O—;
Z is —O—;
W is —CH₂— or —C(CH₃)H—;
V is —CH₂—, —CH₂CH₂— or —CH₂CH₂CH₂—;
L is halogen;
R¹ and R² are each independently Cl or —CN;
R⁵ and R⁶ are each independently hydrogen or methyl;
R⁷ is H or C₁-C₆ alkyl;
n1 and n2 are each independently 0, 1, or 2; and
t is 1.

In one embodiment the present disclosure provides compounds comprising the structure of formula (E-II):

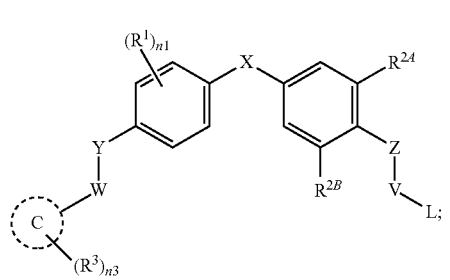

(E-II)

or a pharmaceutically acceptable salt, tautomer, stereoisomer or prodrug thereof, wherein:

C is

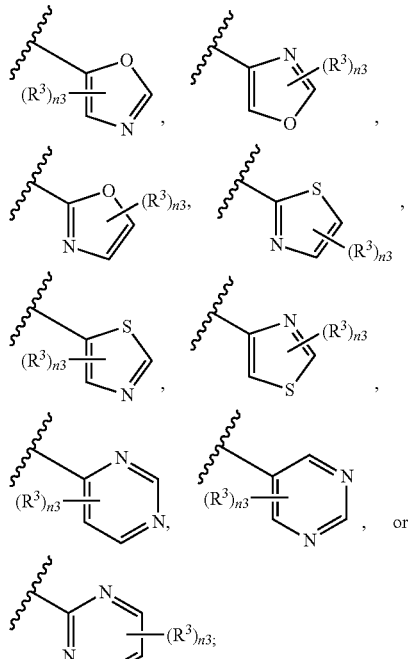

X is —(CR⁵R⁶)—;
Y is a bond, —CH₂—, —O—, or —NH—;
Z is a bond, —CH₂—, —O—, or —NH—;
W is a bond, —CH₂—, or —C(CH₃)H—;
V is —CH₂—, —CH₂CH₂—, or —CH₂CH₂CH₂—;
L is halogen;
R¹, R²ᴬ and R²ᴮ are each independently hydrogen, halogen, —CN, —CF₃, methyl, or —CONH₂;
R³ is selected from hydrogen, F, Cl, Br, I, oxo, —CN, —CF₃, —OH, C₁-C₃ alkyl, C₂-C₃ alkenyl, C₂-C₃ alkynyl, C₁-C₃ alkoxy, —S(C₁-C₃ alkyl), —SO₂(C₁-C₃ alkyl), —NH₂, —NHSO₂CH₃, —NHSO₂CF₃, —N(CH₃)SO₂CH₃, —CH₂NHSO₂CH₃, —CH₂N(CH₃)SO₂CH₃, —SO₂NH₂, —CONH₂, —CON(C₁-C₃ alkyl)₂, —CONH(C₁-C₃ alkyl), —NHCO(C₁-C₃ alkyl), —N(CH₃)COO(C₁-C₃ alkyl), —NHCO(C₁-C₃ alkyl), or —N(CH₃)COO(C₁-C₃ alkyl);
R⁵ and R⁶ are each independently hydrogen or C₁-C₃ alkyl;
n1 is 0, 1, or 2; and
n3 is 1 or 2;
wherein when C—R³ is

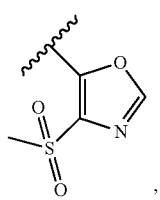 [SMILES: *c1ocnc1S(C)(=O)=O]

R²ᴬ and R²ᴮ are not both Cl.

In one embodiment the present disclosure provides compounds comprising the structure of formula (E-III):

(E-III)

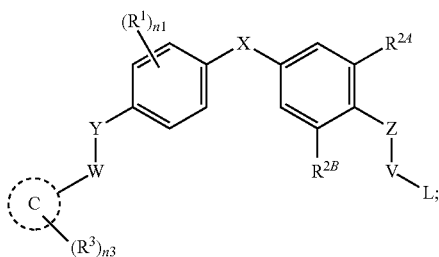

or a pharmaceutically acceptable salt, tautomer, stereoisomer or prodrug thereof, wherein:

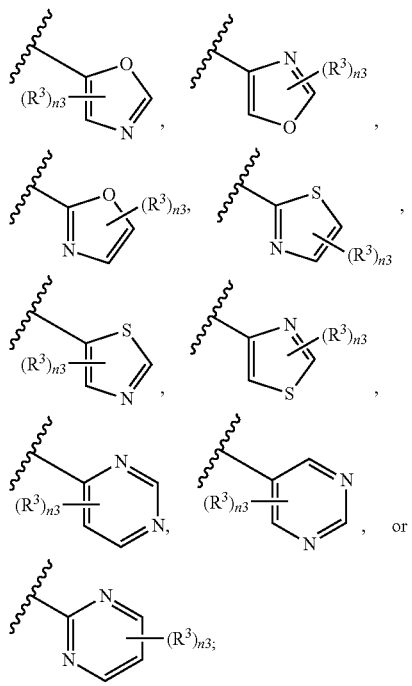

X is —(CR$^5$R$^6$)—;
Y is a bond, —CH$_2$—, —O—, or —NH—;
Z is a bond, —CH$_2$—, —O—, or —NH—;
W is a bond, —CH$_2$—, or —C(CH$_3$)H—;
V is —CH$_2$—, —CH$_2$CH$_2$—, or —CH$_2$CH$_2$CH$_2$—;
L is halogen;
R$^1$, R$^{2A}$ and R$^{2B}$ are each independently hydrogen, halogen, —CN, —CF$_3$, methyl, or —CONH$_2$;
R$^3$ is selected from hydrogen, F, Cl, Br, I, oxo, —CN, —CF$_3$, —OH, C$_1$-C$_3$ alkyl, C$_2$-C$_3$ alkenyl, C$_2$-C$_3$ alkynyl, C$_1$-C$_3$ alkoxy, —S(C$_1$-C$_3$ alkyl), —SO$_2$(C$_1$-C$_3$ alkyl), —NH$_2$, —NHSO$_2$CH$_3$, —NHSO$_2$CF$_3$, —N(CH$_3$)SO$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), —N(CH$_3$)COO(C$_1$-C$_3$ alkyl), —NHCO(C$_1$-C$_3$ alkyl), or —N(CH$_3$)COO(C$_1$-C$_3$ alkyl);
R$^5$ and R$^6$ are each independently hydrogen or C$_1$-C$_3$ alkyl;
n1 is 0, 1, or 2; and
n3 is 1 or 2;

wherein when C—R$^3$ is

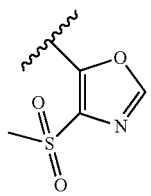 [SMILES: *c1ocnc1S(C)(=O)=O]

and one of R$^{2A}$ and R$^{2B}$ is Cl, then the other of R$^{2A}$ and R$^{2B}$ is not —CN.

In one embodiment the present disclosure provides compounds comprising the structure of formula (E-IV):

(E-IV)

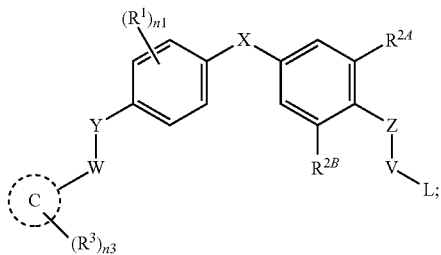

or a pharmaceutically acceptable salt, tautomer, stereoisomer or prodrug thereof, wherein:
C is

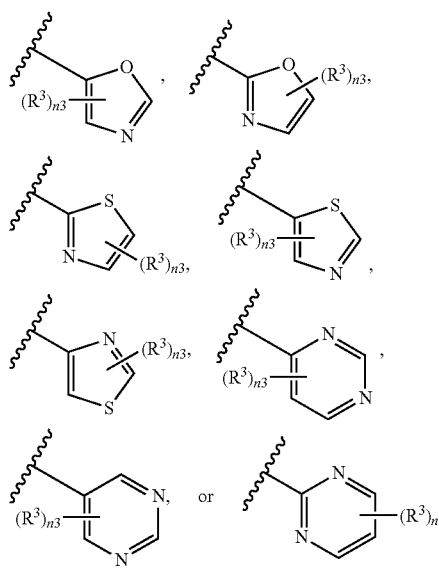

X is —(CR$^5$R$^6$)—;
Y is a bond, —CH$_2$—, —O—, or —NH—;
Z is a bond, —CH$_2$—, —O—, or —NH—;
W is a bond, —CH$_2$—, or —C(CH$_3$)H—;
V is —CH$_2$—, —CH$_2$CH$_2$—, or —CH$_2$CH$_2$CH$_2$—;
L is halogen;
R$^1$, R$^{2A}$ and R$^{2B}$ are each independently hydrogen, halogen, —CN, —CF$_3$, methyl, or —CONH$_2$;
R$^3$ is selected from hydrogen, F, Cl, Br, I, oxo, —CN, —CF$_3$, —OH, C$_1$-C$_3$ alkyl, C$_2$-C$_3$ alkenyl, C$_2$-C$_3$ alkynyl, C$_1$-C$_3$ alkoxy, —S(C$_1$-C$_3$ alkyl), —SO$_2$(C$_1$-C$_3$ alkyl), —NH$_2$, —NHSO$_2$CH$_3$, —NHSO$_2$CF$_3$, —N(CH$_3$)SO$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), —N(CH$_3$)COO(C$_1$-C$_3$ alkyl), —NHCO(C$_1$-C$_3$ alkyl), or —N(CH$_3$)COO(C$_1$-C$_3$ alkyl);

$R^5$ and $R^6$ are each independently hydrogen or C$_1$-C$_3$ alkyl;

n1 is 0, 1, or 2; and n3 is 1 or 2.

In one embodiment the present disclosure provides compounds comprising the structure of formula (E-V):

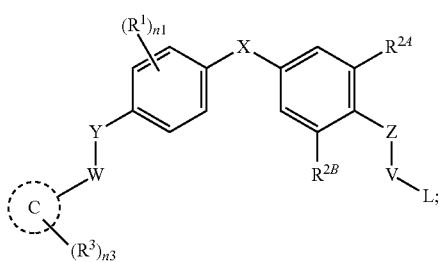

(E-V)

or a pharmaceutically acceptable salt, tautomer, stereoisomer or prodrug thereof, wherein:

C is

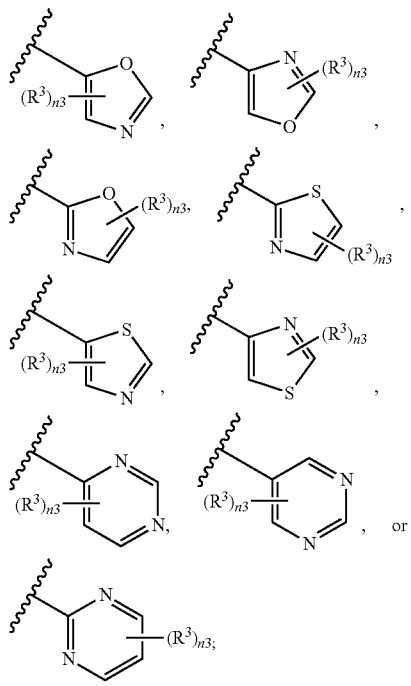

X is —(CR$^5$R$^6$)—;
Y is a bond, —CH$_2$—, —O—, or —NH—;
Z is a bond, —CH$_2$—, —O—, or —NH—;
W is a bond, —CH$_2$—, or —C(CH$_3$)H—;
V is —CH$_2$—, —CH$_2$CH$_2$—, or —CH$_2$CH$_2$CH$_2$—;
L is halogen;
R$^1$, R$^{2A}$ and R$^{2B}$ are each independently hydrogen, halogen, —CN, —CF$_3$, methyl, or —CONH$_2$;
R$^3$ is selected from hydrogen, F, Cl, Br, I, oxo, —CN, —CF$_3$, —OH, C$_1$-C$_3$ alkyl, C$_2$-C$_3$ alkenyl, C$_2$-C$_3$ alkynyl, C$_1$-C$_3$ alkoxy, —S(C$_1$-C$_3$ alkyl), —SO$_2$(C$_1$-C$_3$ alkyl), —NH$_2$, —NHSO$_2$CH$_3$, —NHSO$_2$CF$_3$, —N(CH$_3$)SO$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), —N(CH$_3$)COO(C$_1$-C$_3$ alkyl), —NHCO(C$_1$-C$_3$ alkyl), or —N(CH$_3$)COO(C$_1$-C$_3$ alkyl);

$R^5$ and $R^6$ are each independently hydrogen or C$_1$-C$_3$ alkyl;

n1 is 0, 1, or 2; and n3 is 1 or 2;

wherein when C—R$^3$ is

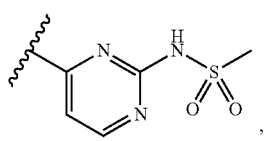 [SMILES: *c1ccnc(NS(C)(=O)=O)n1]

R$^{2A}$ and R$^{2B}$ are not both Cl.

In one embodiment the present disclosure provides compounds comprising the structure of formula (E-VI):

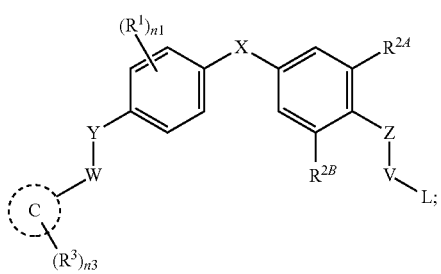

(E-VI)

or a pharmaceutically acceptable salt, tautomer, stereoisomer or prodrug thereof, wherein:

C is

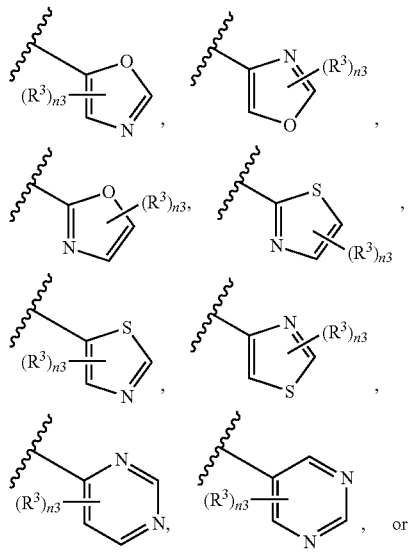

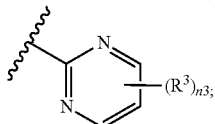

X is —(CR⁵R⁶)—;
Y is a bond, —CH₂—, —O—, or —NH—;
Z is a bond, —CH₂—, —O—, or —NH—;
W is a bond, —CH₂—, or —C(CH₃)H—;
V is —CH₂—, —CH₂CH₂—, or —CH₂CH₂CH₂—;
L is halogen;
R¹, R²ᴬ and R²ᴮ are each independently hydrogen, halogen, —CN, —CF₃, methyl, or —CONH₂;
R³ is selected from hydrogen, F, Cl, Br, I, oxo, —CN, —CF₃, —OH, C₁-C₃ alkyl, C₂-C₃ alkenyl, C₂-C₃ alkynyl, C₁-C₃ alkoxy, —S(C₁-C₃ alkyl), —SO₂(C₁-C₃ alkyl), —NH₂, —NHSO₂CH₃, —NHSO₂CF₃, —N(CH₃)SO₂CH₃, —CH₂NHSO₂CH₃, —CH₂N(CH₃)SO₂CH₃, —SO₂NH₂, —CONH₂, —CON(C₁-C₃ alkyl)₂, —CONH(C₁-C₃ alkyl), —NHCO(C₁-C₃ alkyl), —N(CH₃)COO(C₁-C₃ alkyl), —NHCO(C₁-C₃ alkyl), or —N(CH₃)COO(C₁-C₃ alkyl);
R⁵ and R⁶ are each independently hydrogen or C₁-C₃ alkyl;
n1 is 0, 1, or 2; and
n3 is 1 or 2;
wherein when C—R³ is

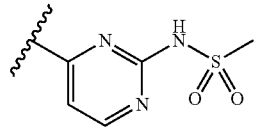 [SMILES: *c1ccnc(NS(C)(=O)=O)n1]

and one of R²ᴬ and R²ᴮ is C₁, then the other of R²ᴬ and R²ᴮ is not —CN.

In one embodiment the present disclosure provides compounds comprising the structure of formula (E-VII):

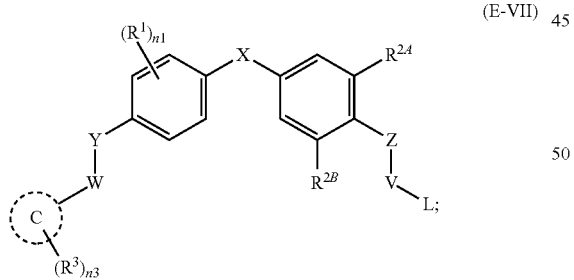

(E-VII)

or a pharmaceutically acceptable salt, tautomer, stereoisomer or prodrug thereof, wherein:
C is

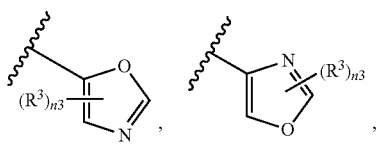

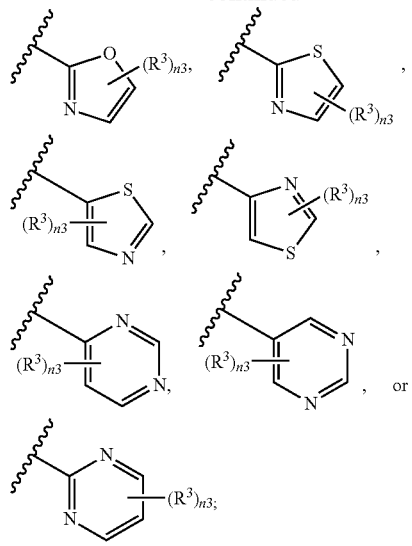

X is —(CR⁵R⁶)—;
Y is a bond, —CH₂—, —O—, or —NH—;
Z is a bond, —CH₂—, —O—, or —NH—;
W is a bond, —CH₂—, or —C(CH₃)H—;
V is —CH₂—, —CH₂CH₂—, or —CH₂CH₂CH₂—;
L is halogen;
R¹, R²ᴬ and R²ᴮ are each independently hydrogen, halogen, —CN, —CF₃, methyl, or —CONH₂;
R³ is selected from hydrogen, F, Cl, Br, I, oxo, —CN, —CF₃, —OH, C₁-C₃ alkyl, C₂-C₃ alkenyl, C₂-C₃ alkynyl, C₁-C₃ alkoxy, —S(C₁-C₃ alkyl), —SO₂(C₁-C₃ alkyl), —NH₂, —NHSO₂CH₃, —NHSO₂CF₃, —N(CH₃)SO₂CH₃, —CH₂NHSO₂CH₃, —CH₂N(CH₃)SO₂CH₃, —SO₂NH₂, —CONH₂, —CON(C₁-C₃ alkyl)₂, —CONH(C₁-C₃ alkyl), —NHCO(C₁-C₃ alkyl), —N(CH₃)COO(C₁-C₃ alkyl), —NHCO(C₁-C₃ alkyl), or —N(CH₃)COO(C₁-C₃ alkyl);
R⁵ and R⁶ are each independently hydrogen or C₁-C₃ alkyl;
n1 is 0, 1, or 2; and
n3 is 1 or 2.

In one embodiment of the compounds of formula (I), (IA), (IB), (IC), (II), (IIA), (IIB), (III), (IIIA), (IV), (V), (VA), or (VI) (denoted as formula "(I)-(VI)"), A and B are each independently 5- or 6-membered aryl or heteroaryl. In one embodiment, A and B are each independently selected from phenyl, pyridyl, pyrimidyl, or thiophene. In one embodiment, A and B are each phenyl.

In another embodiment, A has a meta or para connectivity with X and Y. In some embodiments, B has a meta or para connectivity with X and Z.

In one embodiment of the compounds of formula (I)-(VI), A and B are phenyl and has one of the connectivity as shown:

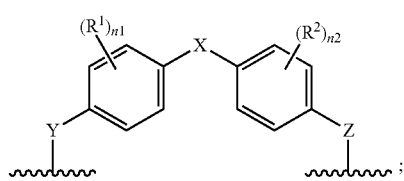

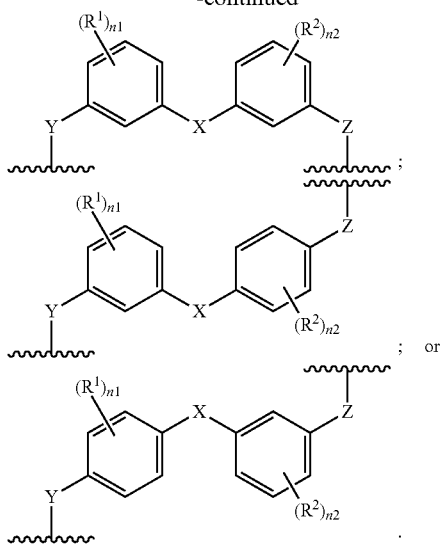

In one embodiment of the compounds of formula (I)-(VA) and (A) (e.g., formula (I), (IA), (IB), (IC), (II), (IIA), (IIB), (III), (IIIA), (IV), (V) (VA), and (A)), C is aryl or heteroaryl. In some embodiments, C is 5- to 10-membered aryl or heteroaryl. In other embodiments, C is aryl. In some embodiments, C is phenyl or naphthyl. In other embodiments, C is aryl. In some embodiments, C is phenyl.

In one embodiment of the compounds of formula (I)-(VA) and (A), C is heteroaryl. In one embodiment, C monocyclic or bicyclic heteroaryl. In another embodiment, C is monocyclic heteroaryl. In some embodiments, C is 5- or 10-membered heteroaryl. In some embodiments, C is 5- or 6-membered heteroaryl, which is optionally substituted with 1, 2, 3, 4, or 5 $R^3$. In some embodiments, C is 5- or 6-membered heteroaryl containing 1, 2, or 3 heteroatoms selected from O, S, or N, wherein the heteroaryl is optionally substituted with 1, 2, 3, 4, or 5 $R^3$. In some embodiments, C is 5- or 6-membered heteroaryl containing 1 or 2 heteroatoms selected from O, S, or N, wherein the heteroaryl is optionally substituted with 1, 2, 3, 4, or 5 $R^3$.

In one embodiment of the compounds of formula (I)-(VA), (A), or (D), C is pyrazole, imidazole, oxazole, oxadiazole, oxazolone, isoxazole, thiazole, pyridyl, or pyrimidyl, which are each optionally substituted with 1, 2, 3, 4, or 5 $R^3$. In one embodiment, C, which is substituted with $(R^3)n3$, is pyrazole, imidazole, oxazole, oxadiazole, oxazolone, isoxazole, thiazole, pyridyl, pyrazine, furan or pyrimidyl. In one embodiment, C is pyrazole, imidazole, oxazole, oxadiazole, oxazolone, isoxazole, thiazole, pyridyl, pyrazine, furan or pyrimidyl, which are each substituted with 1, 2, 3, 4, or 5 $R^3$.

In one embodiment of the compounds of formula (I)-(VA), (A), or (D), C is selected from

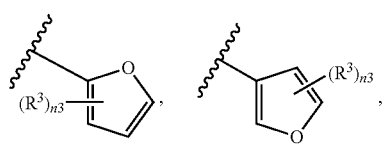

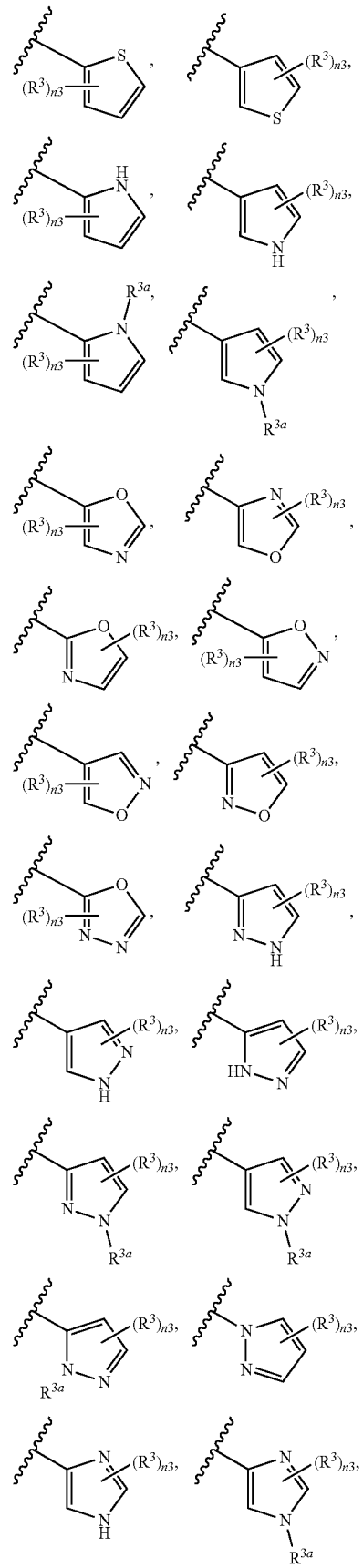

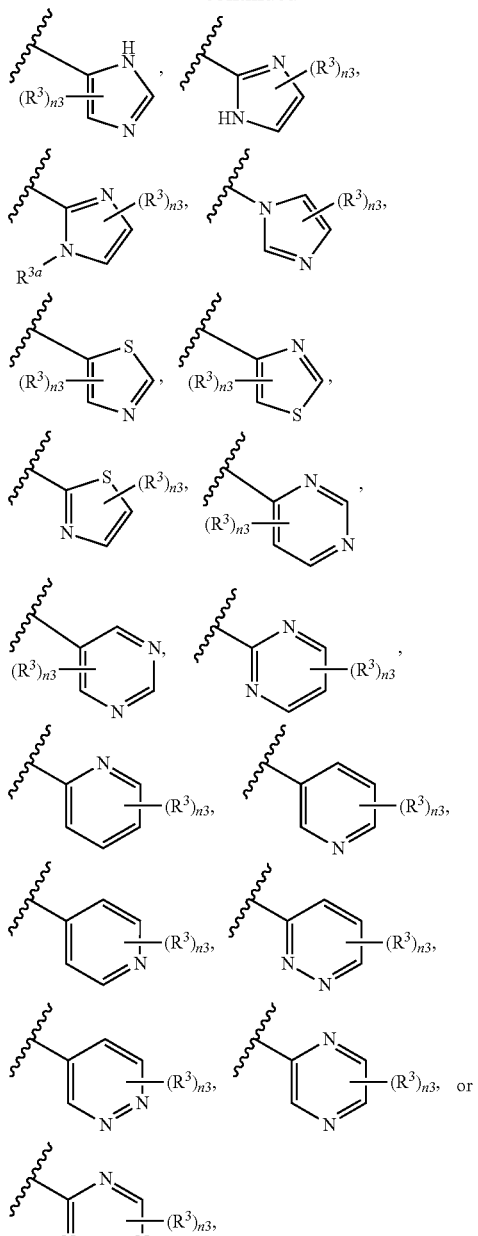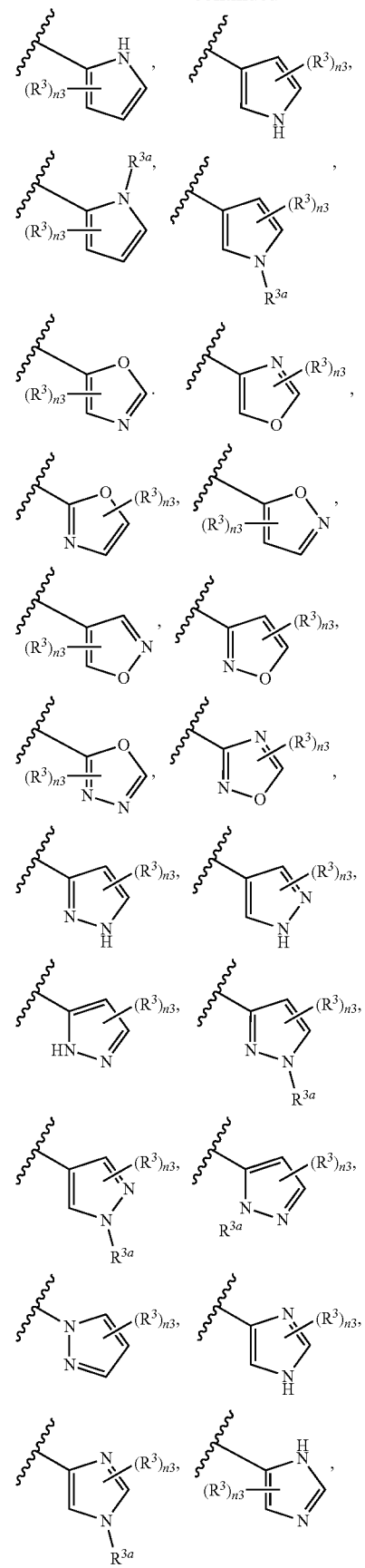
wherein $R^{3a}$ is $C_1$-$C_3$ alkyl. In one embodiment of the compounds of formula (I)-(VA), (A) or (D), C is selected from
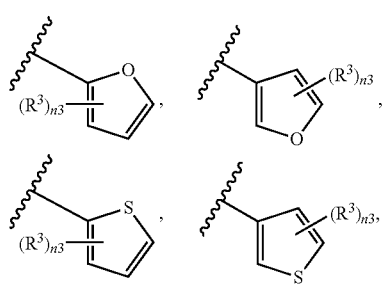

-continued

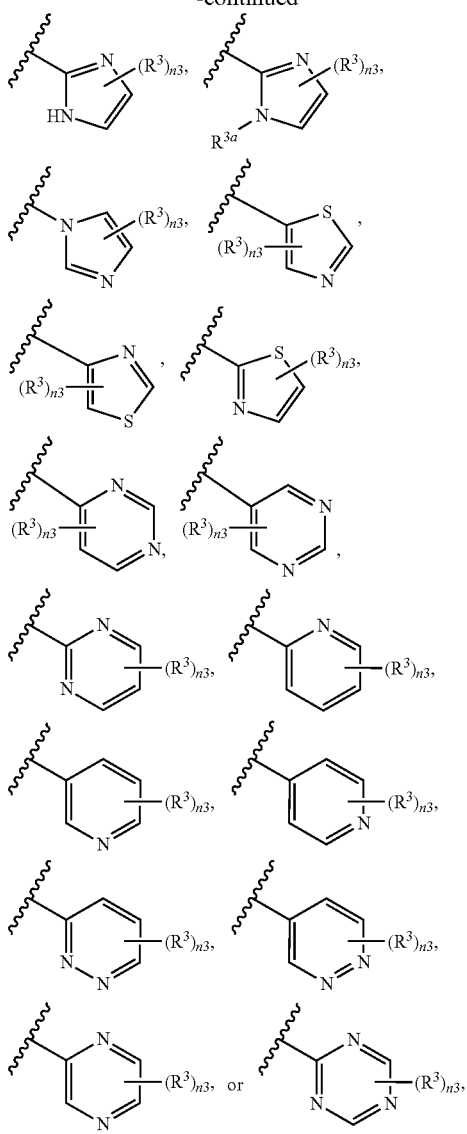

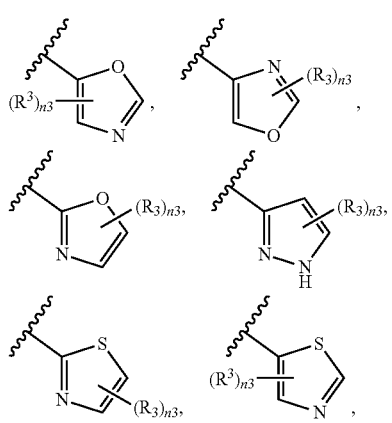

wherein R³ᵃ is $C_1$-$C_3$ alkyl.

In one embodiment of the compounds of formula (I)-(VA), (A), or (D), C is

-continued

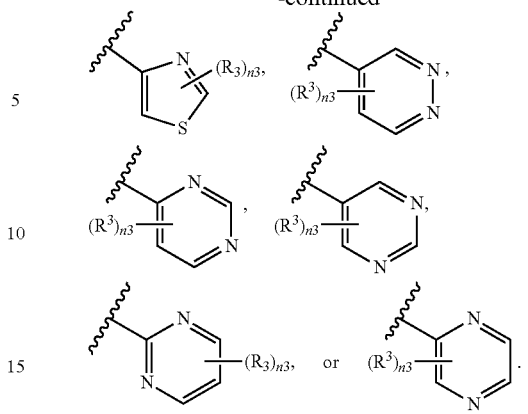

In one embodiment, C is

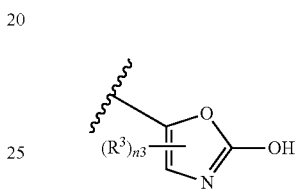

or in its tautomeric form

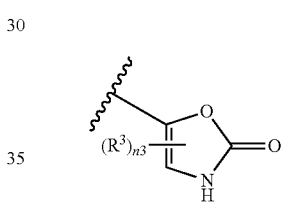

In one embodiment, C is

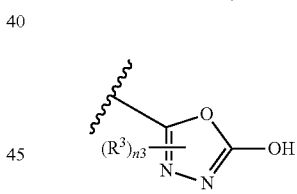

or in its tautomeric form

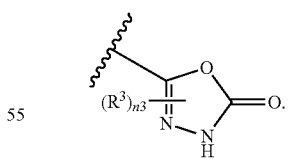

In one embodiment of the compounds of formula (I)-(IV), C is heterocyclyl. In one embodiment, C is saturated or partially saturated heterocycle. In some embodiments, C is monocyclic or bicyclic. In some embodiments, C is 5- to 7-membered heterocyclyl comprising 1, 2, or 3 heteroatoms selected from O, S, or N as a ring member.

In one embodiment of the compounds of formula (I)-(VA), (B) and (C), C is imidazolidine, imidazolidine-dione, or dihydrooxazole. In one embodiment, C is selected from

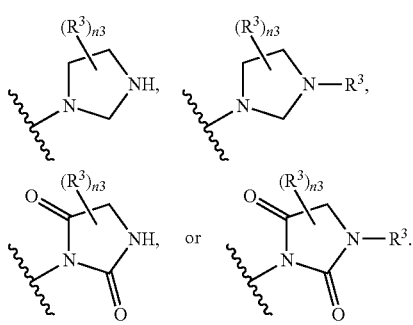

In one embodiment of the compounds of formula (I)-(VA), (B) and (C), C is

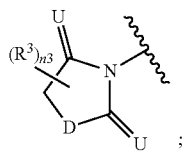

D is —O—, —NH— or —NR$^3$—; and U is each independently O, S, or NR$^{16}$. In one embodiment, D is —NH— or —NR$^3$—. In some embodiments, at least one U is O. In other embodiments, each U is O. In some embodiments, at least one R$^3$ is —SO$_2$CH$_3$, —NHSO$_2$CH$_3$, —CH$_2$NHSO$_2$CH$_3$, —SO$_2$NH$_2$, —CONH$_2$, or —NHCOCH$_3$.

In one embodiment of the compounds of formula (I)-(VA), C is aryl. In some embodiments, C is phenyl or naphthyl. In one embodiment of the compounds of formula (I)-(VA) or (A), C is phenyl.

In on embodiment compounds of formula (I)-(VI), C is bicyclic heteroaryl or heterocyclyl. In one embodiment, C is

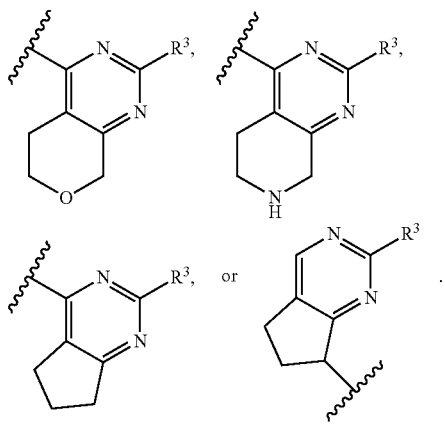

In one embodiment of the compounds of formula (I), Z is a bond, —(CR$^8$R$^9$)$_m$—, —O—, —C(=O)—, —S—, —S(=O)—, —SO$_2$—, or —NR$^7$—. In one embodiment, Z is —(CR$^8$R$^9$)$_m$—, —O—, —C(=O)—, —S—, —S(=O)—, —SO$_2$—, or —NR$^7$—. In some embodiments, Z is —C(=O)—.

In one embodiment of the compounds of formula (I)-(VI), (A), (B), and (C), Z is a bond, —CH$_2$—, —C(CH$_3$)H—, —O—, —S—, —NH—, —NCH$_3$—, or —N(COCH$_3$)—. In one embodiment, Z is —CH$_2$—, —C(CH$_3$)H—, —O—, —S—, —NH—, —NCH$_3$—, or —N(COCH$_3$)—. In some embodiments, Z is a bond, —CH$_2$—, —O—, or —NCH$_3$—. In some embodiments, Z is a bond, —CH$_2$—, —O—, or —NH—. In some embodiments of the compounds of formula (I)-(VI) and (A)-(H-I), Z is —O—. As used herein, "compounds of formula (I)-(IV) and (A)-(H-I)" refers to compounds of formula (I), (IA), (IB), (IC), (II), (IIA), (IIIA), (IIB), (III), (IV), (IVA), (V), (VA), (VI), (A), (A-I), (B)-(D), (E), (E-I)-(E-VII), (F), (G), (G-I), (G-II), (H), and (H-I).

In one embodiment of the compounds of formula (I), Y is a bond, —(CR$^8$R$^9$)$_m$—, —O—, —C(=O)—, —S—, —S(=O)—, —SO$_2$—, or —NR$^7$—. In one embodiment, Y is —(CR$^8$R$^9$)$_m$—, —O—, —C(=O)—, —S—, —S(=O)—, —SO$_2$—, or —NR$^7$—. In some embodiments, Y is —C(=O)—.

In one embodiment of the compounds of formula (I)-(VI), (A), (A-I), (B), and (C), Y is a bond, —CH$_2$—, —C(CH$_3$)H—, —O—, —S—, —NH—, —NCH$_3$—, or —N(COCH$_3$)—. In one embodiment, Y is —CH$_2$—, —C(CH$_3$)H—, —O—, —S—, —NH—, —NCH$_3$—, or —N(COCH$_3$)—. In some embodiments, Y is a bond, —CH$_2$—, —O—, or —NCH$_3$—. In some embodiments, Y is a bond, —CH$_2$—, —O—, or —NH—. In some embodiments of the compounds of formula (I)-(VI) and (A)-(H-I), Y is —O—.

In one embodiment of the compounds of formula (I)-(VI), (A), (B), and (C), V is a bond, —(CR$^{8a}$R$^{9a}$)$_m$—, or —C(=O)—. In some embodiments, V is bond, or —(CR$^{8a}$R$^{9a}$)$_m$—.

In one embodiment of the compounds of formula (I)-(VI), (A), (A-I), (B), and (C), V is —(CR$^{8a}$R$^{9a}$)$_m$—, wherein m is 1, 2, or 3. In one embodiment of the compounds of formula (I)-(VI), (A), (B), and (C), V is —(CR$^{8a}$R$^{9a}$)$_m$—, wherein R$^{8a}$ and R$^{8b}$ are each independently hydrogen, —OH, halogen, optionally substituted C$_1$-C$_3$ alkyl, optionally substituted C$_2$-C$_3$ alkenyl, optionally substituted C$_2$-C$_3$ alkynyl, C$_1$-C$_3$ alkoxy, —NR$^{13}$R$^{14}$, optionally substituted —(C$_1$-C$_3$ alkyl)-NR$^{13}$R$^{14}$, —NR$^{14}$COR$^{16}$, optionally substituted —(C$_1$-C$_3$ alkyl)-NR$^{14}$COR$^{16}$, —CONR$^{14}$R$^{15}$, or optionally substituted —(C$_1$-C$_3$ alkyl)-CONR$^{14}$R$^{15}$; or R$^{8a}$ and R$^{8b}$ taken together form an optionally substituted 3- to 6-membered carbocyclyl or heterocyclyl. In one embodiment, V is —(CR$^{8a}$R$^{9a}$)$_m$—, wherein R$^{8a}$ and R$^{8b}$ are each independently hydrogen, —OH, halogen, C$_1$-C$_3$ alkyl, C$_2$-C$_3$ alkenyl, C$_2$-C$_3$ alkynyl, C$_1$-C$_3$ alkoxy, —NR$^{13}$R$^{14}$, —(C$_1$-C$_3$ alkyl)-NR$^{13}$R$^{14}$, —NR$^{14}$COR$^{16}$, —(C$_1$-C$_3$ alkyl)-NR$^{14}$COR$^{16}$, —CONR$^{14}$R$^{15}$, or —(C$_1$-C$_3$ alkyl)-CONR$^{14}$R$^{15}$; or R$^{8a}$ and R$^{8b}$, on the same carbon atom or on a different carbon atom, taken together form an optionally substituted 3- to 6-membered carbocyclyl or heterocyclyl.

In one embodiment of the compounds of formula (I)-(IIB) and (VA), V is —CH$_2$—, —CH$_2$CH$_2$—, —CH(CH$_3$)CH$_2$—, —CH$_2$CH(CH$_3$)—, or —CH$_2$CH$_2$CH$_2$—.

In one embodiment of the compounds of formula (I)-(VI), (A), (B), and (C), V is —CH$_2$—, —CH$_2$CH$_2$—, or —CH$_2$CH$_2$CH$_2$—, each optionally substituted with one or more of —OH, halogen, or C$_1$-C$_3$ alkyl. In other embodiments, V is —CH$_2$—, —CH$_2$CH$_2$—, —CH$_2$CH(OH)CH$_2$— or —CH$_2$CH$_2$CH$_2$—. In some embodiments of the compounds of formula (I)-(VI) and (A)-(H-I), V is —CH$_2$—, —CH$_2$CH$_2$—, or —CH$_2$CH$_2$CH$_2$—. In some embodiments of the compounds of formula (I)-(VI) and (A)-(H-I), V is —CH$_2$— or —CH$_2$CH$_2$—.

In some embodiments of the compounds of formula (I)-(VI) and (A)-(D), V is —CH$_2$— and L is halogen, —NH$_2$, or —CF$_3$; or V is —CH$_2$CH$_2$— and L is halogen or —NH$_2$.

In one embodiment of the compounds of formula (I)-(VI), (A), (B), and (C), L is hydrogen, halogen, —CF$_2$H, —CF$_3$, —CN, —O(C$_1$-C$_3$ alkyl), —NR$^{11}$R$^{12}$, or —CONR$^{11}$R$^{12}$. In one embodiment, L is hydrogen, halogen, —CF$_2$H, —CF$_3$, —CN, —O(C$_1$-C$_3$ alkyl), —NH$_2$, —NH(C$_1$-C$_3$ alkyl), —N(C$_1$-C$_3$ alkyl)$_2$, —CONH$_2$, —CONH(C$_1$-C$_3$ alkyl), or —CON(C$_1$-C$_3$ alkyl)$_2$. In some embodiments, L is hydrogen, halogen, —CF$_3$, or —NH$_2$.

In some embodiments of the compounds of formula (IC) and (IIIA), L is halogen, —CCl$_3$, —CCl$_2$, —CF$_3$, or —NH$_2$. In some embodiments of the compounds of formula (I)-(VI) and (A)-(H-I), L is halogen, —CF$_3$, or —NH$_2$. In one embodiment, L is hydrogen or halogen. In one embodiment, L is halogen. In other embodiments, L is C$_1$, or Br. In one embodiment, L is C$_1$.

In one embodiment of the compounds of formula (I)-(VI), (A), (B), and (C), W is a bond. In one embodiment, W is —(CR$^{8a}$R$^{9a}$)$_m$—, —C(=O)—, —N(R$^7$)CO—, —CONR$^7$—, or —NSO$_2$R$^7$—. In one embodiment, W is —(CR$^{8a}$R$^{9a}$)$_m$—, wherein m is 1, 2, or 3. In some embodiments, W is a bond, —CH$_2$—, —C(CH$_3$)H—, —C(=O)—, —N(R$^7$)CO—, or —CONR$^7$—, wherein R$^7$ is H or C$_1$-C$_6$ alkyl. In some embodiments, W is a bond, —CH$_2$—, —C(CH$_3$)H—, —C(=O)—, —NHCO—, —N(C$_1$-C$_3$ alkyl)CO—, —CONH—, or —CON(C$_1$-C$_3$ alkyl)-. In one embodiment of the compounds of formula (I)-(VI) and (A)-(E-VI), W is a bond, —CH$_2$—, or —C(CH$_3$)H—. In one embodiment of the compounds of formula (I)-(VI) and (A)-(H-I), W is a —CH$_2$— or —C(CH$_3$)H—.

In one embodiment of the compounds of formula (I)-(VI), (A), (B), and (C), —Y—W— is a bond, —OCH$_2$—, —OCH$_2$CH$_2$—, —OCH(CH$_3$)—, —NH—, —NHCH$_2$—, —NHC(=O)—, or —C(=O)NH—. In one embodiment of the compounds of formula (I)-(VI) and (A)-(H-I), —Y—W— is —OCH$_2$—, —OCH$_2$CH$_2$—, or —OCH(CH$_3$)—.

In one embodiment of the compounds of formula (I)-(VI), (A), (B), and (C),
Z is a bond, —CH$_2$—, —C(CH$_3$)H—, —O—, —S—, —NH—, —NCH$_3$—, or —N(COCH$_3$)—; and
V is —CH$_2$—, —CH$_2$CH$_2$—, or —CH$_2$CH$_2$CH$_2$—.

In one embodiment of the compounds of formula (I)-(VI), (A), (B), and (C),
Z is a bond, —CH$_2$—, —C(CH$_3$)H—, —O—, —S—, —NH—, —NCH$_3$—, or —N(COCH$_3$)—;
V is —CH$_2$—, —CH$_2$CH$_2$—, or —CH$_2$CH$_2$CH$_2$—; and
L is halogen, —NH$_2$, or —CF$_3$.

In one embodiment of the compounds of formula (I)-(VI), (A), (B), and (C), —Z—V-L is —Z—CH$_2$CH$_2$C$_1$, —Z—CH$_2$CH$_2$CH$_2$C$_1$, —Z—CH$_2$CH$_2$NH$_2$, or —Z—CH$_2$CH$_2$CH$_2$NH$_2$, wherein Z is a bond, —O—, —NH—, or —N(COCH$_3$)—. In one embodiment, —Z—V-L is —OCH$_3$.

In one embodiment of the compounds of formula (I)-(VI) and (A)-(H-I), —Z—V-L is —O—CH$_2$CH$_2$C$_1$ or —O—CH$_2$CH$_2$CH$_2$C$_1$.

In one embodiment of the compounds of formula (I)-(VI), (A), (B), and (C), —V-L is —CH$_2$CH$_2$C$_1$, —CH$_2$CH$_2$CH$_2$C$_1$, —CH$_2$CH$_2$NH$_2$, or —CH$_2$CH$_2$CH$_2$NH$_2$. In one embodiment, —V-L is —CH$_3$.

In one embodiment of the compounds of formula (I)-(VI), (A), (B), and (C), X is a bond, —(CR$^5$R$^6$)$_t$—, —O—, —C(=O)—, —S—, —S(=O)—, —SO$_2$—, or —NR$^7$—. In one embodiment, X is a bond, —(CR$^5$R$^6$)$_t$—, —O—, —C(=O)—, —S—, —S(=O)—, —SO$_2$—, or —NR$^7$—, wherein R$^7$ is H or C$_1$-C$_6$ alkyl. In some embodiments, X is a bond, —(CR$^5$R$^6$)$_t$—, or —NR$^7$—. In some embodiments, X is a bond or —(CR$^5$R$^6$)$_t$—. In some embodiments, X is a bond, —CH$_2$—, —C(CH$_3$)H—, —C(CH$_3$)$_2$—, —CH$_2$CH$_2$—, —NH—, or —N(C$_1$-C$_6$ alkyl)-. In some embodiments, X is a bond, —CH$_2$—, —C(CH$_3$)H—, —C(CH$_3$)$_2$—, —CH$_2$CH$_2$—, —NH—, —N(CH$_3$)—, —N(CH$_2$CH$_3$)—, —N(iPr)-, or —N(tBu)-. In some embodiments, X is a bond, —CH$_2$—, —C(CH$_3$)H—, —C(CH$_3$)$_2$—, or —CH$_2$CH$_2$—.

In one embodiment of the compounds of formula (I)-(VI) and (A)-(H-I), X is —CH$_2$—, —C(CH$_3$)H—, or —C(CH$_3$)$_2$—. In one embodiment, X is —C(CH$_3$)$_2$—.

In one embodiment of the compounds of formula (I)-(VI), (A), (B), and (C), R$^1$ and R$^2$ are each independently halogen, —CN, —CF$_3$, —OH, C$_1$-C$_3$ alkyl, C$_1$-C$_3$ alkoxy, —(C$_1$-C$_3$ alkyl)-(C$_1$-C$_3$ alkoxy), —(C$_1$-C$_3$ alkyl)-OH, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl)NR$^{14}$SO$_2$R$^{16}$, —NR$^{14}$COR$^{16}$, —(C$_1$-C$_3$ alkyl)-NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO$_2$R$^{16}$, —(C$_1$-C$_3$ alkyl)-SO$_2$R$^{16}$, 3- to 7-membered carbocyclyl, 3- to 7-membered heterocyclyl, phenyl, or 5- to 6-membered heteroaryl.

In one embodiment of the compounds of formula (I)-(VI), (A), (A-I), (B), and (C), R$^1$ and R$^2$ are each independently hydrogen, halogen, —CN, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$, or optionally substituted —(C$_1$-C$_6$ alkyl)-SO$_2$R$^{16}$. In one embodiment, R$^1$ and R$^2$ are each independently hydrogen, halogen, —CN, —CF$_3$, —OH, optionally substituted C$_1$-C$_3$ alkyl, C$_1$-C$_3$ alkoxy, optionally substituted —(C$_1$-C$_3$ alkyl)-(C$_1$-C$_3$ alkoxy), optionally substituted —(C$_1$-C$_3$ alkyl)-OH, —NR$^{13}$R$^{14}$, —(C$_1$-C$_3$ alkyl)-NR$^{13}$R$^{14}$, —NR$^{14}$SO$_2$R$^{16}$ optionally substituted —(C$_1$-C$_3$ alkyl)NR$^{14}$SO$_2$R$^{16}$, —NR$^{14}$COR$^{16}$, optionally substituted —(C$_1$-C$_3$ alkyl)-NR$^{14}$COR$^{16}$, —CONR$^{14}$R$^{15}$, optionally substituted —(C$_1$-C$_3$ alkyl)-CONR$^{14}$R$^{15}$, —SO$_2$NR$^{14}$R$^{15}$, optionally substituted —(C$_1$-C$_3$ alkyl)-SO$_2$NR$^{14}$R$^{15}$, —SO$_2$R$^{16}$, or optionally substituted —(C$_1$-C$_3$ alkyl)-SO$_2$R$^{16}$. In one embodiment, R$^1$ and R$^2$ are each independently hydrogen, halogen, —CN, —CF$_3$, —OH, C$_1$-C$_3$ alkyl, C$_1$-C$_3$ alkoxy, —(C$_1$-C$_3$ alkyl)-(C$_1$-C$_3$ alkoxy), —(C$_1$-C$_3$ alkyl)-OH, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl)NR$^{14}$SO$_2$R$^{16}$, —NR$^{14}$COR$^{16}$, —(C$_1$-C$_3$ alkyl)-NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO$_2$R$^{16}$, or —(C$_1$-C$_3$ alkyl)-SO$_2$R$^{16}$.

In one embodiment of the compounds of formula (I)-(VI), (A), (A-I), (B), and (C), R$^1$ and R$^2$ are each independently hydrogen, halogen, —CN, —CF$_3$, —OH, C$_1$-C$_3$ alkyl, or —CONR$^{14}$R$^{15}$. In some embodiments, R$^1$ and R$^2$ are each independently hydrogen, halogen, —CN, —CF$_3$, —OH, methyl, methoxy, or —CONH$_2$. In one embodiment, R$^1$ and R$^2$ are each independently hydrogen, Cl, —CN, —CF$_3$, —OH, methyl, methoxy, or —CONH$_2$. In one embodiment, R$^1$ and R$^2$ are each independently hydrogen, halogen, —CN, —CF$_3$, —OH, or methyl. In one embodiment, R$^1$ and R$^2$ are each independently Cl, —CN, —CF$_3$, —OH, methyl, methoxy, or —CONH$_2$. In one embodiment of the compounds of formula (I)-(VI), R$^1$ and R$^2$ are each independently halogen, —CN, —CF$_3$, —OH, or methyl.

In one embodiment of the compounds of formula (I)-(VI) and (A)-(E-I), R$^1$ and R$^2$ are each halogen, methyl, —CF$_3$, or —CN. In one embodiment of the compounds of formula (I)-(VI) and (A)-(F), R$^1$ and R$^2$ are each halogen or —CN. In one embodiment of the compounds of formula (I)-(VI) and (A)-(H-I), at least one of R$^1$ and R$^2$ is C$_1$ or —CN. In one embodiment of the compounds of formula (I)-(VI) and (A)-(H-I), at least two of R$^1$ and R$^2$ are each independently Cl or —CN. In one embodiment of the compounds of formula (I)-(VI) and (A)-(H-I), R$^1$ and R$^2$ are each C$_1$ or —CN.

In one embodiment of the compounds of formula (I)-(VI), (A), (B), and (C), R$^1$ and R$^2$ are each independently optionally substituted carbocyclyl, optionally substituted heterocyclyl, optionally substituted aryl, or optionally substituted heteroaryl. In one embodiment, R$^1$ and R$^2$ are each independently 3- to 7-membered carbocyclyl, 3- to 7-membered heterocyclyl, phenyl, or 5- to 6-membered heteroaryl.

In one embodiment of the compounds of formula (I)-(VI), (A), (A-I), (B), and (C), R$^1$ have one of the connectivity as shown below with respect to X and Y:

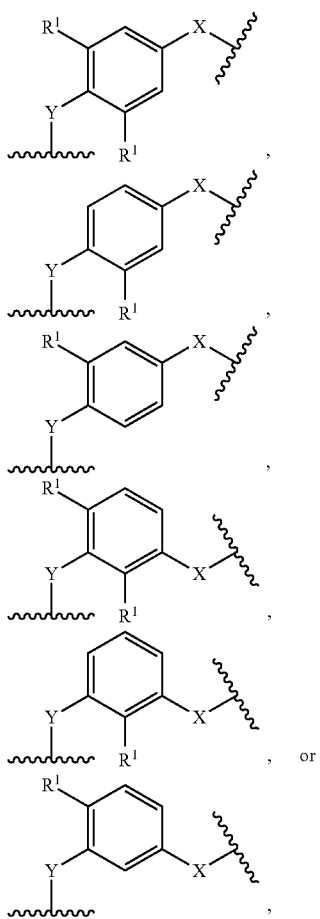

In one embodiment of the compounds of formula (I)-(VI), (A), (A-I), (B), and (C), R$^2$ have one of the connectivity as shown below with respect to X and Z:

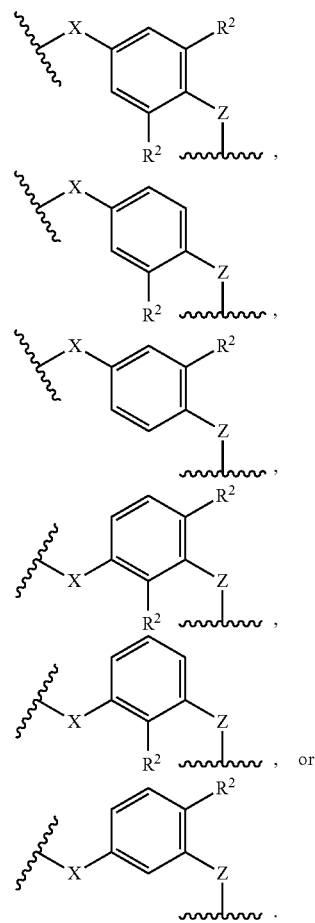

In one embodiment of the compounds of formula (I)-(VI), (A), (A-I), (B), and (C), n1 is 0, 1, or 2. In some embodiments, n1 is 0 or 1. In other embodiments, n1 is 0. In some embodiments, n1 is 1. In one embodiment, the sum of n1 and n2 is 0, 1, 2, 3, or 4. In some embodiments, the sum of n1 and n2 is 1, 2, 3, or 4. In one embodiment, the sum of n1 and n2 is 2.

In one embodiment of the compounds of formula (I)-(VI), (A), (A-I), (B), and (C), n2 is 0, 1, or 2. In some embodiments, n2 is 1 or 2. In other embodiments, n2 is 0. In some embodiments, n2 is 1. In some embodiments, n2 is 2.

In some embodiments of the compounds of (I)-(VI), (A), (A-I), (B), and (C), n3 is 1, 2, 3, 4, or 5. In some embodiments, n3 is 1, 2, 3, or 4. In one embodiment, n3 is 1, 2, or 3. In one embodiment, n3 is 1 or 2.

In one embodiment of the compounds of formula (I)-(VI), (A), (A-I), (B), and (C), R$^3$ is selected from hydrogen, halogen, oxo, =S, =NR$^{16}$, —CN, —CF$_3$, —OH, —SR$^{16}$, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, —$SO_2NR^{14}R^{15}$, optionally substituted —($C_1$-$C_6$ alkyl)-$SO_2NR^{14}R^{15}$, optionally substituted —$SO_2R^{16}$, optionally substituted —($C_1$-$C_6$ alkyl)-$SO_2R^{16}$, optionally substituted carbocyclyl, optionally substituted heterocyclyl, optionally substituted aryl, or optionally substituted heteroaryl. In some embodiments, $R^3$ is selected from hydrogen, halogen, oxo, =S, =$NR^{16}$, —CN, —$CF_3$, —OH, —$SR^{16}$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —$NR^{13}R^{14}$, optionally substituted —($C_1$-$C_6$ alkyl)-$NR^{13}R^{14}$, —$NR^{14}SO_2R^{16}$, optionally substituted —($C_1$-$C_6$ alkyl)$NR^{14}SO_2R^{16}$, —$NR^{14}COR^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, —$SO_2NR^{14}R^{15}$, optionally substituted —($C_1$-$C_6$ alkyl)-$SO_2NR^{14}R^{15}$, optionally substituted —$SO_2R^{16}$, or optionally substituted —($C_1$-$C_6$ alkyl)-$SO_2R^{16}$. In another embodiment, $R^3$ is hydrogen, halogen, oxo, =S, =$NR^{16}$, —CN, —$CF_3$, —OH, —$SR^{16}$, optionally substituted $C_1$-$C_3$ alkyl, optionally substituted $C_2$-$C_3$ alkenyl, optionally substituted $C_2$-$C_3$ alkynyl, optionally substituted $C_1$-$C_3$ alkoxy, optionally substituted —($C_1$-$C_3$ alkyl)-($C_1$-$C_3$ alkoxy), optionally substituted —($C_1$-$C_3$ alkyl)-OH, —$NR^{13}R^{14}$, optionally substituted —($C_1$-$C_3$ alkyl)-$NR^{13}R^{14}$, —$NR^{14}SO_2R^{16}$, optionally substituted —($C_1$-$C_3$ alkyl)$NR^{14}SO_2R^{16}$, —$NR^{14}COR^{16}$, optionally substituted —($C_1$-$C_3$ alkyl)-$NR^{14}COR^{16}$, —$CONR^{14}R^{15}$, optionally substituted —($C_1$-$C_3$ alkyl)-$CONR^{14}R^{15}$, —$SO_2NR^{14}R^{15}$, optionally substituted —($C_1$-$C_3$ alkyl)-$SO_2NR^{14}R^{15}$, optionally substituted —$SO_2R^{16}$, or optionally substituted —($C_1$-$C_3$ alkyl)-$SO_2R^{16}$.

In one embodiment of the compounds of formula (I)-(VI), (A), (A-I), (B), and (C), $R^3$ is selected from —$NR^{14}SO_2R^{16}$, optionally substituted —($C_1$-$C_6$ alkyl)$NR^{14}SO_2R^{16}$, or optionally substituted —$SO_2R^{16}$; wherein $R^{16}$ is hydrogen, optionally substituted $C_1$-$C_3$ alkyl, optionally substituted $C_2$-$C_3$ alkenyl, optionally substituted $C_2$-$C_3$ alkynyl, $C_3$-$C_6$ cycloalkyl, or phenyl. In one embodiment, $R^3$ is selected from —$NR^{14}SO_2R^{16}$, —($C_1$-$C_6$ alkyl)$NR^{14}SO_2R^{16}$, or —$SO_2R^{16}$; wherein $R^{16}$ is hydrogen, $C_1$-$C_3$ alkyl, —($C_1$-$C_3$ alkyl)-$NH_2$, $C_3$-$C_6$ cycloalkyl, or phenyl.

In one embodiment of the compounds of formula (I)-(VI), (A), (A-I), (B), and (C), $R^3$ is selected from hydrogen, halogen, oxo, =S, =$NR^{16}$, —CN, —$CF_3$, —OH, —S($C_1$-$C_3$ alkyl), $C_1$-$C_3$ alkyl, $C_2$-$C_3$ alkenyl, $C_2$-$C_3$ alkynyl, $C_1$-$C_3$ alkoxy, —($C_1$-$C_3$ alkyl)-($C_1$-$C_3$ alkoxy), —($C_1$-$C_3$ alkyl)-OH, —$NR^{13}R^{14}$, —($C_1$-$C_3$ alkyl)-$NR^{13}R^{14}$, —$NR^{14}SO_2R^{16}$, —($C_1$-$C_3$ alkyl)$NR^{14}SO_2R^{16}$, —$NR^{14}COR^{16}$, —($C_1$-$C_6$ alkyl)-$NR^{14}COR^{16}$, —$CONR^{14}R^{15}$, —($C_1$-$C_3$ alkyl)-$CONR^{14}R^{15}$, —$SO_2NR^{14}R^{15}$, —($C_1$-$C_3$ alkyl)-$SO_2NR^{14}R^{15}$, —SO($C_1$-$C_3$ alkyl), —$SO_2$($C_1$-$C_3$ alkyl), or —($C_1$-$C_6$ alkyl)-$SO_2$($C_1$-$C_3$ alkyl). In some embodiments, $R^3$ is selected from hydrogen, F, Cl, Br, I, oxo, =S, =$NR^{16}$, —CN, —$CF_3$, —OH, $C_1$-$C_3$ alkyl, $C_2$-$C_3$ alkenyl, $C_2$-$C_3$ alkynyl, —S($C_1$-$C_3$ alkyl), —SO($C_1$-$C_3$ alkyl), —$SO_2$($C_1$-$C_3$ alkyl), —$NHSO_2CH_3$, —N($CH_3$)$SO_2CH_3$, —$NHSO_2CH_2CH_3$, —N($CH_3$)$SO_2CH_2CH_3$, —$CH_2NHSO_2CH_3$, —$CH_2N(CH_3)SO_2CH_3$, —$SO_2NH_2$, —$CONH_2$, —CON($C_1$-$C_3$ alkyl)$_2$, —CONH($C_1$-$C_3$ alkyl), —NHCO($C_1$-$C_3$ alkyl), or —N($CH_3$)CO($C_1$-$C_3$ alkyl). In some embodiments, $R^3$ is selected from F, Cl, Br, I, oxo, =S, =$NR^{16}$, —CN, —$CF_3$, —OH, $C_1$-$C_3$ alkyl, $C_2$-$C_3$ alkenyl, $C_2$-$C_3$ alkynyl, —S($C_1$-$C_3$ alkyl), —SO($C_1$-$C_3$ alkyl), —$SO_2$($C_1$-$C_3$ alkyl), —$NHSO_2CH_3$, —N($CH_3$)$SO_2CH_3$, —$NHSO_2CH_2CH_3$, —N($CH_3$)$SO_2CH_2CH_3$, —$CH_2NHSO_2CH_3$, —$CH_2N(CH_3)SO_2CH_3$, —$SO_2NH_2$, —$CONH_2$, —CON($C_1$-$C_3$ alkyl)$_2$, —CONH($C_1$-$C_3$ alkyl), —NHCO($C_1$-$C_3$ alkyl), or —N($CH_3$)CO($C_1$-$C_3$ alkyl). In one embodiment, $R^3$ is selected from hydrogen, F, Cl, Br, I, oxo, =S, =$NR^{16}$, —CN, —$CF_3$, —OH, methyl, —$SCH_3$, —$SO_2CH_3$, —$NHSO_2CH_3$, —$NHSO_2CH_2CH_3$, —$CH_2NHSO_2CH_3$, —$SO_2NH_2$, —$CONH_2$, or —$NHCOCH_3$. In one embodiment, $R^3$ is selected from hydrogen, F, Cl, Br, I, oxo, =S, =$NR^{16}$, —CN, —$CF_3$, —OH, methyl, —$SCH_3$, —$SO_2CH_3$, —$NHSO_2CH_3$, —$CH_2NHSO_2CH_3$, —$SO_2NH_2$, —$CONH_2$, or —$NHCOCH_3$. In some embodiments, $R^3$ is selected from F, Cl, Br, I, oxo, =S, =$NR^{16}$, —CN, —$CF_3$, —OH, $C_1$-$C_3$ alkyl, $C_2$-$C_3$ alkenyl, $C_2$-$C_3$ alkynyl, —S($C_1$-$C_3$ alkyl), —SO($C_1$-$C_3$ alkyl), —$SO_2$($C_1$-$C_3$ alkyl), —$NHSO_2CH_3$, —N($CH_3$)$SO_2CH_3$, —$CH_2NHSO_2CH_3$, —$CH_2N(CH_3)SO_2CH_3$, —$SO_2NH_2$, —$CONH_2$, —CON($C_1$-$C_3$ alkyl)$_2$, —CONH($C_1$-$C_3$ alkyl), —NHCO($C_1$-$C_3$ alkyl), or —N($CH_3$)CO($C_1$-$C_3$ alkyl). In some embodiments, $R^3$ is selected from F, Cl, Br, I, oxo, =S, =$NR^{16}$, —CN, —$CF_3$, —OH, $C_1$-$C_3$ alkyl, $C_2$-$C_3$ alkenyl, $C_2$-$C_3$ alkynyl, —S($C_1$-$C_3$ alkyl), —SO($C_1$-$C_3$ alkyl), —$SO_2$($C_1$-$C_3$ alkyl), —$NHSO_2CH_3$, —N($CH_3$)$SO_2CH_3$, —$NHSO_2CH_2CH_3$, —N($CH_3$)$SO_2CH_2CH_3$, —$CH_2NHSO_2CH_3$, —$CH_2N(CH_3)SO_2CH_3$, —$SO_2NH_2$, —$CONH_2$, —CON($C_1$-$C_3$ alkyl)$_2$, —CONH($C_1$-$C_3$ alkyl), —NHCO($C_1$-$C_3$ alkyl), or —N($CH_3$)CO($C_1$-$C_3$ alkyl). In one embodiment, $R^3$ is selected from F, Cl, Br, I, oxo, =S, =$NR^{16}$, —CN, —$CF_3$, —OH, methyl, —$SCH_3$, —$SO_2CH_3$, —$NHSO_2CH_3$, —$CH_2NHSO_2CH_3$, —$SO_2NH_2$, —$CONH_2$, or —$NHCOCH_3$. In another embodiment, $R^3$ is —$SO_2CH_3$, —$NHSO_2CH_3$, —$CH_2NHSO_2CH_3$, —$SO_2NH_2$, —$CONH_2$, or —$NHCOCH_3$. In one embodiment, $R^3$ is oxo, =S, =$NR^{16}$, $C_1$-$C_3$ alkyl, —$SO_2$($C_1$-$C_3$ alkyl), or —$NHSO_2$($C_1$-$C_3$ alkyl). In one embodiment, at least one of $R^3$ is oxo, =S, or =$NR^{16}$. In one embodiment, at least one of $R^3$ is oxo, =S, or =$NR^{16}$, wherein $R^{16}$ is H or $C_1$-$C_3$ alkyl.

In one embodiment of the compounds of formula (I)-(VI) and (A)-(E-VII), $R^3$ is selected from hydrogen, F, Cl, Br, I, oxo, —CN, —$CF_3$, —OH, $C_1$-$C_3$ alkyl, $C_2$-$C_3$ alkenyl, $C_2$-$C_3$ alkynyl, $C_1$-$C_3$ alkoxy, —S($C_1$-$C_3$ alkyl), —$SO_2$($C_1$-$C_3$ alkyl), —$NH_2$, —$NHSO_2CH_3$, —$NHSO_2CF_3$, —N($CH_3$)$SO_2CH_3$, —$NHSO_2CH_2CH_3$, —N($CH_3$)$SO_2CH_2CH_3$, —$CH_2NHSO_2CH_3$, —$CH_2N(CH_3)SO_2CH_3$, —$SO_2NH_2$, —$CONH_2$, —CON($C_1$-$C_3$ alkyl)$_2$, —CONH($C_1$-$C_3$ alkyl), —NHCO($C_1$-$C_3$ alkyl), —N($CH_3$)COO($C_1$-$C_3$ alkyl), —NHCO($C_1$-$C_3$ alkyl), or —N($CH_3$)COO($C_1$-$C_3$ alkyl). In one embodiment of the compounds of formula (I)-(VI) and (A)-(E-VII), $R^3$ is selected from hydrogen, F, Cl, Br, I, oxo, —CN, —$CF_3$, —OH, $C_1$-$C_3$ alkyl, $C_2$-$C_3$ alkenyl, $C_2$-$C_3$ alkynyl, $C_1$-$C_3$ alkoxy, —S($C_1$-$C_3$ alkyl), —$SO_2$($C_1$-$C_3$ alkyl), —$NH_2$, —$NHSO_2CH_3$, —$NHSO_2CF_3$, —N($CH_3$)$SO_2CH_3$, —$CH_2NHSO_2CH_3$, —$CH_2N(CH_3)SO_2CH_3$, —$SO_2NH_2$, —$CONH_2$, —CON($C_1$-$C_3$ alkyl)$_2$, —CONH($C_1$-$C_3$ alkyl), —NHCO($C_1$-$C_3$ alkyl), —N($CH_3$)COO($C_1$-$C_3$ alkyl), —NHCO($C_1$-$C_3$ alkyl), or —N($CH_3$)COO($C_1$-$C_3$ alkyl).

In one embodiment of the compounds of formula (I)-(VI), (A), (A-I), (B), and (C), $R^3$ on a $sp^3$ carbon is each selected from hydrogen, halogen, oxo, =S, =$NR^{16}$, —CN, —$CF_3$, —OH, —S($C_1$-$C_3$ alkyl), $C_1$-$C_3$ alkyl, $C_2$-$C_3$ alkenyl, $C_2$-$C_3$ alkynyl, $C_1$-$C_3$ alkoxy, —($C_1$-$C_3$ alkyl)-($C_1$-$C_3$ alkoxy), —($C_1$-$C_3$ alkyl)-OH, —$NR^{13}R^{14}$, —($C_1$-$C_3$ alkyl)-$NR^{13}R^{14}$, —$NR^{14}SO_2R^{16}$, —($C_1$-$C_3$ alkyl)$NR^{14}SO_2R^{16}$, —$NR^{14}COR^{16}$, —($C_1$-$C_6$ alkyl)-$NR^{14}COR^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO(C$_1$-C$_3$ alkyl), —SO$_2$(C$_1$-C$_3$ alkyl), or —(C$_1$-C$_6$ alkyl)-SO$_2$(C$_1$-C$_3$ alkyl). When R$^3$ on a sp$^3$ carbon is oxo, =S, or =NR$^{16}$, the carbon becomes sp$^2$.

In one embodiment of the compounds of formula (I)-(VI), (A), (A-I), (B), and (C), R$^3$ on a sp$^2$ carbon is each selected from hydrogen, halogen, —CN, —CF$_3$, —OH, —S(C$_1$-C$_3$ alkyl), C$_1$-C$_3$ alkyl, C$_2$-C$_3$ alkenyl, C$_2$-C$_3$ alkynyl, C$_1$-C$_3$ alkoxy, —(C$_1$-C$_3$ alkyl)-(C$_1$-C$_3$ alkoxy), —(C$_1$-C$_3$ alkyl)-OH, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl)NR$^{14}$SO$_2$R$^{16}$, —NR$^{14}$COR$^{16}$, —(C$_1$-C$_6$ alkyl)-NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO(C$_1$-C$_3$ alkyl), —SO$_2$(C$_1$-C$_3$ alkyl), or —(C$_1$-C$_6$ alkyl)-SO$_2$(C$_1$-C$_3$ alkyl).

In one embodiment of the compounds of formula (I)-(VI), (A), (A-I), (B), and (C), R$^3$ on a nitrogen atom is each selected from C$_1$-C$_3$ alkyl, C$_2$-C$_3$ alkenyl, C$_2$-C$_3$ alkynyl, C$_1$-C$_3$ alkoxy, —(C$_1$-C$_3$ alkyl)-(C$_1$-C$_3$ alkoxy), —(C$_1$-C$_3$ alkyl)-OH, —(C$_1$-C$_3$ alkyl)-NR$^{13}$R$^{14}$, —(C$_1$-C$_3$ alkyl) NR$^{14}$SO$_2$R$^{16}$, —(C$_1$-C$_6$ alkyl)-NR$^{14}$COR$^{16}$, —CONR$^{14}$R$^{15}$, —(C$_1$-C$_3$ alkyl)-CONR$^{14}$R$^{15}$, —(C$_1$-C$_3$ alkyl)-SO$_2$NR$^{14}$R$^{15}$, or —(C$_1$-C$_6$ alkyl)-SO$_2$(C$_1$-C$_3$ alkyl).

In one embodiment of the compounds of formula (I)-(VI) and (A)-(G-II), at least one R$^3$ is selected from —CN, C$_1$-C$_3$ alkoxy, —CONH$_2$, —NHSO$_2$CH$_3$, —N(CH$_3$)SO$_2$CH$_3$, —NHSO$_2$CH$_2$CH$_3$, —N(CH$_3$)SO$_2$CH$_2$CH$_3$, or —SO$_2$CH$_3$ and the other R$^3$, if present, is selected from —CN, —CF$_3$, C$_1$-C$_3$ alkyl, C$_2$-C$_3$ alkenyl, C$_2$-C$_3$ alkynyl, C$_1$-C$_3$ alkoxy, —S(C$_1$-C$_3$ alkyl), —SO$_2$(C$_1$-C$_3$ alkyl), —NH$_2$, —(C$_1$-C$_3$ alkyl)NH$_2$, —NHSO$_2$CH$_3$, —NHSO$_2$CF$_3$, —N(CH$_3$) SO$_2$CH$_3$, —NHSO$_2$CH$_2$CH$_3$, —N(CH$_3$)SO$_2$CH$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), —N(CH$_3$)COO(C$_1$-C$_3$ alkyl), —NHCO(C$_1$-C$_3$ alkyl), or —N(CH$_3$)COO(C$_1$-C$_3$ alkyl). In one embodiment, at least one R$^3$ is selected from —NHSO$_2$CH$_3$, —NHSO$_2$CH$_2$CH$_3$, or —SO$_2$CH$_3$ and the other R$^3$, if present, is selected from —CN, C$_1$-C$_3$ alkyl, C$_1$-C$_3$ alkoxy, —SO$_2$(C$_1$-C$_3$ alkyl), —NH$_2$, —(C$_1$-C$_3$ alkyl) NH$_2$, —NHSO$_2$CH$_3$, —N(CH$_3$)SO$_2$CH$_3$, —NHSO$_2$CH$_2$CH$_3$, —N(CH$_3$)SO$_2$CH$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), —N(CH$_3$)COO(C$_1$-C$_3$ alkyl), —NHCO(C$_1$-C$_3$ alkyl), or —N(CH$_3$)COO(C$_1$-C$_3$ alkyl).

In one embodiment of the compounds of formula (I)-(VI) and (A)-(E-II), R$^3$ is not hydrogen.

In one embodiment of the compounds of formula (I)-(VI) and (A)-(G-II), at least one R$^3$ is —SO$_2$CH$_3$, —NHSO$_2$CH$_3$, —NCH$_3$SO$_2$CH$_3$, —NHSO$_2$CH$_2$CH$_3$, or —N(CH$_3$)SO$_2$CH$_2$CH$_3$. In one embodiment of the compounds of formula (I)-(VI) and (A)-(G-II), at least one R$^3$ is —SO$_2$CH$_3$, —NHSO$_2$CH$_3$, or —NCH$_3$SO$_2$CH$_3$.

In one embodiment the compounds of formula (I), (IA), (IB), or (IC), R$^3$ is heterocyclyl. In one embodiment, R$^3$ is heterocyclyl selected from

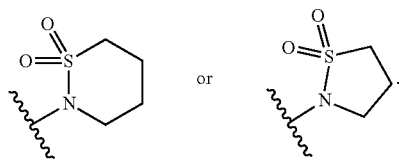 [SMILES: *N1CCCCS1(=O)=O ; *N1CCCS1(=O)=O]

In one embodiment of the compounds of formula (IB), (IC), (IIA), or (IIB), R$^3$ is —NR$^{14}$SO$_2$R$^{16}$, wherein R$^{14}$ and R$^{16}$ together form a 5 or 6 membered ring including the nitrogen and sulfur atoms.

In one embodiment of the compounds of formula (I), (IA), (IB), or (IC), R$^3$ is —NR$^{14}$SO$_2$R$^{16}$, wherein R$^{16}$ is optionally substituted C$_1$-C$_6$ alkyl. In one embodiment, R$^3$ is —NR$^{14}$SO$_2$R$^{16}$, wherein R$^{16}$ is C$_1$-C$_6$ alkyl optionally substituted with one or more groups selected from halogen, —CN, —CF$_3$, —OH, C$_1$-C$_3$ alkyl, C$_1$-C$_3$ alkoxy, —NH$_2$, —NH(C$_1$-C$_3$ alkyl), —N(C$_1$-C$_3$ alkyl)$_2$, —SCH$_3$. In one embodiment, R$^3$ is —NR$^{14}$SO$_2$R$^{16}$, wherein R$^{16}$ is C$_1$-C$_3$ alkyl substituted with —NH$_2$.

In one embodiment of the compounds of formula (I)-(VI), (A), (B), and (C), R$^5$ and R$^6$ are each independently hydrogen, halogen, —OH, C$_1$-C$_3$ alkyl, C$_2$-C$_3$ alkenyl, C$_2$-C$_3$ alkynyl, or C$_1$-C$_3$ alkoxy; or R$^5$ and R$^6$ taken together form an optionally substituted 3- to 6-membered carbocyclyl or heterocyclyl. In some embodiments, R$^5$ and R$^6$ are each independently hydrogen, halogen, —OH, optionally substituted C$_1$-C$_6$ alkyl, optionally substituted C$_2$-C$_6$ alkenyl, optionally substituted C$_2$-C$_6$ alkynyl. In one embodiment, R$^5$ and R$^6$ are hydrogen, halogen, —OH, or C$_1$-C$_3$ alkyl. In one embodiment, R$^5$ and R$^6$ are each independently hydrogen, F, —OH, or C$_1$-C$_3$ alkyl. In one embodiment, R$^5$ and R$^6$ are each independently, hydrogen, F, —OH, or methyl. In one embodiment, R$^5$ and R$^6$ are each H. In one embodiment, R$^5$ and R$^6$ are each methyl. In one embodiment of the compounds of formula (I)-(VI) and (A)-(H-I), R$^5$ and R$^6$ are each H or methyl.

In one embodiment of the compounds of formula (I)-(VI), (A), (B), and (C), R$^7$ is hydrogen, optionally substituted C$_1$-C$_6$ alkyl, optionally substituted C$_2$-C$_6$ alkenyl, optionally substituted C$_2$-C$_6$ alkynyl, optionally substituted carbocyclyl, optionally substituted heterocyclyl, optionally substituted aryl, or optionally substituted heteroaryl. In some embodiments, R$^7$ is hydrogen, optionally substituted C$_1$-C$_3$ alkyl, optionally substituted C$_2$-C$_3$ alkenyl, optionally substituted C$_2$-C$_3$ alkynyl, optionally substituted carbocyclyl, optionally substituted heterocyclyl, optionally substituted aryl, or optionally substituted heteroaryl. In some embodiments, R$^7$ is hydrogen, C$_1$-C$_6$ alkyl, C$_2$-C$_6$ alkenyl, C$_2$-C$_6$ alkynyl, carbocyclyl, heterocyclyl, aryl, or heteroaryl. In some embodiments, R$^7$ is hydrogen, C$_1$-C$_3$ alkyl, C$_2$-C$_3$ alkenyl, C$_2$-C$_3$ alkynyl, carbocyclyl, heterocyclyl, aryl, or heteroaryl. In some embodiments, R$^7$ is hydrogen, C$_1$-C$_6$ alkyl, C$_2$-C$_6$ alkenyl, or C$_2$-C$_6$ alkynyl. In some embodiments, R$^7$ is hydrogen, C$_1$-C$_3$ alkyl, C$_2$-C$_3$ alkenyl, or C$_2$-C$_3$ alkynyl. In some embodiments, R$^7$ is hydrogen or C$_1$-C$_6$ alkyl. In some embodiments, R$^7$ is hydrogen or C$_1$-C$_4$ alkyl. In some embodiments of the compounds of formula (I)-(VI) and (A)-(H-I), R$^7$ is hydrogen or C$_1$-C$_3$ alkyl.

In one embodiment of the compounds of formula (I)-(VI), (A), (B), and (C), R$^{8a}$ and R$^{9a}$ are each independently hydrogen, halogen, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, —NR$^{13}$R$^{14}$, optionally substituted —(C$_1$-C$_6$ alkyl)-NR$^{13}$R$^{14}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, optionally substituted carbocyclyl, optionally substituted heterocyclyl, optionally substituted aryl, or optionally substituted heteroaryl, or R$^{8a}$ and R$^{9a}$ taken together form an optionally substituted carbocyclyl or optionally substituted heterocyclyl. In some embodiments, R$^{8a}$ and R$^{8b}$ are each independently hydrogen, —OH, halogen, C$_1$-C$_3$ alkyl, C$_2$-C$_3$ alkenyl, C$_2$-C$_3$ alkynyl, C$_1$-C$_3$ alkoxy, —NR$^{13}$R$^{14}$, —(C$_1$-C$_3$ alkyl)-NR$^{13}$R$^{14}$, —NR$^{14}$COR$^{16}$, —(C$_1$-C$_3$ alkyl)-NR$^{14}$COR$^{16}$, —CONR$^{14}$R$^{15}$, or —(C$_1$-C$_3$ alkyl)-CONR$^{14}$R$^{15}$; or R$^{8a}$ and R$^{8b}$ taken together form an optionally substituted 3- to 6-membered carbocyclyl or heterocyclyl. In one embodiment, R$^{8a}$ and R$^{9a}$ are each independently hydrogen, halogen, C$_1$-C$_3$ alkyl, C$_2$-C$_3$ alkenyl, C$_2$-C$_3$ alkynyl, C$_1$-C$_3$ alkoxy, —NR$^{13}$R$^{14}$, —(C$_1$-C$_3$ alkyl)-NR$^{13}$R$^{14}$, —NR$^{14}$COR$^{16}$, —(C$_1$-C$_3$ alkyl)-NR$^{14}$COR$^{16}$, —CONR$^{14}$R$^{15}$, or —(C$_1$-C$_3$ alkyl)-CONR$^{14}$R$^{15}$. In one embodiment of the compounds of formula (IB), (IC), (III), or (IIIA), R$^{8a}$ and R$^{9a}$ are not —OH. In one embodiment, R$^{8a}$ and R$^{9a}$ are not —OH.

In one embodiment of the compounds of formula (I)-(VI), (A), (B), and (C), R$^7$ and R$^{8a}$ taken together form an optionally substituted heterocyclyl. In one embodiment, R$^7$ and R$^{8a}$ taken together form an optionally substituted 3- to 7-membered heterocycle.

In one embodiment of the compounds of formula (I)-(VI), (A), (B), and (C), R$^8$ and R$^9$ are each independently hydrogen, halogen, or C$_1$-C$_3$ alkyl.

In one embodiment of the compounds of formula (I)-(IIB), R$^{10}$ is hydrogen, optionally substituted C$_1$-C$_6$ alkyl, optionally substituted C$_2$-C$_6$ alkenyl, optionally substituted C$_2$-C$_6$ alkynyl, optionally substituted carbocyclyl, optionally substituted heterocyclyl, optionally substituted aryl, or optionally substituted heteroaryl. In some embodiments, R$^{10}$ is hydrogen, optionally substituted C$_1$-C$_3$ alkyl, optionally substituted C$_2$-C$_3$ alkenyl, optionally substituted C$_2$-C$_3$ alkynyl, optionally substituted carbocyclyl, optionally substituted heterocyclyl, optionally substituted aryl, or optionally substituted heteroaryl. In some embodiments, R$^{10}$ is hydrogen, C$_1$-C$_3$ alkyl, C$_2$-C$_3$ alkenyl, C$_2$-C$_3$ alkynyl, carbocyclyl, heterocyclyl, aryl, or heteroaryl. In some embodiments, R$^{10}$ is hydrogen, C$_1$-C$_3$ alkyl, C$_2$-C$_3$ alkenyl, C$_2$-C$_3$ alkynyl. In some embodiments, R$^{10}$ is hydrogen or C$_1$-C$_3$ alkyl.

In one embodiment of the compounds of formula (I)-(IIB), R$^{11}$ and R$^{12}$ are each independently hydrogen, optionally substituted C$_1$-C$_6$ alkyl, optionally substituted C$_2$-C$_6$ alkenyl, optionally substituted C$_2$-C$_6$ alkynyl, optionally substituted carbocyclyl, optionally substituted heterocyclyl, optionally substituted aryl, or optionally substituted heteroaryl. In one embodiment, R$^{11}$ and R$^{12}$ are each independently hydrogen, optionally substituted C$_1$-C$_6$ alkyl, optionally substituted C$_2$-C$_6$ alkenyl, or optionally substituted C$_2$-C$_6$ alkynyl. In some embodiments. R$^{11}$ and R$^{12}$ are each independently hydrogen, C$_1$-C$_6$ alkyl, C$_2$-C$_6$ alkenyl, or C$_2$-C$_6$ alkynyl. In some embodiments. R$^{11}$ and R$^{12}$ are each independently hydrogen or C$_1$-C$_3$ alkyl.

In one embodiment of the compounds of formula (I)-(IIB), R$^{11}$ and R$^{12}$ taken together form an optionally substituted heterocyclyl. In one embodiment, R$^{11}$ and R$^{12}$ taken together form an optionally substituted 3- to 7-membered heterocyclyl. In other embodiments, R$^{11}$ and R$^{12}$ taken together form 3- to 7-membered heterocyclyl.

In one embodiment of the compounds of formula (I)-(VI), (A), (B), and (C), R$^{13}$ and R$^{14}$ are each independently hydrogen, optionally substituted C$_1$-C$_6$ alkyl, optionally substituted C$_2$-C$_6$ alkenyl, optionally substituted C$_2$-C$_6$ alkynyl, optionally substituted carbocyclyl, optionally substituted heterocyclyl, optionally substituted aryl, or optionally substituted heteroaryl. In one embodiment, R$^{13}$ and R$^{14}$ are each independently hydrogen, optionally substituted C$_1$-C$_6$ alkyl, optionally substituted C$_2$-C$_6$ alkenyl, or optionally substituted C$_2$-C$_6$ alkynyl. In some embodiments R$^{13}$ and R$^{14}$ are each independently hydrogen, C$_1$-C$_6$ alkyl, C$_2$-C$_6$ alkenyl, or C$_2$-C$_6$ alkynyl. In some embodiments R$^{13}$ and R$^{14}$ are each independently hydrogen or C$_1$-C$_3$ alkyl.

In one embodiment of the compounds of formula (I)-(VI), (A), (B), and (C), R$^{15}$ is hydrogen, optionally substituted C$_1$-C$_6$ alkyl, optionally substituted C$_2$-C$_6$ alkenyl, optionally substituted C$_2$-C$_6$ alkynyl, optionally substituted carbocyclyl, optionally substituted heterocyclyl, optionally substituted aryl, or optionally substituted heteroaryl. In one embodiment, R$^{15}$ is hydrogen, optionally substituted C$_1$-C$_6$ alkyl, optionally substituted C$_2$-C$_6$ alkenyl, or optionally substituted C$_2$-C$_6$ alkynyl. In some embodiments, R$^{15}$ is hydrogen, C$_1$-C$_6$ alkyl, C$_2$-C$_6$ alkenyl, or C$_2$-C$_6$ alkynyl. In some embodiments, R$^{15}$ is hydrogen or C$_1$-C$_3$ alkyl.

In one embodiment of the compounds of formula (I)-(VI), (A), (B), and (C), R$^{14}$ and R$^{15}$ taken together form an optionally substituted heterocyclyl. In one embodiment, R$^{14}$ and R$^{15}$ taken together form an optionally substituted 3- to 7-membered heterocyclyl. In other embodiments, R$^{14}$ and R$^{15}$ taken together form 3- to 7-membered heterocyclyl.

In one embodiment of the compounds of formula (I)-(VI), (A), (B), and (C), R$^{16}$ is hydrogen, optionally substituted C$_1$-C$_6$ alkyl, optionally substituted C$_2$-C$_6$ alkenyl, optionally substituted C$_2$-C$_6$ alkynyl, optionally substituted carbocyclyl, optionally substituted heterocyclyl, optionally substituted aryl, or optionally substituted heteroaryl. In some embodiments, R$^{16}$ is hydrogen, optionally substituted C$_1$-C$_3$ alkyl, optionally substituted C$_2$-C$_3$ alkenyl, optionally substituted C$_2$-C$_3$ alkynyl, optionally substituted carbocyclyl, optionally substituted heterocyclyl, optionally substituted aryl, or optionally substituted heteroaryl. In some embodiments, R$^{16}$ is hydrogen, C$_1$-C$_3$ alkyl, C$_2$-C$_3$ alkenyl, C$_2$-C$_3$ alkynyl, carbocyclyl, heterocyclyl, aryl, or heteroaryl. In some embodiments, R$^{16}$ is hydrogen, C$_1$-C$_3$ alkyl, C$_2$-C$_3$ alkenyl, or C$_2$-C$_3$ alkynyl. In some embodiments, R$^{16}$ is hydrogen or C$_1$-C$_3$ alkyl.

In one embodiment of the compounds of formula (I)-(IIIA), m is 1 or 2.

In one embodiment of the compounds of formula (I)-(VI) and (A)-(F), t is 1 or 2. In one embodiment of the compounds of formula (I)-(VI) and (A)-(H-I), t is 1.

In one embodiment of the compounds of formula (I)-(VI), (A), (B), and (C), optional substituent is selected from halogen, —CN, —CF$_3$, —OH, —S(C$_1$-C$_3$ alkyl), C$_1$-C$_3$ alkyl, C$_2$-C$_3$ alkenyl, C$_2$-C$_3$ alkynyl, C$_1$-C$_3$ alkoxy, —(C$_1$-C$_3$ alkyl)-(C$_1$-C$_3$ alkoxy), —(C$_1$-C$_3$ alkyl)-OH, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl) NR$^{14}$SO$_2$R$^{16}$, —NR$^{14}$COR$^{16}$, —(C$_1$-C$_6$ alkyl)-NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO(C$_1$-C$_3$ alkyl), —SO$_2$(C$_1$-C$_3$ alkyl), or —(C$_1$-C$_6$ alkyl)-SO$_2$(C$_1$-C$_3$ alkyl). In another embodiment, the optional substituent is selected from halogen, —CN, —CF$_3$, —OH, C$_1$-C$_3$ alkyl, C$_1$-C$_3$ alkoxy, —NH$_2$, —SCH$_3$, —SO$_2$CH$_3$, —NHSO$_2$CH$_3$, —CH$_2$NHSO$_2$CH$_3$, —SO$_2$NH$_2$, —CONH$_2$, or —NHCOCH$_3$.

In one embodiment of the compounds of formula (I)-(VI), A and B are each monocyclic ring.

In one embodiment of the compounds of formula (I)-(VI), B is phenyl, pyridyl, or pyrimidyl.

In one embodiment of the compounds of formula (I)-(IIIA), Z and V are not both a bond.

In one embodiment of the compounds of formula (I)-(VI), (A)-(C), Y and W are not both a bond.

In one embodiment of the compounds of formula (I)-(VI), C is a 4- to 10-membered ring.

In one embodiment of the compounds of formula (D)-(H-I), X is a bond, —CH$_2$—, —C(CH$_3$)H—, —C(CH$_3$)$_2$—, or —CH₂CH₂—. In one embodiment, X is —CH₂—, —C(CH₃)H—, or —C(CH₃)₂—. In some embodiments, X is —C(CH₃)₂—.

In one embodiment of the compounds of formula (D)-(H), X is —NR⁷—. In one embodiment, X is —NH—, —N(CH₃)—, —N(CH₂CH₃)—, —N(iPr)-, or —N(tBu)-.

In one embodiment of the compounds of formula (D)-(H-I), Y is —O—. In one embodiment of the compounds of formula (D)-(H-I), Z is —O—. In one embodiment of the compounds of formula (D)-(H-I), Y and Z are both —O—.

In one embodiment of the compounds of formula (D)-(H-I), —V-L is CH₂CH₂C₁, —CH₂CH₂CH₂C₁, or —CH₃. In some embodiments, —V-L is CH₂CH₂C₁ or —CH₂CH₂CH₂C₁.

In one embodiment of the compounds of formula (D)-(H-I), n1 is 0.

In one embodiment of the compounds of formula (D)-(H-I), n2 is 0, 1, or 2. In some embodiments, n2 is 2. In some embodiments, n2 is 2 and R² are each ortho to Z. In other embodiments, n2 is 2 and R² are each ortho to Z, wherein R² is halogen or —CN.

In one embodiment of the compound of formula (I)-(VI) and (A)-(H-I), the compound can be a stereoisomer. For example, if X is —(CR⁵R⁶)— and R⁵ and R⁶ are different, the carbon attached to R⁵ and R⁶ can be in an S configuration or an R configuration.

In some embodiments of the compounds of formula (I)-(VI) and (A)-(H-I), a hydrogen atom can be replaced with a deuterium atom.

In one embodiment of the compound of formula (I)-(VA), (A), (A-I), or (D)-(H-I), the compound is selected from Table A below, or a pharmaceutically acceptable salt, tautomer, stereoisomer or prodrug thereof. In one embodiment of the compound of formula (I)-(VA), (A), or (D)-(H-I), the compound is selected from Compounds A3, A5, A7, A13, A17, A18, A22, A23, A24, A25, A28, A30, A31, A32, A34, A35, A38, A40, A41, A42, A45, A49, A52, A53, A54, A56, A57, A58, A62, A63, A64, A65, A68, A73, A74, A75, or A76, or a pharmaceutically acceptable salt, tautomer, stereoisomer or prodrug thereof. In one embodiment of the compound of formula (I)-(VA), (A), (A-I), or (D)-(H-I), the compound is selected from Compounds A1, A2, A4, A6, A8, A9, A10, A11, A12, A14, A15, A16, A19, A20, A21, A26, A27, A29, A33, A36, A37, A39, A43, A44, A46, A47, A48, A50, A51, A55, A59, A60, A61, A66, A67, A69, A70, A71, A72, A77, A78, A79, A80, A81, A82, A83, A84, A85, A86, A87, A88, A89, A90, A91, A92, A93, A94, A95, A96, or A97, or a pharmaceutically acceptable salt, tautomer, stereoisomer or prodrug thereof. In one embodiment of the compound of formula (I)-(VA), (A), (A-I), or (D)-(H-I), the compound is selected from Compounds A98-A186, or a pharmaceutically acceptable salt, tautomer, stereoisomer or prodrug thereof. In one embodiment of the compound of formula (I)-(VA), (A), (A-I), or (D)-(H-I), the compound is selected from Compounds A187-A211, or a pharmaceutically acceptable salt, tautomer, stereoisomer or prodrug thereof. In one embodiment of the compound of formula (I)-(VA), (A), (A-I), or (D)-(H-I), the compound is selected from Compounds A1-A211, or a pharmaceutically acceptable salt, tautomer, stereoisomer or prodrug thereof. In one embodiment of the compound of formula (I)-(VA), (A), (A-I), or (D)-(H-I), the compound is selected from Compounds A212-A234, or a pharmaceutically acceptable salt, tautomer, stereoisomer or prodrug thereof. In one embodiment of the compound of formula (I)-(VA), (A), (A-I), or (D)-(H-I), the compound is selected from Compounds A1-A234, or a pharmaceutically acceptable salt, tautomer, stereoisomer or prodrug thereof. In one embodiment of the compound of formula (I)-(VA), (A), (A-I), or (D)-(H-I), the compound is selected from Compounds A1-A96, A98-A116, A118-A159, A161-A175, and A177-A234, or a pharmaceutically acceptable salt, tautomer, stereoisomer or prodrug thereof.

In one embodiment of the compound of formula (I)-(VA), (A), (A-I), or (D)-(H-I), the compound is selected from A13, A57, A74, A93, A109, A112, A122, A126, A131, A134, A136, A137, A164, A168, A169, A170, A171, A172, A184, A185, A195, and/or A204, or a pharmaceutically acceptable salt, tautomer, stereoisomer or prodrug thereof.

TABLE A

| Compound ID | Structure |
|---|---|
| A1 | (structure) |
| A2 | (structure) |

TABLE A-continued

Compounds

| Compound ID | Structure |
|---|---|
| A3 | 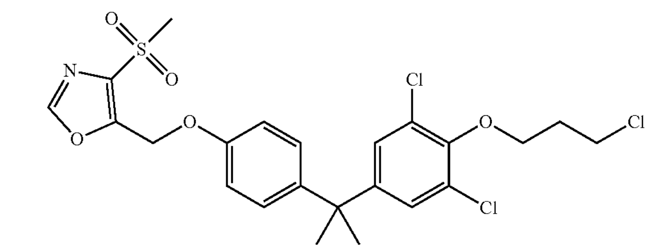 [SMILES: CC(C)(c1ccc(OCc2ocnc2S(C)(=O)=O)cc1)c1cc(Cl)c(OCCCCl)c(Cl)c1] |
| A4 | 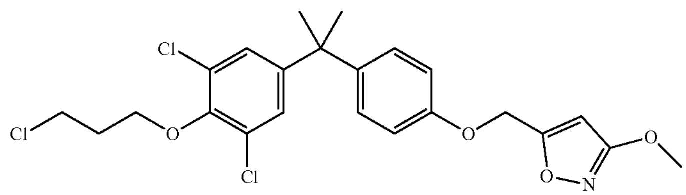 [SMILES: COc1cc(COc2ccc(C(C)(C)c3cc(Cl)c(OCCCCl)c(Cl)c3)cc2)on1] |
| A5 | 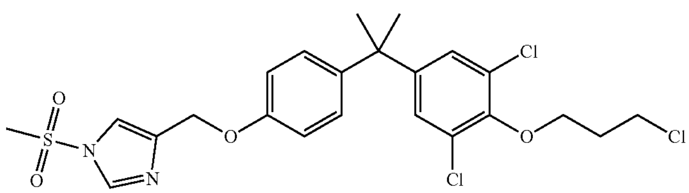 [SMILES: CC(C)(c1ccc(OCc2cn(S(C)(=O)=O)cn2)cc1)c1cc(Cl)c(OCCCCl)c(Cl)c1] |
| A6 | 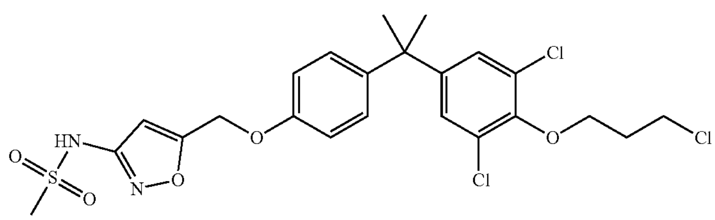 [SMILES: CC(C)(c1ccc(OCc2cc(NS(C)(=O)=O)no2)cc1)c1cc(Cl)c(OCCCCl)c(Cl)c1] |
| A7 | 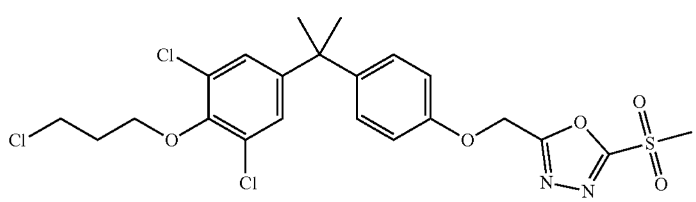 [SMILES: CC(C)(c1ccc(OCc2nnc(S(C)(=O)=O)o2)cc1)c1cc(Cl)c(OCCCCl)c(Cl)c1] |
| A8 | 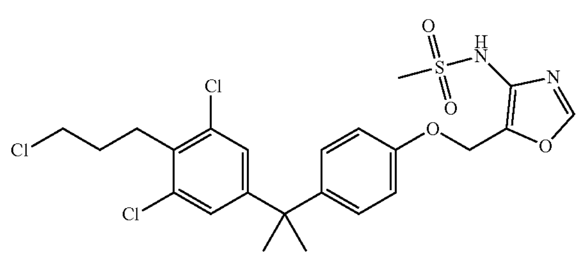 [SMILES: CC(C)(c1ccc(OCc2ocnc2NS(C)(=O)=O)cc1)c1cc(Cl)c(CCCCl)c(Cl)c1] |

TABLE A-continued

| Compound ID | Structure |
|---|---|
| A9 | (structure) |
| A10 | (structure) |
| A11 | (structure) |
| A12 | (structure) |
| A13 | (structure) |
| A14 | (structure) |

TABLE A-continued

| Compound ID | Structure |
|---|---|
| A15 | 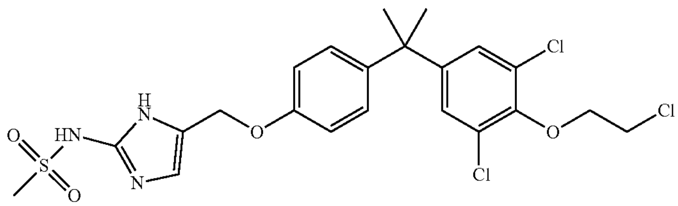 [SMILES: CC(C)(c1ccc(OCc2cnc(NS(C)(=O)=O)[nH]2)cc1)c1cc(Cl)c(OCCCl)c(Cl)c1] |
| A16 | 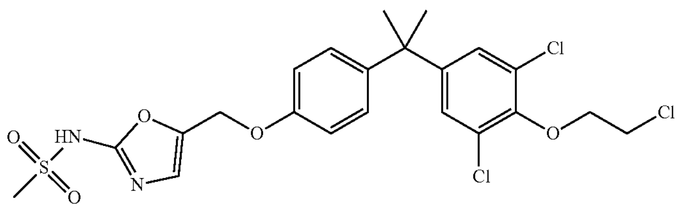 [SMILES: CC(C)(c1ccc(OCc2cnc(NS(C)(=O)=O)o2)cc1)c1cc(Cl)c(OCCCl)c(Cl)c1] |
| A17 | 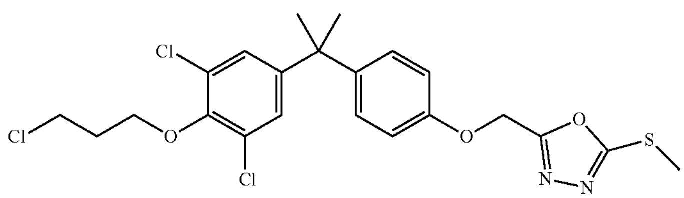 [SMILES: CSc1nnc(COc2ccc(C(C)(C)c3cc(Cl)c(OCCCCl)c(Cl)c3)cc2)o1] |
| A18 | 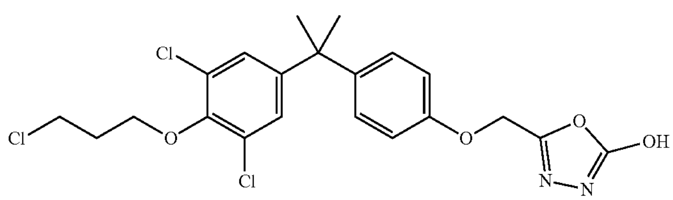 [SMILES: CC(C)(c1ccc(OCc2nnc(O)o2)cc1)c1cc(Cl)c(OCCCCl)c(Cl)c1] |
| A19 | 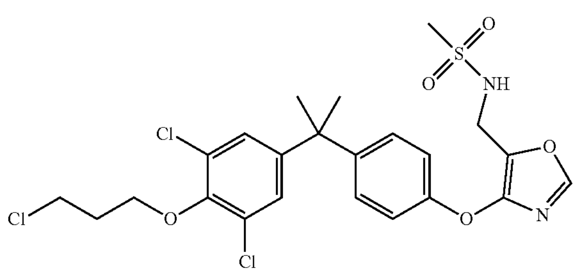 [SMILES: CC(C)(c1ccc(Oc2ncoc2CNS(C)(=O)=O)cc1)c1cc(Cl)c(OCCCCl)c(Cl)c1] |
| A20 | 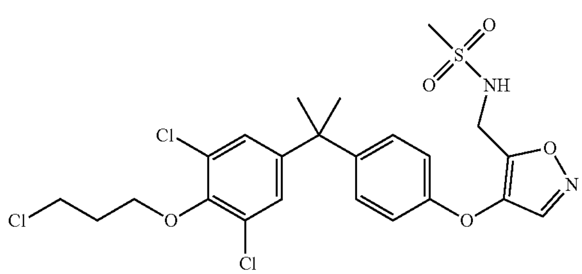 [SMILES: CC(C)(c1ccc(Oc2cnoc2CNS(C)(=O)=O)cc1)c1cc(Cl)c(OCCCCl)c(Cl)c1] |

TABLE A-continued

| Compound ID | Structure |
|---|---|
| A21 | 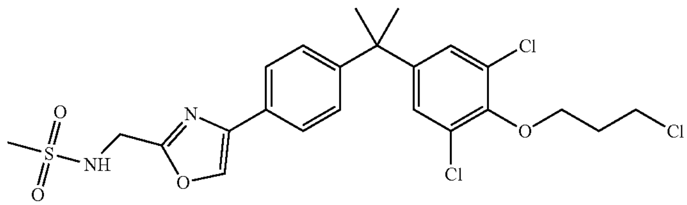 [SMILES: CC(C)(c1ccc(-c2coc(CNS(C)(=O)=O)n2)cc1)c1cc(Cl)c(OCCCCl)c(Cl)c1] |
| A22 | 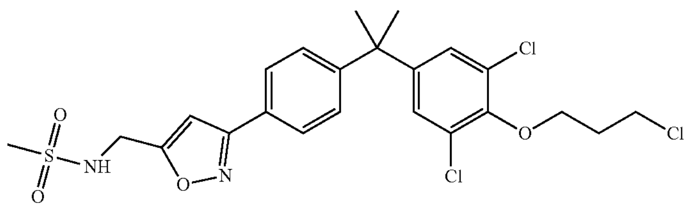 [SMILES: CC(C)(c1ccc(-c2cc(CNS(C)(=O)=O)on2)cc1)c1cc(Cl)c(OCCCCl)c(Cl)c1] |
| A23 | 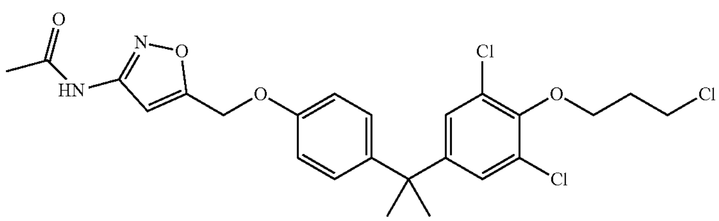 [SMILES: CC(=O)Nc1cc(COc2ccc(C(C)(C)c3cc(Cl)c(OCCCCl)c(Cl)c3)cc2)on1] |
| A24 | 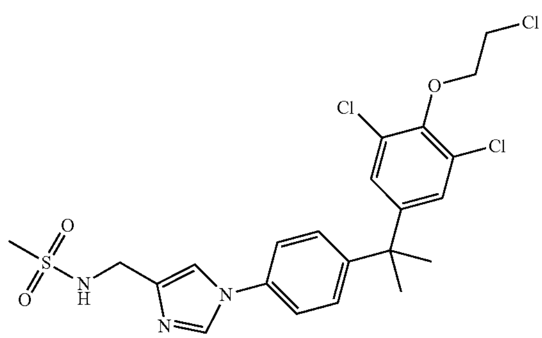 [SMILES: CC(C)(c1ccc(-n2cnc(CNS(C)(=O)=O)c2)cc1)c1cc(Cl)c(OCCCl)c(Cl)c1] |
| A25 | 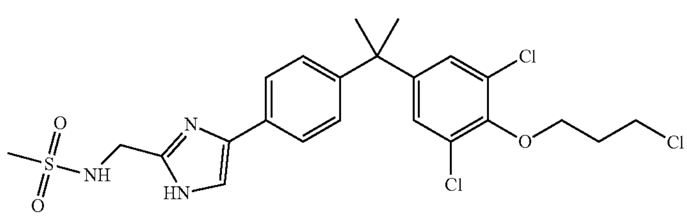 [SMILES: CC(C)(c1ccc(-c2c[nH]c(CNS(C)(=O)=O)n2)cc1)c1cc(Cl)c(OCCCCl)c(Cl)c1] |
| A26 | 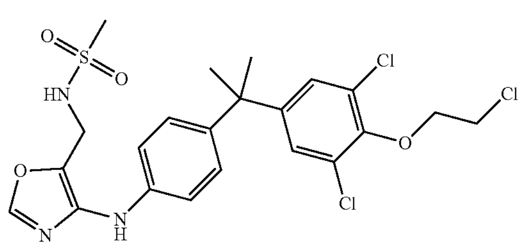 [SMILES: CC(C)(c1ccc(Nc2ncoc2CNS(C)(=O)=O)cc1)c1cc(Cl)c(OCCCl)c(Cl)c1] |

TABLE A-continued

Compounds

| Compound ID | Structure |
|---|---|
| A27 | 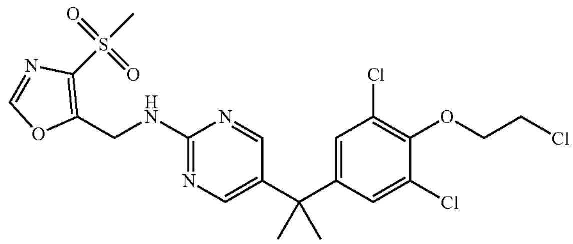 |
| A28 | 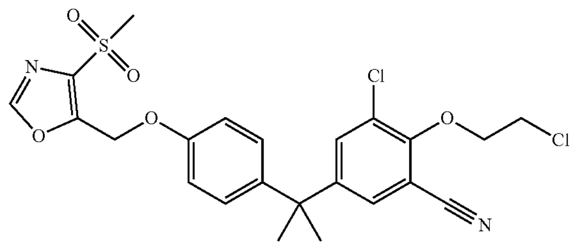 [SMILES: CC(C)(c1ccc(OCc2ocnc2S(C)(=O)=O)cc1)c1cc(Cl)c(OCCCl)c(C#N)c1] |
| A29 | 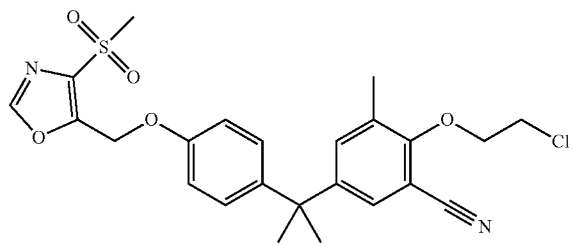 [SMILES: Cc1cc(C(C)(C)c2ccc(OCc3ocnc3S(C)(=O)=O)cc2)cc(C#N)c1OCCCl] |
| A30 | 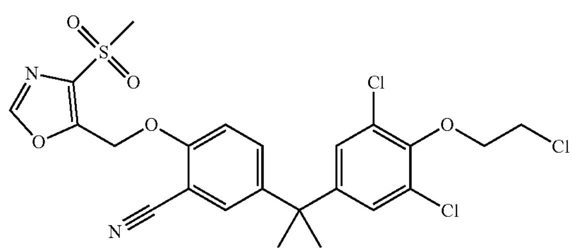 [SMILES: CC(C)(c1cc(Cl)c(OCCCl)c(Cl)c1)c1ccc(OCc2ocnc2S(C)(=O)=O)c(C#N)c1] |
| A31 | 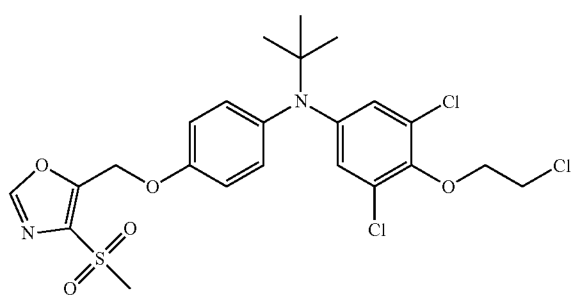 [SMILES: CC(C)(C)N(c1ccc(OCc2ocnc2S(C)(=O)=O)cc1)c1cc(Cl)c(OCCCl)c(Cl)c1] |
| A32 | 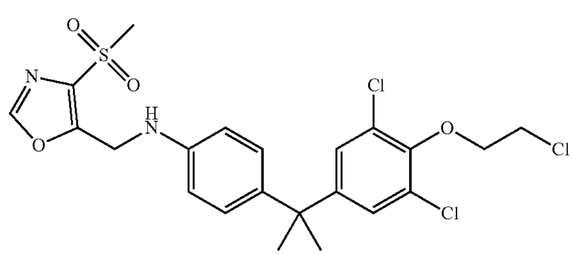 |

TABLE A-continued

| Compound ID | Structure |
|---|---|
| A33 | 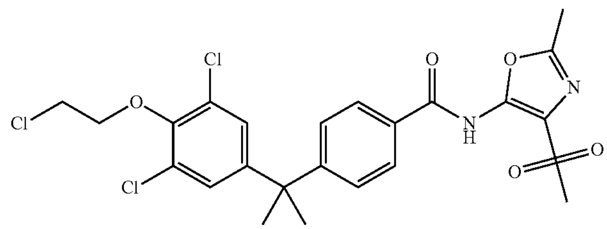 |
| A34 | 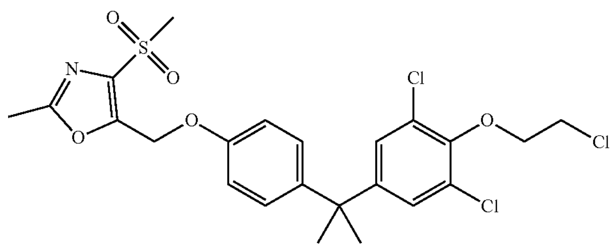 [SMILES: Cc1nc(S(C)(=O)=O)c(COc2ccc(C(C)(C)c3cc(Cl)c(OCCCl)c(Cl)c3)cc2)o1] |
| A35 | 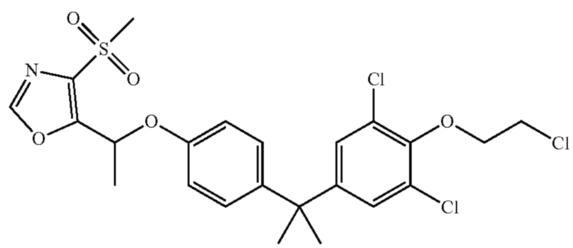 |
| A36 | 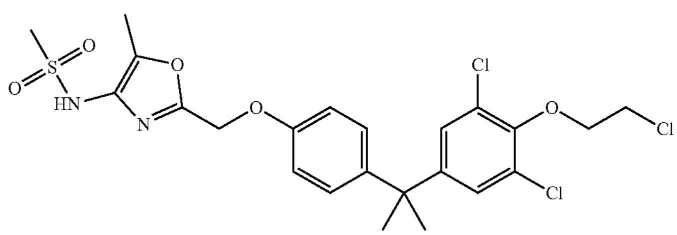 [SMILES: Cc1oc(COc2ccc(C(C)(C)c3cc(Cl)c(OCCCl)c(Cl)c3)cc2)nc1NS(C)(=O)=O] |
| A37 | 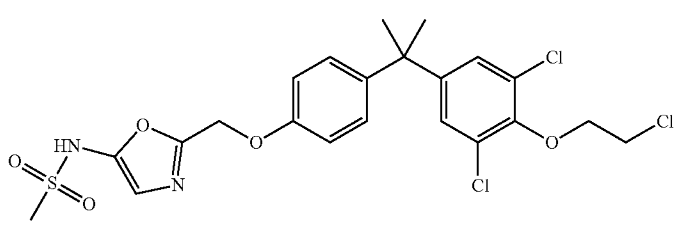 [SMILES: CC(C)(c1ccc(OCc2ncc(NS(C)(=O)=O)o2)cc1)c1cc(Cl)c(OCCCl)c(Cl)c1] |
| A38 | 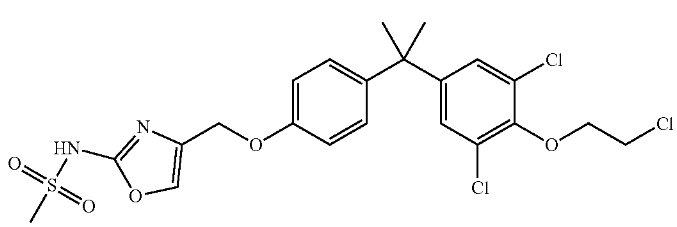 [SMILES: CC(C)(c1ccc(OCc2coc(NS(C)(=O)=O)n2)cc1)c1cc(Cl)c(OCCCl)c(Cl)c1] |

TABLE A-continued
Compounds
| Compound ID | Structure |
|---|---|
| A39 | 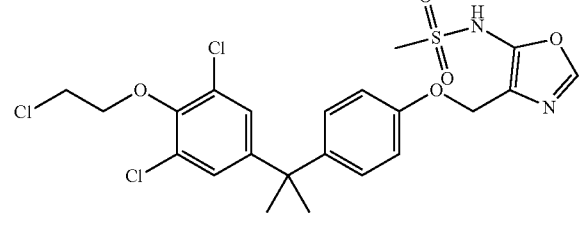 |
| A40 | 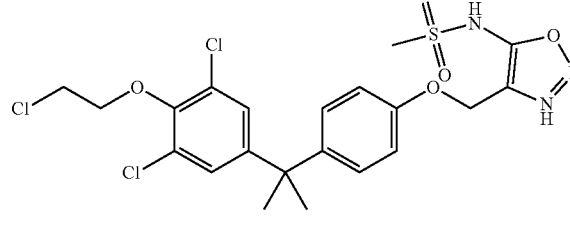 |
| A41 | 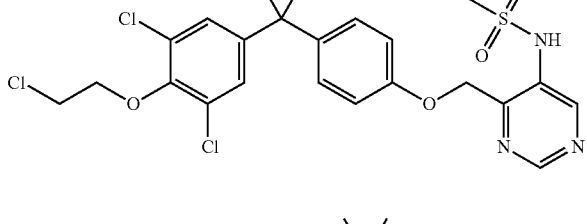 |
| A42 | 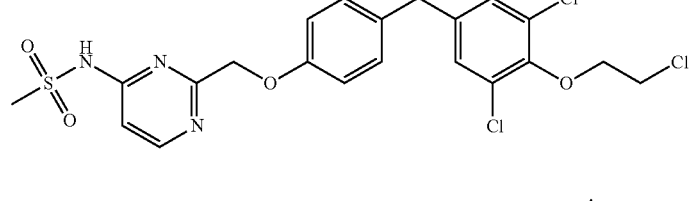 |
| A43 | 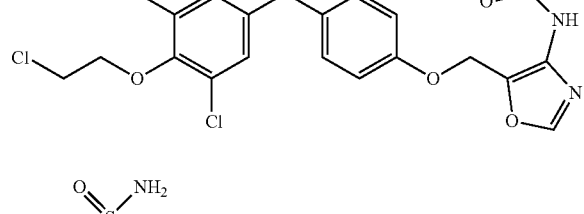 |
| A44 | 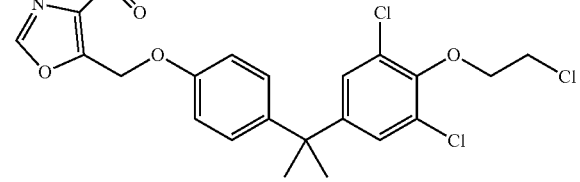 |

TABLE A-continued

| Compound ID | Structure |
|---|---|
| A45 | 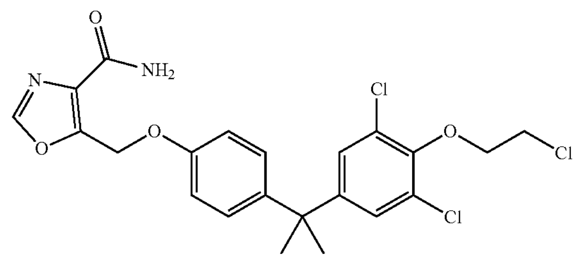 [SMILES: CC(C)(c1ccc(OCc2ocnc2C(N)=O)cc1)c1cc(Cl)c(OCCCl)c(Cl)c1] |
| A46 | 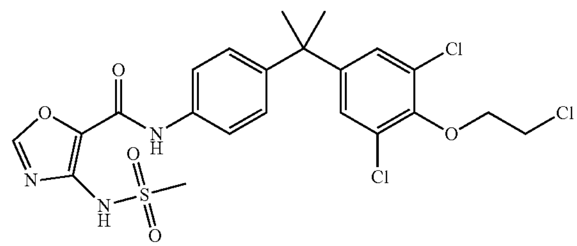 [SMILES: CC(C)(c1ccc(NC(=O)c2ocnc2NS(C)(=O)=O)cc1)c1cc(Cl)c(OCCCl)c(Cl)c1] |
| A47 | 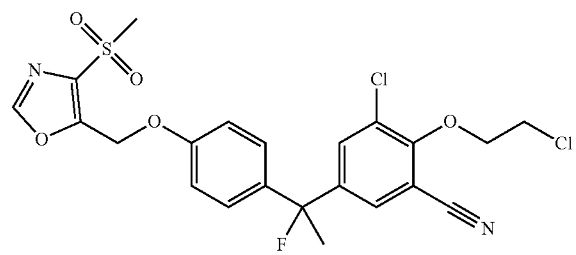 [SMILES: CC(F)(c1ccc(OCc2ocnc2S(C)(=O)=O)cc1)c1cc(Cl)c(OCCCl)c(C#N)c1] |
| A48 | 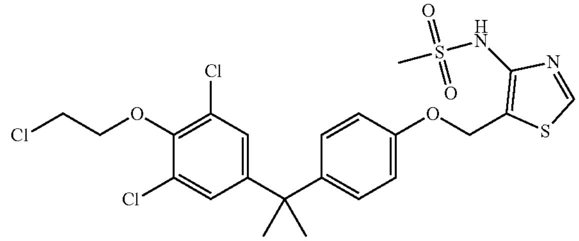 [SMILES: CC(C)(c1ccc(OCc2scnc2NS(C)(=O)=O)cc1)c1cc(Cl)c(OCCCl)c(Cl)c1] |
| A49 | 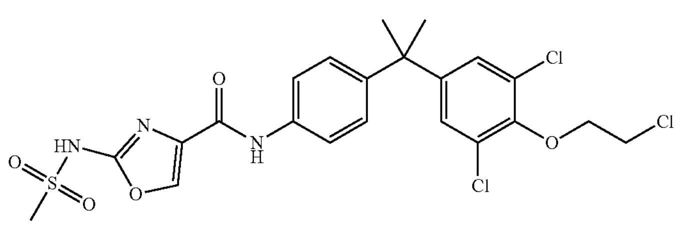 [SMILES: CC(C)(c1ccc(NC(=O)c2coc(NS(C)(=O)=O)n2)cc1)c1cc(Cl)c(OCCCl)c(Cl)c1] |
| A50 | 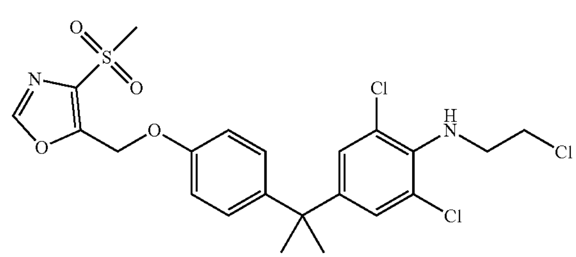 [SMILES: CC(C)(c1ccc(OCc2ocnc2S(C)(=O)=O)cc1)c1cc(Cl)c(NCCCl)c(Cl)c1] |

TABLE A-continued
| Compound ID | Structure |
|---|---|
| A51 | 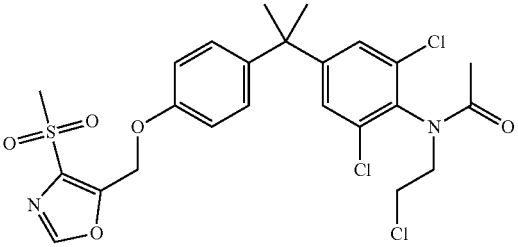 [SMILES: CC(=O)N(CCCl)c1c(Cl)cc(C(C)(C)c2ccc(OCc3ocnc3S(C)(=O)=O)cc2)cc1Cl] |
| A52 | 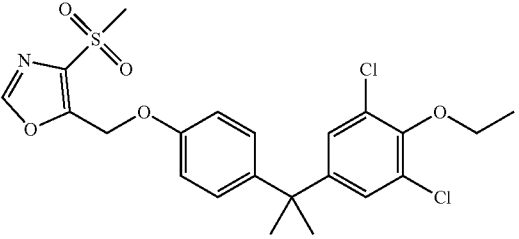 [SMILES: CCOc1c(Cl)cc(C(C)(C)c2ccc(OCc3ocnc3S(C)(=O)=O)cc2)cc1Cl] |
| A53 | 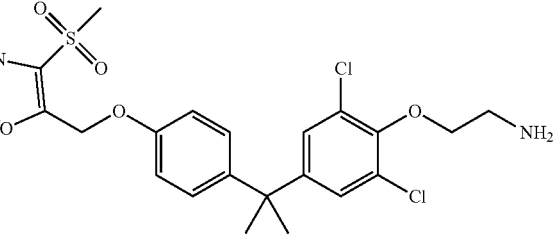 |
| A54 | 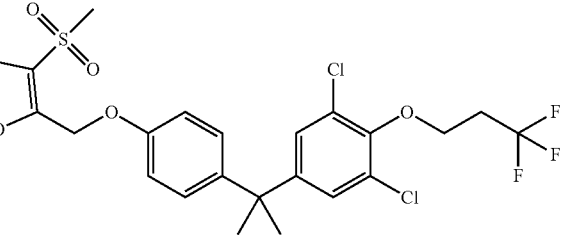 |
| A55 | 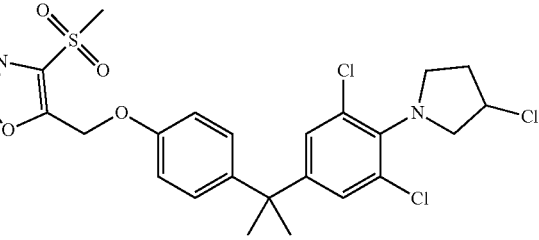 |
| A56 | 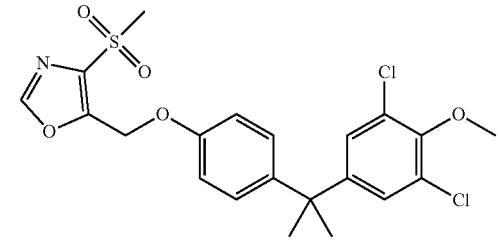 [SMILES: COc1c(Cl)cc(C(C)(C)c2ccc(OCc3ocnc3S(C)(=O)=O)cc2)cc1Cl] |

TABLE A-continued

| Compound ID | Structure |
|---|---|
| A57 | (structure) |
| A58 | (structure) |
| A59 | (structure) |
| A60 | (structure) |
| A61 | (structure) |
| A62 | (structure) |

TABLE A-continued

Compounds

| Compound ID | Structure |
|---|---|
| A63 | 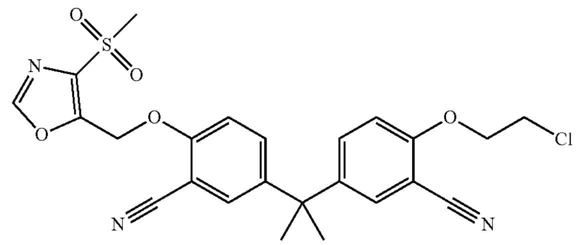 [SMILES: CC(C)(c1ccc(OCCCl)c(C#N)c1)c1ccc(OCc2ocnc2S(C)(=O)=O)c(C#N)c1] |
| A64 | 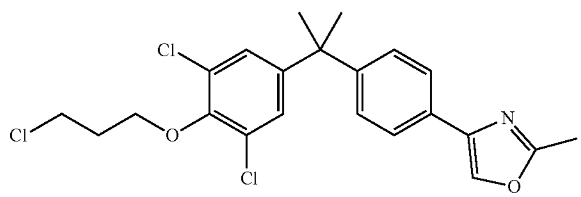 [SMILES: Cc1nc(-c2ccc(C(C)(C)c3cc(Cl)c(OCCCCl)c(Cl)c3)cc2)co1] |
| A65 | 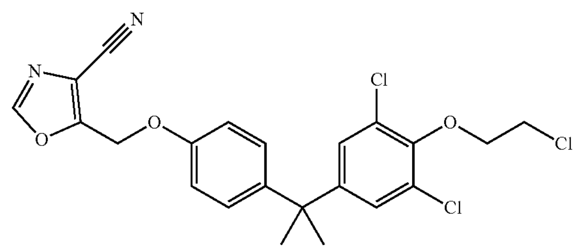 [SMILES: CC(C)(c1ccc(OCc2ocnc2C#N)cc1)c1cc(Cl)c(OCCCl)c(Cl)c1] |
| A66 | 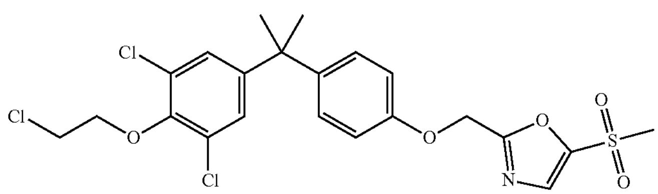 [SMILES: CC(C)(c1ccc(OCc2ncc(S(C)(=O)=O)o2)cc1)c1cc(Cl)c(OCCCl)c(Cl)c1] |
| A67 | 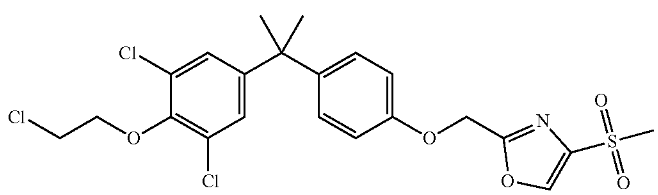 [SMILES: CC(C)(c1ccc(OCc2nc(S(C)(=O)=O)co2)cc1)c1cc(Cl)c(OCCCl)c(Cl)c1] |
| A68 | 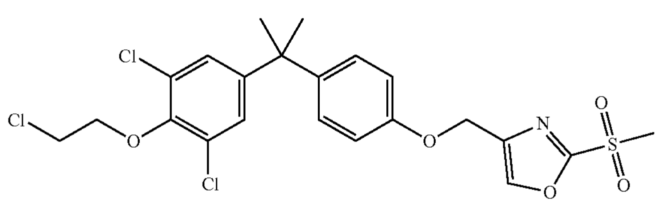 [SMILES: CC(C)(c1ccc(OCc2coc(S(C)(=O)=O)n2)cc1)c1cc(Cl)c(OCCCl)c(Cl)c1] |
| A69 | 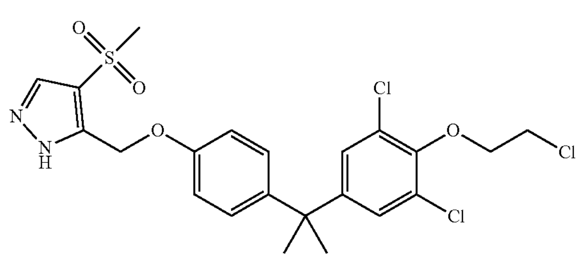 [SMILES: CC(C)(c1ccc(OCc2[nH]ncc2S(C)(=O)=O)cc1)c1cc(Cl)c(OCCCl)c(Cl)c1] |

TABLE A-continued
| Compound ID | Structure |
|---|---|
| A70 | 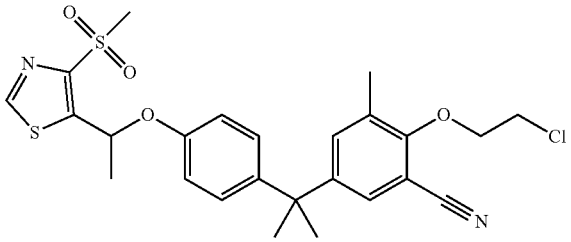 [SMILES: Cc1cc(C(C)(C)c2ccc(OC(C)c3scnc3S(C)(=O)=O)cc2)cc(C#N)c1OCCCl] |
| A71 | 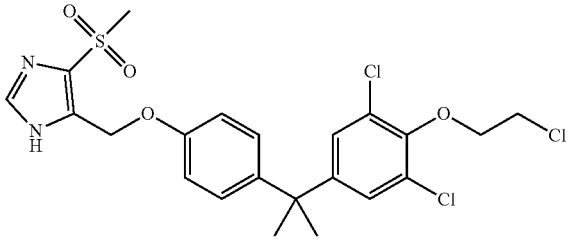 [SMILES: CC(C)(c1ccc(OCc2[nH]cnc2S(C)(=O)=O)cc1)c1cc(Cl)c(OCCCl)c(Cl)c1] |
| A72 | 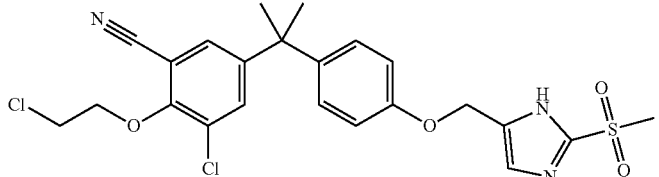 |
| A73 | 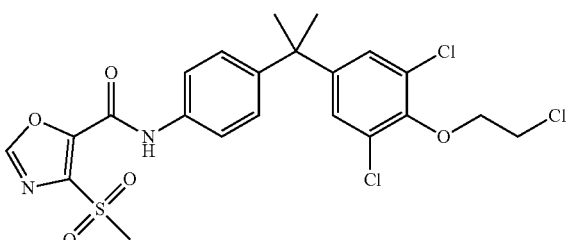 |
| A74 | 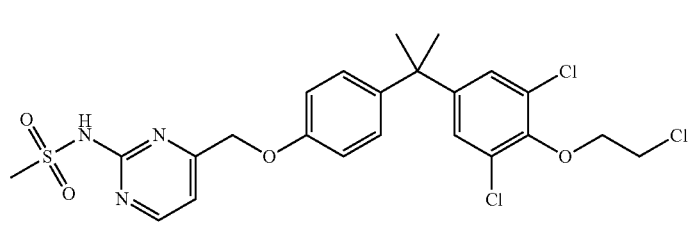 |
| A75 | 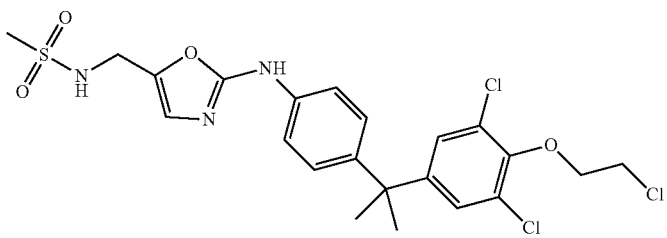 [SMILES: CC(C)(c1ccc(Nc2ncc(CNS(C)(=O)=O)o2)cc1)c1cc(Cl)c(OCCCl)c(Cl)c1] |

TABLE A-continued

Compounds

| Compound ID | Structure |
|---|---|
| A76 | 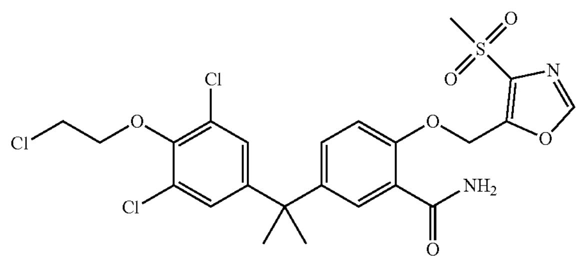 [SMILES: CC(C)(c1cc(Cl)c(OCCCl)c(Cl)c1)c1ccc(OCc2ocnc2S(C)(=O)=O)c(C(N)=O)c1] |
| A77 | 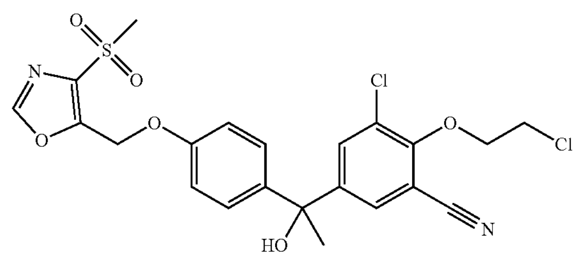 [SMILES: CC(O)(c1ccc(OCc2ocnc2S(C)(=O)=O)cc1)c1cc(Cl)c(OCCCl)c(C#N)c1] |
| A78 | 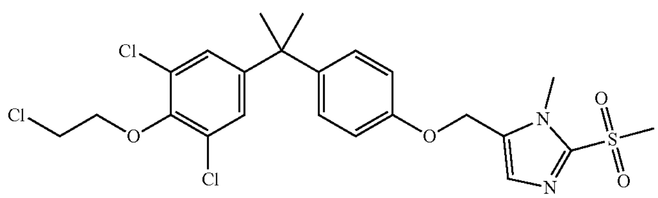 [SMILES: Cn1c(COc2ccc(C(C)(C)c3cc(Cl)c(OCCCl)c(Cl)c3)cc2)cnc1S(C)(=O)=O] |
| A79 | 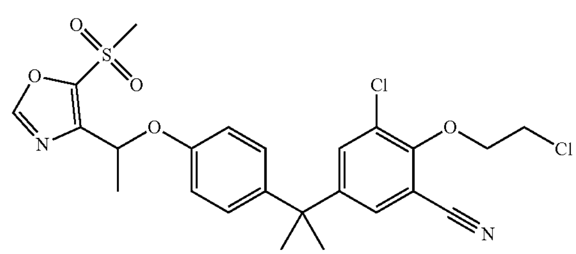 [SMILES: CC(Oc1ccc(C(C)(C)c2cc(Cl)c(OCCCl)c(C#N)c2)cc1)c1ncoc1S(C)(=O)=O] |
| A80 | 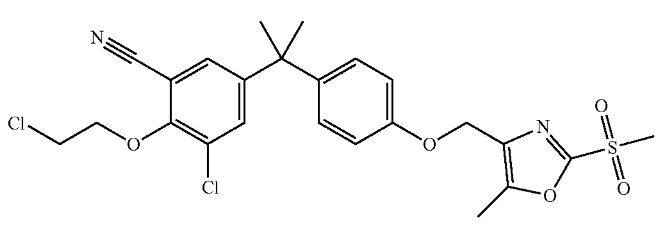 [SMILES: Cc1oc(S(C)(=O)=O)nc1COc1ccc(C(C)(C)c2cc(Cl)c(OCCCl)c(C#N)c2)cc1] |
| A81 | 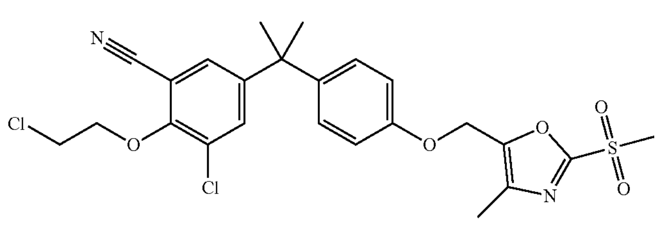 [SMILES: Cc1nc(S(C)(=O)=O)oc1COc1ccc(C(C)(C)c2cc(Cl)c(OCCCl)c(C#N)c2)cc1] |

TABLE A-continued

Compounds

| Compound ID | Structure |
|---|---|
| A82 | 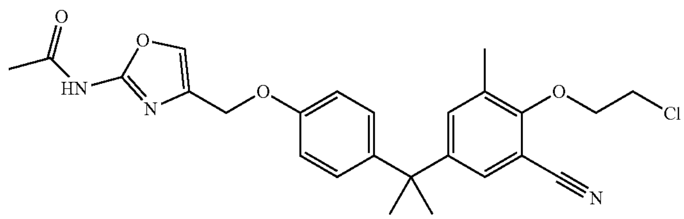 [SMILES: CC(=O)Nc1nc(COc2ccc(C(C)(C)c3cc(C)c(OCCCl)c(C#N)c3)cc2)co1] |
| A83 | 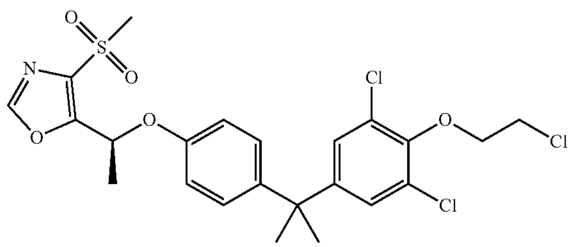 [SMILES: C[C@H](Oc1ccc(C(C)(C)c2cc(Cl)c(OCCCl)c(Cl)c2)cc1)c1ocnc1S(C)(=O)=O] |
| A84 | 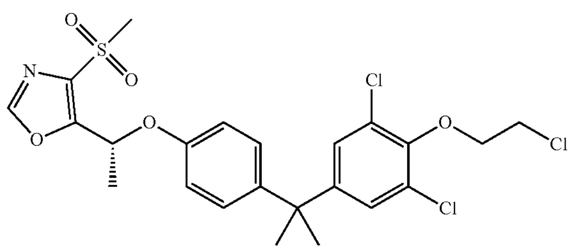 |
| A85 | 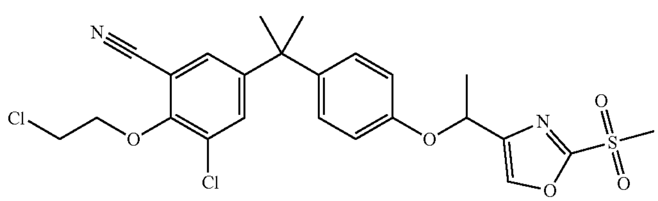 [SMILES: CC(Oc1ccc(C(C)(C)c2cc(Cl)c(OCCCl)c(C#N)c2)cc1)c1coc(S(C)(=O)=O)n1] |
| A86 | 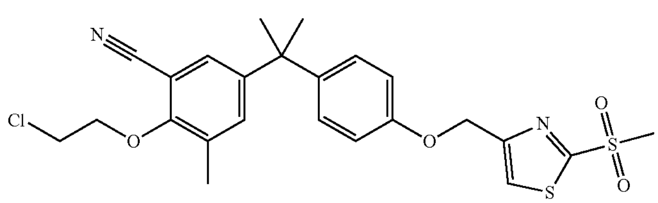 [SMILES: Cc1cc(C(C)(C)c2ccc(OCc3csc(S(C)(=O)=O)n3)cc2)cc(C#N)c1OCCCl] |
| A87 | 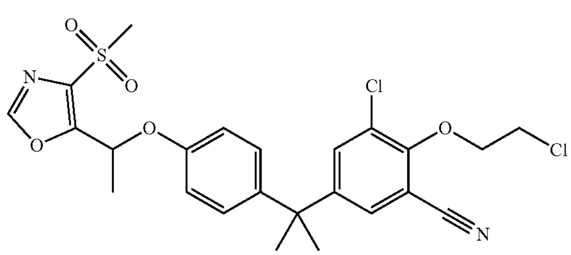 [SMILES: Cc1cc(C(C)(C)c2ccc(OC(C)c3ocnc3S(C)(=O)=O)cc2)cc(C#N)c1OCCCl] |

TABLE A-continued

Compounds

| Compound ID | Structure |
|---|---|
| A88 | 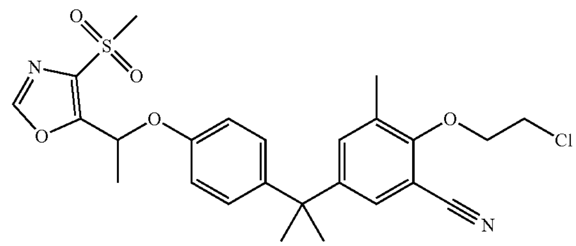 |
| A89 | 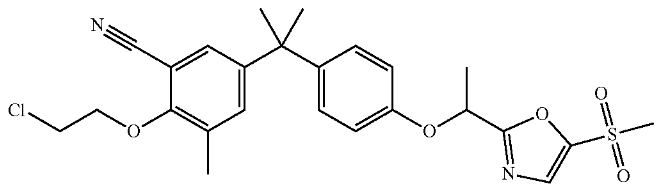 [SMILES: Cc1cc(C(C)(C)c2ccc(OC(C)c3ncc(S(C)(=O)=O)o3)cc2)cc(C#N)c1OCCCl] |
| A90 | 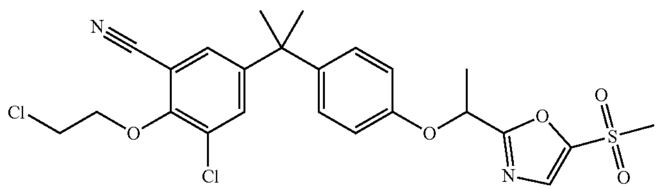 [SMILES: CC(Oc1ccc(C(C)(C)c2cc(Cl)c(OCCCl)c(C#N)c2)cc1)c1ncc(S(C)(=O)=O)o1] |
| A91 | 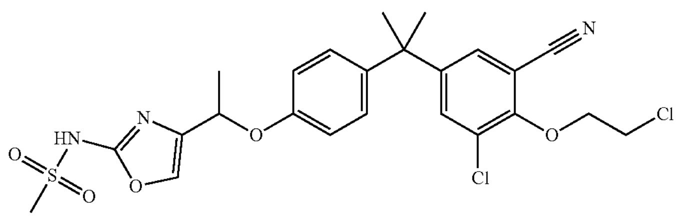 [SMILES: CC(Oc1ccc(C(C)(C)c2cc(Cl)c(OCCCl)c(C#N)c2)cc1)c1coc(NS(C)(=O)=O)n1] |
| A92 | 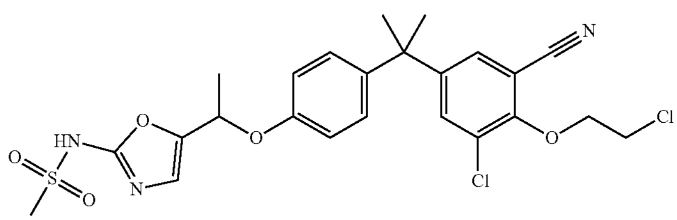 [SMILES: CC(Oc1ccc(C(C)(C)c2cc(Cl)c(OCCCl)c(C#N)c2)cc1)c1cnc(NS(C)(=O)=O)o1] |
| A93 | 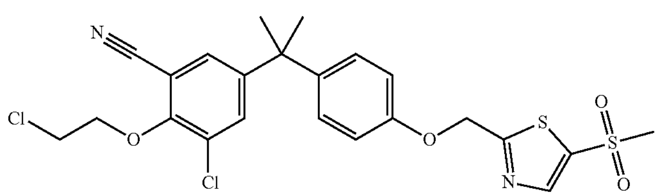 [SMILES: CC(C)(c1ccc(OCc2ncc(S(C)(=O)=O)s2)cc1)c1cc(Cl)c(OCCCl)c(C#N)c1] |
| A94 | 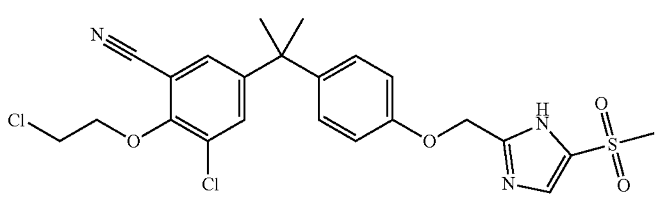 [SMILES: CC(C)(c1ccc(OCc2ncc(S(C)(=O)=O)[nH]2)cc1)c1cc(Cl)c(OCCCl)c(C#N)c1] |

TABLE A-continued
Compounds
| Compound ID | Structure |
|---|---|
| A95 | 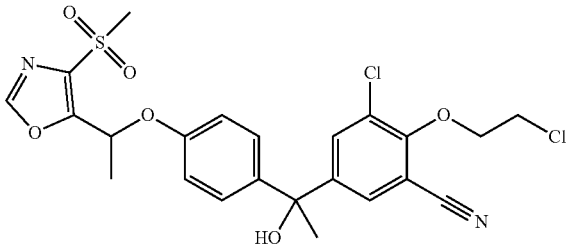 [SMILES: CC(Oc1ccc(C(C)(O)c2cc(Cl)c(OCCCl)c(C#N)c2)cc1)c1ocnc1S(C)(=O)=O] |
| A96 | 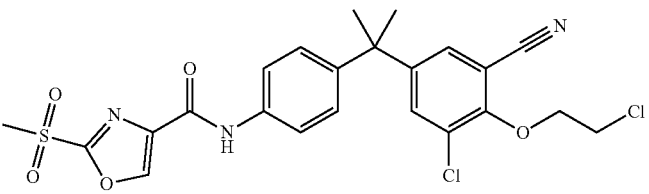 [SMILES: CC(C)(c1ccc(NC(=O)c2coc(S(C)(=O)=O)n2)cc1)c1cc(Cl)c(OCCCl)c(C#N)c1] |
| A97 | 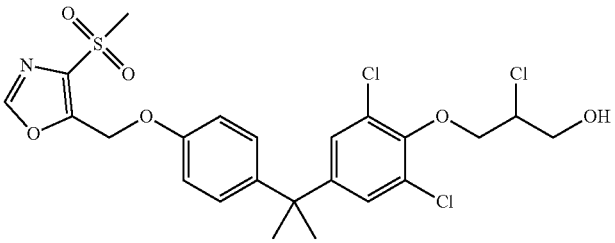 [SMILES: CC(C)(c1ccc(OCc2ocnc2S(C)(=O)=O)cc1)c1cc(Cl)c(OCC(Cl)CO)c(Cl)c1] |
| A98 | 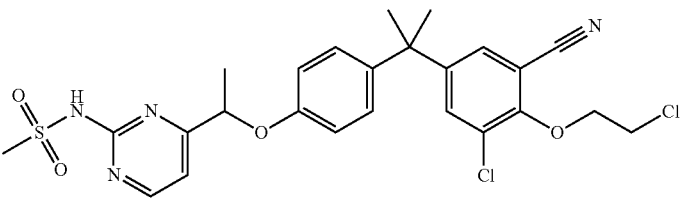 [SMILES: CC(Oc1ccc(C(C)(C)c2cc(Cl)c(OCCCl)c(C#N)c2)cc1)c1ccnc(NS(C)(=O)=O)n1] |
| A99 | 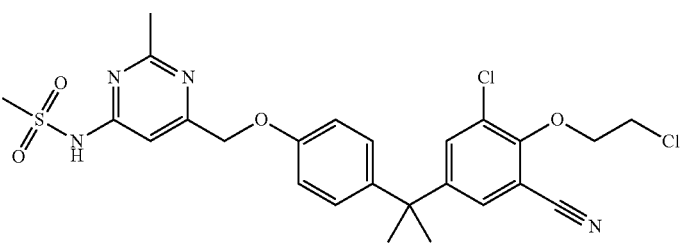 [SMILES: Cc1nc(COc2ccc(C(C)(C)c3cc(Cl)c(OCCCl)c(C#N)c3)cc2)cc(NS(C)(=O)=O)n1] |
| A100 | 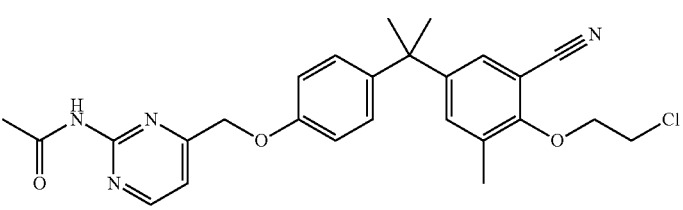 [SMILES: CC(=O)Nc1nccc(COc2ccc(C(C)(C)c3cc(C)c(OCCCl)c(C#N)c3)cc2)n1] |

TABLE A-continued

| Compound ID | Structure |
|---|---|
| A101 | 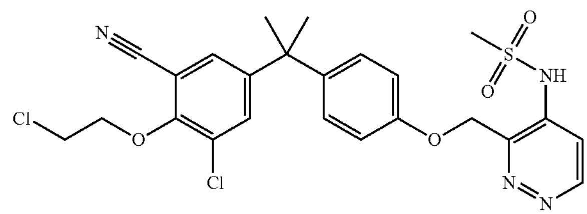 [SMILES: CC(C)(c1ccc(OCc2nnccc2NS(C)(=O)=O)cc1)c1cc(Cl)c(OCCCl)c(C#N)c1] |
| A102 | 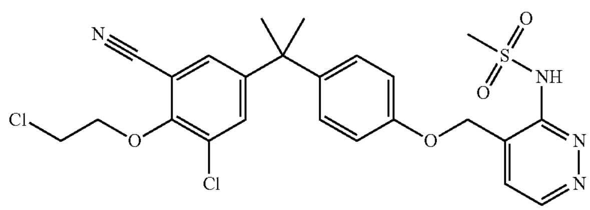 [SMILES: CC(C)(c1ccc(OCc2ccnnc2NS(C)(=O)=O)cc1)c1cc(Cl)c(OCCCl)c(C#N)c1] |
| A103 | 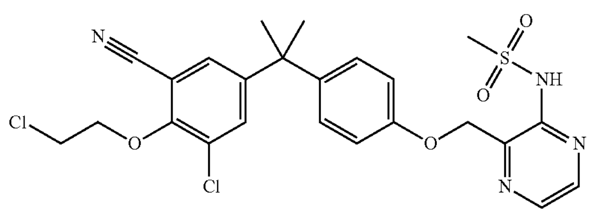 [SMILES: CC(C)(c1ccc(OCc2nccnc2NS(C)(=O)=O)cc1)c1cc(Cl)c(OCCCl)c(C#N)c1] |
| A104 | 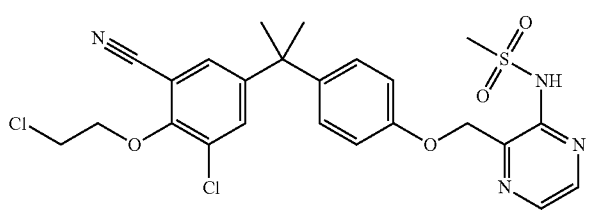 [SMILES: CC(C)(c1ccc(OCc2nccnc2NS(C)(=O)=O)cc1)c1cc(Cl)c(OCCCl)c(C#N)c1] |
| A105 | 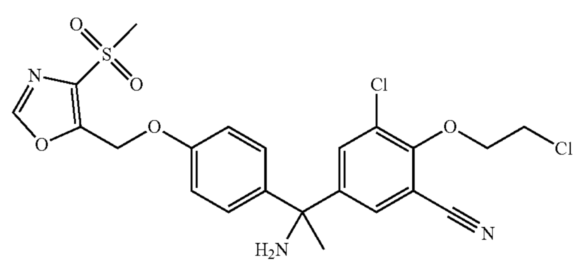 [SMILES: CC(N)(c1ccc(OCc2ocnc2S(C)(=O)=O)cc1)c1cc(Cl)c(OCCCl)c(C#N)c1] |
| A106 | 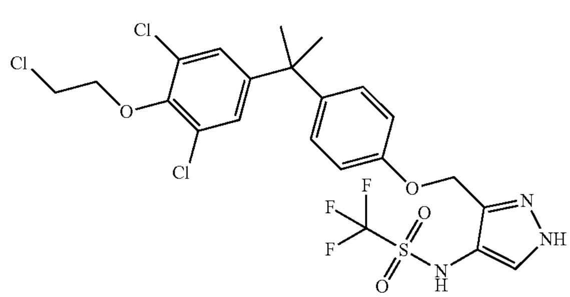 [SMILES: CC(C)(c1ccc(OCc2n[nH]cc2NS(=O)(=O)C(F)(F)F)cc1)c1cc(Cl)c(OCCCl)c(Cl)c1] |

TABLE A-continued

Compounds

| Compound ID | Structure |
|---|---|
| A107 | 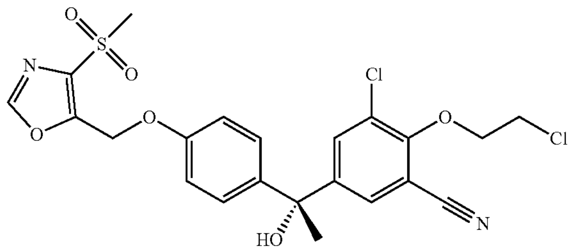 [SMILES: C[C@@](O)(c1ccc(OCc2ocnc2S(C)(=O)=O)cc1)c1cc(Cl)c(OCCCl)c(C#N)c1] |
| A108 | 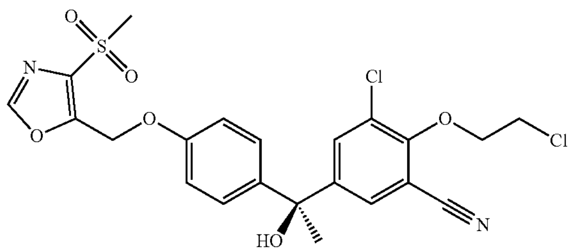 [SMILES: C[C@](O)(c1ccc(OCc2ocnc2S(C)(=O)=O)cc1)c1cc(Cl)c(OCCCl)c(C#N)c1] |
| A109 | 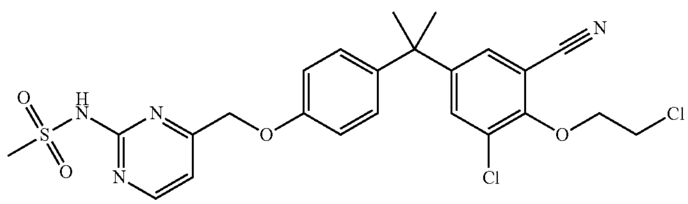 |
| A110 | 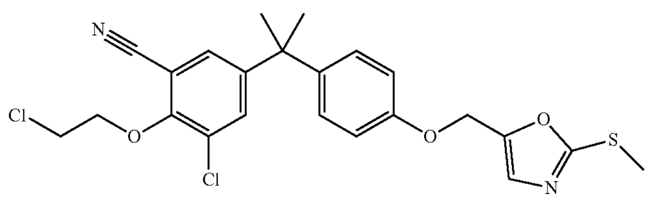 |
| A111 | 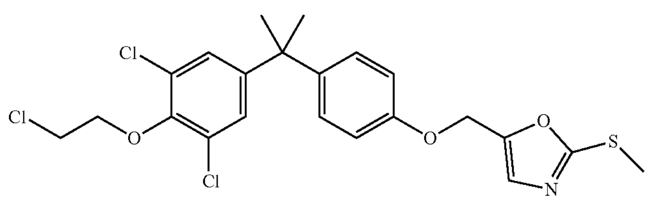 [SMILES: CSc1ncc(COc2ccc(C(C)(C)c3cc(Cl)c(OCCCl)c(Cl)c3)cc2)o1] |
| A112 | 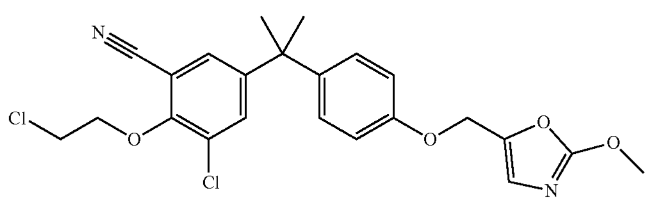 [SMILES: COc1ncc(COc2ccc(C(C)(C)c3cc(Cl)c(OCCCl)c(C#N)c3)cc2)o1] |
| A113 | 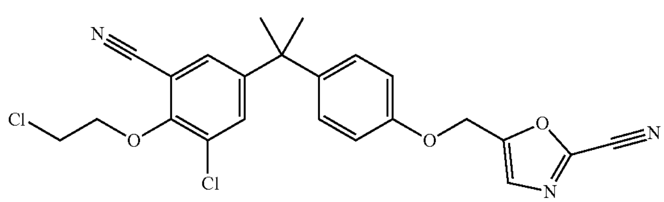 [SMILES: CC(C)(c1ccc(OCc2cnc(C#N)o2)cc1)c1cc(Cl)c(OCCCl)c(C#N)c1] |

TABLE A-continued
Compounds
| Compound ID | Structure |
|---|---|
| A114 | 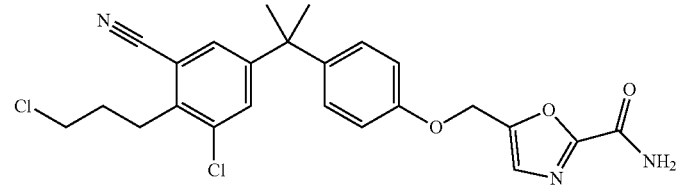 [SMILES: CC(C)(c1ccc(OCc2cnc(C(N)=O)o2)cc1)c1cc(Cl)c(CCCCl)c(C#N)c1] |
| A115 | 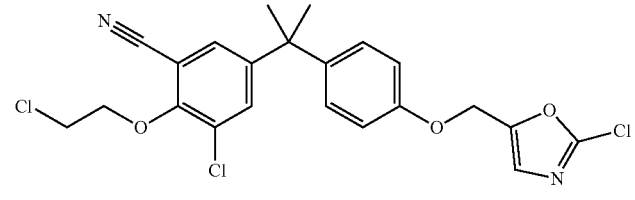 [SMILES: CC(C)(c1ccc(OCc2cnc(Cl)o2)cc1)c1cc(Cl)c(OCCCl)c(C#N)c1] |
| A116 | 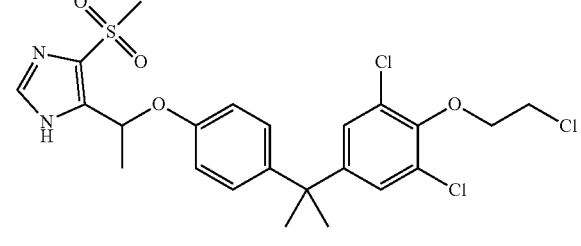 |
| A117 | 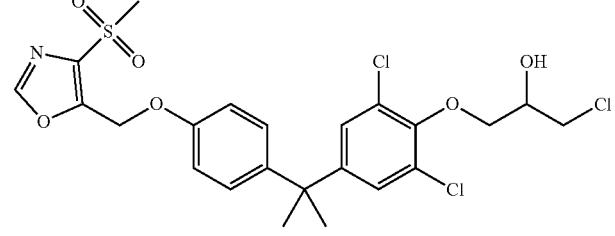 |
| A118 | 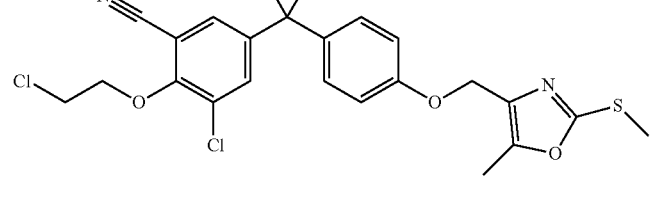 |
| A119 | 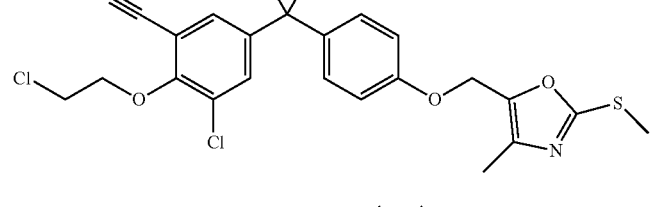 |
| A120 | 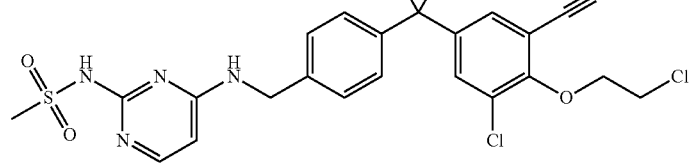 |

TABLE A-continued

Compounds

| Compound ID | Structure |
|---|---|
| A121 | 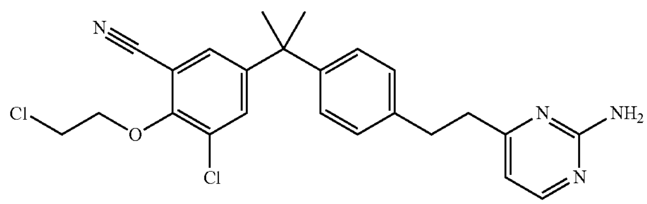 [SMILES: CC(C)(c1ccc(CCc2ccnc(N)n2)cc1)c1cc(Cl)c(OCCCl)c(C#N)c1] |
| A122 | 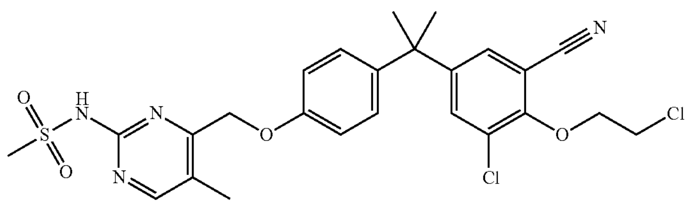 [SMILES: Cc1cnc(NS(C)(=O)=O)nc1COc1ccc(C(C)(C)c2cc(Cl)c(OCCCl)c(C#N)c2)cc1] |
| A123 | 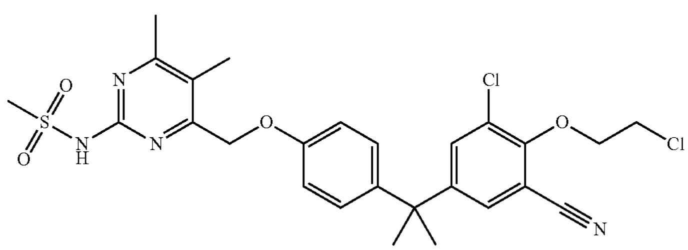 [SMILES: Cc1nc(NS(C)(=O)=O)nc(COc2ccc(C(C)(C)c3cc(Cl)c(OCCCl)c(C#N)c3)cc2)c1C] |
| A124 | 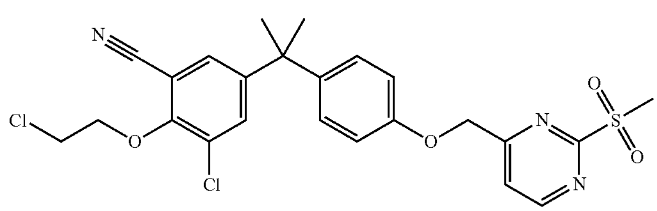 [SMILES: CC(C)(c1ccc(OCc2ccnc(S(C)(=O)=O)n2)cc1)c1cc(Cl)c(OCCCl)c(C#N)c1] |
| A125 | 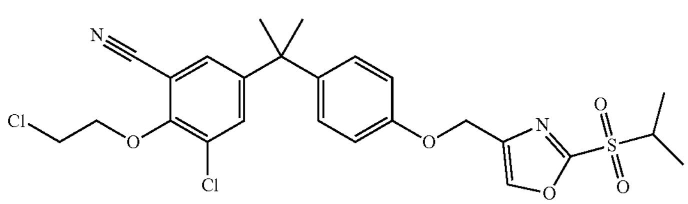 [SMILES: CC(C)S(=O)(=O)c1nc(COc2ccc(C(C)(C)c3cc(Cl)c(OCCCl)c(C#N)c3)cc2)co1] |
| A126 | 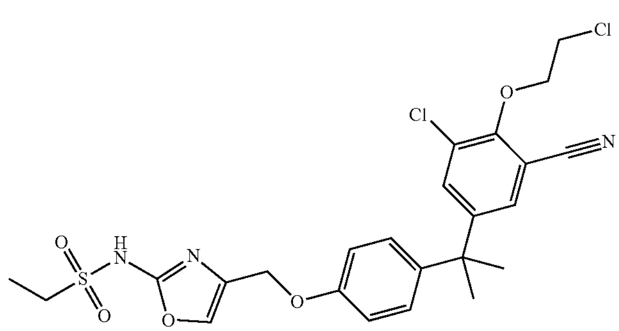 [SMILES: CCS(=O)(=O)Nc1nc(COc2ccc(C(C)(C)c3cc(Cl)c(OCCCl)c(C#N)c3)cc2)co1] |

TABLE A-continued
Compounds
| Compound ID | Structure |
|---|---|
| A127 | 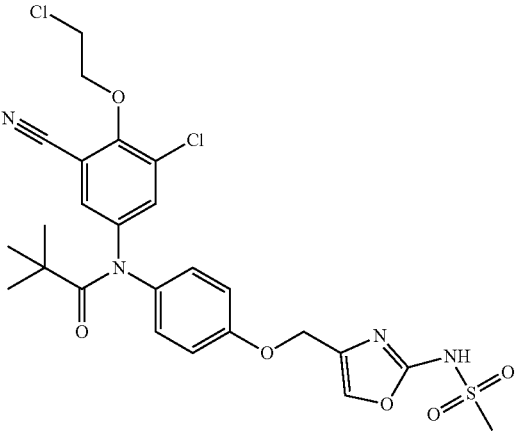 [SMILES: CC(C)(C)C(=O)N(c1ccc(OCc2coc(NS(C)(=O)=O)n2)cc1)c1cc(Cl)c(OCCCl)c(C#N)c1] |
| A128 | 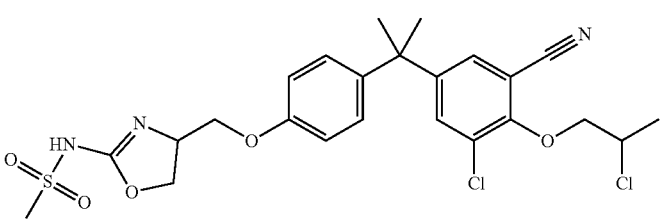 [SMILES: CC(Cl)COc1c(Cl)cc(C(C)(C)c2ccc(OCC3COC(NS(C)(=O)=O)=N3)cc2)cc1C#N] |
| A129 | 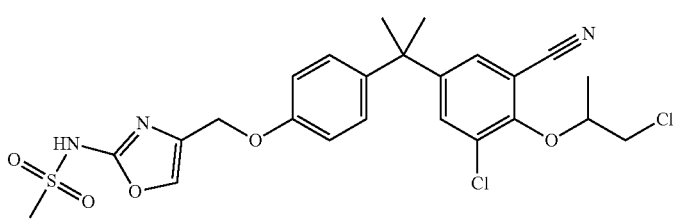 [SMILES: CC(CCl)Oc1c(Cl)cc(C(C)(C)c2ccc(OCc3coc(NS(C)(=O)=O)n3)cc2)cc1C#N] |
| A130 | 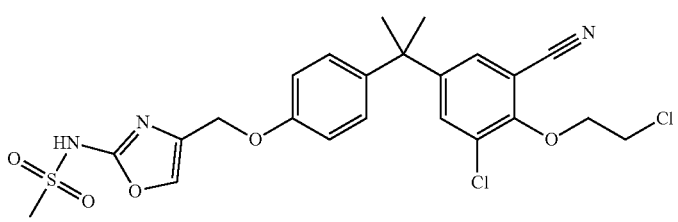 [SMILES: CC(C)(c1ccc(OCc2coc(NS(C)(=O)=O)n2)cc1)c1cc(Cl)c(OCCCl)c(C#N)c1] |
| A131 | 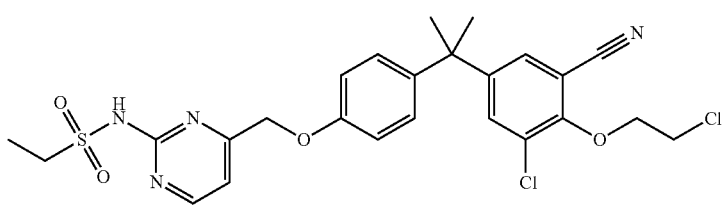 [SMILES: CCS(=O)(=O)Nc1nccc(COc2ccc(C(C)(C)c3cc(Cl)c(OCCCl)c(C#N)c3)cc2)n1] |
| A132 | 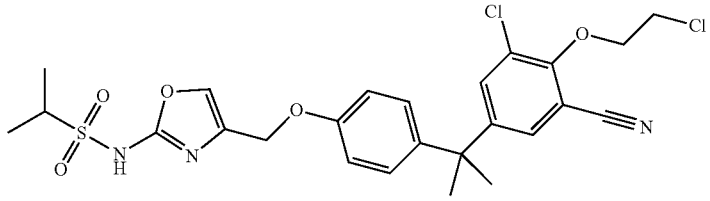 [SMILES: CC(C)S(=O)(=O)Nc1nc(COc2ccc(C(C)(C)c3cc(Cl)c(OCCCl)c(C#N)c3)cc2)co1] |

TABLE A-continued

Compounds

| Compound ID | Structure |
|---|---|
| A133 | 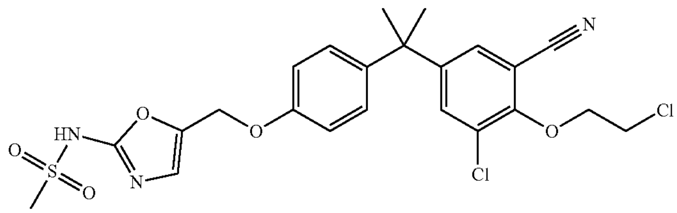 [SMILES: CC(C)(c1ccc(OCc2cnc(NS(C)(=O)=O)o2)cc1)c1cc(Cl)c(OCCCl)c(C#N)c1] |
| A134 | 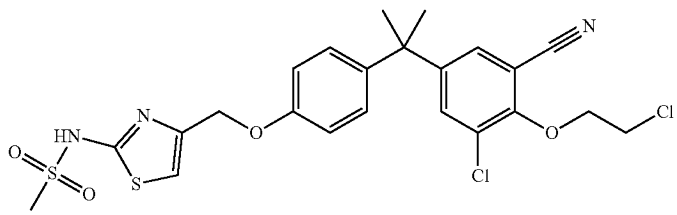 |
| A135 | 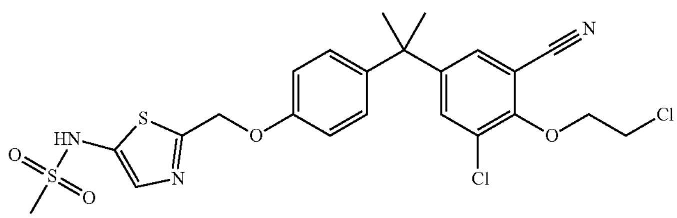 |
| A136 | 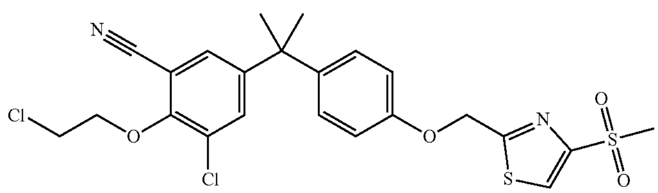 [SMILES: CC(C)(c1ccc(OCc2nc(S(C)(=O)=O)cs2)cc1)c1cc(Cl)c(OCCCl)c(C#N)c1] |
| A137 | 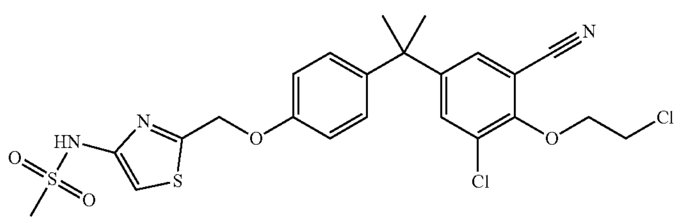 [SMILES: CC(C)(c1ccc(OCc2nc(NS(C)(=O)=O)co2)cc1)c1cc(Cl)c(OCCCl)c(C#N)c1] |
| A138 | 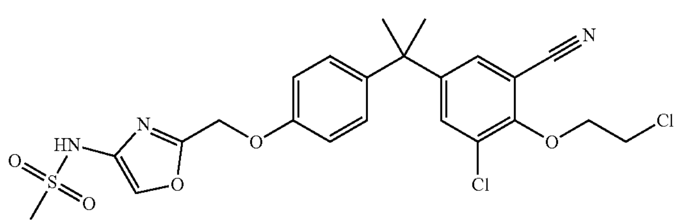 |
| A139 | 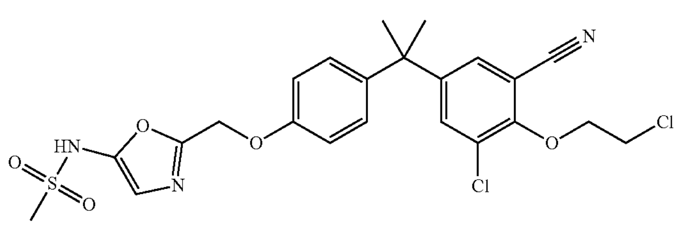 [SMILES: CC(C)(c1ccc(OCc2ncc(NS(C)(=O)=O)o2)cc1)c1cc(Cl)c(OCCCl)c(C#N)c1] |

TABLE A-continued

| Compound ID | Structure |
|---|---|
| A140 | 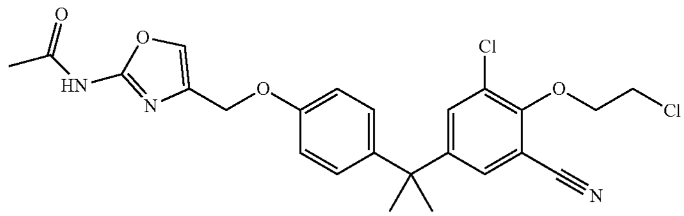 [SMILES: CC(=O)Nc1nc(COc2ccc(C(C)(C)c3cc(Cl)c(OCCCl)c(C#N)c3)cc2)co1] |
| A141 | 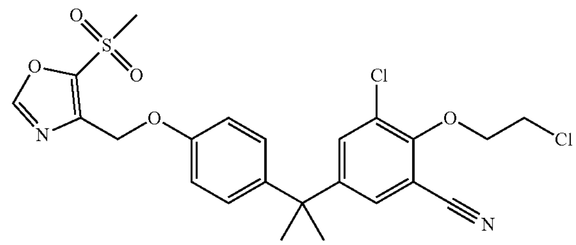 [SMILES: CC(C)(c1ccc(OCc2ncoc2S(C)(=O)=O)cc1)c1cc(Cl)c(OCCCl)c(C#N)c1] |
| A142 | 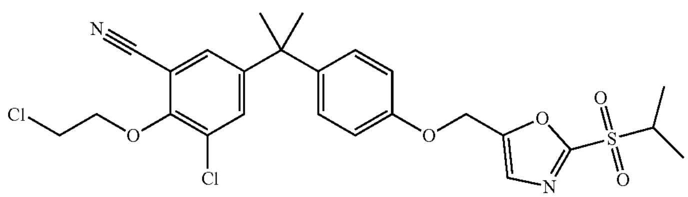 [SMILES: CC(C)S(=O)(=O)c1ncc(COc2ccc(C(C)(C)c3cc(Cl)c(OCCCl)c(C#N)c3)cc2)o1] |
| A143 | 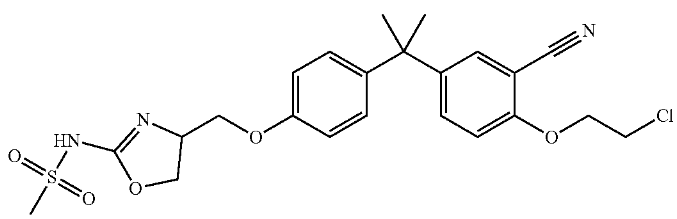 [SMILES: CC(C)(c1ccc(OCC2COC(NS(C)(=O)=O)=N2)cc1)c1ccc(OCCCl)c(C#N)c1] |
| A144 | 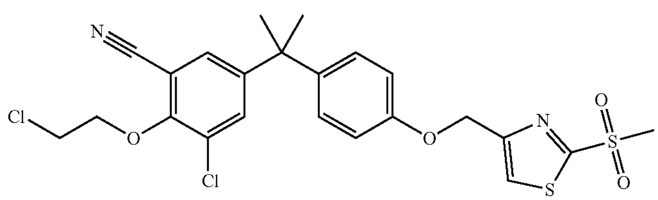 [SMILES: CC(C)(c1ccc(OCc2csc(S(C)(=O)=O)n2)cc1)c1cc(Cl)c(OCCCl)c(C#N)c1] |
| A145 | 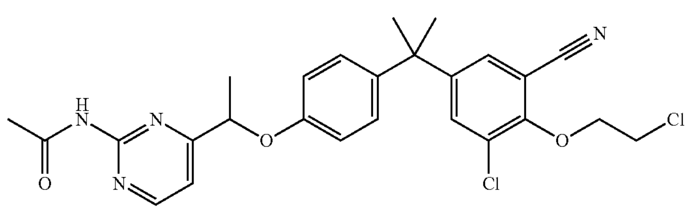 [SMILES: CC(=O)Nc1nccc(C(C)Oc2ccc(C(C)(C)c3cc(Cl)c(OCCCl)c(C#N)c3)cc2)n1] |
| A146 | 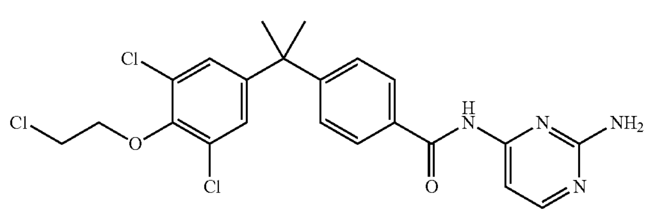 [SMILES: CC(C)(c1ccc(C(=O)Nc2ccnc(N)n2)cc1)c1cc(Cl)c(OCCCl)c(Cl)c1] |

TABLE A-continued
Compounds
| Compound ID | Structure |
|---|---|
| A147 | 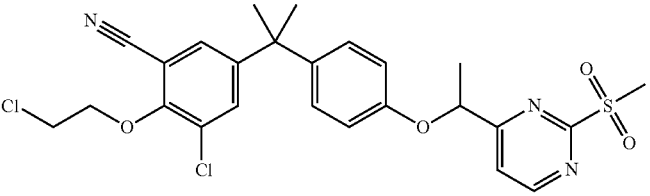 [SMILES: CC(Oc1ccc(C(C)(C)c2cc(Cl)c(OCCCl)c(C#N)c2)cc1)c1ccnc(S(C)(=O)=O)n1] |
| A148 | 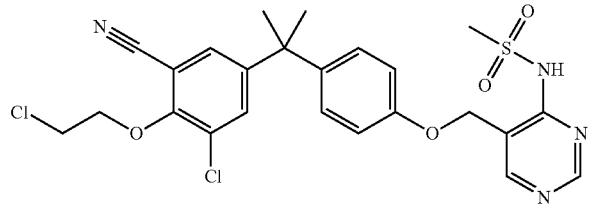 [SMILES: CC(C)(c1ccc(OCc2cncnc2NS(C)(=O)=O)cc1)c1cc(Cl)c(OCCCl)c(C#N)c1] |
| A149 | 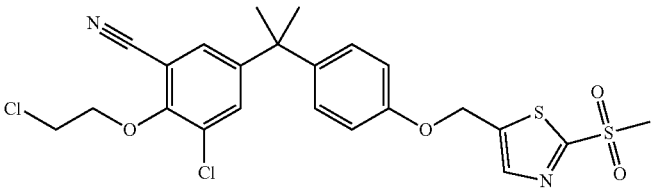 [SMILES: CC(C)(c1ccc(OCc2cnc(S(C)(=O)=O)s2)cc1)c1cc(Cl)c(OCCCl)c(C#N)c1] |
| A150 | 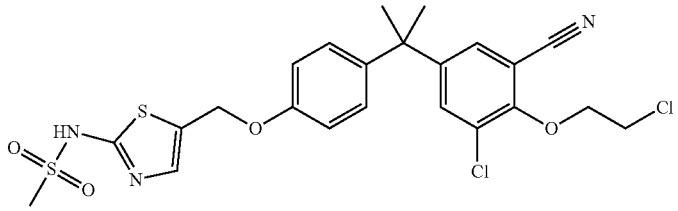 [SMILES: CC(C)(c1ccc(OCc2cnc(NS(C)(=O)=O)s2)cc1)c1cc(Cl)c(OCCCl)c(C#N)c1] |
| A151 | 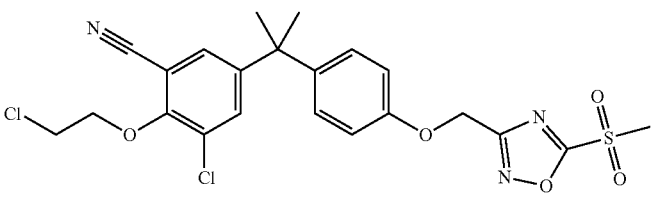 [SMILES: CC(C)(c1ccc(OCc2noc(S(C)(=O)=O)n2)cc1)c1cc(Cl)c(OCCCl)c(C#N)c1] |
| A152 | 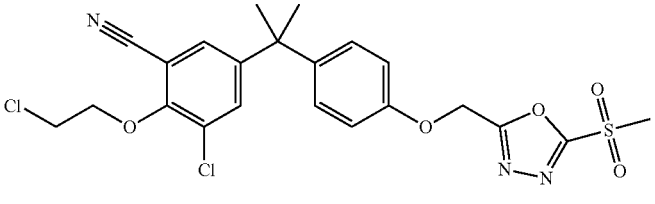 [SMILES: CC(C)(c1ccc(OCc2nnc(S(C)(=O)=O)o2)cc1)c1cc(Cl)c(OCCCl)c(C#N)c1] |
| A153 | 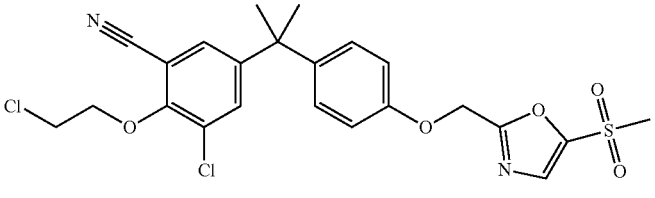 [SMILES: CC(C)(c1ccc(OCc2ncc(S(C)(=O)=O)o2)cc1)c1cc(Cl)c(OCCCl)c(C#N)c1] |

TABLE A-continued
| Compound ID | Structure |
|---|---|
| A154 | 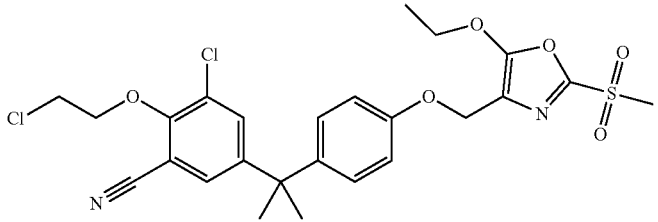 [SMILES: CCOc1oc(S(C)(=O)=O)nc1COc1ccc(C(C)(C)c2cc(Cl)c(OCCCl)c(C#N)c2)cc1] |
| A155 | 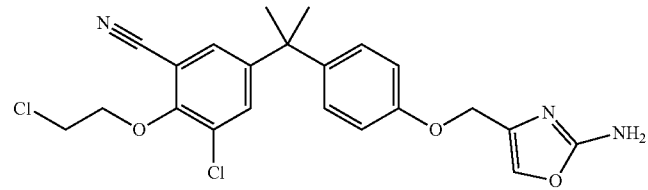 [SMILES: CC(C)(c1ccc(OCc2coc(N)n2)cc1)c1cc(Cl)c(OCCCl)c(C#N)c1] |
| A156 | 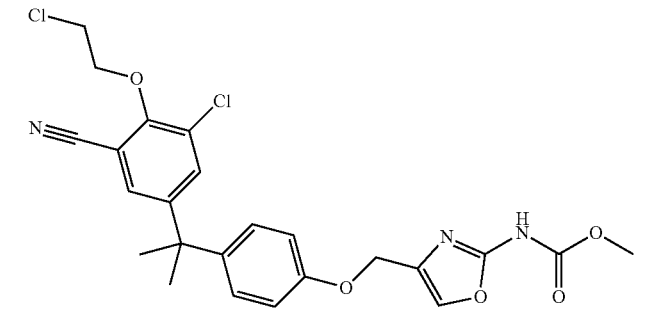 [SMILES: COC(=O)Nc1nc(COc2ccc(C(C)(C)c3cc(Cl)c(OCCCl)c(C#N)c3)cc2)co1] |
| A157 | 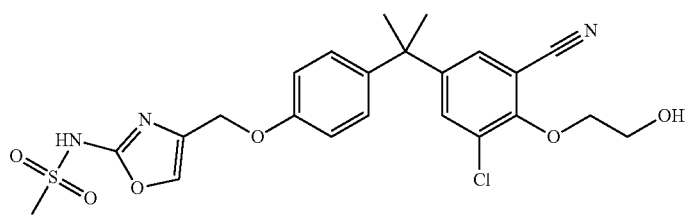 [SMILES: CC(C)(c1ccc(OCc2coc(NS(C)(=O)=O)n2)cc1)c1cc(Cl)c(OCCO)c(C#N)c1] |
| A158 | 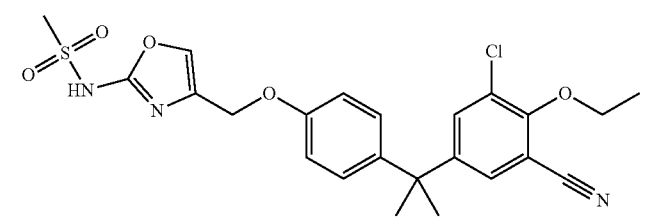 [SMILES: CCOc1c(Cl)cc(C(C)(C)c2ccc(OCc3coc(NS(C)(=O)=O)n3)cc2)cc1C#N] |
| A159 | 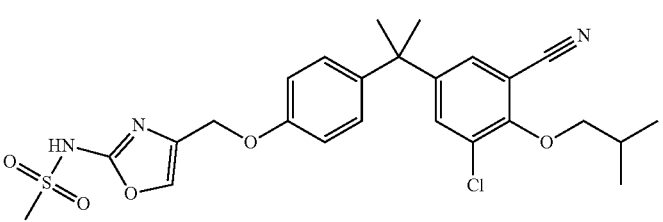 [SMILES: CC(C)COc1c(Cl)cc(C(C)(C)c2ccc(OCc3coc(NS(C)(=O)=O)n3)cc2)cc1C#N] |

TABLE A-continued

| Compound ID | Structure |
|---|---|
| A160 | 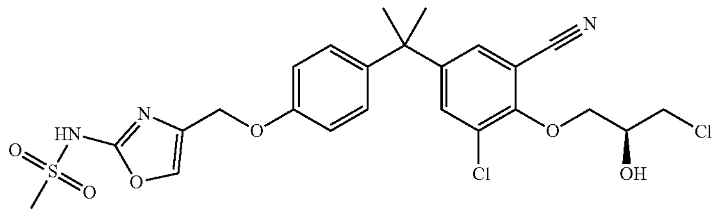 [SMILES: CC(C)(c1ccc(OCc2coc(NS(C)(=O)=O)n2)cc1)c1cc(Cl)c(OC[C@H](O)CCl)c(C#N)c1] |
| A161 | 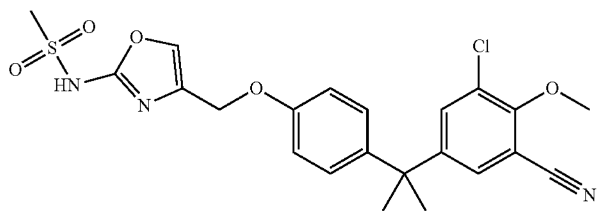 [SMILES: COc1c(Cl)cc(C(C)(C)c2ccc(OCc3coc(NS(C)(=O)=O)n3)cc2)cc1C#N] |
| A162 | 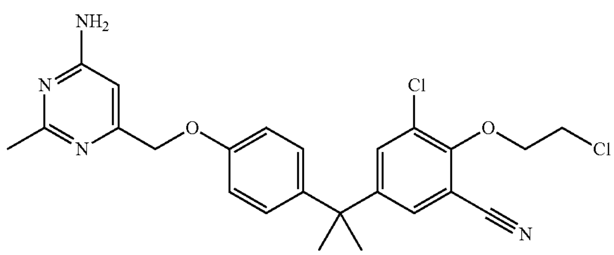 [SMILES: Cc1nc(N)cc(COc2ccc(C(C)(C)c3cc(Cl)c(OCCCl)c(C#N)c3)cc2)n1] |
| A163 | 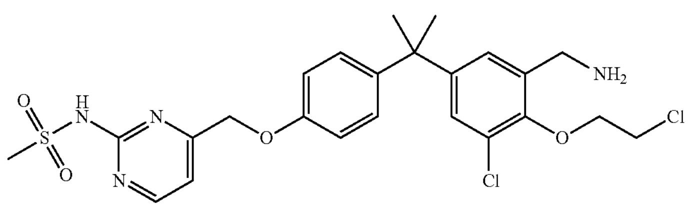 [SMILES: CC(C)(c1ccc(OCc2ccnc(NS(C)(=O)=O)n2)cc1)c1cc(Cl)c(OCCCl)c(CN)c1] |
| A164 | 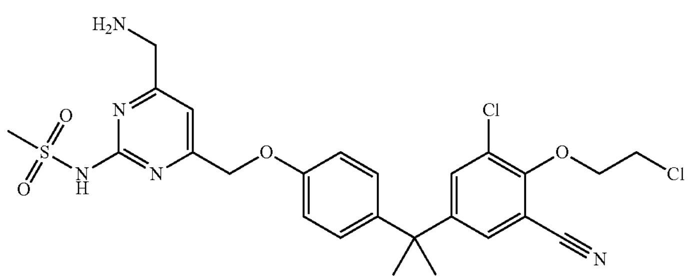 [SMILES: CC(C)(c1ccc(OCc2cc(CN)nc(NS(C)(=O)=O)n2)cc1)c1cc(Cl)c(OCCCl)c(C#N)c1] |
| A165 | 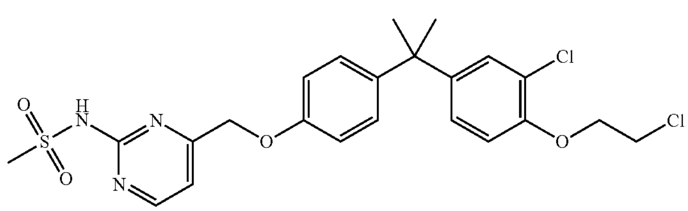 [SMILES: CC(C)(c1ccc(OCc2ccnc(NS(C)(=O)=O)n2)cc1)c1ccc(OCCCl)c(Cl)c1] |

TABLE A-continued

| Compound ID | Structure |
|---|---|
| A166 | 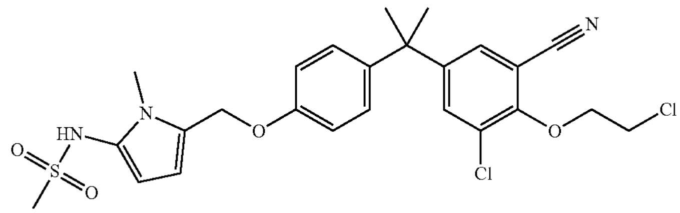 [SMILES: Cn1c(COc2ccc(C(C)(C)c3cc(Cl)c(OCCCl)c(C#N)c3)cc2)ccc1NS(C)(=O)=O] |
| A167 | 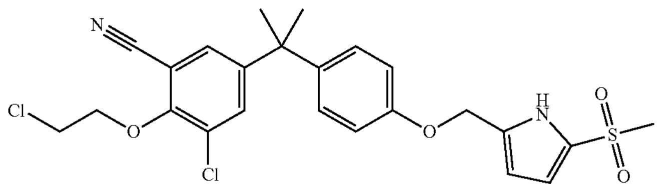 [SMILES: CC(C)(c1ccc(OCc2ccc(S(C)(=O)=O)[nH]2)cc1)c1cc(Cl)c(OCCCl)c(C#N)c1] |
| A168 | 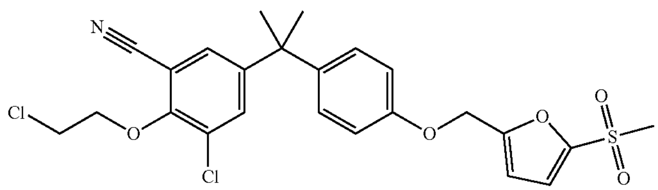 [SMILES: CC(C)(c1ccc(OCc2ccc(S(C)(=O)=O)o2)cc1)c1cc(Cl)c(OCCCl)c(C#N)c1] |
| A169 | 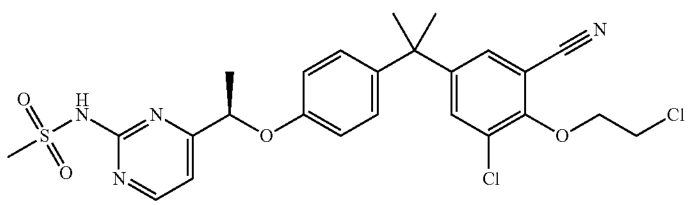 [SMILES: C[C@@H](Oc1ccc(C(C)(C)c2cc(Cl)c(OCCCl)c(C#N)c2)cc1)c1ccnc(NS(C)(=O)=O)n1] |
| A170 | 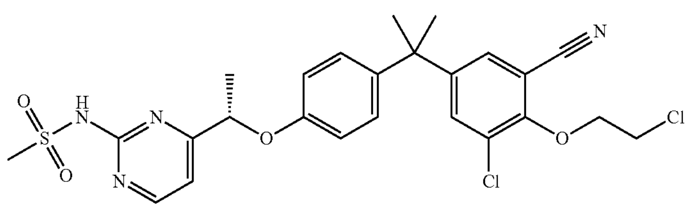 [SMILES: C[C@H](Oc1ccc(C(C)(C)c2cc(Cl)c(OCCCl)c(C#N)c2)cc1)c1ccnc(NS(C)(=O)=O)n1] |
| A171 | 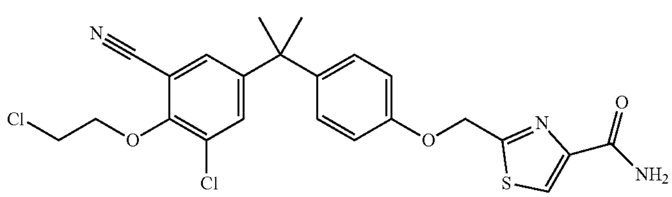 [SMILES: CC(C)(c1ccc(OCc2nc(C(N)=O)cs2)cc1)c1cc(Cl)c(OCCCl)c(C#N)c1] |
| A172 | 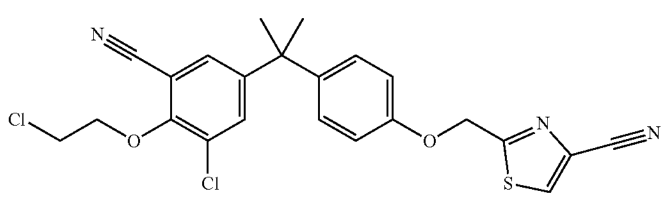 |

TABLE A-continued

Compounds

| Compound ID | Structure |
|---|---|
| A173 | 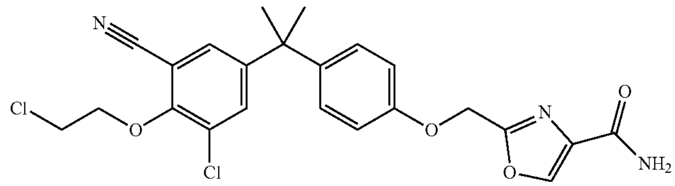 [SMILES: CC(C)(c1ccc(OCc2nc(C(N)=O)co2)cc1)c1cc(Cl)c(OCCCl)c(C#N)c1] |
| A174 | 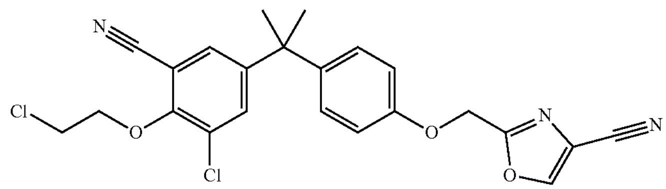 [SMILES: CC(C)(c1ccc(OCc2nc(C#N)co2)cc1)c1cc(Cl)c(OCCCl)c(C#N)c1] |
| A175 | 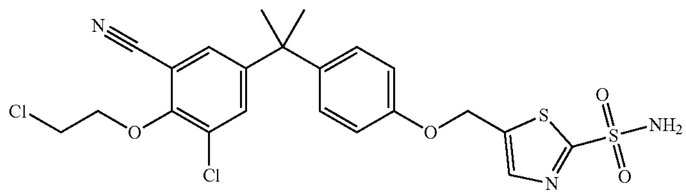 [SMILES: CC(C)(c1ccc(OCc2cnc(S(N)(=O)=O)s2)cc1)c1cc(Cl)c(OCCCl)c(C#N)c1] |
| A176 | 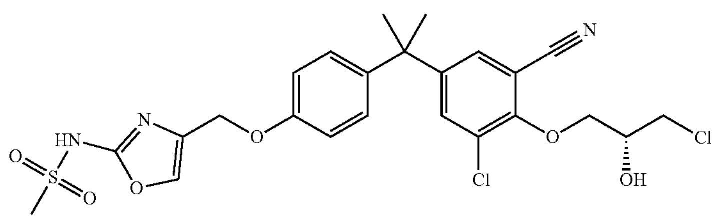 [SMILES: CC(C)(c1ccc(OCc2coc(NS(C)(=O)=O)n2)cc1)c1cc(Cl)c(OC[C@@H](O)CCl)c(C#N)c1] |
| A177 | 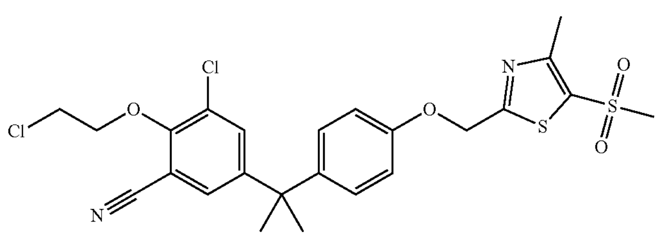 [SMILES: Cc1nc(COc2ccc(C(C)(C)c3cc(Cl)c(OCCCl)c(C#N)c3)cc2)sc1S(C)(=O)=O] |
| A178 | 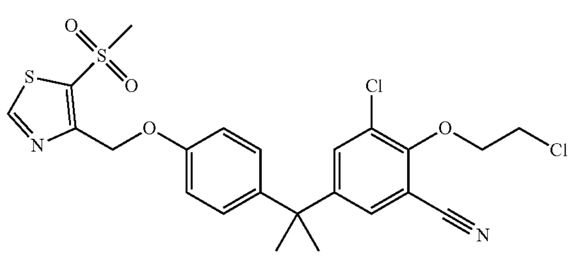 |
| A179 | 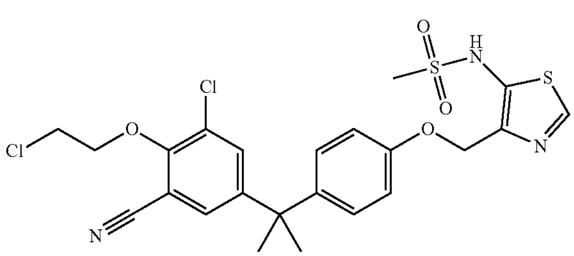 [SMILES: CC(C)(c1ccc(OCc2ncsc2NS(C)(=O)=O)cc1)c1cc(Cl)c(OCCCl)c(C#N)c1] |

TABLE A-continued

Compounds

| Compound ID | Structure |
|---|---|
| A180 | 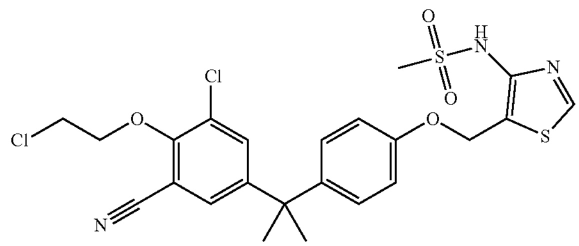 [SMILES: CC(C)(c1ccc(OCc2scnc2NS(C)(=O)=O)cc1)c1cc(Cl)c(OCCCl)c(C#N)c1] |
| A181 | 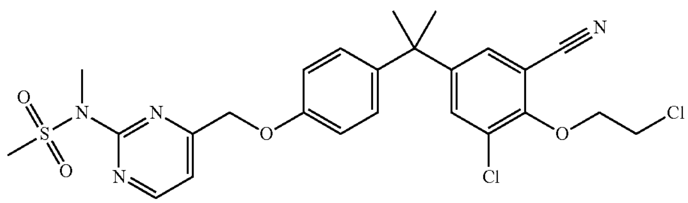 [SMILES: CN(c1nccc(COc2ccc(C(C)(C)c3cc(Cl)c(OCCCl)c(C#N)c3)cc2)n1)S(C)(=O)=O] |
| A182 | 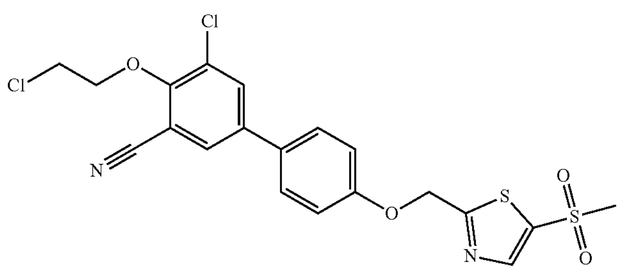 [SMILES: CS(=O)(=O)c1cnc(COc2ccc(-c3cc(Cl)c(OCCCl)c(C#N)c3)cc2)s1] |
| A183 | 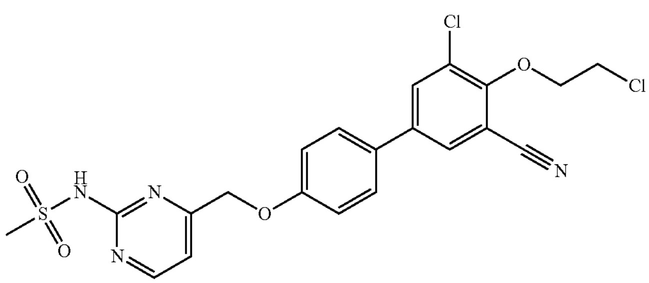 [SMILES: CS(=O)(=O)Nc1nccc(COc2ccc(-c3cc(Cl)c(OCCCl)c(C#N)c3)cc2)n1] |
| A184 | 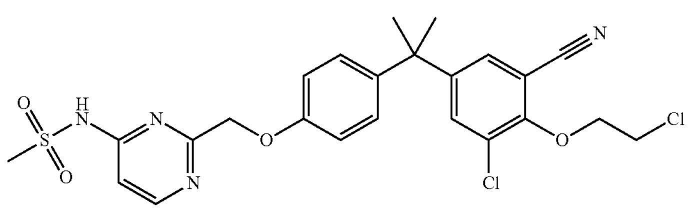 [SMILES: CC(C)(c1ccc(OCc2nccc(NS(C)(=O)=O)n2)cc1)c1cc(Cl)c(OCCCl)c(C#N)c1] |
| A185 | 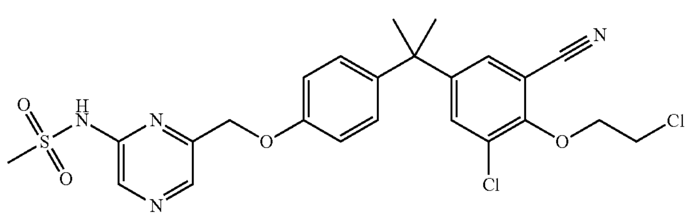 [SMILES: CC(C)(c1ccc(OCc2cncc(NS(C)(=O)=O)n2)cc1)c1cc(Cl)c(OCCCl)c(C#N)c1] |

TABLE A-continued
Compounds
| Compound ID | Structure |
|---|---|
| A186 | 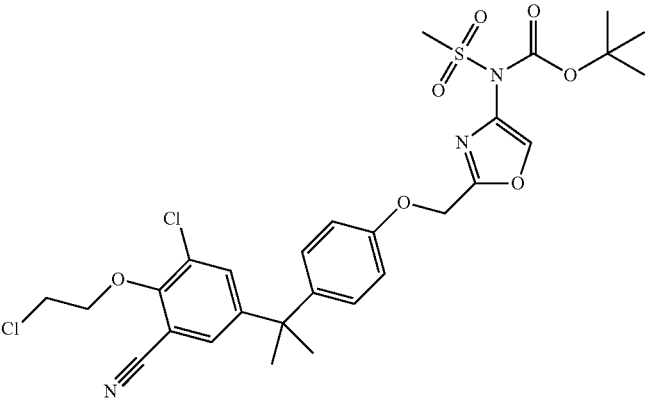 [SMILES: CC(C)(C)OC(=O)N(c1coc(COc2ccc(C(C)(C)c3cc(Cl)c(OCCCl)c(C#N)c3)cc2)n1)S(C)(=O)=O] |
| A187 | 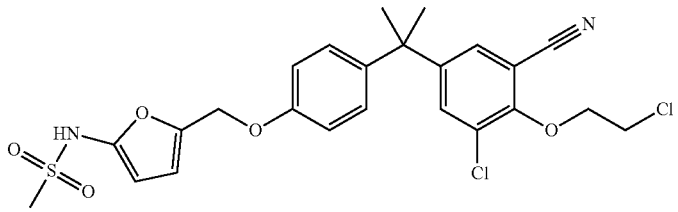 [SMILES: CC(C)(c1ccc(OCc2ccc(NS(C)(=O)=O)o2)cc1)c1cc(Cl)c(OCCCl)c(C#N)c1] |
| A188 | 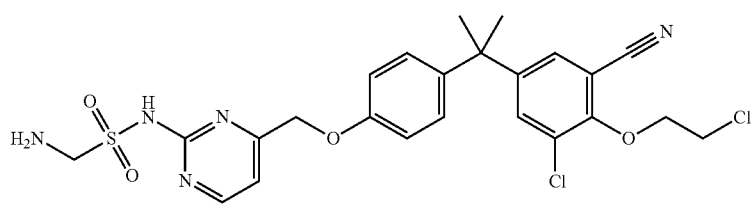 [SMILES: CC(C)(c1ccc(OCc2ccnc(NS(=O)(=O)CN)n2)cc1)c1cc(Cl)c(OCCCl)c(C#N)c1] |
| A189 | 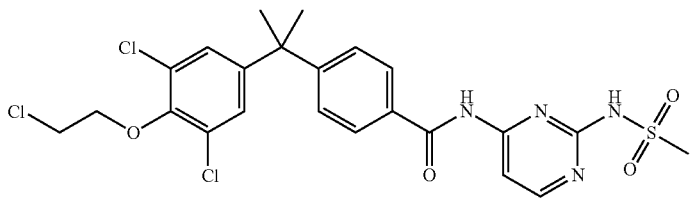 [SMILES: CC(C)(c1ccc(C(=O)Nc2ccnc(NS(C)(=O)=O)n2)cc1)c1cc(Cl)c(OCCCl)c(Cl)c1] |
| A190 | 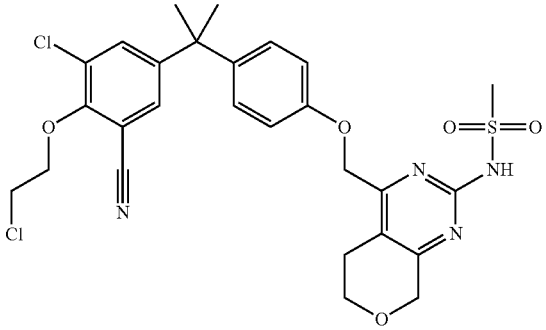 [SMILES: CC(C)(c1ccc(OCc2nc(NS(C)(=O)=O)nc3c2CCOC3)cc1)c1cc(Cl)c(OCCCl)c(C#N)c1] |

TABLE A-continued

Compounds

| Compound ID | Structure |
|---|---|
| A191 | 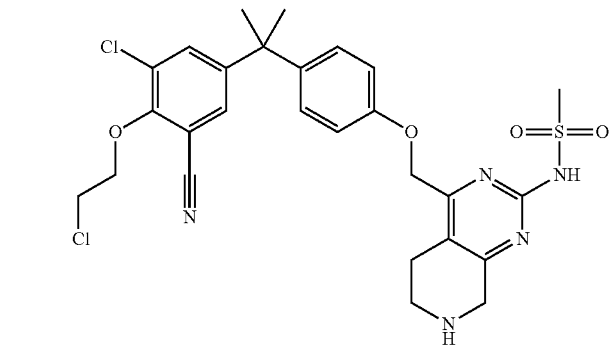 [SMILES: CC(C)(c1ccc(OCc2nc(NS(C)(=O)=O)nc3c2CCNC3)cc1)c1cc(Cl)c(OCCCl)c(C#N)c1] |
| A192 | 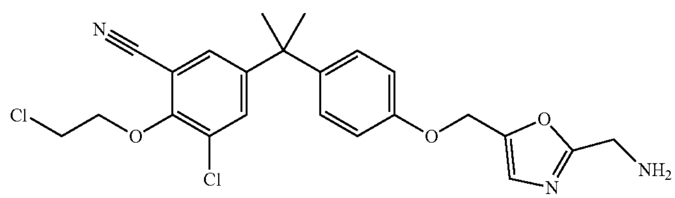 [SMILES: CC(C)(c1ccc(OCc2cnc(CN)o2)cc1)c1cc(Cl)c(OCCCl)c(C#N)c1] |
| A193 | 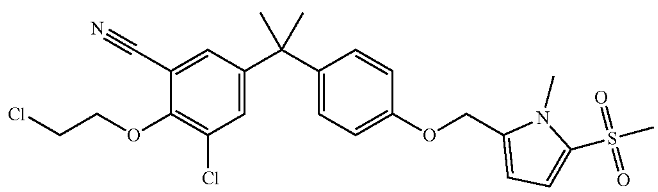 [SMILES: Cn1c(COc2ccc(C(C)(C)c3cc(Cl)c(OCCCl)c(C#N)c3)cc2)ccc1S(C)(=O)=O] |
| A194 | 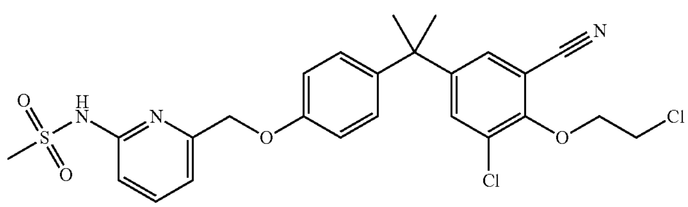 |
| A195 | 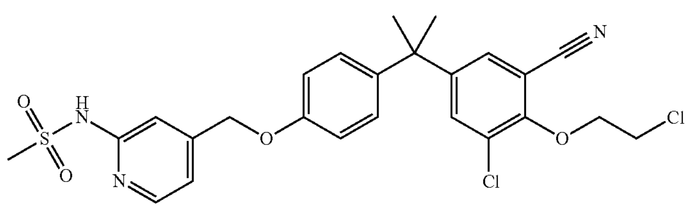 [SMILES: CC(C)(c1ccc(OCc2ccnc(NS(C)(=O)=O)c2)cc1)c1cc(Cl)c(OCCCl)c(C#N)c1] |
| A196 | 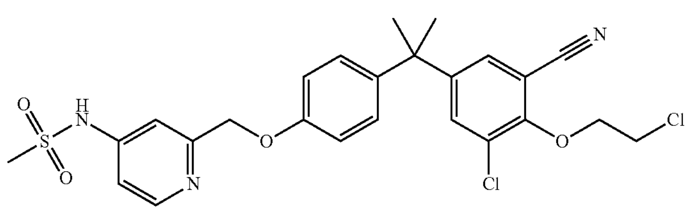 [SMILES: CC(C)(c1ccc(OCc2cc(NS(C)(=O)=O)ccn2)cc1)c1cc(Cl)c(OCCCl)c(C#N)c1] |

TABLE A-continued

Compounds

| Compound ID | Structure |
|---|---|
| A197 | 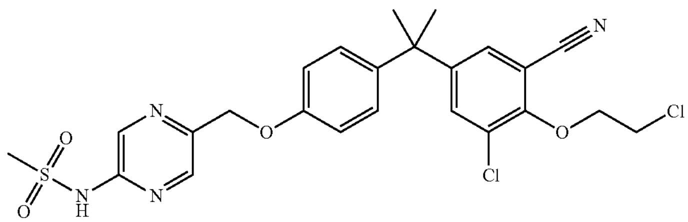 [SMILES: CC(C)(c1ccc(OCc2cnc(NS(C)(=O)=O)cn2)cc1)c1cc(Cl)c(OCCCl)c(C#N)c1] |
| A198 | 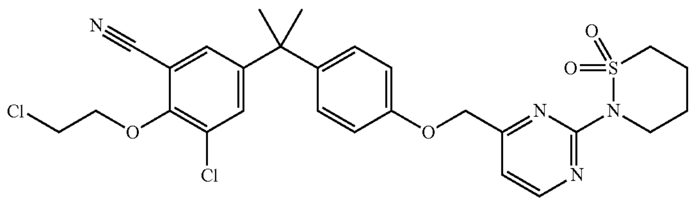 [SMILES: CC(C)(c1ccc(OCc2ccnc(N3CCCCS3(=O)=O)n2)cc1)c1cc(Cl)c(OCCCl)c(C#N)c1] |
| A199 | 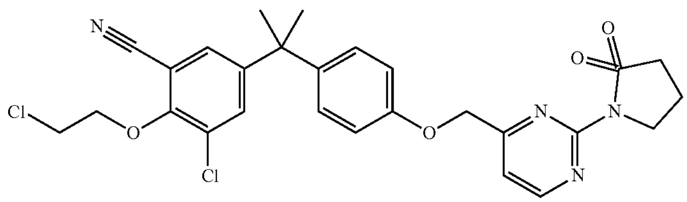 |
| A200 | 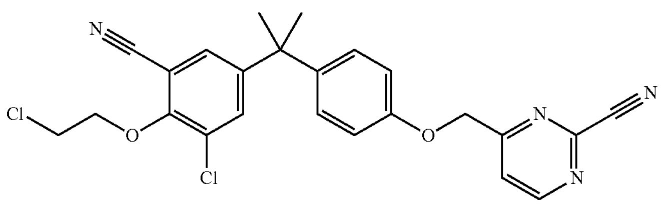 [SMILES: CC(C)(c1ccc(OCc2ccnc(C#N)n2)cc1)c1cc(Cl)c(OCCCl)c(C#N)c1] |
| A201 | 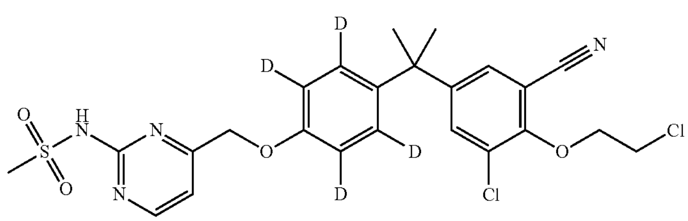 [SMILES: [2H]c1c([2H])c(C(C)(C)c2cc(Cl)c(OCCCl)c(C#N)c2)c([2H])c([2H])c1OCc1ccnc(NS(C)(=O)=O)n1] |
| A202 | 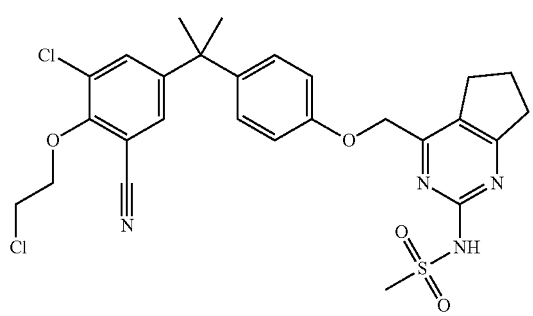 [SMILES: CC(C)(c1ccc(OCc2nc(NS(C)(=O)=O)nc3c2CCC3)cc1)c1cc(Cl)c(OCCCl)c(C#N)c1] |

TABLE A-continued

Compounds

| Compound ID | Structure |
|---|---|
| A203 | 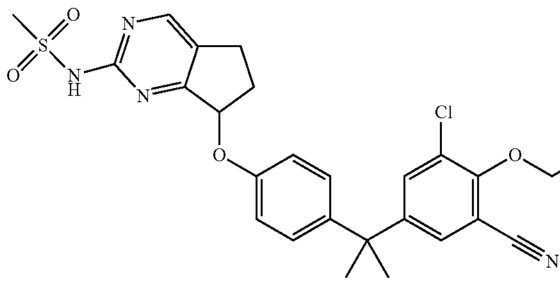 |
| A204 | 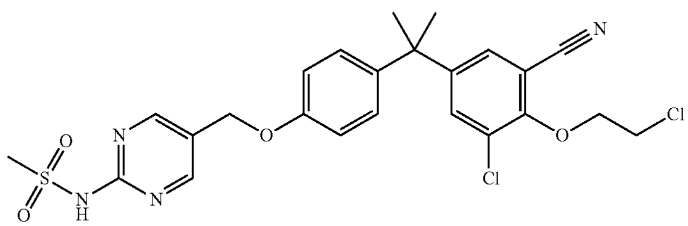 [SMILES: CC(C)(c1ccc(OCc2cnc(NS(C)(=O)=O)nc2)cc1)c1cc(Cl)c(OCCCl)c(C#N)c1] |
| A205 | 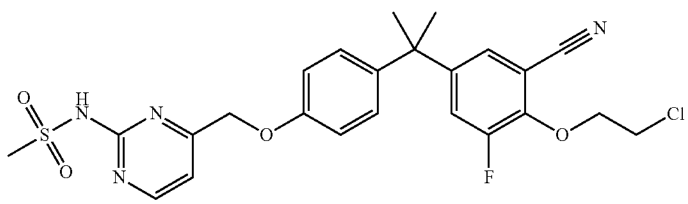 [SMILES: CC(C)(c1ccc(OCc2ccnc(NS(C)(=O)=O)n2)cc1)c1cc(F)c(OCCCl)c(C#N)c1] |
| A206 | 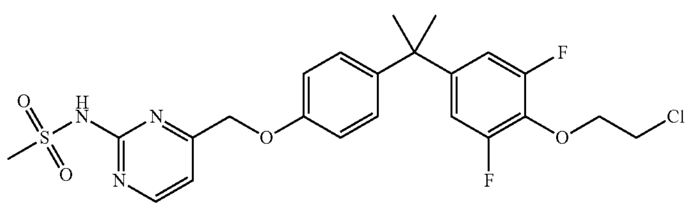 [SMILES: CC(C)(c1ccc(OCc2ccnc(NS(C)(=O)=O)n2)cc1)c1cc(F)c(OCCCl)c(F)c1] |
| A207 | 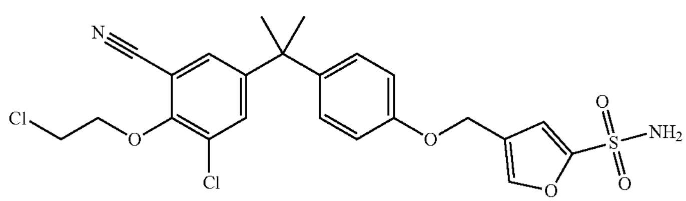 |
| A208 | 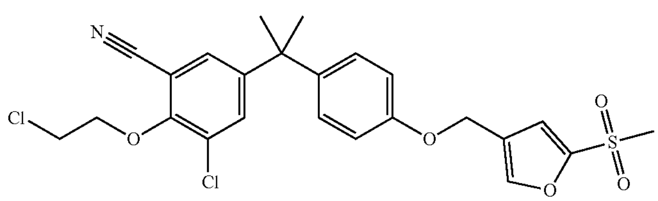 [SMILES: CC(C)(c1ccc(OCc2coc(S(C)(=O)=O)c2)cc1)c1cc(Cl)c(OCCCl)c(C#N)c1] |
| A209 | 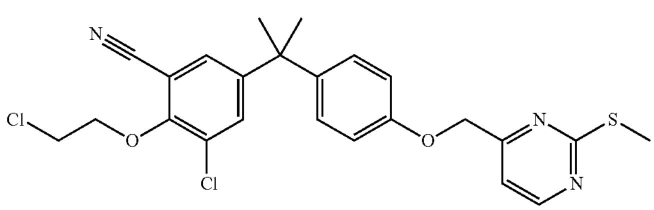 [SMILES: CSc1nccc(COc2ccc(C(C)(C)c3cc(Cl)c(OCCCl)c(C#N)c3)cc2)n1] |

TABLE A-continued

Compounds

| Compound ID | Structure |
|---|---|
| A210 | 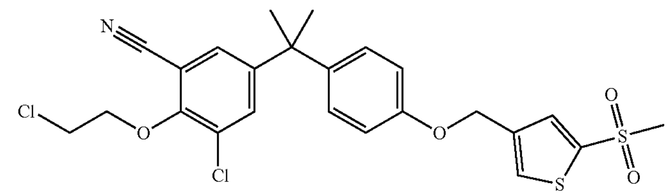 [SMILES: CC(C)(c1ccc(OCc2csc(S(C)(=O)=O)c2)cc1)c1cc(Cl)c(OCCCl)c(C#N)c1] |
| A211 | 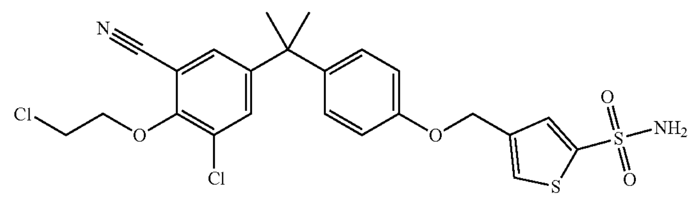 [SMILES: CC(C)(c1ccc(OCc2csc(S(N)(=O)=O)c2)cc1)c1cc(Cl)c(OCCCl)c(C#N)c1] |
| A212 | 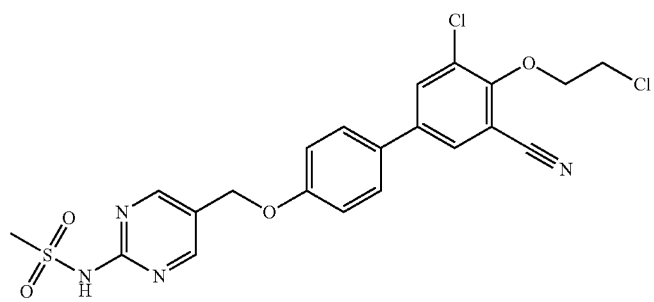 [SMILES: CS(=O)(=O)Nc1ncc(COc2ccc(-c3cc(Cl)c(OCCCl)c(C#N)c3)cc2)cn1] |
| A213 | 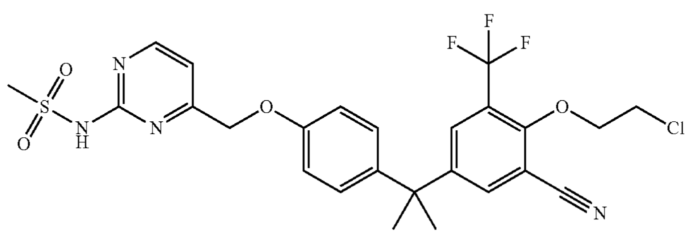 [SMILES: CC(C)(c1ccc(OCc2ccnc(NS(C)(=O)=O)n2)cc1)c1cc(C#N)c(OCCCl)c(C(F)(F)F)c1] |
| A214 | 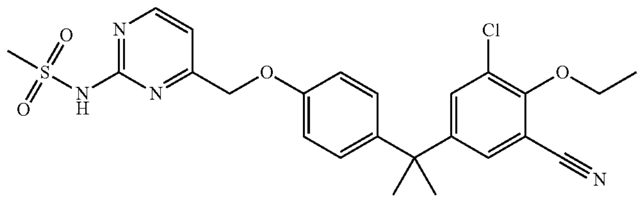 [SMILES: CCOc1c(Cl)cc(C(C)(C)c2ccc(OCc3ccnc(NS(C)(=O)=O)n3)cc2)cc1C#N] |
| A215 | 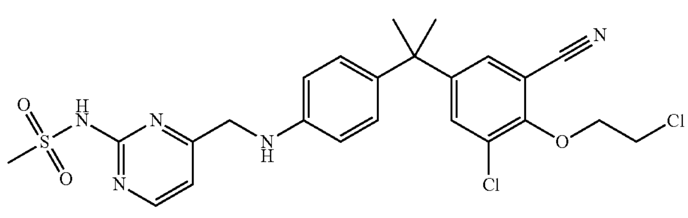 [SMILES: CC(C)(c1ccc(NCc2ccnc(NS(C)(=O)=O)n2)cc1)c1cc(Cl)c(OCCCl)c(C#N)c1] |

TABLE A-continued

| Compound ID | Structure |
|---|---|
| A216 | 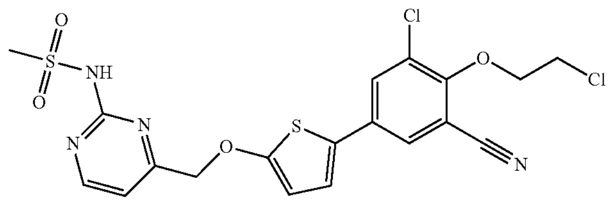 [SMILES: CS(=O)(=O)Nc1nccc(COc2ccc(-c3cc(Cl)c(OCCCl)c(C#N)c3)s2)n1] |
| A217 | 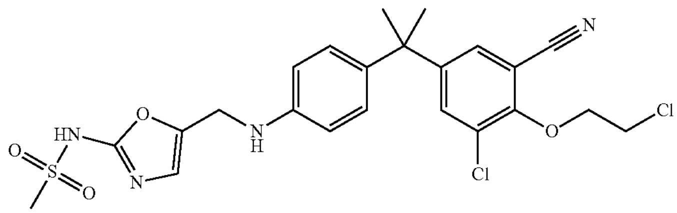 |
| A218 | 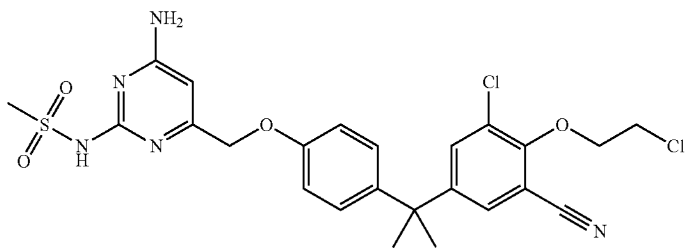 [SMILES: CC(C)(c1ccc(OCc2cc(N)nc(NS(C)(=O)=O)n2)cc1)c1cc(Cl)c(OCCCl)c(C#N)c1] |
| A219 | 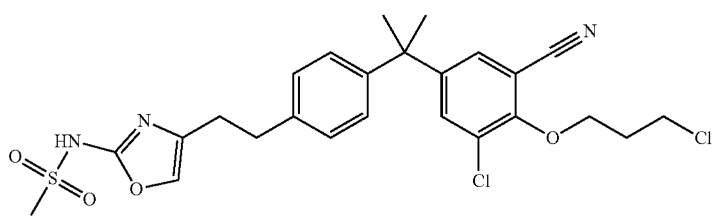 [SMILES: CC(C)(c1ccc(CCc2coc(NS(C)(=O)=O)n2)cc1)c1cc(Cl)c(OCCCCl)c(C#N)c1] |
| A220 | 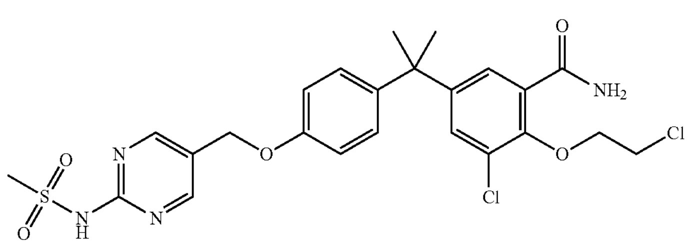 [SMILES: CC(C)(c1ccc(OCc2cnc(NS(C)(=O)=O)nc2)cc1)c1cc(Cl)c(OCCCl)c(C(N)=O)c1] |
| A221 | 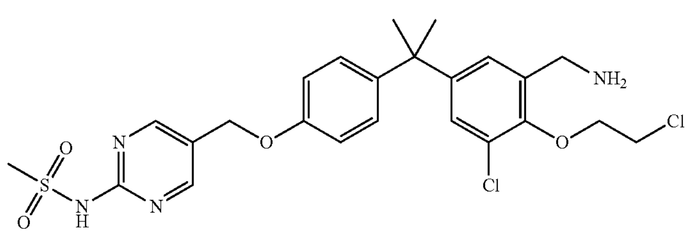 [SMILES: CC(C)(c1ccc(OCc2cnc(NS(C)(=O)=O)nc2)cc1)c1cc(Cl)c(OCCCl)c(CN)c1] |

TABLE A-continued

| Compound ID | Structure |
|---|---|
| A222 | (structure) |
| A223 | (structure) |
| A224 | (structure) |
| A225 | (structure) |
| A226 | (structure) |
| A227 | (structure) |
| A228 | (structure) |

TABLE A-continued

Compounds

| Compound ID | Structure |
|---|---|
| A229 | 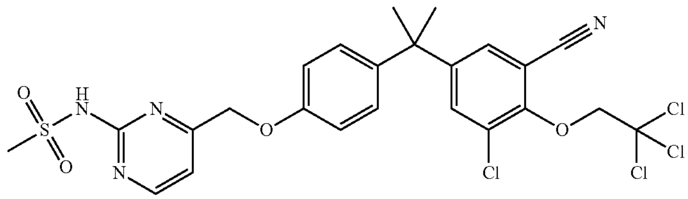 [SMILES: CC(C)(c1ccc(OCc2ccnc(NS(C)(=O)=O)n2)cc1)c1cc(Cl)c(OCC(Cl)(Cl)Cl)c(C#N)c1] |
| A230 | 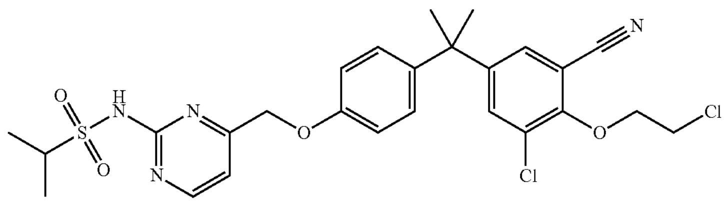 [SMILES: CC(C)S(=O)(=O)Nc1nccc(COc2ccc(C(C)(C)c3cc(Cl)c(OCCCl)c(C#N)c3)cc2)n1] |
| A231 | 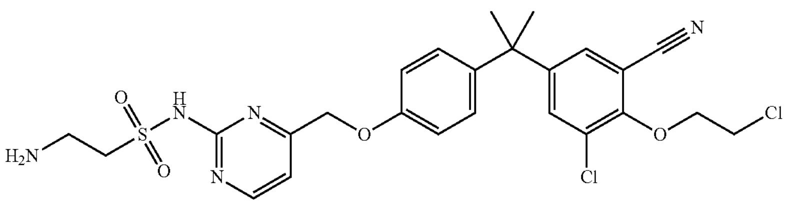 [SMILES: CC(C)(c1ccc(OCc2ccnc(NS(=O)(=O)CCN)n2)cc1)c1cc(Cl)c(OCCCl)c(C#N)c1] |
| A232 | 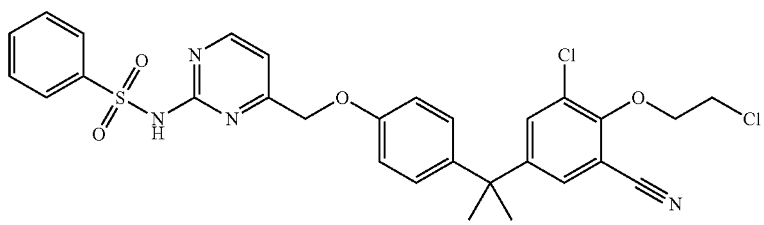 [SMILES: CC(C)(c1ccc(OCc2ccnc(NS(=O)(=O)c3ccccc3)n2)cc1)c1cc(Cl)c(OCCCl)c(C#N)c1] |
| A233 | 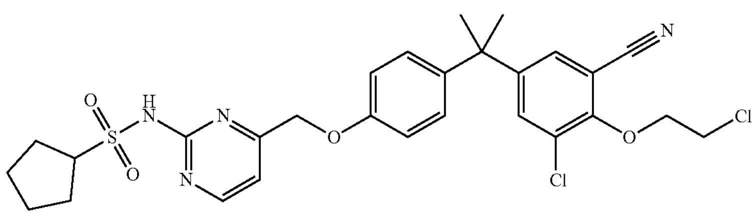 [SMILES: CC(C)(c1ccc(OCc2ccnc(NS(=O)(=O)C3CCCC3)n2)cc1)c1cc(Cl)c(OCCCl)c(C#N)c1] |
| A234 | 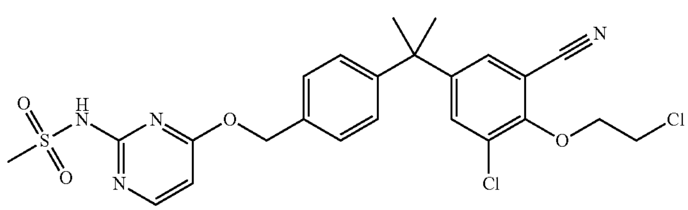 [SMILES: CC(C)(c1ccc(COc2ccnc(NS(C)(=O)=O)n2)cc1)c1cc(Cl)c(OCCCl)c(C#N)c1] |

In one embodiment of the compound of formula (I)-(IV), (VI), (B) or (C), the compound is selected from Table B below, or a pharmaceutically acceptable salt, tautomer, stereoisomer or prodrug thereof. In one embodiment of the compound of formula (I)-(IV), (VI), (B) or (C), the compound is selected from Compounds B1, B2, B3, or B6 or a pharmaceutically acceptable salt, tautomer, stereoisomer or prodrug thereof. In one embodiment of the compound of formula (I)-(IV), (VI), (B) or (C), the compound is selected from Compounds B4, B5, B7, B8, B9, B10, or B11 or a pharmaceutically acceptable salt, tautomer, stereoisomer or prodrug thereof. In one embodiment of the compound of formula (I)-(IV), (VI), (B) or (C), the compound is selected from Compounds B1-B11 or a pharmaceutically acceptable salt, tautomer, stereoisomer or prodrug thereof.

TABLE B

Compounds

| Compound ID | Structure |
|---|---|
| B1 | 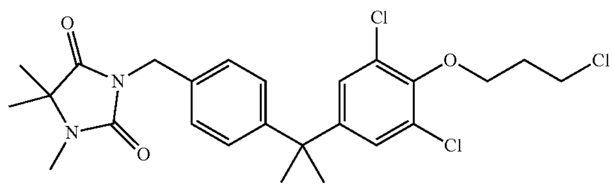 [SMILES: CN1C(=O)N(Cc2ccc(C(C)(C)c3cc(Cl)c(OCCCCl)c(Cl)c3)cc2)C(=O)C1(C)C] |
| B2 | 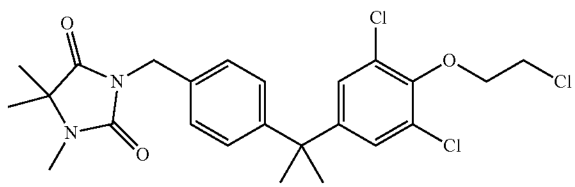 [SMILES: CN1C(=O)N(Cc2ccc(C(C)(C)c3cc(Cl)c(OCCCl)c(Cl)c3)cc2)C(=O)C1(C)C] |
| B3 | 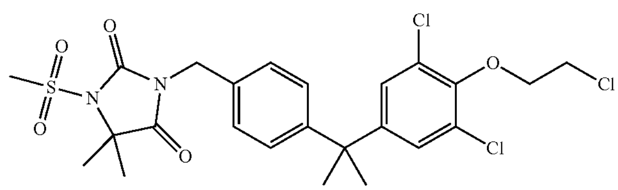 [SMILES: CC(C)(c1ccc(CN2C(=O)N(S(C)(=O)=O)C(C)(C)C2=O)cc1)c1cc(Cl)c(OCCCl)c(Cl)c1] |
| B4 | 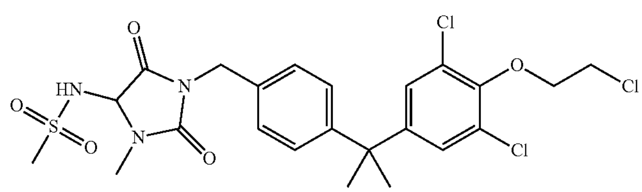 [SMILES: CN1C(=O)N(Cc2ccc(C(C)(C)c3cc(Cl)c(OCCCl)c(Cl)c3)cc2)C(=O)C1NS(C)(=O)=O] |
| B5 | 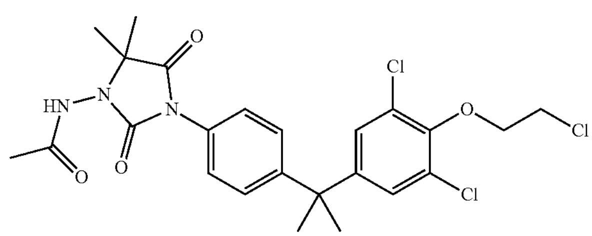 [SMILES: CC(=O)NN1C(=O)N(c2ccc(C(C)(C)c3cc(Cl)c(OCCCl)c(Cl)c3)cc2)C(=O)C1(C)C] |
| B6 | 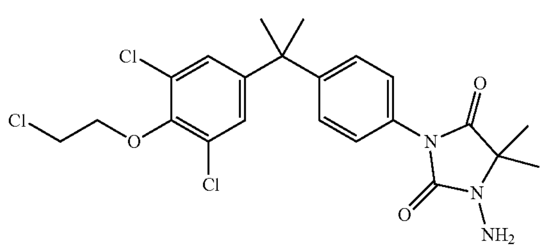 [SMILES: CC(C)(c1ccc(N2C(=O)N(N)C(C)(C)C2=O)cc1)c1cc(Cl)c(OCCCl)c(Cl)c1] |
| B7 | 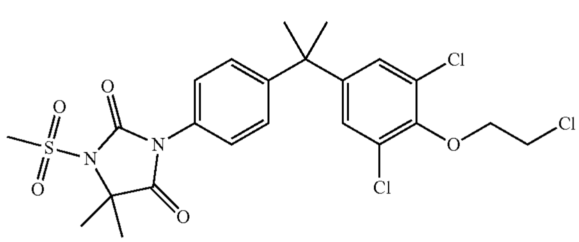 [SMILES: CC(C)(c1ccc(N2C(=O)N(S(C)(=O)=O)C(C)(C)C2=O)cc1)c1cc(Cl)c(OCCCl)c(Cl)c1] |

TABLE B-continued

Compounds

| Compound ID | Structure |
|---|---|
| B8 | 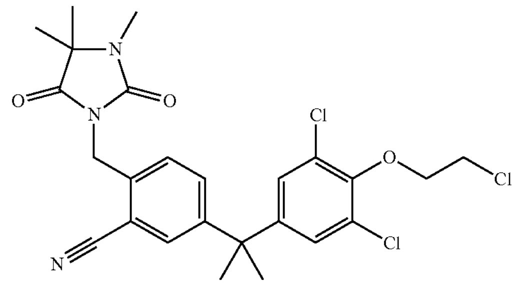 [SMILES: CN1C(=O)N(Cc2ccc(C(C)(C)c3cc(Cl)c(OCCCl)c(Cl)c3)cc2C#N)C(=O)C1(C)C] |
| B9 | 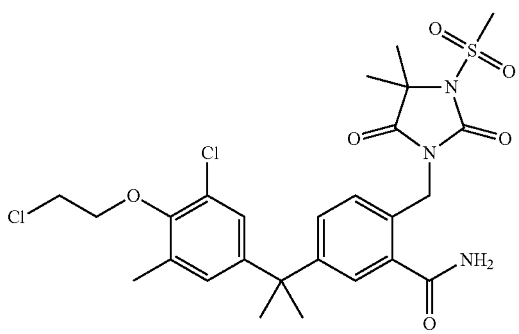 [SMILES: Cc1cc(C(C)(C)c2ccc(CN3C(=O)N(S(C)(=O)=O)C(C)(C)C3=O)c(C(N)=O)c2)cc(Cl)c1OCCCl] |
| B10 | 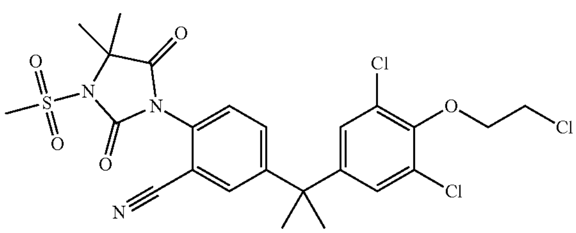 [SMILES: CC(C)(c1cc(Cl)c(OCCCl)c(Cl)c1)c1ccc(N2C(=O)N(S(C)(=O)=O)C(C)(C)C2=O)c(C#N)c1] |
| B11 | 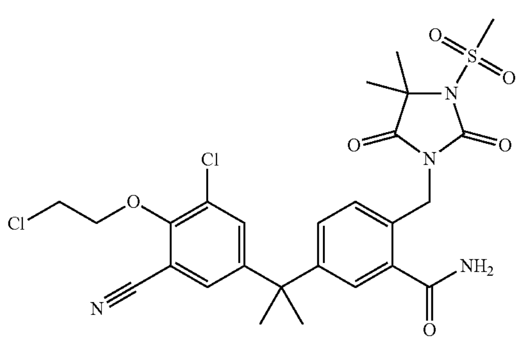 [SMILES: CC(C)(c1cc(Cl)c(OCCCl)c(C#N)c1)c1ccc(CN2C(=O)N(S(C)(=O)=O)C(C)(C)C2=O)c(C(N)=O)c1] |

In one embodiment, the present disclosure provides a pharmaceutical composition comprising a pharmaceutically acceptable carrier or a pharmaceutically acceptable excipient and a compound of any one of formula (I), (IA), (IB), (IC), (II), (IIA), (IIIA), (IIB), (III), (IV), (IVA), (V), (VA), (VI), (A), (A-I), (B)-(D), (E), (E-I)-(E-VII), (F), (G), (G-I), (G-II), (H), and (H-I) ("formula (I)-(VI) and (A)-(H-I)") or compounds of Tables A and B, or a pharmaceutically acceptable salt, tautomer, stereoisomer or prodrug thereof. In one embodiment, the present disclosure provides a pharmaceutical composition comprising a pharmaceutically acceptable carrier or a pharmaceutically acceptable excipient and a compound selected from Compounds A3, A5, A7, A13, A17, A18, A22, A23, A24, A25, A28, A30, A31, A32, A34, A35, A38, A40, A41, A42, A45, A49, A52, A53, A54, A56, A57, A58, A62, A63, A64, A65, A68, A73, A74, A75, A76, B1, B2, B3, or B6 or a pharmaceutically acceptable salt, tautomer, stereoisomer or prodrug thereof. In one embodiment, the present disclosure provides a pharmaceutical composition comprising a pharmaceutically acceptable carrier or a pharmaceutically acceptable excipient and a compound selected from Compounds A1, A2, A4, A6, A8, A9, A10, A11, A12, A14, A15, A16, A19, A20, A21, A26, A27, A29, A33, A36, A37, A39, A43, A44, A46, A47, A48, A50, A51, A55, A59, A60, A61, A66, A67, A69, A70, A71, A72, A77, A78, A79, A80, A81, A82, A83, A84, A85, A86, A87, A88, A89, A90, A91, A92, A93, A94, A95, A96, A97, B4, B5, B7, B8, B9, B10, or B11, or a pharmaceutically acceptable salt, tautomer, stereoisomer or prodrug thereof. In one embodiment, the present disclosure provides a pharmaceutical composition comprising a pharmaceutically acceptable carrier or a pharmaceutically acceptable excipient and a compound selected from Compounds A98-A186, or a pharmaceutically acceptable salt, tautomer, stereoisomer or prodrug thereof. In one embodiment, the present disclosure provides a pharmaceutical composition comprising a pharmaceutically acceptable carrier or a pharmaceutically acceptable excipient and a compound selected from Compounds A187-A211, or a pharmaceutically acceptable salt, tautomer, stereoisomer or prodrug thereof. In one embodiment, the present disclosure provides a pharmaceutical composition comprising a pharmaceutically acceptable carrier or a pharmaceutically acceptable excipient and a compound selected from Compounds A212-A234, or a pharmaceutically acceptable salt, tautomer, stereoisomer or prodrug thereof. In one embodiment, the present disclosure provides a pharmaceutical composition comprising a pharmaceutically acceptable carrier or a pharmaceutically acceptable excipient and a compound selected from Compounds A1-A96, A98-A116, A118-A159, A161-A175, and A177-A234, or a pharmaceutically acceptable salt, tautomer, stereoisomer or prodrug thereof. In one embodiment, the present disclosure provides a pharmaceutical composition comprising a pharmaceutically acceptable carrier or a pharmaceutically acceptable excipient and a compound selected from Compounds A13, A57, A74, A93, A109, A112, A122, A126, A131, A134, A136, A137, A164, A168, A169, A170, A171, A172, A184, A185, A195, and/or A204, or a pharmaceutically acceptable salt, tautomer, stereoisomer or prodrug thereof. In one embodiment, the present disclosure provides a pharmaceutical composition comprising a pharmaceutically acceptable carrier or a pharmaceutically acceptable excipient and a compound selected from Compounds A1-A211 or B1-B11, or a pharmaceutically acceptable salt, tautomer, stereoisomer or prodrug thereof. In one embodiment, the present disclosure provides a pharmaceutical composition comprising a pharmaceutically acceptable carrier or a pharmaceutically acceptable excipient and a compound selected from Compounds A1-A234 or B1-B11, or a pharmaceutically acceptable salt, tautomer, stereoisomer or prodrug thereof. In one embodiment, the present disclosure provides a pharmaceutical composition comprising a pharmaceutically acceptable carrier or a pharmaceutically acceptable excipient and a compound of any one of formula (D)-(H-I), or a pharmaceutically acceptable salt, tautomer, stereoisomer or prodrug thereof.

Therapeutic Use

The present compounds find use in any number of methods. For example, in some embodiments the compounds are useful in methods for modulating androgen receptor (AR). Accordingly, in one embodiment, the present disclosure provides the use of any one of the foregoing compounds of formula (I)-(VI) and (A)-(H-I), or a pharmaceutically acceptable salt, tautomer, stereoisomer or prodrug thereof, for modulating androgen receptor (AR) activity. For example in some embodiments, modulating androgen receptor (AR) activity is in a mammalian cell. Modulating androgen receptor (AR) can be in a subject in need thereof (e.g., a mammalian subject) and for treatment of any of the described conditions or diseases.

In one embodiment, the modulating AR is binding to AR. In other embodiments, the modulating AR is inhibiting AR. In one embodiment, the modulating AR is modulating AR N-terminal domain (NTD). In one embodiment, the modulating AR is binding to AR NTD. In other embodiments, the modulating AR is inhibiting AR NTD. In one embodiment, the modulating AR is modulating AR N-terminal domain (NTD). In some embodiments, modulating the AR is inhibiting transactivation of androgen receptor N-terminal domain (NTD).

In other embodiments, modulating androgen receptor (AR) activity is for treatment of at least one indication selected from the group consisting of: prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy, age related macular degeneration, and combinations thereof. For example in some embodiments, the indication is prostate cancer. In other embodiments, the prostate cancer is primary/localized prostate cancer, locally advanced prostate cancer, recurrent prostate cancer, non-metastatic castration-resistant prostate cancer, metastatic prostate cancer, advanced prostate cancer, or metastatic castration-resistant prostate cancer (CRPC), or hormone-sensitive prostate cancer. While in other embodiments, the prostate cancer is androgen dependent prostate cancer. In other embodiments, the spinal and bulbar muscular atrophy is Kennedy's disease. In other embodiments, the prostate cancer is primary/localized prostate cancer, locally advanced prostate cancer, recurrent prostate cancer, metastatic prostate cancer, advanced prostate cancer, or metastatic castration-resistant prostate cancer (CRPC), or hormone-sensitive prostate cancer. While in other embodiments, the prostate cancer is androgen dependent prostate cancer. In other embodiments, the spinal and bulbar muscular atrophy is Kennedy's disease.

In one embodiment of the present disclosure, a method of treating a condition associated with cell proliferation in a patient in need thereof is provided, comprising administering a compounds of formula (I)-(VI) and (A)-(H-I), or a pharmaceutically acceptable salt, tautomer, stereoisomer or prodrug thereof, to a subject in need thereof. In one embodiment, the present invention provides a method of treating cancer or tumors. In another embodiment, the present invention provides a method of treating prostate cancer or breast cancer.

In one embodiment of the present disclosure, a method of reducing, inhibiting, or ameliorating proliferation, comprising administering a therapeutically effective amount of a compound of formula (I)-(VI) and (A)-(H-I), or a pharmaceutically acceptable salt, tautomer or stereoisomer thereof is provided. In one embodiment, the reducing, inhibiting, or ameliorating in the method disclosed herein, is in vivo. In another embodiment, the reducing, inhibiting, or ameliorating is in vitro.

In one embodiment, the cells in the method disclosed herein, are a cancer cells. In one embodiment, the cancer cells are a prostate cancer cells. In one embodiment, the prostate cancer cells are cells of primary/localized prostate cancer (newly diagnosed or early stage), locally advanced prostate cancer, recurrent prostate cancer (e.g., prostate cancer which was not responsive to primary therapy), metastatic prostate cancer, non-metastatic castration-resistant prostate cancer, advanced prostate cancer (e.g., after castration for recurrent prostate cancer), metastatic castration-resistant prostate cancer (CRPC), or hormone-sensitive prostate cancer. In one embodiment, the prostate cancer cells are cells of primary/localized prostate cancer (newly diagnosed or early stage), locally advanced prostate cancer, recurrent prostate cancer (e.g., prostate cancer which was not responsive to primary therapy), metastatic prostate cancer, advanced prostate cancer (e.g., after castration for recurrent prostate cancer), metastatic castration-resistant prostate cancer (CRPC), or hormone-sensitive prostate cancer. In another embodiment, the prostate cancer cells are cells of a metastatic castration-resistant prostate cancer. In other embodiments, the prostate cancer cells are an androgen-dependent prostate cancer cells or an androgen-independent prostate cancer cells. In one embodiment, the cancer cells are breast cancer cells.

In one embodiment, the condition or disease associated with cell proliferation is cancer. In one embodiment of any one of the methods disclosed herein, the cancer is selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration. In one embodiment, the condition or disease is prostate cancer. In one embodiment, prostate cancer is selected from primary/localized prostate cancer, locally advanced prostate cancer, recurrent prostate cancer, metastatic prostate cancer, non-metastatic castration-resistant prostate cancer, advanced prostate cancer, metastatic castration-resistant prostate cancer (CRPC), or hormone-sensitive prostate cancer. In one embodiment, prostate cancer is selected from primary/localized prostate cancer, locally advanced prostate cancer, recurrent prostate cancer, metastatic prostate cancer, advanced prostate cancer, metastatic castration-resistant prostate cancer (CRPC), or hormone-sensitive prostate cancer. In another embodiment, the prostate cancer is a metastatic castration-resistant prostate cancer. In some embodiments, the prostate cancer is an androgen-dependent prostate cancer cells or an androgen-independent prostate cancer. In one embodiment, the condition or disease is breast cancer.

In another embodiment of the present disclosure, a method for reducing or preventing tumor growth, comprising contacting tumor cells with a therapeutically effective amount of a compound of (I)-(VI) and (A)-(H-I), or a pharmaceutically acceptable salt, tautomer or stereoisomer thereof is provided.

In one embodiment, reducing or preventing tumor growth includes reduction in tumor volume. In one embodiment, reducing or preventing tumor growth includes complete elimination of tumors. In one embodiment, reducing or preventing tumor growth includes stopping or halting the existing tumor to grow. In one embodiment, reducing or preventing tumor growth includes reduction in the rate of tumor growth. In one embodiment, reducing or preventing tumor growth includes reduction in the rate of tumor growth such that the rate of tumor growth before treating a patient with the methods disclosed herein (r1) is faster than the rate of tumor growth after said treatment (r2) such that r1>r2.

In one embodiment, the reducing or preventing in the method disclosed herein is in vivo. In another embodiment, the treating is in vitro.

In one embodiment, the tumor cell in the method disclosed herein is selected from prostate cancer, breast cancer, ovarian cancer, endometrial cancer, or salivary gland carcinoma. In one embodiment, the tumor cells are prostate cancer tumor cells. In one embodiment, the prostate cancer tumor cells are tumor cells of primary/localized prostate cancer, locally advanced prostate cancer, recurrent prostate cancer, metastatic prostate cancer, non-metastatic castration-resistant prostate cancer, advanced prostate cancer, metastatic castration-resistant prostate cancer (CRPC), or hormone-sensitive prostate cancer. In one embodiment, the prostate cancer tumor cells are tumor cells of primary/localized prostate cancer, locally advanced prostate cancer, recurrent prostate cancer, metastatic prostate cancer, advanced prostate cancer, metastatic castration-resistant prostate cancer (CRPC), or hormone-sensitive prostate cancer. In other embodiments, the prostate cancer is a metastatic castration-resistant prostate cancer. In some embodiments, the prostate cancer is androgen-dependent prostate cancer or androgen-independent prostate cancer. In another embodiment, the tumor cells are is breast cancer tumor cells.

In accordance with another embodiment, there is provided a use of the compounds of formula (I)-(VI) and (A)-(H-I), or a pharmaceutically acceptable salt, tautomer or stereoisomer thereof for preparation of a medicament for modulating androgen receptor (AR). In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds provide metabolic stability. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in human liver microsomes (HLMs) of less than about 500 µL/min/mg protein, less than about 450 µL/min/mg protein, less than about 400 µL/min/mg protein, less than about 350 µL/min/mg protein, less than about 300 µL/min/mg protein, less than about 250 µL/min/mg protein, less than about 225 µL/min/mg protein, or less than about 200 µL/min/mg protein. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in HLMs of less than about 200 µL/min/mg protein, less than about 190 µL/min/mg protein, less than about 180 µL/min/mg protein, less than about 170 µL/min/mg protein, less than about 160 µL/min/mg protein, less than about 150 µL/min/mg protein, less than about 140 µL/min/mg protein, less than about 130 µL/min/mg protein, less than about 120 µL/min/mg protein, less than about 110 µL/min/mg protein, less than about 100 µL/min/mg protein, less than about 90 µL/min/mg protein, less than about 80 µL/min/mg protein, less than about 70 µL/min/mg protein, less than about 60 µL/min/mg protein, or less than about 50 µL/min/mg protein. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in HLMs of less than about 50 µL/min/mg protein, less than about 48 µL/min/mg protein, less than about 45 µL/min/mg protein, less than about 40 µL/min/mg protein, less than about 35 µL/min/mg protein, less than about 30 µL/min/mg protein, less than about 25 µL/min/mg protein, less than about 20 µL/min/mg protein, or less than about 15 µL/min/mg protein. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in HLMs of less than about 15 µL/min/mg protein, less than about 14 µL/min/mg protein, less than about 13 µL/min/mg protein, less than about 12 µL/min/mg protein, less than about 11 µL/min/mg protein, or less than about 10 µL/min/mg protein.

In a specific embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in HLMs of less than 12 µL/min/mg protein. In a specific embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in HLMs in the range of about 0.1 µL/min/mg protein to about 12 µL/min/mg protein. In a specific embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in HLMs of less than 48 µL/min/mg protein. In a specific embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in HLMs in the range of about 12 µL/min/mg protein to about 48 µL/min/mg protein. In a specific embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in HLMs in the range of about 0.1 µL/min/mg protein to about 48 µL/min/mg protein.

In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an HLM in vitro metabolic clearance of less than about 20 µL/min/mg protein. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an HLM in vitro metabolic clearance of less than about 15 µL/min/mg protein. In another embodi- ment, the compounds of the present disclosure are com- pounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoi- somer thereof, wherein the compounds have an HLM in vitro metabolic clearance of less than about 12 µL/min/mg protein. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically accept- able salt, tautomer or stereoisomer thereof, wherein the compounds have an HLM in vitro metabolic clearance of less than about 11.55 µL/min/mg protein.

In another embodiment, the compounds of the present disclosure are any compound of Tables A or B, or a phar- maceutically acceptable salt, tautomer or stereoisomer thereof, wherein the compounds have an HLM in vitro metabolic clearance of less than about 20 µL/min/mg pro- tein. In another embodiment, the compounds of the present disclosure are any compound of Tables A or B, or a phar- maceutically acceptable salt, tautomer or stereoisomer thereof, wherein the compounds have an HLM in vitro metabolic clearance of less than about 15 µL/min/mg pro- tein. In another embodiment, the compounds of the present disclosure are any compound of Tables A or B, or a phar- maceutically acceptable salt, tautomer or stereoisomer thereof, wherein the compounds have an HLM in vitro metabolic clearance of less than about 12 µL/min/mg pro- tein. In another embodiment, the compounds of the present disclosure are any compound of Tables A or B, or a phar- maceutically acceptable salt, tautomer or stereoisomer thereof, wherein the compounds have an HLM in vitro metabolic clearance of less than about 11.55 µL/min/mg protein.

In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in mouse liver microsomes (MLMs) of less than about 500 µL/min/mg protein, less than about 450 µL/min/mg protein, less than about 400 µL/min/mg protein, less than about 350 µL/min/mg protein, less than about 300 µL/min/mg protein, less than about 250 µL/min/mg protein, less than about 225 µL/min/mg protein, or less than about 200 µL/min/mg protein. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in MLMs of less than about 200 µL/min/mg protein, less than about 190 µL/min/mg protein, less than about 180 µL/min/mg protein, less than about 170 µL/min/mg protein, less than about 160 µL/min/mg protein, less than about 150 µL/min/mg protein, less than about 140 µL/min/mg protein, less than about 130 µL/min/mg protein, less than about 120 µL/min/mg protein, less than about 110 µL/min/mg protein, less than about 100 µL/min/mg protein, less than about 90 µL/min/mg protein, less than about 80 µL/min/mg protein, less than about 70 µL/min/mg protein, less than about 60 µL/min/mg protein, or less than about 50 µL/min/mg protein. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in MLMs of less than about 50 µL/min/mg protein, less than about 48 µL/min/mg protein, less than about 45 µL/min/mg protein, less than about 40 µL/min/mg protein, less than about 35 µL/min/mg protein, less than about 30 µL/min/mg protein, less than about 25 µL/min/mg protein, less than about 20 µL/min/mg protein, or less than about 15 µL/min/mg protein. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in MLMs of less than about 15 µL/min/mg protein, less than about 14 µL/min/mg protein, less than about 13 µL/min/mg protein, less than about 12 µL/min/mg protein, less than about 11 µL/min/mg protein, or less than about 10 µL/min/mg protein.

In a specific embodiment, the compounds of the present disclosure are any compound of Tables A and B, or a pharmaceutically acceptable salt, tautomer or stereoisomer thereof, and wherein the compounds have an in vitro metabolic clearance in MLMs of less than 12 µL/min/mg protein. In a specific embodiment, the compounds of the present disclosure are any compound of Tables A and B, or a pharmaceutically acceptable salt, tautomer or stereoisomer thereof, and wherein the compounds have an in vitro metabolic clearance in MLMs in the range of about 0.1 µL/min/mg protein to about 12 µL/min/mg protein. In a specific embodiment, the compounds of the present disclosure are any compound of Tables A and B, or a pharmaceutically acceptable salt, tautomer or stereoisomer thereof, and wherein the compounds have an in vitro metabolic clearance in MLMs of less than 48 µL/min/mg protein. In a specific embodiment, the compounds of the present disclosure are any compound of Tables A and B, or a pharmaceutically acceptable salt, tautomer or stereoisomer thereof, and wherein the compounds have an in vitro metabolic clearance in MLMs in the range of about 12 µL/min/mg protein to about 48 µL/min/mg protein. In a specific embodiment, the compounds of the present disclosure are any compound of Tables A and B, or a pharmaceutically acceptable salt, tautomer or stereoisomer thereof, and wherein the compounds have an in vitro metabolic clearance in MLMs in the range of about 0.1 µL/min/mg protein to about 48 µL/min/mg protein.

In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an MLM in vitro metabolic clearance of less than about 20 µL/min/mg protein. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an MLM in vitro metabolic clearance of less than about 15 µL/min/mg protein. In another embodi- ment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an MLM in vitro metabolic clearance of less than about 12 µL/min/mg protein. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an MLM in vitro metabolic clearance of less than about 11.55 µL/min/mg protein.

In another embodiment, the compounds of the present disclosure are any compound of Tables A or B, or a pharmaceutically acceptable salt, tautomer or stereoisomer thereof, wherein the compounds have an MLM in vitro metabolic clearance of less than about 20 µL/min/mg protein. In another embodiment, the compounds of the present disclosure are any compound of Tables A or B, or a pharmaceutically acceptable salt, tautomer or stereoisomer thereof, wherein the compounds have an MLM in vitro metabolic clearance of less than about 15 µL/min/mg protein. In another embodiment, the compounds of the present disclosure are any compound of Tables A or B, or a pharmaceutically acceptable salt, tautomer or stereoisomer thereof, wherein the compounds have an MLM in vitro metabolic clearance of less than about 12 µL/min/mg protein. In another embodiment, the compounds of the present disclosure are any compound of Tables A or B, or a pharmaceutically acceptable salt, tautomer or stereoisomer thereof, wherein the compounds have an MLM in vitro metabolic clearance of less than about 11.55 µL/min/mg protein.

In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in human hepatocytes (HHs) of less than about 500 µL/min/million cells, less than about 450 µL/min/million cells, less than about 400 µL/min/million cells, less than about 350 µL/min/million cells, less than about 300 µL/min/million cells, less than about 250 µL/min/million cells, less than about 225 µL/min/million cells, or less than about 200 µL/min/million cells. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in HHs of less than about 200 µL/min/million cells, less than about 190 µL/min/million cells, less than about 180 µL/min/million cells, less than about 170 µL/min/million cells, less than about 160 µL/min/million cells, less than about 150 µL/min/million cells, less than about 140 µL/min/million cells, less than about 130 µL/min/million cells, less than about 120 µL/min/million cells, less than about 110 µL/min/million cells, less than about 100 µL/min/million cells, less than about 90 µL/min/million cells, less than about 80 µL/min/million cells, less than about 70 µL/min/million cells, less than about 60 µL/min/million cells, or less than about 50 µL/min/million cells. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in HHs of less than about 50 μL/min/ million cells, less than about 48 μL/min/million cells, less than about 45 μL/min/million cells, less than about 40 μL/min/million cells, less than about 35 μL/min/million cells, less than about 30 μL/min/million cells, less than about 25 μL/min/million cells, less than about 20 μL/min/million cells, or less than about 15 μL/min/million cells. In some embodiments, the compounds of the present disclosure have an in vitro metabolic clearance in HHs of less than about 15 μL/min/million cells, less than about 14 μL/min/million cells, less than about 13 μL/min/million cells, less than about 12 μL/min/million cells, less than about 11 μL/min/million cells, less than about 10 μL/min/million cells, less than about 9 μL/min/million cells, less than about 8 μL/min/million cells, less than about 8 μL/min/million cells, less than about 6 μL/min/million cells, or less than about 5 μL/min/million cells.

In a specific embodiment, the compounds of the present disclosure are any compound of Tables A and B, or a pharmaceutically acceptable salt, tautomer or stereoisomer thereof, and wherein the compounds have an in vitro metabolic clearance in HHs of less than 4 μL/min/million cells. In a specific embodiment, the compounds of the present disclosure are any compound of Tables A and B, or a pharmaceutically acceptable salt, tautomer or stereoisomer thereof, and wherein the compounds have an in vitro metabolic clearance in HHs in the range of about 0.1 μL/min/ million cells to about 4 μL/min/million cells. In a specific embodiment, the compounds of the present disclosure are any compound of Tables A and B, or a pharmaceutically acceptable salt, tautomer or stereoisomer thereof, and wherein the compounds have an in vitro metabolic clearance in HHs of less than 18 μL/min/million cells. In a specific embodiment, the compounds of the present disclosure are any compound of Tables A and B, or a pharmaceutically acceptable salt, tautomer or stereoisomer thereof, and wherein the compounds have an in vitro metabolic clearance in HHs in the range of about 4 μL/min/million cells to about 18 μL/min/million cells. In a specific embodiment, the compounds of the present disclosure are any compound of Tables A and B, or a pharmaceutically acceptable salt, tautomer or stereoisomer thereof, and wherein the compounds have an in vitro metabolic clearance in HHs in the range of about 0.1 μL/min/million cells to about 18 μL/min/ million cells.

In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in HHs of less than about 20 μL/min/million cells. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in HHs of less than about 10 μL/min/million cells. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in HHs of less than about 5 μL/min/ million cells. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in HHs of less than about 3.85 μL/min/million cells.

In another embodiment, the compounds of the present disclosure are any compound of Tables A or B, or a pharmaceutically acceptable salt, tautomer or stereoisomer thereof, wherein the compounds have an in vitro metabolic clearance in HHs of less than about 20 μL/min/million cells. In another embodiment, the compounds of the present disclosure are any compound of Tables A or B, or a pharmaceutically acceptable salt, tautomer or stereoisomer thereof, wherein the compounds have an in vitro metabolic clearance in HHs of less than about 10 μL/min/million cells. In another embodiment, the compounds of the present disclosure are any compound of Tables A or B, or a pharmaceutically acceptable salt, tautomer or stereoisomer thereof, wherein the compounds have an in vitro metabolic clearance in HHs of less than about 5 μL/min/million cells. In another embodiment, the compounds of the present disclosure are any compound of Tables A or B, or a pharmaceutically acceptable salt, tautomer or stereoisomer thereof, wherein the compounds have an in vitro metabolic clearance in human hepatocytes of less than about 3.85 μL/min/million cells.

In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in mouse hepatocytes (MHs) of less than about 500 μL/min/million cells, less than about 450 μL/min/million cells, less than about 400 μL/min/ million cells, less than about 350 μL/min/million cells, less than about 300 μL/min/million cells, less than about 250 μL/min/million cells, less than about 225 μL/min/million cells, or less than about 200 μL/min/million cells. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in MHs of less than about 200 μL/min/ million cells, less than about 190 μL/min/million cells, less than about 180 μL/min/million cells, less than about 170 μL/min/million cells, less than about 160 μL/min/million cells, less than about 150 μL/min/million cells, less than about 140 μL/min/million cells, less than about 130 L/min/ million cells, less than about 120 μL/min/million cells, less than about 110 μL/min/million cells, less than about 100 μL/min/million cells, less than about 90 μL/min/million cells, less than about 80 μL/min/million cells, less than about 70 μL/min/million cells, less than about 60 μL/min/million cells, or less than about 50 μL/min/million cells. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in MHs of less than about 50 µL/min/million cells, less than about 48 µL/min/million cells, less than about 45 µL/min/million cells, less than about 40 µL/min/million cells, less than about 35 µL/min/million cells, less than about 30 µL/min/million cells, less than about 25 µL/min/million cells, less than about 20 µL/min/million cells, or less than about 15 µL/min/million cells. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in MHs of less than about 15 µL/min/million cells, less than about 14 µL/min/million cells, less than about 13 µL/min/million cells, less than about 12 µL/min/million cells, less than about 11 µL/min/million cells, less than about 10 µL/min/million cells, less than about 9 µL/min/million cells, less than about 8 µL/min/million cells, less than about 8 µL/min/million cells, less than about 6 µL/min/million cells, or less than about 5 µL/min/million cells.

In a specific embodiment, the compounds of the present disclosure are any compound of Tables A and B, or a pharmaceutically acceptable salt, tautomer or stereoisomer thereof, and wherein the compounds have an in vitro metabolic clearance in MHs of less than 4 µL/min/million cells. In a specific embodiment, the compounds of the present disclosure are any compound of Tables A and B, or a pharmaceutically acceptable salt, tautomer or stereoisomer thereof, and wherein the compounds have an in vitro metabolic clearance in MHs in the range of about 0.1 µL/min/million cells to about 4 µL/min/million cells. In a specific embodiment, the compounds of the present disclosure are any compound of Tables A and B, or a pharmaceutically acceptable salt, tautomer or stereoisomer thereof, and wherein the compounds have an in vitro metabolic clearance in MHs of less than 18 µL/min/million cells. In a specific embodiment, the compounds of the present disclosure are any compound of Tables A and B, or a pharmaceutically acceptable salt, tautomer or stereoisomer thereof, and wherein the compounds have an in vitro metabolic clearance in MHs in the range of about 4 µL/min/million cells to about 18 µL/min/million cells. In a specific embodiment, the compounds of the present disclosure are any compound of Tables A and B, or a pharmaceutically acceptable salt, tautomer or stereoisomer thereof, and wherein the compounds have an in vitro metabolic clearance in MHs in the range of about 0.1 µL/min/million cells to about 18 µL/min/million cells.

In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in MHs of less than about 20 µL/min/million cells. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in MHs of less than about 17 µL/min/million cells. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in MHs of less than about 7 µL/min/million cells. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in MHs of less than about 3.85 µL/min/million cells.

In another embodiment, the compounds of the present disclosure are any compound of Tables A or B, or a pharmaceutically acceptable salt, tautomer or stereoisomer thereof, wherein the compounds have an in vitro metabolic clearance in MHs of less than about 20 µL/min/million cells. In another embodiment, the compounds of the present disclosure are any compound of Tables A or B, or a pharmaceutically acceptable salt, tautomer or stereoisomer thereof, wherein the compounds have an in vitro metabolic clearance in MHs of less than about 17 µL/min/million cells. In another embodiment, the compounds of the present disclosure are any compound of Tables A or B, or a pharmaceutically acceptable salt, tautomer or stereoisomer thereof, wherein the compounds have an in vitro metabolic clearance in MHs of less than about 7 µL/min/million cells. In another embodiment, the compounds of the present disclosure are any compound of Tables A or B, or a pharmaceutically acceptable salt, tautomer or stereoisomer thereof, wherein the compounds have an in vitro metabolic clearance in MHs of less than about 3.85 µL/min/million cells.

In another embodiment, the compounds of the present disclosure are any compounds with a combination of in vitro metabolic clearance in HLM, MLM, HHs, and MHs as described herein.

In a specific embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an HLM and MLM in vitro metabolic clearance of less than about 20 µL/min/mg protein. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an HLM and MLM in vitro metabolic clearance of less than about 15 µL/min/mg protein. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an HLM and MLM in vitro metabolic clearance of less than about 12 µL/min/mg protein. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an HLM and MLM in vitro metabolic clearance of less than about 11.55 µL/min/mg protein.

In a specific embodiment, the compounds of the present disclosure are any compound of Tables A and B, or a pharmaceutically acceptable salt, tautomer or stereoisomer thereof, and wherein the compounds have an HLM and MLM in vitro metabolic clearance of less than about 20 µL/min/mg protein. In another embodiment, the compounds of the present disclosure are any compound of Tables A and B, or a pharmaceutically acceptable salt, tautomer or stereoisomer thereof, and wherein the compounds have an HLM and MLM in vitro metabolic clearance of less than about 15 µL/min/mg protein. In another embodiment, the compounds of the present disclosure are any compound of Tables A and B, or a pharmaceutically acceptable salt, tautomer or stereoisomer thereof, and wherein the compounds have an HLM and MLM in vitro metabolic clearance of less than about 12 µL/min/mg protein. In another embodiment, the compounds of the present disclosure are any compound of Tables A and B or a pharmaceutically acceptable salt, tautomer or stereoisomer thereof, and wherein the compounds have an HLM and MLM in vitro metabolic clearance of less than about 11.55 µL/min/mg protein.

In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in human and mouse hepatocytes of less than about 20 µL/min/million cells. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in mouse hepatocytes of less than about 17 µL/min/million cells and a an in vitro metabolic clearance in human hepatocytes of less than about 10 µL/min/million cells. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro metabolic clearance in mouse hepatocytes of less than about 7 µL/min/million cells, and an in vitro metabolic clearance in human hepatocytes of less than about 5 µL/min/million cells. In another embodiment, the compounds of the present disclosure are any compound of Tables A and B, or a pharmaceutically acceptable salt, tautomer or stereoisomer thereof, and wherein the compounds have an in vitro meta- bolic clearance in human and mouse hepatocytes of less than about 20 µL/min/million cells. In another embodiment, the compounds of the present disclosure are any compound of Tables A and B, or a pharmaceutically acceptable salt, tautomer or stereoisomer thereof, and wherein the compounds have an in vitro metabolic clearance in mouse hepatocytes of less than about 17 µL/min/million cells and a an in vitro metabolic clearance in human hepatocytes of less than about 10 µL/min/million cells. In another embodiment, the compounds of the present disclosure are any compound of Tables A and B or a pharmaceutically acceptable salt, tautomer or stereoisomer thereof, and wherein the compounds have an in vitro metabolic clearance in mouse hepatocytes of less than about 7 µL/min/million cells, and an in vitro metabolic clearance in human hepatocytes of less than about 5 µL/min/million cells. In another embodiment, the compounds of the present disclosure are any compound of Tables A and B or a pharmaceutically acceptable salt, tautomer or stereoisomer thereof, and wherein the compounds have an in vitro metabolic clearance in human and mouse hepatocytes of less than about 3.85 µL/min/million cells.

In a specific embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an HLM and MLM in vitro metabolic clearance of less than about 20 µL/min/mg protein and an in vitro metabolic clearance in human and mouse hepatocytes of less than about 20 µL/min/million cells. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an HLM and MLM in vitro metabolic clearance of less than about 15 µL/min/mg protein, an in vitro metabolic clearance in human and mouse hepatocytes of less than about 17 µL/min/million cells. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an HLM and MLM in vitro metabolic clearance of less than about 12 µL/min/mg protein, an in vitro metabolic clearance in human and mouse hepatocytes of less than about 7 µL/min/million cells. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds s have an HLM and MLM in vitro metabolic clearance of less than about 11.55 µL/min/mg protein, an in vitro metabolic clearance in human and mouse hepatocytes of less than about 3.85 µL/min/million cells.

In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an a) HLM or MLM in vitro metabolic clearance of less than about 12 µL/min/mg protein and b) an in vitro metabolic clearance in human or mouse hepatocytes of less than about 4 μL/min/million cells. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an a) HLM or MLM in vitro metabolic clearance of less than 12 μL/min/mg protein and b) an in vitro metabolic clearance in human or mouse hepatocytes of less than 4 μL/min/million cells. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an a) HLM and MLM in vitro metabolic clearance of less than about 12 μL/min/mg protein and b) an in vitro metabolic clearance in human or mouse hepatocytes of less than about 4 μL/min/million cells. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an a) HLM or MLM in vitro metabolic clearance of less than about 12 μL/min/mg protein and b) an in vitro metabolic clearance in human and mouse hepatocytes of less than about 4 μL/min/million cells. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an a) HLM and MLM in vitro metabolic clearance of less than about 12 μL/min/mg protein and b) an in vitro metabolic clearance in human and mouse hepatocytes of less than about 4 μL/min/million cells. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an a) HLM and MLM in vitro metabolic clearance of less than 12 μL/min/mg protein and b) an in vitro metabolic clearance in human and mouse hepatocytes of less than 4 μL/min/million cells. In a specific embodiment, the compounds of the present disclosure are any compound of Tables A and B, or a pharmaceutically acceptable salt, tautomer or stereoisomer thereof, wherein the compounds have an a) HLM and MLM in vitro metabolic clearance of less than 12 μL/min/mg protein and b) an in vitro metabolic clearance in human and mouse hepatocytes of less than 4 μL/min/million cells.

In a specific embodiment, the compounds of the present disclosure are any compound of Tables A and B, or a pharmaceutically acceptable salt, tautomer or stereoisomer thereof, and wherein the compounds have an HLM and MLM in vitro metabolic clearance of less than about 20 μL/min/mg protein and an in vitro metabolic clearance in human and mouse hepatocytes of less than about 20 μL/min/million cells. In another embodiment, the compounds of the present disclosure are any compound of Tables A and B, or a pharmaceutically acceptable salt, tautomer or stereoisomer thereof, and wherein the compounds have an HLM and MLM in vitro metabolic clearance of less than about 15 μL/min/mg protein, an in vitro metabolic clearance in human and mouse hepatocytes of less than about 17 μL/min/million cells. In another embodiment, the compounds of the present are any compound of Tables A and B or a pharmaceutically acceptable salt, tautomer or stereoisomer thereof, and wherein the compounds have an HLM and MLM in vitro metabolic clearance of less than about 12 μL/min/mg protein, an in vitro metabolic clearance in human and mouse hepatocytes of less than about 7 μL/min/million cells. In another embodiment, the compounds of the present disclosure are any compound of Tables A and B or a pharmaceutically acceptable salt, tautomer or stereoisomer thereof, and wherein the compounds have an HLM and MLM in vitro metabolic clearance of less than about 11.55 μL/min/mg protein, an in vitro metabolic clearance in human and mouse hepatocytes of less than about 3.85 μL/min/million cells.

In a specific embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in human, mouse, rat, monkey or dog microsome greater than about 120 minutes. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in human, mouse, rat, monkey or dog microsome greater than about 110 minutes. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in human, mouse, rat, monkey or dog microsome greater than about 100 minutes. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in human, mouse, rat, monkey or dog microsome greater than about 90 minutes. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in human, mouse, rat, monkey or dog microsome greater than about 80 minutes. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in human, mouse, rat, monkey or dog microsome greater than about 70 minutes.

In another embodiment, the compounds of the present disclosure are any compound of Tables A and B or a pharmaceutically acceptable salt, tautomer or stereoisomer thereof, wherein the compounds have an in vitro half-life in human microsomes greater than about 120 min.

In another embodiment, the compounds of the present disclosure are any compound of Tables A and B or a pharmaceutically acceptable salt, tautomer or stereoisomer thereof, wherein the compounds have an in vitro half-life in mouse microsomes greater than about 120 min.

In a specific embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat microsome greater than about 120 minutes. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat microsome greater than about 110 minutes. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat microsome greater than about 100 minutes. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat microsome greater than about 90 minutes. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat microsome greater than about 80 minutes. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat microsome greater than about 70 minutes. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat microsome greater than about 60 minutes. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat microsome greater than about 50 minutes. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat microsome greater than about 40 minutes. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat microsome greater than about 30 minutes. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat microsome greater than about 20 minutes. In some embodiments, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat microsome greater than about 10 minutes. In one embodiment, the compound is selected from any of the compound of Tables A and B or a pharmaceutically acceptable salt, tautomer or stereoisomer thereof.

In a specific embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in human hepatocytes greater than about 360 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in human hepatocytes greater than about 350 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in human hepatocytes greater than about 325 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in human hepatocytes greater than about 310 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in human hepatocytes greater than about 300 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in human hepatocytes greater than about 290 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in human hepatocytes greater than about 250 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in human hepatocytes greater than about 200 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in human hepatocytes greater than about 150 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in human hepatocytes greater than about 100 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in human hepatocytes greater than about 80 minutes. In one embodiment, the compound is selected from any of the compound of Tables A and B or a pharmaceutically acceptable salt, tautomer or stereoisomer thereof.

In a specific embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mouse hepatocytes greater than about 360 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mouse hepatocytes greater than about 350 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mouse hepatocytes greater than about 325 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mouse hepatocytes greater than about 300 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mouse hepatocytes greater than about 250 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mouse hepatocytes greater than about 225 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mouse hepatocytes greater than about 200 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mouse hepatocytes greater than about 150 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mouse hepatocytes greater than about 100 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mouse hepatocytes greater than about 50 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mouse hepatocytes greater than about 30 minutes. In one embodiment, the compound is selected from any of the compound of Tables A and B or a pharmaceutically acceptable salt, tautomer or stereoisomer thereof.

In a specific embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat hepatocytes greater than about 360 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat hepatocytes greater than about 350 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat hepatocytes greater than about 325 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat hepatocytes greater than about 300 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat hepatocytes greater than about 250 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat hepatocytes greater than about 225 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat hepatocytes greater than about 200 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat hepatocytes greater than about 150 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat hepatocytes greater than about 100 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in rat hepatocytes greater than about 50 minutes. In one embodiment, the compounds have an in vitro half-life in rat hepatocytes greater than about 30 minutes. In one embodiment, the compound is selected from any of the compound of Tables A and B or a pharmaceutically acceptable salt, tautomer or stereoisomer thereof.

In a specific embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life stability in mammal microsome of greater than 80 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life stability in mammal microsome of greater than 90 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life stability in mammal microsome of greater than 100 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life stability in mammal microsome of greater than 110 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life stability in mammal microsome of greater than 115 minutes. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life stability in mammal microsome of greater than 120 minutes. In one embodiment, the compound is selected from any of the compound of Tables A and B or a pharmaceutically acceptable salt, tautomer or stereoisomer thereof. In one embodiment, the mammal microsome is human or mouse microsome.

In a specific embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life stability in mammal microsome in the range of about 50 min to about 200 min. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life stability in mammal microsome in the range of about 80 min to about 180 min. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life stability in mammal microsome in the range of about 100 min to about 160 min. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life stability in mammal microsome in the range of about 110 min to about 150 min. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life stability in mammal microsome in the range of about 110 min to about 140 min. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life stability in mammal microsome in the range of about 110 min to about 130 min. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life stability in mammal microsome in the range of about 115 min to about 130 min. In another embodiment, the compounds of the present disclosure are any compound of Tables A and B or a pharmaceutically acceptable salt, tautomer or stereoisomer thereof, having an in vitro half-life stability in mammal microsome in the range of about 115 min to about 130 min. In one embodiment, the mammal microsome is human or mouse microsome.

In one embodiment, the present disclosure provides compounds which demonstrate blocking androgen-induced PSA-luciferase activity (PSA-luciferase assay). In a specific embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 4500 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 4000 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 3500 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 3000 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 2500 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 2000 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 1500 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 1000 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 950 nm. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 900 nM.

In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 890 nM, less than about 880 nM, less than about 870 nM, less than about 860 nM, less than about 850 nM, less than about 840 nM, less than about 830 nM, less than about 820 nM, less than about 810 nM, or less than about 800 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 790 nM, less than about 780 nM, less than about 770 nM, less than about 760 nM, less than about 750 nM, less than about 740 nM, less than about 730 nM, less than about 720 nM, less than about 710 nM, or less than about 700 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 690 nM, less than about 680 nM, less than about 670 nM, less than about 660 nM, less than about 650 nM, less than about 640 nM, less than about 630 nM, less than about 620 nM, less than about 610 nM, or less than about 600 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 590 nM, less than about 580 nM, less than about 570 nM, less than about 560 nM, less than about 550 nM, less than about 540 nM, less than about 530 nM, less than about 520 nM, less than about 510 nM, or less than about 500 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 500 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds having in vitro $IC_{50}$ in a PSA-luciferase assay of less than about 490 nM, less than about 480 nM, less than about 470 nM, less than about 460 nM, less than about 450 nM, less than about 440 nM, less than about 430 nM, less than about 420 nM, less than about 410 nM, or less than about 400 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 390 nM, less than about 380 nM, less than about 370 nM, less than about 360 nM, less than about 350 nM, less than about 340 nM, less than about 330 nM, less than about 320 nM, less than about 310 nM, or less than about 300 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 290 nM, less than about 280 nM, less than about 270 nM, less than about 260 nM, less than about 250 nM, less than about 240 nM, less than about 230 nM, less than about 220 nM, less than about 210 nM, or less than about 200 nM. In one embodiment, the compounds have an in vitro $IC_{50}$ in a PSA-luciferase assay of less than about 200 nM. In one embodiment, the compound is selected from any of the compound of Tables A and B or a pharmaceutically acceptable salt, tautomer or stereoisomer thereof.

In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mammal microsome of greater than about 80 minutes and in vitro $IC_{50}$ in a PSA-luciferase assay of less than about 2000 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mammal microsome of greater than about 90 minutes and in vitro $IC_{50}$ in a PSA-luciferase assay of less than about 1500 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mammal microsome of greater than about 100 minutes and in vitro $IC_{50}$ in a PSA-luciferase assay of less than about 1000 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mammal microsome of greater than about 105 minutes and in vitro $IC_{50}$ in a PSA-luciferase assay of less than about 900 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mammal microsome of greater than about 110 minutes and in vitro $IC_{50}$ in a PSA-luciferase assay of less than about 850 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mammal microsome of greater than about 115 minutes and in vitro $IC_{50}$ in a PSA-luciferase assay of less than about 800 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mammal microsome of greater than about 115 minutes and in vitro $IC_{50}$ in a PSA-luciferase assay of less than about 750 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mammal microsome of greater than about 120 minutes and in vitro $IC_{50}$ in a PSA-luciferase assay of less than about 700 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mammal microsome of greater than about 120 minutes and in vitro $IC_{50}$ in a PSA-luciferase assay of less than about 650 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mammal microsome of greater than about 120 minutes and in vitro $IC_{50}$ in a PSA-luciferase assay of less than about 600 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mammal microsome of greater than about 120 minutes and in vitro $IC_{50}$ in a PSA-luciferase assay of less than about 550 nM. In one embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro half-life in mammal microsome of greater than about 120 minutes and in vitro $IC_{50}$ in a PSA-luciferase assay of less than about 500 nM. In one embodiment, the compound is selected from any of the compound of Tables A and B or a pharmaceutically acceptable salt, tautomer or stereoisomer thereof. In one embodiment, the mammal microsome is human or mouse microsome.

In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 1000 nM and a HLM or MLM in vitro metabolic clearance of less than 12 µL/min/mg protein. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 1000 nM and a HLM and MLM in vitro metabolic clearance of less than 12 µL/min/mg protein. In another embodiment, the compounds of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 1000 nM and an in vitro metabolic clearance in human or mouse hepatocytes of less than 4 µL/min/million cells. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 1000 nM and an in vitro metabolic clearance in human and mouse hepatocytes of less than 4 µL/min/million cells.

In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 1000 nM; a HLM or MLM in vitro metabolic clearance of less than 12 µL/min/mg protein; and an in vitro metabolic clearance in human or mouse hepatocytes of less than 4 µL/min/million cells. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 800 nM; a HLM or MLM in vitro metabolic clearance of less than 12 µL/min/mg protein; and an in vitro metabolic clearance in human or mouse hepatocytes of less than 4 µL/min/million cells. In another embodiment, the compounds of the present disclosure are compounds having the structure of formula (I)-(VI) and/or (A)-(H-I), or a pharmaceutically acceptable salt, tautomer or stereoisomer thereof, or the compounds of Tables A and B, or a pharmaceutically acceptable salt, tautomer or stereoisomer thereof, wherein the compounds have an in vitro $IC_{50}$ in a PSA-luciferase assay of less than about 700 nM; a HLM or MLM in vitro metabolic clearance of less than 12 µL/min/mg protein; and an in vitro metabolic clearance in human or mouse hepatocytes of less than 4 µL/min/million cells. In one embodiment, the compound is selected from any of the compound of Tables A and B or a pharmaceutically acceptable salt, tautomer or stereoisomer thereof.

In a specific embodiment, the compounds of the present disclosure are any compound of Tables A and B, or a pharmaceutically acceptable salt, tautomer or stereoisomer thereof, wherein the compounds have an in vitro $IC_{50}$ in a PSA-luciferase assay of less than about 1000 nM; a HLM or MLM in vitro metabolic clearance of less than 12 µL/min/mg protein; and an in vitro metabolic clearance in human or mouse hepatocytes of less than 4 µL/min/million cells.

In a specific embodiment, the compounds of the present disclosure are compounds having the structure of formula (I)-(VI) and/or (A)-(H-I), or a pharmaceutically acceptable salt, tautomer or stereoisomer thereof, and wherein the compounds have an in vitro metabolic clearance in HHs of less than 4 µL/min/million cells. In a specific embodiment, the compounds of the present disclosure are compounds having the structure of formula (I)-(VI) and/or (A)-(H-I), or a pharmaceutically acceptable salt, tautomer or stereoisomer thereof, and wherein the compounds have an in vitro metabolic clearance in HHs of less than 4 μL/min/million cells and in vitro $IC_{50}$ in a PSA-luciferase assay of less than about 700 nM. In one embodiment, the compounds have an in vitro metabolic clearance in HHs of less than 4 μL/min/million cells and in vitro $IC_{50}$ in a PSA-luciferase assay of less than about 675 nM. In a specific embodiment, the compounds of the present disclosure are compounds having the structure of formula (I)-(VI) and/or (A)-(H-I), or a pharmaceutically acceptable salt, tautomer or stereoisomer thereof, and wherein the compounds have an in vitro half-life in HHs of less than about 350 minutes. In a specific embodiment, the compounds of the present disclosure are compounds having the structure of formula (I)-(VI) and/or (A)-(H-I), or a pharmaceutically acceptable salt, tautomer or stereoisomer thereof, and wherein the compounds have an in vitro half-life in HHs of greater than about 320 minutes and in vitro $IC_{50}$ in a PSA-luciferase assay of less than about 700 nM. In one embodiment, the compounds have an in vitro half-life in HHs of greater than about 350 minutes and in vitro $IC_{50}$ in a PSA-luciferase assay of less than about 700 nM.

In a specific embodiment, the compounds of the present disclosure are compounds having the structure of formula (I)-(VI) and/or (A)-(H-I), or a pharmaceutically acceptable salt, tautomer or stereoisomer thereof, and wherein the compounds have an in vitro metabolic clearance in MLMs of less than 15 μL/min/mg protein. In a specific embodiment, the compounds of the present disclosure are compounds having the structure of formula (I)-(VI) and/or (A)-(H-I), or a pharmaceutically acceptable salt, tautomer or stereoisomer thereof, and wherein the compounds have an in vitro metabolic clearance in MLMs of less than 15 μL/min/mg protein and in vitro $IC_{50}$ in a PSA-luciferase assay of less than about 700 nM. In one embodiment, the compounds have an in vitro metabolic clearance in MLMs of less than 15 μL/min/mg protein and in vitro $IC_{50}$ in a PSA-luciferase assay of less than about 675 nM. In a specific embodiment, the compounds of the present disclosure are compounds having the structure of formula (I)-(VI) and/or (A)-(H-I), or a pharmaceutically acceptable salt, tautomer or stereoisomer thereof, and wherein the compounds have an in vitro metabolic clearance in MHs of less than 10 μL/min/million cells. In one embodiment, the compounds have an in vitro metabolic clearance in MHs of less than 8 μL/min/million cells. In a specific embodiment, the compounds of the present disclosure are compounds having the structure of formula (I)-(VI) and/or (A)-(H-I), or a pharmaceutically acceptable salt, tautomer or stereoisomer thereof, and wherein the compounds have an in vitro metabolic clearance in MHs of less than 10 μL/min/million cells and in vitro $IC_{50}$ in a PSA-luciferase assay of less than about 700 nM. In one embodiment, the compounds have an in vitro metabolic clearance in MHs of less than 8 μL/min/million cells and in vitro $IC_{50}$ in a PSA-luciferase assay of less than about 675 nM. In a specific embodiment, the compounds of the present disclosure are compounds having the structure of formula (I)-(VI) and/or (A)-(H-I), or a pharmaceutically acceptable salt, tautomer or stereoisomer thereof, and wherein the compounds have an in vitro half-life in MLMs of greater than about 100 minutes. In a specific embodiment, the compounds of the present disclosure are compounds having the structure of formula (I)-(VI) and/or (A)-(H-I), or a pharmaceutically acceptable salt, tautomer or stereoisomer thereof, and wherein the compounds have an in vitro half-life in MHs of greater than about 100 minutes. In one embodiment, the compounds have an in vitro half-life in MHs of greater than about 180 minutes.

In a specific embodiment, the compounds of the present disclosure are compounds having the structure of formula (I)-(VI) and/or (A)-(H-I), or a pharmaceutically acceptable salt, tautomer or stereoisomer thereof, and wherein the compounds have an in vitro metabolic clearance in MHs in the range of 3 μL/min/million cells to about 20 μL/min/million cells. In one embodiment, the compounds have an in vitro metabolic clearance in MHs in the range of 3.2 μL/min/million cells to about 18 μL/min/million cells. In one embodiment, the compounds have an in vitro metabolic clearance in MHs in the range of 3.4 μL/min/million cells to about 17 μL/min/million cells.

In a specific embodiment, the compounds of the present disclosure are compounds having the structure of formula (I)-(VI) and/or (A)-(H-I), or a pharmaceutically acceptable salt, tautomer or stereoisomer thereof, and wherein the compounds have an in vitro $IC_{50}$ in a PSA-luciferase assay of less than 650 nM. In one embodiment, the compounds have an in vitro $IC_{50}$ in a PSA-luciferase assay of less than about 640 nM. In one embodiment, the compounds have an in vitro $IC_{50}$ in a PSA-luciferase assay of less than about 635 nM.

In a specific embodiment, the compounds of the present disclosure are compounds having the structure of formula (I)-(VI) and/or (A)-(H-I), or a pharmaceutically acceptable salt, tautomer or stereoisomer thereof, and wherein the compounds have an in vitro $IC_{50}$ in a PSA-luciferase assay in the range of 200 nM to about 700 nM. In one embodiment, the compounds have an in vitro $IC_{50}$ in a PSA-luciferase assay in the range of about 250 nM to about 700 nM. In one embodiment, the compounds have an in vitro $IC_{50}$ in a PSA-luciferase assay in the range of about 300 nM to about 700 nM. In one embodiment, the compounds have an in vitro $IC_{50}$ in a PSA-luciferase assay in the range of about 350 nM to about 675 nM.

In a specific embodiment, the compounds of the present disclosure are compounds having the structure of formula (I)-(VI) and/or (A)-(H-I), or a pharmaceutically acceptable salt, tautomer or stereoisomer thereof, and wherein the compounds have an in vitro $IC_{50}$ in a PSA-luciferase assay of less than 525 nM. In one embodiment, the compounds have an in vitro $IC_{50}$ in a PSA-luciferase assay of less than about 500 nM. In one embodiment, the compounds have an in vitro $IC_{50}$ in a PSA-luciferase assay of less than about 450 nM.

Pharmaceutical Compositions and Formulations

The present disclosure also includes pharmaceutical compositions for modulating androgen receptor (AR) in a subject. In one embodiment, a pharmaceutical composition comprises one or more compounds of formula (I)-(VI) and/or (A)-(H-I), or a pharmaceutically acceptable salt or solvate thereof.

In one embodiment of the present disclosure, a pharmaceutical composition comprises a therapeutically effective amounts of one or more compounds of formula (I)-(VI) and/or (A)-(H-I), or a pharmaceutically acceptable salt or solvate thereof.

In a specific embodiment, a pharmaceutical composition, as described herein, comprises one or more compounds selected from Table A, or a pharmaceutically acceptable salt or solvate thereof. In one embodiment, a pharmaceutical composition as described herein comprise one or more compounds selected from Table B, or a pharmaceutically acceptable salt or solvate thereof.

In a specific embodiment, a pharmaceutical composition, as described herein, comprises one or more compounds selected from Compounds A3, A5, A7, A13, A17, A18, A22, A23, A24, A25, A28, A30, A31, A32, A34, A35, A38, A40, A41, A42, A45, A49, A52, A53, A54, A56, A57, A58, A62, A63, A64, A65, A68, A73, A74, A75, A76, B1, B2, B3, or B6, or a pharmaceutically acceptable salt or solvate thereof. In a specific embodiment, a pharmaceutical composition, as described herein, comprises one or more compounds selected from Compounds A1, A2, A4, A6, A8, A9, A10, A11, A12, A14, A15, A16, A19, A20, A21, A26, A27, A29, A33, A36, A37, A39, A43, A44, A46, A47, A48, A50, A51, A55, A59, A60, A61, A66, A67, A69, A70, A71, A72, A77, A78, A79, A80, A81, A82, A83, A84, A85, A86, A87, A88, A89, A90, A91, A92, A93, A94, A95, A96, A97, B4, B5, B7, B8, B9, B10, or B11, or a pharmaceutically acceptable salt or solvate thereof. In a specific embodiment, a pharmaceutical composition, as described herein, comprises one or more compounds selected from Compounds A98-A186. In a specific embodiment, a pharmaceutical composition, as described herein, comprises one or more compounds selected from Compounds A187-A211. In a specific embodiment, a pharmaceutical composition, as described herein, comprises one or more compounds selected from Compounds A212-A234. In a specific embodiment, a pharmaceutical composition, as described herein, comprises one or more compounds selected from Compounds A1-A96, A98-A116, A118-A159, A161-A175, and A177-A234. In a specific embodiment, a pharmaceutical composition, as described herein, comprises one or more compounds selected from Compounds A13, A57, A74, A93, A109, A112, A122, A126, A131, A134, A136, A137, A164, A168, A169, A170, A171, A172, A184, A185, A195, and/or A204, or a pharmaceutically acceptable salt, tautomer, stereoisomer or prodrug thereof. In a specific embodiment, a pharmaceutical composition, as described herein, comprises one or more compounds selected from Compounds A1-A211 or B1-B11. In a specific embodiment, a pharmaceutical composition, as described herein, comprises one or more compounds selected from Compounds A1-A234 or B1-B11.

In one embodiment, a pharmaceutical composition, as described herein, comprising one or more compounds of formula (I)-(VI) and/or (A)-(H-I), or a pharmaceutically acceptable salt or solvate thereof, further comprises one or more additional therapeutically active agents. In one embodiment, one or more additional therapeutically active agents are selected from therapeutics useful for treating cancer, neurological disease, a disorder characterized by abnormal accumulation of α-synuclein, a disorder of an aging process, cardiovascular disease, bacterial infection, viral infection, mitochondrial related disease, mental retardation, deafness, blindness, diabetes, obesity, autoimmune disease, glaucoma, Leber's Hereditary Optic Neuropathy, and rheumatoid arthritis.

In some embodiments, the one or more additional therapeutic agents is a poly (ADP-ribose) polymerase (PARP) inhibitor including but not limited to olaparib, niraparib, rucaparib, talazoparib; an androgen receptor ligand binding domain inhibitor including but not limited to enzalutamide, apalutamide, darolutamide, bicalutamide, nilutamide, flutamide, ODM-204, TAS3681; an inhibitor of CYP17 including but not limited to galeterone, abiraterone, abiraterone acetate; a microtubule inhibitor including but not limited to docetaxel, paclitaxel, cabazitaxel (XRP-6258); a modulator of PD-1 or PD-L1 including but not limited to pembrolizumab, durvalumab, nivolumab, atezolizumab; a gonadotropin releasing hormone agonist including but not limited to cyproterone acetate, leuprolide; a 5-alpha reductase inhibitor including but not limited to finasteride, dutasteride, turosteride, bexlosteride, izonsteride, FCE 28260, SKF 105,111; a vascular endothelial growth factor inhibitor including but not limited to bevacizumab (Avastin); a histone deacetylase inhibitor including but not limited to OSU-HDAC42; an integrin alpha-v-beta-3 inhibitor including but not limited to VITAXIN; a receptor tyrosine kinase inhibitor including but not limited to sunitumib; a phosphoinositide 3-kinase inhibitor including but not limited to alpelisib, buparlisib, idealisib; an anaplastic lymphoma kinase (ALK) inhibitor including but not limited to crizotinib, alectinib; an endothelin receptor A antagonist including but not limited to ZD-4054; an anti-CTLA4 inhibitor including but not limited to MDX-010 (ipilimumab); an heat shock protein 27 (HSP27) inhibitor including but not limited to OGX 427; an androgen receptor degrader including but not limited to ARV-330, ARV-110; a androgen receptor DNA-binding domain inhibitor including but not limited to VPC-14449; a bromodomain and extra-terminal motif (BET) inhibitor including but not limited to BI-894999, GSK25762, GS-5829; an androgen receptor N-terminal domain inhibitor including but not limited to a sintokamide; an alpha-particle emitting radioactive therapeutic agent including but not limited to radium 233 or a salt thereof; niclosamide; or related compounds thereof; a selective estrogen receptor modulator (SERM) including but not limited to tamoxifen, raloxifene, toremifene, arzoxifene, bazedoxifene, pipindoxifene, lasofoxifene, enclomiphene; a selective estrogen receptor degrader (SERD) including but not limited to fulvestrant, ZB716, OP-1074, elacestrant, AZD9496, GDC0810, GDC0927, GW5638, GW7604; an aromitase inhibitor including but not limited to anastrazole, exemestane, letrozole; selective progesterone receptor modulators (SPRM) including but not limited to mifepristone, lonaprison, onapristone, asoprisnil, lonaprisnil, ulipristal, telapristone; a glucocorticoid receptor inhibitor including but not limited to mifepristone, COR108297, COR125281, ORIC-101, PT150; CDK4/6 inhibitors including palbociclib, abemaciclib, ribociclib; HER2 receptor antagonist including but not limited to trastuzumab, neratinib; a mammalian target of rapamycin (mTOR) inhibitor including but not limited to everolimus, temsirolimus.

In a further embodiment of the present disclosure, a pharmaceutical composition comprising one or more compounds of formula (I)-(VI) and/or (A)-(H-I), or a pharmaceutically acceptable salt or solvate thereof, and a pharmaceutically acceptable excipient or adjuvant is provided. The pharmaceutically acceptable excipients and adjuvants are added to the composition or formulation for a variety of purposes. In another embodiment, a pharmaceutical composition comprising one or more compounds of formula (I)-(VI) and/or (A)-(H-I), or a pharmaceutically acceptable salt or solvate thereof, further comprises a pharmaceutically acceptable carrier. In one embodiment, a pharmaceutically acceptable carrier includes a pharmaceutically acceptable excipient, binder, and/or diluent. In one embodiment, suitable pharmaceutically acceptable excipients include, but are not limited to, water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, the pharmaceutical compositions of the present disclosure may additionally contain other adjunct components conventionally found in pharmaceutical compositions, at their art-established usage levels. Thus, for example, the pharmaceutical compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

For the purposes of this disclosure, the compounds of the present disclosure can be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

The compounds disclosed herein can be formulated in accordance with the routine procedures adapted for desired administration route. Accordingly, the compounds disclosed herein can take such forms as suspensions, solutions or emulsions in oily or aqueous vehicles, and can contain formulatory agents such as suspending, stabilizing and/or dispersing agents. The compounds disclosed herein can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in Remington: The Science and Practice of Pharmacy, A. Gennaro, ed., 20th edition, Lippincott, Williams & Wilkins, Philadelphia, Pa.

In certain embodiments, a pharmaceutical composition of the present disclosure is prepared using known techniques, including, but not limited to mixing, dissolving, granulating, dragee-making, levigating, emulsifying, encapsulating, entrapping or tableting processes.

In one embodiment, the present disclosure provides a pharmaceutical composition comprising a compound of formula (I)-(VI) and/or (A)-(H-I), or a pharmaceutically acceptable salt or solvate thereof, as disclosed herein, combined with a pharmaceutically acceptable carrier. In one embodiment, suitable pharmaceutically acceptable carriers include, but are not limited to, inert solid fillers or diluents and sterile aqueous or organic solutions. Pharmaceutically acceptable carriers are well known to those skilled in the art and include, but are not limited to, from about 0.01 to about 0.1 M and preferably 0.05M phosphate buffer or 0.8% saline. Such pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate.

Aqueous carriers suitable for use in the present application include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers suitable for use in the present application can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the present application include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellant.

Solid carriers suitable for use in the present application include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

Parenteral carriers suitable for use in the present application include, but are not limited to, sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like.

Carriers suitable for use in the present application can be mixed as needed with disintegrants, diluents, granulating agents, lubricants, binders and the like using conventional techniques known in the art. The carriers can also be sterilized using methods that do not deleteriously react with the compounds, as is generally known in the art.

Diluents may be added to the formulations of the present invention. Diluents increase the bulk of a solid pharmaceutical composition and/or combination, and may make a pharmaceutical dosage form containing the composition and/or combination easier for the patient and care giver to handle. Diluents for solid compositions and/or combinations include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT(r)), potassium chloride, powdered cellulose, sodium chloride, sorbitol, and talc.

Additional embodiments relate to the pharmaceutical formulations wherein the formulation is selected from the group consisting of a solid, powder, liquid and a gel. In certain embodiments, a pharmaceutical composition of the present invention is a solid (e.g., a powder, tablet, a capsule, granulates, and/or aggregates). In certain of such embodiments, a solid pharmaceutical composition comprising one or more ingredients known in the art, including, but not limited to, starches, sugars, diluents, granulating agents, lubricants, binders, and disintegrating agents.

Solid pharmaceutical compositions that are compacted into a dosage form, such as a tablet, may include excipients whose functions include helping to bind the active ingredient and other excipients together after compression. Binders for solid pharmaceutical compositions and/or combinations include acacia, alginic acid, carbomer (e.g., carbopol), carboxymethylcellulose sodium, dextrin, ethyl cellulose, gelatin, guar gum, gum tragacanth, hydrogenated vegetable oil, hydroxyethyl cellulose, hydroxypropyl cellulose (e.g., KLUCEL), hydroxypropyl methyl cellulose (e.g., METHOCEL), liquid glucose, magnesium aluminum silicate, maltodextrin, methylcellulose, polymethacrylates, povidone (e.g., KOLLIDON, PLASDONE), pregelatinized starch, sodium alginate, and starch.

The dissolution rate of a compacted solid pharmaceutical composition in the patient's stomach may be increased by the addition of a disintegrant to the composition and/or combination. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), potato starch, and starch.

Glidants can be added to improve the flowability of a non-compacted solid composition and/or combination and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition and/or combination to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition and/or combination of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

Liquid pharmaceutical compositions can be prepared using compounds of formula (I)-(VI) and/or (A)-(H-I), or a pharmaceutically acceptable salt or solvate thereof, and any other solid excipients where the components are dissolved or suspended in a liquid carrier such as water, vegetable oil, alcohol, polyethylene glycol, propylene glycol, or glycerin.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Liquid pharmaceutical compositions can contain emulsifying agents to disperse uniformly throughout the composition and/or combination an active ingredient or other excipient that is not soluble in the liquid carrier. Emulsifying agents that may be useful in liquid compositions and/or combinations of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as aspartame, lactose, sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition can also contain a buffer such as guconic acid, lactic acid, citric acid or acetic acid, sodium guconate, sodium lactate, sodium citrate, or sodium acetate. Selection of excipients and the amounts used may be readily determined by the formulation scientist based upon experience and consideration of standard procedures and reference works in the field.

In one embodiment, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the compound is to be administered by infusion, it can be dispensed in a formulation with an infusion bottle containing sterile pharmaceutical grade water, saline or dextrose/water. Where the compound is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80 and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers.

In certain embodiments, sustained-release systems may, depending on their chemical nature, release pharmaceutical agents over a period of hours, days, weeks or months.

Appropriate pharmaceutical compositions of the present disclosure can be determined according to any clinically-acceptable route of administration of the composition to the subject. The manner in which the composition is administered is dependent, in part, upon the cause and/or location. One skilled in the art will recognize the advantages of certain routes of administration. The method includes administering an effective amount of the agent or compound (or composition comprising the agent or compound) to achieve a desired biological response, e.g., an amount effective to alleviate, ameliorate, or prevent, in whole or in part, a symptom of a condition to be treated, e.g., oncology and neurology disorders. In various aspects, the route of administration is systemic, e.g., oral or by injection. The agents or compounds, or pharmaceutically acceptable salts or derivatives thereof, are administered orally, nasally, transdermally, pulmonary, inhalationally, buccally, sublingually, intraperitoneally, subcutaneously, intramuscularly, intravenously, rectally, intrapleurally, intrathecally, intraportally, and parenterally. Alternatively or in addition, the route of administration is local, e.g., topical, intra-tumor and peri-tumor. In some embodiments, the compound is administered orally.

In certain embodiments, a pharmaceutical composition of the present disclosure is prepared for oral administration. In certain of such embodiments, a pharmaceutical composition is formulated by combining one or more agents and pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In other embodiments the compound of the present disclosure are administered by the intravenous route. In further embodiments, the parenteral administration may be provided in a bolus or by infusion.

In certain embodiments, a pharmaceutical composition is prepared for rectal administration, such as a suppository or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more compounds of formula (I)-(VI) and/or (A)-(H-I), or a pharmaceutically acceptable salt or solvate thereof are formulated as a prodrug. In certain embodiments, upon in vivo administration, a prodrug is chemically converted to the biologically, pharmaceutically or therapeutically more active form. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

In various aspects, the amount of the compound of formula (I)-(VI) and/or (A)-(H-I), or a pharmaceutically acceptable salt or solvate thereof, or compounds disclosed in Tables A and B, or a pharmaceutically acceptable salt or solvate thereof, can be administered at about 0.001 mg/kg to about 100 mg/kg body weight (e.g., about 0.01 mg/kg to about 10 mg/kg or about 0.1 mg/kg to about 5 mg/kg).

The concentration of a disclosed compound in a pharmaceutically acceptable mixture will vary depending on several factors, including the dosage of the compound to be administered, the pharmacokinetic characteristics of the compound(s) employed, and the route of administration. The agent may be administered in a single dose or in repeat doses. The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. Treatments may be administered daily or more frequently depending upon a number of factors, including the overall health of a patient, and the formulation and route of administration of the selected compound(s). An ordinarily skilled physician or veterinarian can readily determine and prescribe the effective amount of the drug required to prevent, counter or arrest the progress of the condition.

The compounds or pharmaceutical compositions of the present disclosure may be manufactured and/or administered in single or multiple unit dose forms.

Having now generally described the invention, the same will be more readily understood through reference to the following examples, which are provided by way of illustration and are not intended to be limiting of the present invention.

EXAMPLES

The disclosure now being generally described, it will be more readily understood by reference to the following examples which are included merely for purposes of illustration of certain aspects and embodiments of the present invention, and are not intended to limit the invention.

Synthetic Preparation

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis,* 44th. Ed., Wiley & Sons, 2006, as well as in Jerry March, *Advanced Organic Chemistry,* $4^{th}$ edition, John Wiley & Sons, publisher, New York, 1992 which are incorporated herein by reference in their entirety.

Compounds of the present invention can be prepared by the literature methods cited in the following text. The following schemes depict established, known syntheses of these scaffolds.

The groups and/or the substituents of the compounds of the present invention can be synthesized and attached to these scaffolds by the literature methods cited in the following text. The following schemes depict the known techniques for accomplishing this joinder.

General Synthesis

Compounds of the present invention can be synthesized using the following methods. General reaction conditions are given, and reaction products can be purified by general known methods including crystallization, silica gel chromatography using various organic solvents such as hexane, cyclohexane, ethyl acetate, methanol and the like, preparative high pressure liquid chromatography or preparative reverse phase high pressure liquid chromatography.

Representative Synthesis

Example 1: Synthesis of 5-[[4-[1-[3,5-dichloro-4-(3-chloropropoxy)phenyl]-1-methyl-ethyl]phenoxy]methyl]-4-methylsulfonyl-oxazole (A3)

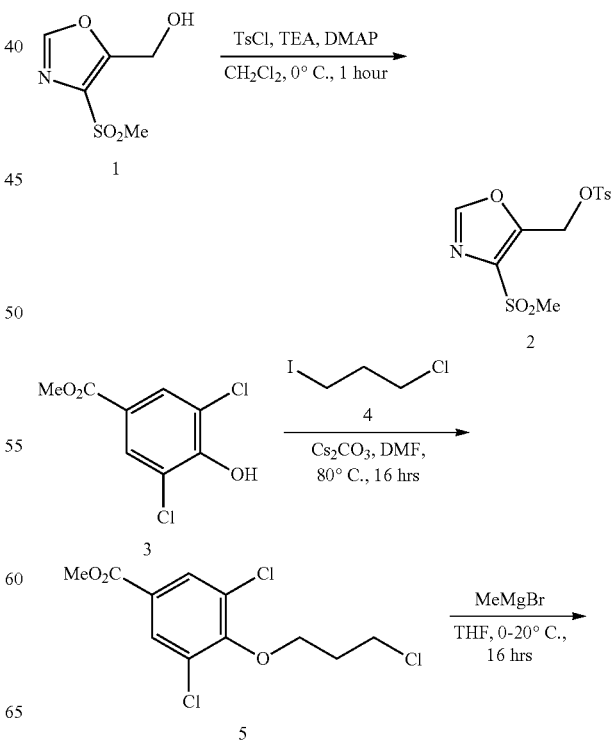

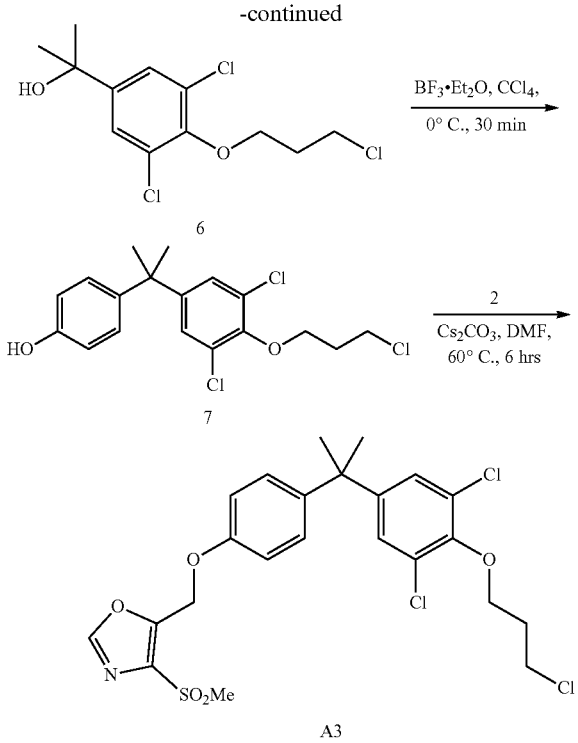

(4-Methylsulfonyloxazol-5-yl) 4-methylbenzenesulfonate (2)

To a solution of 4-methylsulfonyloxazol-5-ol (1) (0.10 g, 0.56 mmol), TEA (0.11 g, 1.1 mmol) and DMAP (14 mg, 0.11 mol) in DCM (3 mL) was added Tosyl chloride (0.10 g, 0.52 mmol) dropwise at 0° C. Then the solution was stirred at the same temperature for 1 hour. TLC showed the reaction was completed. The mixture was poured into $H_2O$ (5 mL), extracted with DCM (3 mL×3). The combined organic layers were washed with brine (5 mL), dried over $Na_2SO_4$, filtered, and concentrated under reduced pressure to give (4-methylsulfonyloxazol-5-yl) 4-methylbenzenesulfonate (2) (0.11 g, yield: 56.6%) as yellow oil. $^1$H NMR (400 MHz, CHCl$_3$-d) δ 7.98 (s, 1H), 7.93 (d, J=8.40 Hz, 2H), 7.42 (d, J=8.80 Hz, 2H), 4.95 (s, 2H), 3.22 (s, 3H).

Methyl 3,5-dichloro-4-(3-chloropropoxy)benzoate (5)

To a mixture of methyl 3, 5-dichloro-4-hydroxybenzoate (3) (100.0 g, 0.45 mol) and $Cs_2CO_3$ (293.2 g, 0.90 mol) in DMF (1.5 L) was added 1-chloro-3-iodopropane (4) (102.2 g, 0.50 mol), and the mixture was stirred at 80° C. for 16 hours. TLC showed the reaction was completed. The mixture was cooled down, quenched with water (3.5 L) and extracted with MTBE (1.0 L×2). The combined organic layers were washed with brine (1 L), dried over $Na_2SO_4$, filtered and concentrated under reduced pressure. The residue was purified by silica-gel column chromatography to give methyl 3,5-dichloro-4-(3-chloropropoxy)benzoate (70.0 g, yield: 52.0%) as yellow oil. $^1$H NMR (400 MHz, CHCl$_3$-d) δ 2.29 (q, J=6.03 Hz, 2H), 3.85 (t, J=6.36 Hz, 2H), 3.91 (s, 3H), 4.22 (t, J=5.70 Hz, 2H), 7.92-8.00 (m, 2H).

2-(3,5-Dichloro-4-(3-chloropropoxy)phenyl)propan-2-ol (6)

To a solution of 3,5-dichloro-4-(3-chloropropoxy)benzoate (5) (70.0 g, 0.24 mol) in THF (500 mL) was added MeMgBr (400 mL, 1.20 mol) at 0° C. under $N_2$ atmosphere. The mixture was stirred at 20° C. for 16 hours under $N_2$ atmosphere. TLC showed the reaction was completed. The mixture was poured into $H_2O$ (500 mL), extracted with EtOAc (200 mL×5), and the combined organic layers were dried over $Na_2SO_4$, filtered and concentrated under reduced pressure to give 2-(3,5-dichloro-4-(3-chloropropoxy)phenyl)propan-2-ol (44.0 g, yield: 62.9%) as yellow oil. $^1$H NMR (400 MHz, CHCl$_3$-d) δ 1.56 (s, 6H), 2.29 (q, J=6.06 Hz, 2H), 3.87 (t, J=6.39 Hz, 2H), 4.13-4.19 (m, 2H), 7.41 (s, 2H).

4-(2-(3,5-Dichloro-4-(3-chloropropoxy)phenyl)propan-2-yl)phenol (7)

To a solution of 2-(3,5-dichloro-4-(3-chloropropoxy)phenyl)propan-2-ol (6) (20.0 g, 67.2 mmol) and phenol (7.0 g, 73.9 mmol) in $CCl_4$ (400 mL) was added $BF_3 \cdot Et_2O$ (16.6 mL, 134.2 mmol) dropwise at 0° C. under $N_2$ atmosphere. The mixture was stirred at 0° C. for 30 min. TLC showed the reaction was completed. The resulting mixture was poured into $H_2O$ (300 mL), extracted with DCM (300 mL×3). The combined organic layers were washed with brine (500 mL), dried over $Na_2SO_4$, filtered and concentrated under reduced pressure. The residue was purified by MPLC to give 4-(2-(3,5-dichloro-4-(3-chloropropoxy)phenyl)propan-2-yl)phenol (18.0 g, yield: 71.7%) as yellow oil. $^1$H NMR (400 MHz, CHCl$_3$-d) δ 7.12 (s, 2H), 7.10-7.05 (m, 2H), 6.79-6.75 (m, 2H), 4.65 (s, 1H), 4.15 (t, J=5.7 Hz, 2H), 3.86 (t, J=6.4 Hz, 2H), 2.28 (q, J=6.1 Hz, 2H), 1.62 (s, 6H).

5-[[4-[1-[3,5-Dichloro-4-(3-chloropropoxy)phenyl]-1-methyl ethyl]phenoxy]methyl]-4-methylsulfonyl-oxazole (A3)

To a suspension of 4-[1-[3,5-dichloro-4-(3-chloropropoxy)phenyl]-1-methyl-ethyl]phenol (7) (0.135 g, 0.36 mmol) and $Cs_2CO_3$ (0.197 g, 0.6 mmol) in DMF (3 mL) was added (4-methylsulfonyloxazol-5-yl)methyl 4-methylbenzenesulfonate (2) (0.1 g, 0.3 mmol) at 25° C. The mixture was stirred at 60° C. for 6 hours. LCMS showed the reaction was completed. The resulting mixture was poured into $H_2O$ (8 mL) and extracted with EtOAc (5 mL×3). The combined organic layers were washed with brine (5 mL×2), dried over $Na_2SO_4$, filtered and concentrated under reduced pressure. The residue was purified by prep-HPLC (HCl) to give 5-[[4-[1-[3,5-dichloro-4-(3-chloropropoxy)phenyl]-1-methyl-ethyl]phenoxy]methyl]-4-methylsulfonyl-oxazole (A1) (37.9 mg, yield: 23.6%) as yellow oil. HPLC purity (220 nm): 96.25%. $^1$H NMR (400 MHz, CHCl$_3$-d) δ 7.99 (s, 1H), 7.16-7.10 (m, 4H), 6.94 (d, J=8.82 Hz, 2H), 5.42 (s, 2H), 4.15 (t, J=5.73 Hz, 2H), 3.86 (t, J=6.50 Hz, 2H) 3.18 (s, 3H), 2.28 (quin, J=6.17 Hz, 2H), 1.62 (s, 6H). LCMS (M+23) m/z: calcd 533; found 556.

Example 2: Synthesis of 4-((4-(2-(3,5-dichloro-4-(3-chloropropoxy)phenyl)propan-2-yl)phenoxy)methyl)-1-(methylsulfonyl)-1H-imidazole (A5)

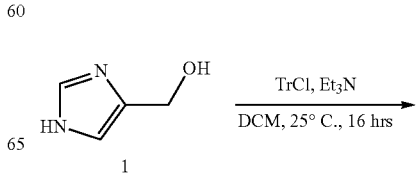

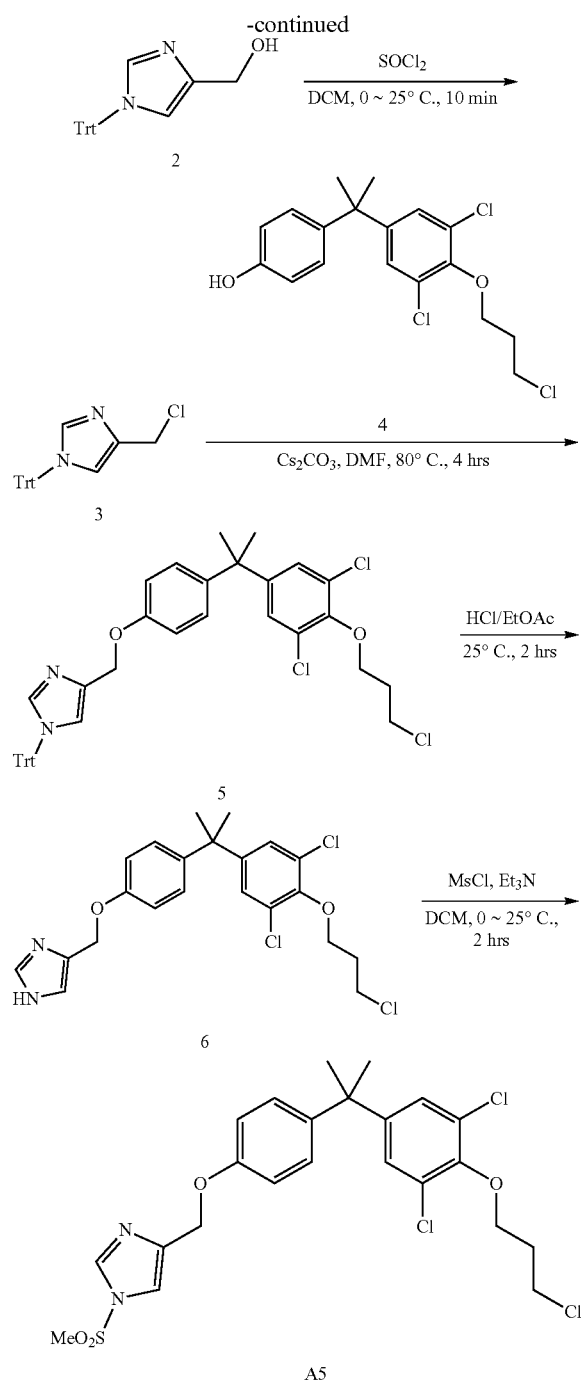

δ=7.37-7.44 (m, 9H), 7.29 (d, J=1.34 Hz, 2H), 7.10 (dd, J=8.01, 1.41 Hz, 6H), 4.87 (t, J=5.56 Hz, 1H), 4.33 (d, J=5.50 Hz, 2H).

4-(Chloromethyl)-1-trityl-1H-imidazole (3)

To a solution of (1-tritylimidazol-4-yl)methanol (2) (200 mg, 0.6 mmol) in DCM (3 mL) was added SOCl$_2$ (0.2 mL, 2.9 mmol) dropwise at 0° C. and the mixture was stirred at 25° C. for 10 min. TLC showed the reaction was completed. The reaction was concentrated under reduced pressure to give 4-(chloromethyl)-1-trityl-1H-imidazole (3) (150 mg, yield: 71.1%) as yellow oil.

4-((4-(2-(3,5-Dichloro-4-(3-chloropropoxy)phenyl)propan-2-yl)phenoxy)methyl) 1-trityl-1H-imidazole (5)

A mixture of 4-(chloromethyl)-1-trityl-1H-imidazole (3) (150 mg, 0.4 mmol), Cs$_2$CO$_3$ (272 mg, 0.8 mmol) and 4-[1-[3,5-dichloro-4-(3-chloropropoxy)phenyl]-1-methyl-ethyl]phenol (4) (156 mg, 0.4 mmol) in MeCN (5 mL) was stirred at 80° C. for 4 hours. TLC showed the reaction was completed. The resulting mixture was cooled down, poured into H$_2$O (10 mL), extracted with EtOAc (4 mL×2), and the combined organic layers were washed with brine (4 mL×5), dried over Na$_2$SO$_4$, filtered and concentrated under reduced pressure. The residue was purified by silica-gel column chromatography to give 4-((4-(2-(3,5-dichloro-4-(3-chloropropoxy)phenyl)propan-2-yl)phenoxy)methyl)-1-trityl-1H-imidazole (5) (150 mg, yield: 71.1%) as white solid. $^1$H NMR (400 MHz, CHCl$_3$-d) δ=7.45 (d, J=1.2 Hz, 1H), 7.38-7.30 (m, 9H), 7.19-7.06 (m, 10H), 6.95-6.86 (m, 3H), 4.99 (s, 2H), 4.14-4.10 (m, 2H), 3.86 (t, J=6.5 Hz, 2H), 2.28 (quin, J=6.1 Hz, 2H), 1.62 (s, 6H).

4-((4-(2-(3,5-Dichloro-4-(3-chloropropoxy)phenyl)propan-2-yl)phenoxy)methyl)-1H-imidazole (6)

A solution of 4-((4-(2-(3,5-dichloro-4-(3-chloropropoxy)phenyl)propan-2-yl)phenoxy)methyl)-1-trityl-1H-imidazole (5) (150 mg, 0.2 mmol) in HCl/EtOAc (4 M, 2 mL) was stirred at 25° C. for 2 hours. LCMS showed the reaction was completed. The reaction was filtered and the filtrate concentrated under reduced pressure to give 4-((4-(2-(3,5-dichloro-4-(3-chloropropoxy)phenyl)propan-2-yl)phenoxy)methyl)-1H-imidazole (6) (95 mg, yield: 97.2%) as colorless oil. LCMS (M+1) m/z: calcd 452.1; found 452.9.

4-((4-(2-(3,5-Dichloro-4-(3-chloropropoxy)phenyl)propan-2-yl)phenoxy)methyl)-1-(methyl sulfonyl)-1H-imidazole (A5)

To a mixture of 4-((4-(2-(3,5-dichloro-4-(3-chloropropoxy)phenyl)propan-2-yl)phenoxy)methyl)-1H-imidazole (6) (80 mg, 0.2 mmol) and TEA (0.1 mL, 0.5 mmol) in DCM (2 mL) was added methanesulfonyl chloride (41 mg, 0.4 mmol) dropwise at 0° C., and the mixture was stirred at 25° C. for 2 hours. TLC showed the reaction was completed. The mixture was diluted with water (20 mL), extracted with DCM (5 mL×3), and the combined organic layers were washed with brine (10 mL), dried over Na$_2$SO$_4$, filtered and concentrated under reduced pressure. The residue was purified by prep-HPLC (NH$_4$HCO$_3$) to give 4-((4-(2-(3,5-dichloro-4-(3-chloropropoxy)phenyl)propan-2-yl)phenoxy)methyl)-1-(methyl sulfonyl)-imidazole (A5) (16 mg, yield: 16.6%) as colorless oil. $^1$H NMR (400 MHz, CHCl$_3$-d) δ=7.99 (d, J=1.3 Hz, 1H), 7.40 (s, 1H), 7.15-7.12 (m, 4H), 6.95-6.90 (m, 2H), 5.05 (s, 2H), 4.15 (t, J=5.7 Hz, 2H), 3.86 (t, J=6.4 Hz, 2H), 3.30 (s, 3H), 2.31-2.26 (m, 2H), 1.63 (s, 6H). LCMS (220 nm): 95.2%. LCMS (M+1) m/z: calcd 530.1; found 531.0.

(1-Trityl-1H-imidazol-4-yl)methanol (2)

To a solution of (1H-imidazol-4-yl)methanol (0.5 g, 5.3 mmol) and Et$_3$N (1.1 g, 10.2 mmol) in DCM (20 mL) was added TrCl (1.5 g, 5.3 mmol) and the mixture was stirred at 50° C. for 4 hours. TLC showed the reaction was completed. The reaction was cooled down, quenched with water (40 mL), extracted with DCM (5 mL×3). The combined organic layers were washed with brine (10 mL), dried over Na$_2$SO$_4$, filtered and concentrated under reduced pressure. The residue was purified by silica-gel column chromatography to give (1-trityl-1H-imidazol-4-yl)methanol (2) (1.0 g, yield: 76.8%) as colorless oil. $^1$H NMR (400 MHz, CHCl$_3$-d)

Example 3: Synthesis of 2-((4-(2-(3,5-dichloro-4-(3-chloropropoxy)phenyl)propan-2-yl)phenoxy)methyl)-5-(methylsulfonyl)-1,3,4-oxadiazole (A7)
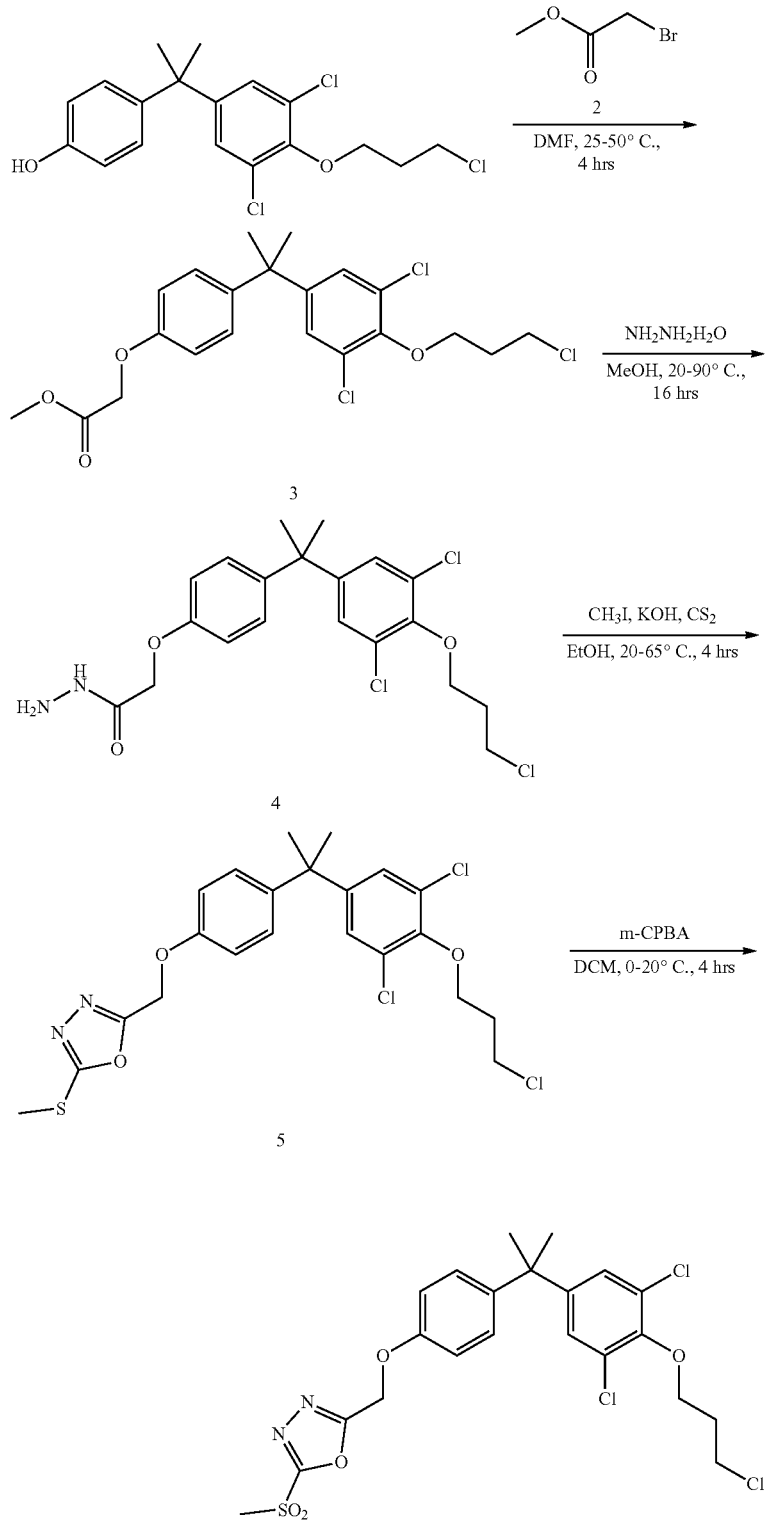

Methyl 2-(4-(2-(3,5-dichloro-4-(3-chloropropoxy) phenyl)propan-2-yl)phenoxy)acetate (3)

To a solution of 4-(2-(3,5-dichloro-4-(3-chloropropoxy) phenyl)propan-2-yl)phenol (1) (1.00 g, 2.6 mmol) and methyl 2-bromoacetate (2) (0.49 g, 3.2 mmol) in DMF (10 mL) was added $Cs_2CO_3$ (1.30 g, 4.0 mmol) at 25° C. The mixture was stirred at 50° C. for 4 hours. LCMS showed the reaction was completed. The mixture was quenched with water (20 mL) and extracted with EtOAc (20 mL×3). The combined organic layers were washed with brine (20 mL×5), dried over $Na_2SO_4$, filtered and concentrated under reduced pressure to give the methyl 2-(4-(2-(3,5-dichloro-4-(3-chloropropoxy)phenyl)propan-2-yl)phenoxy)acetate (3) (1.00 g, yield: 70%) as colorless oil. LCMS (M+23) m/z: calcd 444.07; found 467.1.

2-(4-(2-(3,5-Dichloro-4-(3-chloropropoxy)phenyl) propan-2-yl)phenoxy) Acetohydrazide (4)

To a solution of methyl 2-(4-(2-(3,5-dichloro-4-(3-chloropropoxy)phenyl)propan-2-yl) phenoxy) acetate (3) (1.32 g, 2.9 mmol) in MeOH (10 mL) was added $NH_2NH_2 \cdot H_2O$ (0.59 g, 11.8 mmol) at 20° C. The mixture was stirred at 90° C. for 16 hours. TLC showed of the reaction was completed. The mixture was quenched with water (10 mL) and extracted with EtOAc (20 mL×3). The combined organic layers were washed with brine (10 mL×2), dried over $Na_2SO_4$, filtered and concentrated under reduced pressure. The residue was purified by silica gel column chromatography to give 2-(4-(2-(3,5-dichloro-4-(3-chloropropoxy) phenyl)propan-2-yl)phenoxy) acetohydrazide (4) (1.0 g, yield: 75.8%) as colorless oil. $^1$H NMR (400 MHz, $CHCl_3$-d) δ ppm: 7.73 (br, 1H), 7.11-7.14 (d, J=8.9 Hz, 2H), 7.11 (s, 2H), 6.84 (d, J=8.9 Hz, 2H), 4.58 (s, 2H), 4.14-4.16 (t, J=5.2 Hz, 2H), 3.94 (br, 1H), 3.86 (t, J=6.4 Hz, 2H), 2.28 (m, 2H), 1.62 (s, 6H).

3-(1-(4-(2-(3,5-Dichloro-4-(3-chloropropoxy)phenyl)propan-2-yl)phenoxy)ethyl)-5-methylthio)-4H-pyrazole (5)

To a solution of 2-(4-(2-(3,5-dichloropropoxy)phenyl)propan-2-yl)phenoxy) acetohydrazide (4) (500 mg, 1.12 mmol) in MeOH (2 mL) was added KOH (75 mg, 1.33 mmol) and $CS_2$ (76 mg, 2.8 mmol) at 20° C. The mixture was stirred at 65° C. for 2 hours. Then $CH_3I$ (2 mL) was added to the reaction mixture and stirred at 65° C. for 2 hours. LCMS showed the reaction was completed. The mixture was quenched with water (20 mL) and extracted with EtOAc (10 mL×3). The combined organic layers were washed with brine (20 mL), dried over $Na_2SO_4$, filtered and concentrated under reduced pressure. The residue was purified by silica gel column chromatography to give 3-(1-(4-(2-(3,5-dichloro-4-(3-chloropropoxy)phenyl)propan-2-yl) phenoxy)ethyl)-5-(methylthio)-4H-pyrazole (5) (300 mg, yield: 54.5%) as colorless oil. $^1$H NMR (400 MHz, $CHCl_3$-d) δ ppm 7.14 (d, J=8.9 Hz, 2H), 7.11 (s, 2H), 6.94 (d, J=8.9 Hz, 2H), 5.22 (s, 1H), 4.15 (t, J=5.8 Hz, 2H), 3.86 (t, J=6.4 Hz, 2H), 2.74 (s, 3H), 2.28 (t, J=5.99 Hz, 2H), 1.62 (s, 6H).

2-((4-(2-(3,5-Dichloro-4-(3-chloropropoxy)phenyl) propan-2-yl)phenoxy)methyl)-5-(methylsulfonyl)-1,3,4-oxadiazole (A7)

To a solution of 3-(1-(4-(2-(3,5-dichloro-4-(3-chloropropoxy)phenyl)propan-2-yl)phenoxy)ethyl)-5-(methylthio)-4H-pyrazole (5) (220 mg, 0.49 mmol) in DCM (5 mL) was added m-CPBA (85% purity, 226 mg, 4.03 mmol) at 0° C. The reaction was stirred at 20° C. for 4 hours. LCMS showed the reaction was completed. The mixture was quenched with saturated aqueous $Na_2S_2O_3$ (5 mL) and saturated aqueous $NaHCO_3$ (5 mL), then extracted with DCM (10 mL×3). The combined organic layers were washed with brine (10 mL), dried over $Na_2SO_4$, filtered and concentrated under reduced pressure. The residue was purified by prep-HPLC (TFA) to give 2-((4-(2-(3,5-Dichloro-4-(3-chloropropoxy)phenyl)propan-2-yl)phenoxy)methyl)-5-(methylsulfonyl)-1,3,4-oxadiazole (A7) (74 mg, yield: 31.6%) as colorless oil. $^1$H NMR (400 MHz, DMSO-d6) δ ppm 7.14 (d, J=8.9 Hz, 2H), 7.11 (s, 2H), 6.95 (d, J=8.8 Hz, 2H), 5.35 (s, 2H), 4.15 (t, J=5.73 Hz, 2H), 3.86 (t, J=6.39 Hz, 2H), 3.50 (s, 3H), 2.28 (t, J=6.06 Hz, 2H), 1.63 (s, 6H). LCMS (220 nm): 97%. LCMS M+H$^+$) m/z: calcd 532.04, found 533.1.

Example 4: Synthesis of 5-((4-(2-(3,5-dichloro-4-(2-chloroethoxy)phenyl)propan-2-yl)phenoxy) methyl)-4-(methylsulfonyl)oxazole (A13)

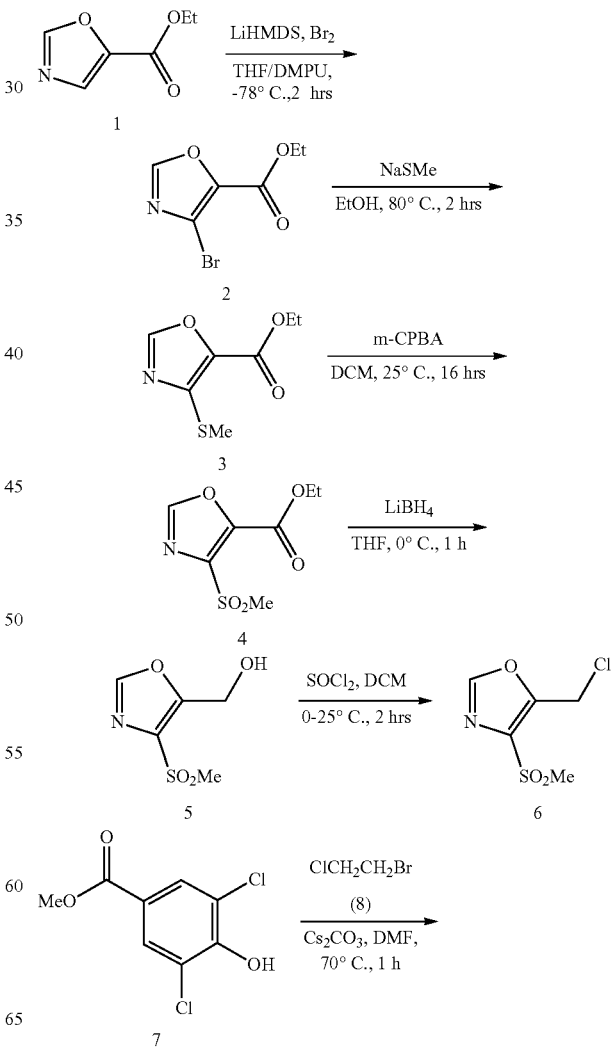

-continued

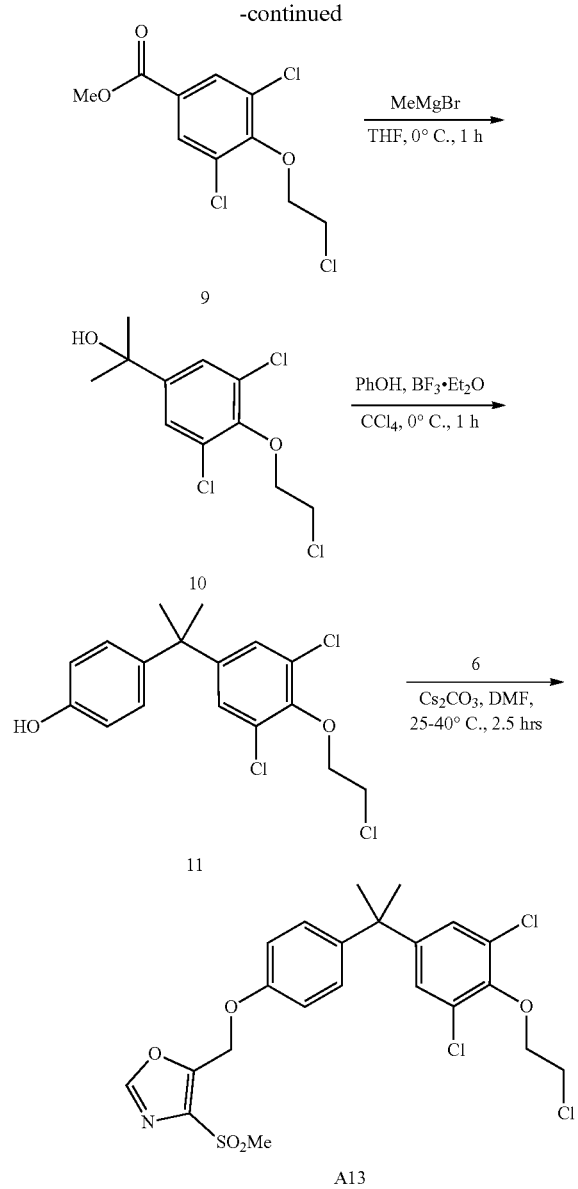

Ethyl 4-bromooxazole-5-carboxylate (2)

To a solution of ethyl oxazole-5-carboxylate (1) (100.0 g, 0.71 mol) in THF (500 mL) and DMPU (500 mL) was added LiHMDS (1.0 M, 921 mL, 921 mmol) dropwise at −78° C. under $N_2$ atmosphere, and the mixture was stirred for 1.5 hours. Then $Br_2$ (54.5 mL, 1.06 mol) was added dropwise at the same temperature and the resulting mixture was stirred for 0.5 hours. TLC showed the starting material disappeared. The resulting solution was poured into a room temperature saturated aqueous $NH_4Cl$ (1000 mL), extracted with EtOAc (500 mL×3). The combined organic layers were washed with brine (500 mL×2), dried over $Na_2SO_4$, filtered and concentrated under reduced pressure. The residue was purified by MPLC to give ethyl 4-bromooxazole-5-carboxylate (25.0 g, purity: 90%, yield: 11%) as yellow oil. $^1H$ NMR (400 MHz, $CHCl_3$-d): 6.7.94 (s, 1H), 4.43 (q, J=7.3 Hz, 2H), 1.42 (t, J=7.2 Hz, 3H)

Ethyl 4-(methylthio)oxazole-5-carboxylate (3)

A mixture of ethyl 4-bromooxazole-5-carboxylate (2) (28.0 g, 127 mmol) and NaSMe (10.8 g, 153 mmol) in EtOH (400 mL) was stirred at 80° C. for 2 hours. LCMS showed the reaction was completed. The resulting solution was cooled down and concentrated under reduced pressure. The residue was diluted with water (300 mL) and extracted with EtOAc (300 mL×3). The combined organic layers were washed with brine (300 mL), dried over $Na_2SO_4$, filtered and concentrated under reduced pressure. The residue was purified by MPLC to give ethyl 4-methylsulfanyloxazole-5-carboxylate (13.0 g, yield: 80%, yield: 43.7%) as yellow oil. $^1H$ NMR (400 MHz, $CHCl_3$-d): δ 7.91 (s, 1H), 4.40 (q, J=7.2 Hz, 2H), 2.62 (s, 3H), 1.41 (t, J=7.2 Hz, 3H).

Ethyl 4-(methylsulfonyl)oxazole-5-carboxylate (4)

A solution of ethyl 4-methylsulfanyloxazole-5-carboxylate (3) (2.9 g, 15.5 mmol) and m-CPBA (10.0 g, 46.5 mmol) in DCM (10 mL) was stirred at 25° C. for 16 hours. The reaction was completed detected by TLC. The reaction was quenched by sat. aqueous $Na_2SO_3$ (100 mL) and sat. aqueous $NaHCO_3$ (100 mL). The mixture was extracted with DCM (60 mL×3). The combined organic layers were washed with brine (50 mL×2), dried over $Na_2SO_4$, filtered and concentrated under reduced pressure. The residue was purified by MPLC to give ethyl 4-methylsulfonyloxazole-5-carboxylate (1.20 g, yield: 35.3%) as colorless oil. $^1H$ NMR (400 MHz, $CHCl_3$-d): δ 8.04 (s, 1H), 4.50 (q, J=7.1 Hz, 2H), 3.38 (s, 3H), 1.44 (t, J=7.2 Hz, 3H).

(4-(Methylsulfonyl)oxazol-5-yl)methanol (5)

To a solution of ethyl 4-methylsulfonyloxazole-5-carboxylate (4) (1.2 g, 5.47 mmol) in THF (10 mL) was added $LiBH_4$ (179 mg, 8.21 mmol) at 0° C. The mixture was stirred at 0° C. for 1 hour. TLC showed the reaction completed. The mixture was quenched with aqueous HCl solution (3M, 2 mL) at 0° C. and extracted with EtOAc (10 mL×3). The combined organic layers were washed with brine (3 mL), dried over $Na_2SO_4$, filtered and concentrated under reduced pressure. The residue was purified by MPLC to give (4-methylsulfonyloxazol-5-yl)methanol (900 mg, yield: 92.8%) as colorless oil. $^1H$ NMR (400 MHz, $CHCl_3$-d): 6=7.92 (s, 1H), 4.93 (s, 2H), 3.24 (s, 3H).

5-(Chloromethyl)-4-(methylsulfonyl)oxazole (6)

To a solution of ethyl 4-methylsulfonyloxazole-5-carboxylate (5) (700 mg, 3.95 mmol) in DCM (10 mL) and DMF (0.5 mL) was added $SOCl_2$ (1.44 mL, 19.8 mmol) at 0° C. The mixture was stirred at 25° C. for 2 hours. TLC showed the reaction completed. The mixture was quenched with $H_2O$ (15 mL), extracted with DCM (10 mL×3). The combined organic layers were washed with brine (10 mL×2), dried over $Na_2SO_4$, filtered and concentrated under reduced pressure to give 5-(chloromethyl)-4-methylsulfonyl-oxazole (700 mg, yield: 90.6%) as yellow oil. 1H NMR (400 MHz, $CHCl_3$-d) δ=7.99 (s, 1H), 4.94 (s, 2H), 3.22 (s, 3H).

Methyl 3,5-dichloro-4-(2-chloroethoxy)benzoate (9)

A mixture of methyl 3,5-dichloro-4-hydroxy-benzoate (7) (10.0 g, 45.2 mmol), $Cs_2CO_3$ (36.9 g, 113 mmol) and 1-bromo-2-chloro-ethane (26.0 g, 181 mmol) in DMF (60.0 mL) was stirred at 70° C. for 1 hour. TLC showed the reaction completed. The resulting solution was cooled down and diluted with water (150 mL), extracted with EtOAc (100 mL×3). The combined organic layers were washed with brine, dried over Na$_2$SO$_4$, filtered and concentrated under reduced pressure to give methyl 3,5-dichloro-4-(2-chloroethoxy)benzoate (10.0 g, yield: 78.0%) as a yellow oil. $^1$H NMR (400 MHz, CHCl$_3$-d) δ=8.01-7.97 (m, 2H), 4.35 (t, J=6.2 Hz, 2H), 3.93 (s, 3H), 3.89 (t, J=6.2 Hz, 2H).

2-(3,5-Dichloro-4-(2-chloroethoxy)phenyl)propan-2-ol (10)

To a solution of MeMgBr (3 M, 65.6 mL, 197 mmol) in THF (30 mL) was added methyl 3,5-dichloro-4-(2-chloroethoxy)benzoate (9) (9.3 g, 32.8 mmol) in THF (50 mL) dropwise at 0° C. The reaction was stirred at 0° C. for 1 hour and TLC showed the reaction completed. The mixture was added to sat. aqueous NH$_4$Cl solution (300 mL) and extracted with EtOAc (200 mL×3). The combined organic layers were washed with brine (200 mL), dried over Na$_2$SO$_4$, filtered and concentrated to give 2-[3,5-dichloro-4-(2-chloroethoxy)phenyl]propan-2-ol (9.0 g, yield: 96.8%) as yellow oil. $^1$H NMR (400 MHz, CHCl$_3$-d) δ=7.42 (s, 2H), 4.27 (t, J=6.3 Hz, 2H), 3.87 (t, J=6.3 Hz, 2H), 1.55 (s, 6H).

4-(2-(3,5-Dichloro-4-(2-chloroethoxy)phenyl)propan-2-yl)phenol (11)

To a solution of 2-[3,5-dichloro-4-(2-chloroethoxy)phenyl]propan-2-ol (9.0 g, 31.7 mmol) (10) and phenol (3.58 g, 38.1 mmol) in CCl$_4$ (100 mL) was added BF$_3$-Et$_2$O (7.83 mL, 63.5 mmol) dropwise at 0° C. under N$_2$ atmosphere. The mixture was stirred at 0° C. for 1 h. LCMS TLC showed the reaction almost completed. The mixture was added to water (150 mL) and extracted with DCM (100 mL×3). The combined organic layers were washed with brine (100 mL), dried over Na$_2$SO$_4$, filtered and concentrated. The crude product was purified by reverse phase MPLC (neutral) to give 4-[1-[3,5-dichloro-4-(2-chloroethoxy)phenyl]-1-methyl-ethyl]phenol (7.0 g, yield: 61.3%) as yellow oil. $^1$H NMR (400 MHz, CHLOROFORM-d) δ=7.13 (s, 2H), 7.10-7.04 (m, 2H), 6.79-6.74 (m, 2H), 4.81 (br s, 1H), 4.26 (t, J=6.3 Hz, 2H), 3.86 (t, J=6.4 Hz, 2H), 1.62 (s, 6H).

5-((4-(2-(3,5-Dichloro-4-(2-chloroethoxy)phenyl) propan-2-yl)phenoxy)methyl)-4-(methylsulfonyl) oxazole (A13)

A solution of 5-(chloromethyl)-4-methyl sulfonyl-oxazole (6) (500 mg, 2.56 mmol), 4-[1-[3,5-dichloro-4-(2-chloroethoxy)phenyl]-1-methyl-ethyl]phenol (11) (919 mg, 2.56 mmol) and Cs$_2$CO$_3$ (1.67 g, 5.11 mmol) in DMF (20 mL) was stirred at 25° C. for 2 hours. Then the resulting solution was stirred at 40° C. for 0.5 hr. The reaction was completed detected by TLC. The reaction was quenched with water (50 mL), and the mixture was extracted with EtOAc (20 mL×3). The combined organic layers were washed with brine (30 mL×2), dried over Na$_2$SO$_4$, filtered, and concentrated under reduced pressure. The residue was purified by MPLC to give 5-[[4-[1-[3,5-dichloro-4-(2-chloroethoxy)phenyl]-1-methyl-ethyl]phenoxy]methyl]-4-methylsulfonyl-oxazole (528 mg, yield: 39.8%) as white solid. $^1$H NMR (400 MHz, CHLOROFORM-d) δ=7.92 (s, 1H), 7.09-7.02 (m, 4H), 6.89-6.83 (m, 2H), 5.34 (s, 2H), 4.18 (t, J=6.4 Hz, 2H), 3.79 (t, J=6.4 Hz, 2H), 3.11 (s, 3H), 1.54 (s, 6H). MS (M+H$^+$) m/z: clcd. 517.0; found 518.1, 540.0.

Example 5: Synthesis of N-((3-(4-(2-(3,5-dichloro-4-(3-chloropropoxy)phenyl)propan-2-yl)phenyl) Isoxazol-5-yl)methyl)methanesulfonamide (A22)

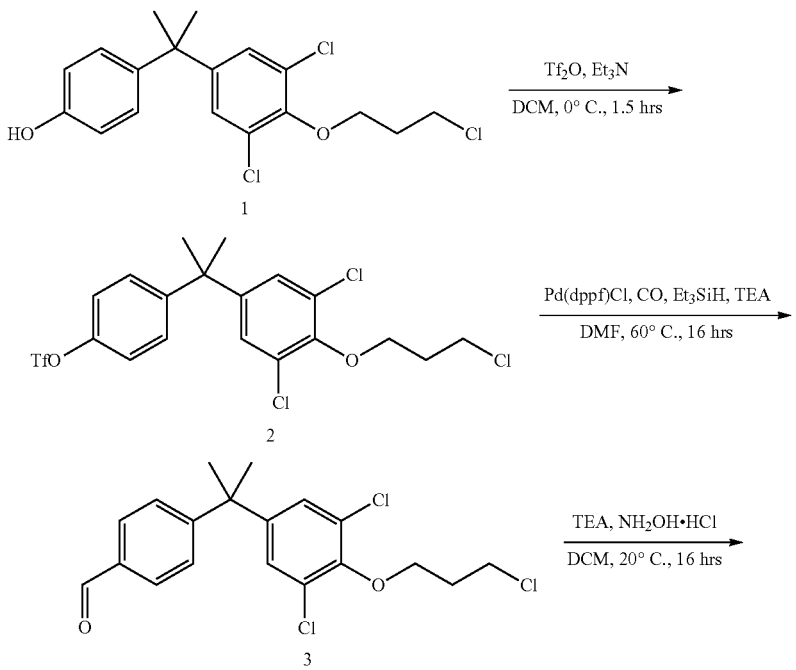

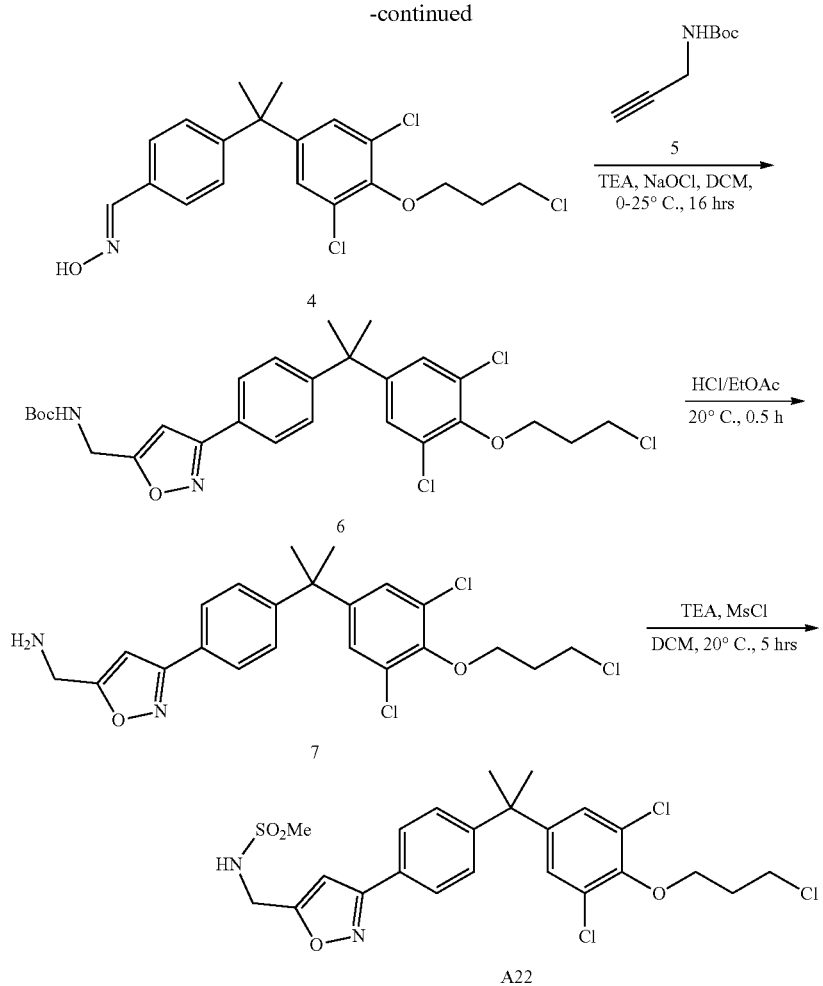

4-(2-(3,5-dichloro-4-(3-chloropropoxy)phenyl)propan-2-yl)phenyl trifluoromethane-sulfonate (2)

To a solution of 4-(2-(3,5-dichloro-4-(3-chloropropoxy)phenyl)propan-2-yl)phenol (1) (4.0 g, 10.7 mmol) and Et₃N (4.5 mL, 54.7 mmol) in DCM (40 mL) was added trifluoromethanesulfonic anhydride (5.4 g, 19.3 mmol) dropwise at 0° C. under N₂ atmosphere. The mixture was stirred at the same temperature for 1.5 hrs. TLC showed the reaction was completed. The mixture was poured into H₂O (60 mL), extracted with DCM (20 mL×3). The combined organic layers were washed with brine (20 mL×3), dried over Na₂SO₄, filtered and concentrated under reduced pressure. The residue was purified by MPLC to give 4-(2-(3,5-dichloro-4-(3-chloropropoxy)phenyl)propan-2-yl)phenyl trifluoromethanesulfonate (4.0 g, yield: 73.4%) as yellow oil. ¹H NMR (400 MHz, CHCl₃-d) δ 7.29-7.27 (m, 2H), 7.22-7.19 (m, 2H), 7.11 (s, 2H), 4.17 (t, J=6.3 Hz, 2H), 3.87 (t, J=6.3 Hz, 2H), 3.87 (t, J=6.2 Hz, 2H), 1.66 (s, 6H).

4-(2-(3,5-dichloro-4-(3-chloropropoxy)phenyl)propan-2-yl)benzaldehyde (3)

To a solution of 4-(2-(3,5-dichloro-4-(3-chloropropoxy)phenyl)propan-2-yl)phenyl trifluoromethanesulfonate (6) (4.0 g, 7.9 mmol), Et₃SiH (1.9 mL, 11.9 mmol) and Et₃N (2.2 mL, 15.8 mmol) in DMF (50 mL) was added Pd(dppf) Cl₂ (290 mg, 0.4 mmol) at 20° C. The reaction was stirred at 60° C. for 16 hours under CO atmosphere at 50 psi. TLC showed the reaction was completed. The resulting mixture was cooled down, poured into H₂O (100 mL), extracted with EtOAc (40 mL×3). The combined organic layers were washed with brine (50 mL×2), dried over Na₂SO₄, filtered and concentrated under reduced pressure. The residue was purified by MPLC to give 4-(2-(3,5-dichloro-4-(3-chloropropoxy)phenyl)propan-2-yl)benzaldehyde (2.6 g, yield: 85.2%) as yellow oil. ¹H NMR (400 MHz, CHCl₃-d) δ 10.02 (s, 1H), 7.83 (d, J=8.8 Hz, 2H), 7.41 (d, J=8.8 Hz, 2H), 7.13 (s, 2H), 4.18 (t, J=5.8 Hz, 2H), 3.88 (t, J=6.4 Hz, 2H), 2.31 (m, 2H), 1.70 (s, 6H).

(E)-4-(2-(3,5-Dichloro-4-(3-chloropropoxy)phenyl)propan-2-yl)benzaldehyde oxime (4)

To a solution of 4-(2-(3,5-dichloro-4-(3-chloropropoxy)phenyl)propan-2-yl)benzaldehyde (0.5 g, 1.3 mmol) (3) in DCM (5 mL) was added NH₂OH.HCl (117 mg, 1.7 mmol) and TEA (0.5 mL, 3.9 mmol) at 20° C. under N₂ atmosphere. The reaction was stirred at the same temperature for 16 hrs. LCMS showed the reaction was completed. The mixture was poured into H₂O (10 mL) and extracted with DCM (10 mL×3). The organic layers were washed with brine (10 mL×2), dried over Na₂SO₄, filtered, and concentrated under reduced pressure to give 4-(2-(3,5-dichloro-4-(3-chloropropoxy)phenyl)propan-2-yl)benzaldehyde oxime (4) (0.410 g, yield: 78.9%) as white solid. ¹H NMR (400 MHz, CHCl₃-d) δ=8.13 (s, 1H), 7.52 (d, J=8.4 Hz, 2H), 7.37 (s, 1H), 7.23 (d, J=8.4 Hz, 2H), 7.12 (s, 2H), 4.15 (t, J=5.6 Hz, 2H), 3.86 (t, J=6.5 Hz, 2H), 2.28 (quin, J=6.1 Hz, 2H), 1.65 (s, 6H). MS (M+H⁺⁾ m/z: clcd. 399.0; found 399.8.

Tert-Butyl ((3-(4-(2-(3,5-dichloro-4-(3-chloropropoxy)phenyl)propan-2-yl)phenyl)isoxazol-5-yl)methyl)carbamate (6)

To a solution of 4-(2-(3,5-dichloro-4-(3-chloropropoxy)phenyl) propan-2-yl)benzaldehyde oxime (4) (320 mg, 0.80 mmol) in DCM (10 mL) was added aqueous NaClO (7.0%, 1.3 g, 1.2 mmol) dropwise at 0° C. The reaction was stirred for 5 min. Tert-butyl prop-2-yn-1-ylcarbamate (5) (120 mg, 0.80 mmol) and TEA (0.22 mL, 1.6 mmol) were added to the reaction mixture at 0° C. The mixture was stirred at 0° C.~25° C. for 16 hours. LCMS showed ~50% of desired product and ~10% of starting material 2 remained. The mixture was poured into H₂O (10 mL), extracted with DCM (10 mL×2). The combined organic layers were washed with brine (10 mL), dried over Na₂SO₄, filtered and concentrated under reduced pressure and purified by MPLC to give tert-butyl ((3-(4-(2-(3,5-dichloro-4-(3-chloropropoxy)phenyl)propan-2-yl)phenyl)isoxazol-5-yl)methyl) carbamate (0.22 g, yield: 51%) as colorless oil. ¹H NMR (400 MHz, CHCl₃-d) δ=7.72 (d, J=8.60 Hz, 2H) 7.31 (d, J=8.60 Hz, 2H) 7.10-7.20 (m, 2H) 6.48 (s, 1H) 5.03 (br s, 1H) 4.48 (br d, J=6.17 Hz, 2H) 4.16 (t, J=5.73 Hz, 2H) 3.86 (t, J=6.39 Hz, 2H) 2.29 (q, J=6.06 Hz, 2H) 1.68 (s, 6H) 1.47 (s, 9H). MS (M+H⁺) m/z: clcd. 552.1; found 553.2.

(3-(4-(2-(3,5-Dichloro-4-(3-chloropropoxy)phenyl) propan-2-yl)phenyl)isoxazol-5-yl) methanamine hydrochloride (7)

A solution of tert-butyl ((3-(4-(2-(3,5-dichloro-4-(3-chloropropoxy) phenyl)propan-2-yl)phenyl)isoxazol-5-yl) methyl)carbamate (6) (190 mg, 0.34 mmol) in HCl/EtOAc (4 M, 3 mL, 12 mmol) was stirred at 20° C. for 0.5 hour. LCMS showed the reaction was completed. The mixture was concentrated under reduced pressure to give (3-(4-(2-(3,5-dichloro-4-(3-chloropropoxy)phenyl)propan-2-yl)phenyl) isoxazol-5-yl)methanamine hydrochloride (7) (60 mg, yield: 36%) as brown oil. MS (M+H⁺) m/z: clcd. 452.1; found 453.1.

N-((3-(4-(2-(3,5-Dichloro-4-(3-chloropropoxy)phenyl)propan-2-yl)phenyl)isoxazol-5-yl)methyl)methanesulfonamide (A22)

To a solution of [3-[4-[1-[3,5-dichloro-4-(3-chloropropoxy)phenyl]-1-methyl-ethyl]phenyl]isoxazol-5-yl]methanamine (7) (60 mg, 0.13 mmol) in DCM (3 mL) was added TEA (40 mg, 0.40 mmol) and MsCl (18 mg, 0.16 mmol) under N₂ atmosphere at 0° C. The reaction was stirred at 20° C. for 5 hrs. TLC showed the reaction was completed. The mixture was poured into H₂O (5 mL) and extracted with DCM (10 mL×3). The combined organic layers were washed with brine (10 mL), dried over Na₂SO₄, filtered and concentrated under reduced pressure. The residue was purified by prep-HPLC (TFA) to give N-((3-(4-(2-(3,5-dichloro-4-(3-chloropropoxy)phenyl)propan-2-yl)phenyl)isoxazol-5-yl)methyl) methanesulfonamide (A22) (5 mg, yield: 7.11%) as brown oil. LCMS purity (220 nm): 89.4%. ¹H NMR (400 MHz, CHCl₃-d) δ=7.73 (br d, J=7.9 Hz, 2H), 7.31 (br d, J=8.2 Hz, 2H), 7.14 (s, 2H), 6.60 (s, 1H), 4.89-4.80 (m, 1H), 4.54 (d, J=6.2 Hz, 2H), 4.16 (t, J=5.6 Hz, 2H), 3.86 (t, J=6.4 Hz, 2H), 2.99 (s, 3H), 2.33-2.25 (m, 2H), 1.68 (s, 6H). LCMS (M+H⁺) m/z: clcd. 530.0; found 531.0.

Example 6: Synthesis of N-(tert-Butyl)-3,5-dichloro-4-(2-chloroethoxy)-N-(4-((4-(methyl-sulfonyl)oxazol-5-yl)methoxy)phenyl)aniline (A31)

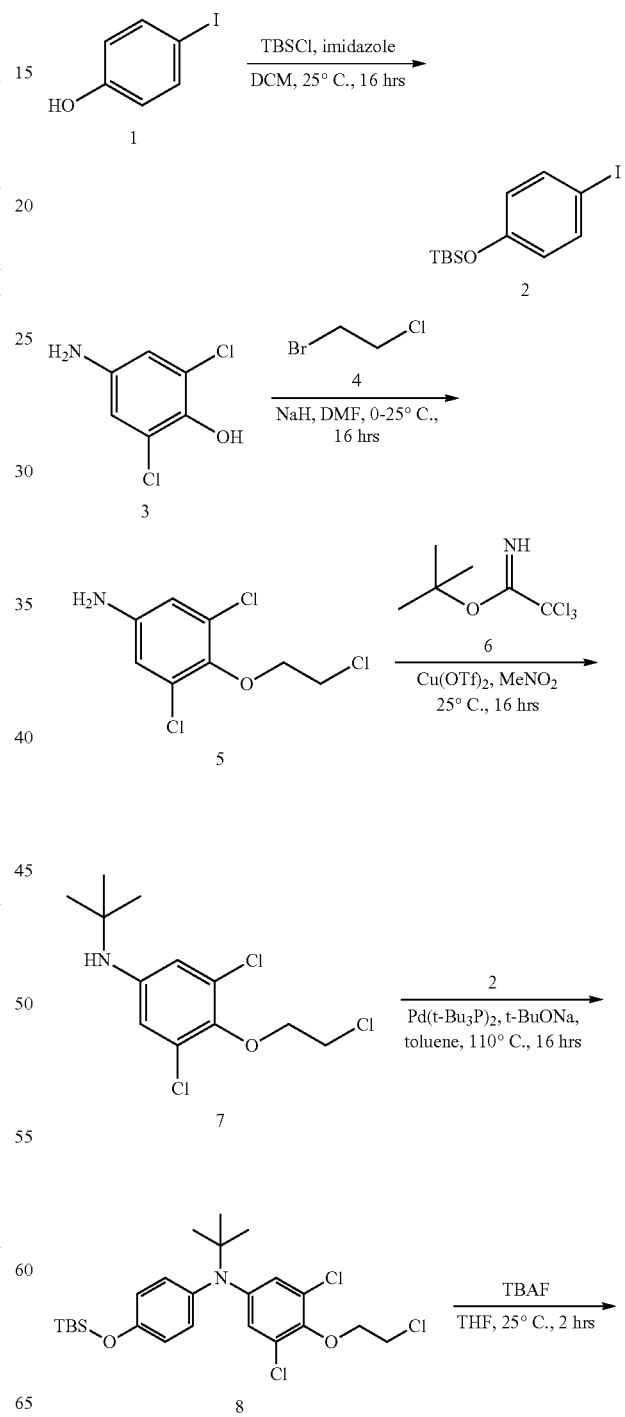

-continued

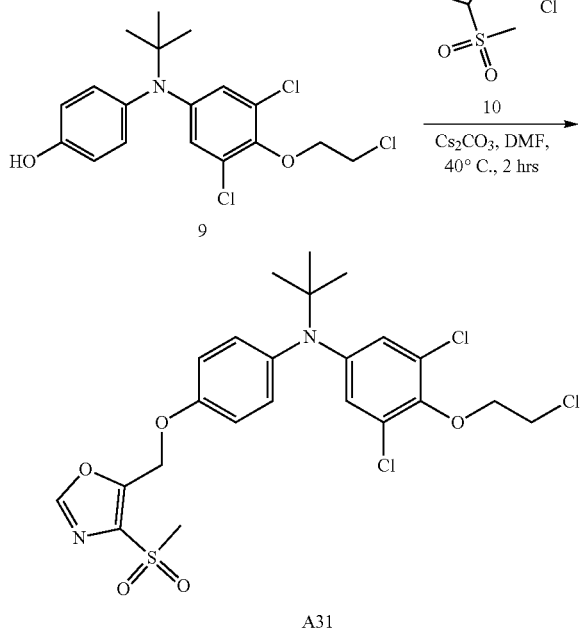

Tert-Butyl-(4-iodophenoxy)-dimethyl-silane (2)

To a solution of 4-iodophenol (1) (3.0 g, 13.6 mmol) and imidazole (1.9 g, 27.3 mmol) in DCM (30 mL) was added TBSCl (1.8 g, 12.3 mmol) at 25° C. Then the mixture was stirred at the same temperature for 16 hours. TLC showed the reaction was completed. The reaction mixture was washed with water (10 mL×2), dried over $Na_2SO_4$, filtered and concentrated under reduced pressure. The residue was purified by MPLC to give tert-butyl-(4-iodophenoxy)-dimethyl-silane (2) (2.5 g, yield: 54.8%) as colorless oil. $^1H$ NMR (400 MHz, $CHCl_3$-d) δ 7.57-7.44 (m, 2H), 6.67-6.55 (m, 2H), 1.02-0.93 (m, 9H), 0.19 (s, 6H).

3,5-Dichloro-4-(2-chloroethoxy)aniline (5)

To a solution of 4-amino-2,6-dichloro-phenol (3) (5.0 g, 28.1 mmol) in DMF (50 mL) was added NaH (60% purity, 1.1 g, 28.1 mmol) in portions at 0° C. under $N_2$ atmosphere. After stirring at the same temperature for 15 min, 1-bromo-2-chloro-ethane (4) (4.4 g, 30.9 mmol) was added and the resulting mixture was stirred at 25° C. for 16 hours. TLC showed the reaction was completed. The resulting mixture was quenched with saturated aqueous $NH_4Cl$ solution (100 mL) and extracted with EtOAc (50 mL×3). The combined organic layers were washed with brine (50 mL×3), dried over $Na_2SO_4$, filtered and concentrated under reduced pressure. The residue was purified by MPLC to give 3,5-dichloro-4-(2-chloroethoxy)aniline (5) (2.5 g, yield: 37%) as yellow solid. $^1H$ NMR (400 MHz, $CHCl_3$-d) 66.64-6.55 (m, 2H), 4.18 (t, J=6.4 Hz, 2H), 3.84 (t, J=6.4 Hz, 2H), 3.69-3.58 (m, 2H).

N-tert-butyl-3,5-dichloro-4-(2-chloroethoxy)aniline (7)

To a solution of 3,5-dichloro-4-(2-chloroethoxy)aniline (5) (1.0 g, 4.16 mmol) and tert-butyl 2,2,2-trichloroetha- nimidate (6) (2.27 g, 10.4 mmol) in $MeNO_2$ (10 mL) was added Copper(II) trifluoromethanesulfonate (1.5 g, 4.16 mmol) under $N_2$ atmosphere. Then the resulting mixture was stirred at 25° C. for 16 hours. TLC showed the reaction completed. The mixture was quenched with aqueous $NaHCO_3$ solution (5 mL) and extracted with EtOAc (5 mL×3). The combined organic layers were washed with brine (5 mL×2), dried over $Na_2SO_4$, filtered and concentrated under reduced pressure. The residue was purified by MPLC to give the N-tert-butyl-3,5-dichloro-4-(2-chloroethoxy)aniline (7) (460 mg, yield: 37.3%) as a brown gum. $^1H$ NMR (400 MHz, $CHCl_3$-d) δ 6.64 (s, 2H), 4.19 (t, J=6.4 Hz, 2H), 3.84 (t, J=6.4 Hz, 2H), 1.37-1.29 (m, 9H).

N-tert-Butyl-N-[4-[tert-butyl(dimethyl)silyl]oxyphenyl]-3,5-dichloro-4-(2 Chloroethoxy)aniline (8)

To a mixture of N-tert-butyl 3,5-dichloro-4-(2-chloro ethoxy) aniline (7) (210 mg, 0.71 mmol), tert-butyl-(4-iodophenoxy)-dimethyl-silane (237 mg, 0.71 mmol) and t-BuONa (162 mg, 1.77 mmol) in toluene (5 mL) was added palladium (I) tritertubutyl phosphine bromide (55 mg, 0.07 mmol) under $N_2$ atmosphere. Then the resulting mixture was stirred at 110° C. for 16 hours. TLC showed the reaction was completed. The resulting mixture was cooled down and quenched with water (2 mL) and extracted with EtOAc (2 mL×3). The combined organic layers were washed with brine (3 mL), dried over $Na_2SO_4$, filtered and concentrated under reduced pressure. The residue was purified by MPLC to give N-tert-butyl-N-[4-[tert-butyl(dimethyl) silyl]oxyphenyl]-3,5-dichloro-4-(2-chloroethoxy)aniline (8): (125 mg, yield: 35.1%) as yellow solid. $^1H$ NMR (400 MHz, $CHCl_3$-d) δ 6.99-6.93 (m, 2H), 6.86-6.77 (m, 2H), 6.70 (s, 2H), 4.18 (t, J=6.4 Hz, 2H), 3.83 (t, J=6.5 Hz, 2H), 1.37 (s, 9H), 1.04-0.94 (m, 9H), 0.26-0.21 (m, 6H).

4-[N-tert-Butyl3,5-dichloro-4-(2-chloroethoxy)anilino]phenol (9)

To a solution of N-tert-butylN-[4-[tert-butyl(dimethyl) silyl]oxyphenyl]-3,5-dichloro-4-(2-chloro-ethoxy)aniline (8) (150 mg, 0.29 mmol) in THF (5 mL) was added TBAF (1 M, 1.0 mL, 1 mmol). Then the resulting mixture was stirred at 25° C. for 2 hours. TLC showed the reaction was completed. The mixture was quenched with water (5 mL) and extracted with EtOAc (3 mL×3). The combined organic layers were washed with water (5 mL×2), dried over $Na_2SO_4$, filtered and concentrated to give the 4-[N-tert-butyl3,5-dichloro-4-(2-chloroethoxy)anilino]phenol (9) (110 mg, yield: 94.9%) as yellow gum. $^1H$ NMR (400 MHz, $CHCl_3$-d) δ 7.03-6.93 (m, 2H), 6.87-6.79 (m, 2H), 6.72 (s, 2H), 4.18 (t, J=6.4 Hz, 2H), 3.83 (t, J=6.4 Hz, 2H), 1.37 (s, 9H).

N-tert-Butyl-3,5-dichloro-4-(2-chloroethoxy)-N-[4-[(4-methylsulfonyloxazol-5-yl)-methoxy]-phenyl] aniline (A31)

To a mixture of 4-[N-tert-butyl-3,5-dichloro-4-(2-chloroethoxy)anilino]phenol (9) (110 mg, 0.283 mmol) and $Cs_2CO_3$ (277 mg, 0.85 mmol) in DMF (5 mL) was added 5-(chloromethyl)-4-methylsulfonyl-oxazole (10) (83 mg, 0.42 mmol). Then the resulting mixture was stirred at 40° C. for 2 hours. LCMS showed the reaction was completed. The mixture was cooled down, quenched with water (5 mL) and extracted with EtAOc (5 mL×3). The combined organic layers were washed with brine (5 mL×3), dried over Na₂SO₄, filtered and concentrated under reduced pressure. The residue was purified by p-HPLC (TFA) to give the N-tert-butyl-3,5-dichloro-4-(2-chloroethoxy)-N-[4-[(4-methylsulfonyl-oxazol-5-yl)-methoxy]-phenyl]aniline (A31) (36.5 mg, yield: 23.5%) as yellow solid. HPLC purity (220 nm): 91.7%. $^1$H NMR (400 MHz, CHCl₃-d) δ 8.01 (s, 1H), 7.06-7.02 (m, 2H), 6.99-6.94 (m, 2H), 6.73 (s, 2H), 5.41 (s, 2H), 4.17 (t, J=6.4 Hz, 2H), 3.82 (t, J=6.4 Hz, 2H), 3.20 (s, 3H), 1.35 (s, 9H). LCMS (M+Na⁺) m/z: calcd 546.1; found 569.1.

Example 7: Synthesis of 4-(2-(3,5-dichloro-4-(2-chloroethoxy)phenyl)propan-2-yl)-N-((4-(methylsulfonyl)oxazol-5-yl)methyl)aniline Hydrochloride (A32)

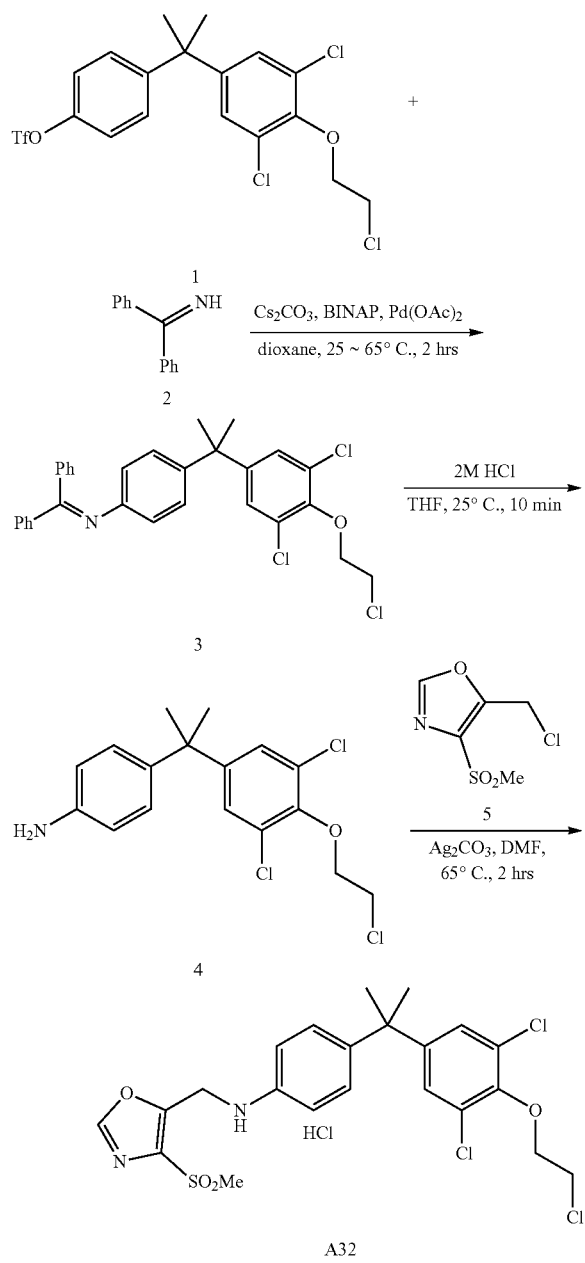

4-(2-(3,5-Dichloro-4-(2-chloroethoxy)phenyl)propan-2-yl)-N-(diphenylmethylene)aniline (3)

To a mixture of 4-(2-(3,5-dichloro-4-(2-chloroethoxy)phenyl)propan-2-yl)phenyl trifluoromethanesulfonate (1) (5.0 g, 10.2 mmol), diphenylmethanimine (2) (1.8 g, 10.2 mmol), Cs₂CO₃ (6.6 g, 20.3 mmol) and BINAP (1.3 g, 5.08 mmol) in 1,4-dioxane (100 mL) was added Pd(OAc)₂ (0.5 g, 2.0 mmol) at 25° C. under N₂ atmosphere. The mixture was stirred at 65° C. for 2 hrs. TLC showed the reaction was completed. The resulting solution was cooled down, quenched with H₂O (100 mL), extracted with EtOAc (30 mL×2). The combined organic layers were washed with brine (40 mL×3), dried over Na₂SO₄, filtered and concentrated under reduced pressure. The residue was purified by silica-gel column chromatography to give 4-(2-(3,5-dichloro-4-(2-chloroethoxy)phenyl)propan-2-yl)-N-(diphenylmethylene)aniline (4.5 g, yield: 84.6%) as colorless oil. $^1$H NMR (400 MHz, CHCl₃-d) δ 7.78-7.74 (m, 2H), 7.63-7.57 (m, 2H), 7.45-7.38 (m, 2H), 7.32-7.27 (m, 2H), 7.14-7.07 (m, 2H), 7.03-6.94 (m, 4H), 6.66 (d, J=8.6 Hz, 2H), 4.26 (t, J=6.4 Hz, 2H), 3.86 (t, J=6.4 Hz, 2H), 1.58 (s, 6H).

4-(2-(3,5-Dichloro-4-(2-chloroethoxy)phenyl)propan-2-yl)aniline Hydrochloride (4)

To a solution of 4-(2-(3,5-dichloro-4-(2-chloroethoxy)phenyl)propan-2-yl)-N-(diphenyl methylene)aniline (3) (4.5 g, 8.6 mmol) in THF (50 mL) was added aqueous HCl (2 M, 15 mL) and the mixture was stirred at 25° C. for 15 min. TLC showed the reaction was completed. The mixture was concentrated under reduced pressure and purified by silica-gel column chromatography to give 4-(2-(3,5-dichloro-4-(2-chloroethoxy)phenyl)propan-2-yl)aniline hydrochloride (2.5 g, yield: 81.0%) as yellow solid. $^1$H NMR (400 MHz, CHCl₃-d) δ 10.54 (br s, 2H), 7.48 (br d, J=8.6 Hz, 2H), 7.31-7.27 (m, 2H), 7.09 (s, 2H), 4.26 (t, J=6.4 Hz, 2H), 3.86 (t, J=6.3 Hz, 2H), 1.63 (s, 6H).

4-(2-(3,5-dichloro-4-(2-chloroethoxy)phenyl)propan-2-yl)-N-((4-(methylsulfonyl)oxazol-5-yl)methyl)aniline Hydrochloride (A32)

To a suspension of 5-(chloromethyl)-4-(methylsulfonyl)oxazole (5) (200 mg, 0.5 mmol) and Ag₂CO₃ (564 mg, 0.2 mmol) in DMF (2 mL) was added 4-(2-(3,5-dichloro-4-(2-chloroethoxy)phenyl)propan-2-yl)aniline (4) (382 mg, 0.1 mmol), and the mixture was stirred at 65° C. for 2 hours. TLC showed the reaction was completed. The resulting mixture was cooled down, poured into H₂O (6 mL), extracted with EtOAc (2 mL×2). The combined organic layers were washed with brine (4 mL×3), dried over Na₂SO₄, filtered and concentrated under reduced pressure. The residue was purified by prep-HPLC (HCl) to give 4-(2-(3,5-dichloro-4-(2-chloroethoxy)phenyl)propan-2-yl)-N-((4-(methylsulfonyl)oxazol-5-yl) methyl)aniline hydrochloride (A32) (20 mg, yield: 3.8%) as white solid. $^1$H NMR (400 MHz, CHCl₃-d) δ 7.85 (s, 1H), 7.16-7.09 (m, 4H), 7.04-6.93 (m, 2H), 4.80 (s, 2H), 4.26 (t, J=6.4 Hz, 2H), 3.86 (t, J=6.4 Hz, 2H), 3.16 (s, 3H), 1.61 (s, 6H). LCMS (M+H⁺) m/z: calcd: 516.0; found 517.0.

Example 8: Synthesis of 5-(1-(4-(2-(3,5-dichloro-4-(2-chloroethoxy)phenyl)propan-2-yl) phenoxy) ethyl)-4-(methylsulfonyl)oxazole (A35)

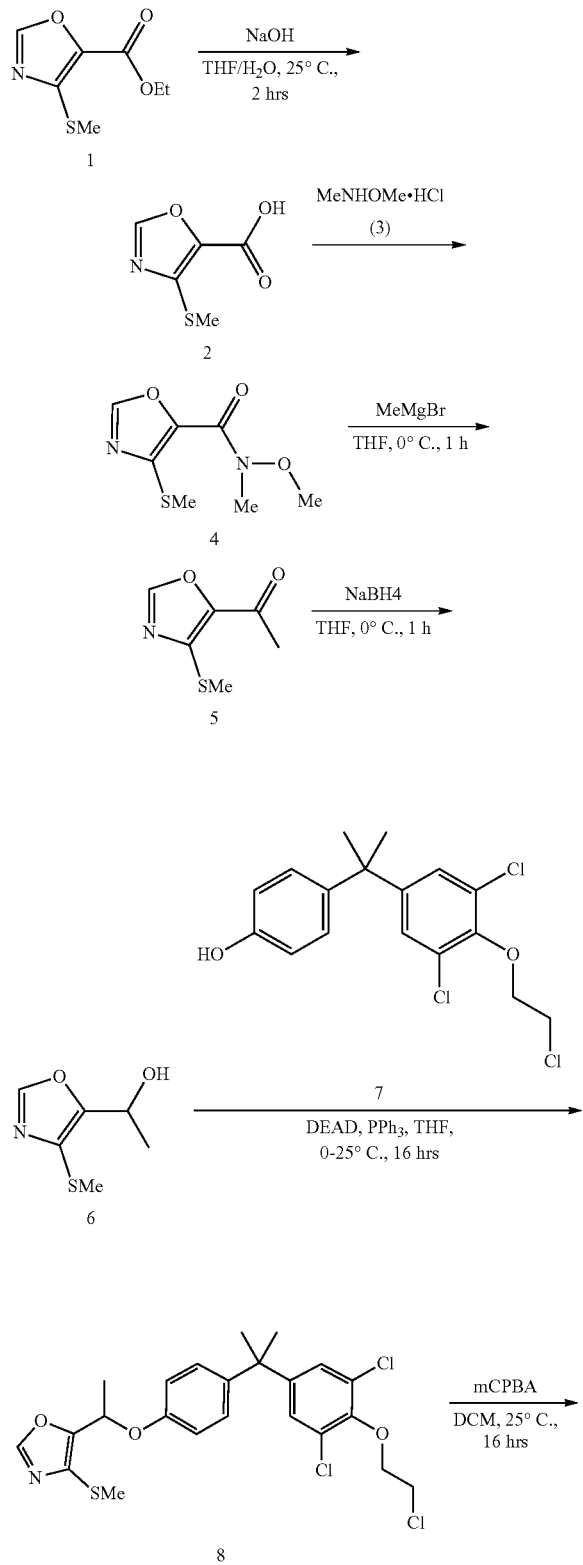

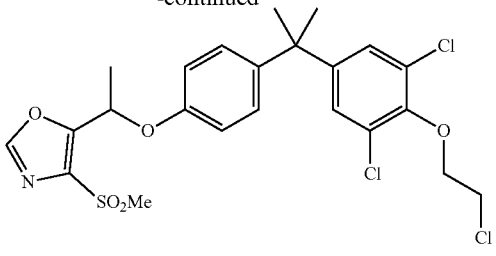

A35

4-(Methylthio)oxazole-5-carboxylic Acid (2)

To a solution of ethyl 4-methylsulfanyloxazole-5-carboxylate (1) (1 g, 80% purity, 4.3 mmol) in THF (10 mL) and H$_2$O (4 mL) was added NaOH (300 mg, 8.6 mmol) at 25° C., and the mixture was stirred at the same temperature for 2 hours. LCMS showed the reaction was completed. The mixture was acidified to pH=3 with aqueous HCl solution (3 M, 3 mL) and extracted with EtOAc (15 mL×3). The combined organic layers were washed with brine (10 mL), dried over Na$_2$SO$_4$, filtered and concentrated under reduced pressure to give 4-(methylthio)oxazole-5-carboxylic acid (2) (0.7 g, 80% purity, yield: 82.3%) as white solid. $^1$H NMR (400 MHz, CHCl$_3$-d) δ 7.99 (s, 1H), 2.65 (s, 3H). LCMS (M+1) m/z: calcd: 531.0; found 532.0.

N-Methoxy-N-methyl-4-(methylthio)oxazole-5-carboxamide (4): To a mixture of 4-(methylthio)oxazole-5-carboxylic acid (2) (0.7 g, 4.4 mmol) in THF (5 mL) and DMF (5 mL) was added HATU (2.5 g, 6.6 mmol) at 25° C. under N$_2$ atmosphere. After stirring at the same temperature for 15 minutes, N-methoxymethanamine hydrochloride (3) (0.6 g, 5.7 mmol) and TEA (3.1 mL, 22.0 mmol) were added and the resulting mixture stirred at 25° C. for 2 hours. TLC showed the reaction was completed. The reaction was diluted with H$_2$O (10 mL), extracted with EtOAc (10 mL×3). The combined organic layers were washed with brine (3 mL), dried over Na$_2$SO$_4$, filtered and concentrated under reduced pressure. The residue was purified by MPLC to give N-methoxy-N-methyl-4-(methylthio)oxazole-5-carboxamide (4) (0.5 g, yield: 56.2%) as yellow oil. $^1$H NMR (400 MHz, CHCl$_3$-d) δ 7.90 (s, 1H), 4.12 (q, J=7.1 Hz, 1H), 3.81 (s, 3H), 3.30 (s, 3H), 2.58 (s, 3H).

1-(4-(Methylthio)oxazol-5-yl)ethenone (5)

To a mixture of N-methoxy-N-methyl-4-(methylthio)oxazole-5-carboxamide (4) (0.4 g, 1.9 mmol) in THF (8 mL) was added MeMgBr (3 M, 0.8 mL, 2.4 mmol) at 0° C. under N$_2$ atmosphere, and the resulting mixture was stirred at the same temperature for 1 hour. TLC showed the reaction was completed. The reaction was quenched with saturated aqueous NH$_4$Cl (4 mL), extracted with EtOAc (5 mL×3). The combined organic layers were washed with brine (3 mL), dried over Na$_2$SO$_4$, filtered and concentrated under reduced pressure to give 1-(4-(methylthio)oxazol-5-yl)ethenone (5) (0.4 g, 75% purity, yield: 96.2%) as yellow oil. $^1$H NMR (400 MHz, CHCl$_3$-d) δ 7.89 (s, 1H), 2.62 (s, 3H), 2.50 (s, 3H).

1-(4-(Methylthio)oxazol-5-yl)ethanol (6)

To a mixture of 1-(4-(methylthio)oxazol-5-yl)ethanone (5) (0.4 g, 2.3 mmol) in THF (8 mL) was added NaBH$_4$ (0.1 g, 2.7 mmol) at 0° C. under N₂ atmosphere, and the mixture was stirred at the same temperature for 1 hour. TLC showed the reaction was completed. The reaction was quenched with saturated aqueous NH₄Cl (4 mL), extracted with EtOAc (5 ml×3). The combined organic layers were washed with brine (3 mL), dried over Na₂SO₄, filtered and concentrated under reduced pressure to give 1-(4-(methylthio)oxazol-5-yl)ethanol (6) (0.2 g, yield: 54.9%) as yellow oil. ¹H NMR (400 MHz, CHCl₃-d) δ 7.83 (s, 1H), 5.12 (br d, J=5.5 Hz, 1H), 2.44 (s, 3H), 1.58 (d, J=6.6 Hz, 3H).

5-(1-(4-(2-(3,5-Dichloro-4-(2-chloroethoxy)phenyl) propan-2-yl)phenoxy)ethyl)-4 (methylthio)oxazole (8)

To a mixture of 1-(4-(methylthio)oxazol-5-yl)ethanol (6) (0.2 g, 1.1 mmol), 4-[1-[3,5-dichloro-4-(2-chloroethoxy)phenyl]-1-methyl-ethyl]phenol (7) (0.4 g, 1.1 mmol) and PPh₃ (0.6 g, 2.3 mmol) in THF (2 mL) was added DEAD (0.3 g, 1.7 mmol) at 0° C. under N₂ atmosphere, and the mixture was stirred at 25° C. for 16 hours. TLC showed the reaction was completed. The reaction was quenched with H₂O (5 mL), extracted with EtOAc (6 mL×3). The combined organic layers were washed with brine (3 mL), dried over Na₂SO₄, filtered and concentrated under reduced pressure. The residue was purified by MPLC to give the 5-(1-(4-(2-(3,5-dichloro-4-(2-chloroethoxy)phenyl)propan-2-yl)phenoxy)ethyl)-4-(methylthio)oxazole (8) (50 mg, yield: 8.83%) as yellow oil. ¹H NMR (400 MHz, CHCl₃-d) 6.7.85-7.82 (m, 1H), 7.11-7.03 (m, 4H), 6.88 (d, J=8.8 Hz, 2H), 5.51 (q, J=6.6 Hz, 1H), 4.24 (t, J=6.4 Hz, 2H), 3.84 (t, J=6.4 Hz, 2H), 2.35 (s, 3H), 1.69 (d, J=6.6 Hz, 3H), 1.58 (s, 6H).

5-(1-(4-(2-(3,5-Dichloro-4-(2-chloroethoxy)phenyl) propan-2-yl)phenoxy)ethyl)-4-(methylsulfonyl)oxazole (A35)

To a mixture of 5-(1-(4-(2-(3,5-dichloro-4-(2-chloroethoxy)phenyl)propan-2-yl)phenoxy)ethyl)-4-(methylthio)oxazole (8) (50 mg, 0.1 mmol) was added mCPBA (80% purity, 64 mg, 0.3 mmol) in DCM (3 mL) at 25° C., and the mixture was stirred at the same temperature for 16 hours. LCMS showed the reaction was completed. The reaction was quenched with H₂O (5 mL), extracted with EtOAc (6 mL×3). The combined organic layers were washed with brine (3 mL), dried over Na₂SO₄, filtered and concentrated under reduced pressure. The residue was purified by p-HPLC (TFA) 5-(1-(4-(2-(3,5-dichloro-4-(2-chloroethoxy) phenyl)propan-2-yl)phenoxy)ethyl)-4-(methylsulfonyl)oxazole (21.7 mg, yield: 40.8%) as white solid. HPLC purity (220 nm): 98.5%. ¹H NMR (400 MHz, CHCl₃-d) δ=7.94 (s, 1H), 7.14-7.03 (m, 4H), 6.92 (d, J=8.9 Hz, 2H), 6.10 (q, J=6.5 Hz, 1H), 4.26 (t, J=6.3 Hz, 2H), 3.86 (t, J=6.3 Hz, 2H), 3.06 (s, 3H), 1.74 (d, J=6.7 Hz, 3H), 1.59 (s, 6H). LCMS (M+H⁺) m/z: calcd: 531.0; found 532.0, 534.0.

Example 9: Synthesis of N-(4-((4-(2-(3,5-dichloro-4-(2-chloroethoxy)phenyl)propan-2-yl)phenoxy) methyl)oxazol-2-yl)methanesulfonamide (A38)

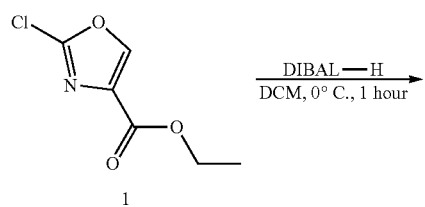

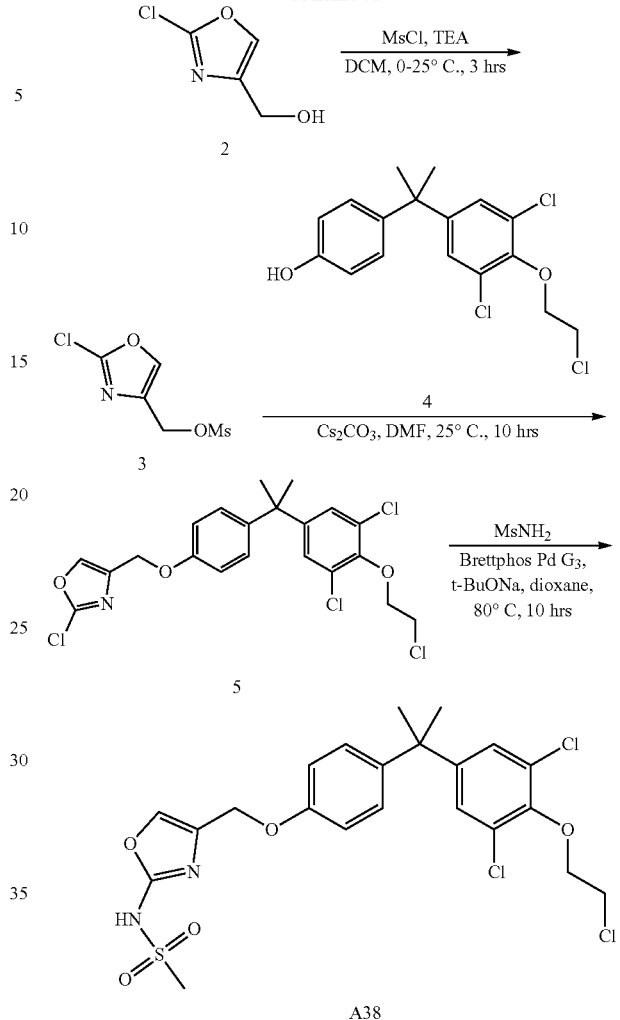

(2-Chlorooxazol-4-yl)methanol (2)

To a solution of ethyl 2-chlorooxazole-4-carboxylate (1) (1.0 g, 5.7 mmol) in DCM (20 mL) was added DIBAL-H (1 M in toluene 8.5 mL, 8.5 mmol) dropwise at 0° C. under N₂ atmosphere. The mixture was stirred at the same temperature for 1 hour. TLC showed the reaction was completed. The mixture was quenched with saturated aqueous NH₄Cl (20 mL), then extracted with EtOAc (20 mL×3). The combined organic layers were washed with brine (20 mL×2), dried over Na₂SO₄, filtered, and concentrated under reduced pressure. The residue was purified by MPLC to give (2-chlorooxazol-4-yl)methanol (2) (470 mg, yield: 62%) as brown oil. ¹H NMR (400 MHz, CHCl₃-d) δ 7.59 (s, 1H), 4.58 (d, J=0.8 Hz, 2H).

(2-Chlorooxazol-4-yl)methyl methanesulfonate (3)

To a mixture of (2-chlorooxazol-4-yl)methanol (2) (0.47 g, 3.52 mmol) and TEA (1 mL, 7.04 mol) in DCM (15 mL) was added methanesulfonyl chloride (444 mg, 3.87 mmol) at 0° C. The mixture was stirred at 0-25° C. for 3 hours. TLC showed the reaction was completed. The mixture was poured into H₂O (30 mL), extracted with DCM (10 mL×2). The combined organic layers were washed with brine (20 mL×2), dried over Na₂SO₄, filtered and concentrated under reduce pressure to give (2-chlorooxazol-4-yl)methyl methanesulfonate (3) (800 mg, 70% purity) as yellow oil. ¹H NMR (400 MHz, CHCl₃-d) δ 7.77 (s, 1H), 5.14 (d, J=0.8 Hz, 2H), 3.08 (s, 3H).

2-Chloro-4-((4-(2-(3,5-dichloro-4-(2-chloroethoxy)phenyl)propan-2-yl)phenoxy)methyl)oxazole (5)

To a solution of (2-chlorooxazol-4-yl)methyl methanesulfonate (3) (0.70 g, 3.31 mmol) in DMF (10 mL) was added 4-[1-[3,5-dichloro-4-(2-chloroethoxy)phenyl]-1-methyl-ethyl]phenol (4) (1.19 g, 3.31 mmol) and Cs₂CO₃ (2.16 g, 6.62 mmol). The resulting mixture was stirred at 25° C. for 10 hours. LCMS showed the reaction was completed. The mixture was poured into H₂O (30 mL) and extracted with EtOAc (30 mL×3). The combined organic layers were washed with brine (20 mL×3), dried over Na₂SO₄, filtered and concentrated under reduce pressure. The residue was purified by silica gel column chromatography to give 2-chloro-4-[[4-[1-[3,5-dichloro-4-(2-chloroethoxy)phenyl]-1-methyl-ethyl]phenoxy]methyl]oxazole (0.50 g, yield: 31.8%) as yellow oil. ¹H NMR (400 MHz, CHCl₃-d) δ 7.68 (s, 1H), 7.15-7.11 (m, 4H), 6.92-6.87 (m, 2H), 4.97 (d, J=0.8 Hz, 2H), 4.26 (t, J=6.4 Hz, 2H), 3.86 (t, J=6.4 Hz, 2H), 1.63 (s, 6H). LCMS (M+H⁺) m/z: calcd: 473.0; found 474.1.

N-(4-((4-(2-(3,5-dichloro-4-(2-chloroethoxy)phenyl)propan-2-yl)phenoxy)methyl)oxazol-2-yl)methanesulfonamide (A38)

To a solution of 2-chloro-4-[[4-[1-[3,5-dichloro-4-(2-chloroethoxy)phenyl]-1-methyl-ethyl]phenoxy]methyl]oxazole (5) (10 mg, 0.02 mmol) in 1,4-dioxane (0.2 mL) was added methanesulfonamide (2.4 mg, 0.02 mmol), Brettphos Pd G3 (2 mg, w20%) and t-BuONa (3 mg, 0.03 mmol). The mixture was stirred at 80° C. for 10 hours under N₂ atmosphere. LCMS showed 5% desired MS and 90% starting material. The resulting 20 reaction mixtures were cooled down and combined. The mixture was filtered and the filtrate concentrated under reduced pressure. The residue was purified by prep-HPLC (TFA) to give N-[[5-bromo-4-[4-[1-[3,5-dichloro-4-(3-chloropropoxy)phenyl]-1-methyl-ethyl]phenyl]oxazol-2-yl]methyl]methanesulfonamide (2 mg, yield: 1.8%) as pale yellow solid. LCMS (220 nm): 85.79%. ¹H NMR (400 MHz, CHCl₃-d) δ 7.16 (d, J=8.8 Hz, 2H), 7.12 (s, 2H), 7.08 (s, 1H), 6.86 (d, J=8.8 Hz, 2H), 4.86 (s, 2H), 4.27 (t, J=6.4 Hz, 2H), 3.86 (t, J=6.4 Hz, 2H), 3.09 (s, 3H), 1.64 (s, 6H). LCMS (M+H⁺) m/z: calcd: 532.04; found 533.0.

Example 10: Synthesis of N-[3-[[4-[1-[3,5-dichloro-4-(2-chloroethoxy)phenyl]-1-methyl-ethyl]phenoxy]methyl]-1H-pyrazol-4-yl]methanesulfonamide (A40)

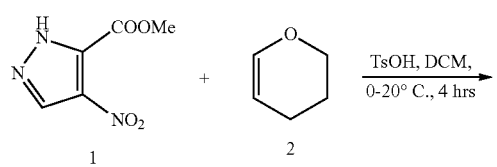

1

2

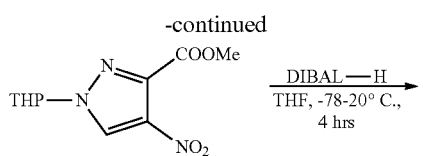

3

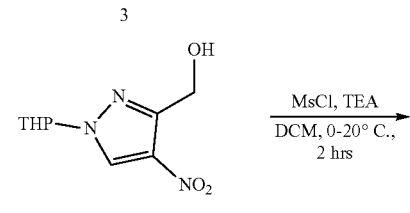

4

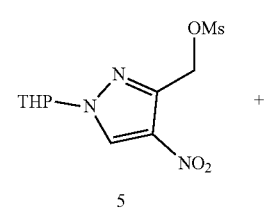

5

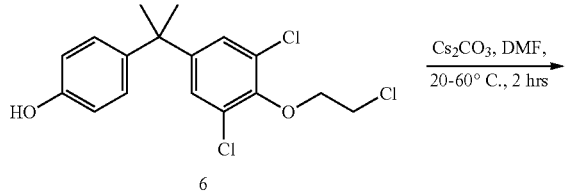

6

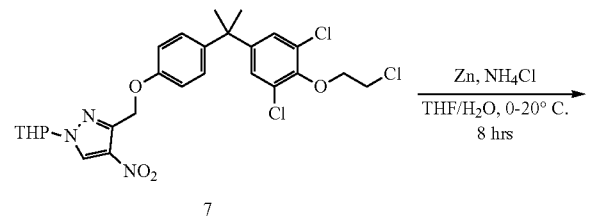

7

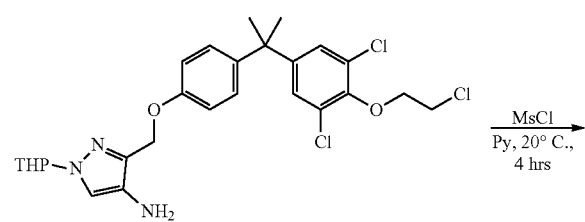

8

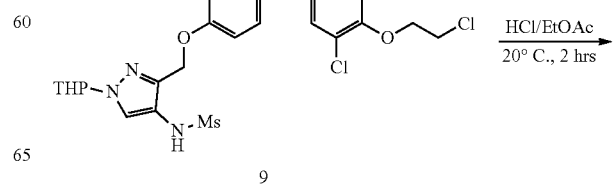

9

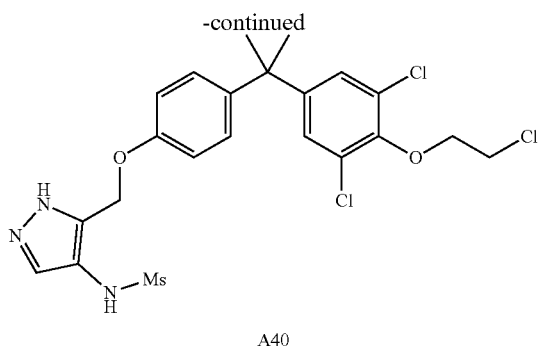

A40

Methyl 4-nitro-1-tetrahydropyran-2-yl-pyrazole-3-carboxylate (3)

To a solution of methyl 4-nitro-1H-pyrazole-5-carboxylate (1) (2.00 g, 1.17 mmol) in DCM (20 mL) was added 3,4-dihydro-2H-pyran (2) (3.11 g, 14.0 mmol) and p-Toluenesulfonic acid (0.20 g, 1.17 mmol) at 20° C. The mixture was stirred at the same temperature for 4 hours. LCMS showed the reaction was completed. The reaction was poured into water (100 mL) and extracted with DCM (30 mL×3). The combined organic layers were washed with brine (50 mL), dried over $Na_2SO_4$, concentrated under reduced pressure. The residue was purified by silica gel column chromatography to give methyl 4-nitro-1-tetrahydropyran-2-yl-pyrazole-3-carboxylate (3) (2.7 g, yield: 90.5%) as colorless oil. $^1$H NMR (400 MHz, CHCl$_3$-d) δ ppm 8.39 (s, 1H), 5.44 (dd, J=9.04, 2.87 Hz, 1H), 4.06-4.15 (m, 1H), 4.00 (s, 3H), 3.74 (ddd, J=11.69, 9.04, 4.41 Hz, 1H), 2.23 (dd, J=12.79, 3.09 Hz, 1H), 1.86-2.07 (m, 3H), 1.63-1.77 (m, 4H), 1.57 (s, 6H). LCMS (220 nm): 68% Exact Mass 255.09; found 256.0.

(4-nitro-1-tetrahydropyran-2-yl-pyrazol-3-yl)Methanol (4)

To a solution of methyl 4-nitro-1-tetrahydropyran-2-yl-pyrazole-3-carboxylate (3) (1.00 g, 3.92 mmol) in THF (10 mL) was added DIBALH (7.8 mL, 7.8 mmol, 1.0 mol/L in toluene) at −78° C. under N2 atmosphere and the mixture was stirred at 20° C. for 4 hours. LCMS showed the reaction was completed. The mixture was quenched with water (20 mL) and extracted with EtOAc (30 mL×5). The combined organic layers were washed with brine (20 mL), dried over $Na_2SO_4$, filtered and concentrated under reduced pressure to give (4-nitro-1-tetrahydropyran-2-yl-pyrazol-3-yl)methanol (70.0%, 0.90 g, yield: 70.8%) as colorless oil. HPLC purity (220 nm): 69%. $^1$H NMR (400 MHz, CHCl3-d) δ ppm 8.39 (s, 1H), 5.37 (dd, J=9.17, 2.69 Hz, 1H), 4.93 (s, 2H), 4.06-4.14 (m, 1H), 3.70-3.77 (m, 1H), 2.13-2.22 (m, 1H), 1.87-2.09 (m, 2H), 1.64-1.77 (m, 4H). LCMS (M+H$^+$) m/z: calcd: 227.09; found 250.2.

3-(Chloromethyl)-4-nitro-1-tetrahydropyran-2-yl-pyrazole (5)

To a solution of (4-nitro-1-tetrahydropyran-2-yl-pyrazol-3-yl) methanol (4) (1.3 g, 5.72 mmol) in DCM (13 mL) was added triethylamine (1.2 g, 1.14 mmol) at 20° C. Methanesulfonyl chloride (0.8 g, 6.87 mmol) was dropwise at 0° C. The reaction was stirred at 20° C. for 4 hours. TLC showed the reaction was completed. The mixture was quenched with water (30 mL) and extracted with DCM (30 mL×3). The combined organic layers were washed with brine (40 mL), dried over $Na_2SO_4$, filtered and concentrated under reduced pressure. The residue was purified by silica gel column chromatography to give 3-(chloromethyl)-4-nitro-1-tetrahydropyran-2-yl-pyrazole (5) (60.0%, yield: 30.9%) as colorless oil. $^1$H NMR (400 MHz, CHCl$_3$-d) δ ppm 8.39 (s, 1H), 5.38 (dd, J=9.26, 2.65 Hz, 1H), 4.88 (s, 2H), 3.75 (m, 2H), 1.86 (m, 2H), 1.67-1.77 (m, 4H).

3-[[4-[1-[3,5-Dichloro-4-(2-chloroethoxy)phenyl]-1-methyl-ethyl]phenoxy]methyl]-4-nitro-1-tetrahydropyran-2-yl-pyrazole (7)

To a solution of 3-(chloromethyl)-4-nitro-1-tetrahydropyran-2-yl-pyrazole (5) (0.20 g, 0.814 mmol) in DMF (2 mL) was added $CS_2CO_3$ (0.4 g, 1.22 mmol) and 4-[1-[3,5-dichloro-4-(2-chloroethoxy)phenyl]-1-methyl-ethyl]phenol (0.18 g, 0.49 mmol) (6) at 20° C. The mixture was stirred for 2 hours at 60° C. LCMS showed the reaction was completed. The mixture was quenched with water (10 mL) and extracted with EtOAc (10 mL×3). The combined organic layers were washed with brine (10 mL×5), dried over $Na_2SO_4$, filtered and concentrated under reduced pressure to give 3-[[4-[1-[3,5-dichloro-4-(2-chloroethoxy)phenyl]-1-methyl-ethyl]phenoxy]methyl]-4-nitro-1-tetrahydropyran-2-yl-pyrazole 3-[[4-[1-[3,5-dichloro-4-(2-chloroethoxy)phenyl]-1-methyl-ethyl]phenoxy]methyl]-4-nitro-1-tetrahydropyran-2-yl-pyrazole (7) (50.0% purity, 0.20 g, yield: 21.6%) as colorless oil. LCMS (M+Na$^+$) m/z: calcd: 567.1; found 590.2.

3-[[4-[1-[3,5-Dichloro-4-(2-chloroethoxy)phenyl]-1-methyl-ethyl]phenoxy]methyl]-1-tetrahydropyran-2-yl-pyrazol-4-amine (8)

To a solution of 3-[[4-[1-[3,5-dichloro-4-(2-chloroethoxy)phenyl]-1-methyl-ethyl]phenoxy]methyl]-4-nitro-1-tetrahydropyran-2-yl-pyrazole (7) (1.0 g, 1.76 mmol) in THF/$H_2O$ (6 mL/3 mL) was added $NH_4Cl$ (0.282 g, 5.27 mmol) at 20° C., Zn (0.575 g, 8.79 mmol) was added to the mixture at 0° C. The mixture was stirred at 20° C. for 8 hours. LCMS showed the reaction was completed. The reaction mixture was quenched with water (10 mL) and extracted with EtOAc (10 mL×3). The combined organic layers were washed with brine (10 mL), dried over $Na_2SO_4$, filtered and concentrated under reduced pressure. The residue was purified by p-HPLC (TFA) to give the 3-[[4-[1-[3,5-dichloro-4-(2-chloroethoxy)phenyl]-1-methyl-ethyl]phenoxy]methyl]-1-tetrahydropyran-2-yl-pyrazol-4-amine (8) (60 mg, yield: 6.3%) as colorless oil. $^1$H NMR (400 MHz, CHCl$_3$-d) δ ppm 7.07-7.17 (m, 4H) 6.89-6.99 (m, 2H), 5.23 (d, J=9.48 Hz, 1H), 5.10 (s, 2H), 4.24-4.30 (m, 2H), 4.05 (d, J=11.47 Hz, 1H), 3.83-3.89 (m, 2H), 3.63-3.72 (m, 1H), 2.06 (m, 2H), 2.02 (s, 1H), 1.62 (s, 6H). LCMS (M+H$^+$) m/z: calcd: 537.14; found 538.2.

N-[3-[[4-[1-[3,5-Dichloro-4-(2-chloroethoxy)phenyl]-1-methyl-ethyl]phenoxy]methyl]-1-tetrahydropyran-2-yl-pyrazol-4-yl]methanesulfonamide (9)

To a solution of 3-[[4-[1-[3,5-dichloro-4-(2-chloroethoxy)phenyl]-1-methyl-ethyl]phenoxy]methyl]-1-tetrahydropyran-2-yl-pyrazol-4-amine (8) (60 mg, 0.111 mmol) in DCM (0.5 mL) was added pyridine (17.6 mg, 0.223 mmol) at 20° C. Mesyl chloride (0.0129 mL, 0.167 mmol) was added dropwise to the reaction mixture at 0° C. The mixture was stirred at 20° C. for 4 hours. LCMS showed the reaction was completed. The reaction mixture was quenched with water (5 mL) and extracted with DCM (1 mL×3). The combined organic layers were washed with brine (10 mL), dried over Na₂SO₄, filtered and concentrated under reduced pressure to give N-[3-[[4-[1-[3,5-dichloro-4-(2-chloroethoxy)phenyl]-1-methyl-ethyl]phenoxy]methyl]-1-tetrahydropyran-2-yl-pyrazol-4-yl]methanesulfonamide (9) (70 mg, yield: 81.5%) as colorless oil. HPLC purity (220 nm): 79%. LCMS (M+Na⁺) m/z: calcd: 615.1; found 616.2.

N-[3-[[4-[1-[3,5-Dichloro-4-(2-chloroethoxy)phenyl]-1-methyl-ethyl]phenoxy]methyl]-1H-pyrazol-4-yl]methanesulfonamide (A40)

A solution of N-[3-[[4-[1-[3,5-dichloro-4-(2-chloroethoxy)phenyl]-1-methyl-ethyl]phenoxy]methyl]-1-tetrahydropyran-2-yl-pyrazol-4-yl]methanesulfonamide (9) (70 mg, 0.113 mmol) in HCl/EtOAc (4M, 2 mL) was stirred at 20° C. for 2 hours. LCMS showed the reaction was completed. The mixture was concentrated under reduced pressure. The residue was purified by prep-HPLC (FA) to give N-[3-[[4-[1-[3,5-dichloro-4-(2-chloroethoxy)phenyl]-1-methyl-ethyl]phenoxy]methyl]-1H-pyrazol-4-yl]methanesulfonamide (A40) (11.6 mg, yield: 18.2%) as white solid. ¹H NMR (400 MHz, CHCl₃-d) δ ppm 7.71 (s, 1H), 7.10-7.17 (m, 4H), 6.89-6.94 (m, 2H), 6.22 (s, 1H), 5.21 (s, 2H), 4.26 (t, J=6.39 Hz, 2H), 3.86 (t, J=6.28 Hz, 2H), 2.90 (s, 3H), 1.62 (s, 6H). LCMS (M+Na⁺) m/z: calcd: 531.06; found 532.1.

Example 11: Synthesis of N-(4-((4-(2-(3, 5-dichloro-4-(2-chloroethoxy)phenyl)propan-2-yl)phenoxy) Methyl) Pyrimidin-5-yl)methanesulfonamide (A41)

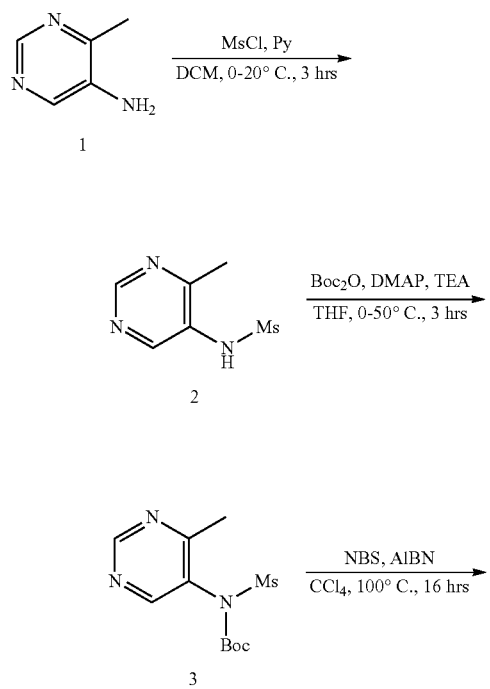

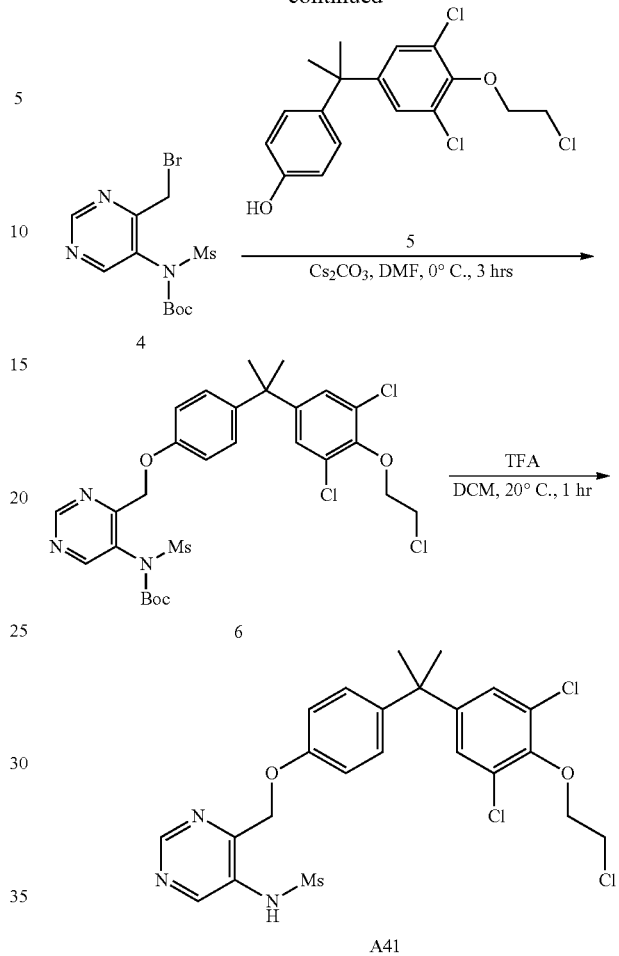

N-(4-Methylpyrimidin-5-yl)methanesulfonamide (2)

To a solution of 4-methylpyrimidin-5-amine (1) (3.0 g, 27.5 mmol) and pyridine (10.9 g, 0.137 mol) in DCM (30 mL) was added methanesulfonyl chloride (6.3 g, 55.0 mmol) at 0° C. and the resulting mixture was stirred at 20° C. for 3 hours. TLC showed the reaction was completed. The mixture was concentrated under reduced pressure. The residue was purified by silica gel column chromatography to give N-(4-methylpyrimidin-5-yl)methanesulfonamide (2) (1.0 g, 19.4%) as yellow solid. ¹H NMR (400 MHz, CHCl3-d) δ ppm 8.98 (s, 1H), 8.76 (s, 1H), 6.68 (br s, 1H), 3.13 (s, 3H), 2.61 (s, 3H).

Tert-Butyl (4-methylpyrimidin-5-yl)(methylsulfonyl)carbamate (3)

To a solution of N-(4-methylpyrimidin-5-yl) methanesulfonamide (2) (1.0 g, 5.34 mmol) and TEA (1.1 g, 10.7 mmol), DMAP (196 mg, 1.60 mmol) in THF (15 mL) was added tert-butoxycarbonyl tert-butyl carbonate (1.75 g, 8.01 mmol) at 0° C. and the resulting mixture was stirred at 50° C. for 3 hours. TLC showed the reaction was completed. The resulting mixture was cooled down and quenched with water (20 mL). The mixture was extracted with EtOAc (10 mL×5). The combined organic layers were washed with brine (20 mL×2), dried over Na$_2$SO$_4$, filtered and concentrated under reduced pressure. The residue was purified by silica gel column chromatography to give tert-butyl N-(4-methylpyrimidin-5-yl)-N-methylsulfonyl-carbamate (3) (1.0 g, yield: 65.2%) as yellow solid. $^1$H NMR (400 MHz, CHCl3-d) δ ppm 9.07 (s, 1H), 8.46 (s, 1H), 3.53 (s, 3H), 2.56 (s, 3H), 1.49 (s, 9H).

Tert-Butyl (4-(bromomethyl)pyrimidin-5-yl)(methylsulfonyl)carbamate (4)

To a mixture of tert-butyl N-(4-methylpyrimidin-5-yl)-N-methylsulfonyl-carbamate (3) (1.0 g, 3.48 mmol) and NBS (929 mg, 5.22 mmol) in CCl$_4$ (20 mL) was added AIBN (495 mg, 3.48 mmol) under N$_2$ atmosphere, and the resulting mixture was stirred at 100° C. for 16 hours. LCMS showed the reaction was completed. The mixture was cooled down and quenched with water (40 mL), and then extracted with DCM (10 mL×3). The combined organic layers were washed with brine (20 mL×2), dried over Na$_2$SO$_4$, filtered and concentrated under reduced pressure. The residue was purified by silica gel column chromatography to give tert-butyl N-(bromomethyl) pyrimidin-5-yl)-N-methylsulfonyl-carbamate (4) (170 mg, yield: 13.3%) as yellow solid. $^1$H NMR (400 MHz, CHCl$_3$-d) δ ppm 9.20 (br s, 1H), 8.60 (br s, 1H), 4.59 (d, J=10.64 Hz, 1H), 4.42 (d, J=10.64 Hz, 1H), 3.57-3.60 (m, 3H), 1.48-1.51 (m, 9H). LCMS (M+H$^+$) m/z: 367.0; found 368.0.

Tert-Butyl (4-((4-(2-(3,5-dichloro-4-(2-chloroethoxy)phenyl)propan-2-yl)phenoxy) methyl) pyrimidin-5-yl)(methylsulfonyl)carbamate (6)

To a mixture of 4-(1-(3,5-dichloro-4-(2-chloroethoxy)phenyl)-1-methyl-ethyl)phenol (5) (134 mg, 0.37 mmol) and Cs$_2$CO$_3$ (181 mg, 0.56 mmol) in DMF (5 mL) was added tert-butyl N-(4-(bromomethyl)pyrimidin-5-yl)-N-methylsulfonyl-carbamate (4) (170 mg, 0.37 mmol) at 0° C. under N$_2$ atmosphere, and the resulting mixture was stirred at the same temperature for 3 hours. TLC showed the reaction was completed. The mixture was poured into water (10 mL) and extracted with EtOAc (5 mL×5). The combined organic layers were washed with brine (10 mL×2), dried over Na$_2$SO$_4$, filtered and concentrated under reduced pressure. The residue was purified by MPLC to give tert-butyl N-(4-((4-(1-(3,5-dichloro-4-(2-chloroethoxy)phenyl)-1-methyl-ethyl)phenoxy)methyl)pyrimidin-5-yl)-N-methylsulfonyl-carbamate (6) (50 mg, yield: 20.9%) as light oil. $^1$H NMR (400 MHz, CHCl$_3$-d) δ ppm 9.18 (s, 1H), 8.62 (s, 1H), 7.12 (s, 2H), 7.09 (s, 2H), 6.85-6.91 (m, 2H), 5.15-5.30 (m, 2H), 4.24 (t, J=6.28 Hz, 2H), 3.85 (t, J=6.28 Hz, 2H), 3.52 (s, 3H), 1.60 (s, 6H), 1.37 (s, 9H).

N-(4-((4-(2-(3,5-Dichloro-4-(2-chloroethoxy)phenyl)propan-2-yl)phenoxy)methyl) pyrimidin-5-yl) methanesulfonamide (A41)

A mixture of tert-butyl N-(4-((4-(1-(3,5-dichloror-4-(2-chloroethoxy)phenyl)-1-methyl-ethyl)phenoxy)methyl)pyrimidin-5-yl)-N-methylsulfonyl-carbamate (6) (50 mg, 0.062 mmol) in DCM (5.0 mL) and TFA (0.5 mL) was stirred at 20° C. for 1 hour. LCMS showed the reaction was completed. The resulting mixture was concentrated under reduced pressure. The residue was purified by prep-HPLC (TFA) to give N-(4-((4-(1-(3,5-dichloro-4-(2-chloroethoxy)phenyl)-1-methyl-ethyl)phenoxy)methyl)pyrimidin-5-yl) methanesulfonamide (A41) (8 mg, yield: 23.7%) as yellow oil. $^1$H NMR (400 MHz, CHCl3-d) δ ppm 9.01 (d, J=4.40 Hz, 2H), 7.81 (br s, 1H), 7.16 (d, J=8.93 Hz, 2H), 7.10 (s, 2H), 6.93 (d, J=8.93 Hz, 2H), 5.36 (s, 2H), 4.26 (t, J=6.36 Hz, 2H), 3.86 (t, J=6.36 Hz, 2H), 3.03 (s, 3H), 1.62 (s, 6H). LCMS (M+H$^+$) m/z: 545.05; found 546.0. HPLC purity (220 nm): 84.4%.

Example 12: Synthesis of N-(4-(2-(3,5-dichloro-4-(2-chloroethoxy)phenyl)propan-2-yl)phenyl)-7-(methylsulfonamido)oxazole-4-carboxamide (A49)

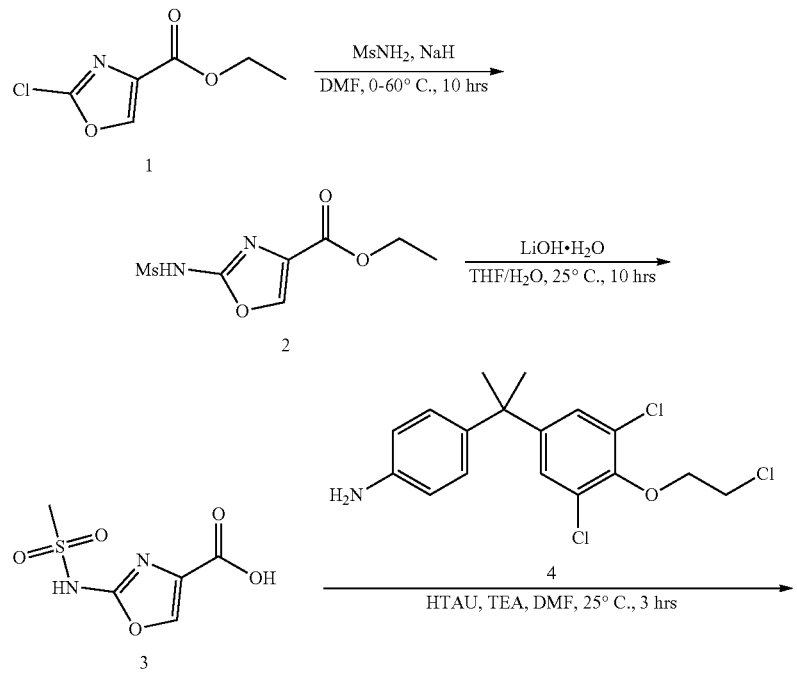

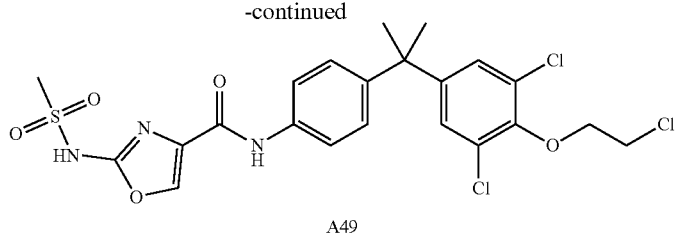

A49

Ethyl 2-(methylsulfonamido)oxazole-4-carboxylate (2)

To a solution of methane sulfonamide (3.3 g, 34.2 mmol) in DMF (30 mL) was added NaH (1.3 g, 60% purity, 34.2 mmol) in portions at 0° C. under $N_2$ atmosphere. The mixture was stirred at 0° C. for 0.5 hour, and then ethyl 2-chlorooxazole-4-carboxylate (1) (3.0 g, 17.1 mmol) was added to the mixture. The resulting mixture was stirred at 60° C. for 10 hours. LCMS showed the reaction was completed. The reaction was quenched with $H_2O$ (10 mL), and directly purified by reversed phase MPLC (TFA) to give ethyl 2-(methanesulfon-amido)oxazole-4-carboxylate (2) (1.17 g, yield: 29.2%) as colorless oil. $^1$H NMR (400 MHz, $CHCl_3$-d) δ 7.61 (s, 1H), 4.39 (q, J=7.2 Hz, 2H), 3.12 (s, 3H), 1.37 (t, J=7.2 Hz, 3H). LCMS $(M+H)^+$ m/z: clcd 234.03; found 235.1.

2-(Methylsulfonamido)oxazole-4-carboxylic Acid (3)

To a mixture of ethyl 2-(methanesulfonamido)oxazole-4-carboxylate (2) (100 mg, 0.43 mmol) in THF (3 mL) and $H_2O$ (1 mL) was added $LiOH \cdot H_2O$ (72 mg, 1.7 mmol) at 25° C. The mixture was stirred at the same temperature for 10 hours. LCMS showed the reaction was completed. The mixture was adjusted pH to 4 by aqueous HCl (2 M), and then concentrated under reduce pressure to give 2-(methanesulfonamido)oxazole-4-carboxylic acid (3) (90 mg, 65% purity) as yellow solid. $^1$H NMR (400 MHz, MeOH-$d_4$) δ 7.94 (s, 1H), 3.08 (s, 3H). LCMS $(M-H)^-$ m/z: clcd 206.0; found 204.9.

N-(4-(2-(3,5-Dichloro-4-(2-chloroethoxy)phenyl)propan-2-yl)phenyl)-2-(methylsulfonamido)oxazole-4-carboxamide (A49)

To a solution of 2-(methane-sulfonamido)oxazole-4-carboxylic acid (3) (60 mg, 0.3 mmol) in DMF (3 mL) was added 4-[1-[3,5-dichloro-4-(2-chloroethoxy)phenyl]-1-methyl-ethyl]aniline (4) (104 mg, 0.3 mmol), HATU (133 mg, 0.35 mmol) and TEA (0.12 mL, 0.9 mmol) at 25° C. The mixture was stirred at the same temperature for 3 hours. LCMS showed the reaction was completed, the mixture was quenched with $H_2O$ (1 mL), and directly purified by prep-HPLC (TFA), to give N-[4-[1-[3,5-dichloro-4-(2-chloroethoxy)phenyl]-1-methyl-ethyl]phenyl]-2-(methanesulfonamido)oxazole-4-carboxamide (A49) (23.2 mg, yield: 14.6%) as white solid. $^1$H NMR (400 MHz, $CHCl_3$-d) δ 8.44 (s, 1H), 7.91 (s, 1H), 7.56 (d, J=8.8 Hz, 2H), 7.21 (d, J=8.8 Hz, 2H), 7.13 (s, 2H), 4.27 (t, J=6.4 Hz, 2H), 3.86 (t, J=6.4 Hz, 2H), 3.32 (s, 3H), 1.65 (s, 6H). LCMS $(M+H)^+$ m/z: clcd 545.03; found 546.0.

Example 13: Synthesis of 5-((4-(2-(3,5-dichloro-4-(3,3,3-trifluoropropoxy)phenyl)propan-2-yl)phenoxy)methyl)-4-(methylsulfonyl)oxazole (A54)

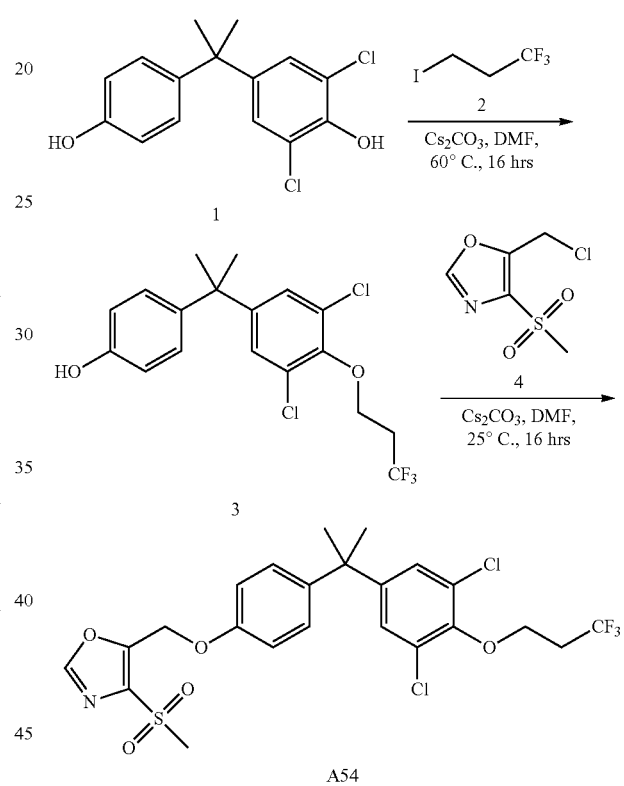

A54

2,6-Dichloro-4-(2-(4-hydroxyphenyl)propan-2-yl)phenol (3)

To a solution of 2,6-dichloro-4-[1-(4-hydroxyphenyl)-1-methyl-ethyl]phenol (1) (0.2 g, 0.67 mmol) in DMF (2 mL) were added 1,1,1-trifluoro-3-iodo-propane (2) (1.5 g, 6.7 mmol) and $Cs_2CO_3$ (0.66 g, 2.0 mmol). The resulting reaction was stirred at 60° C. for 16 hours. TLC showed the reaction was completed. The mixture was cooled down and poured into water (10 mL), extracted with EtOAc (10 mL×3). The combined organic layers were washed with brine (10 mL×3), dried over $Na_2SO_4$, filtered and concentrated. The residue was purified by p-TLC to give 4-[1-[3,5-dichloro-4-(3,3,3-trifluoropropoxy)phenyl]-1-methyl-ethyl]phenol (3) (80 mg, yield: 30.2%) as colorless oil. $^1$H NMR (400 MHz, $CHCl_3$-d) δ 7.13 (s, 2H), 7.09-7.05 (m, 2H), 6.78-6.75 (m, 2H), 4.71 (s, 1H), 4.21 (t, J=6.8 Hz, 2H), 2.78-2.66 (m, 2H), 1.62 (s, 6H).

5-((4-(2-(3,5-Dichloro-4-(3,3,3-trifluoropropoxy)phenyl)propan-2-yl)phenoxy)methyl)-4-(methylsulfonyl)oxazole (A54)

To a mixture of 4-[1-[3,5-dichloro-4-(3,3,3-trifluoropropoxy)phenyl]-1-methyl-ethyl]phenol (3) (40 mg, 0.10 mmol) and 5-(chloromethyl)-4-methylsulfonyl-oxazole (4) (24 mg, 0.12 mmol) in DMF (0.5 mL) was added $Cs_2CO_3$ (66 mg, 0.20 mmol) and the mixture was stirred at 25° C. for 16 hours. LCMS showed the reaction was completed. The mixture was poured into water (2 mL) and extracted with EtOAc (5 mL×3). The combined organic layers were washed with brine (5 mL×3), dried over $Na_2SO_4$, filtered and concentrated under reduced pressure. The residue was purified by p-TLC to give 5-[[4-[1-[3,5-dichloro-4-(3,3,3-trifluoropropoxy)phenyl]-1-methyl-ethyl]phenoxy]methyl]-4-methylsulfonylo-xazole (A54) (18 mg, yield: 29.9%) as yellow oil. LCMS purity: (220 nm): 93.3%. $^1$H NMR (400 MHz, $CHCl_3$-d) δ 8.00 (s, 1H), 7.16-7.12 (m, 4H), 6.94 (d, J=8.8 Hz, 2H), 5.42 (s, 2H), 4.22 (t, J=6.8 Hz, 2H), 3.19 (s, 3H), 2.78-2.64 (m, 2H), 1.62 (s, 6H). LCMS (M+$NH_{4+}$) m/z: calcd 551.1; found 569.0.

Example 14: Synthesis of 2-(2-chloroethoxy)-5-(2-(3-cyano-4-((4-(methyl sulfonyl)oxazol-5-yl)methoxy) phenyl)propan-2-yl)benzonitrile (A63)

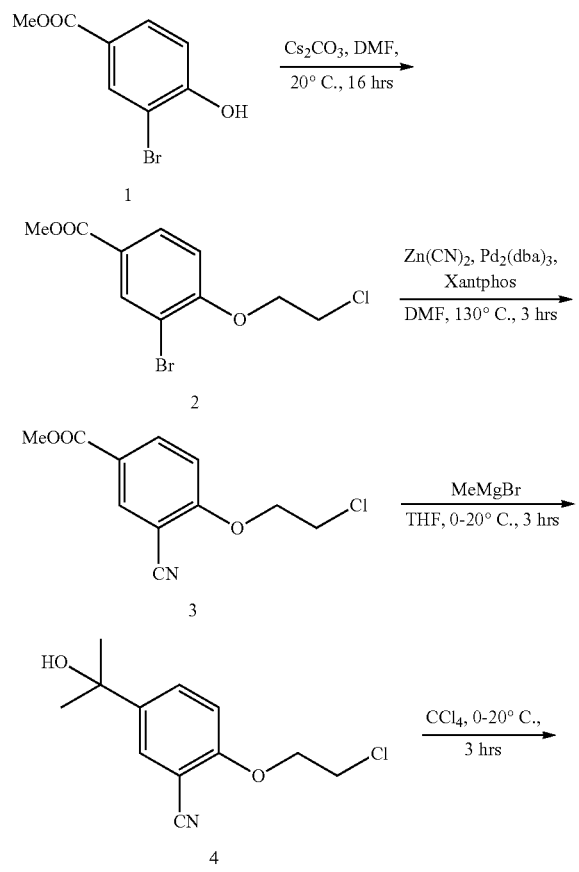

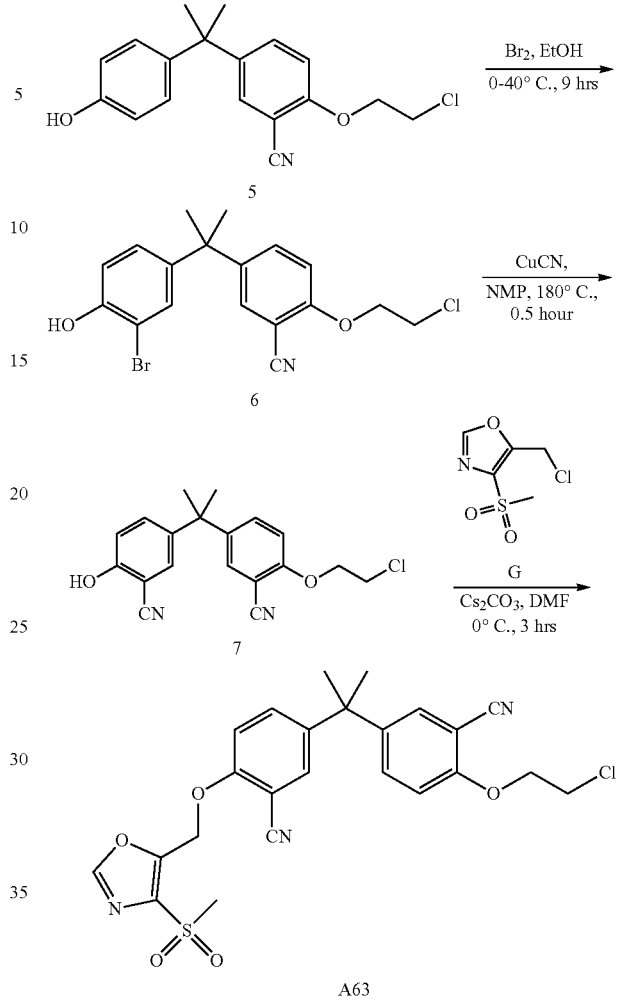

Methyl 3-bromo-4-(2-chloroethoxy)benzoate (2)

To a solution of methyl 3-bromo-4-hydroxybenzoate (1) (15 g, 65 mmol) in DMF (100 mL) was added 1-bromo-2-chloro-ethane (11 g, 78 mmol) and $Cs_2CO_3$ (32 g, 97 mmol) under $N_2$ atmosphere at 20° C. Then the reaction mixture was stirred at the same temperature for 16 hours. TLC showed the reaction was completed. The mixture was poured into $H_2O$ (100 mL), extracted with EtOAc (100 mL×2). The combined organic layers were washed with brine (100 mL×3), dried over $Na_2SO_4$, filtered and concentrated under reduced pressure. The crude product was purified by MPLC to give methyl 3-bromo-4-(2-chloroethoxy)benzoate (2) (13 g, yield: 67%) as white solid. $^1$H NMR (400 MHz, $CHCl_3$-d) δ 8.29-8.21 (m, 1H), 8.02-7.90 (m, 1H), 6.91 (d, J=8.6 Hz, 1H), 4.35 (t, J=6.1 Hz, 2H), 3.95-3.86 (m, 5H).

Methyl 4-(2-chloroethoxy)-3-cyanobenzoate (3)

To a solution of methyl 3-bromo-4-(2-chloroethoxy)benzoate (2) (0.6 g, 2.0 mmol) in DMF (20 mL) was added $Zn(CN)_2$ (0.72 g, 6.1 mmol), Xantphos (0.1 g, 0.2 mmol) and $Pd_2(dba)_3$ (0.18 g, 0.2 mmol) under $N_2$ atmosphere at 20° C. The reaction mixture was stirred at 130° C. for 3 hours. TLC showed the reaction was completed. Thirteen batches of reaction were combined, and then poured into H₂O (50 mL). The mixture was extracted with EtOAc (80 mL×3). The combined organic layers were washed with brine (80 mL×4), dried over Na₂SO₄, filtered, and concentrated under reduced pressure. The crude product was purified by MPLC to give methyl 4-(2-chloroethoxy)-3-cyanobenzoate (3) (4.60 g, yield: 72.2%) as brown solid. $^1$H NMR (400 MHz, CHCl₃-d) δ 8.27 (s, 1H), 8.22 (dd, J=2.1, 8.9 Hz, 1H), 7.02 (d, J=8.8 Hz, 1H), 4.41 (s, 2H), 3.92 (s, 3H), 3.92-3.88 (m, 2H).

2-(2-Chloroethoxy)-5-(2-hydroxypropan-2-yl)benzonitrile (4)

To a solution of MeMgBr (3 M, 24 mL, 72 mmol,) in THF (20 mL) was added methyl 4-(2-chloroethoxy)-3-cyanobenzoate (3) (4.3 g, 18 mmol) in THF (40 mL) dropwise under N₂ atmosphere at 0° C. Then the reaction was stirred at 20° C. for 3 hours. LCMS showed the reaction was completed. The mixture was poured into saturated aqueous NH₄Cl (20 mL) and extracted with EtOAc (20 mL×3). The combined organic layers were washed with brine (20 mL×2), dried over Na₂SO₄, filtered, concentrated under reduced pressure. The residue was purified by MPLC to give 2-(2-chloroethoxy)-5-(2-hydroxypropan-2-yl)benzonitrile (4) (2.9 g, yield: 67.4%) as brown oil. $^1$H NMR (400 MHz, CHCl₃-d) δ=7.71 (d, J=2.4 Hz, 1H), 7.67 (dd, J=2.3, 8.7 Hz, 1H), 6.98-6.92 (m, 1H), 4.34 (t, J=6.1 Hz, 2H), 3.87 (t, J=6.2 Hz, 2H), 1.57 (s, 6H). LCMS (M+H$^+$) m/z: calcd 239.1; found: 240.1.

2-(2-Chloroethoxy)-5-(2-(4-hydroxyphenyl)propan-2-yl)benzonitrile (5)

To a mixture of 2-(2-chloroethoxy)-5-(2-hydroxypropan-2-yl)benzonitrile (4) (2.9 g, 12.1 mmol) and phenol (1.4 g, 14.5 mmol) in CCl₄ (40 mL) was added BF₃-Et₂O (3.0 mL, 24 mmol) dropwise under N₂ atmosphere at 0° C. Then the reaction was stirred at 20° C. for 3 hours. TLC showed the reaction was completed. The mixture was poured into saturated aqueous NaHCO₃ (40 mL), extracted with DCM (20 mL×2). The combined organic layers were dried over Na₂SO₄, filtered and concentrated under reduced pressure. The residue was purified by MPLC to give 2-(2-chloroethoxy)-5-(2-(4-hydroxyphenyl)propan-2-yl)benzonitrile (5) (2.77 g, yield: 72.5%) as brown oil. $^1$H NMR (400 MHz, CHCl₃-d) δ 7.46 (s, 1H), 7.39-7.33 (dd, J=8.8 Hz, 1H), 7.05 (d, J=8.6 Hz, 2H), 6.88-6.83 (d, J=8.8 Hz, 1H), 6.80-6.73 (d, J=8.4 Hz, 2H), 5.00 (s, 1H), 4.31 (t, J=6.2 Hz, 2H), 3.85 (t, J=6.2 Hz, 2H), 1.63 (s, 6H).

5-(2-(3-Bromo-4-hydroxyphenyl)propan-2-yl)-2-(2-chloroethoxy)benzonitrile (6)

To a solution of 2-(2-chloroethoxy)-5-(2-(4-hydroxyphenyl)propan-2-yl)benzonitrile (5) (1.35 g, 4.27 mmol) in EtOH (30 mL) was added Br₂ (0.22 mL, 4.27 mmol) dropwise under N₂ atmosphere at 0° C. Then the reaction was stirred at 20° C. for 3 hours, and then at 40° C. for another 6 hours. LCMS showed 23% of starting material and 73% of desired product in reaction mixture. The mixture was poured into saturated aqueous Na₂SO₃ (20 mL) then concentrated under reduced to remove EtOH. The resulting solution was extracted with EtOAc (20 mL×2). The combined organic layers were washed with brine (20 mL), dried over Na₂SO₄, filtered, and concentrated under reduced. The residue was purified by MPLC to give 5-(2-(3-bromo-4-hydroxyphenyl)propan-2-yl)-2-(2-chloroethoxy)benzonitrile (6) (1.16 g, yield: 68.7%) as brown oil. $^1$H NMR (400 MHz, CHCl₃-d) δ=7.45 (d, J=2.4 Hz, 1H), 7.37-7.31 (d, J=8.8 Hz, 1H), 7.30-7.28 (m, 1H), 7.03-6.98 (m, 1H), 6.96-6.92 (m, 1H), 6.87 (d, J=8.8 Hz, 1H), 5.44 (br s, 1H), 4.32 (t, J=6.2 Hz, 2H), 3.86 (t, J=6.2 Hz, 2H), 1.63 (s, 6H). LCMS (M+H$^+$) m/z: calcd 393.0; found: 393.8.

2-(2-Chloroethoxy)-5-(2-(3-cyano-4-hydroxyphenyl)propan-2-yl)benzonitrile (7)

To a solution of 5-(2-(3-bromo-4-hydroxyphenyl)propan-2-yl)-2-(2-chloroethoxy) benzonitrile (6) (0.60 g, 1.52 mmol) in NMP (5 mL) was added CuCN (0.68 g, 7.6 mol) under N₂ atmosphere at 20° C. The reaction was stirred at 180° C. for 0.5 hour. TLC showed the reaction was completed. The mixture was poured into H₂O (20 mL), extracted with EtOAc (10 mL×2). The combined organic layers were washed with brine (10 mL×6), dried over Na₂SO₄, filtered and concentrated under reduced pressure. The crude product was purified by MPLC to give 2-(2-chloroethoxy)-5-(2-(3-cyano-4-hydroxyphenyl)propan-2-yl)benzonitrile (7) (130 mg, yield: 25.1%) as brown oil. $^1$H NMR (400 MHz, CHCl₃-d) δ=7.44-7.41 (m, 1H), 7.35 (d, J=2.4 Hz, 1H), 7.32 (dd, J=2.5, 8.9 Hz, 1H), 7.23 (dd, J=2.4, 8.8 Hz, 1H), 6.91 (d, J=7.3 Hz, 1H), 6.90-6.88 (dd, J=2.5, 8.9 Hz, 1H), 6.10 (br, 1H), 4.37-4.28 (t, J=6.2 Hz, 2H), 3.87 (t, J=6.2 Hz, 2H), 1.64 (s, 6H).

2-(2-Chloroethoxy)-5-(2-(3-cyano-4-((4-(methylsulfonyl)oxazol-5-yl)methoxy) Phenyl)propan-2-yl) Benzonitrile (A63)

To a solution of 2-(2-chloroethoxy)-5-(2-(3-cyano-4-hydroxyphenyl)propan-2-yl)benzonitrile (7) (130 mg, 0.38 mmol) in DMF (2 mL) was added 5-(chloromethyl)-4-(methylsulfonyl)oxazole (G) (75 mg, 0.38 mol) and Cs₂CO₃ (249 mg, 0.76 mmol) under N₂ atmosphere. The reaction was stirred at 0° C. for 3 hours. LCMS showed the reaction was completed. The mixture was diluted with EtOAc (5 mL) and poured into H₂O (5 mL). The aqueous phase was extracted with EtOAc (5 mL×2). The combined organic layers were washed with brine (5 mL×4), then dried over Na₂SO₄, filtered and concentrated under reduced pressure. The crude product was purified by prep-HPLC(TFA) to give 2-(2-chloroethoxy)-5-(2-(3-cyano-4-((4-(methylsulfonyl) oxazol-5-yl)methoxy)phenyl)propan-2-yl)benzonitrile (A63) (53 mg, yield: 27.8%) as white solid. LCMS purity (220 nm): 91.1%. $^1$H NMR (400 MHz, CHCl₃-d) δ=8.04 (s, 1H), 7.41 (br s, 2H), 7.39-7.29 (m, 2H), 7.15-7.04 (m, 1H), 6.94-6.85 (d, J=8.9 Hz, 1H), 5.51 (s, 2H), 4.33 (br t, J=6.0 Hz, 2H), 3.87 (br t, J=6.0 Hz, 2H), 3.25 (s, 3H), 1.64 (s, 6H). LCMS (M+H$^+$) m/z: calcd 499.1; found 500.1.

Example 15: Synthesis of N-((2-((4-(2-(3,5-dichloro-4-(2-chloroethoxy)phenyl)propan-2-yl) Phenyl)amino)oxazol-5-yl)methyl)methanesulfonamide (A75)
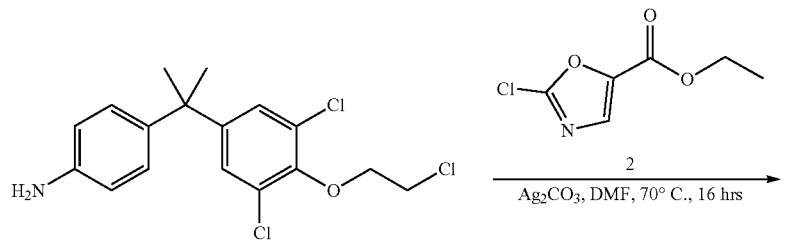
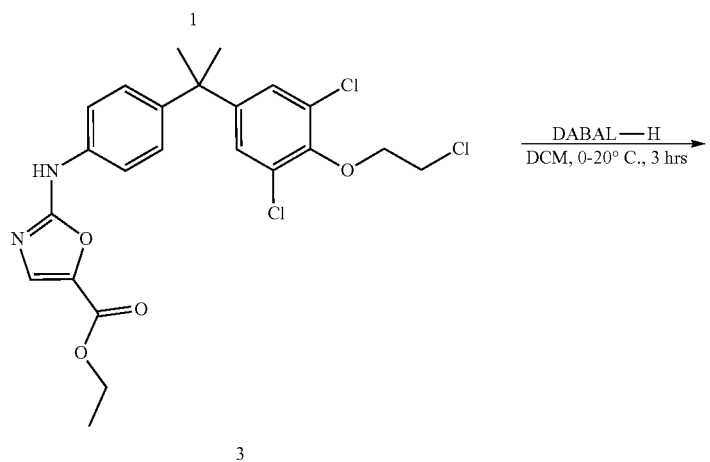
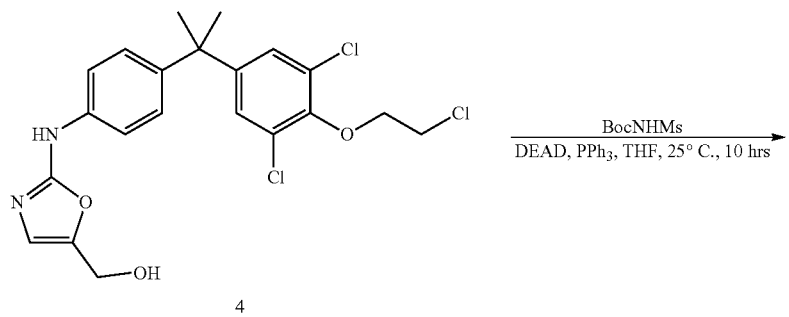
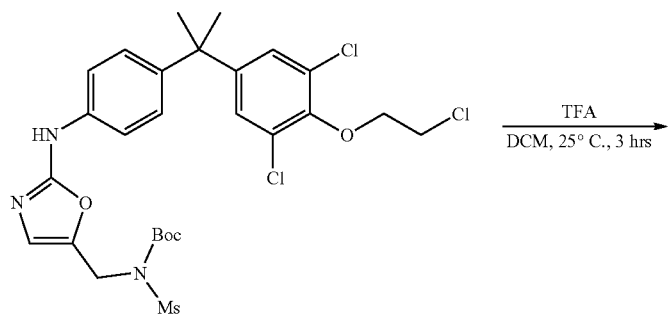

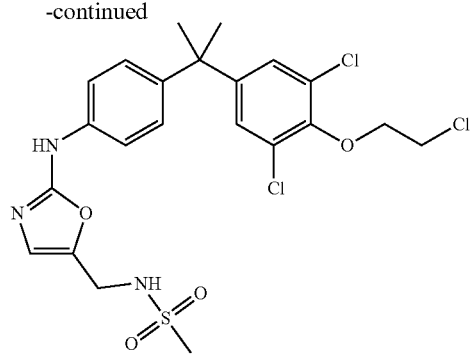

A75

Ethyl 2-((4-(2-(3,5-dichloro-4-(2-chloroethoxy)phenyl)propan-2-yl)phenyl)amino)oxazole-5-carboxylate (3)

To a solution of 4-[1-[3,5-dichloro-4-(2-chloroethoxy)phenyl]-1-methyl-ethyl]aniline (1) (1.00 g, 2.5 mmol) in DMF (10 mL) was added $Ag_2CO_3$ (1.05 g, 3.81 mol) and ethyl 2-chlorooxazole-5-carboxylate (2) (0.668 g, 3.81 mmol) under $N_2$ atmosphere at 20° C. Then the mixture was stirred at 70° C. for 16 hours. TLC showed the reaction was completed. The mixture was cooled down, poured into $H_2O$ (50 mL) and extracted with EtOAc (25 mL×2). The organic layers were combined and washed with brine (20 mL×3), dried over $Na_2SO_4$, filtered and concentrated under reduced pressure. The residue was purified by silica gel column chromatography to give ethyl 2-[4-[1-[3,5-dichloro-4-(2-chloroethoxy)phenyl]-1-methyl-ethyl]anilino]oxazole-5-carboxylate (3) (0.7 g, yield: 56.2%) as brown oil. $^1$H NMR (400 MHz, $CHCl_3$-d) δ 7.62 (s, 1H), 7.46 (s, 1H), 7.43 (d, J=8.8 Hz, 2H), 7.20 (d, J=8.8 Hz, 2H), 7.14 (s, 2H), 4.37 (q, J=7.2 Hz, 2H), 4.26 (t, J=6.4 Hz, 2H), 3.86 (t, J=6.4 Hz, 2H), 1.64 (s, 6H), 1.38 (t, J=7.2 Hz, 3H).

(2-((4-(2-(3,5-Dichloro-4-(2-chloroethoxy)phenyl)propan-2-yl)phenyl)amino)oxazol-5-yl)methanol (4)

To a solution of ethyl 2-[4-[1-[3,5-dichloro-4-(2-chloroethoxy)phenyl]-1-methyl-ethyl]anilino]oxazole-5-carboxylate (3) (0.6 g, 1.2 mmol) in DCM (10 mL) was added DIBAL-H (1 M in toluene, 2.4 mL, 2.4 mmol) under $N_2$ atmosphere at 0° C. Then the resulting mixture was stirred at 20° C. for 3 hours. TLC showed the reaction was completed. The mixture was poured into saturated aqueous $NH_4Cl$ (20 mL) and extracted with DCM (10 mL×3). The organic layers were washed with brine (15 mL×2), dried over $Na_2SO_4$, filtered and concentrated under reduced pressure to give [2-[4-[1-[3,5-dichloro-4-(2-chloroethoxy)phenyl]-1-methyl-ethyl]anilino]oxazol-5-yl]-methanol (4) (410 mg, yield: 74.6%) as brown oil. $^1$H NMR (400 MHz, $CHCl_3$-d) δ 7.38 (d, J=8.8 Hz, 2H), 7.17 (d, J=8.8 Hz, 2H), 7.14 (s, 2H), 6.81 (s, 1H), 4.60 (s, 2H), 4.26 (t, J=6.4 Hz, 2H), 3.86 (t, J=6.4 Hz, 2H), 1.63 (s, 6H).

Tert-Butyl ((2-((4-(2-(3,5-dichloro-4-(2-chloroethoxy)phenyl)propan-2-yl)phenyl)-amino)oxazol-5-yl)methyl)(methylsulfonyl)carbamate (5)

To a mixture of [2-4-[1-[3,5-dichloro-4-(2-chloroethoxy)phenyl]-1-methyl-ethyl]anilino]oxazol-5-yl]methanol (4) (50 mg, 0.1 mmol) and tert-butyl N-methylsulfonylcarbamate (21 mg, 0.1 mmol) in THF (3 mL) was added $PPh_3$ (58 mg, 0.22 mmol) and DEAD (29 mg, 0.16 mmol). The mixture was stirred at 25° C. for 10 hours under $N_2$ atmosphere. LCMS showed 30% desired product was detected. The mixture was concentrated and purified by prep-TLC to give tert-butyl N-[[2-[4-[1-[3,5-dichloro-4-(2-chloroethoxy)phenyl]-1-methyl-ethyl]anilino]oxazol-5-yl]methyl]-N-methylsulfonyl-carbamate (5) (25 mg, yield: 36.0%) as colorless oil. $^1$H NMR (400 MHz, $CHCl_3$-d) δ 7.39 (d, J=8.8 Hz, 2H), 7.16 (d, J=8.8 Hz, 2H), 7.13 (s, 2H), 6.84 (s, 1H), 4.86 (s, 2H), 4.26 (t, J=6.4 Hz, 2H), 3.86 (t, J=6.4 Hz, 2H), 3.24 (s, 3H), 1.63 (s, 9H), 1.53 (s, 6H).

N-((2-((4-(2-(3,5-Dichloro-4-(2-chloroethoxy)phenyl)propan-2-yl)phenyl)amino)oxazol-5-yl)methyl)methanesulfonamide (A75)

A solution of tert-butyl N-[[2-[4-[1-[3,5-dichloro-4-(2-chloroethoxy)phenyl]-1-methyl-ethyl]anilino]oxazol-5-yl]methyl]-N-methylsulfonyl-carbamate (5) (25 mg, 0.04 mmol) in DCM (2 mL) and TFA (0.2 mL) was stirred at 25° C. for 3 hours. LCMS showed the reaction was completed. The mixture was concentrated and purified by prep-HPLC (TFA) to give N-[[2-[4-[1-[3,5-dichloro-4-(2-chloroethoxy)phenyl]-1-methyl-ethyl]anilino]oxazol-5-yl]methyl]methanesulfonamide (4.6 mg, yield: 21.9%) as yellow oil. LCMS purity (220 nm): 86%. $^1$H NMR (400 MHz, $CHCl_3$-d) 6.7.36-7.33 (m, 2H), 7.25-7.22 (m, 2H), 7.11 (s, 2H), 7.02 (s, 1H), 5.18 (s, 1H), 4.36 (s, 2H), 4.27 (t, J=6.4 Hz, 2H), 3.87 (t, J=6.4 Hz, 2H), 3.00 (s, 3H), 1.64 (s, 6H). LCMS (M+H$^+$) m/z: calcd: 531.0; found 531.6.

Example 16: Synthesis of 3-(4-(2-(3,5-dichloro-4-(2-chloroethoxy)phenyl)propan-2-yl)benzyl)-1,5,5-trimethylimidazolidine-2,4-dione (B2)

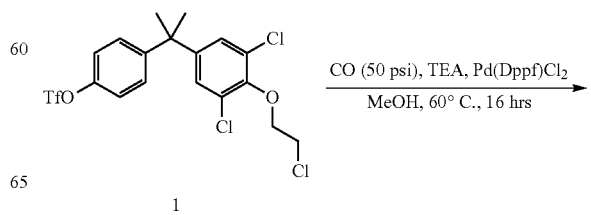

1

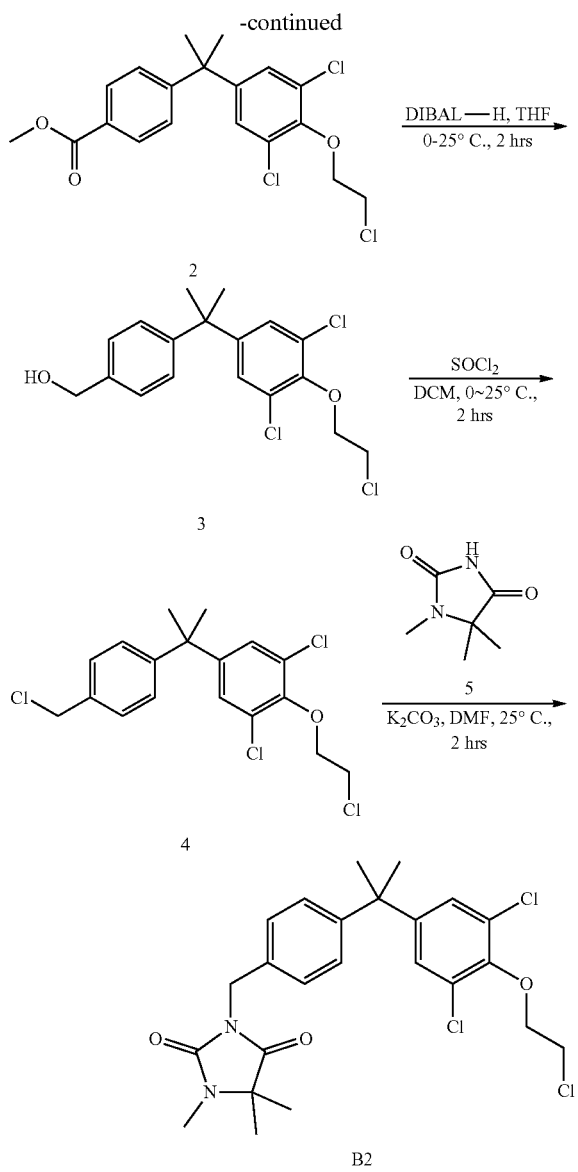

Methyl 4-(2-(3,5-dichloro-4-(2-chloroethoxy)phenyl)propan-2-yl)benzoate (2)

To a solution of 4-(2-(3,5-dichloro-4-(2-chloroethoxy)phenyl)propan-2-yl)phenyl trifluoromethanesulfonate (1) (600 mg, 1.7 mmol) and TEA (1 mL, 5.0 mmol) in MeOH (15 mL) was added Pd(dppf)Cl$_2$ (200 mg, 0.3 mmol). The resulting mixture was stirred at 50 Psi of CO atmosphere and the mixture at 60° C. for 16 hours. TLC showed the reaction was completed. The mixture was poured into H$_2$O (30 mL), extracted with EtOAc (10 mL×2). The combined organic layers were washed with brine (4 mL), dried over Na$_2$SO$_4$, filtered and concentrated under reduced pressure. The residue was purified by prep-TLC to give methyl 4-(2-(3,5-dichloro-4-(2-chloroethoxy)phenyl)propan-2-yl)benzoate (2) (300 mg, yield: 44.5%) as yellow oil. $^1$H NMR (400 MHz, CHCl$_3$-d) δ 8.00-7.90 (m, 2H), 7.27-7.23 (m, 2H), 7.09 (s, 2H), 4.28-4.21 (m, 2H), 3.90 (s, 3H), 3.87-3.81 (m, 2H), 1.68-1.62 (m, 6H).

(4-(2-(3,5-Dichloro-4-(2-chloroethoxy)phenyl)propan-2-yl)phenyl)methanol (3)

To a solution of methyl 4-(2-(3,5-dichloro-4-(2-chloroethoxy)phenyl)propan-2-yl)benzoate (2) (300 mg, 0.7 mmol) in THF (3 mL) was added DIBAL-H (1.00 M, 2 mL) at 0° C. and the mixture was stirred at 0-25° C. for 2 hours. TLC showed the reaction was completed. The mixture was poured into H$_2$O (15 mL), extracted with EtOAc (5 mL×2). The combined organic layers were washed with brine (4 mL), dried over Na$_2$SO$_4$, filtered and concentrated under reduced pressure to give (4-(2-(3,5-dichloro-4-(2-chloroethoxy)phenyl)propan-2-yl)phenyl)methanol (3) (170 mg, yield: 60.9%) as yellow oil. $^1$H NMR (400 MHz, CHCl$_3$-d) δ=7.32 (d, J=8.3 Hz, 2H), 7.24-7.18 (m, 2H), 7.17-7.11 (m, 2H), 4.75-4.63 (m, 2H), 4.31-4.22 (m, 2H), 3.86 (t, J=6.4 Hz, 2H), 1.70-1.61 (m, 6H).

1,3-Dichloro-2-(2-chloroethoxy)-5-(2-(4-(chloromethyl)phenyl)propan-2-yl)benzene (4)

To a solution of (4-(2-(3,5-dichloro-4-(2-chloroethoxy)phenyl)propan-2-yl)phenyl)methanol (3) (40 mg, 0.1 mmol) in DCM (2 mL) was added SOCl$_2$ (0.1 mL, 1.1 mmol) at 0° C. and the mixture was stirred at 0-25° C. for 2 hours. TLC showed the reaction was completed. The mixture was poured into H$_2$O (10 mL), extracted with DCM (3 mL×2). The combined organic layers were washed with brine (4 mL), dried over Na$_2$SO$_4$, filtered and concentrated under reduced pressure to give 1,3-dichloro-2-(2-chloroethoxy)-5-(2-(4-(chloromethyl)phenyl)propan-2-yl)benzene (4) (40 mg, yield: 95.3%) as yellow oil. $^1$H NMR (400 MHz, CHCl$_3$-d) δ=7.36-7.30 (m, 2H), 7.20 (d, J=8.4 Hz, 2H), 7.15-7.15 (m, 1H), 7.14 (s, 1H), 4.59 (s, 2H), 4.27 (t, J=6.4 Hz, 2H), 3.86 (t, J=6.4 Hz, 2H), 1.68-1.62 (m, 6H).

3-(4-(2-(3,5-Dichloro-4-(2-chloroethoxy)phenyl)propan-2-yl)benzyl)-1,5,5-trimethylimidazolidine-2,4-dione (B2)

To a mixture of 1,5,5-trimethylimidazolidine-2,4-dione (5) (20 mg, 0.2 mmol) and K$_2$CO$_3$ (70 mg, 0.5 mmol) in DMF (3 mL) was added 1,3-dichloro-2-(2-chloroethoxy)-5-(2-(4-(chloromethyl)phenyl)propan-2-yl)benzene (4) (50 mg, 0.1 mmol) at 25° C. and the mixture was stirred at the same temperature for 2 hours. LCMS showed the reaction was completed. The mixture was poured into H$_2$O (10 mL), extracted with EtOAc (5 mL×2). The combined organic layers were washed with brine (5 mL), dried over Na$_2$SO$_4$, filtered and concentrated under reduced pressure. The residue was purified by prep-HPLC (HCl) to give 3-(4-(2-(3,5-dichloro-4-(2-chloroethoxy)phenyl)propan-2-yl)benzyl)-1,5,5-trimethylimidazolidine-2,4-dione (B2) (20 mg, yield: 31.8%) as colorless oil. LCMS purity (220 nm): 96.1%. $^1$H NMR (400 MHz, CHCl$_3$-d) δ=7.30-7.25 (m, 1H), 7.28-7.25 (m, 1H), 7.30-7.25 (m, 1H), 7.15-7.10 (m, 2H), 7.10-7.08 (m, 2H), 4.66-4.57 (m, 2H), 4.24 (t, J=6.4 Hz, 2H), 3.89-3.77 (m, 2H), 2.87 (s, 3H), 1.65-1.54 (m, 6H), 1.41-1.34 (m, 6H). LCMS (M+H$^+$) m/z: calcd: 496.1; found 497.1.

Example 17: Synthesis of 3-(4-(2-(3,5-dichloro-4-(2-chloroethoxy)phenyl)propan-2-yl)benzyl)-5,5-dimethyl-1-(methylsulfonyl)imidazolidine-2,4-dione (B3)

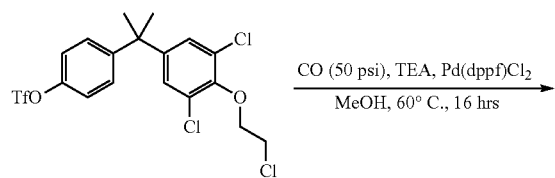
1

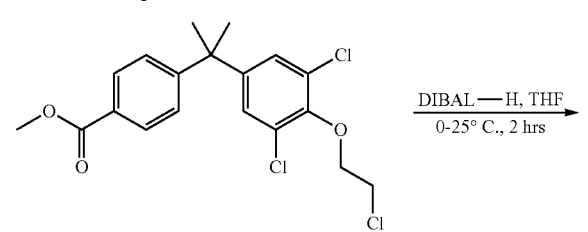
2

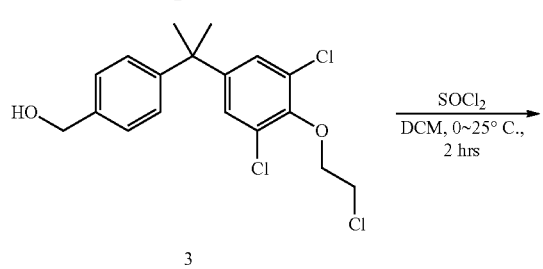
3

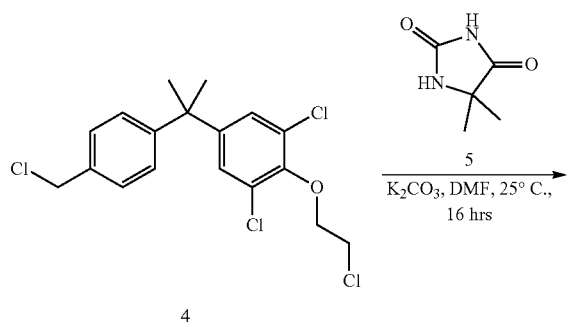
4

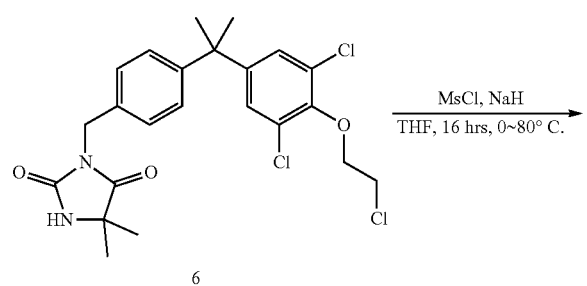
6

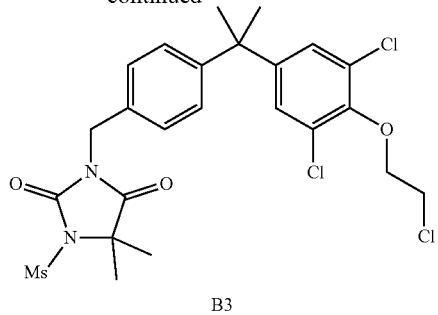
B3

Methyl 4-(2-(3,5-dichloro-4-(2-chloroethoxy)phenyl)propan-2-yl)benzoate (2)

To a solution of 4-(2-(3,5-dichloro-4-(2-chloroethoxy)phenyl)propan-2-yl)phenyl trifluoromethanesulfonate (1) (600 mg, 1.7 mmol) and TEA (1 mL, 5.0 mmol) in MeOH (15 mL) was added Pd(dppf)Cl$_2$ (200 mg, 0.3 mmol). The resulting mixture was stirred at 50 Psi of CO atmosphere and the mixture at 60° C. for 16 hours. TLC showed the reaction was completed. The mixture was poured into H$_2$O (30 mL), extracted with EtOAc (10 mL×2). The combined organic layers were washed with brine (4 mL), dried over Na$_2$SO$_4$, filtered and concentrated under reduced pressure. The residue was purified by prep-TLC to give methyl 4-(2-(3,5-dichloro-4-(2-chloroethoxy)phenyl)propan-2-yl)benzoate (2) (300 mg, yield: 44.5%) as yellow oil. $^1$H NMR (400 MHz, CHCl$_3$-d) δ 8.00-7.90 (m, 2H), 7.27-7.23 (m, 2H), 7.09 (s, 2H), 4.28-4.21 (m, 2H), 3.90 (s, 3H), 3.87-3.81 (m, 2H), 1.68-1.62 (m, 6H).

(4-(2-(3,5-Dichloro-4-(2-chloroethoxy)phenyl)propan-2-yl)phenyl)methanol (3)

To a solution of methyl 4-(2-(3,5-dichloro-4-(2-chloroethoxy)phenyl)propan-2-yl)benzoate (2) (300 mg, 0.7 mmol) in THF (3 mL) was added DIBAL-H (1.00 M, 2 mL) at 0° C. and the mixture was stirred at 0-25° C. for 2 hours. TLC showed the reaction was completed. The mixture was poured into H$_2$O (15 mL), extracted with EtOAc (5 mL×2). The combined organic layers were washed with brine (4 mL), dried over Na$_2$SO$_4$, filtered and concentrated under reduced pressure to give (4-(2-(3,5-dichloro-4-(2-chloroethoxy)phenyl)propan-2-yl)phenyl)methanol (3) (170 mg, yield: 60.9%) as yellow oil. $^1$H NMR (400 MHz, CHCl$_3$-d) δ=7.32 (d, J=8.3 Hz, 2H), 7.24-7.18 (m, 2H), 7.17-7.11 (m, 2H), 4.75-4.63 (m, 2H), 4.31-4.22 (m, 2H), 3.86 (t, J=6.4 Hz, 2H), 1.70-1.61 (m, 6H).

1,3-Dichloro-2-(2-chloroethoxy)-5-(2-(4-(chloromethyl)phenyl)propan-2-yl)benzene (4)

To a solution of (4-(2-(3,5-dichloro-4-(2-chloroethoxy)phenyl)propan-2-yl)phenyl)methanol (3) (40 mg, 0.1 mmol) in DCM (2 mL) was added SOCl$_2$ (0.1 mL, 1.1 mmol) at 0° C. and the mixture was stirred at 0-25° C. for 2 hours. TLC showed the reaction was completed. The mixture was poured into H$_2$O (10 mL), extracted with DCM (3 mL×2). The combined organic layers were washed with brine (4 mL), dried over Na$_2$SO$_4$, filtered and concentrated under reduced pressure to give 1,3-dichloro-2-(2-chloroethoxy)-5-(2-(4-(chloromethyl)phenyl)propan-2-yl)benzene (4) (40 mg, yield: 95.3%) as yellow oil. $^1$H NMR (400 MHz, CHCl$_3$-d) δ=7.36-7.30 (m, 2H), 7.20 (d, J=8.4 Hz, 2H), 7.15-7.15 (m, 1H), 7.14 (s, 1H), 4.59 (s, 2H), 4.27 (t, J=6.4 Hz, 2H), 3.86 (t, J=6.4 Hz, 2H), 1.68-1.62 (m, 6H).

3-(4-(2-(3,5-Dichloro-4-(2-chloroethoxy)phenyl) propan-2-yl)benzyl)-5,5-dimethylimidazolidine-2,4-dione (6)

To a mixture of 1,3-dichloro-2-(2-chloroethoxy)-5-(2-(4-(chloromethyl)phenyl)propan-2-yl)benzene (4) (100 mg, 0.2 mmol) and 5,5-dimethylimidazolidine-2,4-dione (5) (30 mg, 0.2 mmol) in DMF (5 mL) was added K$_2$CO$_3$ (100 mg, 0.8 mmol) at 25° C. and the mixture was stirred at 25° C. for 16 hours. LCMS showed the reaction was completed. The mixture was poured into H$_2$O (15 mL), extracted with EtOAc (5 mL×2). The combined organic layers were washed with brine (5 mL), dried over Na$_2$SO$_4$, filtered and concentrated under reduced pressure to give 3-(4-(2-(3,5-dichloro-4-(2-chloroethoxy)phenyl)propan-2-yl)benzyl)-5,5-dimethylimidazolidine-2,4-dione (6) (40 mg, yield: 64.8%) as yellow oil. LCMS purity (220 nm): 97.7%. $^1$H NMR (400 MHz, CHCl$_3$-d) δ=7.16-7.08 (m, 4H), 6.83 (d, J=8.8 Hz, 2H), 5.27 (s, 1H), 4.51 (s, 2H), 4.45 (s, 2H), 4.17-4.12 (m, 2H), 3.86 (t, J=6.4 Hz, 2H), 3.31 (s, 3H), 2.28 (quin, J=6.1 Hz, 2H), 1.62 (s, 6H), 1.49 (s, 9H). LCMS (M+H$^+$) m/z: calcd: 482.1; found 483.2.

3-(4-(2-(3,5-Dichloro-4-(2-chloroethoxy)phenyl) propan-2-yl)benzyl)-5,5-dimethyl-1-(methylsulfonyl)imidazolidine-2,4-dione (B3)

To a solution of 3-(4-(2-(3,5-dichloro-4-(2-chloroethoxy) phenyl)propan-2-yl)benzyl)-5,5-dimethylimidazolidine-2,4-dione (6) ((40 mg, 0.1 mmol) in THF (2 mL) was added Mesyl chloride (0.1 mL, 0.2 mmol) and NaH (60.0%, 6 mg, 0.2 mmol) at 0° C. and the mixture was stirred at 80° C. for 16 hours. TLC showed the reaction was completed. The reaction was quenched with saturated aqueous NH$_4$Cl (10 mL) and extracted with EtOAc (3 mL×2). The combined organic layers were washed with brine (3 mL), dried over Na$_2$SO$_4$, filtered and concentrated under reduced pressure. The residue was purified by prep-HPLC (HCl) to give 3-(4-(2-(3,5-dichloro-4-(2-chloroethoxy)phenyl)propan-2-yl)benzyl)-5,5-dimethyl-1-(methylsulfonyl)imidazolidine-2,4-dione (5 mg, yield: 10.8%) as yellow oil. LCMS purity (220 nm): 81.8%. $^1$H NMR (400 MHz, CHCl$_3$-d) δ=7.31-7.28 (m, 2H), 7.20-7.14 (m, 2H), 7.14-7.11 (m, 2H), 4.71-4.65 (m, 2H), 4.27 (t, J=6.4 Hz, 2H), 3.86 (t, J=6.4 Hz, 2H), 3.38 (s, 3H), 1.76-1.71 (m, 6H), 1.64 (s, 6H). LCMS (M+H$^+$) m/z: calcd: 526, found: 527.

Example 18: Synthesis of 3-chloro-2-(2-chloroethoxy)-5-(2-(4-((4-(methyl sulfonyl)oxazol-5-yl) methoxy)phenyl)propan-2-yl)benzonitrile (A28)

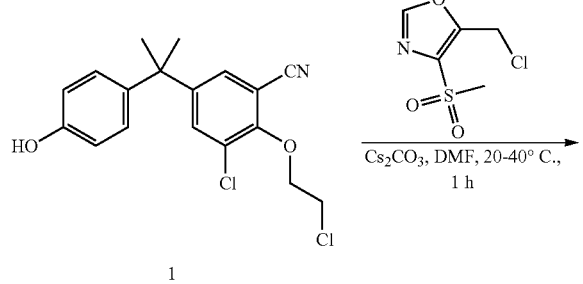

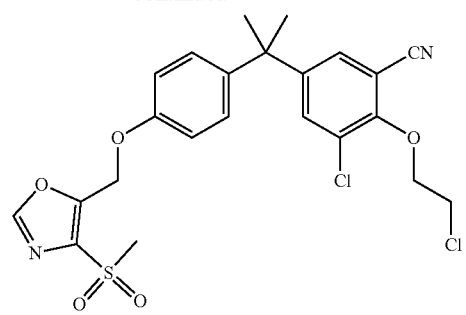

A28

To a mixture of 3-chloro-2-(2-chloro ethoxy)-5-(2-(4-hydroxyphenyl)propan-2-yl)benzonitrile (900 mg, 2.6 mmol) in DMF (10 mL) was added Cs$_2$CO$_3$ (167 mg, 5.1 mmol) and 5-(chloromethyl)-4-(methylsulfonyl)oxazole (750 mg, 3.9 mmol) under N$_2$ atmosphere at 20° C. The mixture was stirred at 40° C. for 1 h. TLC showed the reaction was completed. The mixture was cooled down to room temperature, poured into H$_2$O (40 mL) and extracted with EtOAc (20 mL×3). The combined organic layers were washed with brine (20 mL×4), dried over Na$_2$SO$_4$, filtered, and concentrated under reduced pressure. The residue was purified by MPLC and then triturated with MTBE:EtOAc=10 mL: 2 mL to give 3-chloro-2-(2-chloroethoxy) 5-(2-(4-((4-(methylsulfonyl) xazol-5-yl) ethoxy)phenyl) propan-2-yl)benzonitrile (310 mg, yield: 23.2%) as white solid. $^1$H NMR (400 MHz, CDCl3) δ=8.00 (s, 1H), 7.43 (d, J=2.4 Hz, 1H), 7.32 (d, J=2.4 Hz, 1H), 7.13 (d, J=8.4 Hz, 2H), 6.96 (d, J=8.8 Hz, 2H), 5.42 (s, 2H), 4.43 (t, J=6.4 Hz, 2H), 3.88 (t, J=6.4 Hz, 2H), 3.21 (s, 3H), 1.64 (s, 6H). LCMS (220 nm): 97.8%. Exact Mass: 508.1; found 509.1, 511.1.

Example 19: Synthesis of 2-(2-chloroethoxy)-3-methyl-5-(2-(4-((4-(methylsulfonyl)oxazol-5-yl) methoxy) phenyl)proan-2-yl)benzonitrile (A29)

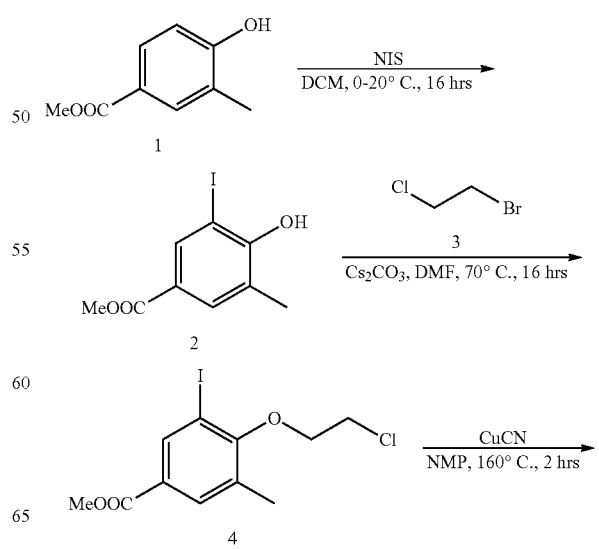

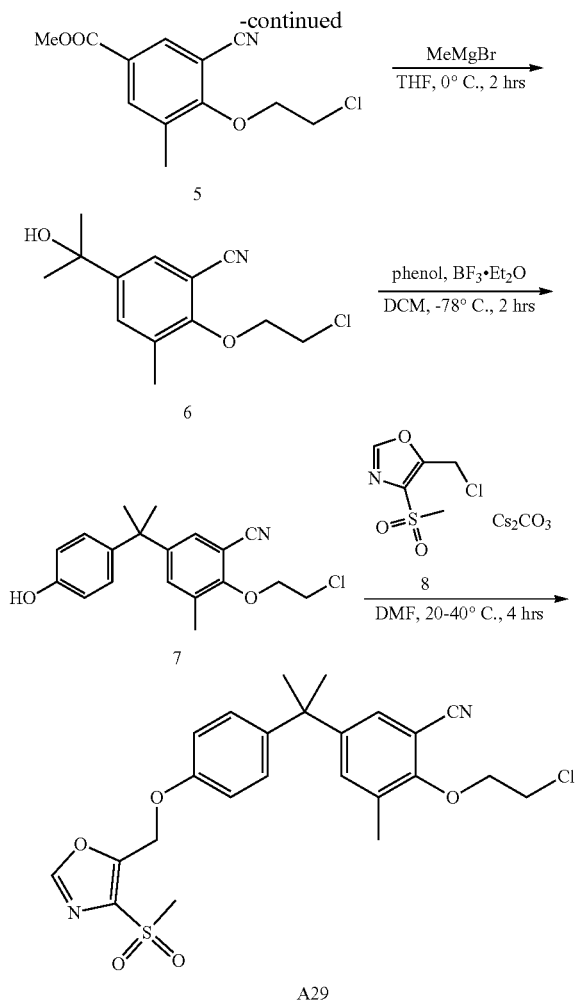

Methyl 4-hydroxy-3-iodo-5-methylbenzoate (2)

To a solution of methyl 4-hydroxy-3-methyl-benzoate (3.0 g, 18.0 mmol) in DCM (30 mL) was added NIS (4.0 g, 18.0 mmol) at 0° C. under $N_2$ atmosphere. The mixture was stirred at 20° C. for 16 hrs. TLC showed the reaction was completed. The mixture was poured into water (20 mL), extracted with DCM (30 mL×3). The combined organic layers were washed with brine (50 mL), dried over $Na_2SO_4$, filtered and concentrated under reduced pressure. The residue was purified by silica gel chromatography to give methyl 4-hydroxy-3-iodo-5-methyl-benzoate (3.6 g, yield: 68.3%) as yellow solid. $^1$H NMR (400 MHz, CDCl$_3$) δ=8.21 (d, J=1.2 Hz, 1H), 7.80 (s, 1H), 5.70 (s, 1H), 3.89 (s, 3H), 2.34 (s, 3H).

Methyl 4-(2-chloroethoxy)-3-iodo-5-methylbenzoate (4)

To a mixture of methyl 4-hydroxy-3-iodo-5-methyl-benzoate (3.6 g, 12.3 mmol) and 1-bromo-2-chloro-ethane (1.9 g, 13.6 mmol) in DMF (80 mL) was added Cs$_2$CO$_3$ (8.0 g, 24.7 mmol) and the mixture was stirred at 70° C. for 16 hrs. TLC showed the reaction was completed. The mixture was cooled down and poured into water (80 mL), extracted with EtOAc (50 mL×3). The combined organic layers were washed with brine (50 mL×3), dried over Na$_2$SO$_4$, filtered and concentrated under reduced pressure. The residue was purified by silica gel chromatography to give methyl 4-(2-chloroethoxy)-3-iodo-5-methyl-benzoate (2.3 g, yield: 52.6%) as colorless oil. $^1$H NMR (400 MHz, CDCl$_3$) δ=8.31 (d, J=1.6 Hz, 1H), 7.87-7.86 (m, 1H), 4.17 (t, J=6.0 Hz, 2H), 3.89-3.95 (m, 5H), 2.41 (s, 3H).

Methyl 4-(2-chloroethoxy)-3-cyano-5-methylbenzoate (5)

To a solution of methyl 4-(2-chloroethoxy)-3-iodo-5-methyl-benzoate (2.1 g, 6.0 mmol) in NMP (20 mL) was added CuCN (637 mg, 7.1 mmol) under N$_2$ atmosphere and the mixture was stirred at 160° C. for 2 hrs. LCMS showed the reaction was completed. The mixture was cooled down and poured into water (60 mL) and extracted with EtOAc (30 mL×3). The combined organic layers were washed with brine (30 mL×3), dried over Na$_2$SO$_4$, filtered and concentrated under reduced pressure. The residue was purified by silica gel chromatography to give methyl 4-(2-chloroethoxy)-3-cyano-5-methyl-benzoate (0.7 g, yield: 46.6%) as yellow solid. $^1$H NMR (400 MHz, CHCl$_3$-d): δ 8.13 (d, J=2.0 Hz, 1H), 8.09 (d, J=1.2 Hz, 1H), 4.54 (t, J=5.6 Hz, 2H), 3.93 (s, 3H), 3.89 (t, J=5.6 Hz, 2H), 2.39 (s, 3H). LCMS (220 nm): 78.1%. Exact Mass: 253.1; found: 254.1.

2-(2-chloroethoxy)-5-(2-hydroxypropan-2-yl)-3-methylbenzonitrile (6)

To a mixture of methyl 4-(2-chloroethoxy)-3-cyano-5-methyl-benzoate (500 mg, 2.1 mmol) and TEA (1.7 mL, 11.8 mmol) in THF (10 mL) was added MeMgBr (3M, 9.8 mmol, 3.3 mL) dropwise at 0° C. under N$_2$ atmosphere and the mixture was stirred at 0° C. for 2 hrs. TLC showed the reaction was completed. The mixture was poured into saturated aqueous NH$_4$Cl (20 mL), extracted with EtOAc (10 mL×4), dried over Na$_2$SO$_4$, filtered and concentrated under reduced pressure. The residue was purified by silica gel chromatography to give 2-(2-chloroethoxy)-5-(2-hydroxypropan-2-yl)-3-methylbenzonitrile (250 mg, yield: 50.0%) as yellow oil. $^1$H NMR (400 MHz, CDCl$_3$) δ=7.55 (s, 2H), 4.38 (t, J=5.6 Hz, 2H), 3.87 (t, J=5.6 Hz, 2H), 2.36 (s, 3H), 1.57 (s, 6H).

2-(2-chloroethoxy)-5-(2-(4-hydroxyphenyl)propan-2-yl)-3-methylbenzonitrile (7)

To a solution of 2-(2-chloroethoxy)-5-(2-hydroxy-2-methyl-ethyl)-3-methyl-benzonitrile (250 mg, 1.0 mmol) and phenol (110 mg, 1.2 mmol) in DCM (3 mL) was added BF$_3$·Et$_2$O (0.5 mL, 2 mmol) at −78° C. under N$_2$ atmosphere and the mixture was stirred at the same temperature for 2 hrs. TLC showed the reaction was completed. The mixture was poured into water (5 mL) and extracted with DCM (5 mL×3). The combined organic layers were washed with brine (15 mL), dried over Na$_2$SO$_4$, filtered and concentrated under reduced pressure. The residue was purified by silica gel chromatography to give 2-(2-chloroethoxy)-5-(2-(4-hydroxyphenyl) propan-2-yl)-3-methylbenzonitrile (220 mg, yield: 67.7%) as colorless oil. $^1$H NMR (400 MHz, CDCl$_3$) δ=7.29 (d, J=2.4 Hz, 1H), 7.21 (d, J=2.0 Hz, 1H), 7.06 (d, J=6.4 Hz, 2H), 6.76 (d, J=6.8 Hz, 2H), 4.73 (s, 1H), 4.36 (t, J=6.0 Hz, 2H), 3.86 (t, J=6.0 Hz, 2H), 2.29 (s, 3H), 1.63 (s, 6H)

2-(2-chloroethoxy)-3-methyl-5-(2-(4-((4-(methylsulfonyl)oxazol-5-yl)methoxy)phenyl)proan-2-yl)benzonitrile (A29)

To a mixture of 2-(2-chloroethoxy)-5-(2-(4-hydroxyphenyl)propan-2-yl)-3-methylbenzonitrile (100 mg, 0.3 mmol)

and 5-(chloromethyl)-4-methylsulfonyl-oxazole (60 mg, 0.3 mmol) in DMF (3 mL) was added Cs$_2$CO$_3$ (200 mg, 0.6 mmol) at 20° C. and the mixture was stirred at 40° C. for 4 hrs. LCMS showed the reaction was completed. The mixture was cooled down, filtered and purified by prep-HPLC (TFA) to give 2-(2-chloroethoxy)-3-methyl-5-(2-(4-((4-(methylsulfonyl)oxazol-5-yl)methoxy)phenyl)propan-2-yl)benzonitrile (26 mg, yield: 17.5%) as yellow oil. $^1$H NMR (400 MHz, MeOD): δ 8.39 (s, 1H), 7.33-7.35 (m, 1H), 7.31-7.32 (m, 1H), 7.16 (d, J=8.8 Hz, 2H), 6.96 (d, J=8.8 Hz, 2H), 5.41 (s, 2H), 4.32 (t, J=5.6 Hz, 2H), 3.88 (t, J=5.4 Hz, 2H), 3.18 (s, 3H), 2.28 (s, 3H), 1.64 (s, 6H). LCMS: (220 nm): 98.8%. Exact Mass: 488.1; found 489.0.

Example 20: Synthesis of N-(4-((4-(2-(3,5-dichloro-4-(2-chloroethoxy)phenyl)propan-2-yl)phenoxy) Methyl)pyrimidin-2-yl)methanesulfonamide (A74)

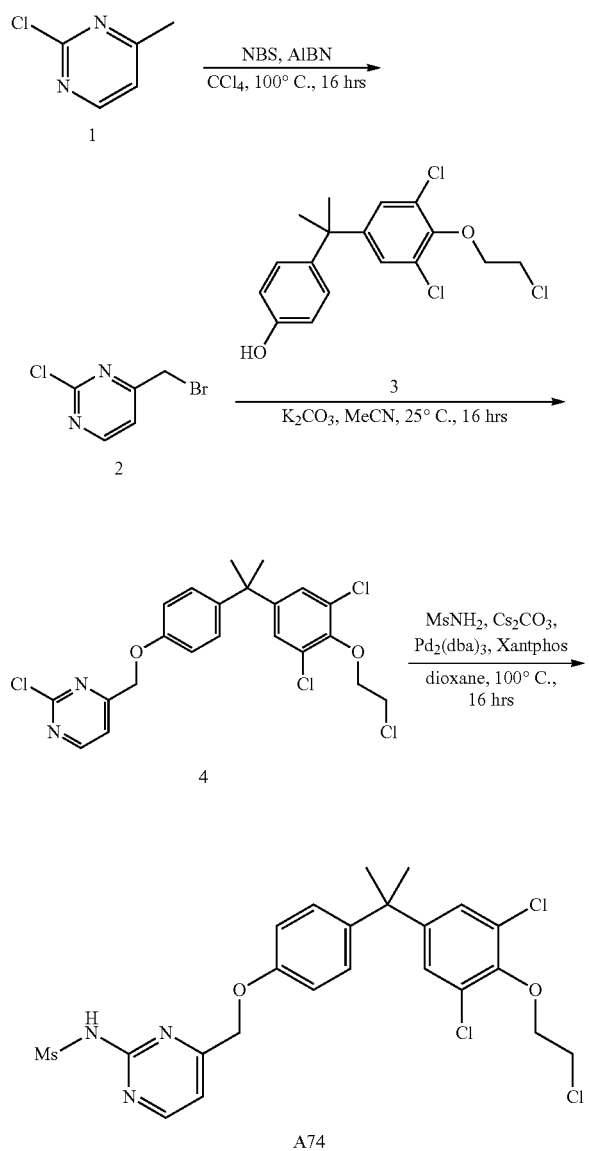

4-(bromomethyl)-2-chloropyrimidine (2)

To a mixture of 2-chloro-4-methyl-pyrimidine (5.0 g, 38.9 mmol) and NBS (10.4 g, 58.3 mmol) in CCl$_4$ (100 mL) was added AIBN (2.18 g, 19.4 mmol) at 20° C. and the mixture was stirred at 100° C. for 16 hrs. LCMS showed most of the starting material consumed. The mixture was cooled down, added to water (200 mL) and extracted with DCM (100 mL×5). The combined organic phases were washed with brine (200 mL), dried over Na$_2$SO$_4$, filtered and concentrated under reduced pressure. The crude product was purified by MPLC to give 4-(bromomethyl)-2-chloropyridine (2.0 g, yield: 24.8%) as brown oil. $^1$H NMR (400 MHz, CDCl3) δ=8.65 (d, J=5.2 Hz, 1H), 7.45 (d, J=5.2 Hz, 1H), 4.43 (s, 2H).

2-chloro-4-((4-(2-(3,5-dichloro-4-(2-chloroethoxy) phenyl)propan-2-yl)phenoxy)methyl) pyrimidine (4)

To a mixture of 4-(2-(3,5-dichloro-4-(2-chloroethoxy) phenyl)propan-2-yl)phenol (0.2 g, 0.6 mmol) and 4-(bromomethyl)-2-chloropyrimidine (127 mg, 0.6 mmol) in MeCN (5 mL) was added K$_2$CO$_3$ (115 mg, 0.83 mmol) and the mixture was stirred at 25° C. for 16 hrs. LCMS showed the reaction was completed. The resulting mixture was quenched with saturated aqueous NH$_4$Cl (5 mL), extracted with EtOAc (5 mL×3). The combined organic layers we washed with brine (10 mL×2), dried over Na$_2$SO$_4$, filtered and concentrated under reduced pressure to give 2-chloro-4-((4-(2-(3,5-dichloro-4-(2-chloroethoxy)phenyl)propan-2-yl)phenoxy)methyl)pyrimidine (270 mg, yield: 82.9%) as yellow solid. $^1$H NMR (400 MHz, CDCl3) δ=8.66 (d, J=5.2 Hz, 1H), 7.56 (d, J=5.2 Hz, 1H), 7.16 (d, J=8.8 Hz, 2H), 7.13 (s, 2H), 6.88 (d, J=8.8 Hz, 2H), 5.15 (s, 2H), 4.26 (t, J=6.4 Hz, 2H), 3.86 (t, J=6.4 Hz, 2H), 1.63 (s, 6H).

N-(4-((4-(2-(3,5-dichloro-4-(2-chloroethoxy)phenyl) propan-2-yl)phenoxy) methyl)pyrimidin-2-yl)methanesulfonamide (A74)

To a mixture of 2-chloro-4-((4-(2-(3,5-dichloro-4-(2-chloroethoxy)phenyl)propan-2-yl)phenoxy)methyl)pyrimidine (200 mg, 0.3 mmol), methanesulfonamide (62.6 mg, 0.66 mmol), Cs$_2$CO$_3$ (322 mg, 0.99 mmol) in anhydrous dioxane (8 mL) was added Pd$_2$(dba)$_3$ (30.1 mg, 0.03 mmol) and Xantphos (38.1 mg, 0.06 mmol) and the mixture was stirred at 100° C. for 16 hrs under N$_2$ atmosphere. LCMS showed the reaction was completed. The mixture was cooled down, poured into water (10 mL), extracted with EtOAc (10 mL×3). The combined organic layers were washed with brine (10 mL), dried over Na$_2$SO$_4$, filtered and concentrated under reduced pressure. The residue was purified by p-HPLC(TFA) to obtain the desired product N-(4-((4-(2-(3,5-dichloro-4-(2-chloroethoxy)phenyl)propan-2-yl)phenoxy) methyl)pyrimidin-2-yl)methanesulfonamide (61.4 mg, yield: 34.2%) as light red solid. $^1$H NMR (400 MHz, CDCl3) δ=8.61 (d, J=5.2 Hz, 1H), 7.29 (d, J=5.2 Hz, 1H), 7.16-7.11 (m, 4H), 6.88 (d, J=8.8 Hz, 2H), 5.09 (s, 2H), 4.26 (t, J=6.4 Hz, 2H), 3.86 (t, J=6.4 Hz, 2H), 3.47 (s, 3H), 1.63 (s, 6H). LCMS: (220 nm): 98.1%. Exact Mass: 543.1; found 544.

Example 21: Synthesis of 3-chloro-2-(2-chloroethoxy)-5-(2-(4-((5-(methylsulfonyl)thiazol-2-yl)methoxy)phenyl)propan-2-yl)benzonitrile (A93)

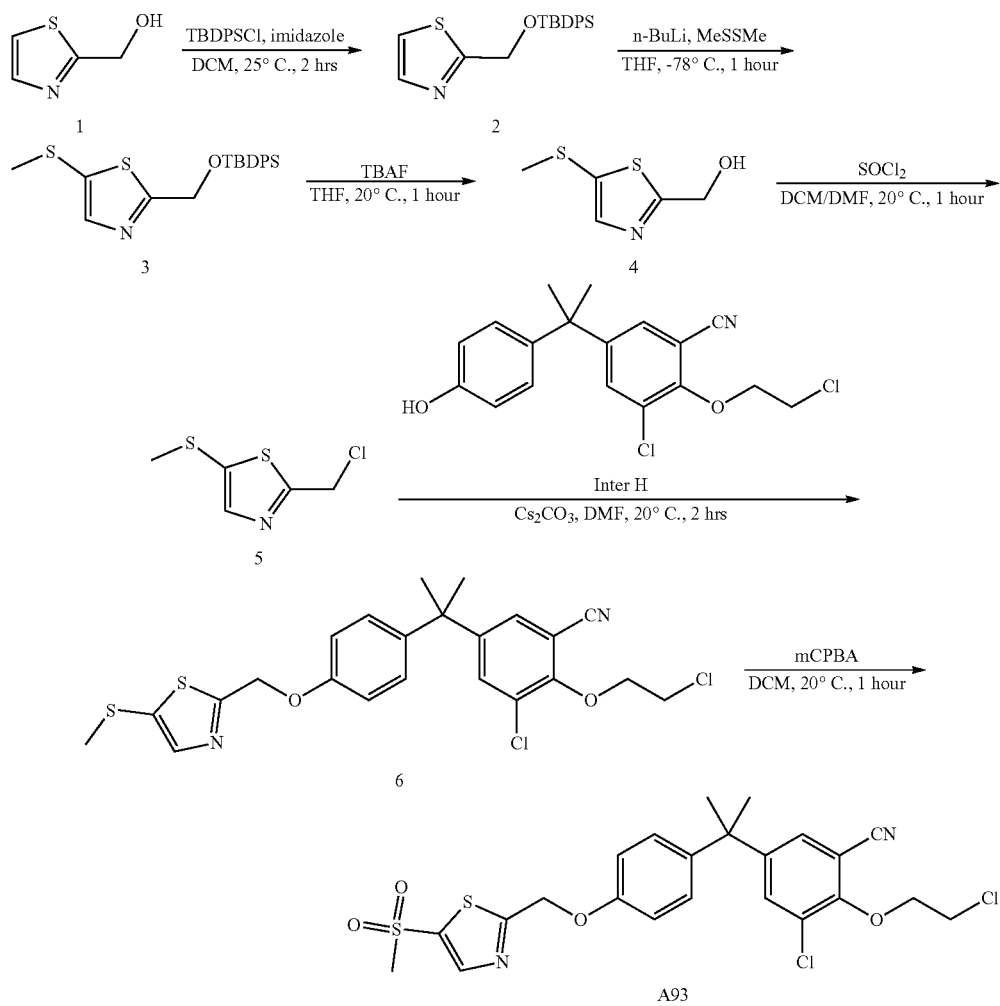

2-(((tert-butyldiphenylsilyl)oxy)methyl)thiazole (2)

To a mixture of thiazol-2-ylmethanol (1.0 g, 8.7 mmol) and imidazole (1.2 g, 17.4 mmol) in DCM (50 mL) was added TBDPSCl (2.9 g, 10.4 mmol) in portions at 25° C. The mixture was stirred at the same temperature for 2 hrs. TLC showed the reaction was completed. The reaction was quenched with water (80 mL) and extracted with DCM (50 mL×3). The combined organic layers were washed with brine (50 mL), dried over $Na_2SO_4$, filtered and concentrated under reduce pressure. The residue was purified by MPLC to give 2-(((tert-butyldiphenylsilyl)oxy)methyl)thiazole (3.0 g, yield: 97.7%) as colorless oil. $^1$H NMR (400 MHz, CDCl3) δ=7.73-7.70 (m, 4H), 7.48-7.45 (m, 1H), 7.44-7.38 (m, 6H), 7.31 (d, J=3.2 Hz, 1H), 5.02 (s, 2H), 1.14 (s, 9H).

2-(((tert-butyldiphenylsilyl)oxy)methyl)-5-(methylthio)thiazole (3)

To a solution of 2-(((tert-butyldiphenylsilyl)oxy)methyl)thiazole (4.2 g, 11.9 mmol) in THF (80 mL) was added n-BuLi (2.50 M, 9.50 mL) dropwise at −78° C. under $N_2$ atmosphere. The mixture was stirred at the same temperature for 30 min. Then 1,2-dimethyldisulfane (2.2 g, 23.8 mmol) was added to the mixture dropwise at −78° C. under $N_2$ atmosphere and stirred for 30 min. TLC showed the reaction was completed. The reaction mixture was poured into saturated aqueous $NH_4Cl$ (100 mL) and extracted with EtOAc (50 mL×3). The combined organic layers were washed with brine (50 mL), dried over $Na_2SO_4$, filtered and concentrated under reduce pressure to give 2-(((tert-butyldiphenylsilyl)oxy)methyl)-5-(methylthio)thiazole (4.6 g, yield: 96.9%) as brown oil. $^1$H NMR (400 MHz, CDCl3) δ=7.74-7.67 (m, 4H), 7.60 (s, 1H), 7.48-7.38 (m, 6H), 4.92 (s, 2H), 2.50 (s, 3H), 1.13 (s, 9H).

(5-(methylthio)thiazol-2-yl)methanol (4)

To a solution of 2-(((tert-butyldiphenylsilyl) oxy)methyl)-5-(methylthio)thiazole (5.4 g, 13.5 mmol) in anhydrous THF (27 mL) was added TBAF (1.00 M, 27.0 mL) dropwise at 20° C. and stirred at the same temperature for 1 hour. TLC showed the reaction was completed. The reaction was quenched with water (50 mL). The aqueous layer was extracted with EtOAc (30 mL×3). The combined organic layers were washed with brine (30 mL×3), dried over Na$_2$SO$_4$, filtered and concentrated under reduce pressure. The residue was purified by MPLC to give (5-(methylthio)thiazol-2-yl)methanol (1.4 g, yield: 64.3%) as yellow oil. $^1$H NMR (400 MHz, CDCl3) δ=7.63 (s, 1H), 4.91 (d, J=5.6 Hz, 2H), 2.72 (t, J=6.0 Hz, 1H), 2.49 (s, 3H).

2-(chloromethyl)-5-(methylthio)thiazole (5)

To a solution of (5-(methylthio)thiazol-2-yl)methanol (0.4 g, 2.5 mmol) in DCM (5 mL) was added SOCl$_2$ (0.5 mL, 7.4 mmol) at 20° C., then DMF (0.1 mL) was added. The mixture was stirred at the same temperature for 1 h. TLC showed the reaction was completed. The reaction was concentrated under reduce pressure. The residue was quenched with water (10 mL) and extracted with DCM (10 mL×3). The combined organic layers were washed with brine (10 mL), dried over Na$_2$SO$_4$, filtered and concentrated under reduce pressure to give 2-(chloromethyl)-5-(methylthio)thiazole (0.4 g, yield: 89.7%) as brown oil. $^1$H NMR (400 MHz, CDCl3) δ=7.63 (s, 1H), 4.82 (s, 2H), 2.52 (s, 3H).

3-chloro-2-(2-chloroethoxy)-5-(2-(4-((5-(methylthio)thiazol-2-yl)methoxy)phenyl)propan-2-yl)benzonitrile (6)

To a mixture of 3-chloro-2-(2-chloroethoxy)-5-(2-(4-hydroxyphenyl) propan-2-yl)benzonitrile (100 mg, 0.3 mmol) and 2-(chloromethyl)-5-(methylthio)thiazole (103 mg, 0.6 mmol) in DMF (3 mL) was added Cs$_2$CO$_3$ (186 mg, 0.6 mmol) and the mixture was stirred at 20° C. for 2 hrs. LCMS showed the reaction was completed. The resulting mixture was quenched with water (10 mL) and extracted with EtOAc (5 mL×3). The combined organic layers were washed with brine (5 mL×2), dried over Na$_2$SO$_4$, filtered and concentrated under reduce pressure. The residue was purified by MPLC to give 3-chloro-2-(2-chloroethoxy)-5-(2-(4-((5-(methylthio)thiazol-2-yl)methoxy)phenyl)propan-2-yl)benzonitrile (80 mg, yield: 56.8%) as yellow oil. $^1$H NMR (400 MHz, CDCl3) δ=7.66 (s, 1H), 7.44 (s, 1H), 7.33 (s, 1H), 7.12 (br d, J=8.4 Hz, 2H), 6.95 (br d, J=8.8 Hz, 2H), 5.30 (s, 2H), 4.42 (t, J=6.0 Hz, 2H), 3.88 (t, J=6.0 Hz, 2H), 2.50 (s, 3H), 1.65 (s, 6H).

3-chloro-2-(2-chloroethoxy)-5-(2-(4-((5-(methylthio)thiazol-2-yl)methoxy)phenyl)propan-2-yl)benzonitrile (A93)

A suspension of 3-chloro-2-(2-chloroethoxy)-5-(2-(4-((5-(methylthio)thiazol-2-yl)methoxy)phenyl)propan-2-yl)benzonitrile (80 mg, 0.16 mmol) and m-CPBA (80.0%, 105 mg, 0.49 mmol) in DCM (3 mL) was stirred at 20° C. for 1 h. LCMS showed the reaction was completed. The resulting mixture was poured into saturated aqueous NaHCO$_3$ (3 mL) and extracted with DCM (3 mL×3). The combined organic layers were washed with brine (5 mL), dried over Na$_2$SO$_4$, filtered and concentrated under reduce pressure. The residue was purified by prep-HPLC (TFA) to give 3-chloro-2-(2-chloroethoxy)-5-(2-(4-((5-(methylsulfonyl)thiazol-2-yl)methoxy)phenyl)propan-2-yl)benzonitrile (64.2 mg, yield: 75.4%) as white solid. $^1$H NMR (400 MHz, CDCl3) δ=8.31 (s, 1H), 7.45 (d, J=2.4 Hz, 1H), 7.32 (d, J=2.4 Hz, 1H), 7.16 (d, J=8.8 Hz, 2H), 6.95 (d, J=8.8 Hz, 2H), 5.40 (s, 2H), 4.43 (t, J=6.0 Hz, 2H), 3.88 (t, J=6.0 Hz, 2H), 3.25 (s, 3H), 1.66 (s, 6H). LCMS (220 nm): 99.5%. Exact Mass: 524.0; found 525.1, 527.1.

Example 22: Synthesis of N-(4-((4-(2-(3-chloro-4-(2-chloroethoxy)-5-cyanophenyl)propan-2-yl)phenoxy) methyl)pyrimidin-2-yl)methanesulfonamide N-(4-((4-(2-(3-chloro-4-(2-chloroethoxy)-5-cyanophenyl) propan-2-yl) phenoxy) methyl)pyrimidin-2-yl)methanesulfonamide (A109)

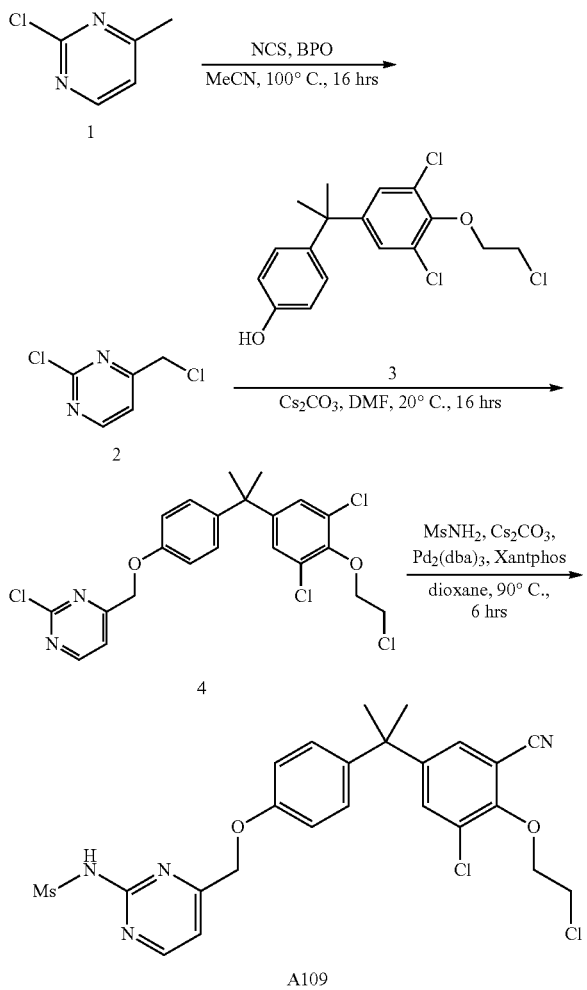

2-chloro-4-(chloromethyl)pyrimidine (2)

To a mixture of 2-chloro-4-methyl-pyrimidine (50.0 g, 398 mmol) and NCS (77.9 g, 583 mmol) in MeCN (250 mL) was added benzoyl benzenecarboperoxoate (28.3 g, 117 mmol) in portions at 20° C. and the mixture was stirred at 100° C. for 16 hrs under N$_2$ atmosphere. TLC showed most of the starting material consumed and two new spots appeared. The mixture was cooled down to room temperature, poured into water (500 mL) and extracted with EtOAc (200 mL×3). The organic layers were combined and washed with brine (200 mL×2), dried over Na$_2$SO$_4$, filtered and concentrated under reduced pressure. The residue was purified by silica gel column chromatography to give 2-chloro- 4-(chloromethyl) pyrimidine (22 g, yield: 31.2%) as yellow oil. ¹H NMR (400 MHz, CDCl3) δ=8.69 (d, J=5.2 Hz, 1H), 7.54 (d, J=5.0 Hz, 1H), 4.61 (s, 2H).

3-chloro-2-(2-chloroethoxy)-5-(2-(4-((2-chloropyrimidin-4-yl)methoxy)phenyl)propan-2-yl)benzonitrile (4)

To a mixture of 3-chloro-2-(2-chloroethoxy)-5-(2-(4-hydroxyphenyl)propan-2-yl)benzonitrile (18.0 g, 51.4 mmol) and 2-chloro-4-(chloromethyl) pyrimidine (10.1 g, 61.7 mmol) in DMF (150 mL) was added Cs₂CO₃ (33.5 g, 103.4 mmol) at 20° C. and the mixture was stirred at the same temperature for 16 hrs. LCMS showed the reaction was completed. The reaction mixture was poured into H₂O (300 mL) and extracted with EtOAc (150 mL×3). The combined organic layers were washed with brine (150 mL×3), dried over Na₂SO₄, filtered and concentrated under reduced pressure. The residue was purified by silica gel column chromatography to give 3-chloro-2-(2-chloroethoxy)-5-(2-(4-((2-chloropyrimidin-4-yl)methoxy)phenyl)propan-2-yl) benzonitrile (15.5 g, yield: 63.3%) as white solid. ¹H NMR (400 MHz, CDCl3) δ=8.67 (d, J=5.2 Hz, 1H), 7.56 (d, J=5.2 Hz, 1H), 7.45 (d, J=2.4 Hz, 1H), 7.35-7.29 (m, 1H), 7.13 (d, J=8.8 Hz, 2H), 6.90 (d, J=8.8 Hz, 2H), 5.16 (s, 2H), 4.43 (t, J=6.0 Hz, 2H), 3.88 (t, J=6.0 Hz, 2H), 1.65 (s, 6H).

N-(4-((4-(2-(3-chloro-4-(2-chloroethoxy)-5-cyanophenyl)propan-2-yl)phenoxy)methyl) pyrimidin-2-yl)methanesulfonamide (A109)

To a mixture of 3-chloro-2-(2-chloroethoxy)-5-(2-(4-((2-chloropyrimidin-4-yl)methoxy)phenyl)propan-2-yl)benzonitrile (15.5 g, 32.5 mmol), methane sulfonamide (9.3 g, 97.5 mmol), Cs₂CO₃ (21.2 g, 65.0 mmol) and Xantphos (1.88 g, 3.25 mmol) in 1,4-dioxane (450 mL) was added Pd₂(dba)₃ (3.0 g, 3.3 mmol) at 20° C. and the mixture was stirred at 90° C. for 6 hrs under N₂ atmosphere. LCMS showed the reaction was completed. The mixture was cooled down to room temperature, poured into water (300 mL) and extracted with EtOAc (300 mL×3). The combined organic layers were washed with brine (300 mL×2), dried over Na₂SO₄, filtered and concentrated under reduced pressure. The residue was purified by silica gel column chromatography to give the crude product and then further purified by p-HPLC (TFA) to give N-(4-((4-(2-(3-chloro-4-(2-chloroethoxy)-5-cyanophenyl)propan-2-yl)phenoxy) methyl)pyrimidin-2-yl)methanesulfonamide (5.30 g, yield: 30.1%) as yellow solid. ¹H NMR (400 MHz, CDCl3) δ=10.02 (br s, 1H), 8.69 (d, J=5.2 Hz, 1H), 7.45 (d, J=2.4 Hz, 1H), 7.34-7.31 (m, 1H), 7.30 (d, J=5.2 Hz, 1H), 7.13 (d, J=8.8 Hz, 2H), 6.91 (d, J=8.8 Hz, 2H), 5.13 (s, 2H), 4.43 (t, J=6.0 Hz, 2H), 3.88 (t, J=6.0 Hz, 2H), 3.47 (s, 3H), 1.65 (s, 6H). LCMS (220 nm): 99.0%. Exact Mass: 534.09; found 535.1, 537.0.

Example 23: Synthesis of N-(4-(1-(4-(2-(3-chloro-4-(2-chloroethoxy)-5-cyanophenyl)propan-2-yl)phenoxy)ethyl)oxazol-2-yl)methanesulfonamide (A122)

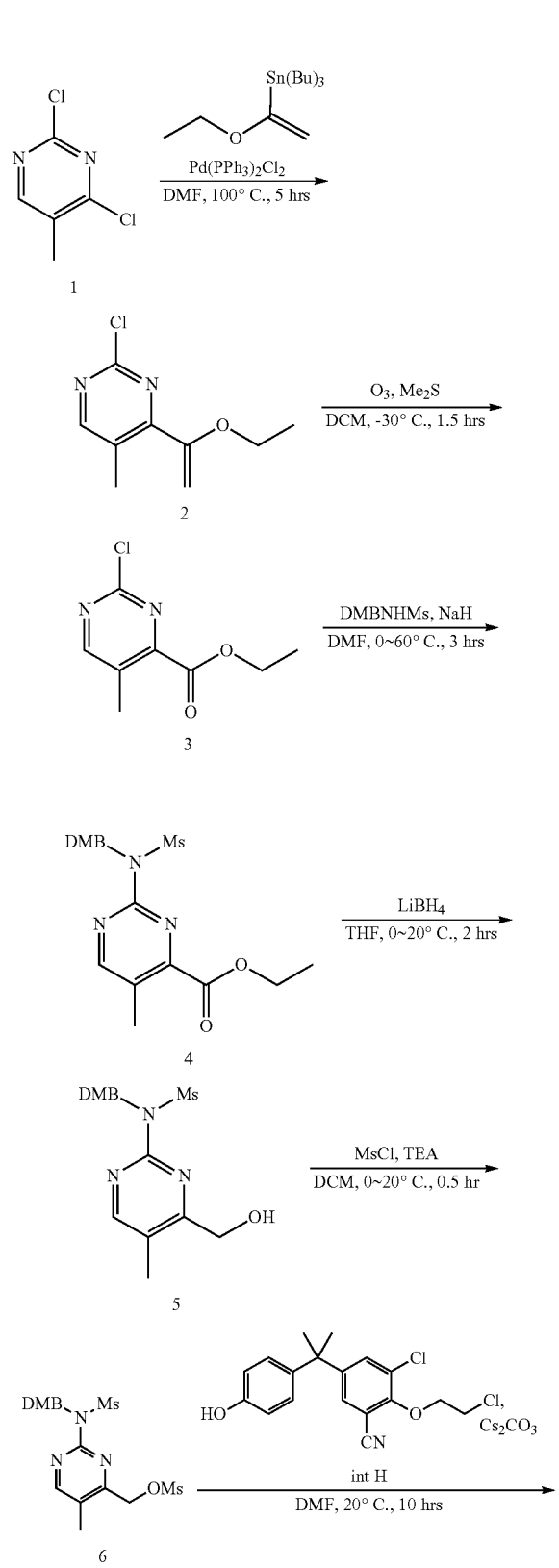

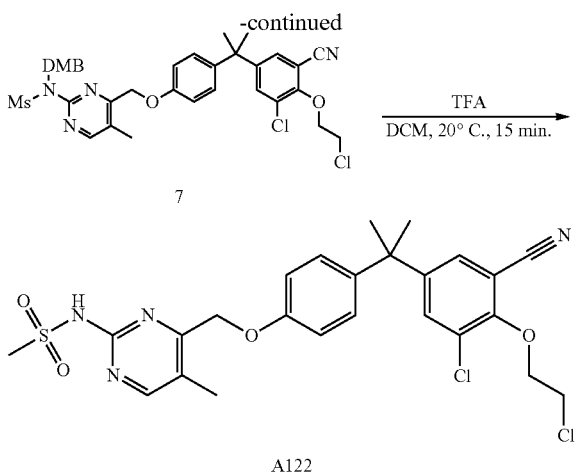

2-Chloro-4-(1-ethoxyvinyl)-5-methylpyrimidine (2)

To a mixture of 2,4-dichloro-5-methyl-pyrimidine (10.0 g, 61.3 mmol) and tributyl(1-ethoxyvinyl)stannane (22.2 g, 0.0613 mol) in DMF (200 mL) was added Pd(PPh$_3$)$_2$Cl$_2$ (2.15 g, 3.1 mmol) at 20° C. and the mixture was stirred at 100° C. for 5 hrs under N$_2$ atmosphere. TLC showed the reaction was completed. The reaction was quenched by KF solution (30 g, 0.172 mol dissolved 500 mL in water), filtered and extracted with EtOAc (100 mL×3). The combined organic layers were washed with brine (100 mL×2), dried over Na$_2$SO$_4$, filtered and concentrated under reduced pressure. The residue was purified by MPLC to give 2-chloro-4-(1-ethoxyvinyl)-5-methyl-pyrimidine (6.0 g, yield: 41.5%) as yellow oil. $^1$H NMR (400 MHz, CDCl$_3$): δ 8.40 (s, 1H), 5.01 (d, J=2.4 Hz, 1H), 4.55 (d, J=2.4 Hz, 1H), 3.94 (q, J=7.2 Hz, 2H), 2.38 (s, 3H), 1.41 (t, J=7.2 Hz, 3H).

Ethyl 2-chloro-5-methylpyrimidine-4-carboxylate (3)

O$_3$ (gas) was bubbled into a solution of 2-chloro-4-(1-ethoxyvinyl)-5-methyl-pyrimidine (2) (purity: 50.0%, 6.0 g, 0.0151 mol) in DCM (60.0 mL) at −30 OC for 0.5 hour. TLC showed the reaction was completed. 02 and N$_2$ was bubbled into the above solution at 10° C. for 0.5 hr. (CH$_3$)$_2$S (10.0 mL, 0.0151 mol) was added into the reaction and the mixture was stirred for 0.5 hr at 20° C. TLC showed the reaction was completed. The mixture was concentrated under reduced pressure. The residue was purified by silica gel column chromatography to give ethyl 2-chloro-5-methylpyrimidine-4-carboxylate (1.70 g, yield: 56.1%) as colorless oil. $^1$H NMR (400 MHz, CDCl$_3$) δ 8.62 (s, 1H), 4.48 (q, J=7.2 Hz, 2H), 2.50 (s, 3H), 1.44 (t, J=7.2 Hz, 3H).

Ethyl 2-(N-(2,4-dimethoxybenzyl)methylsulfonamido)-5-methylpyrimidine-4 carboxylate (4)

To a mixture of ethyl 2-chloro-5-methylpyrimidine-4-carboxylate (3) (0.20 g, 0.997 mmol) and N-[(2,4-dimethoxyphenyl)methyl]methanesulfonamide (0.49 g, 1.99 mmol) in DMF (5.0 mL) was added NaH (60.0%, 0.076 g, 1.99 mmol) at 0° C. The mixture was stirred at 60° C. for 6 hrs. LCMS showed the reaction was completed. The mixture was quenched by saturated aqueous NH$_4$Cl (10 mL) and extracted with EtOAc (15 mL×3). The combined organic layers were combined and washed with brine (15 mL×2), dried over Na$_2$SO$_4$, filtered and concentrated under reduced pressure. The residue was purified by silica gel column chromatography to give ethyl 2-(N-(2,4-dimethoxybenzyl)methylsulfonamido)-5-methylpyrimidine-4-carboxylate (0.180 g, yield: 44.1%) as colorless oil. $^1$H NMR (400 MHz, CDCl$_3$): δ 8.53 (s, 1H), 7.33-7.29 (m, 1H), 6.42-6.37 (m, 2H), 5.29 (s, 2H), 4.44 (q, J=7.2 Hz, 2H), 3.78 (s, 3H), 3.66 (s, 3H), 3.36 (s, 3H), 2.44 (s, 3H), 1.43 (t, J=7.2 Hz, 3H).

N-(2,4-Dimethoxybenzyl)-N-(4-(hydroxymethyl)-5-methylpyrimidin-2-yl)methanesulfonamide (5)

To a solution of ethyl 2-(N-(2,4-dimethoxybenzyl)methyl sulfonamido)-5-methylpyrimidine-4-carboxylate (4) (0.18 g, 0.44 mmol)) in THF (5 mL) was added LiBH$_4$ (0.038 g, 1.8 mmol) in portions at 0° C. The mixture was stirred at 20° C. for 2 hrs. TLC showed the reaction was completed. The mixture was quenched by saturated aqueous NH$_4$Cl (20 mL), extracted with EtOAc (10 mL×2). The combined organic layers were washed with brine (10 mL), dried over Na$_2$SO$_4$, filtered and concentrated under reduced pressure. The residue was purified by silica gel chromatography to give N-(2,4-dimethoxybenzyl)-N-(4-(hydroxymethyl)-5-methylpyrimidin-2-yl) methanesulfonamide (0.080 g, yield: 50%) as colorless oil. $^1$H NMR (400 MHz, CDCl$_3$): δ 8.29 (s, 1H), 7.25 (br s, 1H), 6.45-6.41 (m, 2H), 5.31 (s, 2H), 4.63 (d, J=4.8 Hz, 2H), 4.03 (t, J=4.8 Hz, 1H), 3.78 (s, 3H), 3.74 (s, 3H), 3.41 (s, 3H), 2.12 (s, 3H).

(2-(N-(2,4-Dimethoxybenzyl)methylsulfonamido)-5-methylpyrimidin-4-yl)methyl Methanesulfonate (6)

To a solution of N-(2,4-dimethoxybenzyl)-N-(4-(hydroxymethyl)-5-methylpyrimidin-2-yl)methanesulfonamide (5) (0.10 g, 0.272 mmol) in DCM (2 mL) was added TEA (0.0759 mL, 0.544 mmol) and MsCl (0.047 g, 0.41 mmol) at 0° C. The mixture was stirred at 20° C. for 0.5 hr under N$_2$ atmosphere. LCMS showed the reaction was completed. The reaction was quenched by saturated aqueous NH$_4$Cl solution (2 mL), extracted with DCM (3 mL×3), dried over Na$_2$SO$_4$, filtered and concentrated under reduced pressure to give (2-(N-(2,4-dimethoxybenzyl)methylsulfonamido)-5-methylpyrimidin-4-yl)methyl methanesulfonate (0.15 g, crude). $^1$H NMR (400 MHz, CDCl$_3$): δ 8.39 (s, 1H), 7.24 (s, 1H), 6.39 (s, 2H), 5.29-5.28 (m, 2H), 4.54 (s, 2H), 3.78 (s, 6H), 3.62 (s, 3H), 3.28 (s, 3H), 2.80 (s, 3H).

N-(4-((4-(2-(3-Chloro-4-(2-chloroethoxy)-5-cyanophenyl)propan-2-yl)phenoxy)methyl)-5-methylpyrimidin-2-yl)-N-(2,4-dimethoxybenzyl)methanesulfonamide (7)

To a solution of (2-(N-(2,4-dimethoxybenzyl)methyl sulfonamido)-5-methylpyrimidin-4-yl)methyl methanesulfonate (6) (0.10 g, 0.22 mmol) in DMF (2.0 mL) was added Cs$_2$CO$_3$ (0.15 g, 0.45 mmol) and 3-chloro-2-(2-chloroethoxy)-5-[1-(4-hydroxyphenyl)-1-methyl-ethyl]benzonitrile (Int H) (0.079 g, 0.22 mmol) at 20° C. The mixture was stirred at 20° C. for 10 hrs. TLC showed the reaction was completed. The mixture was quenched with H$_2$O (3 mL), extracted with EtOAc (3 mL×3). The combined organic layers were washed with brine (4 mL×3), dried over Na$_2$SO$_4$, filtered and concentrated under reduced pressure to give N-(4-((4-(2-(3-chloro-4-(2-chloroethoxy)-5-cyanophenyl)propan-2-yl)phenoxy)methyl)-5-methylpyrimidin-2- yl)-N-(2,4-dimethoxybenzyl)methanesulfonamide (0.10 g, crude) as yellow oil which was used directly without further purification.

N-(4-((4-(2-(3-Chloro-4-(2-chloroethoxy)-5-cyanophenyl)propan-2-yl)phenoxy)methyl)-5-methylpyrimidin-2-yl)methanesulfonamide (A122)

To a solution of N-(4-((4-(2-(3-chloro-4-(2-chloroethoxy)-5-cyanophenyl)propan-2-yl)phenoxy)methyl)-5-methylpyrimidin-2-yl)-N-(2,4-dimethoxybenzyl)methanesulfonamide (7) (0.05 g, crude) in DCM (1 mL) was added TFA (0.0159 mL, 0.214 mmol) and the mixture was stirred at 20° C. for 15 min. LCMS showed the reaction was completed. The mixture was quenched with H$_2$O (2 mL), extracted with DCM (3 mL×3). The combined organic layers were washed with brine (2 mL), dried over Na$_2$SO$_4$, filtered and concentrated under reduced pressure. The residue was purified by prep-HPLC (FA) to give N-(4-((4-(2-(3-chloro-4-(2-chloroethoxy)-5-cyanophenyl)propan-2-yl)phenoxy)methyl)-5-methylpyrimidin-2-yl)methanesulfonamide (purify: 100%, 7 mg, yield: 17.8%) as white solid. $^1$H NMR (400 MHz, CDCl$_3$): δ 8.41 (s, 2H), 8.25-8.30 (br, 1H), 7.44 (d, J=2.4 Hz, 1H), 7.31 (d, J=2.4 Hz, 1H), 7.11 (d, J=6.8 Hz, 2H), 6.92 (d, J=6.8 Hz, 2H), 5.12 (s, 2H), 4.42 (t, J=6.1 Hz, 2H), 3.88 (t, J=6.4 Hz, 2H), 3.41 (s, 3H), 2.35 (s, 3H), 1.64 (s, 6H). LCMS: (220 nm): 100%. Exact Mass: 548.1; found 549.2, 551.1.

Example 24: Synthesis of N-(4-((4-(2-(3-chloro-4-(2-chloroethoxy)-5-cyanophenyl)propan-2-yl)phenoxy)methyl)thiazol-2-yl)methanesulfonamide (A134)

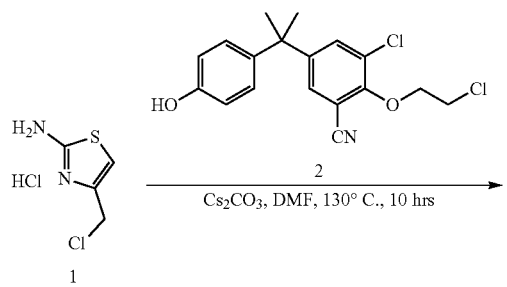

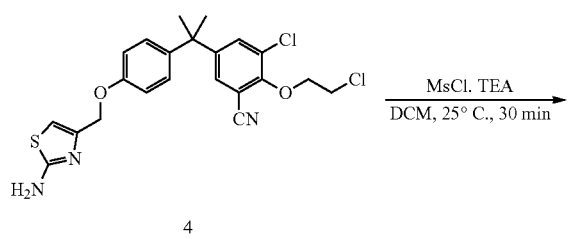

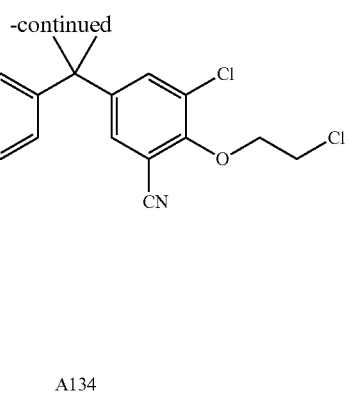

5-(2-(4-((2-Aminothiazol-4-yl)methoxy)phenyl)propan-2-yl)-3-chloro-2-(2-chloro ethoxy)benzonitrile (3)

To a mixture of 4-(chloromethyl)thiazol-2-aminehydrochloride (1) (200 mg, 1.08 mmol) and 3-chloro-2-(2-chloroethoxy)-5-(2-(4-hydroxyphenyl)propan-2-yl)benzonitrile (2) (378 mg, 1.08 mmol) in DMF (5 mL) was added Cs$_2$CO$_3$ (1.4 g, 4.32 mol) at 20° C. and the mixture was stirred at 130° C. for 10 hrs. LCMS showed the reaction was completed. The reaction was cooled down, quenched with water (10 mL). The mixture was extracted with DCM (5 mL×3). The combined organic layers were washed with brine (5 mL×2), dried over Na$_2$SO$_4$, filtered and concentrated under reduced pressure. The residue was purified by HPLC (FA) to obtain 5-(2-(4-((2-aminothiazol-4-yl)methoxy)phenyl)propan-2-yl)-3-chloro-2-(2-chloroethoxy) benzonitrile (3) (15.0 mg, yield: 3%) as yellow solid. $^1$H NMR (400 MHz, CDCl$_3$) δ=7.44 (s, 1H), 7.32 (s, 1H), 7.11 (br d, J=6.6 Hz, 2H), 6.93 (br s, 2H), 6.53 (br s, 1H), 5.06-4.83 (m, 2H), 4.42 (t, J=6.2 Hz, 2H), 3.88 (t, J=6.2 Hz, 2H), 1.64 (s, 6H).

N-(4-((4-(2-(3-chloro-4-(2-chloroethoxy)-5-cyanophenyl)propan-2-yl)phenoxy)methyl)thiazol-2-yl)methanesulfonamide (A134)

To a mixture of 5-(2-(4-((2-aminothiazol-4-yl)methoxy)phenyl)propan-2-yl)-3-chloro-2-(2-chloroethoxy)benzonitrile (3) (15.0 mg, 0.03 mmol) and TEA (0.01 mL, 0.10 mmol) in DCM (1 mL) was added methanesulfonyl chloride (4.46 mg, 0.03 mmol) and the mixture was stirred at 25° C. for 30 min (two Ms groups are installed in LCMS). Then Cs$_2$CO$_3$ (21.1 mg, 0.0649 mol) in H2O (0.5 mL) was added into the reaction. The mixture was stirred at 50° C. for 10 min. LCMS showed the reaction was completed. The reaction was quenched with water (2 mL) and extracted with DCM (3 mL×3). The combined organic layers were washed with brine (3 mL×2), dried over Na$_2$SO$_4$, filtered, and concentrated under reduced pressure. The residue was purified by prep-HPLC (HCOOH) to obtain N-(4-((4-(2-(3-chloro-4-(2-chloroethoxy)-5-cyanophenyl)propan-2-yl)phenoxy)methyl)thiazol-2-yl) methanesulfonamide (A134) (1.8 mg, yield: 10.3%) as yellow oil. $^1$H NMR (400 MHz, CDCl$_3$) δ=7.44 (d, J=2.2 Hz, 1H), 7.32 (d, J=2.2 Hz, 1H), 7.13 (d, J=8.8 Hz, 2H), 6.90 (d, J=8.8 Hz, 2H), 6.49 (s, 1H), 4.98 (s, 2H), 4.43 (t, J=6.2 Hz, 2H), 3.88 (t, J=6.2 Hz, 2H), 3.01 (s, 3H), 1.65 (s, 6H). LCMS: (220 nm): 94.9%. Exact Mass: 539.1; found 540.0/542.0.

Example 25: Synthesis of 3-chloro-2-(2-chloroethoxy)-5-(2-(4-((4-(methylsulfonyl)thiazol-2-yl)methoxy)phenyl)propan-2-yl)benzonitrile (A136)

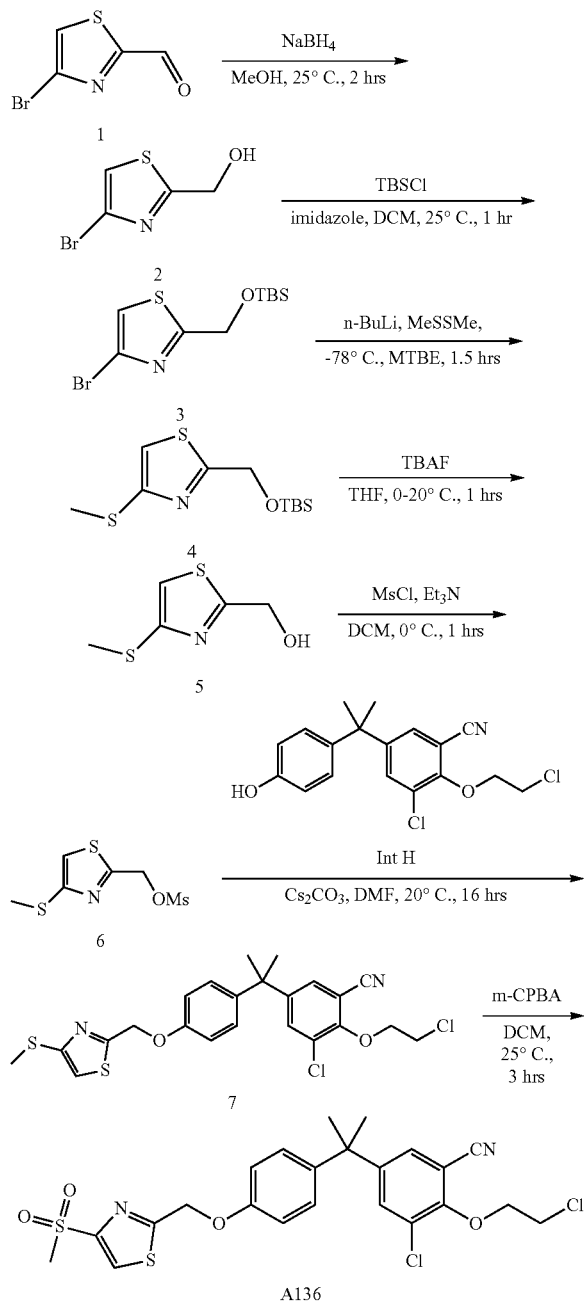

(4-Bromothiazol-2-yl)methanol (2)

To a solution of 4-bromothiazole-2-carbaldehyde (10.4 g, 0.0542 mol) in MeOH (150 mL) was added NaBH$_4$ (4.10 g, 0.108 mol) at 0° C. The mixture was stirred at 25° C. for 2 hrs. TLC showed the reaction was completed and one new spot was observed. The mixture was quenched with water (70 mL), stirred for 0.5 hr and concentrated to remove most of MeOH. The aqueous layer was extracted with EtOAc (30 mL×3). The combined organic layers were washed with brine (50 mL), dried over Na$_2$SO$_4$, filtered and concentrated under reduced pressure. The residue was purified by silica gel column chromatography (SiO$_2$, Petroleum ether/Ethyl acetate=10: to 3:1) to give (4-bromothiazol-2-yl)methanol (10.0 g, 0.0515 mol, yield: 95.2%) as white solid. $^1$H NMR (400 MHz, CDCl$_3$) δ 7.23 (s, 1H), 4.96 (d, J=6.0 Hz, 2H), 2.79 (t, J=6.0 Hz, 1H).

4-Bromo-2-(((tert-butyldimethylsilyl)oxy)methyl)thiazole (3)

To a solution of (4-bromothiazol-2-yl)methanol (11.7 g, 0.0603 mol) in DCM (120 mL) was added imidazole (8.21 g, 0.121 mol) and tert-butyl-chloro-dimethyl-silane (10.0 g, 0.0663 mol). The mixture was stirred at 25° C. for 1 hr. TLC showed the starting material was consumed and one new spot was observed. The reaction was poured into water (100 mL), extracted with DCM (70 mL×2). The combined organic layers were washed with brine (70 mL), dried over Na$_2$SO$_4$, filtered and concentrated under reduced pressure. The residue was purified by silica-gel column chromatography to give (4-bromothiazol-2-yl)methoxy-tert-butyl-dimethyl-silane (17.0 g, 0.0551 mol, yield: 91.5%) as colorless oil. $^1$H NMR (400 MHz, CDCl$_3$) δ 7.18 (s, 1H), 4.95 (s, 2H), 0.96 (s, 9H), 0.14 (s, 6H).

2-(((tert-Butyldimethylsilyl)oxy)methyl)-4-(methylthio)thiazole (4)

To a solution of (4-bromothiazol-2-yl)methoxy-tert-butyl-dimethyl-silane (11.5 g, 0.0373 mol) in MTBE (300 mL) was added n-BuLi (2.50 M, 17.9 mL, 0.0448 mol) dropwise at −78 OC under N$_2$ atmosphere. The mixture was stirred at −78° C. for 30 min. Then MeSSMe (14.3 g, 0.152 mol) was added at −78° C. and stirred at the same temperature for 1 hr. LCMS showed 70% desired MS was detected. The mixture was quenched with sat. NH$_4$Cl solution (100 mL), extracted with EtOAc (30 mL×3). The combined organic layers were washed with brine (50 mL), dried over Na$_2$SO$_4$, filtered and concentrated under reduced pressure to give crude tert-butyl-dimethyl-[(4-methylsulfanylthiazol-2-yl)methoxy]silane (90.0%, 10.0 g, 0.0327 mol, yield: 87.6%) as brown oil. $^1$H NMR (400 MHz, CDCl$_3$) δ 6.87 (s, 1H), 4.95 (s, 2H), 2.53 (s, 3H), 0.96 (s, 9H), 0.14 (s, 6H).

(4-(Methylthio)thiazol-2-yl)methanol (5)

To a solution of (4-bromothiazol-2-yl)methoxy-tert-butyl-dimethyl-silane (12.0 g, 0.0389 mol) in THF (150 mL) was added TBAF (1.00 M, 46.7 mL, 0.0467 mol) at 0° C. The mixture was stirred at 20° C. for 1 hr. TLC showed the reaction was completed. The reaction was poured into water (50 mL), extracted with EtOAc (30 mL×3). The combined organic layers were washed with brine (50 mL), dried over Na$_2$SO$_4$, filtered and concentrated under reduced pressure. The residue was purified by silica-gel column chromatography to give (4-methylsulfanylthiazol-2-yl) methanol (3.60 g, 0.0223 mol, yield: 57.4%) as yellow solid. $^1$H NMR (400 MHz, CDCl$_3$) δ 6.89 (s, 1H), 4.94 (br d, J=2.0 Hz, 2H), 2.95 (br s, 1H), 2.54 (s, 3H).

(4-(Methylthio)thiazol-2-yl)methyl methanesulfonate (6)

To a mixture of (4-methylsulfanylthiazol-2-yl)methanol (3.40 g, 0.0211 mol) and TEA (0.432 mL, 0.00310 mol) in DCM (50 mL) was added MsCl (1.96 mL, 0.0253 mol) at 0°

C. The mixture was stirred at 0° C. for 1 hr. TLC showed the starting material was consumed and one new spot was observed. The reaction was poured into water (30 mL), extracted with DCM (15 mL×3). The combined organic layers were washed with brine (40 mL), dried over Na$_2$SO$_4$, filtered and concentrated under reduced pressure to give (4-methylsulfanylthiazol-2-yl)methyl methanesulfonate (5.40 g, 0.0226 mol, crude) as yellow oil. $^1$H NMR (400 MHz, CDCl$_3$) δ 6.99 (s, 1H), 5.45 (s, 2H), 3.10 (s, 3H), 2.55 (s, 3H).

3-Chloro-2-(2-chloroethoxy)-5-(2-(4-((4-(methyl-thio)thiazol-2-yl)methoxy)phenyl)propan-2-yl)benzonitrile (7)

To a suspension of (4-methylsulfanylthiazol-2-yl)methyl methanesulfonate (80.0%, 3.08 g, 0.0103 mol) and Cs$_2$CO$_3$ (5.58 g, 0.0171 mol) in DMF (20 mL) was added 3-chloro-2-(2-chloroethoxy)-5-[1-(4-hydroxyphenyl)-1-methyl-ethyl]benzonitrile (3.00 g, 0.00857 mol) at 20° C. The mixture was stirred at 20° C. for 16 hrs. LCMS showed the reaction was completed. The reaction was poured into H$_2$O (50 mL), extracted with EtOAc (30 mL×3). The combined organic layers were washed with brine (30 mL×3), filtered and concentrated under reduced pressure to give 3-chloro-2-(2-chloroethoxy)-5-[1-methyl-1-[4-[(4-methyl sulfa-nylthiazol-2-yl)methoxy]phenyl]ethyl]benzonitrile (3.20 g, 0.00648 mol, yield: 75.7%) as yellow oil. $^1$H NMR (400 MHz, CDCl$_3$) δ 7.44 (d, J=2.4 Hz, 1H), 7.32 (d, J=2.4 Hz, 1H), 7.12 (d, J=8.4 Hz, 2H), 6.99-6.91 (m, 3H), 5.34 (s, 2H), 4.42 (t, J=6.4 Hz, 2H), 3.88 (t, J=6.4 Hz, 2H), 2.56 (s, 3H), 1.64 (s, 6H).

3-Chloro-2-(2-chloroethoxy)-5-(2-(4-((4-(methyl-sulfonyl)thiazol-2-yl)methoxy)phenyl) propan-2-yl) benzonitrile (A136)

To a solution of 3-chloro-2-(2-chloroethoxy)-5-[1-methyl-1-[4-[(4-methyl sulfanylthiazol-2-yl)methoxy]phe-nyl]ethyl]benzonitrile (3.00 g, 0.00608 mol) in DCM (50 mL) was added m-CPBA (80.0%, 5.25 g, 0.0243 mol) at 0° C. The mixture was stirred at 25° C. for 3 hrs. LCMS showed the reaction was completed and 60% desired product was detected. The mixture was quenched with water (30 mL). The mixture was extracted with DCM (20 mL×3). The combined organic layers were washed with brine (50 mL×2), dried over Na$_2$SO$_4$, filtered and concentrated under reduced pressure. The residue was purified by prep-HPLC (FA) to give 3-chloro-2-(2-chloroethoxy)-5-[1-methyl-1-[4-[(4-methylsulfonylthiazol-2-yl)methoxy]phenyl]ethyl]ben-zonitrile (A136) (1.71 g, 0.00325 mol, yield: 53.5%) as white solid. $^1$H NMR (400 MHz, CDCl$_3$) δ 8.22 (s, 1H), 7.45 (d, J=2.4 Hz, 1H), 7.32 (d, J=2.0 Hz, 1H), 7.15 (d, J=6.8 Hz, 2H), 6.95 (d, J=6.8 Hz, 2H), 5.39 (s, 2H), 4.43 (t, J=6.4 Hz, 2H), 3.88 (t, J=6.0 Hz, 2H), 3.23 (s, 3H), 1.66 (s, 6H).

Example 26: Synthesis of N-(2-((4-(2-(3-Chloro-4-(2-chloroethoxy)-5-cyanophenyl)propan-2-yl)phe-noxy)methyl)thiazol-4-yl)methanesulfonamide (A137)

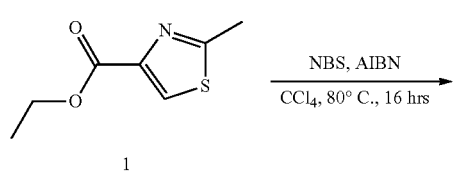

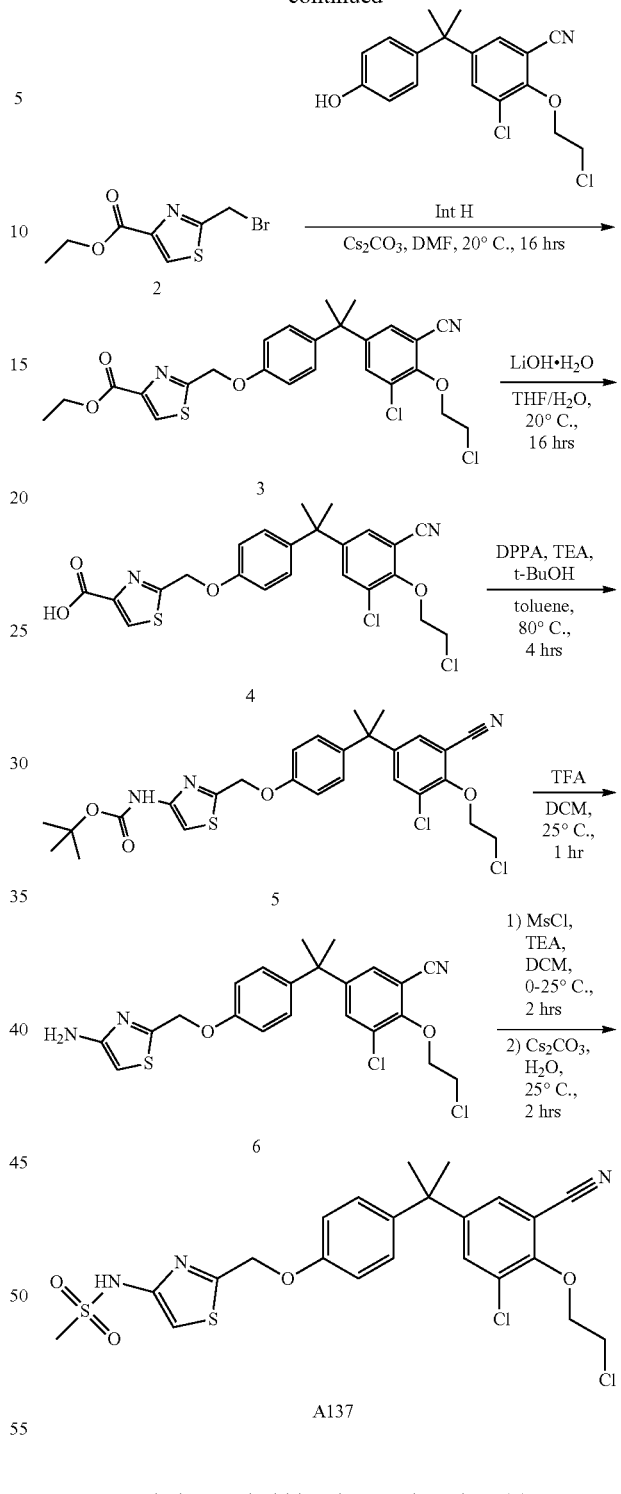

Ethyl 2-methylthiazole-4-carboxylate (2)

To a mixture of ethyl 2-methyloxazole-4-carboxylate (1) (10.0 g, 58.4 mmol) and AIBN (0.959 g, 5.84 mmol) in CCl$_4$ (80 mL) was added NBS (12.5 g, 70.1 mmol) at 20° C. and the mixture was stirred at 80° C. for 16 hrs. TLC showed a new spot appeared and trace of starting material was remained. The reaction was poured into H$_2$O (150 mL) and extracted with DCM (80 mL×2). The combined organic layers were washed with brine (80 mL), dried over Na$_2$SO$_4$, filtered, and concentrated under reduced pressure. The residue was purified by silica gel to give ethyl 2-methyloxazole-4-carboxylate (2) (4.6 g, Yield: 31.5%) as yellow oil. $^1$H NMR (400 MHz, CDCl$_3$) δ=8.23 (s, 1H), 4.77 (s, 2H), 4.41 (q, J=6.8 Hz, 2H), 1.42 (t, J=7.2 Hz, 3H).

Ethyl 2-((4-(2-(3-chloro-4-(2-chloroethoxy)-5-cyanophenyl)propan-2-yl) phenoxy) methyl)thiazole-4-carboxylate (3)

A solution of 3-chloro-2-(2-chloroethoxy)-5-(1-(4-hydroxyphenyl)-1-methyl-ethyl)benzonitrile (int H) (0.5 g, 1.43 mmol), ethyl 2-(bromomethyl) thiazole-4-carboxylate (2) (0.428 g, 1.71 mmol) and Cs$_2$CO$_3$ (0.93, 2.86 mmol) in DMF (10 mL) was stirred at 20° C. for 16 hrs. LCMS showed the reaction was completed. The reaction was poured into H$_2$O (15 mL) and extracted with EtOAc (15 mL×3). The combined organic layers were washed with brine (10 mL×3), dried over Na$_2$SO$_4$, filtered and concentrated under reduced pressure. The residue was purified by silica gel to give ethyl 2-((4-(1-(3-chloro-4-(2-chloroethoxy)-5-cyano-phenyl)-1-methyl-ethyl)phenoxy)methyl)thiazole-4-carboxylate (3) (0.6 g, Yield: 80.9%) as yellow oil. $^1$H NMR (400 MHz, CDCl$_3$) δ=8.27 (s, 1H), 7.44 (d, J=2.4 Hz, 1H), 7.32 (d, J=2.4 Hz, 1H), 7.12 (d, J=8.8 Hz, 2H), 5.41 (s, 2H), 4.44-4.09 (m, 4H), 3.88 (t, J=6.4 Hz, 2H), 1.65 (s, 1H), 1.43 (t, J=7.6 Hz, 3H).

2-((4-(2-(3-Chloro-4-(2-chloroethoxy)-5-cyanophenyl)propan-2-yl)phenoxy)methyl)thiazole-4-carboxylic acid (4)

A solution of ethyl 2-((4-(1-(3-chloro-4-(2-chloroethoxy)-5-cyano-phenyl)-1-methyl-ethyl)phenoxy)methyl)thiazole-4-carboxylate (3) (0.5 g, 0.963 mmol) and LiOH.H$_2$O (0.162 g, 3.85 mmol) in THF (3 mL) and H$_2$O (3 mL) was stirred at 20° C. for 16 hrs. LCMS showed the reaction was completed. The reaction was poured into H$_2$O (8 mL). The pH of the aqueous layer was adjusted to 3-4 by adding aqueous HCl solution (3M). The aqueous layer was separated and extracted with EtOAc (8 mL×3). The combined organic layers were washed with brine (8 mL×2), dried over Na$_2$SO$_4$, filtered and concentrated under reduced pressure to give 2-((4-(2-(3-chloro-4-(2-chloroethoxy)-5-cyanophenyl) propan-2-yl)phenoxy)methyl)thiazole-4-carboxylic acid (4) (0.4 g, yield: 84.6%) as white solid. $^1$H NMR (400 MHz, CDCl$_3$) δ=8.34 (s, 1H), 7.44 (d, J=2.4 Hz, 1H), 7.32 (d, J=2.4 Hz, 1H), 7.14 (d, J=8.8 Hz, 2H), 6.95 (d, J=8.8 Hz, 2H), 5.41 (s, 2H), 4.43 (t, J=6.0 Hz, 2H), 3.88 (t, J=6.4 Hz, 2H), 1.65 (s, 6H).

Tert-Butyl (2-((4-(2-(3-chloro-4-(2-chloroethoxy)-5-cyanophenyl)propan-2-yl) phenoxy)methyl)thiazol-4-yl)carbamate (5)

To a solution of 2-((4-(2-(3-chloro-4-(2-chloroethoxy)-5-cyanophenyl)propan-2-yl)phenoxy)methyl)thiazole-4-carboxylic acid (4) (0.1 g, 0.204 mmol) and TEA (0.0851 mL, 0.000611 mol) in toluene (1.0 mL) was added t-BuOH (1.0 mL) and DPPA (0.132 mL, 0.611 mmol) under N$_2$ atmosphere. The mixture was stirred at 90° C. for 4 hrs. LCMS showed the starting material was consumed. The mixture was poured into H$_2$O (6 mL), extracted with DCM (3 mL×2). And the combined organic layers were washed with brine (4 mL), dried over Na$_2$SO$_4$, filtered and concentrated under reduced pressure. The residue was purified by silica gel tert-butyl (2-((4-(2-(3-chloro-4-(2-chloroethoxy)-5-cya-nophenyl)propan-2-yl)phenoxy)methyl)thiazol-4-yl)carbamate (5) (0.11 g, yield: 96.1%) as white oil. $^1$H NMR (400 MHz, CDCl$_3$) δ=7.43 (d, J=2.4 Hz, 1H), 7.33 (d, J=2.4 Hz, 1H), 7.25 (s, 1H), 7.11 (d, J=8.8 Hz, 2H), 6.93 (d, J=8.8 Hz, 2H), 5.25 (s, 2H), 4.43 (t, J=6.0 Hz, 2H), 3.88 (t, J=6.0 Hz, 2H), 1.65 (s, 6H), 1.53 (s, 9H).

5-(2-(4-((4-Aminothiazol-2-yl)methoxy)phenyl)propan-2-yl)-3-chloro-2-propoxybenzonitrile (6)

To a solution of tert-butyl (2-((4-(2-(3-chloro-4-(2-chloroethoxy)-5-cyanophenyl)propan-2-yl)phenoxy)methyl)thiazol-4-yl)carbamate (5) (0.1 g, 0.0178 mmol) in DCM (1 mL) was added TFA (0.1 mL) and stirred at 25° C. for 2 hrs. LCMS showed the reaction was completed. The reaction was poured into saturated aqueous NaHCO$_3$ solution (4 mL) and extracted with DCM (2 mL×3). The combined organic layers were washed with brine (2 mL), dried over Na$_2$SO$_4$, filtered and concentrated under reduced pressure to give 5-(2-(4-((4-aminothiazol-2-yl)methoxy)phenyl)propan-2-yl)-3-chloro-2-propoxybenzonitrile (6) (30 mg, Yield: 35.1%) as yellow oil. $^1$H NMR (400 MHz, CDCl$_3$) δ=7.44 (d, J=2.0 Hz, 1H), 7.33 (d, J=2.4 Hz, 1H), 7.25 (s, 1H), 7.11 (d, J=8.8 Hz, 2H), 6.94 (d, J=8.8 Hz, 2H), 5.24 (s, 2H), 4.42 (t, J=2.4 Hz, 2H), 3.88 (t, J=2.4 Hz, 2H), 1.65 (s, 6H)

N-(2-((4-(2-(3-Chloro-4-(2-chloroethoxy)-5-cyanophenyl)propan-2-yl)phenoxy)methyl)thiazol-4-yl) methanesulfonamide (A137)

To a solution of 5-(2-(4-((4-aminothiazol-2-yl)methoxy) phenyl)propan-2-yl)-3-chloro-2-propoxybenzonitrile (6) (50 mg, 0.108 mmol) and TEA (21.9 mg, 0,216 mmol) in DCM (2 mL) was added methanesulfonyl chloride (18.6 mg, 0.0649 mmol) dropwisely at 0° C. under nitrogen and the mixture was stirred at 25° C. for 2 hrs. (two Ms groups were installed). Then the mixture was added Cs$_2$CO$_3$ (0.141 g, 0.433 mmol) and H$_2$O (1 mL) and stirred at 25° C. for 2 hrs. LCMS showed the reaction was completed. The reaction was poured into H$_2$O (4 mL). The aqueous layer was extracted with EtOAc (4 mL×3). The combined organic layers were washed with brine (4 m), dried over Na$_2$SO$_4$, filtered, and concentrated under reduced pressure. The residue was purified by prep-HPLC (HCOOH) to give product N-(2-((4-(2-(3-chloro-4-(2-chloroethoxy)-5-cyanophenyl) propan-2-yl)phenoxy) methyl)thiazol-4-yl)methanesulfonamide (A137) (10 mg, yield: 17.1%) as white solid. 1H NMR (400 MHz, CDCl$_3$) δ=7.44 (d, J=2.4 Hz, 1H), 7.32 (d, J=2.4 Hz, 1H), 7.13 (d, J=8.8 Hz, 2H), 7.04 (s, 1H), 7.00 (s, 1H), 6.94 (d, J=8.8 Hz, 2H), 5.29 (s, 2H), 4.46 (t, J=6.0 Hz, 2H), 3.88 (t, J=6.0 Hz, 2H), 3.12 (s, 3H), 1.65 (s, 6H). LCMS: (220 nm): 93.78%. Exact Mass: 540.5; found: 540.1/542.1.

Example 27: Synthesis of 2-((4-(2-(3-chloro-4-(2-chloroethoxy)-5-cyanophenyl)propan-2-yl)phenoxy) methyl)thiazole-4-carboxamide (A171)

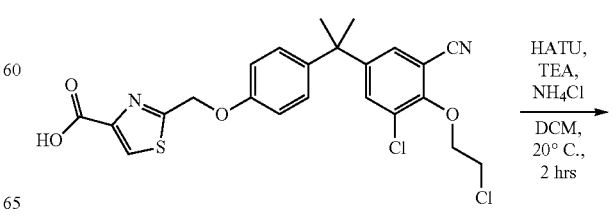

4

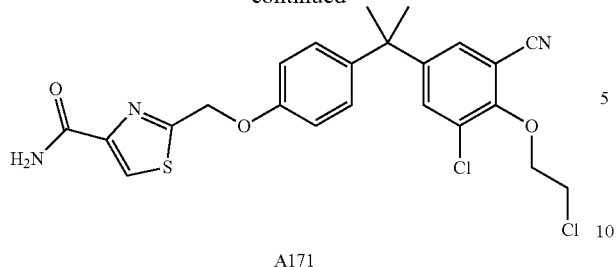

A171

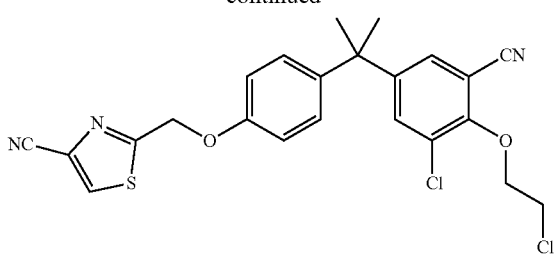

A172

To a solution of 2-((4-(2-(3-chloro-4-(2-chloroethoxy)-5-cyanophenyl)propan-2-yl)phenoxy)methyl)thiazole-4-carboxylic acid (4) (20 mg, 0.0407 mmol), NH₄Cl (5.4 mg, 0.102 mmol), HATU (0.0186 g, 0.0488 mmol) in DCM (1.00 mL) was added TEA (8.2 mg, 0.0814 mmol) at 20° C. The mixture was stirred at same temperature for 2 hrs. LCMS showed the starting material was consumed. The mixture was poured into H₂O (4 mL) and extracted with DCM (3 mL×2). The combined organic layers were washed with brine (4 mL), dried over Na₂SO₄, filtered and concentrated under reduced pressure. The residue was purified prep-HPLC (HCOOH) to give 2-((4-(2-(3-chloro-4-(2-chloroethoxy)-5-cyanophenyl)propan-2-yl)phenoxy)methyl)thiazole-4-carboxamide (A171) (9.2 mg, yield: 46.1%) as white solid. 1H NMR (400 MHz, CDCl₃) δ=8.19 (s, 1H), 7.44 (d, J=2.2 Hz, 1H), 7.32 (d, J=2.2 Hz, 1H), 7.14 (br d, J=8.8 Hz, 2H), 6.95 (d, J=8.8 Hz, 2H), 5.60 (br s, 1H), 5.34 (s, 2H), 4.43 (t, J=6.2 Hz, 2H), 3.88 (t, J=6.2 Hz, 2H), 1.66 (s, 6H). LCMS (220 nm): 99.5%. Exact Mass: 489.0; found 490.

Example 28: Synthesis of 2-((4-(2-(3-chloro-4-(2-chloroethoxy)-5-cyanophenyl)propan-2-yl)phenoxy)methyl)thiazole-4-carbonitrile (A172)

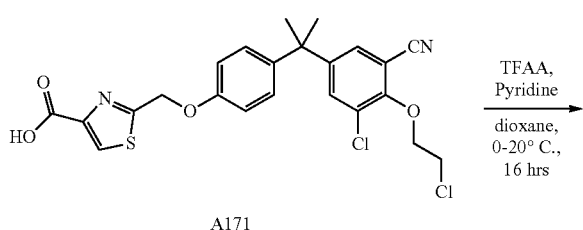

A171

TFAA, Pyridine
dioxane, 0-20° C., 16 hrs
→

To a solution 2-((4-(2-(3-chloro-4-(2-chloroethoxy)-5-cyanophenyl)propan-2-yl)phenoxy)methyl)thiazole-4-carboxamide (A171) (20 mg, 0.0408 mmol) and pyridine (3.27 mg, 0.0413 mmol) in dioxane (2.0 mL) was added TFAA (17.4 mg, 0.00827 mmol) under N₂ at 0° C. Then the reaction was stirred at 20° C. for 16 hrs. LCMS showed the reaction was completed. The reaction was poured into H₂O (4 mL). The reaction mixture were separated and extracted with EtOAc (4 mL×3). The organic layers were washed with brine (4 mL), dried over Na₂SO₄, filtered, and concentrated under reduced pressure. The residue was purified by prep-HPLC (HCOOH) to give the product 2-((4-(2-(3-chloro-4-(2-chloroethoxy)-5-cyanophenyl)propan-2-yl)phenoxy)methyl)thiazole-4-carbonitrile (A172) (10 mg, yield: 52.1%) as white solid. 1H NMR (400 MHz, CDCl₃) δ=8.05 (s, 1H), 7.44 (d, J=2.2 Hz, 1H), 7.31 (d, J=2.2 Hz, 1H), 7.15 (d, J=8.8 Hz, 2H), 6.94 (d, J=8.8 Hz, 2H), 5.37 (s, 2H), 4.43 (t, J=6.2 Hz, 2H), 3.88 (t, J=6.2 Hz, 2H), 1.65 (s, 6H). LCMS (220 nm): 100.0%. Exact Mass: 471.0; found 472.0.

Example 29: Synthesis of N-(4-(aminomethyl)-6-((4-(2-(3-chloro-4-(2-chloroethoxy)-5-cyanophenyl)propan-2-yl)phenoxy)methyl)pyrimidin-2-yl)methanesulfonamide (A164)

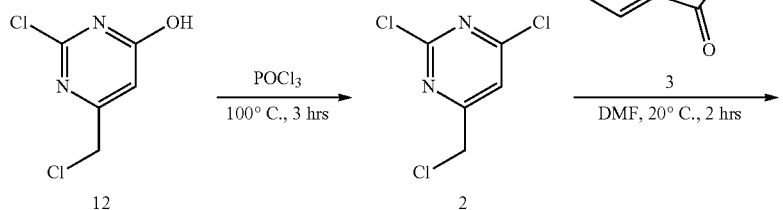

-continued
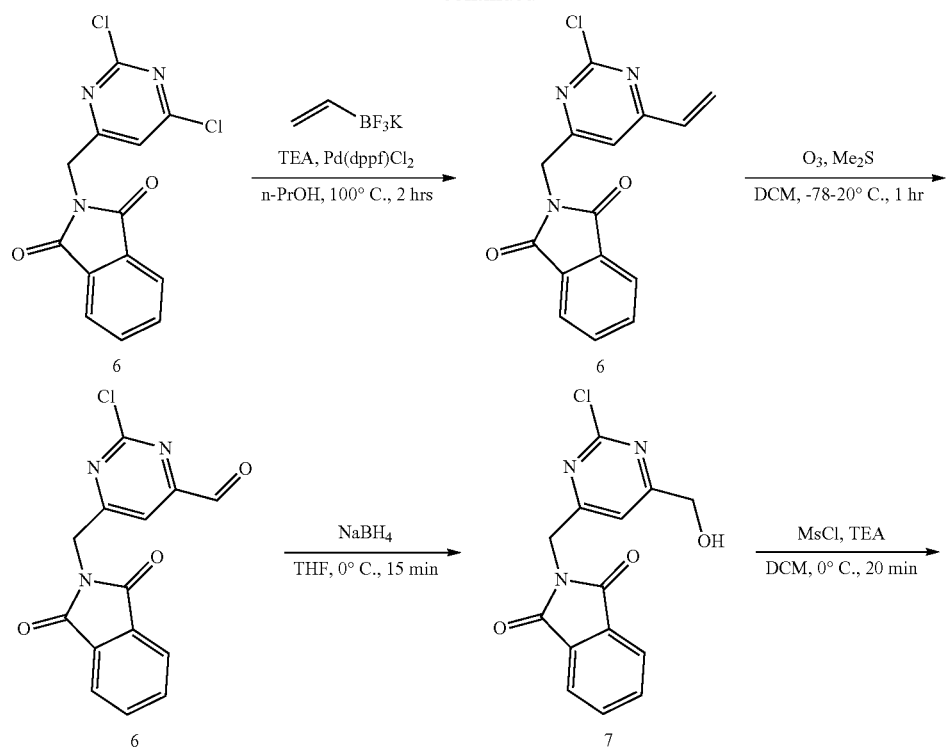
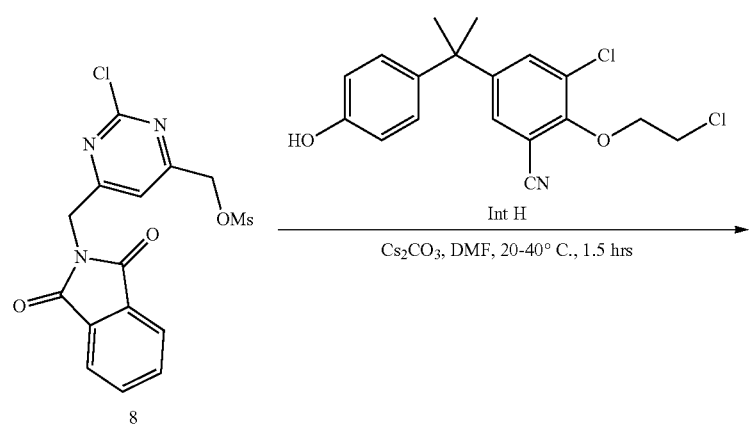
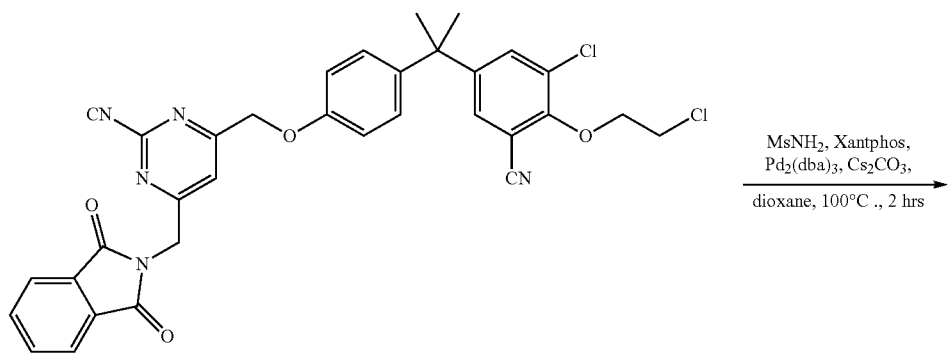

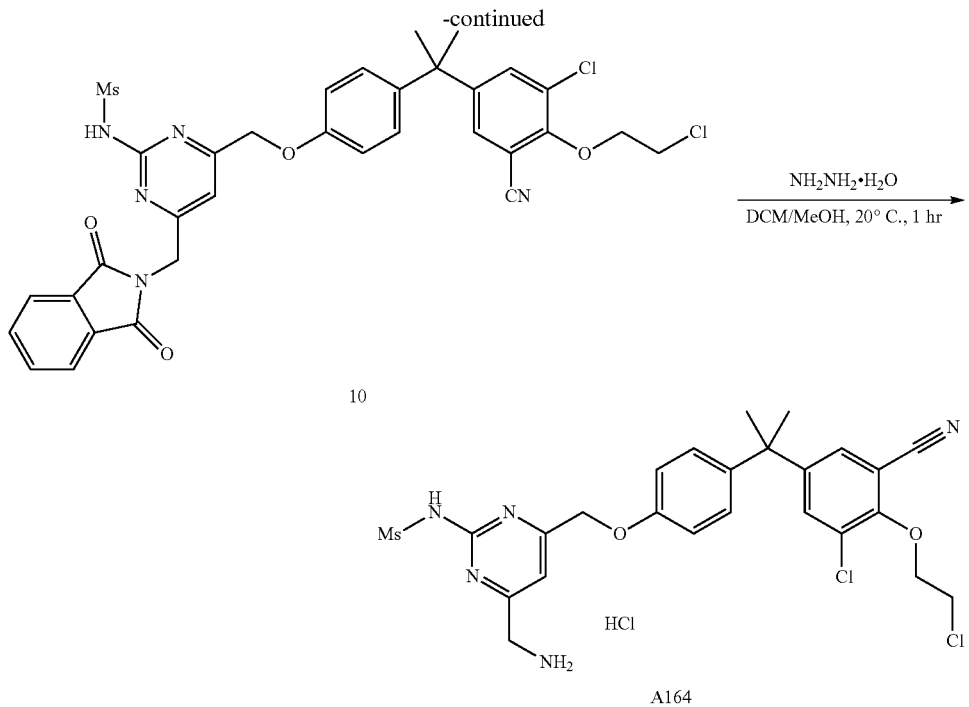

2,4-Dichloro-6-(chloromethyl)pyrimidine (2)

A suspension of 6-(chloromethyl)pyrimidine-2,4-diol (1) (1.50 g, 9.34 mmol) in $POCl_3$ (10 mL) was stirred at 100° C. for 3 hrs. TLC showed the reaction was completed. The solid was dissolved and the reaction became brown. The resulting mixture was cooled down, concentrated under reduced pressure. The residue was quenched with water (20 mL) and extracted with EtOAc (10 mL×2). The combined organic layers were washed with brine (10 mL), dried over $Na_2SO_4$, filtered and concentrated under reduced pressure. The residue was purified by MPLC (petroleum ether/EtOAc=10/1) to obtain 2,4-dichloro-6-(chloromethyl)pyrimidine (2) (1.5 g, yield: 81.3%) as light yellow oil. $^1$H NMR (400 MHz, $CDCl_3$) δ=7.55 (s, 1H), 4.59 (s, 2H).

2-((2,6-Dichloropyrimidin-4-yl)methyl)isoindoline-1,3-dione (4)

A suspension of 2,4-dichloro-6-(chloromethyl)pyrimidine (2) (1.5 g, 7.60 mmol) and potassium 1,3-dioxoisoindolin-2-ide (3) (1.55 g, 8.36 mmol) in DMF (20 mL) was stirred at 20° C. for 2 hrs. LCMS showed the reaction was completed. The reaction was quenched with water (60 mL) and extracted with EtOAc (40 mL×3). The combined organic layers were washed with brine (50 mL), dried over $Na_2SO_4$, filtered and concentrated under reduced pressure. The residue was purified by R-MPLC to obtain 2-((2,6-dichloropyrimidin-4-yl)methyl)isoindoline-1,3-dione (4) (1.5 g, yield: 64.1%) as yellow solid. $^1$H NMR (400 MHz, DMSO-$d_6$) δ=8.00 (s, 1H), 7.96-7.92 (m, 2H), 7.92-7.87 (m, 2H), 4.92 (s, 2H).

2-((2-Chloro-6-vinylpyrimidin-4-yl)methyl)isoindoline 1,3-dione (5):

A suspension of 2-((2,6-dichloropyrimidin-4-yl)methyl)isoindoline-1,3-dione (4) (1.5 g, 4.87 mmol), potassium;trifluoro(vinyl)boranuide (0.587 g, 4.38 mmol), TEA (0.746 mL, 5.36 mmol) and Pd(dppf)$Cl_2$ (0.249 g, 0.34 mmol) in n-PrOH (80 mL) was stirred at 100° C. for 2 hrs under $N_2$ atmosphere. LCMS showed the reaction was completed. Then the resulting mixture was quenched with saturated aqueous $NH_4Cl$ (50 mL) and extracted with EtOAc (30 mL×3). The combined organic layers were washed with brine (80 mL), dried over $Na_2SO_4$, filtered and concentrated under reduced pressure. The residue was purified by MPLC to obtain 2-((2-chloro-6-vinylpyrimidin-4-yl)methyl)isoindoline-1,3-dione (5) (~80.0% in HNMR, 0.8 g) as yellow solid. $^1$H NMR (400 MHz, DMSO-$d_6$) δ=7.96-7.93 (m, 2H), 7.92-7.88 (m, 2H), 7.72 (s, 1H), 6.82-6.73 (m, 1H), 6.55 (dd, J=1.0, 17.4 Hz, 1H), 5.83 (dd, J=1.0, 10.7 Hz, 1H), 4.90 (s, 2H).

2-Chloro-6-((1,3-dioxoisoindolin-2-yl)methyl)pyrimidine-4-carbaldehyde (6)

To a solution of 2-((2-chloro-6-vinylpyrimidin-4-yl)methyl)isoindoline-1,3-dione (5) (80.0%, 0.7 g, 1.87 mmol) in DCM (20 mL) was bubbled with $O_3$ at −78° C. for 15 min. Then the solution was bubbled with $O_2$ for 10 min at same temperature until the reaction turned colorless. $Me_2S$ (2 mL) was added at −78° C. and the mixture was stirred at 20° C. for 1 hr. TLC showed the reaction was completed. The resulting mixture was quenched with water (20 mL) and extracted with DCM (10 mL×2). The combined organic layers were washed with brine (10 mL), dried over $Na_2SO_4$, filtered and concentrated under reduced pressure. The residue was purified by MPLC to give 2-chloro-6-((1,3-dioxoisoindolin-2-yl)methyl)pyrimidine-4-carbaldehyde (6) (470 mg, yield: 83.4%) as yellow solid. $^1$H NMR (400 MHz, DMSO-$d_6$) δ=9.96 (s, 1H), 7.95 (dd, J=3.2, 5.4 Hz, 2H), 7.82 (dd, J=2.8, 5.6 Hz, 2H), 7.63 (s, 1H), 5.08 (s, 2H).

2-((2-Chloro-6-(hydroxymethyl)pyrimidin-4-yl)methyl)isoindoline-1,3-dione (7)

To a solution of 2-chloro-6-((1,3-dioxoisoindolin-2-yl)methyl)pyrimidine-4-carbaldehyde (6) (490 mg, 1.62 mmol)

in THF (10 mL) was added NaBH$_4$ (24.7 mg, 0.65 mmol) in water (0.5 mL) dropwise at 0° C. The reaction was stirred at same temperature for 15 min. LCMS showed the reaction was completed. The residue was partitioned between EtOAc (10 mL) and water (10 mL). The aqueous layer was extracted with EtOAc (5 mL×3). The combined organic layers were washed with brine (5 mL), dried over Na$_2$SO$_4$, filtered and concentrated under reduced pressure to give 2-((2-chloro-6-(hydroxymethyl)pyrimidin-4-yl)methyl) isoindoline-1,3-dione (7) (430 mg, yield: 78.5%) as light yellow solid. $^1$H NMR (400 MHz, DMSO-d$_6$) δ=7.98-7.94 (m, 2H), 7.93-7.89 (m, 2H), 7.61 (s, 1H), 5.76 (t, J=5.9 Hz, 1H), 4.95 (s, 2H), 4.54 (d, J=5.9 Hz, 2H).

(2-Chloro-6-((1,3-dioxoisoindolin-2-yl)methyl)-pyrimidin-4-yl)methyl methanesulfonate (8)

To a solution of 2-((2-chloro-6-(hydroxymethyl)pyrimidin-4-yl)methyl)isoindoline-1,3-dione (7) (410 mg, 1.35 mmol)) and TEA (0.3 mL, 2.03 mmol) in DCM (10 mL) was added MsCl (170 mg, 1.49 mmol) at 0° C. The reaction was stirred at same temperature for 20 min. TLC showed the reaction was completed. The reaction was quenched with saturated aqueous NH$_4$Cl (10 mL) and extracted with DCM (10 mL×2). The combined organic layers were washed with brine (10 mL), dried over Na$_2$SO$_4$, filtered and concentrated under reduced pressure to give (2-chloro-6-((1,3-dioxoisoindolin-2-yl)methyl)pyrimidin-4-yl)methylmethanesulfonate (8) (500 mg, yield: 97.0%) as yellow oil, which was used for next step directly. $^1$H NMR (400 MHz, CDCl$_3$) δ=7.94 (dd, J=2.8, 5.4 Hz, 2H), 7.83-7.79 (m, 2H), 7.35 (s, 1H), 5.25 (s, 2H), 5.01 (s, 2H), 3.15 (s, 3H).

3-Chloro-5-(2-(4-((2-chloro-6-((1,3-dioxoisoindolin-2-yl)methyl)pyrimidin-4-yl)methoxy) phenyl)propan-2-yl)-2-(2-chloroethoxy)benzonitrile (9)

A suspension of (2-chloro-6-((1,3-dioxoisoindolin-2-yl) methyl)pyrimidin-4-yl)methyl methanesulfonate (8) (500 mg, 1.31 mmol), 3-chloro-2-(2-chloroethoxy)-5-(2-(4-hydroxyphenyl)propan-2-yl)benzonitrile (int H) (436 mg, 1.24 mmol) and Cs$_2$CO$_3$ (853 mg, 2.62 mmol) in DMF (10 mL) was stirred at 20° C. for 16 hrs. Then the mixture was stirred at 40° C. for 0.5 hrs. LCMS showed the reaction was completed. The resulting mixture was quenched with saturated aqueous NH$_4$Cl solution (10 mL) and water (10 mL). The aqueous layer was extracted with EtOAc (10 mL×3). The combined organic layers were washed with brine (10 mL), dried over Na$_2$SO$_4$, filtered and concentrated under reduced pressure. The residue was purified by MPLC to obtain 3-chloro-5-(2-(4-((2-chloro-6-((1,3-dioxoisoindolin-2-yl)methyl)pyrimidin-4-yl)methoxy)phenyl)propan-2-yl)-2-(2-chloroethoxy)benzonitrile (9) (300 mg, 36.0%) as yellow solid. $^1$H NMR (400 MHz, CDCl3) δ=7.92 (dd, J=3.0, 5.4 Hz, 2H), 7.80 (dd, J=3.0, 5.4 Hz, 2H), 7.46-7.43 (m, 2H), 7.33 (d, J=2.4 Hz, 1H), 7.11 (d, J=8.8 Hz, 2H), 6.86 (d, J=8.8 Hz, 2H), 5.11 (s, 2H), 4.99 (s, 2H), 4.43 (t, J=6.2 Hz, 2H), 3.88 (t, J=6.2 Hz, 2H), 1.65 (s, 6H).

N-(4-((4-(2-(3-Chloro-4-(2-chloroethoxy)-5-cyanophenyl)propan-2-yl)phenoxy)methyl)-6-((1,3-dioxoisoindolin-2-yl)methyl)pyrimidin-2-yl)methanesulfonamide (10)

A suspension of N-(4-((4-(2-(3-chloro-4-(2-chloroethoxy)-5-cyanophenyl)propan-2-yl)phenoxy)methyl)-6-((1,3-dioxoisoindolin-2-yl)methyl)pyrimidin-2-yl)methanesulfonamide (10) (180 mg, 0.28 mmol), methanesulfonamide (80.8 mg, 0.85 mmol), Cs$_2$CO$_3$ (184 mg, 0.57 mmol), Xantphos (32.8 mg, 0.056 mmol) and Pd$_2$(dba)$_3$ (25.9 mg, 0.028 mmol) in dioxane (6 mL) was stirred at 100° C. for 2 hrs. TLC showed the reaction was completed. The resulting mixture was cooled down, quenched with saturated aqueous NH$_4$Cl (5 mL) and water (5 mL). The aqueous layer was extracted with EtOAc (5 mL×3). The combined organic layers were washed with brine (5 mL), dried over Na$_2$SO$_4$, filtered and concentrated under reduced pressure. The residue was purified by MPLC to obtain N-(4-((4-(2-(3-chloro-4-(2-chloroethoxy)-5-cyanophenyl)propan-2-yl)phenoxy)methyl)-6-((1,3-dioxoisoindolin-2-yl)methyl)pyrimidin-2-yl)methanesulfonamide (10) (150 mg, yield: 76.3%) as yellow oil. $^1$H NMR (400 MHz, CDCl3) δ=7.92 (dd, J=3.2, 5.4 Hz, 2H), 7.79 (dd, J=3.2, 5.4 Hz, 2H), 7.45 (d, J=2.2 Hz, 1H), 7.34 (d, J=2.6 Hz, 1H), 7.25 (s, 1H), 7.12 (d, J=8.8 Hz, 2H), 6.89 (d, J=8.8 Hz, 2H), 5.05 (s, 2H), 4.96 (s, 2H), 4.43 (t, J=6.0 Hz, 2H), 3.88 (t, J=6.0 Hz, 2H), 3.25 (s, 3H), 1.66 (s, 6H).

N-(4-(Aminomethyl)-6-((4-(2-(3-chloro-4-(2-chloroethoxy)-5-cyanophenyl)propan-2-yl)phenoxy) methyl)pyrimidin-2-yl)methanesulfonamide (A164)

A solution of N-(4-((4-(2-(3-chloro-4-(2-chloroethoxy)-5-cyanophenyl)propan-2-yl)phenoxy)methyl)-6-((1,3-dioxoisoindolin-2-yl)methyl)pyrimidin-2-yl)methanesulfonamide (10) (50 mg, 0.072 mmol) and NH$_2$NH$_2$H$_2$O (80.0%, 0.0218 mL, 0.36 mmol) in MeOH (1 mL) and DCM (0.5 mL) was stirred at 20° C. for 1 hr. LCMS showed the reaction was completed. The resulting mixture was adjusted pH to 4-5 by adding aqueous HCl (1 N) and the residue was purified by prep-HPLC (HCl) to obtain N-(4-(aminomethyl)-6-((4-(2-(3-chloro-4-(2-chloroethoxy)-5-cyanophenyl)propan-2-yl) phenoxy)methyl)pyrimidin-2-yl)methanesulfonamide (A164) (5.54 mg, yield: 13.6%) as white solid. $^1$H NMR (400 MHz, DMSO-d$_6$) δ=11.52 (s, 1H), 8.45 (s, 3H), 7.63 (s, 1H), 7.58 (s, 1H), 7.39 (s, 1H), 7.20 (d, J=8.4 Hz, 2H), 6.98 (d, J=8.8 Hz, 2H), 5.14 (s, 2H), 4.41 (t, J=4.8 Hz, 2H), 4.22 (s, 2H), 3.95 (t, J=4.8 Hz, 2H), 3.42 (s, 3H), 1.63 (s, 6H). LCMS (220 nm): 99.7%. Exact Mass: 563.12; found 564.1.

Example 30: Synthesis of 3-chloro-2-(2-chloroethoxy)-5-(2-(4-((5-(methyl sulfonyl)furan-2-yl) methoxy)phenyl)propan-2-yl)benzonitrile (A168)

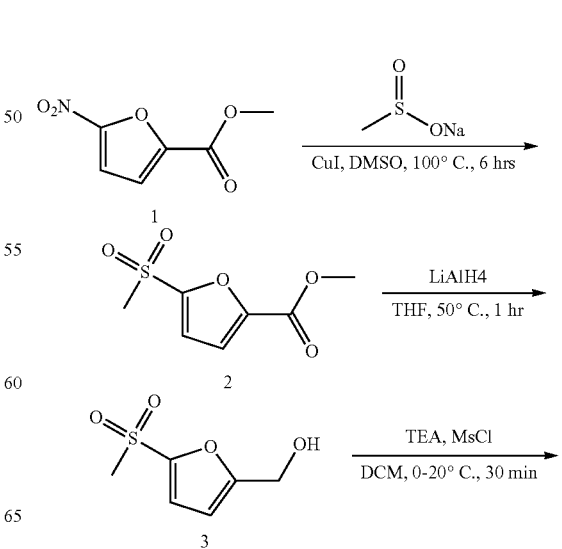

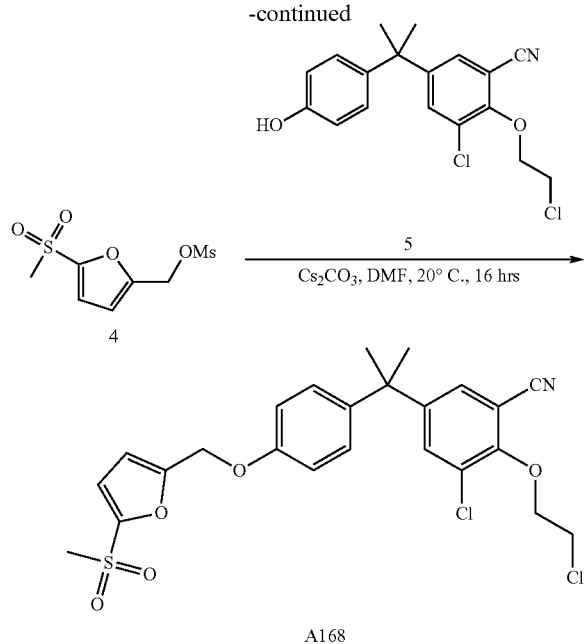

Methyl 5-(methylsulfonyl)furan-2-carboxylate (2)

A suspension of methyl 5-nitrofuran-2-carboxylate (1.0 g, 4.9 mmol), sodium methanesulfonate (115 mg, 9.8 mmol) and CuI (139 mg, 7.3 mmol) in DMSO (30 mL) was stirred at 100° C. for 6 hrs under N$_2$ atmosphere. TLC showed the reaction was completed. The mixture was cooled down. The reaction was diluted with EtOAc (30 mL) and quenched with water (70 mL). The mixture was filtered, and the filtrate was extracted with EtOAc (10 mL). The combined organic layers were washed with brine, dried over Na$_2$SO$_4$, filtered and concentrated under reduced pressure. The residue was purified by MPLC to give methyl 5-(methylsulfonyl)furan-2-carboxylate (0.3 g, yield: 30.1%) as brown oil. $^1$H NMR (400 MHz, CDCl$_3$) δ=7.25 (d, J=3.4 Hz, 1H), 7.22 (d, J=3.4 Hz, 1H), 3.96 (s, 3H), 3.23 (s, 3H).

(5-(Methylsulfonyl)furan-2-yl)methanol (3)

To a solution of methyl 5-(methylsulfonyl)furan-2-carboxylate (0.3 g, 1.5 mmol) in THF (3 mL) was added LiBH$_4$ (128 mg, 5.9 mmol) under N$_2$ atmosphere at 20° C. The mixture was stirred at 50° C. for 1 hr. TLC showed the reaction was completed. The mixture was poured into saturated aqueous NH$_4$Cl (5 mL) and extracted with EtOAc (3 mL×3). The combined organic layers were washed with brine (3 mL×2), dried over Na$_2$SO$_4$, filtered, and concentrated under reduced pressure to give (5-(methylsulfonyl)furan-2-yl)methanol (220 mg, yield: 85.0%) as brown oil. $^1$H NMR (400 MHz, CDCl$_3$) δ=7.14 (d, J=3.4 Hz, 1H), 6.48 (d, J=3.4 Hz, 1H), 4.72 (d, J=6.0 Hz, 2H), 3.17 (s, 3H), 1.97 (t, J=6.4 Hz, 1H).

(5-(Methylsulfonyl)furan-2-yl)methyl methanesulfonate (4)

To a solution of (5-(methylsulfonyl)furan-2-yl)methanol (110 mg, 0.6 mmol) in DCM (2 mL) was added TEA (0.18 g, 1.87 mmol) and MsCl (107 mg, 0.936 mol) at 0° C. under N$_2$ atmosphere. The mixture was stirred at 20° C. for 30 min. TLC showed the reaction was completed. The mixture was poured into saturated aqueous NH$_4$Cl solution (2 mL). The mixture was extracted with DCM (2 mL×3). The combined organic layers were washed with brine (1 mL×2), dried over Na$_2$SO$_4$, filtered, and concentrated under reduced pressure to give (5-(methylsulfonyl)furan-2-yl)methyl methanesulfonate (80.0%, 150 mg, yield: 75.6%) as light yellow solid. $^1$H NMR (400 MHz, CDCl$_3$) δ=7.17 (d, J=3.4 Hz, 1H), 6.70 (d, J=3.4 Hz, 1H), 5.25 (s, 2H), 3.19 (s, 3H), 3.07 (s, 3H)

3-Chloro-2-(2-chloroethoxy)-5-(2-(4-((5-(methylsulfonyl)furan-2-yl)methoxy)phenyl)propan-2-yl)benzonitrile (A168)

To a solution of (5-(methylsulfonyl)furan-2-yl)methyl methanesulfonate (150 mg, 0.6 mmol) in DMF (2.00 mL) was added 3-chloro-2-(2-chloroethoxy)-5-(2-(4-hydroxyphenyl)propan-2-yl)benzonitrile (207 mg, 0.6 mmol) and Cs$_2$CO$_3$ (384 mg, 1.2 mmol) under N$_2$ atmosphere at 20° C. The mixture was stirred at 20° C. for 16 hrs. LCMS showed the reaction was completed. The mixture was poured into H$_2$O (5 mL). The mixture was extracted with EtOAc (3 mL×2). The combined organic layers were washed with brine (2 mL×4), dried over Na$_2$SO$_4$, filtered, and concentrated under reduced pressure. The residue was purified by prep-HPLC (FA) to give 3-chloro-2-(2-chloroethoxy)-5-(2-(4-((5-(methylsulfonyl)furan-2-yl)methoxy)phenyl)propan-2-yl)benzonitrile (A168) (62 mg, yield: 20.7%) as white solid. $^1$H NMR (400 MHz, CDCl$_3$) δ=7.44 (d, J=2.4 Hz, 1H), 7.32 (d, J=2.4 Hz, 1H), 7.17 (d, J=3.2 Hz, 1H), 7.13 (d, J=8.8 Hz, 2H), 6.90 (d, J=8.8 Hz, 2H), 6.59 (d, J=3.2 Hz, 1H), 5.07 (s, 2H), 4.43 (t, J=6.0 Hz, 2H), 3.88 (t, J=6.0 Hz, 2H), 3.18 (s, 3H), 1.65 (s, 6H). LCMS: (220 nm): 32.43%. Exact Mass: 507.1; found 508.1.

Example 31: Synthesis of (R)—N-(4-(1-(4-(2-(3-chloro-4-(2-chloroethoxy)-5-cyanophenyl)propan-2-yl)phenoxy)ethyl)pyrimidin-2-yl)methanesulfonamide (A169) and (S)—N-(4-(1-(4-(2-(3-chloro-4-(2-chloroethoxy)-5-cyanophenyl)propan-2-yl)phenoxy)ethyl)pyrimidin-2-yl)methanesulfonamide (A170)

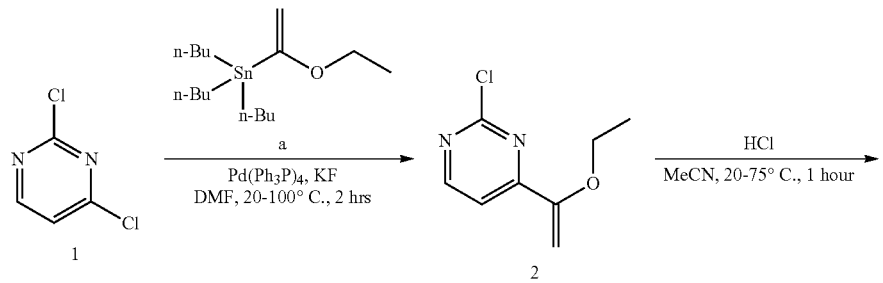

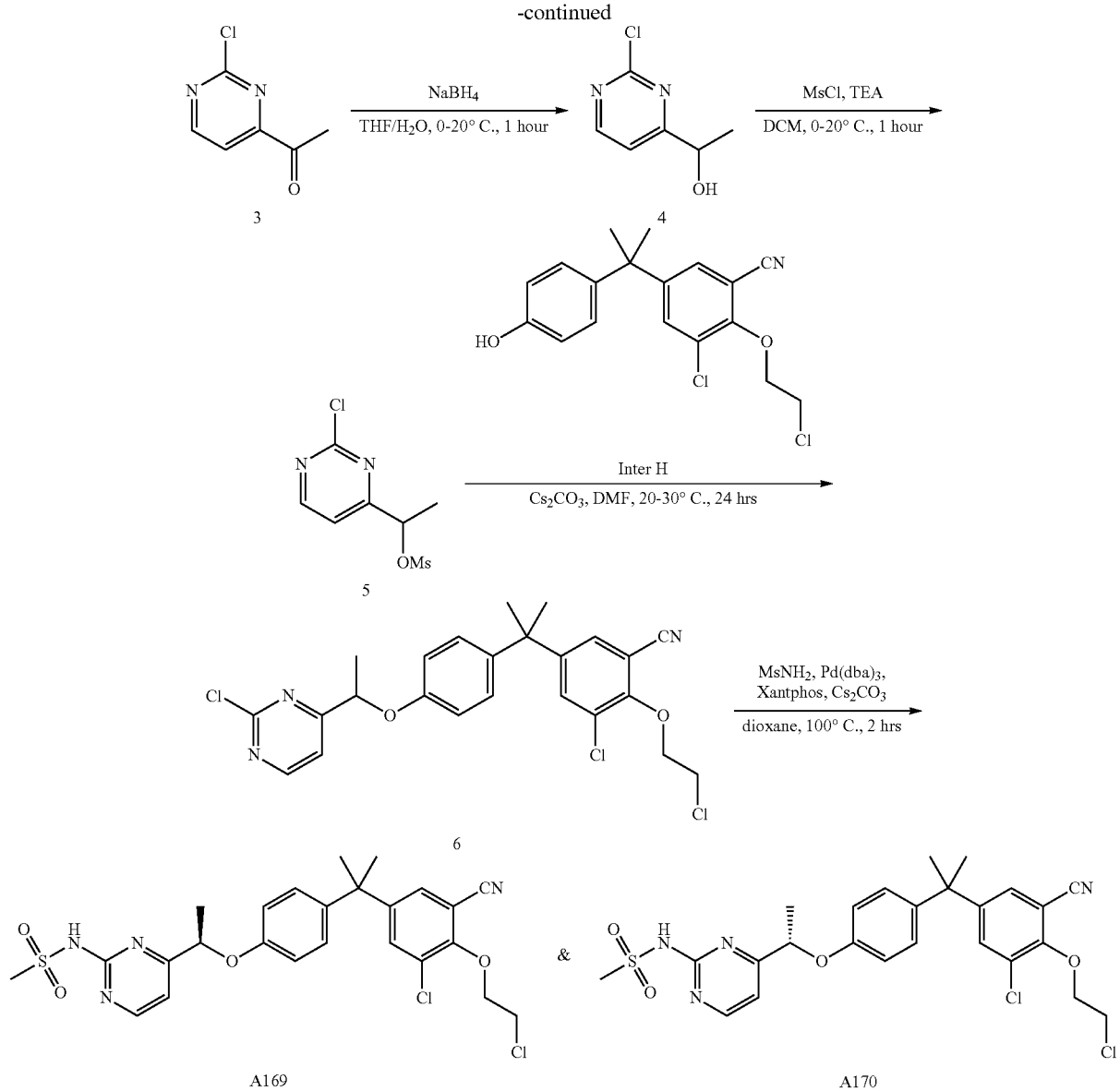

2-Chloro-4-(1-ethoxyvinyl)pyrimidine (2)

To a solution of 2, 4-dichloropyrimidine (1) (20.0 g, 0.134 mol) in DMF (250 mL) was added tributyl(1-ethoxyvinyl) stannane (53.3 g, 0.148 mol), Pd(PPh3)$_4$ (7.7 g, 0.0067 mol) and KF (23.4 g, 0.403 mol) at 20° C. under N2. The mixture was stirred at 100° C. for 2 hrs under $N_2$ atmosphere. TLC showed the reaction was completed. The mixture was poured into water (500 mL). The reaction mixture was filtered and the filter cake was washed with 200 mL water, dried in vacuum to give 2-chloro-4-(1-ethoxyvinyl)pyrimidine (2) (25.0 g, crude) as yellow solid. $^1$H NMR (400 MHz, DMSO-d$_6$) δ ppm 8.79 (d, J=5.0 Hz, 1H), 7.64 (d, J=5.0 Hz, 1H), 5.54 (d, J=2.2 Hz, 1H), 4.72 (d, J=2.2 Hz, 1H), 3.95 (q, J=6.8 Hz, 2H), 1.34 (t, J=7.0 Hz, 3H).

1-(2-Chloropyrimidin-4-yl)ethanone (3)

To a solution of 2-chloro-4-(1-ethoxyvinyl) pyrimidine (2) (25 g, crude) in MeCN (100 mL) was added HCl (10.0%, 100 mL) at 20° C. The mixture was stirred at 75° C. for 1 hour. TLC showed the reaction was completed. The mixture was concentrated to remove MeCN. The mixture was extracted with EtOAc (50 mL×3). The combined organic layers were washed with brine (50 mL), dried over Na$_2$SO$_4$, filtered and concentrated under reduced pressure. The residue was purified by MPLC (petroleum ether:EtOAc=10:1 to 5:1) to give 1-(2-chloropyrimidin-4-yl)ethanone (3) (11.0 g, over two steps yield: 52.3%) as white solid. $^1$H NMR (400 MHz, CDCl$_3$) δ ppm 8.79 (d, J=4.89 Hz, 1H), 7.77 (d, J=4.89 Hz, 1H), 2.61-2.68 (m, 3H).

1-(2-Chloropyrimidin-4-yl)ethanol (4)

To a solution of 1-(2-chloropyrimidin-4-yl)ethanone (3) (11.0 g, 0.0703 mol) in THF (50.0 mL) and H$_2$O (50.0 mL) was added NaBH$_4$ (2.92 g, 0.0773 mol) at 0° C. The mixture was stirred for 1 hour at 20° C. TLC showed the reaction was completed. The mixture was poured into saturated aqueous NH$_4$Cl (100 mL) and extracted with EtOAc (30 mL×3). The combined organic layers were washed with brine (50 mL), dried over Na₂SO₄, filtered and concentrated under reduced pressure. The residue was purified by column (petroleum ether:EtOAc=10:1 to 5:1) to give 1-(2-chloropyrimidin-4-yl)ethanol (4) (5.50 g, yield: 49.4%) as colorless oil. ¹H NMR (400 MHz, CDCl₃) δ ppm 8.62 (d, J=5.0 Hz, 1H), 7.38 (d, J=5.0 Hz, 1H), 4.84-4.94 (m, 1H), 2.98 (d, J=5.0 Hz, 1H), 1.55 (d, J=6.8 Hz, 2H), 1.52-1.53 (m, 1H).

1-(2-Chloropyrimidin-4-yl)ethyl Methanesulfonate (5)

To a solution of 1-(2-chloropyrimidin-4-yl)ethanol (4) (14.0 g, 0.0883 mol) and TEA (24.6 mL, 0.177 mol) in DCM (200 mL) was added methanesulfonyl chloride (15.2 g, 0.132 mol) at 0° C. The mixture was stirred at 20° C. for 1 hr. LCMS showed the reaction was completed. The mixture was poured into water (400 mL) and extracted with DCM (100 mL×3). The combined organic layers were washed with brine (200 mL), dried over Na₂SO₄, filtered and concentrated under reduced pressure to give 1-(2-chloropyrimidin-4-yl)ethyl methanesulfonate (5) (19.0 g, 0.0803 mol, yield: 90.9%) as yellow oil.

3-Chloro-2-(2-chloroethoxy)-5-(2-(4-(1-(2-chloropyrimidin-4-yl)ethoxy)phenyl)propan-2-yl)benzonitrile (6)

To a solution of 3-chloro-2-(2-chloroethoxy)-5-(2-(4-hydroxyphenyl)propan-2-yl)benzonitrile (int H) (20.0 g, 0.0571 mol) in DMF (250 mL) was added 1-(2-chloropyrimidin-4-yl)ethyl methanesulfonate (5) (18.9 g, 0.0799 mol) and Cs₂CO₃ (37.2 g, 0.114 mol) at 20° C. The mixture was stirred at 20° C. for 20 hrs and 30° C. for 4 hrs. TLC showed the reaction was completed. The mixture was poured into saturated aqueous NH₄Cl solution (200 mL) and water (200 mL). The aqueous layer was extracted with EtOAc (300 mL×3). The combined organic layers were washed with brine (300 mL), dried over Na₂SO₄, filtered and concentrated under reduced pressure. The residue was purified by MPLC (petroleum ether:EtOAc=10:1 to 5:1) to give 3-chloro-2-(2-chloroethoxy)-5-(2-(4-(1-(2-chloropyrimidin-4-yl)ethoxy)phenyl)propan-2-yl)benzonitrile (6) (14.8 g, 0.0302 mol, yield: 52.8%) as yellow oil.

¹H NMR (400 MHz, CDCl₃) δ=8.60 (d, J=5.2 Hz, 1H), 7.45-7.41 (m, 2H), 7.29 (d, J=2.4 Hz, 1H), 7.06 (d, J=8.8 Hz, 2H), 6.78 (d, J=8.8 Hz, 2H), 5.33-5.28 (m, 1H), 4.42 (t, J=6.2 Hz, 2H), 3.88 (t, J=6.2 Hz, 2H), 1.69 (d, J=6.6 Hz, 3H), 1.62 (s, 6H).

(R)—N-(4-(1-(4-(2-(3-chloro-4-(2-chloroethoxy)-5-cyanophenyl)propan-2-yl)phenoxy)ethyl)pyrimidin-2-yl)methanesulfonamide (A169) and (S)—N-(4-(1-(4-(2-(3-chloro-4-(2-chloroethoxy)-5-cyanophenyl) propan-2-yl)phenoxy)ethyl)pyrimidin-2-yl) methanesulfonamide (A170)

A suspension of 3-chloro-2-(2-chloroethoxy)-5-(2-(4-(1-(2-chloropyrimidin-4-yl)ethoxy)phenyl)propan-2-yl)benzonitrile (6) (8.00 g, 0.0163 mol), methanesulfonamide (4.65 g, 0.0489 mol), Cs₂CO₃ (10.6 g, 0.0326 mol), Xantphos (1.89 g, 0.00326 mol) and Pd₂(dba)₃ (1.49 g, 0.00163 mol) in dioxane (250 mL) was stirred at 100° C. for 2 hrs under N₂ atmosphere. TLC showed the reaction was completed. The resulting mixture was quenched with saturated aqueous NH₄Cl (100 mL) and water (100 mL). The aqueous layer was extracted with EtOAc (100 mL×3). The combined organic layers were washed with brine (100 mL), dried over Na₂SO₄, filtered and concentrated under reduced pressure. The residue was purified by MPLC to obtain the crude product. The mixture was purified by p-HPLC (FA) and SFC to give (R)—N-(4-(1-(4-(2-(3-chloro-4-(2-chloroethoxy)-5-cyanophenyl)propan-2-yl) phenoxy)ethyl)pyrimidin-2-yl)methanesulfonamide (1.77 g, yield: 19.8%, peak 1 in SFC was named as A169)¹H NMR (400 MHz, CDCl₃) δ=8.56 (d, J=5.1 Hz, 1H), 8.35 (br s, 1H), 7.43 (d, J=2.2 Hz, 1H), 7.29 (d, J=2.1 Hz, 1H), 7.17 (d, J=5.1 Hz, 1H), 7.05 (d, J=8.7 Hz, 2H), 6.79 (d, J=8.8 Hz, 2H), 5.23 (q, J=6.7 Hz, 1H), 4.42 (t, J=6.2 Hz, 2H), 3.88 (t, J=6.2 Hz, 2H), 3.49 (s, 3H), 1.67 (d, J=6.6 Hz, 3H), 1.62 (s, 6H). LCMS (220 nm): 98.4%. Exact Mass: 548.1; found 549.1. (S)—N-(4-(1-(4-(2-(3-chloro-4-(2-chloroethoxy)-5-cyanophenyl)propan-2-yl)phenoxy) ethyl)pyrimidin-2-yl)methanesulfonamide (1.23 g, yield: 13.7%, peak 2 in SFC was named as A170) as light yellow solid. ¹H NMR (400 MHz, CDCl3) δ=8.69 (br s, 1H), 8.58 (d, J=5.3 Hz, 1H), 7.43 (d, J=1.6 Hz, 1H), 7.29 (d, J=1.6 Hz, 1H), 7.17 (d, J=5.1 Hz, 1H), 7.05 (br d, J=8.6 Hz, 2H), 6.79 (d, J=8.7 Hz, 2H), 5.23 (q, J=6.3 Hz, 1H), 4.42 (t, J=6.1 Hz, 2H), 3.88 (t, J=6.1 Hz, 2H), 3.49 (s, 3H), 1.67 (d, J=6.6 Hz, 3H), 1.62 (s, 6H). LCMS (220 nm): 98.6%. Exact Mass: 548.1; found 549.1.

Example 32: Synthesis of N-(2-((4-(2-(3-chloro-4-(2-chloroethoxy)-5-cyanophenyl) propan-2-yl)phenoxy)methyl)pyrimidin-4-yl)methanesulfonamide (A184)

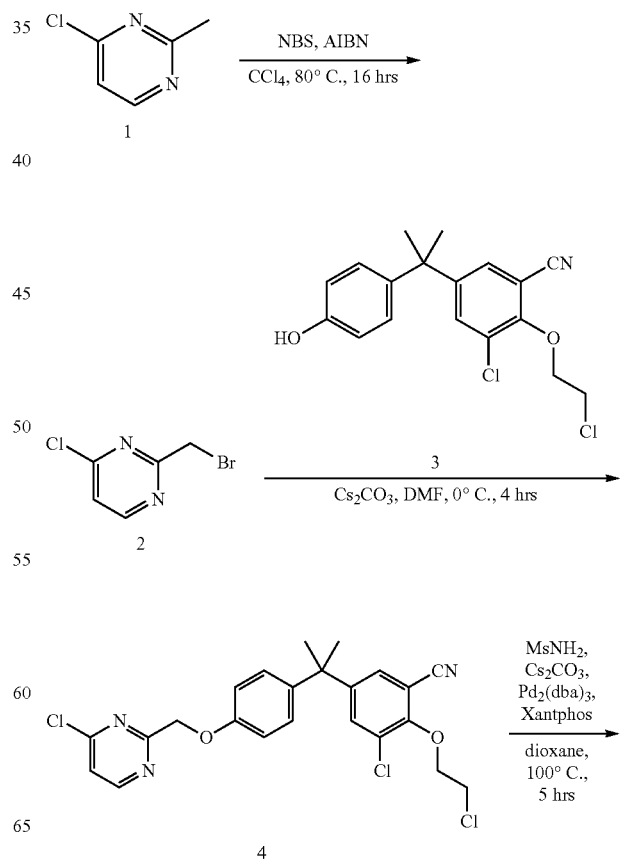

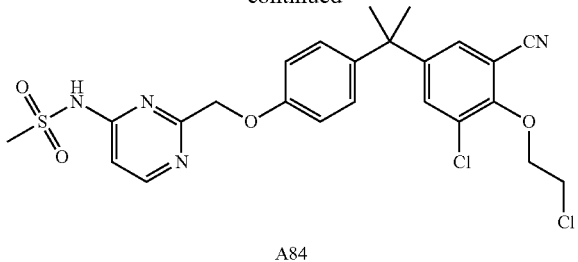

A84

2-(Bromomethyl)-4-chloropyrimidine (2)

To a mixture of 4-chloro-2-methyl-pyrimidine (10.0 g, 7.8 mmol) and AIBN (5.1 g, 31.1 mmol) in CCl$_4$ (100 mL) was added NBS (16.6 g, 93.3 mmol) at 25° C. and the mixture was stirred at 80° C. for 16 hrs. LCMS showed the reaction was completed. The reaction mixture was cooled down to room temperature, poured into H$_2$O (150 mL) and extracted with DCM (80 mL×2). The organic layers were combined and washed with brine (80 mL×2), dried over Na$_2$SO$_4$, filtered and concentrated under reduced pressure. The residue was purified by silica gel column chromatography to give 2-(bromomethyl)-4-chloropyrimidine (1.7 g, yield 10.5%) as yellow oil. $^1$H NMR (400 MHz, CDCl$_3$) δ=8.64 (d, J=5.6 Hz, 1H), 7.29 (d, J=5.2 Hz, 1H), 4.56 (s, 2H).

3-Chloro-2-(2-chloroethoxy)-5-(2-(4-((4-chloropyrimidin-2-yl)methoxy)phenyl)propan-2-yl) Benzonitrile (4)

To a mixture of 3-chloro-2-(2-chloroethoxy)-5-(2-(4-hydroxyphenyl) propan-2-yl)benzonitrile (300 mg, 0.9 mmol) and 2-(bromomethyl)-4-chloropyrimidine (444 mg, 2.1 mmol) in DMF (5 mL) was added NaH (60%, 39 mg, 1.0 mmol) in portions at 0° C. under N2 and the mixture was stirred at 0° C. for 4 hrs. LCMS showed the reaction was completed. The reaction was poured into H$_2$O (10 mL), extracted with EtOAc (8 mL×3). The combined organic layers were washed with brine (12 mL×4), dried over Na$_2$SO$_4$, filtered and concentrated under reduced pressure. The residue was purified by silica gel column chromatography to give 3-chloro-2-(2-chloroethoxy)-5-(2-(4-((4-chloropyrimidin-2-yl) methoxy)phenyl)propan-2-yl) benzonitrile (300 mg, Yield: 73.5%) as yellow oil. $^1$H NMR (400 MHz, CDCl3) δ=8.68 (d, J=5.2 Hz, 1H), 7.43 (d, J=2.4 Hz, 1H), 7.33-7.32 (m, 2H), 7.09 (d, J=8.8 Hz, 2H), 6.94 (d, J=9.2 Hz, 2H), 5.27 (s, 2H), 4.42 (t, J=6.4 Hz, 2H), 3.88 (t, J=6.0 Hz, 2H), 1.64 (s, 6H).

N-(2-((4-(2-(3-Chloro-4-(2-chloroethoxy)-5-cyanophenyl)propan-2-yl)phenoxy)methyl) pyrimidin-4-yl)methanesulfonamide (A184)

To a solution of 3-chloro-2-(2-chloroethoxy)-5-(2-(4-((4-chloropyrimidin-2-yl)methoxy)phenyl)propan-2-yl)benzonitrile (100 mg, 0.2 mmol) in dioxane (2 mL) was added methanesulfonamide (60 mg, 6.3 mmol), Xantphos (24.3 mg, 0.06 mmol), Cs$_2$CO$_3$ (137 mg, 0.4 mmol) and Pd$_2$(dba)$_3$ (19.2 mg, 0.02 mmol) at 100° C. under N$_2$ atmosphere. The mixture was stirred at 100° C. for 5 hrs. LCMS showed the mixture was completed. The reaction was cooled down to room temperature, quenched with water (4 mL) and extracted with DCM (3 mL×3). The combined organic layers were washed with brine (6 mL×2), dried over Na$_2$SO$_4$, filtered, and concentrated under reduced pressure. The crude was purified by silica gel column chromatography and prep-HPLC (FA) to give N-(2-((4-(2-(3-chloro-4-(2-chloroethoxy)-5-cyanophenyl)propan-2-yl)phenoxy)methyl)pyrimidin-4-yl) methanesulfonamide (A184) (8.4 mg, yield: 7.84%) as while solid. 1H NMR (400 MHz, DMSO) δ=8.31-8.36 (m, 1H), 7.63 (d, J=2.4 Hz, 1H), 7.55 (d, J=2.4 Hz, 1H), 7.13 (d, J=8.8 Hz, 1H), 7.13 (d, J=8.8 Hz, 2H), 7.06 (s, 1H), 6.93 (d, J=8.8 Hz, 2H), 5.16 (s, 2H), 4.43 (t, J=6.4 Hz, 2H), 3.88 (t, J=6.0 Hz, 2H), 3.39 (s, 3H), 1.61 (s, 6H). LCMS (220 nm): 98.6%. Exact Mass: 534.10; found 535.1.

Example 33: Synthesis of N-(6-((4-(2-(3-chloro-4-(2-chloroethoxy)-5-cyanophenyl)propan-2-yl)phenoxy)methyl)pyrazin-2-yl)methanesulfonamide (A185)

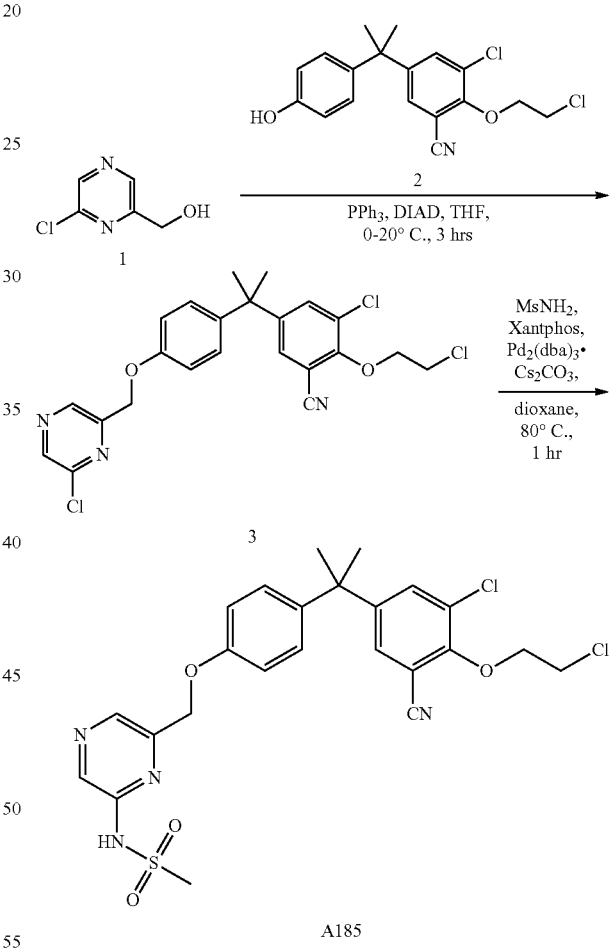

A185

3-Chloro-2-(2-chloroethoxy)-5-(2-(4-((6-chloropyrazin-2-yl)methoxy)phenyl)propan-2-yl)benzonitrile (3)

To a solution of (6-chloropyrazin-2-yl)methanol (1) (0.500 g, 3.46 mmol), 3-chloro-2-(2-chloroethoxy)-5-(1-(4-hydroxyphenyl)-1-methyl-ethyl)benzonitrile (2) (0.606 g, 1.73 mmol) and triphenylphosphane (1.09 g, 4.15 mmol) in THF (10.0 mL) was added DIAD (0.817 mg, 4.15 mmol) at 0° C. and stirred at 25° C. for 3 hrs under N$_2$. TLC showed the reaction was completed. The mixture was poured into water (20 mL) and extracted with EtOAc (15 mL×3), the combined organic layers were washed with brine (5 mL×2), dried over Na$_2$SO$_4$, filtered and concentrated to give the crude product which was purified by silica gel column chromatography to give 3-chloro-2-(2-chloroethoxy)-5-(2-(4-((6-chloropyrazin-2-yl)methoxy)phenyl)propan-2-yl) benzonitrile (3) (purity: 90.0%, 0.400 g, yield: 21.8%) as colorless oil. $^1$H NMR (400 MHz, CDCl$_3$) δ=8.75 (s, 1H), 8.58 (s, 1H), 7.44 (d, J=2.4 Hz, 1H), 7.33 (d, J=2.0 Hz, 1H), 7.13 (d, J=8.8 Hz, 2H), 6.93 (d, J=8.8 Hz, 2H), 5.22 (s, 2H), 4.43 (t, J=6.4 Hz, 2H), 3.88 (t, J=6.0 Hz, 2H), 1.65 (s, 6H).

N-(6-((4-(2-(3-Chloro-4-(2-chloroethoxy)-5-cyanophenyl)propan-2-yl)phenoxy)methyl) Pyrazin-2-yl) methanesulfonamide (A185)

To a solution of 3-chloro-2-(2-chloroethoxy)-5-(2-(4-((6-chloropyrazin-2-yl)methoxy)phenyl)propan-2-yl) benzonitrile (3) (120 mg, 0.25 mmol) in 1,4-Dioxane (3.00 mL) was added methanesulfonamide (71.8 mg, 0.76 mmol), tris (dibenzylideneacetone)dipalladium(0) (14.5 mg, 0.025 mmol), Xantphos (14.6 mg, 0.025 mmol), and Cs2CO3 (0.164 g, 0.50 mmol) at 20° C. under N2. The mixture was stirred at 100° C. for 3 hrs. LCMS showed the reaction was completed. The reaction was poured into water (10 mL) and extracted with EtOAc (3 mL×3). The combined organic layers were washed with brine (10 mL), dried over Na$_2$SO$_4$, filtered and concentrated under reduced pressure. The residue was purified by prep-HPLC (FA) to give N-(6-((4-(2-(3-chloro-4-(2-chloroethoxy)-5-cyanophenyl)propan-2-yl) phenoxy)methyl)pyrazin-2-yl)methanesulfonamide (A185) (38 mg, purity: 96.0%, yield: 27.1%) as white solid. 1H NMR (400 MHz, CDCl$_3$) δ=8.58 (s, 1H), 8.48 (s, 1H), 7.45 (d, J=2.4 Hz, 1H), 7.32 (d, J=2.4 Hz, 1H), 7.14 (d, J=8.8 Hz, 2H), 6.95 (d, J=8.8 Hz, 2H), 5.16 (s, 2H), 4.43 (t, J=6.0 Hz, 2H), 3.88 (t, J=6.4 Hz, 2H), 3.33 (s, 3H), 1.66 (s, 6H). LCMS (220 nm): 96.8%. Exact Mass: 534.09; found 535.0.

Example 34: Synthesis of 3-chloro-2-(2-chloroethoxy)-5-(2-(4-((2-methoxyoxazol-5-yl)methoxy)phenyl)propan-2-yl)benzonitrile (A112)

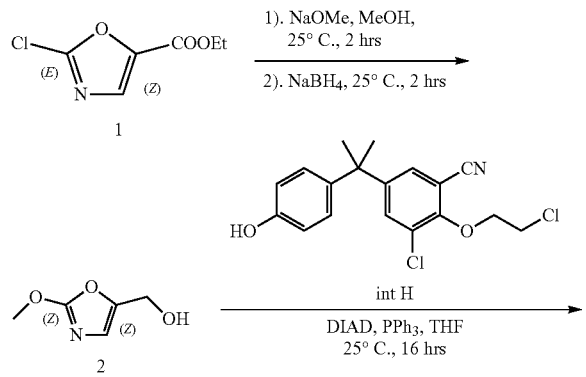

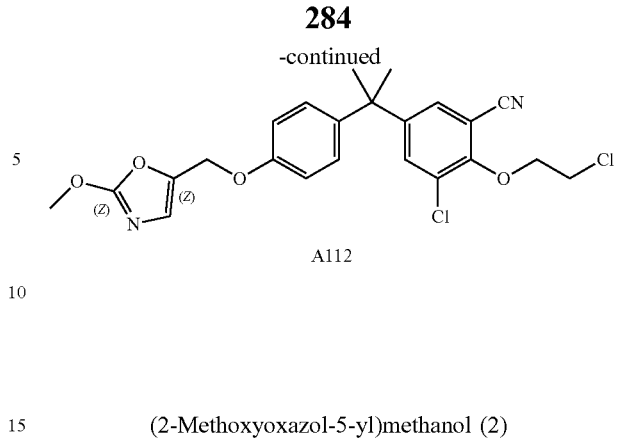

A112

(2-Methoxyoxazol-5-yl)methanol (2)

To a mixture of ethyl 2-chlorooxazole-5-carboxylate (300 mg, 1.7 mmol) in MeOH (5 mL) was added NaOMe (138 mg, 2.6 mmol) at 25° C. and the mixture was stirred at 25° C. for 2 hrs. Then NaBH$_4$ (259 mg, 6.8 mmol) was added to the mixture and stirred at 25° C. for another 2 hrs. TLC showed the starting material was consumed and one new spot was observed. The mixture was filtered and concentrated under reduced pressure. The residue was purified by silica-gel column chromatography to give (2-methoxyoxazol-5-yl)methanol (110 mg, yield: 49.9%) as yellow oil. $^1$H NMR (400 MHz, CD$_3$OD) δ=6.74 (s, 1H), 4.44 (s, 2H), 4.04 (s, 3H).

3-Chloro-2-(2-chloroethoxy)-5-(2-(4-((2-methoxyoxazol-5-yl)methoxy)phenyl)propan-2-yl) benzonitrile (A112)

To a mixture of (2-methoxyoxazol-5-yl)methanol (35 mg, 0.27 mmol), 3-chloro-2-(2-chloroethoxy)-5-(2-(4-hydroxyphenyl)propan-2-yl)benzonitrile (95 mg, 0.27 mmol) and (C$_6$H$_5$)$_3$P (142 mg, 0.5 mmol) in THF (4 mL) was added DIAD (0.1 mL, 0.5 mmol) at 25° C. under N$_2$ atmosphere. The mixture was stirred at 25° C. for 2 hrs. LCMS showed the starting material was consumed and one new peak was observed. The mixture was poured into water (15 mL), extracted with EtOAc (4 mL×2). The combined organic layers were washed with brine (6 mL), dried over Na$_2$SO$_4$, filtered and concentrated under reduced pressure. The residue was purified by prep-HPLC (FA) to give 3-chloro-2-(2-chloroethoxy)-5-(2-(4-((2-methoxyoxazol-5-yl)methoxy) phenyl)propan-2-yl)benzonitrile (A112) (9.05 mg, yield: 7.6%) as yellow oil. $^1$H NMR (400 MHz, CDCl$_3$) δ=7.43 (d, J=2.4 Hz, 1H), 7.33 (d, J=2.4 Hz, 1H), 7.11 (d, J=8.8 Hz, 2H), 6.91 (d, J=2.4 Hz, 2H), 6.85 (s, 1H), 4.92 (s, 2H), 4.42 (t, J=6.4 Hz, 2H), 4.08 (s, 3H), 3.88 (t, J=6.0 Hz, 2H), 1.65 (s, 6H). LCMS (220 nm): 98.1%. Exact Mass: 460.1; found: 461.2.

Characterization of representative compounds synthesized are shown in Table C.

TABLE C

Characterization of compounds

| Compound ID | $^1$HNMR and LCMS |
|---|---|
| A185 | $^1$H NMR (400 MHz, CDCl$_3$): δ = 8.58 (s, 1H), 8.48 (s, 1H), 7.45 (d, J = 2.4 Hz, 1H), 7.32 (d, J = 2.4 Hz, 1H), 7.14 (d, J = 8.8 Hz, 2H), 6.95 (d, J = 8.8 Hz, 2H), 5.16 (s, 2H), 4.43 (t, J = 6.0 Hz, 2H), 3.88 (t, J = 6.4 Hz, 2H), 3.33 |

TABLE C-continued

Characterization of compounds

| Compound ID | $^1$HNMR and LCMS |
| --- | --- |
| | (s, 3H), 1.66 (s, 6H). LCMS (220 nm): 96.8%. Exact Mass: 534.09; found 535.0, 537.0. |
| A189 | $^1$H NMR(400 MHz, CDCl$_3$): δ = 8.67 (s, 1H), 8.53 (br d, J = 6.0 Hz, 1H), 8.02 (br d, J = 6.0 Hz, 1H), 7.87 (d, J = 8.4 Hz, 2H), 7.38 (d, J = 8.4 Hz, 2H), 7.13 (s, 2H), 4.28 (t, J = 6.0 Hz, 2H), 3.87 (t, J = 6.8 Hz, 2H), 3.42 (s, 3H), 1.69 (s, 6H). LCMS (220 nm): 95.2%. Exact Mass: 556.1; found 557.0/559.0. |
| A190 | $^1$H NMR (400 MHz, CDCl$_3$): δ = 7.51 (br s, 1H), 7.44 (d, J = 2.0 Hz, 1H), 7.31 (d, J = 2.4 Hz, 1H), 7.10 (d, J = 8.8 Hz, 2H), 6.88 (d, J = 8.8 Hz, 2H), 5.04 (s, 2H), 4.84 (s, 2H), 4.43 (t, J = 6.4 Hz, 2H), 4.03 (t, J = 6.0 Hz, 2H), 3.88 (t, J = 2.0 Hz, 2H), 3.45 (s, 3H), 2.95 (t, J = 5.6 Hz, 2H), 1.64 (s, 6H). LCMS (220 nm): 97.8%. Exact Mass: 590.1; found: 591.1/593.1. |
| A191 | $^1$H NMR (400 MHz, CDCl$_3$) δ = 9.34 (br s, 1H), 7.62 (d, J = 2.2 Hz, 1H), 7.57 (d, J = 2.2 Hz, 1H), 7.18 (d, J = 8.8 Hz, 2H), 6.96 (d, J = 8.8 Hz, 2H), 5.17 (s, 2H), 4.41 (t, J = 7.2 Hz, 2H), 4.34 (s, 2H), 3.95 (t, J = 7.2 Hz, 2H), 3.51-3.42 (m, 2H), 3.30 (s, 3H), 3.03 (br s, 2H), 1.63 (s, 6H). LCMS (220 nm): 97.6%. Exact Mass: 589.1; found: 590.1/592.2. |
| A192 | $^1$H NMR (400 MHz, DMSO-d6) δ = 7.61 (d, J = 2.2 Hz, 1H), 7.56 (d, J = 2.2 Hz, 1H), 7.40 (s, 1H), 7.17 (d, J = 8.8 Hz, 2H), 6.96 (d, J = 8.8 Hz, 2H), 5.14 (s, 2H), 4.39 (t, J = 4.8 Hz, 2H), 4.28 (s, 2H), 3.94 (t, J = 4.8 Hz, 2H), 1.62 (s, 6H). LCMS (220 nm): 99.7%. Exact Mass: 459.1; found: 460.1/462.1. |
| A193 | $^1$H NMR (400 MHz, CDCl3) δ = 7.46 (d, J = 2.0 Hz, 1H), 7.31 (d, J = 2.4 Hz, 1H), 7.13 (d, J = 8.4 Hz, 2H), 6.95-6.89 (m, 3H), 6.32 (d, J = 4.0 Hz, 1H), 5.00 (s, 2H), 4.43 (t, J = 6.4 Hz, 2H), 3.94 (s, 3H), 3.88 (t, J = 6.4 Hz, 2H), 3.14 (s, 3H), 1.66 (s, 6H). LCMS (220 nm): 99.3%. Exact Mass: 520.10; found 521.1, 523.1. |
| A194 | $^1$H NMR (400 MHz, CDCl$_3$) δ = 7.73 (t, J = 7.6 Hz, 1H), 7.45 (d, J = 2.4 Hz, 1H), 7.32 (d, J = 2.4 Hz, 1H), 7.24 (d, J = 7.6 Hz, 1H), 7.14-7.10 (m, 3H), 6.92 (d, J = 8.8 Hz, 2H), 5.09 (s, 2H), 4.42 (t, J = 6.0 Hz, 2H), 3.88 (t, J = 6.8 Hz, 2H), 3.22 (s, 3H), 1.65 (s, 6H). LCMS (220 nm): 94.7%. Exact Mass: 533.1; found 534.1/536.1. |
| A195 | $^1$H NMR (400 MHz, CDCl3) δ = 8.17 (d, J = 5.6 Hz, 1H), 7.44 (d, J = 2.4 Hz, 1H), 7.37 (s, 1H), 7.32 (d, J = 2.4 Hz, 1H), 7.12 (d, J = 8.8 Hz, 2H), 6.98 (d, J = 5.6 Hz, 1H), 6.89 (d, J = 8.8 Hz, 2H), 5.08 (s, 2H), 4.43 (t, J = 6.4 Hz, 2H), 3.88 (t, J = 6.4 Hz, 2H), 3.12 (s, 3H), 1.65 (s, 6H) LCMS: (220 nm): 97.5%. Exact Mass: 533.1; found 534.1/536.1 |
| A196 | $^1$H NMR (400 MHz, CDCl3) δ = 8.48 (br s, 1H), 7.44 (d, J = 2.8 Hz, 1H), 7.31 (d, J = 2.4 Hz, 1H), 7.23 (s, 1H), 7.12 (d, J = 8.8 Hz, 2H), 7.09 (br s, 1H), 6.93 (d, J = 8.8 Hz, 2H), 6.79 (br s, 1H), 5.17 (s, 2H), 4.42 (t, J = 6.0 Hz, 2H), 3.88 (t, J = 6.0 Hz, 2H), 3.12 (s, 3H), 1.65 (s, 6H). LCMS (220 nm): 97% Exact Mass: 533; found 534.1/536.1. |
| A197 | $^1$H NMR (400 MHz, CDCl3) δ = 8.51 (br d, J = 4.6 Hz, 2H), 7.45 (s, 1H), 7.32 (s, 1H), 7.13 (br d, J = 8.6 Hz, 2H), 6.94 (br d, J = 8.2 Hz, 2H), 5.21 (s, 2H), 4.43 (t, J = 6.2 Hz, 2H), 3.88 (t, J = 6.2 Hz, 2H), 3.33 (s, 3H), 1.65 (s, 6H). LCMS: (220 nm): 95.8 Exact Mass: 534.1; found 535.1/537.1 |
| A198 | $^1$H NMR (400 MHz, CDCl3) δ = 8.67 (d, J = 5.0 Hz, 1H), 7.45 (d, J = 2.4 Hz, 1H), 7.34 (d, J = 5.2 Hz, 1H), 7.32 (d, J = 2.4 Hz, 1H), 7.12 (d, J = 8.8 Hz, 2H), 6.90 (d, J = 8.8 Hz, 2H), 5.13 (s, 2H), 4.43 (t, J = 6.2 Hz, 2H), 4.30-4.26 (m, 2H), 3.88 (t, J = 6.2 Hz, 2H), 3.36-3.31 (m, 2H), 2.34 (quin, J = 6.2 Hz, 2H), 1.85 (td, J = 5.8, 11.7 Hz, 2H), 1.65 (s, 6H) LCMS: (220 nm): 90.5%. Exact Mass: 574.1; found 575.2/9,577.2. |
| A199 | $^1$H NMR (400 MHz, CDCl3) δ = 8.59 (d, J = 5.0 Hz, 1H), 7.44 (s, 1H), 7.33 (s, 1H), 7.21 (d, J = 5.0 Hz, 1H), 7.11 (br d, J = 8.4 Hz, 2H), 6.89 (br d, J = 8.4 Hz, 2H), 5.11 (s, 2H), 4.43 (t, J = 6.4 Hz, 2H), 4.07 (t, J = 6.4 Hz, 2H), 3.88 (t, J = 6.4 Hz, 2H), 3.48 (t, J = 7.2 Hz, 2H), 2.52 (br t, J = 6.8 Hz, 2H), 1.65 (s, 6H) LCMS: (220 nm): 95.2%. Exact Mass: 560.1; found 561.1/563.1 |
| A200 | $^1$H NMR (400 MHz, CDCl3) δ = 8.88 (d, J = 5.2 Hz, 1H), 7.82 (d, J = 5.2 Hz, 1H), 7.45 (d, J = 2.4 Hz, 1H), 7.30 (d, J = 2.4 Hz, 1H), 7.14 (d, J = 6.8 Hz, 2H), 6.90 (d, J = 8.8 Hz, 2H), 5.21 (s, 2H), 4.43 (t, J = 6.0 Hz, 2H), 3.88 (t, J = 6.4 Hz, 2H), 1.66 (s, 6H). LCMS (220 nm): 91.1%. Exact Mass: 466.1; found 467.0, 469.0. |
| A201 | $^1$H NMR (400 MHz, CDCl$_3$) δ = 8.80 (brs, 1H), 8.64 (d, J = 5.2 Hz, 1H), 7.45 (d, J = 2.4 Hz, 1H), 7.32 (d, J = 2.4 Hz, 1H), 7.29 (d, J = 5.2 Hz, 1H), 5.11 (s, 2H), 4.43 (t, J = 6.4 Hz, 2H), 3.88 (t, J = 5.6 Hz, 2H), 3.47 (s, 3H), 1.65 (s, 6H) LCMS: (220 nm): 98.53%. Exact Mass: 538.1; found 539.2/541.1 |
| A202 | $^1$H NMR (400 MHz, CDCl$_3$) δ = 7.66 (br s, 1H), 7.44 (d, J = 2.4 Hz, 1H), 7.31 (d, J = 2.4 Hz, 1H), 7.10 (d, J = 8.8 Hz, 2H), 6.88 (d, J = 8.8 Hz, 2H), 5.08 (s, 2H), 4.43 (t, J = 6.0 Hz, 2H), 3.88 (t, J = 6.4 Hz, 2H), 3.45 (s, 3H), 3.02-2.93 (m, 4H), 2.16-2.12 (m, 2H), 1.64 (s, 6H). LCMS (220 nm): 92.0%. Exact Mass: 574.1; found 575.1/577.1 |
| A203 | $^1$H NMR (400 MHz, CDCl$_3$) δ = 8.56 (s, 1H), 8.48 (br s, 1H), 7.45 (d, J = 2.4 Hz, 1H), 7.34 (d, J = 1.6 Hz, 1H), 7.16-7.11 (m, 2H), 7.10-7.05 (m, 2H), 5.70-5.59 (m, 1H), 4.43 (t, J = 6.4 Hz, 2H), 3.89 (t, J = 6.4 Hz, 2H), 3.31 (s, 3H), 3.19-3.07 (m, 1H), 2.96-2.85 (m, 1H), 2.72-2.59 (m, 1H), 2.41-2.27 (m, 1H), 1.66 (s, 6H) LCMS: (220 nm): 97.7% Exact Mass: 560.1; found 561.1./563.1 |

TABLE C-continued

Characterization of compounds

| Compound ID | $^1$HNMR and LCMS |
|---|---|
| A204 | $^1$H NMR (400 MHz, CDCl3) δ = 10.14 (br s, 1H), 8.74 (s, 2H), 7.45 (d, J = 2.2 Hz, 1H), 7.33 (d, J = 2.2 Hz, 1H), 7.14 (d, J = 8.8 Hz, 2H), 6.91 (d, J = 8.8 Hz, 2H), 5.02 (s, 2H), 4.43 (t, J = 6.4 Hz, 2H), 3.88 (t, J = 6.4 Hz, 2H), 3.49 (s, 3H), 1.66 (s, 6H) LCMS: (220 nm): 98.6% Exact Mass: 534.1; found 535.0/537.0 |
| A205 | $^1$H NMR (400 MHz, CDCl$_3$) δ = 8.61 (d, J = 5.2 Hz, 1H), 7.27-7.29 (m, 1H), 7.17-7.19 (m, 1H),7.13-7.14 (m, 1H), 7.12 (d, J = 8.8 Hz, 1H), 6.89 (d, J = 8.8 Hz, 1H), 5.10 (s, 2H), 4.48 (t, J = 6.0 Hz, 2H), 3.83 (t, J = 5.6 Hz, 2H), 3.48 (s, 3H), 1.64 (s, 6H) LCMS: (220 nm): 99.74%. Exact Mass: 518.1; found 519.1/521.1 |
| A206 | $^1$H NMR (400 MHz, CDCl$_3$) δ = 8.62 (d, J = 5.2 Hz, 1H),8.60 (brs, 1H), 7.29 (d, J = 5.2 Hz, 1H), 7.15 (d, J = 8.8 Hz, 1H), 7.02 (d, J = 2.0 Hz, 1H), 6.89 (d, J = 9.2 Hz, 1H), 6.86-6.83 (dd, J = 12.4 Hz, 2.0 Hz, 1H), 5.10 (s, 2H), 4.31 (t, J = 6.0 Hz, 2H), 3.81 (t, J = 6.0 Hz, 2H), 3.47 (s, 3H), 1.63 (s, 6H) LCMS: (220 nm): 99.51%. Exact Mass: 527.1; found 528.0/529.9 |
| A207 | $^1$H NMR (400 MHz, CDCl$_3$) δ = 7.63 (d, J = 0.8 Hz, 1H), 7.46 (d, J = 2.4 Hz, 1H), 7.30 (d, J = 2.4 Hz, 1H), 7.16-7.07 (m, 3H), 6.89 (d, J = 8.8 Hz, 2H), 5.01-4.96 (m, 1H), 4.96 (br s, 1H), 4.95 (s, 2H), 4.43 (t, J = 6.4 Hz, 2H), 3.88 (t, J = 6.4 Hz, 2H), 1.65 (s, 6H) LCMS: (220 nm): 99.2% Exact Mass: 508.1; found 509.0/511.0 |
| A208 | $^1$H NMR (400 MHz, CDCl$_3$) δ = 7.71 (s, 1H), 7.45 (d, J = 2.4 Hz, 1H), 7.32 (d, J = 2.2 Hz, 1H), 7.26 (br s, 1H), 7.13 (d, J = 8.8 Hz, 2H), 6.89 (d, J = 8.8 Hz, 2H), 4.96 (s, 2H), 4.43 (t, J = 6.2 Hz, 2H), 3.88 (t, J = 6.2 Hz, 2H), 3.18 (s, 3H), 1.66 (s, 6H) LCMS: (220 nm): 99.7% Exact Mass: 507.1; found 508.1/510.1 |
| A209 | $^1$H NMR (400 MHz, CDCl3) δ = 8.53 (d, J = 4.8 Hz, 1H), 7.44 (d, J = 2.4 Hz, 1H), 7.32 (d, J = 2.4 Hz, 1H), 7.21 (d, J = 5.2 Hz, 1H), 7.11 (d, J = 8.8 Hz, 2H), 6.89 (d, J = 8.8 Hz, 2H), 5.09 (s, 2H), 4.42 (t, J = 6.0 Hz, 2H), 3.88 (t, J = 6.0 Hz, 2H), 2.59 (s, 3H), 1.65 (s, 6H). |
| A210 | $^1$H NMR (400 MHz, CDCl$_3$) δ = 7.79 (s, 1H), 7.70 (s, 1H), 7.47 (d, J = 1.8 Hz, 1H), 7.34 (d, J = 1.8 Hz, 1H), 7.14 (d, J = 8.8 Hz, 2H), 6.91 (d, J = 8.6 Hz, 2H), 5.07 (s, 2H), 4.44 (t, J = 6.2 Hz, 2H), 3.90 (t, J = 6.2 Hz, 2H), 3.23 (s, 3H), 1.67 (s, 6H) LCMS: (220 nm): 99.4% Exact Mass: 523.1; found 524.1/526.1 |
| A211 | $^1$H NMR (400 MHz, CDCl$_3$) δ = 7.72 (s, 1H), 7.58 (s, 1H), 7.46 (d, J = 2.2 Hz, 1H), 7.31 (d, J = 2.2 Hz, 1H), 7.12 (d, J = 8.8 Hz, 2H), 6.89 (d, J = 8.8 Hz, 2H), 5.03 (s, 2H), 4.99 (s, 2H), 4.43 (t, J = 6.2 Hz, 2H), 3.88 (t, J = 6.2 Hz, 2H), 1.65 (s, 6H). LCMS: (220 nm): 99.4% Exact Mass: 524.0; found 524.9/522.8 |

Biological Assays

Example 35: Activity of Exemplary Compounds in Cellular Assays

The PSA (6.1 kb)-luciferase reporter contains functional AREs (androgen response elements) to which AR binds in response to androgen to induce luciferase activity. LNCaP cells were transiently transfected with the PSA (6.1 kb)-luciferase reporter for 24 h, and then pretreated with vehicle (DMSO) or indicated concentration of representative compounds for one hour prior to the addition of synthetic androgen, R1881 (1 nM). After 24 h of incubation with R1881, the cells were harvested, and relative luciferase activities were determined (FIG. 1). To determine the IC$_{50}$, treatments were normalized to vehicle control activity induced by R1881 (Table 1A).

Luciferase Assay:

Cells were lysed using Passive Lysis Buffer (Promega) and then collected into V-bottom 96-well tissue culture plates. Lysates were centrifuged at 4° C. for 5 minutes at 3000 rpm. To measure luminescence of LNCaP cell lysates the Firefly Luciferase Assay System (Promega) was employed, according to manufacturer's protocol. Relative luminescence units (RLU) in cell lysates were detected for 10 seconds using Promega GloMax-Multi Detection Luminometer (Promega). Values were normalized to protein content. GraphPad Prism graphing software was used to calculate IC$_{50}$ values.

Statistical analyses were performed using GraphPad Prism (Version 6.01 for Windows; La Jolla, Calif., USA). Comparisons between treatment and control groups were compared using Two-Way ANOVA with post-hoc Dunnett's and Tukey's tests. Differences were considered statistically significant at P values less than 0.05.

Table 1A shows IC$_{50}$ ranges of Compounds from Tables A and B from the luciferase assay. FIG. 1 shows dose dependent curve of representative compounds shown in Table 1A. Compound X and EPI-002 have the following structures:

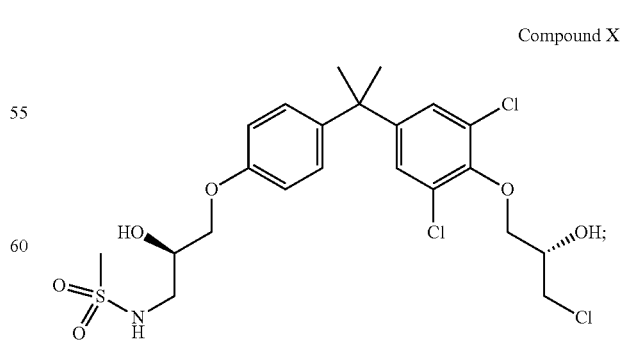

Compound X

EPI-002

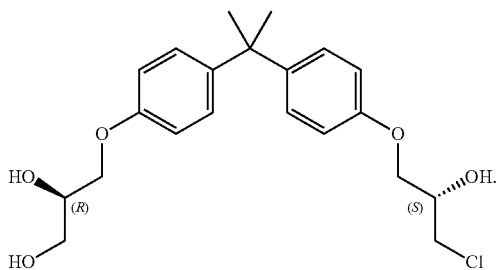

The PSA-Luc % inhibition $IC_{50}$ values of the representative compounds are shown in Table 1B.

LBD-Expressing Reporter Assay:

To assess if the representative compounds (Compounds A13, A28, A38, A74, A93, and A109) compete with ligand (agonist) for the ligand-binding domain (LBD) of steroid hormone receptors (which would be off-target), the GeneBLAzer assay was employed (Thermo Fisher). This assay uses cells that stably express a chimera fusion protein comprising the LBD of a steroid hormone receptor fused to the DNA-binding domain (DBD) of GAL4 along with beta-lactamase reporter under transcriptional control of an upstream activator sequence (UAS). When agonist binds to the LBD of the GAL4 (DBD)-steroid hormone (LBD) chimera fusion protein, the protein binds to the UAS, resulting in expression of beta-lactamase. LBDs of androgen receptor (AR), progesterone receptor-beta (PRβ), glucocorticoid receptor (GR), estrogen receptor-α (ERα), and estrogen receptor-β (ERβ) were tested and $IC_{50}$s calculated for inhibiting maximal activity attained with agonist. See Table 1C.

Figure 7:
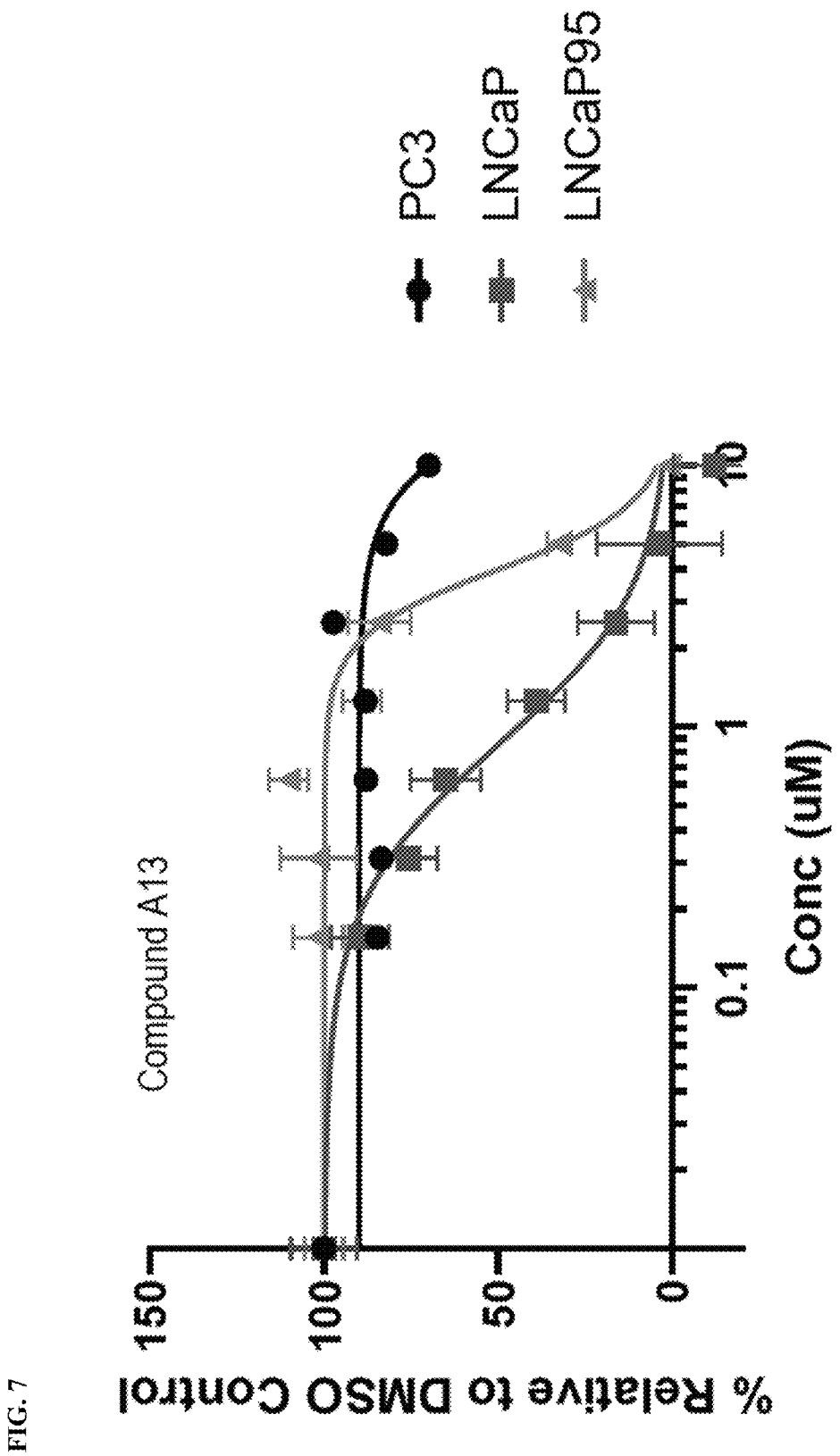
FIG. 7 shows concentration dependent effects on cell proliferation of LNCaP, PC3, and LNCaP95 cells treated with Compound A13.

Cell Proliferation Assay:

Cell proliferation/viability was measured in LNCaP and PC3 cells with Alamar blue, and proliferation was measured in LN-CaP95 cells with BrdU incorporation. In LNCaP cells, AR specific proliferation is calculated by measuring the difference between control cells treated with or without 0.1 nM R1881. See Table 1D and FIG. 7.

Figure 2A:
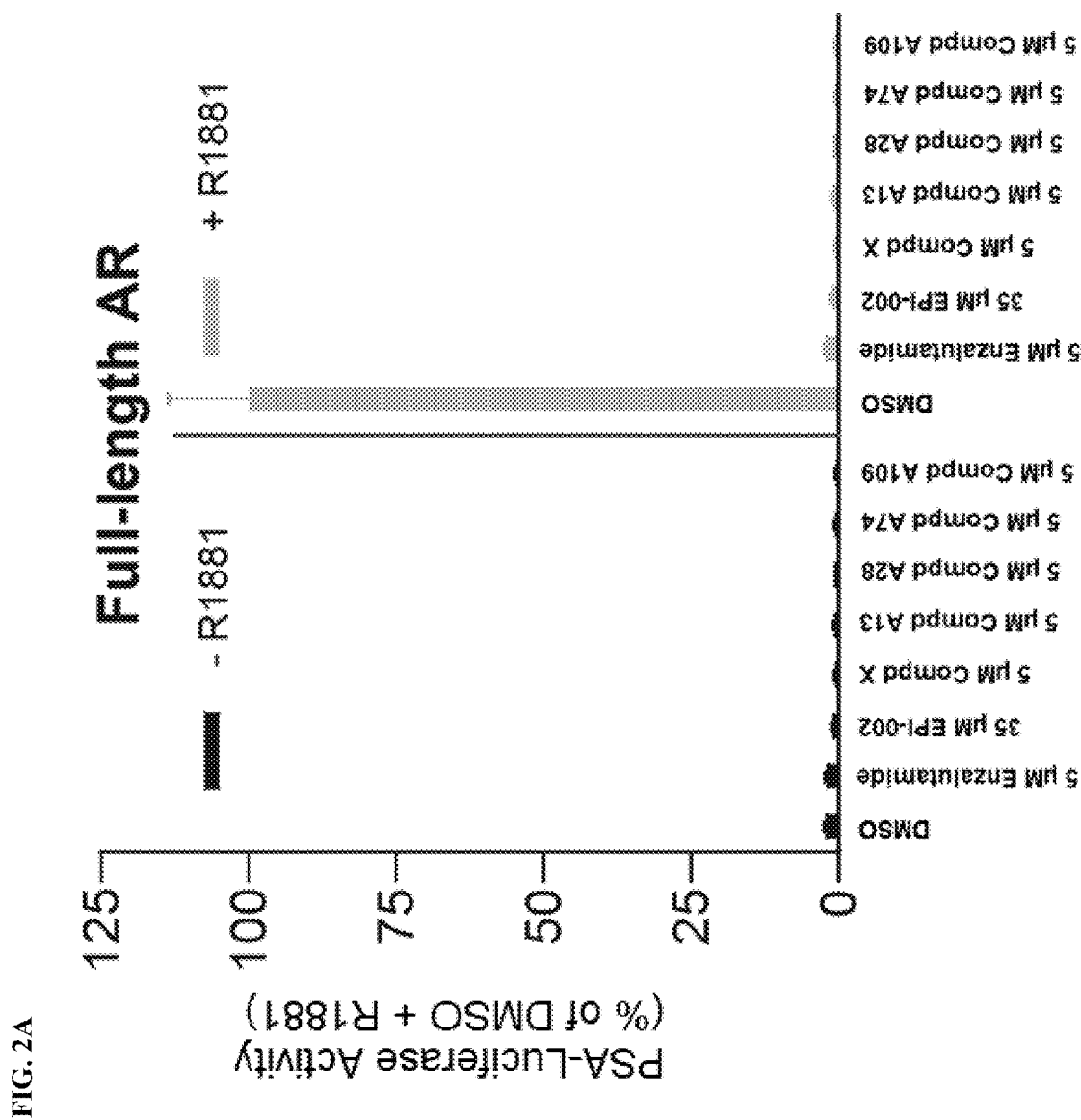
FIG. 2A shows the percent PSA-luciferase activities of representative compounds in LNCaP cells transiently transfected with the PSA(6.1 kb)-luciferase reporter and treated without or with R1881.
Figure 2B:
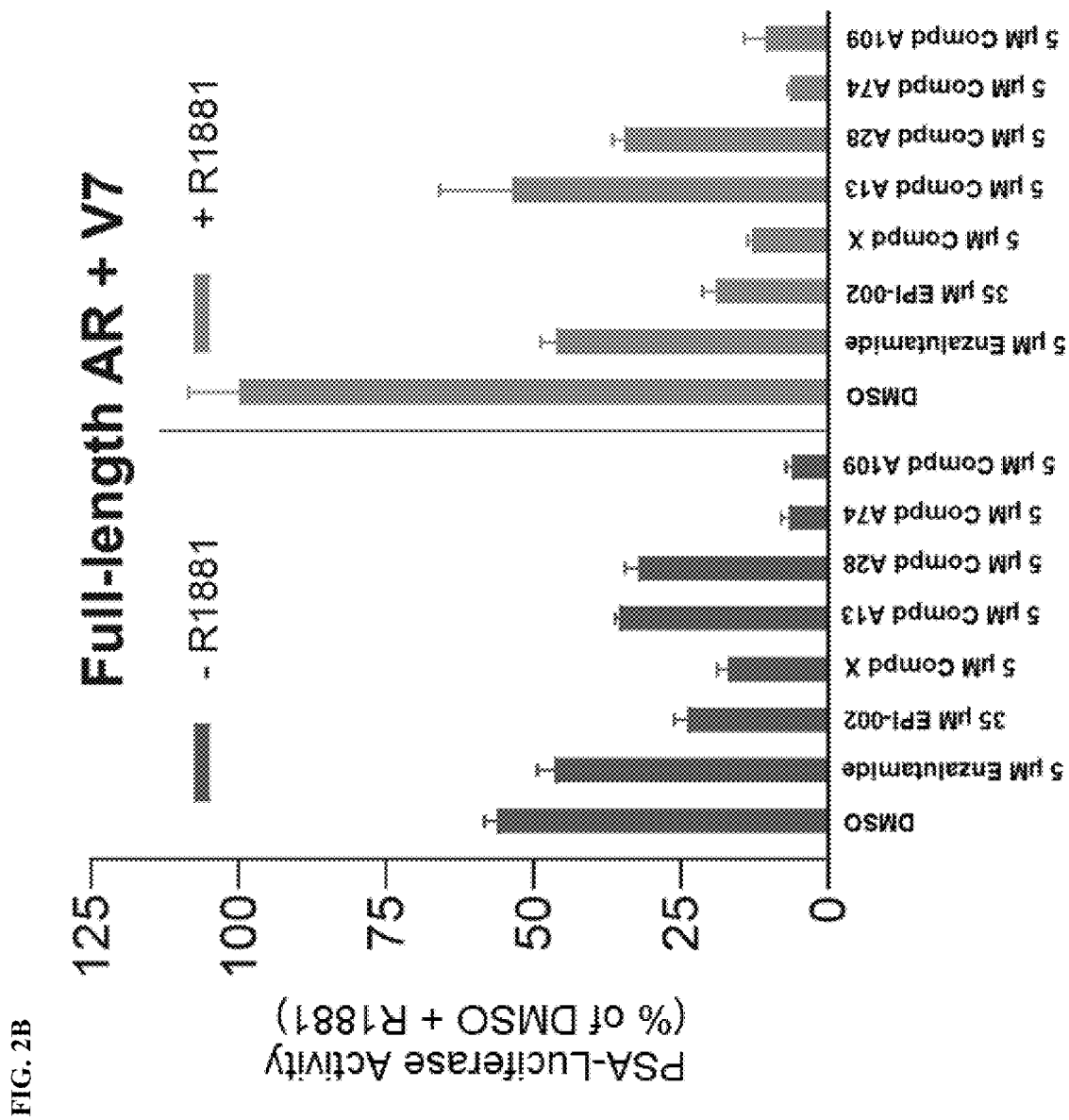
FIG. 2B shows the percent PSA-luciferase activities of representative compounds in LNCaP cells co-transfected with an expression vector for AR-V7 and the PSA-luciferase reporter and treated without or with R1881.

AR-V7 Transcriptional Activity Assay:

Transcriptional activity of AR-V7 was measured in LNCaP cells transiently cotransfected with an expression vector for AR-V7 and the PSA-luciferase reporter and incubated with the representative compounds in the presence or absence of synthetic androgen, R1881. As a control, LNCaP cells were transfected with pcDNA plasmid (absent of AR-V7 insert) with or without R1881. See FIGS. 2A-2B.

The results from this Example supports that the compounds of the present disclosure are selective to AR NTD.

TABLE 1A $IC_{50}$ Ranges of Various Compounds in Androgen-Induced PSA-Luciferase Assay

| Compound ID | PSA-Luc $IC_{50}$ Range |
| --- | --- |
| A1 | N/A |
| A2 | N/A |
| A3 | ** |
| A4 | N/A |
| A5 | ** |
| A6 | N/A |
| A7 | * |
| A8 | N/A |

TABLE 1A-continued $IC_{50}$ Ranges of Various Compounds in Androgen-Induced PSA-Luciferase Assay

| Compound ID | PSA-Luc $IC_{50}$ Range |
| --- | --- |
| A9 | N/A |
| A10 | N/A |
| A11 | N/A |
| A12 | N/A |
| A13 | ** |
| A14 | N/A |
| A15 | N/A |
| A16 | N/A |
| A17 | ** |
| A18 | * |
| A19 | N/A |
| A20 | N/A |
| A21 | N/A |
| A22 | * |
| A23 | * |
| A24 | ** |
| A25 | * |
| A26 | N/A |
| A27 | * |
| A28 | *** |
| A29 | *** |
| A30 | ** |
| A31 | *** |
| A32 | * |
| A33 | N/A |
| A34 | ** |
| A35 | ** |
| A36 | N/A |
| A37 | N/A |
| A38 | ** |
| A39 | N/A |
| A40 | ** |
| A41 | * |
| A42 | ** |
| A43 | N/A |
| A44 | N/A |
| A45 | ** |
| A46 | N/A |
| A47 | N/A |
| A48 | N/A |
| A49 | * |
| A50 | ** |
| A51 | N/A |
| A52 | * |
| A53 | * |
| A54 | ** |
| A55 | N/A |
| A56 | ** |
| A57 | *** |
| A58 | * |
| A59 | N/A |
| A60 | N/A |
| A61 | N/A |
| A62 | * |
| A63 | ** |
| A64 | * |
| A65 | ** |
| A66 | ** |
| A67 | N/A |
| A68 | *** |
| A69 | N/A |
| A70 | *** |
| A71 | ** |
| A72 | N/A |
| A73 | ** |
| A74 | ** |
| A75 | ** |
| A76 | ** |
| A77 | ** |
| A78 | ** |
| A79 | *** |
| A80 | *** |
| A81 | *** |
| A82 | N/A |

TABLE 1A-continued

IC$_{50}$ Ranges of Various Compounds in Androgen-Induced PSA-Luciferase Assay

| Compound ID | PSA-Luc IC$_{50}$ Range |
|---|---|
| A83 | N/A |
| A84 | N/A |
| A85 | *** |
| A86 | *** |
| A87 | ** |
| A88 | ** |
| A89 | ** |
| A90 | ** |
| A91 | ** |
| A92 | *** |
| A93 | *** |
| A94 | ** |
| A95 | * |
| A96 | * |
| A97 | *** |
| A98 | ** |
| A99 | ** |
| A100 | *** |
| A101 | ** |
| A102 | *** |
| A103 | *** |
| A104 | *** |
| A105 | * |
| A106 | *** |
| A107 | * |
| A108 | ** |
| A109 | ** |
| A110 | N/A |
| A111 | *** |
| A112 | *** |
| A113 | * |
| A114 | ** |
| A115 | *** |
| A116 | ** |
| A117 | ** |
| A118 | ** |
| A119 | *** |
| A120 | * |
| A121 | ** |
| A122 | *** |
| A123 | *** |
| A124 | * |
| A125 | *** |
| A126 | ** |
| A127 | N/A |
| A128 | N/A |
| A129 | N/A |
| A130 | ** |
| A131 | ** |
| A132 | ** |
| A133 | *** |
| A134 | ** |
| A135 | *** |
| A136 | ** |
| A137 | *** |
| A138 | N/A |
| A139 | N/A |
| A140 | *** |
| A141 | *** |
| A142 | *** |
| A143 | * |
| A144 | N/A |
| A145 | ** |
| A146 | N/A |
| A147 | * |
| A148 | ** |
| A149 | *** |
| A150 | N/A |
| A151 | ** |
| A152 | N/A |
| A153 | ** |
| A154 | N/A |
| A155 | *** |
| A156 | *** |
| A157 | N/A |
| A158 | N/A |
| A159 | N/A |
| A160 | N/A |
| A161 | N/A |
| A162 | *** |
| A163 | N/A |
| A164 | ** |
| A165 | N/A |
| A166 | N/A |
| A167 | N/A |
| A168 | *** |
| A169 | *** |
| A170 | ** |
| A171 | ** |
| A172 | *** |
| A173 | * |
| A174 | ** |
| A175 | N/A |
| A176 | N/A |
| A177 | N/A |
| A178 | N/A |
| A179 | N/A |
| A180 | N/A |
| A181 | N/A |
| A182 | N/A |
| A183 | N/A |
| A184 | * |
| A185 | *** |
| A186 | N/A |
| A187 | N/A |
| A188 | N/A |
| A189 | ** |
| A190 | ** |
| A191 | ** |
| A192 | *** |
| A193 | ** |
| A194 | ** |
| A195 | *** |
| A196 | ** |
| A197 | ** |
| A198 | *** |
| A199 | *** |
| A200 | ** |
| A201 | ** |
| A202 | ** |
| A203 | ** |
| A204 | *** |
| A205 | ** |
| A206 | ** |
| A207 | *** |
| A208 | *** |
| A209 | NA |
| A210 | NA |
| A211 | NA |
| B1 | ** |
| B2 | *** |
| B3 | ** |
| B4 | N/A |
| B5 | ** |
| B6 | * |
| B7 | * |
| B8 | ** |
| B9 | *** |
| B10 | * |

Note:
*** represent IC$_{50}$ < 500 nM,
** represents IC$_{50}$ in the range of 500-2000 nM,
* represents IC$_{50}$ in the range of ≥2000 nM

TABLE 1B

IC$_{50}$ of Representative Compounds in
Androgen-Induced PSA-Luciferase Assay

| Compound ID | PSA-Luc IC$_{50}$ (nM) | n |
|---|---|---|
| X | 1054 | 3 |
| A13 | 592 | 8 |
| A28 | 400 | 5 |
| A38 | 631 | 6 |
| A74 | 658 | 6 |
| A93 | 205 | 4 |
| A109 | 535 | 2 |
| EPI-002 | 9580 | 2 |
| Enzalutamide | 189 | 8 |
| Bicalutamide | 306 | 2 |

TABLE 1C

IC5$_0$ of Representative Compounds in LBD-Expressing
Reporter Cell Lines

| | Steroid Receptor LBD IC$_{50}$ (µM) | | | | |
|---|---|---|---|---|---|
| Compound ID | AR | ERα | ERβ | PR | GR |
| X | 9.83 | 5.82 | 7.37 | 4.96 | >10 |
| A13 | >10 | >10 | >10 | 0.97 | >10 |
| A28 | >10 | >10 | >10 | 0.93 | >10 |
| A38 | >10 | >10 | >10 | 5.07 | >10 |
| A74 | >10 | >10 | >10 | 5.41 | 9.51 |
| A93 | >10 | >10 | >10 | 5.04 | >10 |
| A109 | >10 | >10 | >10 | 5.61 | >10 |
| EPI-002 | >10 | >10 | >10 | >10 | >10 |
| Enzalutamide | 0.54 | >10 | >10 | 4.49 | >10 |

TABLE 1D

IC$_{50}$ of Represenatative Compounds on Cell Proliferation/Viability

| | Cellular Proliferation/Viability IC$_{50}$ (µM) | | |
|---|---|---|---|
| Compound ID | LNCaP | PC-3 | LNCaP95 |
| X | 3.00 | >10 | 4.00 |
| A13 | 0.85 | >10 | 4.00 |
| A28 | 0.68 | >10 | 6.43 |
| A74 | 1.16 | >10 | 2.65 |
| A109 | 0.44 | >10 | 3.78 |
| EPI-002 | 9.00 | >10 | ~20 |
| Enzalutamide | 0.35 | >10 | >10 |

Example 36: Stability Assays

Microsomal Stability Assay:

Microsomal stability assay is a widely used in vitro model to characterize the metabolic conversion by phase I enzymes, such as cytochrome P450 (CYP) enzymes. Since metabolism is known to be highly variable in different species, microsomal stability assay is commonly run in multiple species. Metabolic stability of testing compound can be evaluated using human, rat, mouse, or other animal liver or intestine microsomes to predict intrinsic clearance.

The assay was carried out in 96-well microtiter plates at 37° C. Reaction mixtures (25 µL) contained a final concentration of 1 µM test compound, 0.5 mg/mL liver microsomes protein, and 1 mM NADPH and/or 1 mM UDPGA (with alamethicin) in 100 mM potassium phosphate, pH 7.4 buffer with 3 mM MgCl$_2$. The incubation was done with N=1, but duplicate incubation at each time point can be prepared if necessary. At each of the time points (for example, 0, 15, 30, and 60 minutes), 150 µL of quench solution (100% acetonitrile with 0.1% formic acid) with internal standard was transferred to each well. Besides the zero minute controls, mixtures containing the same components except the NADPH can also be prepared as the negative control. Verapamil was included as a positive control to verify assay performance. Plates were sealed, vortexed, and centrifuged at 4° C. for 15 minutes at 4000 rpm. The supernatant is transferred to fresh plates for LC/MS/MS analysis.

Summarized conditions: [Compound]=1 M, [LM]=0.5 mg/mL, [NADPH]=1 mM and/or [UDPGA]=1 mM, Buffer=100 mM Potassium Phosphate, pH 7.4 with 3 mM MgCl$_2$, Time=0, 15, 30, and 60 min, and Temperature=37° C.

All samples were analyzed on LC/MS/MS using an AB Sciex API 4000 instrument, coupled to a Shimadzu LC-20AD LC Pump system. Analytical samples were separated using a Waters Atlantis T3 dC18 reverse phase HPLC column (20 mm×2.1 mm) at a flow rate of 0.5 mL/min. The mobile phase consisted of 0.1% formic acid in water (solvent A) and 0.1% formic acid in 100% acetonitrile (solvent B).

The extent of metabolism is calculated as the disappearance of the test compound, compared to the 0-min time incubation. Initial rates are calculated for the compound concentration and used to determine half-life (t½) values and subsequently, the intrinsic clearance ($Cl_{int}$).

$Cl_{int}$=(0.693)(1/t½ (min))(g of liver/kg of body weight)(mL incubation/mg of microsomal protein)(45 mg of microsomal protein/g of liver weight)

Hepatocyte Stability Assay:

The termination of in vitro intrinsic clearance ($Cl_{int}$) for drug candidates in the early discovery stage is common practice in the pharmaceutical industry. The $Cl_{int}$ values of drug candidates can help to confirm whether metabolism is the main clearance pathway when it is compared with the total body clearance in vivo. Hepatocytes are among the routinely used in vitro systems for measuring clearance. Hepatocytes have been reported to retain most of the phase I and phase II metabolic activities, and therefore, it is a useful tool to estimate the intrinsic clearance for potential drug candidates.

Metabolic stability of testing compound were be evaluated using human and mouse hepatocytes and can also be use rat, mouse, or other animal hepatocytes to predict intrinsic clearance. Cryopreserved hepatocytes were removed from the liquid nitrogen tank and thawed in a 37° C. water bath. As soon as the cells pulled away from the vial wall, they were decanted into 48 ml of warm HT medium. Cells were centrifuged for four minutes at 420 rpm (50 g). After removing the supernatant, pellet was re-suspended in warm DMEM medium. Cell density was counted by a hemacytometer.

The assay was carried out in 96-well microtiter plates. Compounds were incubated for 0, 60, 120, and 180 minutes at 37° C. with hepatocytes. Reaction mixtures (50 µL) contained a final concentration of 1 µM test compound, 0.5 million cells/mL hepatocytes in the DMEM medium. At each of the time points (for example, 0, 1, 2, and 3 hours), 200 µL of quench solution (100% acetonitrile with 0.1% formic acid) with internal standard was transferred to each well. Midazolam was included as a positive control to verify assay performance. Plates were sealed and centrifuged at 4° C. for 15 minutes at 4000 rpm. The supernatant is transferred to fresh plates for LC/MS/MS analysis.

Summarized conditions (customizable): [Compound]=1 M, Positive control: midazolam and/or naloxone, [Hepatocyte]=0.5 million cells/Ml, time=0, 60, 120, and 180 min, t=37° C.

All samples were analyzed on LC/MS/MS using an AB Sciex API 4000 instrument, coupled to a Shimadzu LC-20AD LC Pump system. Analytical samples were separated using a Waters Atlantis T3 dC18 reverse phase HPLC column (20 mm×2.1 mm) at a flow rate of 0.5 mL/min. The mobile phase consisted of 0.1% formic acid in water (solvent A) and 0.1% formic acid in 100% acetonitrile (solvent B).

The extent of metabolism was calculated as the disappearance of the test compound, compared to the 0-min control reaction incubations. Initial rates were calculated for the compound concentration and used to determine t½ values and subsequently, the intrinsic clearance, $Cl_{int}$.

$$Cl_{int}=(0.693)(1/t½(min))(mL\ incubation/million\ cells)$$

Metabolic stability assay results of representative compounds from Tables A and B are listed in Table 2A, below. Metabolic stability assay results of representative compounds from Tables A and B for human hepatocytes are demonstrated in Table 2B. Liver microsome and hepatocyte half life of representative compounds are shown in Tables 2C and 2D.

TABLE 2A

Stability Results of Representative Compounds from Tables A and B

| Compound ID | MLM +30/− NADPH: $Cl_{int}$ (μL/min/mg protein)[1] | HLM +/− NADPH: $Cl_{int}$ (μL/min/mg protein)[1] | MH +/− NADPH: $Cl_{int}$ (μL/min/ million cells)[2] |
|---|---|---|---|
| A3 | *** | *** | NA |
| A5 | NA | *** | NA |
| B1 | * | ** | NA |
| A7 | NA | * | NA |
| A13 | *** | *** | ** |
| A17 | NA | *** | NA |
| A18 | NA | * | NA |
| A21 | NA | *** | NA |
| A22 | NA | *** | NA |
| A23 | NA | ** | NA |
| A24 | NA | *** | NA |
| A25 | NA | *** | NA |
| A27 | * | *** | NA |
| B2 | * | * | NA |
| B3 | *** | *** | NA |
| B5 | *** | *** | ** |
| A28 | ** | *** | ** |
| A29 | ** | ** | NA |
| A30 | ** | ** | NA |
| A31 | NA | ** | NA |
| A32 | * | ** | NA |
| A34 | ** | *** | NA |
| A35 | ** | *** | NA |
| A38 | *** | *** | *** |
| A40 | NA | ** | NA |
| A41 | NA | * | NA |
| A42 | *** | *** | NA |
| A45 | *** | *** | NA |
| A49 | *** | ** | NA |
| A50 | NA | ** | NA |
| A52 | NA | *** | NA |
| A53 | NA | *** | NA |
| A54 | NA | *** | NA |
| A56 | NA | *** | NA |
| A57 | * | ** | NA |
| A58 | NA | ** | NA |
| B8 | NA | * | NA |
| A62 | NA | *** | NA |

TABLE 2A-continued

Stability Results of Representative Compounds from Tables A and B

| Compound ID | MLM +30/− NADPH: $Cl_{int}$ (μL/min/mg protein)[1] | HLM +/− NADPH: $Cl_{int}$ (μL/min/mg protein)[1] | MH +/− NADPH: $Cl_{int}$ (μL/min/ million cells)[2] |
|---|---|---|---|
| A63 | NA | ** | NA |
| B9 | ** | ** | NA |
| A64 | NA | * | NA |
| A65 | ** | ** | NA |
| A66 | *** | *** | NA |
| A68 | *** | *** | NA |
| A70 | * | ** | ** |
| A71 | *** | ** | ** |
| A73 | *** | *** | NA |
| A74 | *** | *** | NA |
| A75 | NA | *** | NA |
| B6 | NA | ** | NA |
| A76 | NA | *** | NA |
| B7 | *** | *** | NA |
| A77 | * | ** | NA |
| B10 | ** | *** | NA |
| A78 | *** | *** | NA |
| A79 | * | *** | * |
| A80 | ** | *** | * |
| A81 | * | ** | * |
| A85 | * | *** | * |
| A86 | ** | ** | * |
| A87 | ** | *** | * |
| A88 | * | * | * |
| A89 | * | ** | * |
| A90 | * | *** | * |
| A91 | *** | *** | ** |
| A92 | ** | ** | * |
| A93 | *** | *** | *** |
| A94 | ** | ** | ** |
| A95 | * | ** | * |
| A96 | * | * | * |
| A97 | ** | ** | * |
| A98 | *** | *** | *** |
| A99 | ** | *** | ** |
| A100 | * | * | * |
| A101 | ** | * | ** |
| A102 | *** | ** | *** |
| A103 | ** | ** | *** |
| A104 | * | ** | * |
| A105 | * | ** | * |
| A106 | NA | ** | NA |
| A107 | NA | ** | NA |
| A108 | * | *** | * |
| A109 | *** | *** | *** |
| A110 | NA | NA | NA |
| A111 | ** | ** | ** |
| A112 | ** | *** | ** |
| A113 | ** | ** | * |
| A114 | ** | *** | * |
| A115 | *** | *** | * |
| A116 | ** | ** | ** |
| A117 | ** | ** | * |
| A118 | * | * | ** |
| A119 | * | * | ** |
| A120 | *** | * | ** |
| A121 | ** | ** | ** |
| A122 | ** | *** | ** |
| A123 | * | *** | ** |
| A124 | * | *** | * |
| A125 | * | *** | * |
| A126 | *** | *** | *** |
| A127 | ** | ** | ** |
| A128 | NA | NA | NA |
| A129 | NA | NA | NA |
| A130 | *** | ** | *** |
| A131 | *** | *** | *** |
| A132 | *** | *** | *** |
| A133 | * | * | * |
| A134 | *** | ** | *** |
| A135 | ** | ** | * |
| A136 | ** | ** | ** |
| A137 | ** | *** | *** |

TABLE 2A-continued

Stability Results of Representative Compounds from Tables A and B

| Compound ID | MLM +30/− NADPH: Cl$_{int}$ (μL/min/mg protein)[1] | HLM +/− NADPH: Cl$_{int}$ (μL/min/mg protein)[1] | MH +/− NADPH: Cl$_{int}$ (μL/min/million cells)[2] |
|---|---|---|---|
| A138 | NA | NA | NA |
| A139 | NA | NA | NA |
| A140 | * | * | * |
| A141 | * | *** | * |
| A142 | * | ** | * |
| A143 | *** | *** | *** |
| A144 | ** | ** | * |
| A145 | * | * | * |
| A146 | *** | ** | * |
| A147 | * | ** | * |
| A148 | *** | * | *** |
| A149 | *** | *** | * |
| A150 | NA | NA | NA |
| A151 | NA | NA | NA |
| A152 | NA | NA | NA |
| A153 | ** | *** | ** |
| A154 | NA | NA | NA |
| A155 | * | ** | ** |
| A156 | ** | ** | * |
| A157 | NA | NA | NA |
| A158 | NA | NA | NA |
| A159 | NA | NA | NA |
| A160 | NA | NA | NA |
| A161 | *** | *** | NA |
| A162 | * | ** | * |
| A163 | NA | NA | NA |
| A164 | *** | *** | *** |
| A165 | NA | NA | NA |
| A166 | NA | NA | NA |
| A167 | NA | NA | NA |
| A168 | *** | *** | ** |
| A169 | *** | *** | *** |
| A170 | *** | *** | *** |
| A171 | *** | *** | ** |
| A172 | *** | *** | *** |
| A173 | *** | *** | NA |
| A174 | ** | *** | NA |
| A175 | NA | NA | NA |
| A176 | NA | NA | NA |
| A177 | NA | NA | NA |
| A178 | NA | NA | NA |
| A179 | NA | NA | NA |
| A180 | NA | NA | NA |
| A181 | NA | NA | NA |
| A182 | NA | NA | NA |
| A183 | NA | NA | NA |
| A184 | *** | *** | *** |
| A185 | ** | *** | ** |
| A186 | NA | NA | NA |
| A187 | NA | NA | NA |
| A188 | NA | NA | NA |
| A189 | *** | *** | NA |
| A190 | * | *** | * |
| A191 | NA | NA | NA |
| A192 | ** | ** | * |
| A193 | * | * | ** |
| A194 | *** | *** | *** |
| A195 | *** | *** | ** |
| A196 | *** | ** | *** |
| A197 | *** | *** | *** |
| A198 | ** | *** | ** |
| A199 | * | *** | ** |
| A200 | *** | *** | ** |
| A201 | *** | *** | *** |
| A202 | * | *** | * |
| A203 | NA | NA | NA |
| A204 | *** | *** | *** |
| A205 | NA | NA | NA |
| A206 | *** | *** | *** |
| A207 | *** | *** | *** |
| A208 | *** | *** | *** |
| A209 | NA | NA | NA |
| A210 | NA | NA | NA |
| A211 | NA | NA | NA |

[1]For MLM and HLM: * represent Cl < 12 μL/min/mg protein,  represents Cl in the range of 12-48 μL/min/mg protein, * represents Cl in the range of ≥48 μL/min/mg protein.
[2]For MH: * represent Cl < 4 cells μL/min/million cells,  represents Cl in the range of 4-18 μL/min/million cells, * represents Cl in the range of ≥18 μL/min/million cells.

TABLE 2B

Human Hepatocyce Stability Results of Representative Compounds from Tables A and B

|  | Number of Compounds |
|---|---|
| Cl < 4 μL/min/million cells | 14 compounds |
| Cl in the range of 4-18 μL/min/million cells | 31 compounds |
| Cl in the range of ≥18 μL/min/million cells | 36 compounds |

TABLE 2C

Liver Microsome Half-Life

| Compound ID | Liver microsome T½ (min) | | | | |
|---|---|---|---|---|---|
|  | Human | Mouse | Rat | Dog | Monkey |
| A13 | >120 | >120 | 64 | >120 | >120 |
| A28 | >120 | 74 | 23 | >120 | 73 |
| A38 | >120 | >120 | 12 | >120 | >120 |
| A74 | >120 | >120 | >120 | >120 | >120 |
| A93 | >120 | >120 | 83 | >120 | 101 |
| A109 | >120 | >120 | >120 | >120 | >120 |
| X | >120 | NA | NA | NA | NA |
| Enzalutamide | >120 | >120 | >120 | >120 | >120 |

TABLE 2D

Hepatocytes Half-Life

| Compound ID | Hepatocytes T½ (min) | | |
|---|---|---|---|
|  | Human | Mouse | Rat |
| A13 | 290 | 203 | 75 |
| A28 | >360 | 86 | 31 |
| A38 | >360 | >360 | 56 |
| A74 | >360 | NA | >360 |
| A93 | >360 | >360 | 94 |
| A109 | >360 | >360 | >360 |
| X | >360 | 33 | NA |
| Enzalutamide | >360 | NA | NA |

Example 37: In Vivo Pharmakokinetic Properties

The purpose of this study is to determine the pharmacokinetics of the tested compounds in plasma, following oral gavage administration (PO) to male CD-1 mice.

Animal Husbandry: Animals were group housed during acclimation and the study. The animal room environment were controlled (target conditions: temperature 18 to 26° C., relative humidity 30 to 70%, 12 hours artificial light and 12 hours dark). Temperature and relative humidity were monitored daily. Animals were fasted at least 12 hours prior to the administration. All animals had access to Certified Rodent Diet ad libitum 4 hours post dosing.

Dose Formulation: prepared 85-100 uL of a stock solution of representative compounds of the disclosure in DMSO at 50 mM; 1.5% v/v of Tween 80 were added and mixed gently; 95.5% v/v saline was added gently to the organic phase. The solution was mixed slowly by reverse pipetting to get a clear solution.

Dose Administration: the dose formulations were administered via oral gavage per facility SOPs. The dose volume were determined by the animals' body weight collected on the morning of dosing day Sample Collection: blood collection (about 0.05 mL per time point) was performed from saphenous vein of each animal into polypropylene tubes at each timepoints (0, 0.25, 0.5, 1, 2, 4, 8, 12, and 24 hr). All blood samples were transferred into pre-chilled tubes containing 2 μL of K2-EDTA (0.5M) and placed on wet ice until centrifugation. Each collected blood sample was in the wet-ice before centrifugation. Each collected blood was under centrifugation for 15 minutes at 4° C. and 3000 g for plasma collection. Plasma samples were stored in polypropylene tubes, quickly frozen over dry ice and kept at −70±10° C. until LC/MS/MS analysis.

Bioanalytical analysis: A LC-MS/MS method for the quantitative determination of tested compound in biological matrix were developed under non-GLP compliance. A calibration curve with at least 7 non-zero calibration standards were applied for the method including LLOQ.

Figure 3:
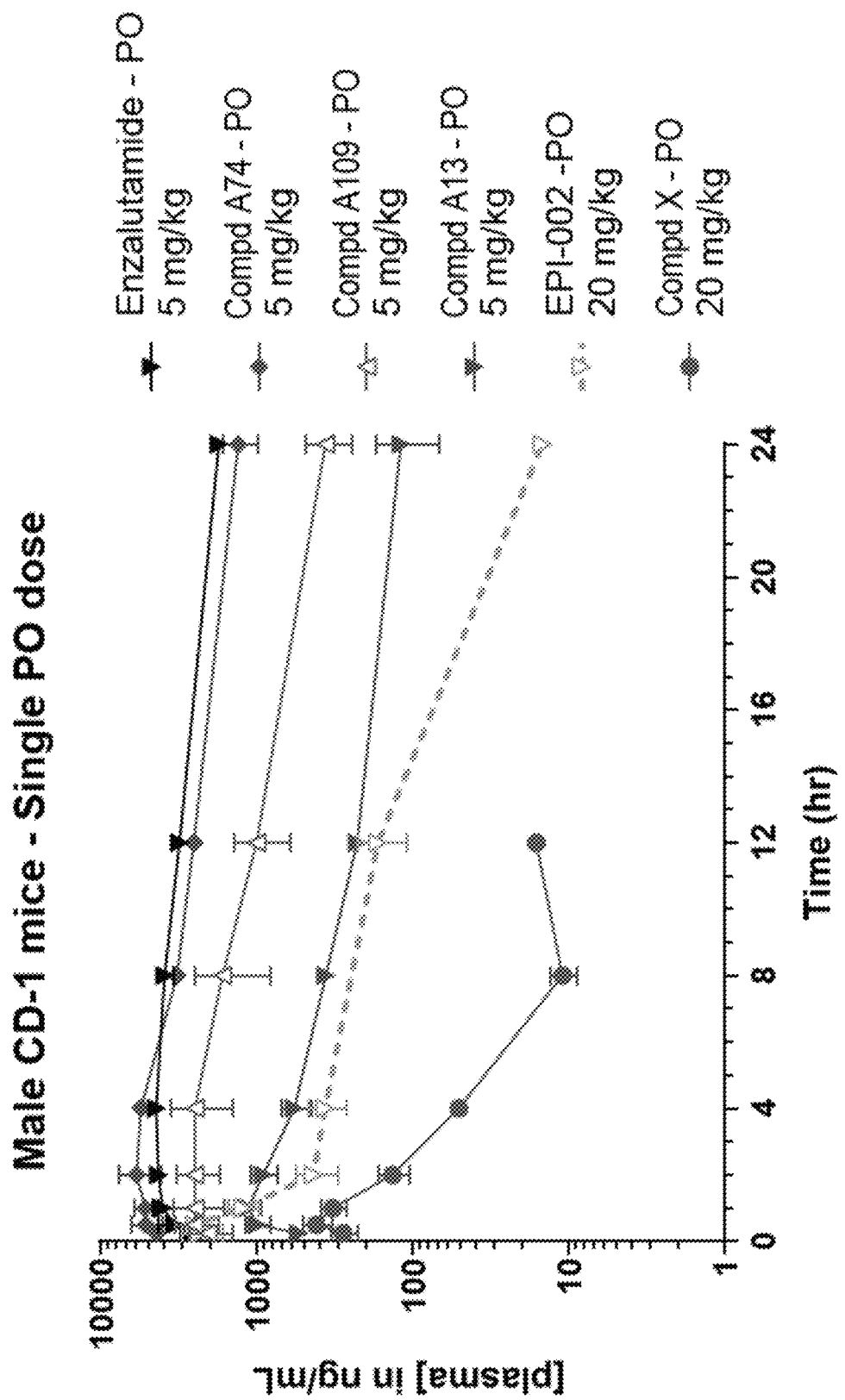
FIG. 3 shows concentration of representative compounds in plasma of male CD-1 mice after a single dose PO (oral) dose.

Plasma concentration versus time data were analyzed by non-compartmental approaches using the Phoenix WinNonlin 6.3 software program. Cl, Vdss, C0, Cmax, Tmax, $T^{1/2}$, AUC(0-t), AUC(0-inf), MRT(0-t), MRT(0-inf), % F (oral availability) and graphs of plasma concentration versus time profile were reported. FIG. 3 shows the time-concentration curve of representative compounds in mice as measured in plasma.

Tables 3A shows PK parameters determined from single PO dose of representative compounds in mice (5 mg/kg).

TABLE 3A

Summary of PO PK Parameters After Single Dose (5 mg/kg) in Male CD-1 Mice

| Compound ID | t½ (hr) | tmax (hr) | Cmax (ng/mL) | AUClast (hr*ng/mL) | AUC/D (hr*kg*ng/mL/mg) | F (%) |
|---|---|---|---|---|---|---|
| A13 | 8.3 | 1.0 | 1143.3 | 8309.3 | 1661.9 | 85.8 |
| A28 | 2.8 | 0.5 | 2013.3 | 8425.4 | 1685.1 | 50.3 |
| A29 | 2.5 | 0.5 | 2010.0 | 5186.6 | 1037.3 | 60.6 |
| A35 | 4.0 | 0.5 | 818.7 | 2415.1 | 483.0 | 49.6 |
| A38 | 4.9 | 3.3 | 1270.0 | 12805.1 | 2561.0 | 86.4 |
| A66 | 12.0 | 0.8 | 1613.3 | 11927.2 | 2385.4 | 71.4 |
| A74 | 12.5 | 2.7 | 6306.7 | 72711.4 | 14542.3 | 71.9 |
| A93 | 17.1 | 0.8 | 2973.3 | 32878.6 | 6575.7 | 62.8 |
| A109 | 8.1 | 2.2 | 2673.3 | 30714.8 | 6143.0 | 33.6 |
| A122 | 1.1 | 0.5 | 4080.0 | 6800.0 | 1360.0 | 92.4 |
| A126 | 4.7 | 1.3 | 3113.0 | 24547.0 | 4909.4 | 86.0 |
| A131 | 5.0 | 1.3 | 7053.0 | 76047.0 | 15209.4 | 81.0 |
| A136 | 10.2 | 1.5 | 3427.0 | 42038.0 | 8407.6 | 14.0 |
| A170 | 3.0 | 3.0 | 8503.0 | 80038.0 | 16007.6 | 150.0 |

Figure 4:
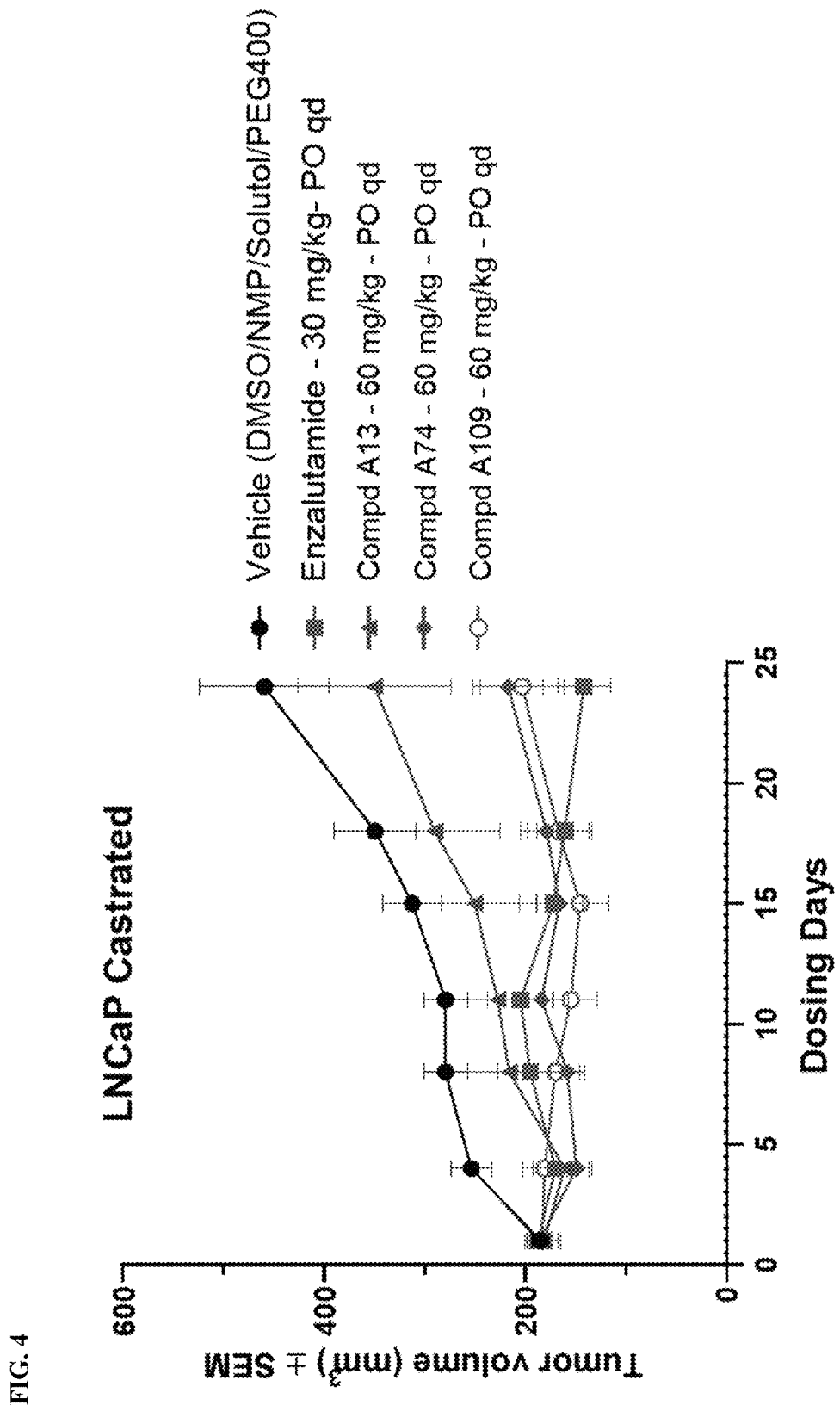
FIG. 4 shows change in tumor volume in male NCG mice bearing LNCaP tumors after oral administration of representative compounds.
Figure 5:
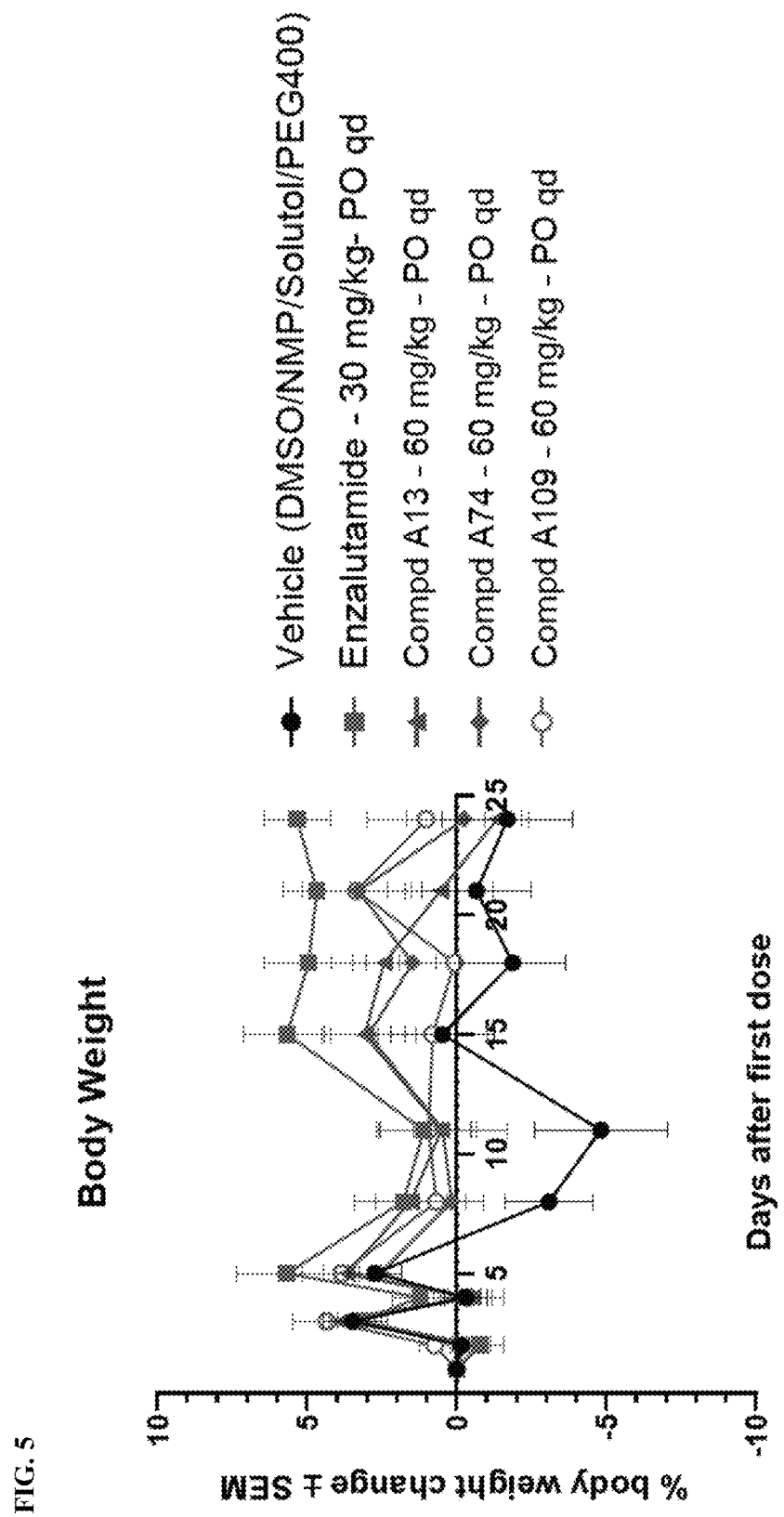
FIG. 5 shows change in % body weight in male NCG mice bearing LNCaP tumors after oral administration of representative compounds.
Figure 6:
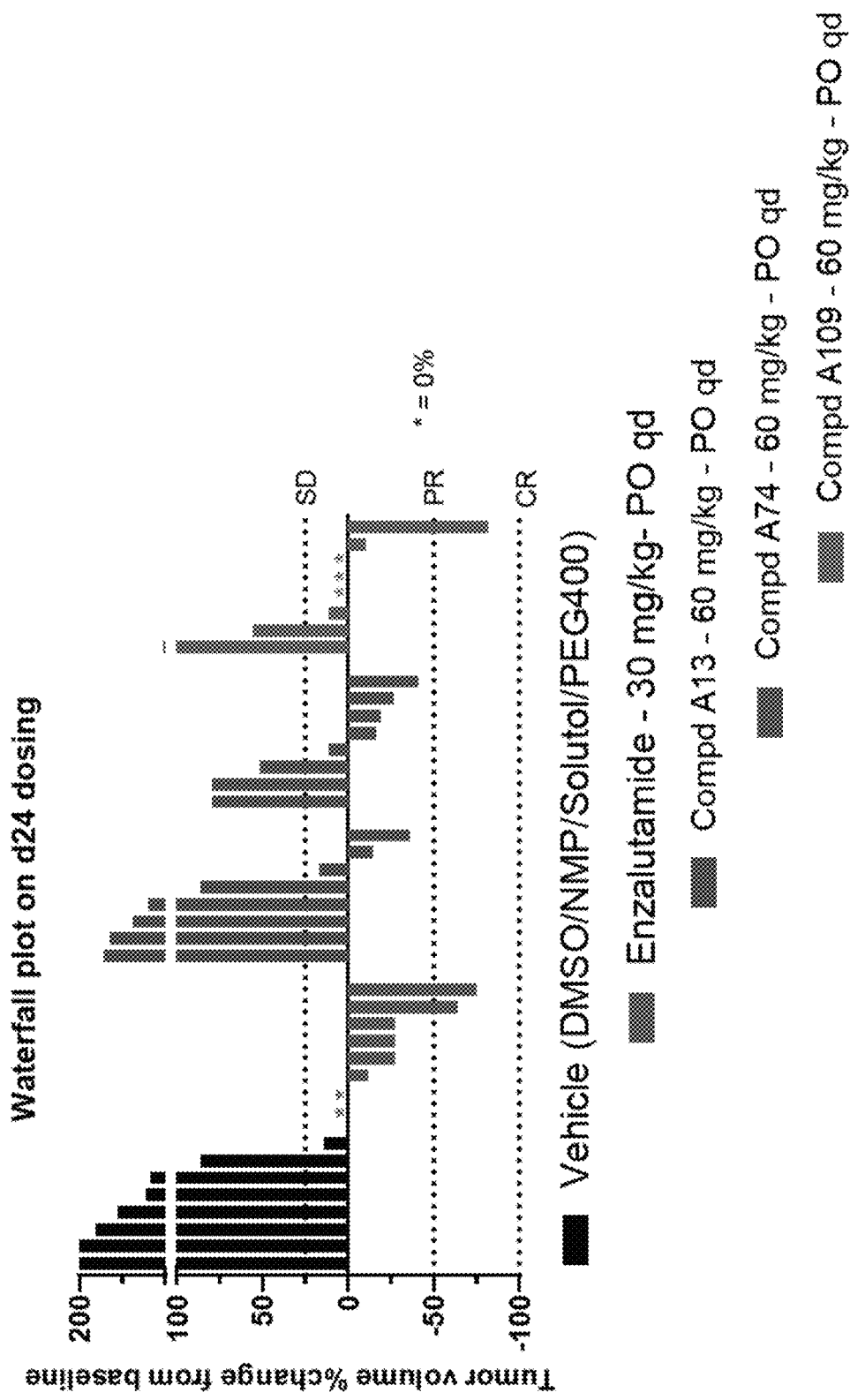
FIG. 6 shows individual tumor volume change from baseline measured at the end of experiment for oral administration of representative compounds to male NCG mice bearing LNCaP tumors.

Example 38: In Vivo Activity of Representative Compounds in LNCaP Xenografts Model Tumor growth was measured in male NCG mice bearing LNCaP tumors. Castration was performed when tumors reached ~100 mm³ and dosing (60 mg/kg PO qd) started 1 week after castration. See FIG. 4. Body weight of the mice were captured biweekly in the animals which showed no drug related toxicity. See FIG. 5. Individual tumor volume change from baseline measured at the end of the experiment. See FIG. 6. Data demonstrated in FIGS. 4-6 shows that the representative compounds showed activity and induced partial regressions of tumor growth. The $C_{min}$ at 5 mg/kg PO and extrapolated $C_{min}$ in efficacy of the representative compounds are shown in Table 4.

TABLE 4

| | $C_{min}$ at 5 mg/kg PO and $C_{min}$ at 5 mg/kg PO | |
|---|---|---|
| Compound ID | $C_{min}$ at 5 mg/kg PO (μM) | $C_{min}$ at 5 mg/kg PO (μM) |
| A13 | 0.23 | 2.78 |
| A74 | 2.42 | 29.1 |
| A109 | 0.68 | 8.18 |
| Enzalutamide | 3.80 | 22.8 |

Numbered Embodiments

In some embodiments, the present disclosure relates to the following embodiments.

Embodiment 1

A compound having a structure of formula (I):

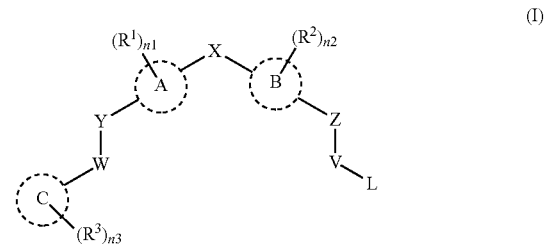

(I)

or a pharmaceutically acceptable salt, tautomer, stereoisomer or prodrug thereof, wherein:

A and B are each independently aryl or heteroaryl;

C is a 3- to 10-membered ring;

X is a bond, —$(CR^5R^6)_r$—, —O—, —C(=O)—, —S—, —S(=O)—, —$SO_2$—, —$NR^7$—, —$N(R^7)CO$—, —$CON(R^7)$—, or —$NSO_2R^7$—;

Y and Z are each independently a bond, —$(CR^8R^9)_m$—, —O—, —C(=O)—, —S—, —S(=O)—, —$SO_2$—, or —$NR^7$—;

W and V are each independently a bond, —$(CR^{8a}R^{9a})_m$—, —C(=O)—, —$N(R^7)CO$—, —$CONR^7$—, or —$NSO_2R^7$—;

L is hydrogen, halogen, —$CF_2R^{10}$, —$CF_3$, —CN, —$OR^1$; —$NR^{11}R^{12}$, or —$CONR^{11}R^{12}$;

$R^1$ and $R^2$ are each independently hydrogen, halogen, —CN, —$CF_3$, —OH, optionally substituted $C_1$-$C_6$ alkyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —$NR^{13}R^{14}$, optionally substituted —($C_1$-$C_6$ alkyl)-$NR^{13}R^{14}$, —$NR^{14}SO_2R^{16}$, optionally substituted —($C_1$-$C_6$ alkyl) $NR^{14}SO_2R^{16}$, —$NR^{14}COR^{16}$, optionally substituted —($C_1$-$C_6$ alkyl)-$NR^{14}COR^{16}$, —$CONR^{14}R^{15}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$, optionally substituted —(C$_1$-C$_6$ alkyl)-SO$_2$R$^{16}$, optionally substituted carbocyclyl, optionally substituted heterocyclyl, optionally substituted aryl, or optionally substituted heteroaryl;

R$^3$ is hydrogen, halogen, oxo, =S, =NR$^{16}$, —CN, —CF$_3$, —OH, —SR$^{16}$, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$, optionally substituted —(C$_1$-C$_6$ alkyl)-SO$_2$R$^{16}$ optionally substituted carbocyclyl, optionally substituted heterocyclyl, optionally substituted aryl, or optionally substituted heteroaryl;

R$^5$ and R$^6$ are each independently hydrogen, halogen, —OH, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, —NR$^{13}$R$^{14}$, optionally substituted —(C$_1$-C$_6$ alkyl)-NR$^{13}$R$^{14}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, optionally substituted carbocyclyl, optionally substituted heterocyclyl, optionally substituted aryl, or optionally substituted heteroaryl; or R$^5$ and R$^6$ taken together form an optionally substituted carbocyclyl or optionally substituted heterocyclyl;

R$^8$ and R$^9$ are each independently hydrogen, halogen, or C$_1$-C$_3$ alkyl;

R$^{8a}$ and R$^{9a}$ are each independently hydrogen, —OH, halogen, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, optionally substituted —OCO(C$_1$-C$_6$ alkyl), —NR$^{13}$R$^{14}$, optionally substituted —(C$_1$-C$_6$ alkyl)-NR$^{13}$R$^{14}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, optionally substituted carbocyclyl, optionally substituted heterocyclyl, optionally substituted aryl, or optionally substituted heteroaryl; or R$^{8a}$ and R$^{8b}$ taken together form an optionally substituted carbocyclyl or optionally substituted heterocyclyl;

R$^7$, R$^{10}$ and R$^{16}$ are each independently hydrogen, optionally substituted C$_1$-C$_6$ alkyl, optionally substituted C$_2$-C$_6$ alkenyl, optionally substituted C$_2$-C$_6$ alkynyl, optionally substituted carbocyclyl, optionally substituted heterocyclyl, optionally substituted aryl, or optionally substituted heteroaryl; or R$^7$ and R$^{8a}$ taken together form an optionally substituted heterocyclyl;

R$^{11}$, R$^{12}$, R$^{13}$, R$^{14}$ and R$^{15}$ are each independently hydrogen, optionally substituted C$_1$-C$_6$ alkyl, optionally substituted C$_2$-C$_6$ alkenyl, optionally substituted C$_2$-C$_6$ alkynyl, optionally substituted carbocyclyl, optionally substituted heterocyclyl, optionally substituted aryl, or optionally substituted heteroaryl; or (R$^{11}$ and R$^{12}$) or (R$^{14}$ and R$^{15}$) taken together form an optionally substituted heterocyclyl;

each m is independently 0, 1 or 2;
n1 and n2 are each independently 0, 1, 2, 3, or 4;
n3 is 0, 1, 2, 3, 4 or 5; and
each t is independently 0, 1 or 2.

Embodiment 2

The compound of Embodiment 1, wherein A and B are each independently 5- or 6-membered aryl or heteroaryl.

Embodiment 3

The compound of Embodiment 1 or 2, wherein A and B are each independently selected from phenyl, pyridyl, pyrimidyl, or thiophene.

Embodiment 4

The compound of any one of Embodiments 1-3, wherein A has a meta or para connectivity with X and Y.

Embodiment 5

The compound of any one of Embodiments 1-4, wherein B has a meta or para connectivity with X and Z.

Embodiment 6

The compound of any one of Embodiments 1-5, wherein C is 5- to 10-membered heteroaryl or aryl.

Embodiment 7

The compound of any one of Embodiments 1-6, wherein C is 5- to 7-membered heteroaryl comprising 1, 2, or 3 heteroatoms selected from O, S, or N as a ring member.

Embodiment 8

The compound of any one of Embodiments 1-7, wherein C is pyrazole, imidazole, oxazole, oxadiazole, oxazolone, isoxazole, thiazole, pyridyl, or pyrimidyl.

Embodiment 9

The compound of any one of Embodiments 1-7, wherein C, which is optionally substituted with R$^3$, is selected from

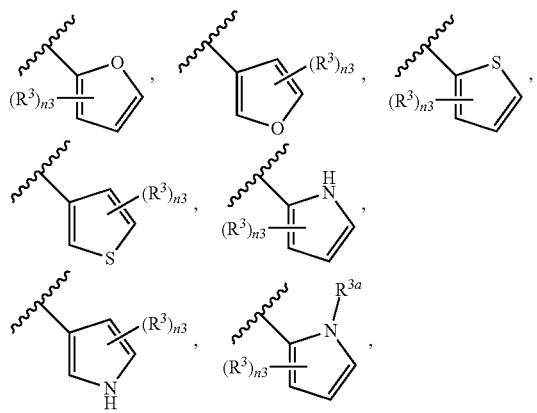

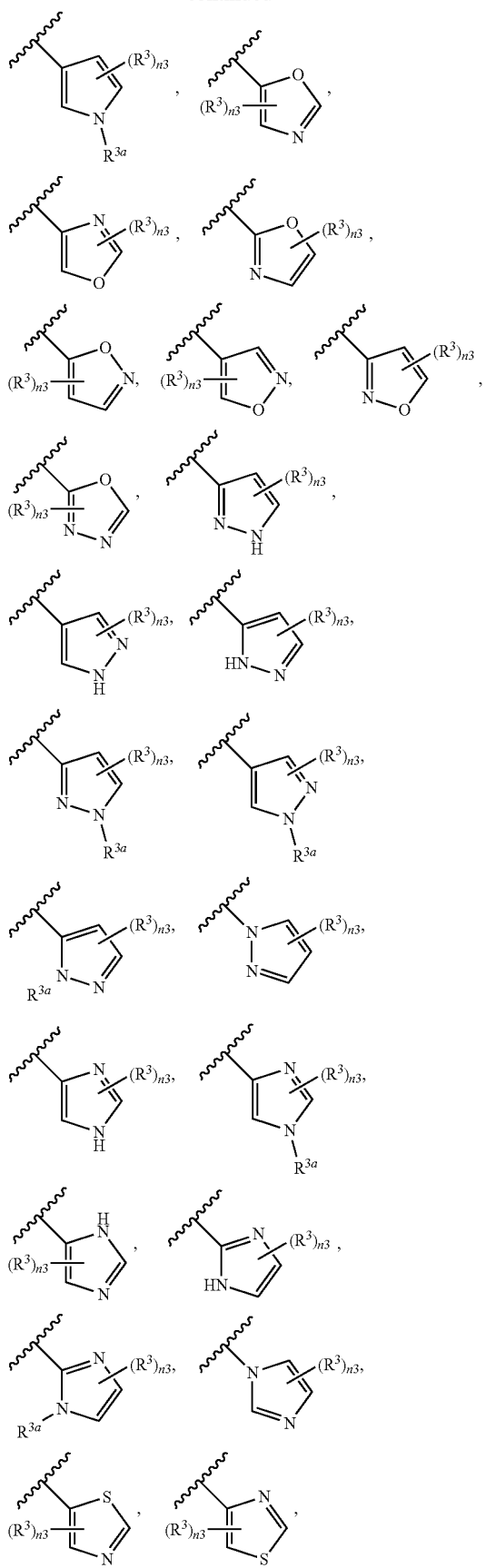

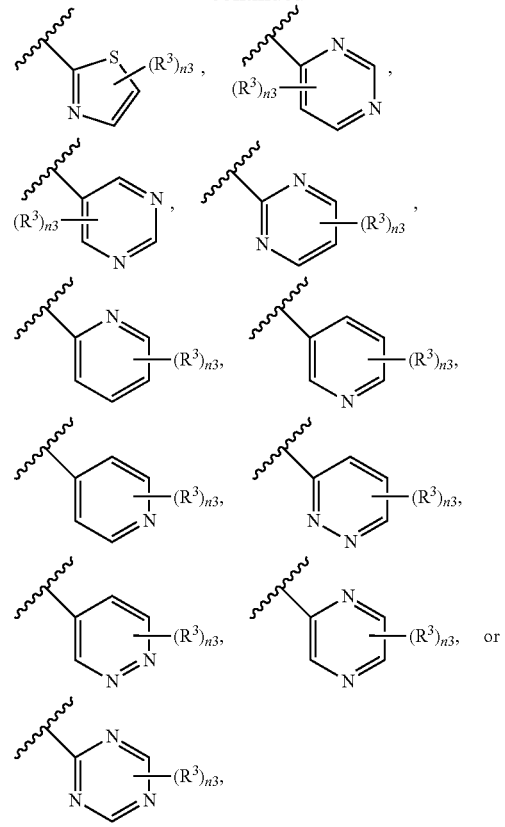

wherein $R^{3a}$ is $C_1$-$C_3$ alkyl.

Embodiment 10

The compound of any one of Embodiments 1-6, wherein C is phenyl or naphthyl.

Embodiment 11

The compound of any one of Embodiments 1-5, wherein C is 5- to 10-membered heterocyclyl comprising 1, 2, or 3 heteroatoms selected from O, S, or N as a ring member.

Embodiment 12

The compound of Embodiment 11, wherein C is

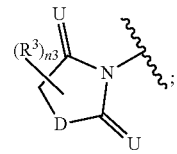

D is —O—, —NH— or —$NR^3$—; and
U is each independently O, S, or $NR^{16}$.

Embodiment 13

The compound of Embodiment 11, wherein C is imidazolidine, imidazolidine-dione, or dihydrooxazole.

Embodiment 14

The compound of any one of Embodiments 1-13, wherein Y is a bond, —CH$_2$—, —C(CH$_3$)H—, —O—, —S—, —NH—, —NCH$_3$—, or —N(COCH$_3$)—.

Embodiment 15

The compound of any one of Embodiments 1-14, wherein W is a bond, —CH$_2$—, —C(CH$_3$)H—, —C(=O)—, —N(R$^7$)CO—, or —CONR$^7$—, wherein R$^7$ is H or C$_1$-C$_3$ alkyl.

Embodiment 16

The compound of any one of Embodiments 1-15, wherein:
Z is a bond, —CH$_2$—, —C(CH$_3$)H—, —O—, —S—, —NH—, —NCH$_3$—, or —N(COCH$_3$)—; and
V is —CH$_2$—, —CH$_2$CH$_2$—, or —CH$_2$CH$_2$CH$_2$—.

Embodiment 17

The compound of any one of Embodiments 1-16, wherein:
Z is a bond, —CH$_2$—, —C(CH$_3$)H—, —O—, —S—, —NH—, —NCH$_3$—, or —N(COCH$_3$)—;
V is —CH$_2$—, —CH$_2$CH$_2$—, —CH$_2$CH$_2$CH$_2$—; and
L is halogen, —NH$_2$, or —CF$_3$.

Embodiment 18

The compound of any one of Embodiments 1-17, wherein X is a bond or —(CR$^5$R$^6$)$_t$—.

Embodiment 19

The compound of any one of Embodiments 1-18, wherein X is a bond, —CH$_2$—, —C(CH$_3$)H—, —C(CH$_3$)$_2$—, or —CH$_2$CH$_2$—.

Embodiment 20

The compound of any one of Embodiments 1-19, wherein R$^1$ and R$^2$ are each independently hydrogen, halogen, —CN, —CF$_3$, —OH, C$_1$-C$_3$ alkyl, C$_1$-C$_3$ alkoxy, —(C$_1$-C$_3$ alkyl)-(C$_1$-C$_3$ alkoxy), —(C$_1$-C$_3$ alkyl)-OH, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl) NR$^{14}$SO$_2$R$^{16}$, —NR$^{14}$COR$^{16}$, —(C$_1$-C$_3$ alkyl)-NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO$_2$R$^{16}$, —(C$_1$-C$_3$ alkyl)-SO$_2$R$^{16}$, 3- to 7-membered carbocyclyl, 3- to 7-membered heterocyclyl, phenyl, or 5- to 6-membered heteroaryl.

Embodiment 21

The compound of any one of Embodiments 1-20, wherein R$^1$ and R$^2$ are each independently hydrogen, halogen, —CN, —CF$_3$, —OH, C$_1$-C$_3$ alkyl, C$_1$-C$_3$ alkoxy, —(C$_1$-C$_3$ alkyl)-(C$_1$-C$_3$ alkoxy), —(C$_1$-C$_3$ alkyl)-OH, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl) NR$^{14}$SO$_2$R$^{16}$, —NR$^{14}$COR$^{16}$, —(C$_1$-C$_3$ alkyl)-NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO$_2$R$^{16}$, or —(C$_1$-C$_3$ alkyl)-SO$_2$R$^{16}$.

Embodiment 22

The compound of any one of Embodiments 1-21, wherein R$^1$ and R$^2$ are each independently halogen, —CN, —CF$_3$, —OH, methyl, methoxy, or —CONH$_2$.

Embodiment 23

The compound of any one of Embodiments 1-22, wherein R$^1$ and R$^2$ are each independently Cl, —CN, —CF$_3$, —OH, methyl, methoxy, or —CONH$_2$.

Embodiment 24

The compound of any one of Embodiments 1-23, wherein n1 and n2 are each independently 0, 1, or 2.

Embodiment 25

The compound of any one of Embodiments 1-24, wherein the sum of n1 and n2 is 0, 1, 2, 3, or 4.

Embodiment 26

The compound of any one of Embodiments 1-25, wherein R$^3$ is selected from hydrogen, halogen, oxo, =S, or =NR$^{16}$, —CN, —CF$_3$, —OH, —S(C$_1$-C$_3$ alkyl), C$_1$-C$_3$ alkyl, C$_2$-C$_3$ alkenyl, C$_2$-C$_3$ alkynyl, C$_1$-C$_3$ alkoxy, —(C$_1$-C$_3$ alkyl)-(C$_1$-C$_3$ alkoxy), —(C$_1$-C$_3$ alkyl)-OH, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl) NR$^{14}$SO$_2$R$^{16}$, —NR$^{14}$COR$^{16}$, —(C$_1$-C$_6$ alkyl)-NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO(C$_1$-C$_3$ alkyl), —SO$_2$(C$_1$-C$_3$ alkyl), or —(C$_1$-C$_6$ alkyl)-SO$_2$(C$_1$-C$_3$ alkyl).

Embodiment 27

The compound of any one of Embodiments 1-26, wherein R$^3$ is selected from hydrogen, F, Cl, Br, I, oxo, =S, =NR$^{16}$, —CN, —CF$_3$, —OH, C$_1$-C$_3$ alkyl, C$_2$-C$_3$ alkenyl, C$_2$-C$_3$ alkynyl, —S(C$_1$-C$_3$ alkyl), —SO(C$_1$-C$_3$ alkyl), —SO$_2$(C$_1$-C$_3$ alkyl), —NHSO$_2$CH$_3$, —N(CH$_3$)SO$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), or —N(CH$_3$)CO(C$_1$-C$_3$ alkyl).

Embodiment 28

The compound of any one of Embodiments 1-27, wherein R$^3$ is selected from hydrogen, F, Cl, Br, I, oxo, =S, =NR$^{16}$, —CN, —CF$_3$, —OH, methyl, —SCH$_3$, —SO$_2$CH$_3$, —NHSO$_2$CH$_3$, —CH$_2$NHSO$_2$CH$_3$, —SO$_2$NH$_2$, —CONH$_2$, or —NHCOCH$_3$.

Embodiment 29

The compound of any one of Embodiments 1-28, wherein at least one of R$^3$ is —SO$_2$CH$_3$, —NHSO$_2$CH$_3$, —CH$_2$NHSO$_2$CH$_3$, —SO$_2$NH$_2$, —CONH$_2$, or —NHCOCH$_3$.

Embodiment 30

The compound of any one of Embodiments 1-29, wherein at least one of R$^3$ is oxo, =S, =NR$^{16}$.

Embodiment 31

The compound of any one of Embodiments 1-30, wherein $R^{8a}$ and $R^{9a}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, —$NR^{13}R^{14}$, optionally substituted —($C_1$-$C_6$ alkyl)-$NR^{13}R^{14}$, —$NR^{14}COR^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, optionally substituted carbocyclyl, optionally substituted heterocyclyl, optionally substituted aryl, or optionally substituted heteroaryl.

Embodiment 32

The compound of any one of Embodiments 1-30, wherein $R^{8a}$ and $R^{9a}$ are not —OH.

Embodiment 33

The compound of Embodiment 1, wherein the compound has the structure of formula (II):

(II)

or a pharmaceutically acceptable salt, tautomer, stereoisomer or prodrug thereof, wherein:

A and B are each independently selected from phenyl, pyridyl, pyrimidyl, or thiophene;
C is a 3- to 10-membered ring;
X is a bond, —$(CR^5R^6)_t$—, or —$NR^7$;
Y is a bond, —$CH_2$—, —$C(CH_3)H$—, —O—, —S—, —NH—, —$NCH_3$—, or —$N(COCH_3)$—;
Z is a bond, —$(CR^8R^9)_m$—, —O—, —S—, —$S(=O)$—, —$SO_2$—, or —$NR^7$—;
W is a bond, —$CH_2$—, —$C(CH_3)H$—, —$C(=O)$—, —NHCO—, —$N(C_1$-$C_3$ alkyl)CO—, or —CONH—, or —$CON(C_1$-$C_3$ alkyl)-;
V is a bond, —$(CR^{8a}R^{9a})_m$—, —$C(=O)$—, —$N(R^7)CO$—, —$CONR^7$—, or —$NSO_2R^7$—;
L is hydrogen, halogen, —$CF_2R^{10}$, —$CF_3$, —CN, —$OR^{10}$; —$NR^{11}R^{12}$, or —$CONR^{11}R^{12}$;
$R^1$ and $R^2$ are each independently hydrogen, halogen, —CN, —$CF_3$, —OH, optionally substituted $C_1$-$C_6$ alkyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —$NR^{13}R^{14}$, optionally substituted —($C_1$-$C_6$ alkyl)-$NR^{13}R^{14}$, —$NR^{14}SO_2R^{16}$, optionally substituted —($C_1$-$C_6$ alkyl) $NR^{14}SO_2R^{16}$, —$NR^{14}COR^{16}$, optionally substituted —($C_1$-$C_6$ alkyl)-$NR^{14}COR^{16}$, —$CONR^{13}R^{14}$, optionally substituted —($C_1$-$C_6$ alkyl)-$CONR^{14}R^{15}$, —$SO_2NR^{14}R^{15}$, optionally substituted —($C_1$-$C_6$ alkyl)-$SO_2NR^{14}R^{15}$, optionally substituted —$SO_2R^{16}$ or optionally substituted —($C_1$-$C_6$ alkyl)-$SO_2R^{16}$;

$R^3$ is selected from hydrogen, halogen, oxo, =S, =$NR^{16}$, —CN, —$CF_3$, —OH, —$S(C_1$-$C_3$ alkyl), $C_1$-$C_3$ alkyl, $C_2$-$C_3$ alkenyl, $C_2$-$C_3$ alkynyl, $C_1$-$C_3$ alkoxy, —$NR^{13}R^{14}$, —($C_1$-$C_3$ alkyl)-$NR^{13}R^{14}$, —$NR^{14}SO_2R^{16}$, —($C_1$-$C_3$ alkyl)$NR^{14}SO_2R^{16}$, —$NR^{14}COR^{16}$, —($C_1$-$C_6$ alkyl)-$NR^{14}COR^{16}$, —$CONR^{14}R^{15}$, —($C_1$-$C_3$ alkyl)-$CONR^{14}R^{15}$, —$SO_2NR^{14}R^{15}$, —($C_1$-$C_3$ alkyl)-$SO_2NR^{14}R^{15}$, —$SO_2(C_1$-$C_3$ alkyl), or —($C_1$-$C_6$ alkyl)-$SO_2(C_1$-$C_3$ alkyl);
$R^5$ and $R^6$ are each independently hydrogen, halogen, —OH, $C_1$-$C_3$ alkyl, $C_2$-$C_3$ alkenyl, $C_2$-$C_3$ alkynyl, or $C_1$-$C_3$ alkoxy; or $R^5$ and $R^6$ taken together form an optionally substituted 3- to 6-membered carbocyclyl or heterocyclyl;
$R^8$ and $R^9$ are each independently hydrogen, halogen, or $C_1$-$C_3$ alkyl;
$R^{8a}$ and $R^{9a}$ are each independently hydrogen, —OH, halogen, $C_1$-$C_3$ alkyl, $C_2$-$C_3$ alkenyl, $C_2$-$C_3$ alkynyl, $C_1$-$C_3$ alkoxy, —$NR^{13}R^{14}$, —($C_1$-$C_3$ alkyl)$NR^{13}R^{14}$, —$NR^{14}COR^{16}$, —($C_1$-$C_3$ alkyl)-$NR^{14}COR^{16}$, —$CONR^{14}R^{15}$, or —($C_1$-$C_3$ alkyl)-$CONR^{14}R^{15}$; or $R^{8a}$ and $R^{8b}$ taken together form an optionally substituted 3- to 6-membered carbocyclyl or heterocyclyl;
$R^{11}$, $R^{12}$, $R^{13}$, $R^{14}$ and $R^{15}$ are each independently hydrogen, $C_1$-$C_3$ alkyl, $C_2$-$C_3$ alkenyl, or $C_2$-$C_3$ alkynyl; or $R^{14}$ and $R^{15}$ taken together form a 3- to 6-membered heterocyclyl;
$R^7$, $R^{10}$ and $R^{16}$ are each independently hydrogen, $C_1$-$C_3$ alkyl, $C_2$-$C_3$ alkenyl, or $C_2$-$C_3$ alkynyl;
each m is independently 0, 1 or 2;
n1 and n2 are each independently 0, 1, or 2;
n3 is 0, 1, 2, 3, 4 or 5; and
t is 0, 1 or 2.

Embodiment 34

The compound of Embodiment 1, wherein the compound has the structure of formula (III):

(III)

or a pharmaceutically acceptable salt, tautomer, stereoisomer or prodrug thereof, wherein:

A and B are each independently selected from phenyl, pyridyl, pyrimidyl, or thiophene;
C is a 3- to 10-membered ring;
X is a bond, —$(CR^5R^6)_t$—, or —$NR^7$;
Y is a bond, —$(CR^8R^9)_m$—, —O—, —S—, —$S(=O)$—, —$SO_2$—, or —$NR^7$—;
W is a bond, —$(CR^{8a}R^{9a})_m$—, —$C(=O)$—, —$N(R^7)CO$—, —$CONR^7$—, or —$NSO_2R^7$—;
Z is a bond, —$CH_2$—, —$C(CH_3)H$—, —O—, —S—, —NH—, —$NCH_3$—, or —$N(COCH_3)$—;
V is —$CH_2$—, —$CH_2CH_2$—, or —$CH_2CH_2CH_2$—;
L is halogen, —$NH_2$, or —$CF_3$;
$R^1$ and $R^2$ are each independently hydrogen, halogen, —CN, —$CF_3$, —OH, optionally substituted $C_1$-$C_6$ alkyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —$NR^{13}R^{14}$, optionally substituted —($C_1$-$C_6$ alkyl)-$NR^{13}R^{14}$, —$NR^{14}SO_2R^{16}$, optionally substituted —($C_1$-$C_6$ alkyl) $NR^{14}SO_2R^{16}$, —$NR^{14}COR^{16}$, optionally substituted —($C_1$-$C_6$ alkyl)-$NR^{14}COR^{16}$, —$CONR^{13}R^{14}$, optionally substituted —($C_1$-$C_6$ alkyl)-$CONR^{14}R^{15}$, —$SO_2NR^{14}R^{15}$, optionally substituted —($C_1$-$C_6$ alkyl)-$SO_2NR^{14}R^{15}$, optionally substituted —$SO_2R^{16}$ or optionally substituted —($C_1$-$C_6$ alkyl)-$SO_2R^{16}$;

$R^3$ is selected from hydrogen, halogen, oxo, =S, =$NR^{16}$, —CN, —$CF_3$, —OH, —S($C_1$-$C_3$ alkyl), $C_1$-$C_3$ alkyl, $C_2$-$C_3$ alkenyl, $C_2$-$C_3$ alkynyl, $C_1$-$C_3$ alkoxy, —$NR^{13}R^{14}$, —($C_1$-$C_3$ alkyl)-$NR^{13}R^{14}$, —$NR^{14}SO_2R^{16}$, —($C_1$-$C_3$ alkyl)$NR^{14}SO_2R^{16}$, —$NR^{14}COR^{16}$, —($C_1$-$C_6$ alkyl)- $NR^{14}COR^{16}$, —$CONR^{14}R^{15}$, —($C_1$-$C_3$ alkyl)-$CONR^{14}R^{15}$, —$SO_2NR^{14}R^{15}$, —($C_1$-$C_3$ alkyl)-$SO_2NR^{14}R^{15}$, —$SO_2$($C_1$-$C_3$ alkyl), or —($C_1$-$C_6$ alkyl)-$SO_2$($C_1$-$C_3$ alkyl);

$R^5$ and $R^6$ are each independently hydrogen, halogen, —OH, $C_1$-$C_3$ alkyl, $C_2$-$C_3$ alkenyl, $C_2$-$C_3$ alkynyl, or $C_1$-$C_3$ alkoxy; or $R^5$ and $R^6$ taken together form an optionally substituted 3- to 6-membered carbocyclyl or heterocyclyl;

$R^7$ is hydrogen, $C_1$-$C_6$ alkyl, $C_2$-$C_6$ alkenyl, or $C_2$-$C_6$ alkynyl;

$R^8$ and $R^9$ are each independently hydrogen, halogen, or $C_1$-$C_3$ alkyl;

$R^{8a}$ and $R^{9a}$ are each independently hydrogen, —OH, halogen, $C_1$-$C_3$ alkyl, $C_2$-$C_3$ alkenyl, $C_2$-$C_3$ alkynyl, $C_1$-$C_3$ alkoxy, —$NR^{13}R^{14}$, —($C_1$-$C_3$ alkyl)-$NR^{13}R^{14}$, —$NR^{14}COR^{16}$, —($C_1$-$C_3$ alkyl)-$NR^{14}COR^{16}$, —$CONR^{14}R^{15}$, or —($C_1$-$C_3$ alkyl)-$CONR^{14}R^{15}$; or $R^{8a}$ and $R^{8b}$ taken together form an optionally substituted 3- to 6-membered carbocyclyl or heterocyclyl;

$R^{13}$, $R^{14}$ and $R^{15}$ are each independently hydrogen, $C_1$-$C_3$ alkyl, $C_2$-$C_3$ alkenyl, or $C_2$-$C_3$ alkynyl; or $R^{14}$ and $R^{15}$ taken together form a 3- to 6-membered heterocyclyl;

$R^{16}$ is hydrogen, $C_1$-$C_3$ alkyl, $C_2$-$C_3$ alkenyl, or $C_2$-$C_3$ alkynyl;

each m is independently 0, 1 or 2;

n1 and n2 are each independently 0, 1, or 2;

n3 is 0, 1, 2, 3, 4 or 5; and t is 0, 1 or 2.

Embodiment 35

The compound of Embodiment 33 or 34, wherein $R^{8a}$ and $R^{9a}$ are each independently hydrogen, halogen, $C_1$-$C_3$ alkyl, $C_2$-$C_3$ alkenyl, $C_2$-$C_3$ alkynyl, $C_1$-$C_3$ alkoxy, —$NR^{13}R^{14}$, —($C_1$-$C_3$ alkyl)-$NR^{13}R^{14}$, —$NR^{14}COR^{16}$, —($C_1$-$C_3$ alkyl)-$NR^{14}COR^{16}$, —$CONR^{14}R^{15}$, or —($C_1$-$C_3$ alkyl)-$CONR^{14}R^{15}$.

Embodiment 36

The compound of Embodiment 33 or 34, wherein $R^{8a}$ and $R^9$ are not —OH.

Embodiment 37

The compound of Embodiments 1, wherein the compound has the structure of formula (IV):

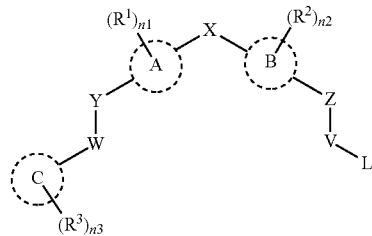

(IV)

or a pharmaceutically acceptable salt, tautomer, stereoisomer or prodrug thereof, wherein:

A and B are each independently selected from phenyl, pyridyl, pyrimidyl, or thiophene;

C is a 3- to 10-membered ring;

X is a bond, —($CR^5R^6$)$_t$—, or —$NR^7$;

Y and Z are each independently a bond, —$CH_2$—, —C($CH_3$)H—, —O—, —S—, —NH—, —$NCH_3$—, or —N(COCH$_3$)—;

W is a bond, —$CH_2$—, —C($CH_3$)H—, —C(=O)—, —N($R^7$)CO—, or —$CONR^7$—;

V is —$CH_2$—, —$CH_2CH_2$—, or —$CH_2CH_2CH_2$—;

L is halogen, —$NH_2$, or —$CF_3$;

$R^1$ and $R^2$ are each independently hydrogen, halogen, —CN, —$CF_3$, —OH, optionally substituted $C_1$-$C_6$ alkyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —$NR^{13}R^{14}$, optionally substituted —($C_1$-$C_6$ alkyl)-$NR^{13}R^{14}$, —$NR^{14}SO_2R^{16}$, optionally substituted —($C_1$-$C_6$ alkyl) $NR^{14}SO_2R^{16}$, —$NR^{14}COR^{16}$, optionally substituted —($C_1$-$C_6$ alkyl)-$NR^{14}COR^{16}$, —$CONR^{13}R^{14}$, optionally substituted —($C_1$-$C_6$ alkyl)-$CONR^{14}R^{15}$, —$SO_2NR^{14}R^{15}$, optionally substituted —($C_1$-$C_6$ alkyl)-$SO_2NR^{14}R^{15}$, optionally substituted —$SO_2R^{16}$ or optionally substituted —($C_1$-$C_6$ alkyl)-$SO_2R^{16}$;

$R^3$ is selected from hydrogen, halogen, oxo, =S, =$NR^{16}$, —CN, —$CF_3$, —OH, —S($C_1$-$C_3$ alkyl), $C_1$-$C_3$ alkyl, $C_2$-$C_3$ alkenyl, $C_2$-$C_3$ alkynyl, $C_1$-$C_3$ alkoxy, —$NR^{13}R^{14}$, —($C_1$-$C_3$ alkyl)-$NR^{13}R^{14}$, —$NR^{14}SO_2R^{16}$, —($C_1$-$C_3$ alkyl)$NR^{14}SO_2R^{16}$, —$NR^{14}COR^{16}$, —($C_1$-$C_6$ alkyl)- $NR^{14}COR^{16}$, —$CONR^{14}R^{15}$, —($C_1$-$C_3$ alkyl)-$CONR^{14}R^{15}$, —$SO_2NR^{14}R^{15}$, —($C_1$-$C_3$ alkyl)-$SO_2NR^{14}R^{15}$, —$SO_2$($C_1$-$C_3$ alkyl), or —($C_1$-$C_6$ alkyl)-$SO_2$($C_1$-$C_3$ alkyl);

$R^5$ and $R^6$ are each independently hydrogen, halogen, —OH, $C_1$-$C_3$ alkyl, $C_2$-$C_3$ alkenyl, $C_2$-$C_3$ alkynyl, or $C_1$-$C_3$ alkoxy; or $R^5$ and $R^6$ taken together form an optionally substituted 3- to 6-membered carbocyclyl or heterocyclyl;

$R^7$ is H or $C_1$-$C_6$ alkyl;

$R^{13}$, $R^{14}$ and $R^{15}$ are each independently hydrogen, $C_1$-$C_3$ alkyl, $C_2$-$C_3$ alkenyl, or $C_2$-$C_3$ alkynyl; or $R^{14}$ and $R^{15}$ taken together form a 3- to 6-membered heterocyclyl;

$R^{16}$ is hydrogen, $C_1$-$C_3$ alkyl, $C_2$-$C_3$ alkenyl, or $C_2$-$C_3$ alkynyl;

n1 and n2 are each independently 0, 1, or 2;

n3 is 0, 1, 2, 3, 4 or 5; and t is 0, 1 or 2.

Embodiment 38

The compound of any one of Embodiments 33-37, wherein C is 5- to 10-membered heteroaryl or aryl.

Embodiment 39

The compound of any one of Embodiments 33-38, wherein C is 5- to 7-membered heteroaryl comprising 1, 2, or 3 heteroatoms selected from O, S, or N as a ring member.

Embodiment 40

The compound of any one of Embodiments 33-39, wherein C is pyrazole, imidazole, oxazole, oxadiazole, oxazolone, isoxazole, thiazole, pyridyl, or pyrimidyl.

Embodiment 41

The compound of any one of Embodiments 33-39, wherein C, which is optionally substituted with $R^3$, is selected from

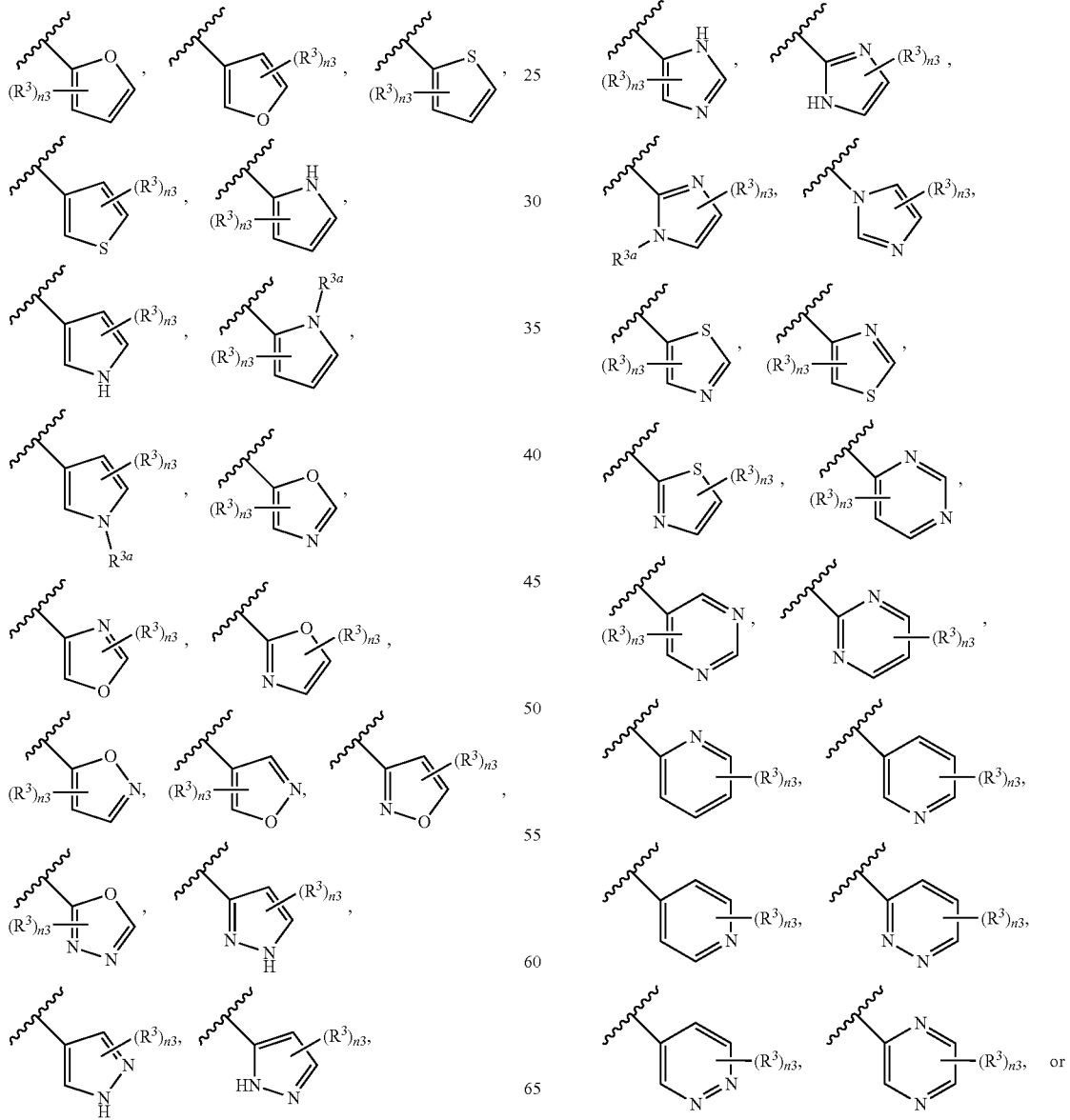

or

-continued

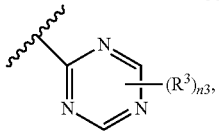

wherein $R^{3a}$ is $C_1$-$C_3$ alkyl.

Embodiment 42

The compound of any one of Embodiments 33-38, wherein C is phenyl or naphthyl.

Embodiment 43

The compound of any one of Embodiments 33-37, wherein C is 5- to 10-membered heterocyclyl comprising 1, 2, or 3 heteroatoms selected from O, S, or N as a ring member.

Embodiment 44

The compound of Embodiment 43, wherein
C is

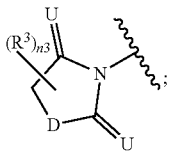

D is —O—, —NH— or —NR³—; and
U is each independently O, S, or NR¹⁶.

Embodiment 45

The compound of Embodiment 43, wherein C is imidazolidine, imidazolidine-dione, or dihydrooxazole.

Embodiment 46

The compound of any one of Embodiments 33-45, wherein A has a meta or para connectivity with X and Y.

Embodiment 47

The compound of any one of Embodiments 33-46, wherein B has a meta or para connectivity with X and Z.

Embodiment 48

The compound of any one of Embodiments 33-47, wherein n1 and n2 are each independently 0, 1, or 2.

Embodiment 49

The compound of Embodiments 1, wherein the compound has the structure of formula (V): n3 (V):

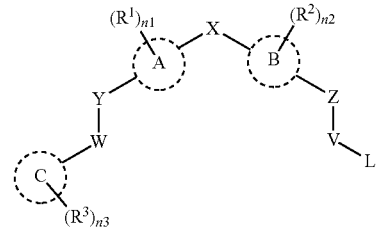

or a pharmaceutically acceptable salt, tautomer, stereoisomer or prodrug thereof, wherein:

A and B are each independently selected from phenyl, pyridyl, pyrimidyl, or thiophene;

C is a 5- to 10-membered heteroaryl or aryl;

X is a bond, —(CR⁵R⁶)$_t$—, or —NR⁷;

Y is a bond, —CH₂—, —C(CH₃)H—, —O—, —S—, —NH—, —NCH₃—, or —N(COCH₃)—;

Z is a bond, —CH₂—, —C(CH₃)H—, —O—, —S—, —NH—, —NCH₃—, or —N(COCH₃)—;

W is a bond, —CH₂—, —C(CH₃)H—, —C(=O)—, —N(R⁷)CO—, or —CONR⁷—;

V is —CH₂—, —CH₂CH₂—, or —CH₂CH₂CH₂—;

L is halogen, —NH₂, or —CF₃;

R¹ and R² are each independently hydrogen, halogen, —CN, —CF₃, —OH, optionally substituted $C_1$-$C_6$ alkyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —NR¹³R¹⁴, optionally substituted —($C_1$-$C_6$ alkyl)-NR¹³R¹⁴, —NR¹⁴SO₂R¹⁶, optionally substituted —($C_1$-$C_6$ alkyl)NR¹⁴SO₂R¹⁶, —NR¹⁴COR¹⁶, optionally substituted —($C_1$-$C_6$ alkyl)-NR¹⁴COR¹⁶, —CONR¹³R¹⁴, optionally substituted —($C_1$-$C_6$ alkyl)-CONR¹⁴R¹⁵, —SO₂NR¹⁴R¹⁵, optionally substituted —($C_1$-$C_6$ alkyl)-SO₂NR¹⁴R¹⁵, optionally substituted —SO₂R¹⁶ or optionally substituted —($C_1$-$C_6$ alkyl)-SO₂R¹⁶;

R³ is selected from hydrogen, halogen, oxo, =S, —CN, —CF₃, —OH, —S($C_1$-$C_3$ alkyl), $C_1$-$C_3$ alkyl, $C_2$-$C_3$ alkenyl, $C_2$-$C_3$ alkynyl, $C_1$-$C_3$ alkoxy, —NR¹³R¹⁴, —($C_1$-$C_3$ alkyl)-NR¹³R¹⁴, —NR¹⁴SO₂R¹⁶, —($C_1$-$C_3$ alkyl)NR¹⁴SO₂R¹⁶, —NR¹⁴COR¹⁶, —($C_1$-$C_6$ alkyl)-NR¹⁴COR¹⁶, —CONR¹⁴R¹⁵, —($C_1$-$C_3$ alkyl)-CONR¹⁴R¹⁵, —SO₂NR¹⁴R¹⁵, —($C_1$-$C_3$ alkyl)-SO₂NR¹⁴R¹⁵, —SO₂($C_1$-$C_3$ alkyl), or —($C_1$-$C_6$ alkyl)-SO₂($C_1$-$C_3$ alkyl);

R⁵ and R⁶ are each independently hydrogen, halogen, —OH, $C_1$-$C_3$ alkyl, $C_2$-$C_3$ alkenyl, $C_2$-$C_3$ alkynyl, or $C_1$-$C_3$ alkoxy; or R⁵ and R⁶ taken together form an optionally substituted 3- to 6-membered carbocyclyl or heterocyclyl;

R⁷ is H or $C_1$-$C_6$ alkyl;

R¹³, R¹⁴ and R¹⁵ are each independently hydrogen, $C_1$-$C_3$ alkyl, $C_2$-$C_3$ alkenyl, or $C_2$-$C_3$ alkynyl; or R¹⁴ and R¹⁵ taken together form a 3- to 6-membered heterocyclyl;

R¹⁶ is hydrogen, $C_1$-$C_3$ alkyl, $C_2$-$C_3$ alkenyl, or $C_2$-$C_3$ alkynyl;

n1 and n2 are each independently 0, 1, or 2;

n3 is 0, 1, 2, 3, 4 or 5; and t is 0, 1 or 2.

Embodiment 50

The compound of Embodiment 49, wherein C is 5- to 7-membered heteroaryl comprising 1, 2, or 3 heteroatoms selected from O, S, or N as a ring member.

Embodiment 51

The compound of Embodiment 49 or 50, wherein C is pyrazole, imidazole, oxazole, oxadiazole, oxazolone, isoxazole, thiazole, pyridyl, or pyrimidyl.

Embodiment 52

The compound of Embodiment 49, wherein C, which is optionally substituted with $R^3$, is selected from

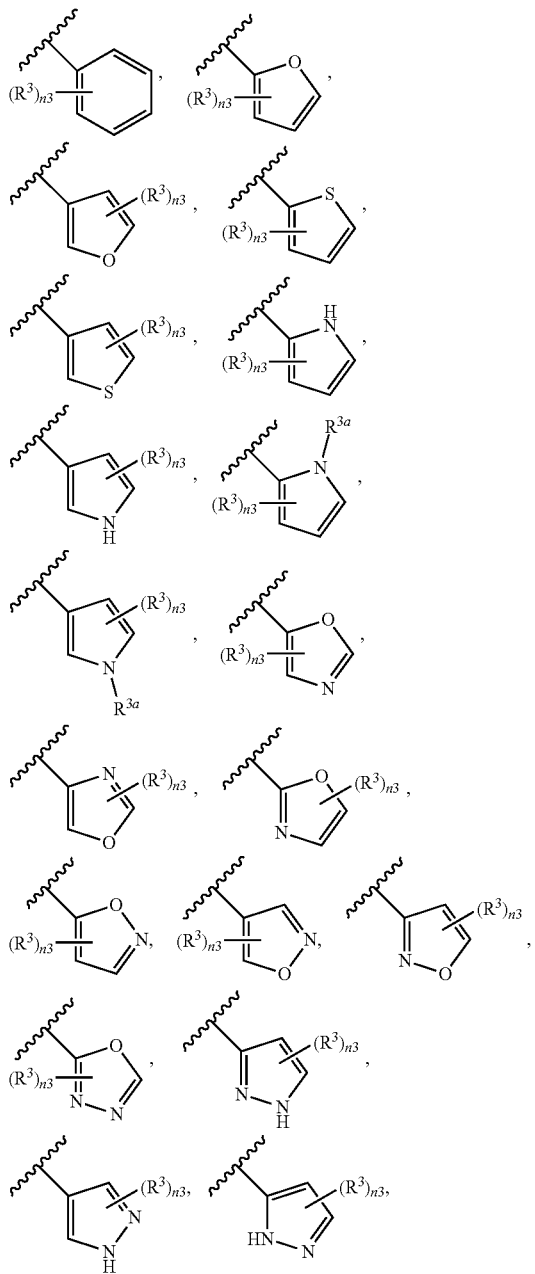

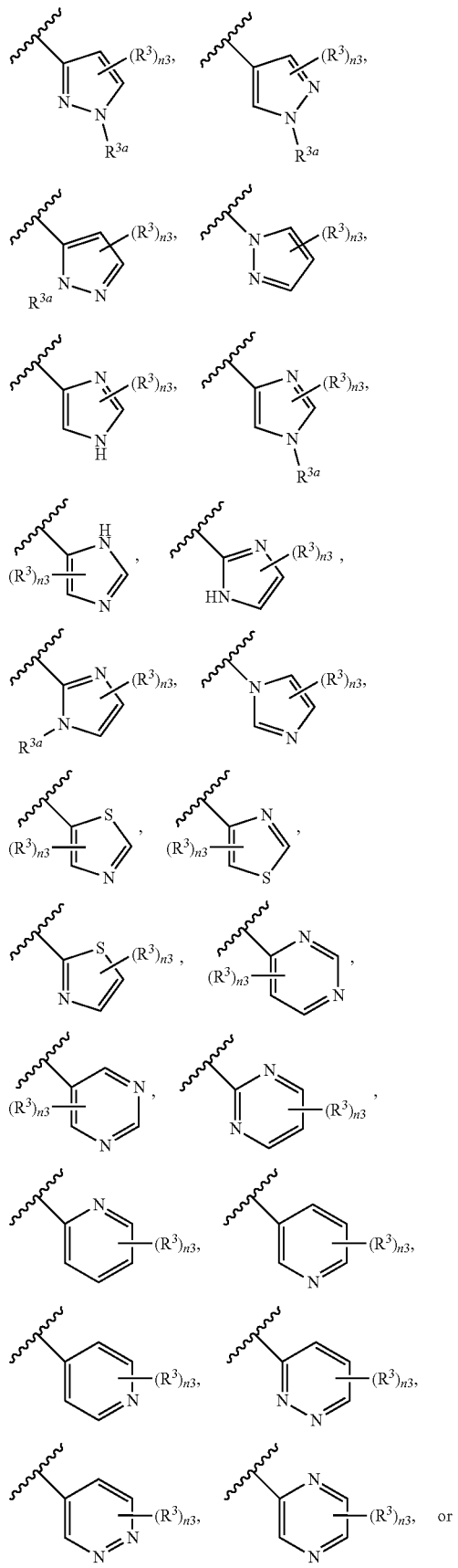

or

-continued

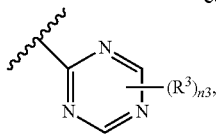

wherein $R^{3a}$ is $C_1$-$C_3$ alkyl.

Embodiment 53

The compound of any one of Embodiments 49-52, wherein A has a meta or para connectivity with X and Y.

Embodiment 54

The compound of any one of Embodiments 49-53, wherein B has a meta or para connectivity with X and Z.

Embodiment 55

The compound of any one of Embodiments 49-54, wherein A and B are each phenyl.

Embodiment 56

The compound of any one of Embodiments 49-55, wherein —Z-V-L is —Z—CH$_2$CH$_2$C$_1$, —Z—CH$_2$CH$_2$CH$_2$C$_1$, —Z—CH$_2$CH$_2$NH$_2$, or —Z—CH$_2$CH$_2$CH$_2$NH$_2$, wherein Z is a bond, —O—, —NH—, or —N(COCH$_3$)—.

Embodiment 57

The compound of any one of Embodiments 49-56, wherein —Y—W— is a bond, —OCH$_2$—, —OCH$_2$CH$_2$—, —OCH(CH$_3$)—, —NH—, —NHCH$_2$—, —NHC(=O)—, or —C(=O)NH—.

Embodiment 58

The compound of any one of Embodiments 49-57, wherein X is a bond, —CH$_2$—, —C(CH$_3$)H—, —C(CH$_3$)$_2$—, or —CH$_2$CH$_2$—.

Embodiment 59

The compound of Embodiment 1, wherein the compound has the structure of formula (VI):

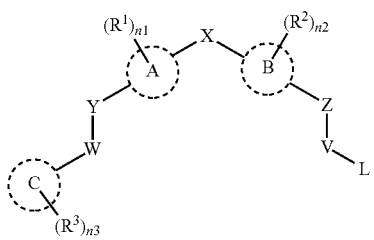

(VI)

wherein:
A and B are each independently selected from phenyl, pyridyl, pyrimidyl, or thiophene;
C is a 5- to 10-membered heterocyclyl;
X is a bond, —(CR$^5$R$^6$)$_t$—, or —NR$^7$;

Y is a bond, —CH$_2$—, —C(CH$_3$)H—, —O—, —S—, —NH—, —NCH$_3$—, or —N(COCH$_3$)—;
Z is a bond, —CH$_2$—, —C(CH$_3$)H—, —O—, —S—, —NH—, —NCH$_3$—, or —N(COCH$_3$)—;
W is a bond, —CH$_2$—, —C(CH$_3$)H—, —C(=O)—, —N(R$^7$)CO—, or —CONR$^7$—;
V is —CH$_2$—, —CH$_2$CH$_2$—, or —CH$_2$CH$_2$CH$_2$—;
L is halogen, —NH$_2$, or —CF$_3$;
R$^1$ and R$^2$ are each independently hydrogen, halogen, —CN, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{13}$R$^{14}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$ or optionally substituted —(C$_1$-C$_6$ alkyl)-SO$_2$R$^{16}$;
R$^3$ is selected from hydrogen, halogen, oxo, =S, =NR$^{16}$, —CN, —CF$_3$, —OH, —S(C$_1$-C$_3$ alkyl), C$_1$-C$_3$ alkyl, C$_2$-C$_3$ alkenyl, C$_2$-C$_3$ alkynyl, C$_1$-C$_3$ alkoxy, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl)NR$^{14}$SO$_2$R$^{16}$, —NR$^{14}$COR$^{16}$, —(C$_1$-C$_6$ alkyl)- NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO$_2$(C$_1$-C$_3$ alkyl), or —(C$_1$-C$_6$ alkyl)-SO$_2$(C$_1$-C$_3$ alkyl);
R$^5$ and R$^6$ are each independently hydrogen, halogen, —OH, C$_1$-C$_3$ alkyl, C$_2$-C$_3$ alkenyl, C$_2$-C$_3$ alkynyl, or C$_1$-C$_3$ alkoxy; or R$^5$ and R$^6$ taken together form an optionally substituted 3- to 6-membered carbocyclyl or heterocyclyl;
R$^7$ is H or C$_1$-C$_6$ alkyl;
R$^{13}$, R$^{14}$ and R$^{15}$ are each independently hydrogen, C$_1$-C$_3$ alkyl, C$_2$-C$_3$ alkenyl, or C$_2$-C$_3$ alkynyl; or R$^{14}$ and R$^{15}$ taken together form a 3- to 6-membered heterocyclyl; and
R$^{16}$ is hydrogen, C$_1$-C$_3$ alkyl, C$_2$-C$_3$ alkenyl, or C$_2$-C$_3$ alkynyl;
n1 and n2 are each independently 0, 1, or 2;
n3 is 0, 1, 2, 3, 4 or 5; and
t is 0, 1 or 2.

Embodiment 60

The compound of Embodiment 57, wherein C is 5- to 7-membered saturated or partially saturated heterocycle comprising 1, 2, or 3 heteroatoms selected from O, S, or N as a ring member.

Embodiment 61

The compound of Embodiment 59 or 60, wherein C is imidazolidine, imidazolidine-dione, or dihydrooxazole.

Embodiment 62

The compound of any one of Embodiments 59-61, wherein C, which is optionally substituted with R$^3$, is selected from

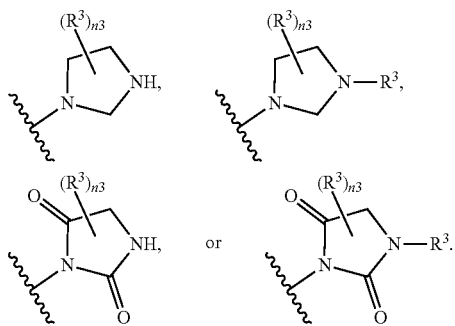

Embodiment 63

The compound of any one of Embodiments 59-62, wherein A has a meta or para connectivity with X and Y.

Embodiment 64

The compound of any one of Embodiments 59-63, wherein B has a meta or para connectivity with X and Z.

Embodiment 65

The compound of any one of Embodiments 59-64, wherein A and B are each phenyl.

Embodiment 66

The compound of any one of Embodiments 59-65, wherein —V-L is —CH$_2$CH$_2$Cl, —CH$_2$CH$_2$CH$_2$Cl, —CH$_2$CH$_2$NH$_2$, or —CH$_2$CH$_2$CH$_2$NH$_2$, and Z is a bond, —O—, —NH—, or —N(COCH$_3$)—.

Embodiment 67

The compound of any one of Embodiments 59-66, wherein —Y—W— is a bond, —OCH$_2$—, —OCH$_2$CH$_2$—, —OCH(CH$_3$)—, —NH—, —NHCH$_2$—, —NHC(=O)—, or —C(=O)NH—.

Embodiment 68

The compound of any one of Embodiments 59-67, wherein X is a bond, —CH$_2$—, —C(CH$_3$)H—, —C(CH$_3$)$_2$—, or —CH$_2$CH$_2$—.

Embodiment 69

The compound of any one of Embodiments 59-68, R$^3$ is oxo, =S, =NR$^{16}$, C$_1$-C$_3$ alkyl, —SO$_2$(C$_1$-C$_3$ alkyl), or —NHSO$_2$(C$_1$-C$_3$ alkyl).

Embodiment 70

The compound of Embodiment 1, wherein the compound has the structure of formula (A):

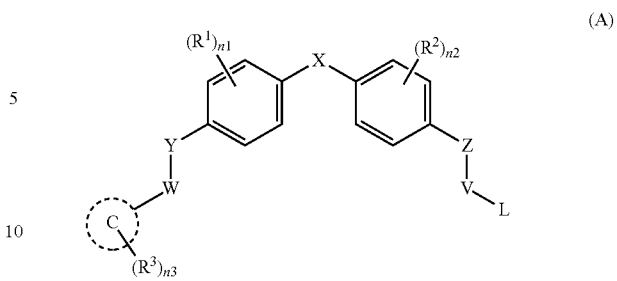

(A)

or a pharmaceutically acceptable salt, tautomer, stereoisomer or prodrug thereof, wherein:

C is a phenyl or a 5- to 7-membered monocyclic heteroaryl comprising 1, 2, or 3 heteroatoms selected from O, S, or N as a ring member;

X is a bond, —(CR$^5$R$^6$)$_t$—, or —NR$^7$;

Y is a bond, —CH$_2$—, —C(CH$_3$)H—, —O—, —S—, —NH—, —NCH$_3$—, or —N(COCH$_3$)—;

Z is a bond, —CH$_2$—, —O—, or —NH—;

W is a bond, —CH$_2$—, —C(CH$_3$)H—, —C(=O)—, —N(R$^7$)CO—, or —CONR$^7$—;

V is —CH$_2$—, —CH$_2$CH$_2$—, or —CH$_2$CH$_2$CH$_2$—;

L is halogen, —NH$_2$, or —CF$_3$;

R$^1$ and R$^2$ are each independently hydrogen, halogen, —CN, —CF$_3$, methyl, or —CONH$_2$;

R$^3$ is selected from hydrogen, F, Cl, Br, I, oxo, —CN, —CF$_3$, —OH, C$_1$-C$_3$ alkyl, C$_2$-C$_3$ alkenyl, C$_2$-C$_3$ alkynyl, —S(C$_1$-C$_3$ alkyl), —SO$_2$(C$_1$-C$_3$ alkyl), —NHSO$_2$CH$_3$, —N(CH$_3$)SO$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), or —N(CH$_3$)CO(C$_1$-C$_3$ alkyl);

R$^5$ and R$^6$ are each independently hydrogen, halogen, —OH, or C$_1$-C$_3$ alkyl;

R$^7$ is H or C$_1$-C$_6$ alkyl;

n1 and n2 are each independently 0, 1, or 2;

n3 is 0, 1, 2, 3, 4 or 5; and t is 0, 1 or 2.

Embodiment 71

The compound of Embodiment 70, wherein C is 5- to 7-membered monocyclic heteroaryl comprising 1, 2, or 3 heteroatoms selected from O, S, or N as a ring member.

Embodiment 72

The compound of Embodiment 1, wherein the compound has the structure of formula (B)

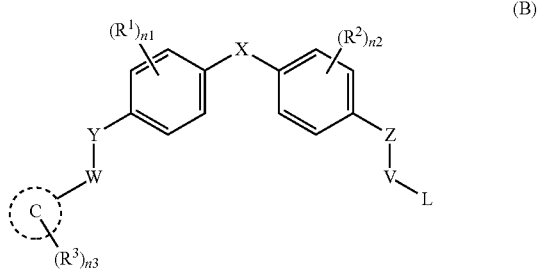

(B)

or a pharmaceutically acceptable salt, tautomer, stereoisomer or prodrug thereof, wherein:

C is a 5- to 7-membered saturated or partially saturated monocyclic heterocycle comprising 1, 2, or 3 heteroatoms selected from O, S, or N as a ring member;

X is a bond, —(CR$^5$R$^6$)$_t$—, or —NR$^7$;

Y is a bond, —CH$_2$—, —C(CH$_3$)H—, —O—, —S—, —NH—, —NCH$_3$—, or —N(COCH$_3$)—;

Z is a bond, —CH$_2$—, —O—, or —NH—;

W is a bond, —CH$_2$—, —C(CH$_3$)H—, —C(=O)—, —N(R$^7$)CO—, or —CONR$^7$—;

V is —CH$_2$—, —CH$_2$CH$_2$—, or —CH$_2$CH$_2$CH$_2$—;

L is halogen, —NH$_2$, or —CF$_3$;

R$^1$ and R$^2$ are each independently hydrogen, halogen, —CN, —CF$_3$, methyl, or —CONH$_2$;

R$^3$ is selected from hydrogen, F, Cl, Br, I, oxo, =S, =NR$^{16}$, —CN, —CF$_3$, —OH, C$_1$-C$_3$ alkyl, C$_2$-C$_3$ alkenyl, C$_2$-C$_3$ alkynyl, —S(C$_1$-C$_3$ alkyl), —SO$_2$(C$_1$-C$_3$ alkyl), —NHSO$_2$CH$_3$, —N(CH$_3$)SO$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), or —N(CH$_3$)CO(C$_1$-C$_3$ alkyl);

R$^5$ and R$^6$ are each independently hydrogen, halogen, —OH, or C$_1$-C$_3$ alkyl;

R$^7$ is H or C$_1$-C$_6$ alkyl;

R$^{16}$ is hydrogen or C$_1$-C$_3$ alkyl;

n1 and n2 are each independently 0, 1, or 2;

n3 is 0, 1, 2, 3, 4 or 5; and t is 0, 1 or 2.

Embodiment 73

The compound of any one of Embodiments 70-72, wherein —V-L is —CH$_2$CH$_2$C$_1$, —CH$_2$CH$_2$CH$_2$C$_1$, —CH$_2$CH$_2$NH$_2$, or —CH$_2$CH$_2$CH$_2$NH$_2$.

Embodiment 74

The compound of any one of Embodiments 70-73, wherein —Y—W— is a bond, —OCH$_2$—, —OCH$_2$CH$_2$—, —OCH(CH$_3$)—, —NH—, —NHCH$_2$—, —NHC(=O)—, or —C(=O)NH—.

Embodiment 75

The compound of any one of Embodiments 70-74, wherein X is a bond, —CH$_2$—, —C(CH$_3$)H—, —C(CH$_3$)$_2$—, or —CH$_2$CH$_2$—.

Embodiment 76

The compound of Embodiment 1, wherein the compound has the structure of formula (C):

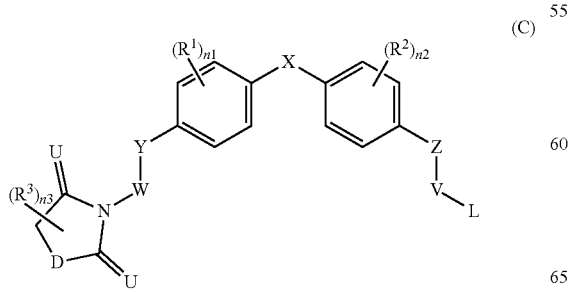

(C)

or a pharmaceutically acceptable salt, tautomer, stereoisomer or prodrug thereof, wherein:

A and B are each independently selected from phenyl, pyridyl, pyrimidyl, or thiophene;

X is a bond, —(CR$^5$R$^6$)$_t$—, or —NR$^7$;

Y is a bond, —CH$_2$—, —C(CH$_3$)H—, —O—, —S—, —NH—, —NCH$_3$—, or —N(COCH$_3$)—;

Z is a bond, —CH$_2$—, —C(CH$_3$)H—, —O—, —S—, —NH—, —NCH$_3$—, or —N(COCH$_3$)—;

W is a bond, —CH$_2$—, —C(CH$_3$)H—, —C(=O)—, —N(R$^7$)CO—, or —CONR$^7$;

V is —CH$_2$—, —CH$_2$CH$_2$—, or —CH$_2$CH$_2$CH$_2$—;

L is halogen, —NH$_2$, or —CF$_3$;

D is —NH or —NR$^3$;

U is each independently O, S, or NR$^{16}$;

R$^1$ and R$^2$ are each independently hydrogen, halogen, —CN, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{13}$R$^{14}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$ or optionally substituted —(C$_1$-C$_6$ alkyl)-SO$_2$R$^{16}$;

R$^3$ is selected from hydrogen, halogen, —CN, —CF$_3$, —OH, —S(C$_1$-C$_3$ alkyl), C$_1$-C$_3$ alkyl, C$_2$-C$_3$ alkenyl, C$_2$-C$_3$ alkynyl, C$_1$-C$_3$ alkoxy, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl)NR$^{14}$SO$_2$R$^{16}$, —NR$^{14}$COR$^{16}$, —(C$_1$-C$_6$ alkyl)-NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO$_2$(C$_1$-C$_3$ alkyl), or —(C$_1$-C$_6$ alkyl)-SO$_2$(C$_1$-C$_3$ alkyl);

R$^5$ and R$^6$ are each independently hydrogen, halogen, —OH, C$_1$-C$_3$ alkyl, C$_2$-C$_3$ alkenyl, C$_2$-C$_3$ alkynyl, C$_1$-C$_3$ alkoxy; or R$^5$ and R$^6$ taken together form an optionally substituted 3- to 6-membered carbocyclyl or heterocyclyl;

R$^7$ is H or C$_1$-C$_6$ alkyl;

R$^{13}$, R$^{14}$ and R$^{15}$ are each independently hydrogen, C$_1$-C$_3$ alkyl, C$_2$-C$_3$ alkenyl, C$_2$-C$_3$ alkynyl; or R$^{14}$ and R$^{15}$ taken together form a 3- to 6-membered heterocyclyl;

R$^{16}$ is hydrogen, C$_1$-C$_3$ alkyl, C$_2$-C$_3$ alkenyl, or C$_2$-C$_3$ alkynyl;

n1 and n2 are each independently 0, 1, or 2;

n3 is 0, 1, 2, or 3; and t is 0, 1 or 2.

Embodiment 77

The compound of Embodiment 1, wherein the compound has the structure of formula (D):

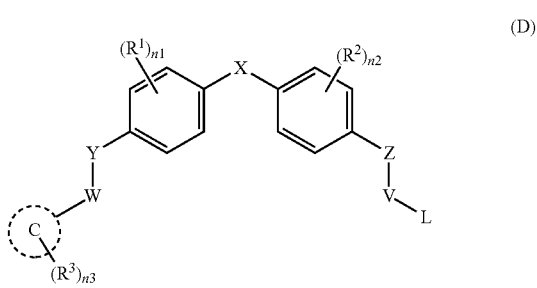

(D)

or a pharmaceutically acceptable salt, tautomer, stereoisomer or prodrug thereof, wherein:
C is a 5- or 6-membered heteroaryl comprising 1 or 2 heteroatoms selected from O, S, or N as a ring member;
X is —(CR$^5$R$^6$)$_t$— or —NR$^7$—;
Y is a bond, —CH$_2$—, —O—, or —NH—;
Z is a bond, —CH$_2$—, —O—, or —NH—;
W is a bond, —CH$_2$—, or —C(CH$_3$)H—;
V is —CH$_2$—, —CH$_2$CH$_2$—, or —CH$_2$CH$_2$CH$_2$—;
L is hydrogen, halogen, —NH$_2$, or —CF$_3$;
R$^1$ and R$^2$ are each independently hydrogen, halogen, —CN, —CF$_3$, methyl, or —CONH$_2$;
R$^3$ is selected from hydrogen, F, Cl, Br, I, oxo, —CN, —CF$_3$, —OH, C$_1$-C$_3$ alkyl, C$_2$-C$_3$ alkenyl, C$_2$-C$_3$ alkynyl, —S(C$_1$-C$_3$ alkyl), —SO$_2$(C$_1$-C$_3$ alkyl), —NHSO$_2$CH$_3$, —N(CH$_3$)SO$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), or —N(CH$_3$)CO(C$_1$-C$_3$ alkyl);
R$^5$ and R$^6$ are each independently hydrogen, halogen, —OH, or C$_1$-C$_3$ alkyl;
R$^7$ is H or C$_1$-C$_6$ alkyl;
n1 and n2 are each independently 0, 1, or 2;
n3 is 0, 1, 2, 3, 4 or 5; and
t is 0, 1 or 2.

Embodiment 78

The compound of Embodiments 1, wherein the compound has the structure of formula (E)

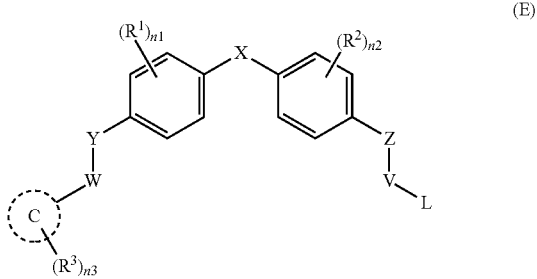

(E)

or a pharmaceutically acceptable salt, tautomer, stereoisomer or prodrug thereof, wherein:
C is

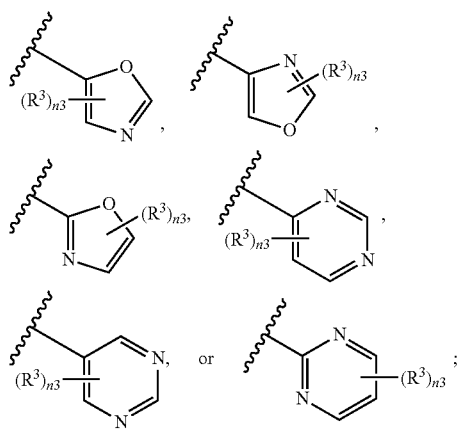

X is —(CR$^5$R$^6$)$_t$— or —NR$^7$—;
Y is a bond, —CH$_2$—, —O—, or —NH—;
Z is a bond, —CH$_2$—, —O—, or —NH—;
W is a bond, —CH$_2$—, or —C(CH$_3$)H—;
V is —CH$_2$—, —CH$_2$CH$_2$—, or —CH$_2$CH$_2$CH$_2$—;
L is hydrogen or halogen;
R$^1$ and R$^2$ are each independently hydrogen, halogen, —CN, —CF$_3$, methyl, or —CONH$_2$;
R$^3$ is selected from hydrogen, F, Cl, Br, I, oxo, —CN, —CF$_3$, —OH, C$_1$-C$_3$ alkyl, C$_2$-C$_3$ alkenyl, C$_2$-C$_3$ alkynyl, —S(C$_1$-C$_3$ alkyl), —SO$_2$(C$_1$-C$_3$ alkyl), —NHSO$_2$CH$_3$, —N(CH$_3$)SO$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), or —N(CH$_3$)CO(C$_1$-C$_3$ alkyl);
R$^5$ and R$^6$ are each independently hydrogen or C$_1$-C$_3$ alkyl;
R$^7$ is H or C$_1$-C$_6$ alkyl;
n1 and n2 are each independently 0, 1, or 2;
n3 is 0, 1, or 2; and
t is 1 or 2.

Embodiment 79

The compound of Embodiment 1, wherein the compound has the structure of formula (F):

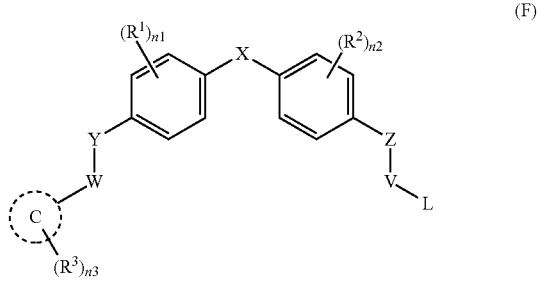

(F)

or a pharmaceutically acceptable salt, tautomer, stereoisomer or prodrug thereof, wherein:
C is

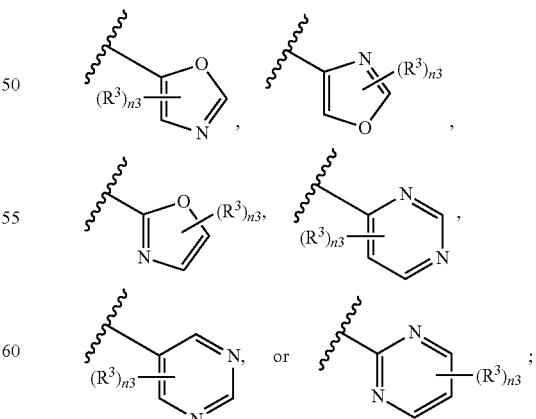

X is —(CR$^5$R$^6$)$_t$— or —NR$^7$—;
Y is —O—;
Z is —O—;

W is —CH$_2$— or —C(CH$_3$)H—;
V is —CH$_2$—, —CH$_2$CH$_2$—, or —CH$_2$CH$_2$CH$_2$—;
L is hydrogen or halogen;
R$^1$ and R$^2$ are each independently halogen or —CN;
R$^3$ is selected from —NHSO$_2$CH$_3$, —N(CH$_3$)SO$_2$CH$_3$, or —SO$_2$CH$_3$;
R$^5$ and R$^6$ are each independently hydrogen or C$_1$-C$_3$ alkyl;
R$^7$ is H or C$_1$-C$_6$ alkyl;
n1 and n2 are each independently 0, 1, or 2;
n3 is 0, 1, or 2; and
is 1 or 2.

Embodiment 80

The compound of Embodiment 1, wherein the compound has the structure of formula (G):

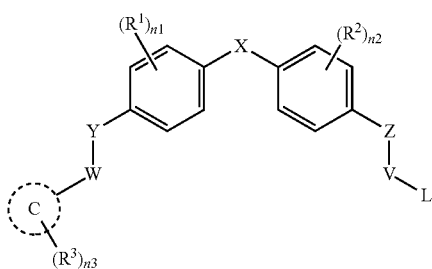

(G)

or a pharmaceutically acceptable salt, tautomer, stereoisomer or prodrug thereof, wherein:
C is

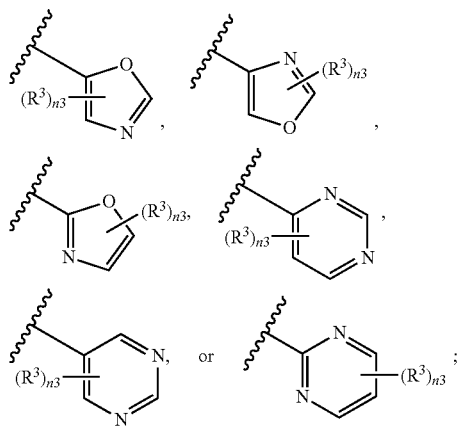

X is —(CR$^5$R$^6$)$_t$— or —NR$^7$—;
Y is —O—;
Z is —O—;
W is —CH$_2$— or —C(CH$_3$)H—;
V is —CH$_2$— and L is hydrogen;
or alternatively, V is —CH$_2$CH$_2$- or —CH$_2$CH$_2$CH$_2$—, and L is halogen
R$^1$ and R$^2$ are each independently Cl or —CN;
R$^3$ is selected from —NHSO$_2$CH$_3$, —N(CH$_3$)SO$_2$CH$_3$, or —SO$_2$CH$_3$;
R$^5$ and R$^6$ are each independently hydrogen or methyl;
R$^7$ is H or C$_1$-C$_6$ alkyl;
n1 and n2 are each independently 0, 1, or 2;
n3 is 1, or 2; and
t is 1.

Embodiment 81

The compound of Embodiment 1, wherein the compound has the structure of formula (H)

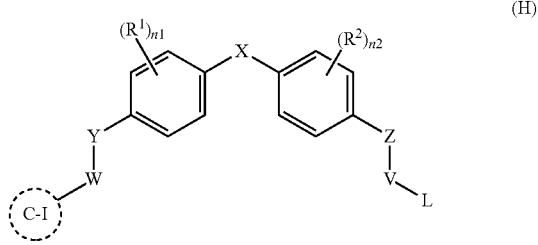

(H)

or a pharmaceutically acceptable salt, tautomer, stereoisomer or prodrug thereof, wherein:
C-I is

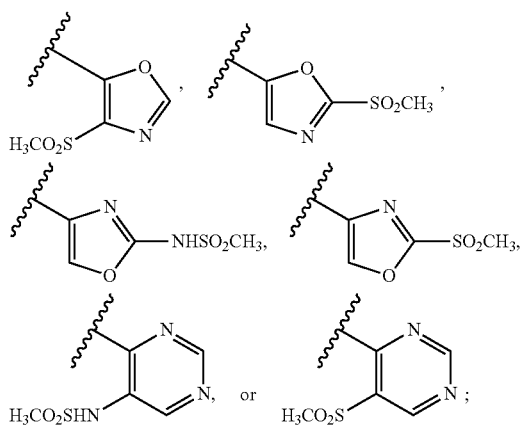

X is —(CR$^5$R$^6$)$_t$— or —NR$^7$—;
Y is —O—;
Z is —O—;
W is —CH$_2$— or —C(CH$_3$)H—;
V is —CH$_2$—, —CH$_2$CH$_2$- or —CH$_2$CH$_2$CH$_2$—;
L is halogen;
R$^1$ and R$^2$ are each independently Cl or —CN;
R$^5$ and R$^6$ are each independently hydrogen or methyl;
R$^7$ is H or C$_1$-C$_6$ alkyl;
n1 and n2 are each independently 0, 1, or 2; and
t is 1.

Embodiment 82

The compound of any one of Embodiments 1-69, wherein A and B are each monocyclic ring.

Embodiment 83

The compound of any one of Embodiments 1-69, wherein B is phenyl, pyridyl, or pyrimidyl.

Embodiment 84

The compound of any one of Embodiments 1-36, wherein Z and V are not both a bond.

Embodiment 85

The compound of any one of Embodiments 1-78, wherein Y and W are not both a bond.

Embodiment 86

The compound of any one of Embodiments 1-48, wherein C is a 4- to 10-membered ring.

Embodiment 87

A compound selected from Compounds A1-A97 or a pharmaceutically acceptable salt, tautomer, stereoisomer or prodrug thereof.

Embodiment 88

A compound selected from Compounds A98-A186 or a pharmaceutically acceptable salt, tautomer, stereoisomer or prodrug thereof.

Embodiment 89

A compound selected from Compounds A187-A211 or a pharmaceutically acceptable salt thereof.

Embodiment 90

A compound selected from Compounds B1-B11 or a pharmaceutically acceptable salt, tautomer, stereoisomer or prodrug thereof.

Embodiment 91

A compound having a structure of formula (IA):

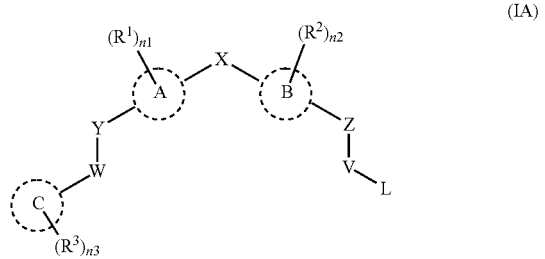

(IA)

or a pharmaceutically acceptable salt, tautomer, stereoisomer or prodrug thereof, wherein:
A and B are each independently aryl or heteroaryl;
C is a 3- to 10-membered ring;
X is a bond, $-(CR^5R^6)_t-$, $-O-$, $-C(=O)-$, $-S-$, $-S(=O)-$, $-SO_2-$, $-NR^7-$, $-N(R^7)CO-$, $-CON(R^7)-$, or $-NSO_2R^7-$;
Y and Z are each independently a bond, $-(CR^8R^9)_m-$, $-O-$, $-C(=O)-$, $-S-$, $-S(=O)-$, $-SO_2-$, or $-NR^7-$;
W and V are each independently a bond, $-(CR^{8a}R^{9a})_m-$, $-C(=O)-$, $-N(R^7)CO-$, $-CONR^7-$, or $-NSO_2R^7-$;

L is hydrogen, halogen, $-CF_2R^{10}$, $-CF_3$, $-CN$, $-OR^{10}$, $-NR^{11}R^{12}$, or $-CONR^{11}R^{12}$;
$R^1$ and $R^2$ are each independently hydrogen, halogen, $-CN$, $-CF_3$, $-OH$, optionally substituted $C_1$-$C_6$ alkyl, optionally substituted $C_1$-$C_6$ alkoxy, optionally substituted $-(C_1$-$C_6$ alkyl)-$(C_1$-$C_6$ alkoxy), optionally substituted $-(C_1$-$C_6$ alkyl)-OH, $-NR^{13}R^{14}$, optionally substituted $-(C_1$-$C_6$ alkyl)-$NR^{13}R^{14}$, $-NR^{14}SO_2R^{16}$, optionally substituted $-(C_1$-$C_6$ alkyl)$NR^{14}SO_2R^{16}$, $-NR^{14}COR^{16}$, optionally substituted $-(C_1$-$C_6$ alkyl)-$NR^{14}COR^{16}$, $-CONR^{14}R^{15}$, optionally substituted $-(C_1$-$C_6$ alkyl)-$CONR^{14}R^{15}$, $-SO_2NR^{14}R^{15}$, optionally substituted $-(C_1$-$C_6$ alkyl)-$SO_2NR^{14}R^{15}$, optionally substituted $-SO_2R^{16}$, optionally substituted $-(C_1$-$C_6$ alkyl)-$SO_2R^{16}$, optionally substituted carbocyclyl, optionally substituted heterocyclyl, optionally substituted aryl, or optionally substituted heteroaryl;
$R^3$ is hydrogen, halogen, oxo, $=S$, $=NR^{16}$, $-CN$, $-CF_3$, $-OH$, $-SR^{16}$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted $-(C_1$-$C_6$ alkyl)-$(C_1$-$C_6$ alkoxy), optionally substituted $-(C_1$-$C_6$ alkyl)-OH, $-NR^{13}R^{14}$, optionally substituted $-(C_1$-$C_6$ alkyl)-$NR^{13}R^{14}$, $-NR^{14}SO_2R^{16}$, optionally substituted $-(C_1$-$C_6$ alkyl)$NR^{14}SO_2R^{16}$, $NR^{14}COOR^{16}$, $-NR^{14}COR^{16}$, $-NR^{14}CONR^{14}R^{15}$, optionally substituted $-(C_1$-$C_6$ alkyl)-$NR^{14}COR^{16}$, $-CONR^{14}R^{15}$, optionally substituted $-(C_1$-$C_6$ alkyl)-$CONR^{14}R^{15}$, $-SO_2NR^{14}R^{15}$, optionally substituted $-(C_1$-$C_6$ alkyl)-$SO_2NR^{14}R^{15}$, optionally substituted $-SO_2R^{16}$, optionally substituted $-(C_1$-$C_6$ alkyl)-$SO_2R^{16}$, optionally substituted carbocyclyl, optionally substituted heterocyclyl, optionally substituted aryl, or optionally substituted heteroaryl;
$R^5$ and $R^6$ are each independently hydrogen, halogen, $-OH$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, $-NR^{13}R^{14}$, optionally substituted $-(C_1$-$C_6$ alkyl)-$NR^{13}R^{14}$, $-NR^{14}COR^{16}$, optionally substituted $-(C_1$-$C_6$ alkyl)-$NR^{14}COR^{16}$, $-CONR^{14}R^{15}$, optionally substituted $-(C_1$-$C_6$ alkyl)-$CONR^{14}R^{15}$, optionally substituted carbocyclyl, optionally substituted heterocyclyl, optionally substituted aryl, or optionally substituted heteroaryl; or $R^5$ and $R^6$ taken together form an optionally substituted carbocyclyl or optionally substituted heterocyclyl;
$R^8$ and $R^9$ are each independently hydrogen, halogen, or $C_1$-$C_3$ alkyl;
$R^{8a}$ and $R^{9a}$ are each independently hydrogen, $-OH$, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted $-OCO(C_1$-$C_6$ alkyl), $-NR^{13}R^{14}$, optionally substituted $-(C_1$-$C_6$ alkyl)-$NR^{13}R^{14}$, $-NR^{14}COR^{16}$, optionally substituted $-(C_1$-$C_6$ alkyl)-$NR^{14}COR^{16}$, $-CONR^{14}R^{15}$, optionally substituted $-(C_1$-$C_6$ alkyl)-$CONR^{14}R^{15}$, optionally substituted carbocyclyl, optionally substituted heterocyclyl, optionally substituted aryl, or optionally substituted heteroaryl; or $R^{8a}$ and $R^{8b}$ taken together form an optionally substituted carbocyclyl or optionally substituted heterocyclyl;
$R^7$, $R^{10}$ and $R^{16}$ are each independently hydrogen, optionally substituted $C_1$-$C_6$ alkyl, optionally substituted $C_2$-$C_6$ alkenyl, optionally substituted $C_2$-$C_6$ alkynyl, $C_1$-$C_6$ haloalkyl, $C_2$-$C_6$ haloalkenyl, $C_2$-$C_6$ haloalkynyl, optionally substituted carbocyclyl, optionally substituted —CO($C_1$-$C_6$ alkyl), —CO (optionally substituted heterocyclyl), optionally substituted heterocyclyl, optionally substituted aryl, or optionally substituted heteroaryl; or $R^7$ and $R^{8a}$ taken together form an optionally substituted heterocyclyl;

$R^{11}$, $R^{12}$, $R^{13}$, $R^{14}$ and $R^{15}$ are each independently hydrogen, optionally substituted $C_1$-$C_6$ alkyl, optionally substituted $C_2$-$C_6$ alkenyl, optionally substituted $C_2$-$C_6$ alkynyl, optionally substituted —COO($C_1$-$C_6$ alkyl), optionally substituted carbocyclyl, optionally substituted heterocyclyl, optionally substituted aryl, or optionally substituted heteroaryl; or ($R^{11}$ and $R^{12}$) or ($R^{14}$ and $R^{15}$) taken together form an optionally substituted heterocyclyl;

each m is independently 0, 1 or 2;
n1 and n2 are each independently 0, 1, 2, 3, or 4;
n3 is 0, 1, 2, 3, 4 or 5; and
each t is independently 0, 1 or 2.

Embodiment 92

The compound of Embodiment 91, wherein the compound has the structure of formula (VA):

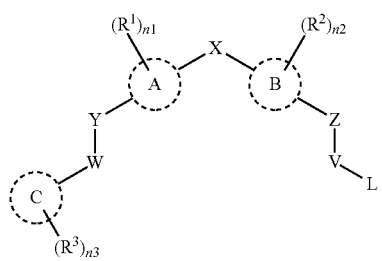

(VA)

or a pharmaceutically acceptable salt, tautomer, stereoisomer or prodrug thereof, wherein:
A and B are each independently selected from phenyl, pyridyl, pyrimidyl, or thiophene;
C is a 5- to 10-membered heteroaryl or aryl;
X is a bond, —($CR^5R^6$)$_t$—, or —$NR^7$;
Y is a bond, —$CH_2$—, —$C(CH_3)H$—, —O—, —S—, —NH—, —$NCH_3$—, or —$N(COCH_3)$—;
Z is a bond, —$CH_2$—, —$C(CH_3)H$—, —O—, —S—, —NH—, —$NCH_3$—, or —$N(COCH_3)$—;
W is a bond, —$CH_2$—, —$C(CH_3)H$—, —C(=O)—, —$N(R^7)CO$—, or —$CONR^7$—;
V is —$CH_2$—, —$CH_2CH_2$—, —$CH(CH_3)CH_2$—, —$CH_2CH(CH_3)$—, or —$CH_2CH_2CH_2$—;
L is hydrogen, halogen, —OH, —$NH_2$, or —$CF_3$;
$R^1$ and $R^2$ are each independently hydrogen, halogen, —CN, —$CF_3$, —OH, optionally substituted $C_1$-$C_6$ alkyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —$NR^{13}R^{14}$, optionally substituted —($C_1$-$C_6$ alkyl)-$NR^{13}R^{14}$, —$NR^{14}SO_2R^{16}$, optionally substituted —($C_1$-$C_6$ alkyl)$NR^{14}SO_2R^{16}$, —$NR^{14}COR^{16}$, optionally substituted —($C_1$-$C_6$ alkyl)-$NR^{14}COR^{16}$, —$CONR^{13}R^{14}$, optionally substituted —($C_1$-$C_6$ alkyl)-$CONR^{14}R^{15}$, —$SO_2NR^{14}R^{15}$, optionally substituted —($C_1$-$C_6$ alkyl)-$SO_2NR^{14}R^{15}$, optionally substituted —$SO_2R^{16}$ or optionally substituted —($C_1$-$C_6$ alkyl)-$SO_2R^{16}$;

$R^3$ is selected from hydrogen, halogen, oxo, =S, —CN, —$CF_3$, —OH, —S($C_1$-$C_3$ alkyl), $C_1$-$C_3$ alkyl, $C_2$-$C_3$ alkenyl, $C_2$-$C_3$ alkynyl, $C_1$-$C_3$ alkoxy, —$NR^{13}R^{14}$, —($C_1$-$C_3$ alkyl)-$NR^{13}R^{14}$, —$NR^{14}SO_2R^{16}$, —($C_1$-$C_3$ alkyl)$NR^{14}SO_2R^{16}$, —$NR^{14}COR^{16}$, —$NR^{14}COOR^{16}$, —$NR^{14}CONR^{14}R^{15}$, —($C_1$-$C_6$ alkyl)-$NR^{14}COR^{16}$, —$CONR^{14}R^{15}$, —($C_1$-$C_3$ alkyl)-$CONR^{14}R^{15}$, —$SO_2NR^{14}R^{15}$, —($C_1$-$C_3$ alkyl)-$SO_2NR^{14}R^{15}$, —$SO_2$($C_1$-$C_3$ alkyl), or —($C_1$-$C_6$ alkyl)-$SO_2$($C_1$-$C_3$ alkyl);
$R^5$ and $R^6$ are each independently hydrogen, halogen, —OH, —$NH_2$, $C_1$-$C_3$ alkyl, $C_2$-$C_3$ alkenyl, $C_2$-$C_3$ alkynyl, or $C_1$-$C_3$ alkoxy; or $R^5$ and $R^6$ taken together form an optionally substituted 3- to 6-membered carbocyclyl or heterocyclyl;
$R^7$ is H, $C_1$-$C_6$ alkyl, —CO($C_1$-$C_6$ alkyl);
$R^{13}$, $R^{14}$ and $R^{15}$ are each independently hydrogen, $C_1$-$C_3$ alkyl, $C_2$-$C_3$ alkenyl, $C_2$-$C_3$ alkynyl, or —COO($C_1$-$C_6$ alkyl); or $R^{14}$ and $R^{15}$ taken together form a 3- to 6-membered heterocyclyl;
$R^{16}$ is hydrogen, $C_1$-$C_3$ alkyl, $C_1$-$C_3$ haloalkyl, $C_2$-$C_3$ alkenyl, or $C_2$-$C_3$ alkynyl;
n1 and n2 are each independently 0, 1, or 2;
n3 is 0, 1, 2, 3, 4 or 5; and
t is 0, 1 or 2.

Embodiment 93

The compound of any one of Embodiments 1-7, 33-39, and 49, wherein C, which is optionally substituted with $R^3$, is selected from

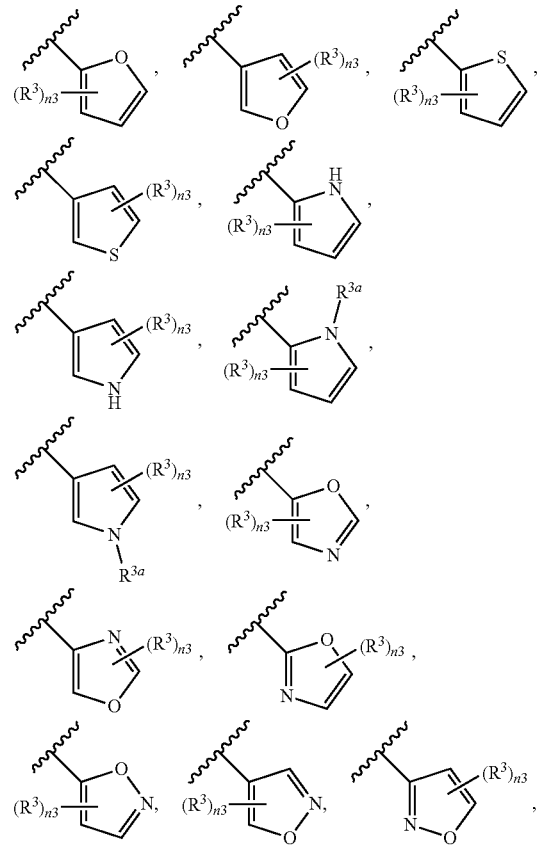

331
-continued
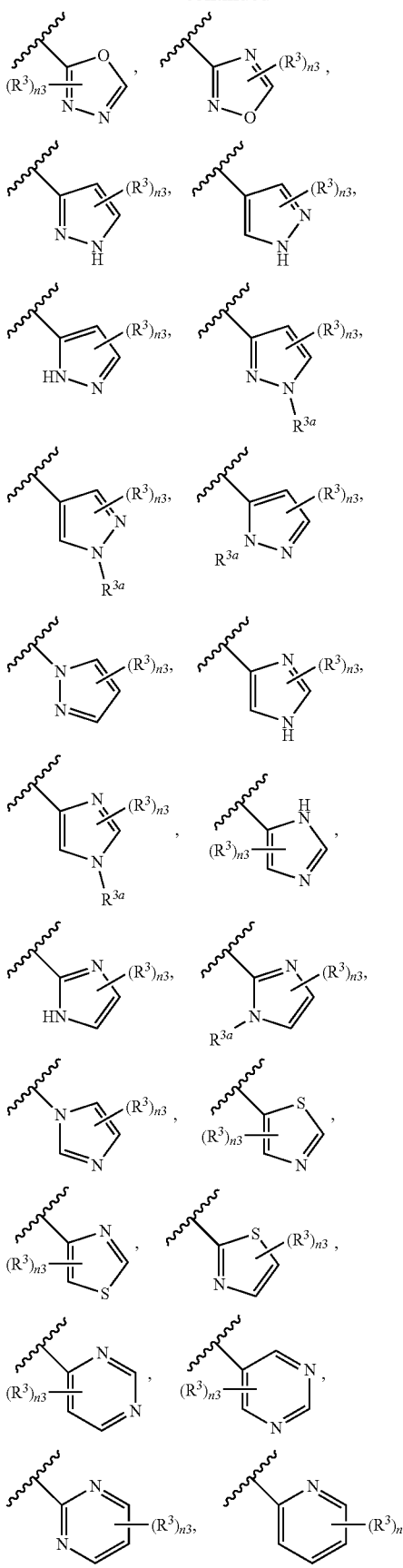
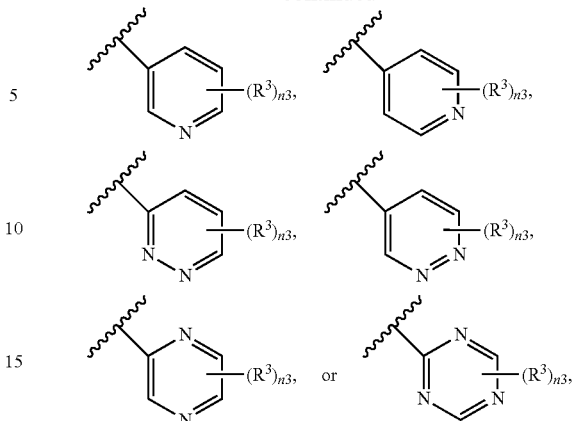
wherein $R^{3a}$ is $C_1$-$C_3$ alkyl.
Embodiment 94
The compound of Embodiment 1, wherein the compound has the structure of formula (E-I):
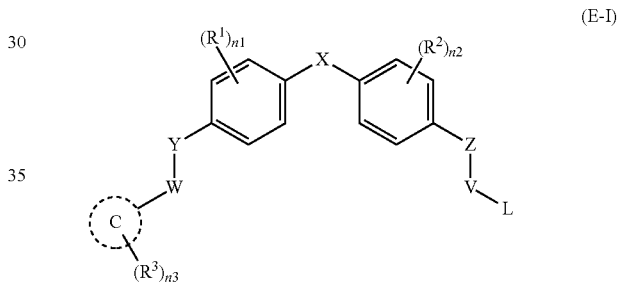
(E-I)
or a pharmaceutically acceptable salt, tautomer, stereoisomer or prodrug thereof, wherein:
C is
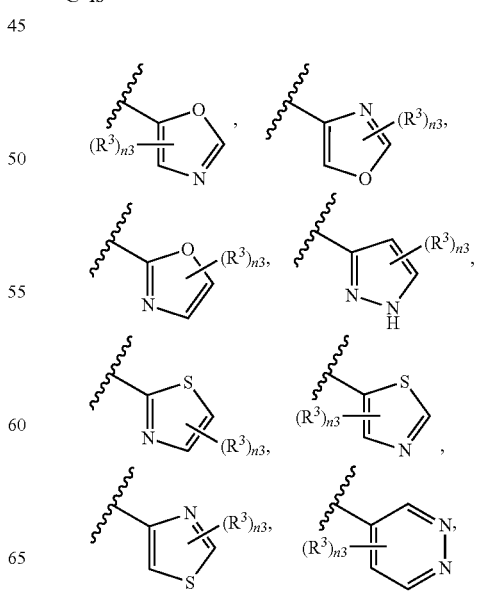

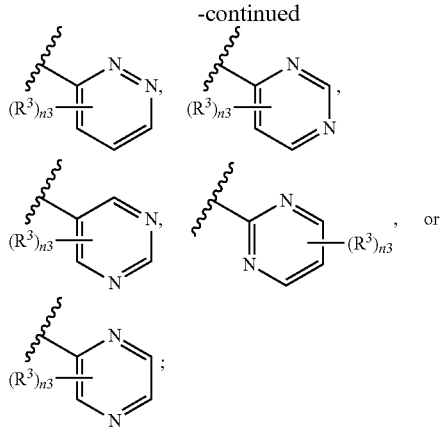

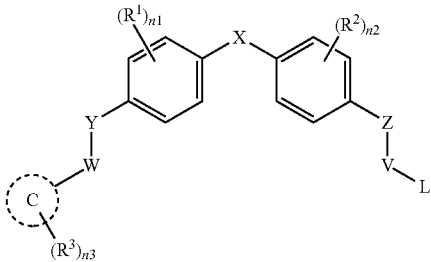

(G-I)

or a pharmaceutically acceptable salt, tautomer, stereoisomer or prodrug thereof, wherein:

C is

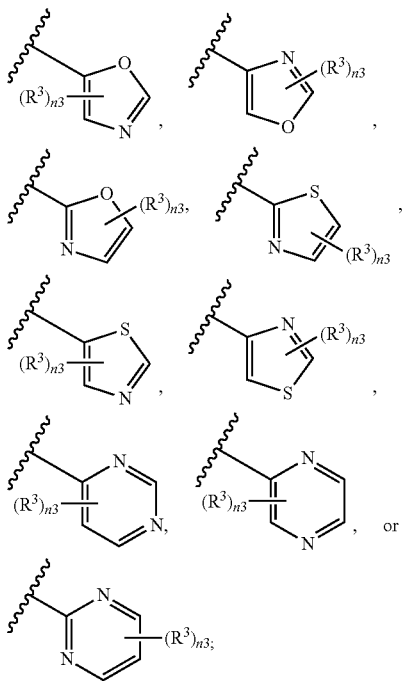

X is —(CR$^5$R$^6$)$_t$— or —NR$^7$—;
Y is a bond, —CH$_2$—, —O—, or —NH—;
Z is a bond, —CH$_2$—, —O—, or —NH—;
W is a bond, —CH$_2$—, or —C(CH$_3$)H—;
V is —CH$_2$—, —CH$_2$CH$_2$—, —CH$_2$CH$_2$CH$_2$—, or —CH$_2$CHClCH$_2$—;
L is hydrogen, —OH, or halogen;
R$^1$ and R$^2$ are each independently hydrogen, halogen, —CN, —CF$_3$, methyl, or —CONH$_2$;
R$^3$ is selected from hydrogen, F, Cl, Br, I, oxo, —CN, —CF$_3$, —OH, C$_1$-C$_3$ alkyl, C$_2$-C$_3$ alkenyl, C$_2$-C$_3$ alkynyl, C$_1$-C$_3$ alkoxy, —S(C$_1$-C$_3$ alkyl), —SO$_2$(C$_1$-C$_3$ alkyl), —NH$_2$, —NHSO$_2$CH$_3$, —NHSO$_2$CF$_3$, —N(CH$_3$)SO$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), —N(CH$_3$)COO(C$_1$-C$_3$ alkyl), —NHCO(C$_1$-C$_3$ alkyl), or —N(CH$_3$)COO(C$_1$-C$_3$ alkyl);
R$^5$ and R$^6$ are each independently hydrogen or C$_1$-C$_3$ alkyl;
R$^7$ is H or C$_1$-C$_6$ alkyl;
n1 and n2 are each independently 0, 1, or 2;
n3 is 0, 1, or 2; and
t is 1 or 2.

Embodiment 95

The compound of Embodiment 94, wherein R$^3$ is selected from hydrogen, F, Cl, Br, I, —CN, —CF$_3$, —OH, methyl, methoxy, —S(C$_1$-C$_3$ alkyl), —SO$_2$(C$_1$-C$_3$ alkyl), —NH$_2$, —NHSO$_2$CH$_3$, —NHSO$_2$CF$_3$, —N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), or —NHCO(C$_1$-C$_3$ alkyl).

Embodiment 96

The compound of Embodiment 1, wherein the compound has the structure of formula (G-I):

X is —(CR$^5$R$^6$)$_t$—;
Y is —O—;
Z is —O—;
W is —CH$_2$— or —C(CH$_3$)H—;
V is —CH$_2$CH$_2$- or —CH$_2$CH$_2$CH$_2$—;
L is halogen
R$^1$ and R$^2$ are each independently Cl or —CN;
R$^3$ is selected from —NHSO$_2$CH$_3$, —N(CH$_3$)SO$_2$CH$_3$, or —SO$_2$CH$_3$;
R$^5$ and R$^6$ are each independently hydrogen or methyl;
n1 and n2 are each independently 0, 1, or 2;
n3 is 1 or 2; and
t is 1.

Embodiment 97

The compound of Embodiment 1, wherein the compound has the structure of formula (H-I):

(H-I)

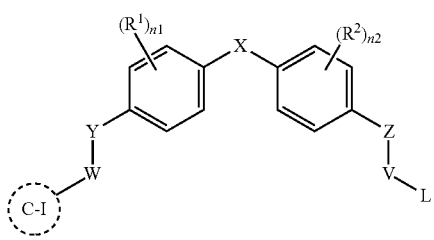

or a pharmaceutically acceptable salt, tautomer, stereoisomer or prodrug thereof, wherein:

C-I is

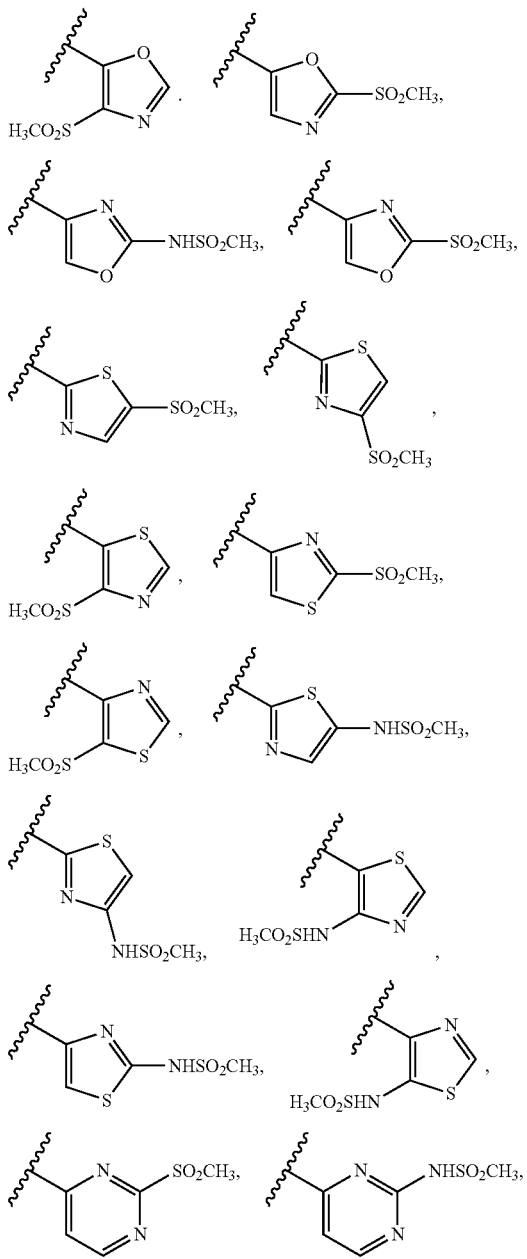

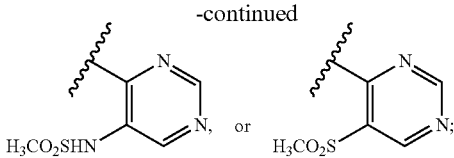

X is $-(CR^5R^6)_t-$;
Y is —O—;
Z is —O—;
W is $-CH_2-$ or $-C(CH_3)H-$;
V is $-CH_2-$, $-CH_2CH_2-$ or $-CH_2CH_2CH_2-$;
L is halogen;
$R^1$ and $R^2$ are each independently Cl or —CN;
$R^5$ and $R^6$ are each independently hydrogen or methyl;
$R^7$ is H or $C_1$-$C_6$ alkyl;
n1 and n2 are each independently 0, 1, or 2; and
t is 1.

Embodiment 98

The compound of Embodiment 1, wherein the compound has the structure of formula (E-II)

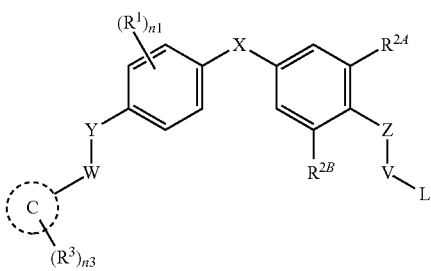

(E-II)

or a pharmaceutically acceptable salt, tautomer, stereoisomer or prodrug thereof, wherein:

C is

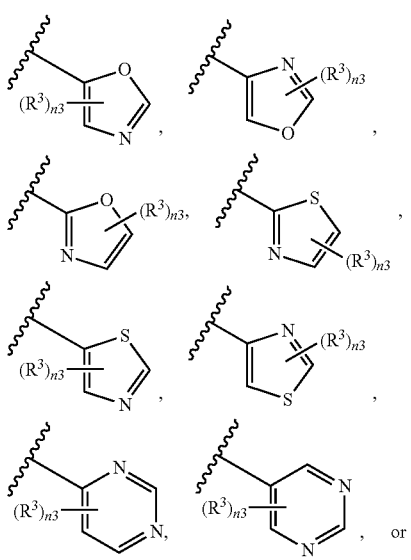

-continued

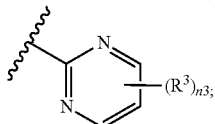

X is —(CR$^5$R$^6$)—;
Y is a bond, —CH$_2$—, —O—, or —NH—;
Z is a bond, —CH$_2$—, —O—, or —NH—;
W is a bond, —CH$_2$—, or —C(CH$_3$)H—;
V is —CH$_2$—, —CH$_2$CH$_2$—, or —CH$_2$CH$_2$CH$_2$—;
L is halogen;
R$^1$, R$^{2A}$ and R$^{2B}$ are each independently hydrogen, halogen, —CN, —CF$_3$, methyl, or —CONH$_2$;
R$^3$ is selected from hydrogen, F, Cl, Br, I, oxo, —CN, —CF$_3$, —OH, C$_1$-C$_3$ alkyl, C$_2$-C$_3$ alkenyl, C$_2$-C$_3$ alkynyl, C$_1$-C$_3$ alkoxy, —S(C$_1$-C$_3$ alkyl), —SO$_2$(C$_1$-C$_3$ alkyl), —NH$_2$, —NHSO$_2$CH$_3$, —NHSO$_2$CF$_3$, —N(CH$_3$)SO$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), —N(CH$_3$)COO(C$_1$-C$_3$ alkyl), —NHCO(C$_1$-C$_3$ alkyl), or —N(CH$_3$)COO(C$_1$-C$_3$ alkyl);
R$^5$ and R$^6$ are each independently hydrogen or C$_1$-C$_3$ alkyl;
n1 is 0, 1, or 2; and
n3 is 1 or 2;
wherein when C-R$^3$ is

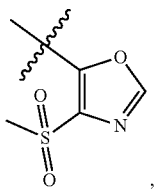 [SMILES: *c1ocnc1S(C)(=O)=O]

,

R$^{2A}$ and R$^{2B}$ are not both Cl.

Embodiment 99

A compound having the structure of formula (IB):

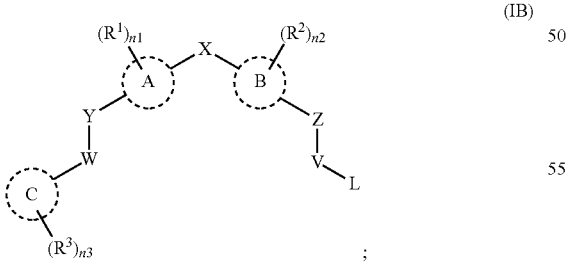

or a pharmaceutically acceptable salt, tautomer, stereoisomer or prodrug thereof, wherein:
A and B are each independently aryl or heteroaryl;
C is a 3- to 10-membered ring;
X is a bond, —(CR$^5$R$^6$)$_t$—, —O—, —C(=O)—, —S—, —S(=O)—, —SO$_2$—, —NR$^7$—, —N(R$^7$)CO—, —CON(R$^7$)—, or —NSO$_2$R$^7$—;
Y is a bond, —(CR$^8$R$^9$)$_m$—, —O—, —S—, —S(=O)—, —SO$_2$—, or —NR$^7$—;
W is a bond, —(CR$^{8a}$R$^{9a}$)$_m$—, —N(R$^7$)CO—, —CONR$^7$—, or —NSO$_2$R$^7$—;
Z is a bond, —CH$_2$—, —C(CH$_3$)H—, —O—, —S—, —NH—, —NCH$_3$—, or —N(COCH$_3$)—;
V is —CH$_2$—, —CH$_2$CH$_2$—, —CH(CH$_3$)CH$_2$—, —CH$_2$CH(CH$_3$)—, or —CH$_2$CH$_2$CH$_2$—;
L is hydrogen, halogen, —CF$_2$R$^{10}$, —CF$_3$, —CN, —OR$^{10}$, —NR$^{11}$R$^{12}$, or —CONR$^{11}$R$^{12}$;
R$^1$ and R$^2$ are each independently hydrogen, deuterium, halogen, —CN, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$, optionally substituted —(C$_1$-C$_6$ alkyl)-SO$_2$R$^{16}$, optionally substituted carbocyclyl, optionally substituted heterocyclyl, optionally substituted aryl, or optionally substituted heteroaryl;
R$^3$ is hydrogen, halogen, oxo, =S, =NR$^{16}$, —CN, —CF$_3$, —OH, —SR$^{16}$, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, NR$^{14}$COOR$^{16}$, —NR$^{14}$COR$^{16}$, —NR$^{14}$CONR$^{14}$R$^{15}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$, optionally substituted —(C$_1$-C$_6$ alkyl)-SO$_2$R$^{16}$, optionally substituted carbocyclyl, optionally substituted heterocyclyl, optionally substituted aryl, or optionally substituted heteroaryl;
R$^5$ and R$^6$ are each independently hydrogen, halogen, —OH, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, —NR$^{13}$R$^{14}$, optionally substituted —(C$_1$-C$_6$ alkyl)-NR$^{13}$R$^{14}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, optionally substituted carbocyclyl, optionally substituted heterocyclyl, optionally substituted aryl, or optionally substituted heteroaryl; or R$^5$ and R$^6$ taken together form an optionally substituted carbocyclyl or optionally substituted heterocyclyl;
R$^8$ and R$^9$ are each independently hydrogen, halogen, or C$_1$-C$_3$ alkyl;
R$^{8a}$ and R$^{9a}$ are each independently hydrogen, halogen, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, —NR$^{13}$R$^{14}$, optionally substituted —(C$_1$-C$_6$ alkyl)-NR$^{13}$R$^{14}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, optionally substituted carbocyclyl, optionally substituted heterocyclyl, optionally substituted aryl, or optionally substituted heteroaryl; or $R^{8a}$ and $R^{8b}$ taken together form an optionally substituted carbocyclyl or optionally substituted heterocyclyl;

$R^7$, $R^{10}$ and $R^{16}$ are each independently hydrogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkyl-$NH_2$, $C_1$-$C_6$ haloalkyl, $C_2$-$C_6$ haloalkenyl, $C_2$-$C_6$ haloalkynyl, optionally substituted carbocyclyl, optionally substituted —CO($C_1$-$C_6$ alkyl), —CO (optionally substituted heterocyclyl), optionally substituted heterocyclyl, optionally substituted aryl, or optionally substituted heteroaryl; or $R^7$ and $R^{8a}$ taken together form an optionally substituted heterocyclyl;

$R^{11}$, $R^{12}$, $R^{13}$, $R^{14}$ and $R^{15}$ are each independently hydrogen, optionally substituted $C_1$-$C_6$ alkyl, optionally substituted $C_2$-$C_6$ alkenyl, optionally substituted $C_2$-$C_6$ alkynyl, optionally substituted —COO($C_1$-$C_6$ alkyl), optionally substituted carbocyclyl, optionally substituted heterocyclyl, optionally substituted aryl, or optionally substituted heteroaryl; or ($R^{11}$ and $R^{12}$) or ($R^{14}$ and $R^{15}$) or ($R^{14}$ and $R^{16}$) taken together form an optionally substituted heterocyclyl;

each m is independently 0, 1 or 2;
n1 and n2 are each independently 0, 1, 2, 3, or 4;
n3 is 0, 1, 2, 3, 4 or 5; and
each t is independently 0, 1 or 2.

Embodiment 100

A compound having the structure of formula (IIA):

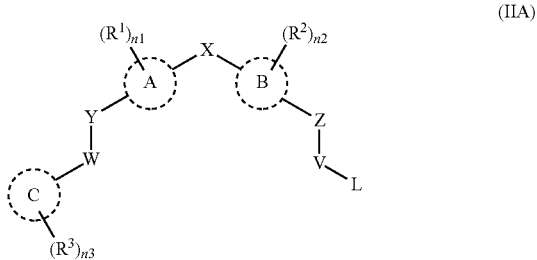

(IIA)

or a pharmaceutically acceptable salt, tautomer, stereoisomer or prodrug thereof, wherein:

A and B are each independently selected from phenyl, pyridyl, pyrimidyl, or thiophene;
C is a 3- to 10-membered ring;
X is a bond, —($CR^5R^6$)$_t$—, or —$NR^7$—;
Y is a bond, —$CH_2$—, —$C(CH_3)H$—, —O—, —S—, —NH—, —$NCH_3$—, or —$N(COCH_3)$—;
Z is a bond, —($CR^8R^9$)$_m$—, —O—, —S—, —S(=O)—, —$SO_2$—, or —$NR^7$—;
W is a bond, —$CH_2$—, —$C(CH_3)H$—, —NHCO—, —N($C_1$-$C_3$ alkyl)CO—, or —CONH—, or —CON($C_1$-$C_3$ alkyl)-;
V is —$CH_2$—, —$CH_2CH_2$—, —$CH(CH_3)CH_2$—, —$CH_2CH(CH_3)$—, or —$CH_2CH_2CH_2$—;
L is hydrogen, halogen, —$CF_2R^1$, —$CF_3$, —CN, —$OR^{10}$; —$NR^{11}R^{12}$, or —$CONR^{11}R^{12}$;
$R^1$ and $R^2$ are each independently hydrogen, deuterium, halogen, —CN, —$CF_3$, —OH, optionally substituted $C_1$-$C_6$ alkyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —$NR^{13}R^{14}$, optionally substituted —($C_1$-$C_6$ alkyl)-$NR^{13}R^{14}$, —$NR^{14}SO_2R^{16}$, optionally substituted —($C_1$-$C_6$ alkyl)$NR^{14}SO_2R^{16}$, —$NR^{14}COR^{16}$, optionally substituted —($C_1$-$C_6$ alkyl)-$NR^{14}COR^{16}$, —$CONR^{13}R^{14}$, optionally substituted —($C_1$-$C_6$ alkyl)-$CONR^{14}R^{15}$, —$SO_2NR^{14}R^{15}$, optionally substituted —($C_1$-$C_6$ alkyl)-$SO_2NR^{14}R^{15}$, optionally substituted —$SO_2R^{16}$ or optionally substituted —($C_1$-$C_6$ alkyl)-$SO_2R^{16}$;

$R^3$ is selected from hydrogen, halogen, oxo, =S, =$NR^{16}$, —CN, —$CF_3$, —OH, —S($C_1$-$C_3$ alkyl), $C_1$-$C_3$ alkyl, $C_2$-$C_3$ alkenyl, $C_2$-$C_3$ alkynyl, $C_1$-$C_3$ alkoxy, —$NR^{13}R^{14}$, —($C_1$-$C_3$ alkyl)-$NR^{13}R^{14}$, —$NR^{14}SO_2R^{16}$, —($C_1$-$C_3$ alkyl)$NR^{14}SO_2R^{16}$, —$NR^{14}COR^{16}$, —($C_1$-$C_6$ alkyl)-$NR^{14}COR^{16}$, —$CONR^{14}R^{15}$, —($C_1$-$C_3$ alkyl)-$CONR^{14}R^{15}$, —$SO_2NR^{14}R^{15}$, —($C_1$-$C_3$ alkyl)-$SO_2NR^{14}R^{15}$, —$SO_2$($C_1$-$C_3$ alkyl), or —($C_1$-$C_6$ alkyl)-$SO_2$($C_1$-$C_3$ alkyl);

$R^5$ and $R^6$ are each independently hydrogen, halogen, —OH, $C_1$-$C_3$ alkyl, $C_2$-$C_3$ alkenyl, $C_2$-$C_3$ alkynyl, or $C_1$-$C_3$ alkoxy; or $R^5$ and $R^6$ taken together form an optionally substituted 3- to 6-membered carbocyclyl or heterocyclyl;

$R^8$ and $R^9$ are each independently hydrogen, halogen, or $C_1$-$C_3$ alkyl;

$R^{11}$, $R^{12}$, $R^{13}$, $R^{14}$ and $R^{15}$ are each independently hydrogen, $C_1$-$C_3$ alkyl, $C_2$-$C_3$ alkenyl, or $C_2$-$C_3$ alkynyl; or $R^{14}$ and $R^{15}$ taken together form a 3- to 6-membered heterocyclyl;

$R^7$, $R^{10}$ and $R^{16}$ are each independently hydrogen, $C_1$-$C_6$ alkyl, $C_2$-$C_6$ alkenyl, $C_2$-$C_6$ alkynyl or $C_1$-$C_6$ alkyl-$NH_2$; or $R^{14}$ and $R^{16}$ taken together form a 3- to 6-membered heterocyclyl;

each m is independently 0, 1 or 2;
n1 and n2 are each independently 0, 1, or 2;
n3 is 0, 1, 2, 3, 4 or 5; and
t is 0, 1 or 2.

Embodiment 101

A compound having the structure of formula (IIB):

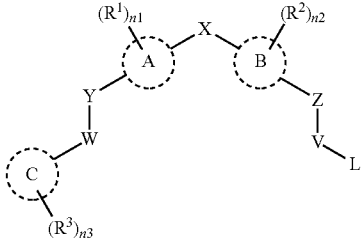

(IIB)

or a pharmaceutically acceptable salt, tautomer, stereoisomer or prodrug thereof, wherein:

A and B are each independently selected from phenyl, pyridyl, pyrimidyl, or thiophene;
C is a 3- to 10-membered ring;
X is a bond, —($CR^5R^6$)$_t$—, or —$NR^7$—;
Y is a bond, —$CH_2$—, —$C(CH_3)H$—, —O—, —S—, —NH—, —$NCH_3$—, or —$N(COCH_3)$—;
Z is a bond, —($CR^8R^9$)$_m$—, —O—, —S—, —S(=O)—, —$SO_2$—, or —$NR^7$—;
W is a bond, —$CH_2$—, or —$C(CH_3)H$—;
V is a bond, —($CR^{8a}R^{9a}$)$_m$—, —C(=O)—, —$N(R^7)$CO—, —$CONR^7$—, or —$NSO_2R^7$—;

L is hydrogen, halogen, —$CF_2R^{10}$, —$CF_3$, —CN, —$OR^{10}$; —$NR^{11}R^{12}$, or —$CONR^{11}R^{12}$;

$R^1$ and $R^2$ are each independently hydrogen, deuterium, halogen, —CN, —$CF_3$, —OH, optionally substituted $C_1$-$C_6$ alkyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —$NR^{13}R^{14}$, optionally substituted —($C_1$-$C_6$ alkyl)-$NR^{13}R^{14}$, —$NR^{14}SO_2R^{16}$, optionally substituted —($C_1$-$C_6$ alkyl)$NR^{14}SO_2R^{16}$, —$NR^{14}COR^{16}$, optionally substituted —($C_1$-$C_6$ alkyl)-$NR^{14}COR^{16}$, —$CONR^{13}R^{14}$, optionally substituted —($C_1$-$C_6$ alkyl)-$CONR^{14}R^{15}$, —$SO_2NR^{14}R^{15}$, optionally substituted —($C_1$-$C_6$ alkyl)-$SO_2NR^{14}R^{15}$, optionally substituted —$SO_2R^{16}$ or optionally substituted —($C_1$-$C_6$ alkyl)-$SO_2R^{16}$;

$R^3$ is selected from hydrogen, halogen, oxo, =S, =$NR^{16}$, —CN, —$CF_3$, —OH, —S($C_1$-$C_3$ alkyl), $C_1$-$C_3$ alkyl, $C_2$-$C_3$ alkenyl, $C_2$-$C_3$ alkynyl, $C_1$-$C_3$ alkoxy, —$NR^{13}R^{14}$, —($C_1$-$C_3$ alkyl)-$NR^{13}R^{14}$, —$NR^{14}SO_2R^{16}$, —($C_1$-$C_3$ alkyl)$NR^{14}SO_2R^{16}$, —$NR^{14}COR^{16}$, —($C_1$-$C_6$ alkyl)- $NR^{14}COR^{16}$, —$CONR^{14}R^{15}$, —($C_1$-$C_3$ alkyl)-$CONR^{14}R^{15}$, —$SO_2NR^{14}R^{15}$, —($C_1$-$C_3$ alkyl)-$SO_2NR^{14}R^{15}$, —$SO_2$($C_1$-$C_3$ alkyl), or —($C_1$-$C_6$ alkyl)-$SO_2$($C_1$-$C_3$ alkyl);

$R^5$ and $R^6$ are each independently hydrogen, halogen, —OH, $C_1$-$C_3$ alkyl, $C_2$-$C_3$ alkenyl, $C_2$-$C_3$ alkynyl, or $C_1$-$C_3$ alkoxy; or $R^5$ and $R^6$ taken together form an optionally substituted 3- to 6-membered carbocyclyl or heterocyclyl;

$R^8$ and $R^9$ are each independently hydrogen, halogen, or $C_1$-$C_3$ alkyl;

$R^{8a}$ and $R^{9a}$ are each independently hydrogen, —OH, halogen, $C_1$-$C_3$ alkyl, $C_2$-$C_3$ alkenyl, $C_2$-$C_3$ alkynyl, $C_1$-$C_3$ alkoxy, —$NR^{13}R^{14}$, —($C_1$-$C_3$ alkyl)-$NR^{13}R^{14}$, —$NR^{14}COR^{16}$, —($C_1$-$C_3$ alkyl)-$NR^{14}COR^{16}$, —$CONR^{14}R^{15}$, or —($C_1$-$C_3$ alkyl)-$CONR^{14}R^{15}$; or $R^{8a}$ and $R^{8b}$ taken together form an optionally substituted 3- to 6-membered carbocyclyl or heterocyclyl;

$R^{11}$, $R^{12}$, $R^{13}$, $R^{14}$ and $R^{15}$ are each independently hydrogen, $C_1$-$C_3$ alkyl, $C_2$-$C_3$ alkenyl, or $C_2$-$C_3$ alkynyl; or $R^{14}$ and $R^{15}$ taken together form a 3- to 6-membered heterocyclyl;

$R^7$, $R^{10}$ and $R^{16}$ are each independently hydrogen, $C_1$-$C_6$ alkyl, $C_2$-$C_6$ alkenyl, $C_2$-$C_6$ alkynyl or $C_1$-$C_6$ alkyl-$NH_2$; or $R^{14}$ and $R^{16}$ taken together form a 3- to 6-membered heterocyclyl;

each m is independently 0, 1 or 2;

n1 and n2 are each independently 0, 1, or 2;

n3 is 1, 2, 3, 4 or 5; and t is 0, 1 or 2.

Embodiment 102

A compound having the structure of formula (IC):

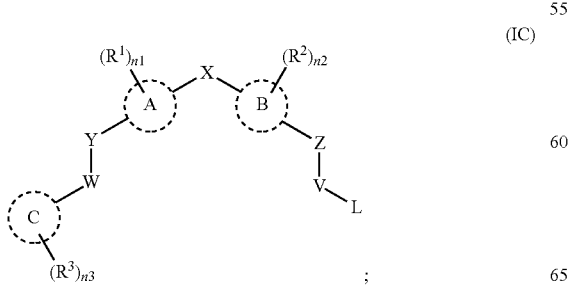

(IC)

or a pharmaceutically acceptable salt, tautomer, stereoisomer or prodrug thereof, wherein:

A and B are each independently aryl or heteroaryl;

C is a 3- to 10-membered ring;

X is a bond, —($CR^5R^6$)$_t$—, —O—, —C(=O)—, —S—, —S(=O)—, —$SO_2$—, —$NR^7$—, —N($R^7$)CO—, —CON($R^7$)—, or —$NSO_2R^7$—;

Y is a bond, —($CR^8R^9$)$_m$—, —O—, —S—, —S(=O)—, —$SO_2$—, or —$NR^7$—;

W is a bond, —($CR^{8a}R^{9a}$)$_m$—, —C(=O)—, N($R^7$)CO—, —$CONR^7$—, or —$NSO_2R^7$—;

Z is a bond, —($CR^8R^9$)$_m$—, —O—, —S—, —S(=O)—, —$SO_2$—, or —$NR^7$—;

V is —$CH_2$—, —$CH_2CH_2$—, —CH($CH_3$)$CH_2$—, —$CH_2$CH($CH_3$)—, or —$CH_2CH_2CH_2$—;

L is hydrogen, halogen, —$CF_2R^{10}$, —$CF_3$, —$CCl_2R^{10}$, —$CCl_3$, —CN, —$OR^{10}$; —$NR^{11}R^{12}$ or —$CONR^{11}R^{12}$;

$R^1$ and $R^2$ are each independently hydrogen, deuterium, halogen, —CN, —$CF_3$, —OH, optionally substituted $C_1$-$C_6$ alkyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —$NR^{13}R^{14}$, optionally substituted —($C_1$-$C_6$ alkyl)-$NR^{13}R^{14}$, —$NR^{14}SO_2R^{16}$, optionally substituted —($C_1$-$C_6$ alkyl)$NR^{14}SO_2R^{16}$, —$NR^{14}COR^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, —$SO_2NR^{14}R^{15}$, optionally substituted —($C_1$-$C_6$ alkyl)-$SO_2NR^{14}R^{15}$, optionally substituted —$SO_2R^{16}$, optionally substituted —($C_1$-$C_6$ alkyl)-$SO_2R^{16}$, optionally substituted carbocyclyl, optionally substituted heterocyclyl, optionally substituted aryl, or optionally substituted heteroaryl;

$R^3$ is hydrogen, halogen, oxo, =S, =$NR^{16}$, —CN, —$CF_3$, —OH, —$SR^{16}$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —$NR^{13}R^{14}$, optionally substituted —($C_1$-$C_6$ alkyl)-$NR^{13}R^{14}$, —$NR^{14}SO_2R^{16}$, optionally substituted —($C_1$-$C_6$ alkyl)$NR^{14}SO_2R^{16}$, $NR^{14}COOR^{16}$, —$NR^{14}COR^{16}$, —$NR^{14}CONR^{14}R^{15}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, —$SO_2NR^{14}R^{15}$, optionally substituted —($C_1$-$C_6$ alkyl)-$SO_2NR^{14}R^{15}$, optionally substituted —$SO_2R^{16}$, optionally substituted —($C_1$-$C_6$ alkyl)-$SO_2R^{16}$, optionally substituted carbocyclyl, optionally substituted heterocyclyl, optionally substituted aryl, or optionally substituted heteroaryl;

$R^5$ and $R^6$ are each independently hydrogen, halogen, —OH, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, —$NR^{13}R^{14}$, optionally substituted —($C_1$-$C_6$ alkyl)-$NR^{13}R^{14}$, —$NR^{14}COR^{16}$, optionally substituted —($C_1$-$C_6$ alkyl)-$NR^{14}COR^{16}$, —$CONR^{13}R^{14}$, —$CONR^{14}R^{15}$, optionally substituted —($C_1$-$C_6$ alkyl)-$CONR^{14}R^{15}$, optionally substituted carbocyclyl, optionally substituted heterocyclyl, optionally substituted aryl, or optionally substituted heteroaryl; or $R^5$ and $R^6$ taken together form an optionally substituted carbocyclyl or optionally substituted heterocyclyl;

$R^8$ and $R^9$ are each independently hydrogen, halogen, or $C_1$-$C_3$ alkyl;

$R^{8a}$ and $R^{9a}$ are each independently hydrogen, —OH, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, —$NR^{13}R^{14}$, optionally substituted —($C_1$-$C_6$ alkyl)-$NR^{13}R^{14}$, —$NR^{14}COR^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, optionally substituted carbocyclyl, optionally substituted heterocyclyl, optionally substituted aryl, or optionally substituted heteroaryl; or $R^{8a}$ and $R^{8b}$ taken together form an optionally substituted carbocyclyl or optionally substituted heterocyclyl;

$R^7$, $R^{10}$ and $R^{16}$ are each independently hydrogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkyl-$NH_2$, $C_1$-$C_6$ haloalkyl, $C_2$-$C_6$ haloalkenyl, $C_2$-$C_6$ haloalkynyl, optionally substituted carbocyclyl, optionally substituted —CO($C_1$-$C_6$ alkyl), —CO (optionally substituted heterocyclyl), optionally substituted heterocyclyl, optionally substituted aryl, or optionally substituted heteroaryl; or $R^7$ and $R^{8a}$ taken together form an optionally substituted heterocyclyl;

$R^{11}$, $R^{12}$, $R^{13}$, $R^{14}$ and $R^{15}$ are each independently hydrogen, optionally substituted $C_1$-$C_6$ alkyl, optionally substituted $C_2$-$C_6$ alkenyl, optionally substituted $C_2$-$C_6$ alkynyl, optionally substituted —$COO(C_1$-$C_6$ alkyl), optionally substituted carbocyclyl, optionally substituted heterocyclyl, optionally substituted aryl, or optionally substituted heteroaryl; or ($R^{11}$ and $R^{12}$) or ($R^{14}$ and $R^{15}$) or ($R^{14}$ and $R^{16}$) taken together form an optionally substituted heterocyclyl;

each m is independently 0, 1 or 2;
n1 and n2 are each independently 0, 1, 2, 3, or 4;
n3 is 0, 1, 2, 3, 4 or 5; and
each t is independently 0, 1 or 2.

Embodiment 103

A compound having a structure of formula (IIIA):

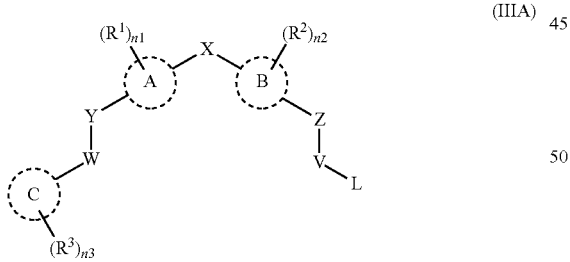

(IIIA)

or a pharmaceutically acceptable salt, tautomer, stereoisomer or prodrug thereof, wherein:
A and B are each independently selected from phenyl, pyridyl, pyrimidyl, or thiophene;
C is a 3- to 10-membered ring;
X is a bond, —($CR^5R^6$)$_t$—, or —$NR^7$;
Y is a bond, —($CR^8R^9$)$_m$—, —O—, —S—, —S(=O)—, —$SO_2$—, —$NR^7$— or —$N(COCH_3)$—;
W is a bond, —($CR^{8a}R^{9a}$)$_m$—, —C(=O)—, —$N(R^7)$CO—, —$CONR^7$—, or —$NSO_2R^7$—;
Z is a bond, —$CH_2$—, —$C(CH_3)H$—, —O—, —S—, —NH—, —$NCH_3$—, or —$N(COCH_3)$—;

V is —$CH_2$— and L is halogen, —$NH_2$, —$CHCl_2$, —$CCl_3$, or —$CF_3$; or
V is —$CH_2CH_2$- and L is halogen or —$NH_2$;
$R^1$ and $R^2$ are each independently hydrogen, halogen, —CN, —$CF_3$, —OH, optionally substituted $C_1$-$C_6$ alkyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —$NR^{13}R^{14}$, optionally substituted —($C_1$-$C_6$ alkyl)-$NR^{13}R^{14}$, —$NR^{14}SO_2R^{16}$, optionally substituted —($C_1$-$C_6$ alkyl)$NR^{14}SO_2R^{16}$, —$NR^{14}COR^{16}$, optionally substituted —($C_1$-$C_6$ alkyl)-$NR^{14}COR^{16}$, —$CONR^{13}R^{14}$, optionally substituted —($C_1$-$C_6$ alkyl)-$CONR^{14}R^{15}$, —$SO_2NR^{14}R^{15}$, optionally substituted —($C_1$-$C_6$ alkyl)-$SO_2NR^{14}R^{15}$, optionally substituted —$SO_2R^{16}$ or optionally substituted —($C_1$-$C_6$ alkyl)-$SO_2R^{16}$;

$R^3$ is selected from halogen, oxo, =S, =$NR^{16}$, —CN, —$CF_3$, —OH, —$S(C_1$-$C_3$ alkyl), $C_1$-$C_3$ alkyl, $C_2$-$C_3$ alkenyl, $C_2$-$C_3$ alkynyl, $C_1$-$C_3$ alkoxy, —$NR^{13}R^{14}$, —($C_1$-$C_3$ alkyl)-$NR^{13}R^{14}$, —$NR^{14}SO_2R^{16}$, —($C_1$-$C_3$ alkyl)$NR^{14}SO_2R^{16}$, —$NR^{14}COR^{16}$, —($C_1$-$C_6$ alkyl)-$NR^{14}COR^{16}$, —$CONR^{14}R^{15}$, —($C_1$-$C_3$ alkyl)-$CONR^{14}R^{15}$, —$SO_2NR^{14}R^{15}$, —($C_1$-$C_3$ alkyl)-$SO_2NR^{14}R^{15}$, —$SO_2(C_1$-$C_3$ alkyl), or —($C_1$-$C_6$ alkyl)-$SO_2(C_1$-$C_3$ alkyl);

$R^5$ and $R^6$ are each independently hydrogen, halogen, —OH, $C_1$-$C_3$ alkyl, $C_2$-$C_3$ alkenyl, $C_2$-$C_3$ alkynyl, or $C_1$-$C_3$ alkoxy; or $R^5$ and $R^6$ taken together form an optionally substituted 3- to 6-membered carbocyclyl or heterocyclyl;

$R^7$ is hydrogen, $C_1$-$C_6$ alkyl, $C_2$-$C_6$ alkenyl, or $C_2$-$C_6$ alkynyl;

$R^8$ and $R^9$ are each independently hydrogen, halogen, or $C_1$-$C_3$ alkyl;

$R^{8a}$ and $R^{9a}$ are each independently hydrogen, —OH, halogen, $C_1$-$C_3$ alkyl, $C_2$-$C_3$ alkenyl, $C_2$-$C_3$ alkynyl, $C_1$-$C_3$ alkoxy, —$NR^{13}R^{14}$, —($C_1$-$C_3$ alkyl)$NR^{13}R^{14}$, —$NR^{14}COR^{16}$, —($C_1$-$C_3$ alkyl)-$NR^{14}COR^{16}$, —$CONR^{14}R^{15}$, or —($C_1$-$C_3$ alkyl)-$CONR^{14}R^{15}$; or $R^{8a}$ and $R^{8b}$ taken together form an optionally substituted 3- to 6-membered carbocyclyl or heterocyclyl;

$R^{13}$, $R^{14}$ and $R^{15}$ are each independently hydrogen, $C_1$-$C_3$ alkyl, $C_2$-$C_3$ alkenyl, or $C_2$-$C_3$ alkynyl; or $R^{14}$ and $R^{15}$ taken together form a 3- to 6-membered heterocyclyl;

$R^{16}$ is hydrogen, optionally substituted $C_1$-$C_3$ alkyl, optionally substituted $C_2$-$C_3$ alkenyl, optionally substituted $C_2$-$C_3$ alkynyl, $C_3$-$C_6$ cycloalkyl, or phenyl;
each m is independently 0, 1 or 2;
n1 and n2 are each independently 0, 1, or 2;
n3 is 1, 2, 3, 4 or 5; and
t is 0, 1 or 2.

Embodiment 104

A compound having a structure of formula (G-II)

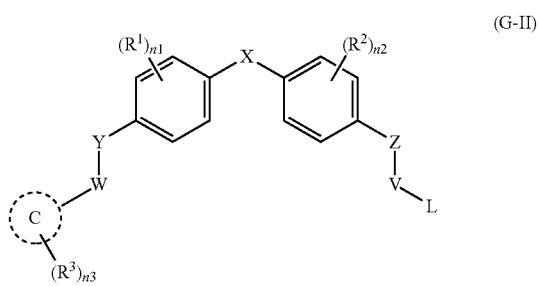

(G-II)

or a pharmaceutically acceptable salt, tautomer, stereoisomer or prodrug thereof, wherein:

C is

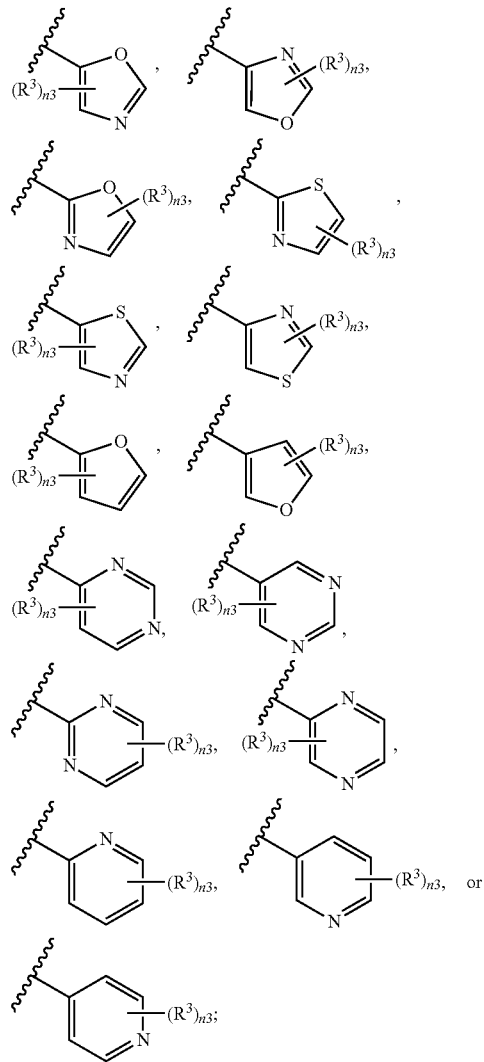

X is —(CR$^5$R$^6$)$_t$—;
Y is —O—;
Z is —O—;
W is —CH$_2$— or —C(CH$_3$)H—;
V is —CH$_2$CH$_2$—;
L is halogen;
R$^1$ and R$^2$ are each independently Cl or —CN;
at least one R$^3$ is selected from —CN, C$_1$-C$_3$ alkoxy, —CONH$_2$, —NHSO$_2$CH$_3$, —N(CH$_3$)SO$_2$CH$_3$, —NHSO$_2$CH$_2$CH$_3$, —N(CH$_3$)SO$_2$CH$_2$CH$_3$, or —SO$_2$CH$_3$ and the other R$^3$, if present, is selected from —CN, —CF$_3$, C$_1$-C$_3$ alkyl, C$_2$-C$_3$ alkenyl, C$_2$-C$_3$ alkynyl, C$_1$-C$_3$ alkoxy, —S(C$_1$-C$_3$ alkyl), —SO$_2$(C$_1$-C$_3$ alkyl), —NH$_2$, —(C$_1$-C$_3$ alkyl)NH$_2$, —NHSO$_2$CH$_3$, —NHSO$_2$CF$_3$, —N(CH$_3$)SO$_2$CH$_3$, —NHSO$_2$CH$_2$CH$_3$, —N(CH$_3$)SO$_2$CH$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C-C$_3$ alkyl), —NHCO(C$_1$-C$_3$ alkyl), —N(CH$_3$)COO(C$_1$-C$_3$ alkyl), —NHCO(C$_1$-C$_3$ alkyl), or —N(CH$_3$)COO(C$_1$-C$_3$ alkyl);

R$^5$ and R$^6$ are each independently hydrogen or methyl;
n1 and n2 are each independently 0, 1, or 2;
n3 is 1 or 2; and
t is 1.

Embodiment 105

The compound of any one of Embodiments 1-104, wherein at least one of R$^3$ is —CN, —OCH$_3$, —SO$_2$CH$_3$, —NHSO$_2$CH$_3$, —CH$_2$NHSO$_2$CH$_3$, —SO$_2$NH$_2$, —CONH$_2$, or —NHCOCH$_3$.

Embodiment 106

A compound selected from Compounds A212-A234 or a pharmaceutically acceptable salt thereof.

Embodiment 107

A pharmaceutical composition comprising a compound of any one of Embodiments 1-106 and a pharmaceutically acceptable carrier.

Embodiment 108

The pharmaceutical composition of Embodiment 107, further comprising one or more additional therapeutic agents.

Embodiment 109

The pharmaceutical composition of Embodiment 108, wherein the one or more additional therapeutic agents is for treating prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy, or age-related macular degeneration.

Embodiment 110

The pharmaceutical composition of Embodiment 108, wherein the one or more additional therapeutic agents is a poly (ADP-ribose) polymerase (PARP) inhibitor including but not limited to olaparib, niraparib, rucaparib, talazoparib; an androgen receptor ligand binding domain inhibitor including but not limited to enzalutamide, apalutamide, darolutamide, bicalutamide, nilutamide, flutamide, ODM-204, TAS3681; an inhibitor of CYP17 including but not limited to galeterone, abiraterone, abiraterone acetate; a microtubule inhibitor including but not limited to docetaxel, paclitaxel, cabazitaxel (XRP-6258); a modulator of PD-1 or PD-L1 including but not limited to pembrolizumab, durvalumab, nivolumab, atezolizumab; a gonadotropin releasing hormone agonist including but not limited to cyproterone acetate, leuprolide; a 5-alpha reductase inhibitor including but not limited to finasteride, dutasteride, turosteride, bexlosteride, izonsteride, FCE 28260, SKF105,111; a vascular endothelial growth factor inhibitor including but not limited to bevacizumab (Avastin); a histone deacetylase inhibitor including but not limited to OSU-HDAC42; an integrin alpha-v-beta-3 inhibitor including but not limited to VITAXIN; a receptor tyrosine kinase inhibitor including but not limited to sunitumib; a phosphoinositide 3-kinase inhibitor including but not limited to alpelisib, buparlisib, idealisib; an anaplastic lymphoma kinase (ALK) inhibitor including but not limited to crizotinib, alectinib; an endothelin receptor A antagonist including but not limited to ZD-4054; an anti-CTLA4 inhibitor including but not limited to MDX-010 (ipilimumab); an heat shock protein 27 (HSP27) inhibitor including but not limited to OGX 427; an androgen receptor degrader including but not limited to ARV-330, ARV-110; a androgen receptor DNA-binding domain inhibitor including but not limited to VPC-14449; a bromodomain and extra-terminal motif (BET) inhibitor including but not limited to BI-894999, GSK25762, GS-5829; an androgen receptor N-terminal domain inhibitor including but not limited to a sintokamide; an alpha-particle emitting radioactive therapeutic agent including but not limited to radium 233 or a salt thereof; niclosamide; or related compounds thereof; a selective estrogen receptor modulator (SERM) including but not limited to tamoxifen, raloxifene, toremifene, arzoxifene, bazedoxifene, pipindoxifene, lasofoxifene, enclomiphene; a selective estrogen receptor degrader (SERD) including but not limited to fulvestrant, ZB716, OP-1074, elacestrant, AZD9496, GDC0810, GDC0927, GW5638, GW7604; an aromitase inhibitor including but not limited to anastrazole, exemestane, letrozole; selective progesterone receptor modulators (SPRM) including but not limited to mifepristone, lonaprison, onapristone, asoprisnil, lonaprisnil, ulipristal, telapristone; a glucocorticoid receptor inhibitor including but not limited to mifepristone, COR108297, COR125281, ORIC-101, PT150; CDK4/6 inhibitors including palbociclib, abemaciclib, ribociclib; HER2 receptor antagonist including but not limited to trastuzumab, neratinib; or a mammalian target of rapamycin (mTOR) inhibitor including but not limited to everolimus, temsirolimus.

Embodiment 111

A method for modulating androgen receptor activity, comprising administering a compound of any one of Embodiments 1-106, to a subject in need thereof.

Embodiment 112

The method of any one of Embodiment 111, wherein the modulating androgen receptor activity is for treating a condition or disease selected from prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy, or age-related macular degeneration.

Embodiment 113

A method for treating cancer, comprising administering a compound of any one of Embodiments 1-106, to a subject in need thereof.

Embodiment 114

The method of Embodiment 113, wherein the cancer is selected from prostate cancer, breast cancer, ovarian cancer, bladder cancer, pancreatic cancer, hepatocellular cancer, endometrial cancer, or salivary gland carcinoma.

Embodiment 115

The method of Embodiment 113, wherein the cancer is prostate cancer.

Embodiment 116

The method of Embodiment 115, wherein the prostate cancer is primary or localized prostate cancer, locally advanced prostate cancer, recurrent prostate cancer, advanced prostate cancer, metastatic prostate cancer, metastatic castration-resistant prostate cancer, and hormone-sensitive prostate cancer. The method of Embodiment 115, wherein the prostate cancer is primary or localized prostate cancer, locally advanced prostate cancer, recurrent prostate cancer, advanced prostate cancer, metastatic prostate cancer, non-metastatic castration-resistant prostate cancer, metastatic castration-resistant prostate cancer, and hormone-sensitive prostate cancer.

Embodiment 117

The method of Embodiment 115, wherein the prostate cancer is metastatic castration-resistant prostate cancer.

Embodiment 118

The method of Embodiment 115, wherein the prostate cancer expresses full-length androgen receptor or truncated androgen receptor splice variant.

Embodiment 119

The compound of any one of Embodiments 1-106, wherein the compound has an in vitro $IC_{50}$ in a PSA-luciferase assay of less than about 1000 nM.

Embodiment 120

The compound of any one of Embodiments 1-106, wherein the compound has an in vitro $IC_{50}$ in a PSA-luciferase assay of less than about 900 nM.

Embodiment 121

The compound of any one of Embodiments 1-106, wherein the compound has an in vitro $IC_{50}$ in a PSA-luciferase assay of less than about 800 nM.

Embodiment 122

The compound of any one of Embodiments 1-106, wherein the compound has an in vitro $IC_{50}$ in a PSA-luciferase assay of less than about 700 nM.

Embodiment 123

The compound of any one of Embodiments 1-106, wherein the compound has an in vitro $IC_{50}$ in a PSA-luciferase assay of less than about 600 nM.

Embodiment 124

The compound of any one of Embodiments 1-106, wherein the compound has an in vitro $IC_{50}$ in a PSA-luciferase assay of less than about 500 nM.

Embodiment 125

The compound of any one of Embodiments 1-106, wherein the compound has an in vitro $IC_{50}$ in a PSA-luciferase assay of less than about 400 nM.

Embodiment 126

The compound of any one of Embodiments 1-106, wherein the compound has an in vitro IC$_{50}$ in a PSA-luciferase assay of less than about 300 nM.

Embodiment 127

The compound of any one of Embodiments 1-106 or 119-126, wherein the compound has an in vitro metabolic clearance of less than 12 µL/min/mg protein in mammalian microsomes.

Embodiment 128

The compound of Embodiment 126, wherein the mammalian microsomes are human microsomes.

Embodiment 129

The compound of any one of Embodiments 1-106 or 119-128, wherein the compound has an in vitro metabolic clearance in mammalian hepatocytes of less than 4 µL/min/million cells.

Embodiment 130

The compound of Embodiment 128, wherein the mammalian microsomes are human microsomes.

Embodiment 131

The compound of any one of Embodiment 1-106, wherein the compound has:
(a) an in vitro IC$_{50}$ in a PSA-luciferase assay of less than about 1000 nM;
(b) an in vitro metabolic clearance of less than 12 µL/min/mg protein in mammalian microsomes; and
(c) in vitro metabolic clearance in mammalian hepatocytes of less than 4 µL/min/million cells.

Embodiment 132

The compound of any one of Embodiments 1-106, wherein the compound has:
(a) an in vitro IC$_{50}$ in a PSA-luciferase assay of less than about 1000 nM;
(b) an in vitro metabolic clearance of less than 12 µL/min/mg protein in human microsomes; and
(c) in vitro metabolic clearance in human hepatocytes of less than 4 µL/min/million cells.

Embodiment 133

The compounds of any one of Embodiments 119-132, wherein the PSA-luciferase assay is performed as described in Example 35.

Embodiment 134

The compounds of any one of Embodiments 119-132, wherein the metabolic clearance is measured according to Example 36.

Embodiment 135

A compound having the structure of formula (IIIA):

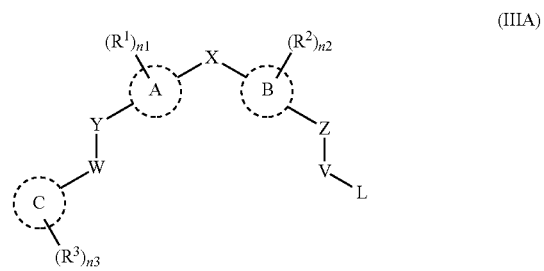

(IIIA)

or a pharmaceutically acceptable salt, tautomer, stereoisomer or prodrug thereof, wherein:
A and B are each independently selected from phenyl, pyridyl, pyrimidyl, or thiophene;
C is a 3- to 10-membered ring;
X is a bond, —(CR$^5$R$^6$)$_t$—, or —NR$^7$;
Y is a bond, —(CR$^8$R$^9$)$_m$—, —O—, —S—, —S(=O)—, —SO$_2$—, —NR$^7$—, or —N(COCH$_3$)—;
W is a bond, —(CR$^{8a}$R$^{9a}$)$_m$—, —C(=O)—, —N(R$^7$)CO—, —CONR$^7$—, or —NSO$_2$R$^7$—;
Z is a bond, —CH$_2$—, —C(CH$_3$)H—, —O—, —S—, —NH—, —NCH$_3$—, or —N(COCH$_3$)—;
V is —CH$_2$— and L is halogen, —NH$_2$, —CHCl$_2$, —CCl$_3$, or —CF$_3$; or
V is —CH$_2$CH$_2$- and L is halogen or —NH$_2$;
R$^1$ and R$^2$ are each independently hydrogen, halogen, —CN, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{13}$R$^{14}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$ or optionally substituted —(C$_1$-C$_6$ alkyl)-SO$_2$R$^{16}$;
R$^3$ is selected from halogen, oxo, =S, =NR$^{16}$, —CN, —CF$_3$, —OH, —S(C$_1$-C$_3$ alkyl), C$_1$-C$_3$ alkyl, C$_2$-C$_3$ alkenyl, C$_2$-C$_3$ alkynyl, C$_1$-C$_3$ alkoxy, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl)NR$^{14}$SO$_2$R$^{16}$, —NR$^{14}$COR$^{16}$, —(C$_1$-C$_6$ alkyl)-NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO$_2$(C$_1$-C$_3$ alkyl), or —(C$_1$-C$_6$ alkyl)-SO$_2$(C$_1$-C$_3$ alkyl);
R$^5$ and R$^6$ are each independently hydrogen, halogen, —OH, C$_1$-C$_3$ alkyl, C$_2$-C$_3$ alkenyl, C$_2$-C$_3$ alkynyl, or C$_1$-C$_3$ alkoxy; or R$^5$ and R$^6$ taken together form an optionally substituted 3- to 6-membered carbocyclyl or heterocyclyl;
R$^7$ is hydrogen, C$_1$-C$_6$ alkyl, C$_2$-C$_6$ alkenyl, or C$_2$-C$_6$ alkynyl;
R$^8$ and R$^9$ are each independently hydrogen, halogen, or C$_1$-C$_3$ alkyl;
R$^{8a}$ and R$^{9a}$ are each independently hydrogen, —OH, halogen, C$_1$-C$_3$ alkyl, C$_2$-C$_3$ alkenyl, C$_2$-C$_3$ alkynyl, C$_1$-C$_3$ alkoxy, —NR$^{13}$R$^{14}$, —(C$_1$-C$_3$ alkyl)NR$^{13}$R$^{14}$, —NR$^{14}$COR$^{16}$, —(C$_1$-C$_3$ alkyl)-NR$^{14}$COR$^{16}$, —CONR$^{14}$R$^{15}$, or —(C$_1$-C$_3$ alkyl)-CONR$^{14}$R$^{15}$; or R$^{8a}$ and R$^{8b}$ taken together form an optionally substituted 3- to 6-membered carbocyclyl or heterocyclyl;

R$^{13}$, R$^{14}$ and R$^{15}$ are each independently hydrogen, C$_1$-C$_3$ alkyl, C$_2$-C$_3$ alkenyl, or C$_2$-C$_3$ alkynyl; or R$^{14}$ and R$^{15}$ taken together form a 3- to 6-membered heterocyclyl;

R$^{16}$ is hydrogen, optionally substituted C$_1$-C$_3$ alkyl, optionally substituted C$_2$-C$_3$ alkenyl, optionally substituted C$_2$-C$_3$ alkynyl, C$_3$-C$_6$ cycloalky, or phenyl;

each m is independently 0, 1, or 2;

n1 and n2 are each independently 0, 1, or 2;

n3 is 1, 2, 3, 4 or 5; and t is 0, 1 or 2.

Embodiment 136

The compound of embodiment 135, wherein the compound has the structure of formula (IVA):

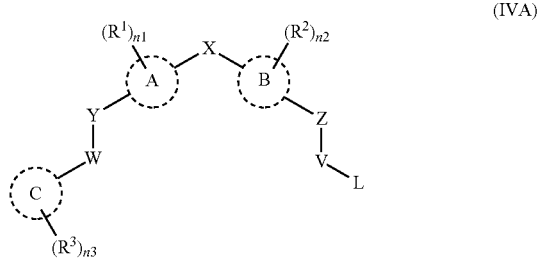

(IVA)

or a pharmaceutically acceptable salt, tautomer, stereoisomer or prodrug thereof, wherein:

A and B are each independently selected from phenyl, pyridyl, pyrimidyl, or thiophene;

C is a 3- to 10-membered ring;

X is a bond, —(CR$^5$R$^6$)$_t$—, or —NR$^7$;

Y and Z are each independently a bond, —CH$_2$—, —C(CH$_3$)H—, —O—, —S—, —NH—, —NCH$_3$—, or —N(COCH$_3$)—;

W is a bond, —CH$_2$—, —C(CH$_3$)H—, —C(=O)—, —N(R$^7$)CO—, or —CONR$^7$—;

V is —CH$_2$— and L is halogen, —NH$_2$, or —CF$_3$; or V is —CH$_2$CH$_2$- and L is halogen or —NH$_2$;

R$^1$ and R$^2$ are each independently hydrogen, halogen, —CN, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{13}$R$^{14}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$, optionally substituted —(C$_1$-C$_6$ alkyl)-SO$_2$R$^{16}$;

R$^3$ is selected from halogen, oxo, =S, =NR$^{16}$, —CN, —CF$_3$, —OH, —S(C$_1$-C$_3$ alkyl), C$_1$-C$_3$ alkyl, C$_2$-C$_3$ alkenyl, C$_2$-C$_3$ alkynyl, C$_1$-C$_3$ alkoxy, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl)NR$^{14}$SO$_2$R$^{16}$, —NR$^{14}$COR$^{16}$, —(C$_1$-C$_6$ alkyl)-NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —S$_2$(C$_1$-C$_3$ alkyl), or —(C$_1$-C$_6$ alkyl)-SO$_2$(C$_1$-C$_3$ alkyl);

R$^5$ and R$^6$ are each independently hydrogen, halogen, —OH, C$_1$-C$_3$ alkyl, C$_2$-C$_3$ alkenyl, C$_2$-C$_3$ alkynyl, or C$_1$-C$_3$ alkoxy; or R$^5$ and R$^6$ taken together form an optionally substituted 3- to 6-membered carbocyclyl or heterocyclyl;

R$^7$ is H or C$_1$-C$_6$ alkyl;

R$^{13}$, R$^{14}$ and R$^{15}$ are each independently hydrogen, C$_1$-C$_3$ alkyl, C$_2$-C$_3$ alkenyl, or C$_2$-C$_3$ alkynyl; or R$^{14}$ and R$^{15}$ taken together form a 3- to 6-membered heterocyclyl;

R$^{16}$ is hydrogen, C$_1$-C$_3$ alkyl, C$_2$-C$_3$ alkenyl, or C$_2$-C$_3$ alkynyl;

n1 and n2 are each independently 0, 1, or 2;

n3 is 1, 2, 3, 4 or 5; and t is 0, 1 or 2.

Embodiment 137

The compound of embodiment 135 or 136, wherein C is 5- to 10-membered heteroaryl or aryl Embodiment 138

The compound of embodiment 137, wherein C is 5- to 7-membered heteroaryl comprising 1, 2, or 3 heteroatoms selected from O, S, or N as a ring member.

Embodiment 139

The compound of embodiment 138, wherein C, which is substituted with (R$^3$)n3, is pyrazole, imidazole, oxazole, oxadiazole, oxazolone, isoxazole, thiazole, pyridyl, pyrazine, furan or pyrimidyl.

Embodiment 140

The compound of any one of embodiments 135-139, wherein C, which is substituted with (R$^3$)n3, is selected from

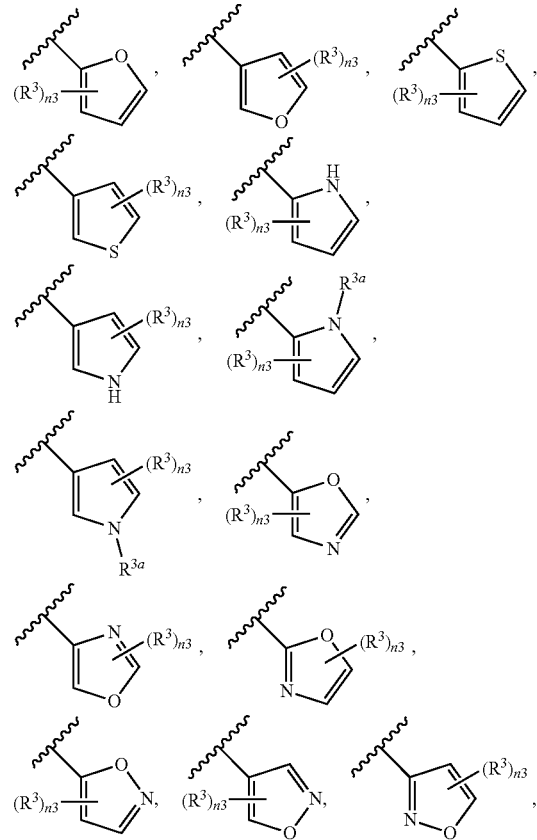

353
-continued

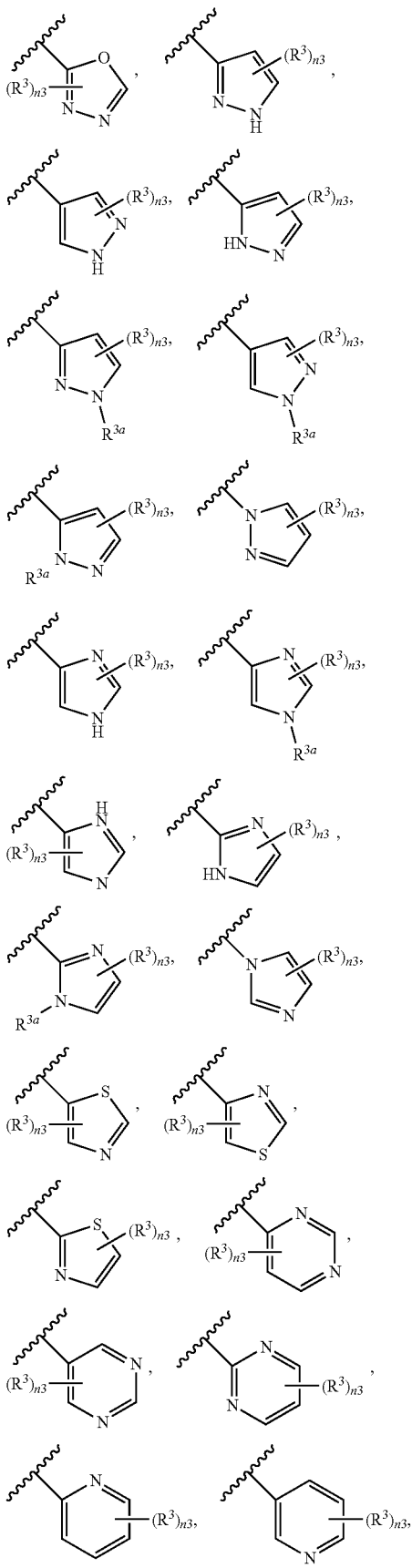

354
-continued

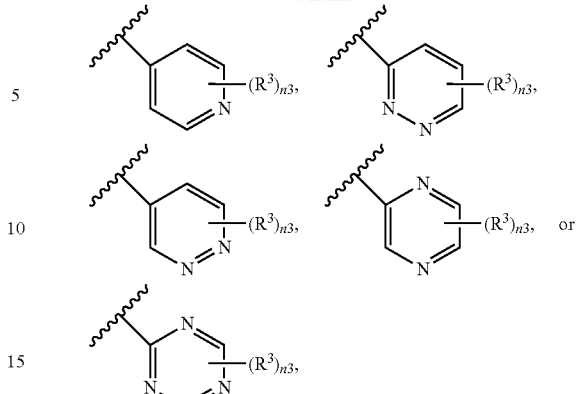

wherein $R^{3a}$ is $C_1$-$C_3$ alkyl.

Embodiment 141

The compound of any one of Embodiments 135-140, wherein $R^1$ and $R^2$ are each independently Cl, —CN, —CF$_3$, —OH, methyl, methoxy, or —CONH$_2$.

Embodiment 142

The compound of any one of Embodiments 135-141, wherein:
A and B are phenyl;
X is —(CR$^5$R$^6$)$_t$—;
Y and Z are each —O—,
V is —CH$_2$— or —CH$_2$CH$_2$—;
L is halogen;
$R^1$ and $R^2$ are each independently hydrogen, halogen, —CN, —CF$_3$, —OH, or optionally substituted $C_1$-$C_6$ alkyl;
$R^5$ and $R^6$ are each independently hydrogen, halogen, —OH, or $C_1$-$C_3$ alkyl; and
$R^{16}$ is hydrogen, $C_1$-$C_3$ alkyl, $C_2$-$C_3$ alkenyl, or $C_2$-$C_3$ alkynyl.

Embodiment 143

The compound of any one of Embodiments 135-142, wherein:
$R^5$ and $R^6$ are each independently hydrogen, or $C_1$-$C_3$ alkyl;
W is —CH$_2$— or —C(CH$_3$)H—;
V is —CH$_2$CH$_2$—; and
$R^1$ and $R^2$ are each independently hydrogen, halogen, or —CN.

Embodiment 144

The compound of any one of Embodiments 135-143, wherein the compound has the structure of formula (A-I):

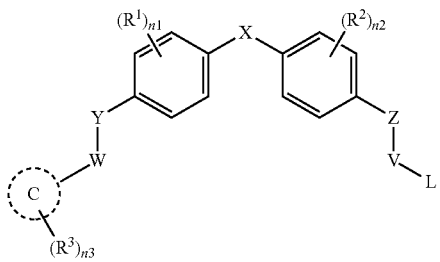

(A-I)

or a pharmaceutically acceptable salt, tautomer, stereoisomer or prodrug thereof, wherein:
C is a 5- to 7-membered monocyclic heteroaryl comprising 1, 2, or 3 heteroatoms selected from O, S, or N as a ring member;
X is a bond, —(CR$^5$R$^6$)$_t$—, or —NR$^7$;
Y is a bond, —CH$_2$—, —C(CH$_3$)H—, —O—, —S—, —NH—, —NCH$_3$—, or —N(COCH$_3$)—;
Z is a bond, —CH$_2$—, —O—, or —NH—;
W is a bond, —CH$_2$—, —C(CH$_3$)H—, —C(=O)—, —N(R$^7$)CO—, or —CONR$^7$—;
V is —CH$_2$— and L is halogen, —NH$_2$, or —CF$_3$; or
V is —CH$_2$CH$_2$- and L is halogen or —NH$_2$;
R$^1$ and R$^2$ are each independently hydrogen, halogen, —CN, —CF$_3$, methyl, or —CONH$_2$;
R$^3$ is selected from —CN, C$_1$-C$_3$ alkoxy, CF$_3$, C$_1$-C$_3$ alkyl, C$_2$-C$_3$ alkenyl, C$_2$-C$_3$ alkynyl, —S(C$_1$-C$_3$ alkyl), —SO$_2$(C$_1$-C$_3$ alkyl), —NH$_2$, —(C$_1$-C$_3$ alkyl)NH$_2$, —NHSO$_2$CH$_3$, —NHSO$_2$CF$_3$, —N(CH$_3$)SO$_2$CH$_3$, —NHSO$_2$CH$_2$CH$_3$, —N(CH$_3$)SO$_2$CH$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), —N(CH$_3$)COO(C$_1$-C$_3$ alkyl), —NHCO(C$_1$-C$_3$ alkyl), or —N(CH$_3$)COO(C$_1$-C$_3$ alkyl);
R$^5$ and R$^6$ are each independently hydrogen, halogen, —OH, or C$_1$-C$_3$ alkyl;
R$^7$ is H or C$_1$-C$_6$ alkyl;
n1 and n2 are each independently 0, 1, or 2;
n3 is 1, 2, 3, 4 or 5; and
t is 0, 1 or 2.

Embodiment 145

The compound of any one of Embodiments 135-144, wherein: at least one R$^3$ is selected from —CN, C$_1$-C$_3$ alkoxy, —CONH$_2$, —NHSO$_2$CH$_3$, —N(CH$_3$)SO$_2$CH$_3$, —NHSO$_2$CH$_2$CH$_3$, —N(CH$_3$)SO$_2$CH$_2$CH$_3$, or —SO$_2$CH$_3$ and the other R$^3$, if present, is selected from —CN, —CF$_3$, C$_1$-C$_3$ alkyl, C$_2$-C$_3$ alkenyl, C$_2$-C$_3$ alkynyl, C$_1$-C$_3$ alkoxy, —S(C$_1$-C$_3$ alkyl), —SO$_2$(C$_1$-C$_3$ alkyl), —NH$_2$, —(C$_1$-C$_3$ alkyl)NH$_2$, —NHSO$_2$CH$_3$, —NHSO$_2$CF$_3$, —N(CH$_3$)SO$_2$CH$_3$, —NHSO$_2$CH$_2$CH$_3$, —N(CH$_3$)SO$_2$CH$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), —N(CH$_3$)COO(C$_1$-C$_3$ alkyl), —NHCO(C$_1$-C$_3$ alkyl), or —N(CH$_3$)COO(C$_1$-C$_3$ alkyl).

Embodiment 146

The compound of any one of Embodiments 135-145, wherein:
X is a bond or —(CR$^5$R$^6$)$_t$;
W is a bond, —CH$_2$—, or —C(CH$_3$)H—;
Y is —O—;
Z is —O—;
V is —CH$_2$— or —CH$_2$CH$_2$—; and
L is halogen.

Embodiment 147

The compound of any one of Embodiments 135-146, wherein the compound has the structure of formula (G-II):

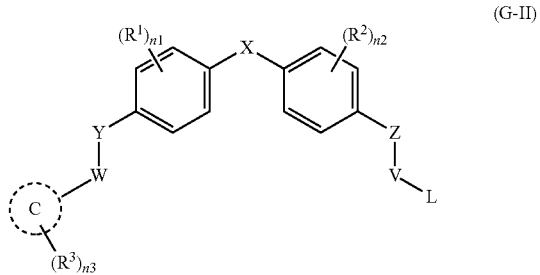

(G-II)

or a pharmaceutically acceptable salt, tautomer, stereoisomer or prodrug thereof, wherein:
C is O

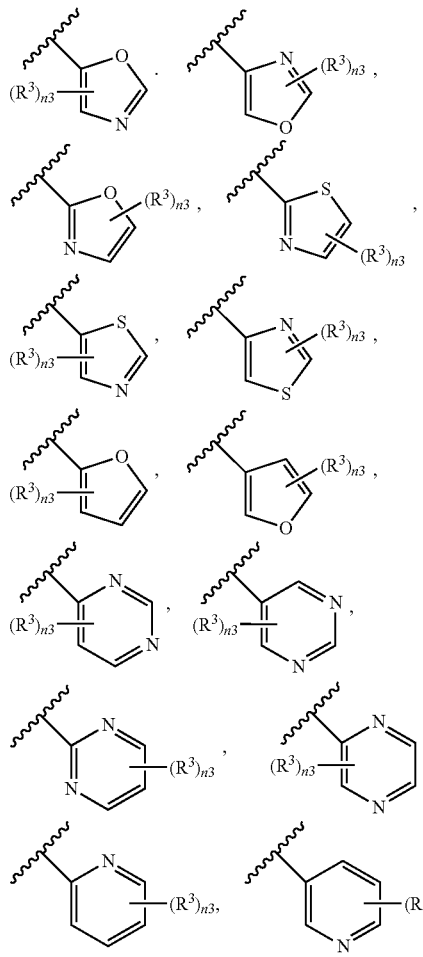

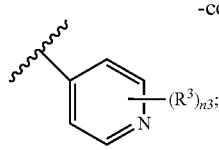

X is —(CR⁵R⁶)$_t$—;
Y is —O—;
Z is —O—;
W is —CH$_2$— or —C(CH$_3$)H—;
V is —CH$_2$CH$_2$—;
L is halogen;
$R^1$ and $R^2$ are each independently Cl or —CN;
at least one $R^3$ is selected from —CN, $C_1$-$C_3$ alkoxy, —CONH$_2$, —NHSO$_2$CH$_3$, —N(CH$_3$)SO$_2$CH$_3$, —NHSO$_2$CH$_2$CH$_3$, —N(CH$_3$)SO$_2$CH$_2$CH$_3$, or —SO$_2$CH$_3$ and the other $R^3$, if present, is selected from —CN, —CF$_3$, $C_1$-$C_3$ alkyl, $C_2$-$C_3$ alkenyl, $C_2$-$C_3$ alkynyl, $C_1$-$C_3$ alkoxy, —S($C_1$-$C_3$ alkyl), —SO$_2$($C_1$-$C_3$ alkyl), —NH$_2$, —($C_1$-$C_3$ alkyl)NH$_2$, —NHSO$_2$CH$_3$, —NHSO$_2$CF$_3$, —N(CH$_3$)SO$_2$CH$_3$, —NHSO$_2$CH$_2$CH$_3$, —N(CH$_3$)SO$_2$CH$_2$CH$_3$, —CH$_2$NHSO$_2$CH$_3$, —CH$_2$N(CH$_3$)SO$_2$CH$_3$, —SO$_2$NH$_2$, —CONH$_2$, —CON($C_1$-$C_3$ alkyl)$_2$, —CONH($C_1$-$C_3$ alkyl), —NHCO($C_1$-$C_3$ alkyl), —N(CH$_3$)COO($C_1$-$C_3$ alkyl), —NHCO($C_1$-$C_3$ alkyl), or —N(CH$_3$)COO($C_1$-$C_3$ alkyl);
$R^5$ and $R^6$ are each independently hydrogen or methyl;
n1 and n2 are each independently 0, 1, or 2;
n3 is 1 or 2; and
t is 1.

Embodiment 148

The compound of any one of Embodiments 135-147, wherein: at least one $R^3$ is selected from —NHSO$_2$CH$_3$, —NHSO$_2$CH$_2$CH$_3$, or —SO$_2$CH$_3$ and the other $R^3$, if present, is selected from —CN, $C_1$-$C_3$ alkyl, $C_1$-$C_3$ alkoxy, —SO$_2$($C_1$-$C_3$ alkyl), —NH$_2$, —($C_1$-$C_3$ alkyl)NH$_2$, —NHSO$_2$CH$_3$, —N(CH$_3$)SO$_2$CH$_3$, —NHSO$_2$CH$_2$CH$_3$, —N(CH$_3$)SO$_2$CH$_2$CH$_3$, —SO$_2$NH$_2$, —CONH$_2$, —CON($C_1$-$C_3$ alkyl)$_2$, —CONH($C_1$-$C_3$ alkyl), —NHCO($C_1$-$C_3$ alkyl), —N(CH$_3$)COO($C_1$-$C_3$ alkyl), —NHCO($C_1$-$C_3$ alkyl), or —N(CH$_3$)COO($C_1$-$C_3$ alkyl).

Embodiment 149

A compound selected from Compounds A1-A96, A98-A116, A118-A159, A161-A175, or A177-A234 or a pharmaceutically acceptable salt, tautomer, stereoisomer or prodrug thereof.

Embodiment 150

The compound of Embodiment 149, wherein the compound is selected from

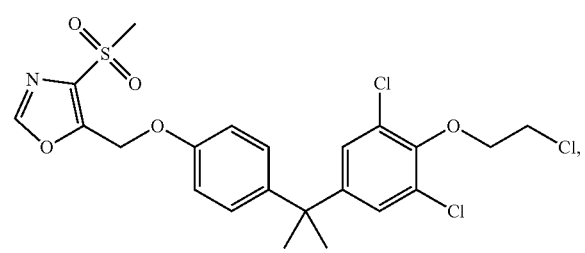

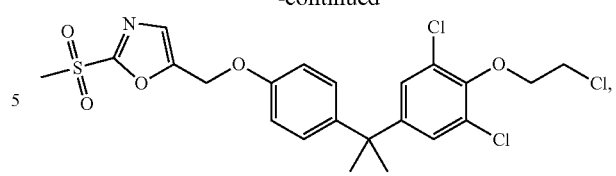

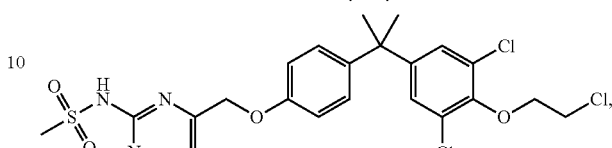

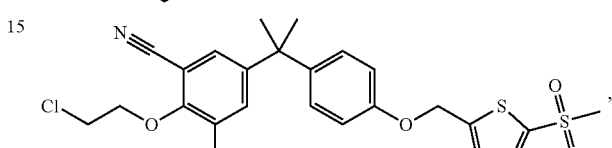

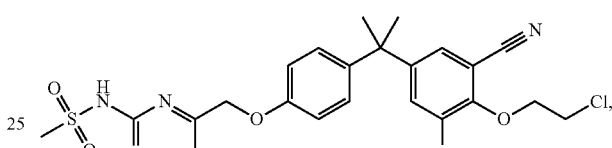

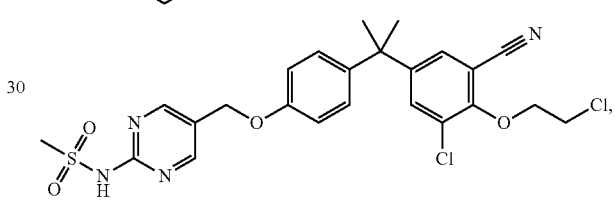

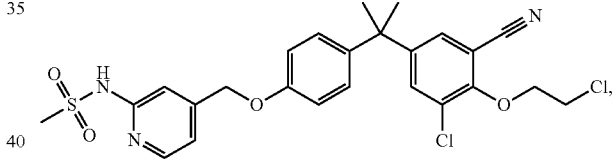

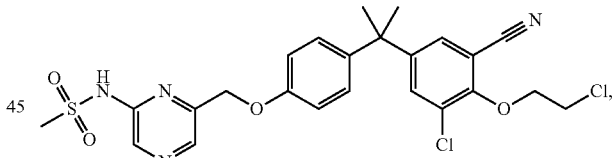

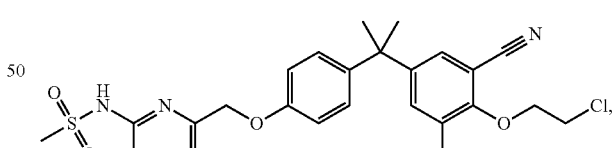

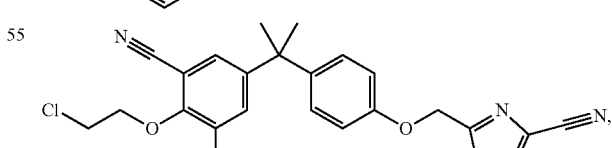

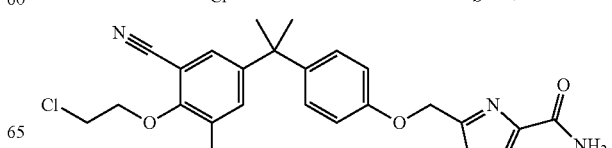

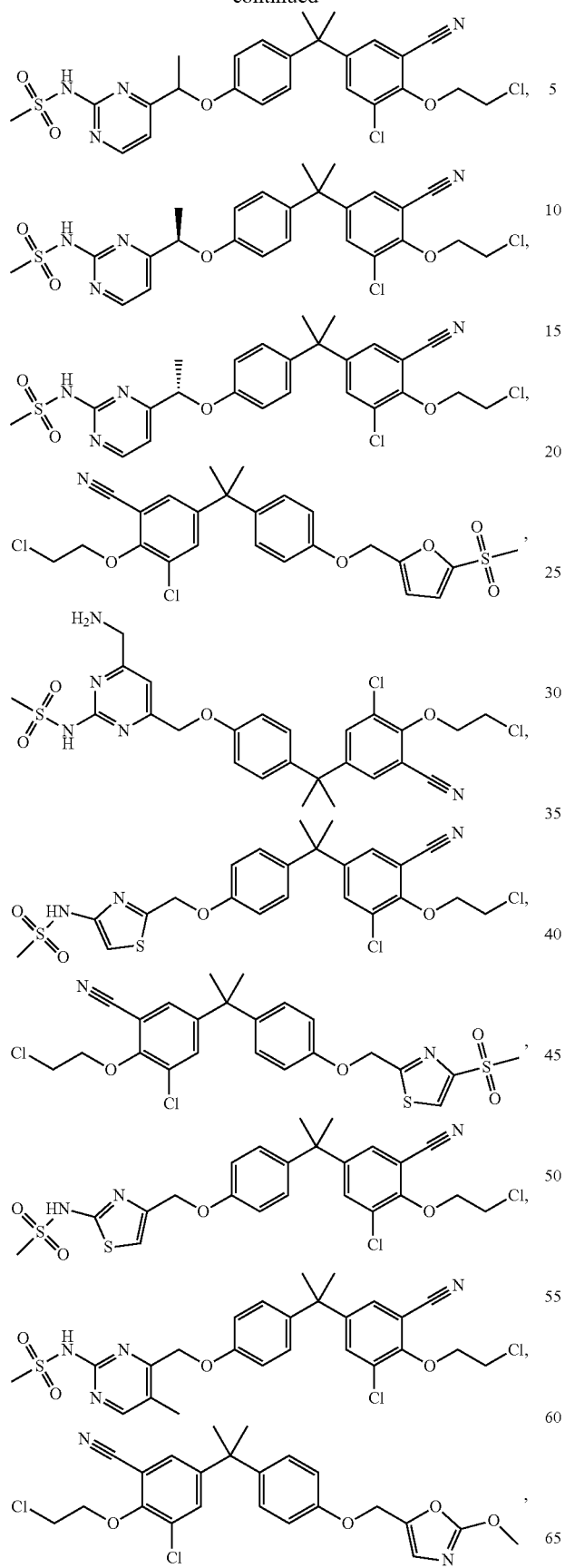

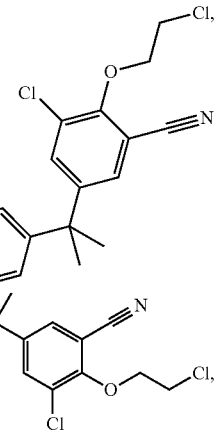

or a pharmaceutically acceptable salt, tautomer, stereoisomer or prodrug thereof.

Embodiment 151

A pharmaceutical composition comprising a compound of any one of Embodiments 135-150 and a pharmaceutically acceptable carrier Embodiment 152

A method for treating cancer, comprising administering the compound, pharmaceutically acceptable salt, tautomer, stereoisomer or prodrug of any one of the compound of Embodiments 135-150 or any pharmaceutical composition of Embodiment 151, to a subject in need thereof.

Embodiment 153

The method of Embodiment 152, wherein the cancer is prostate cancer.

Embodiment 154

The method of Embodiment 153, wherein the prostate cancer is metastatic castration-resistant prostate cancer.

Embodiment 155

The method of Embodiment 154, wherein the prostate cancer expresses full-length androgen receptor or truncated androgen receptor splice variant.

The publications discussed herein are provided solely for their disclosure prior to the filing date of the present application. Nothing herein is to be construed as an admission that the present invention is not entitled to antedate such publication by virtue of prior invention.

While the invention has been described in connection with proposed specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A compound having the structure of formula (A-I):

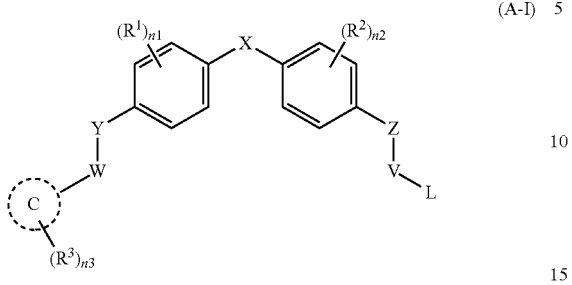

or a pharmaceutically acceptable salt, tautomer, or stereoisomer thereof, wherein:

C is a 5- to 7-membered monocyclic heteroaryl comprising 1, 2, or 3 heteroatoms selected from O, S, or N as a ring member;

X is a bond, —(CR$^5$R$^6$)$_t$—, or —NR$^7$;

Y is a bond, —CH$_2$—, —C(CH$_3$)H—, —O—, —S—, —NH—, —NCH$_3$—, or —N(COCH$_3$)—;

Z is a bond, —CH$_2$—, —O—, or —NH—;

W is a bond, —CH$_2$—, —C(CH$_3$)H—, —C(=O)—, —N(R$^7$)CO—, or —CONR$^7$—;

V is —CH$_2$— and L is halogen, —NH$_2$, or —CF$_3$; or
V is —CH$_2$CH$_2$— and L is halogen or —NH$_2$;

R$^1$ and R$^2$ are each independently hydrogen, halogen, —CN, —CF$_3$, methyl, or —CONH$_2$;

R$^3$ is selected from —CN, C$_1$-C$_3$ alkoxy, —CF$_3$, C$_1$-C$_3$ alkyl, C$_2$-C$_3$ alkenyl, C$_2$-C$_3$ alkynyl, —S(C$_1$-C$_3$ alkyl), —SO$_2$(C$_1$-C$_3$ alkyl), —NH$_2$, —(C$_1$-C$_3$ alkyl)NH$_2$, —NHSO$_2$CH$_3$, —NHSO$_2$CF$_3$, —N(CH$_3$)SO$_2$CH$_3$, —NHSO$_2$CH$_2$CH$_3$, —N(CH$_3$)SO$_2$CH$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), —N(CH$_3$)COO(C$_1$-C$_3$ alkyl), —NHCO(C$_1$-C$_3$ alkyl), or —N(CH$_3$)COO(C$_1$-C$_3$ alkyl);

R$^5$ and R$^6$ are each independently hydrogen, halogen, —OH, or C$_1$-C$_3$ alkyl;

R$^7$ is H or C$_1$-C$_6$ alkyl;

n1 and n2 are each independently 0, 1, or 2;

n3 is 1, 2, 3, 4 or 5; and t is 0, 1 or 2.

2. The compound of claim 1, wherein C, which is substituted with (R$^3$)n3, is pyrazole, imidazole, oxazole, oxadiazole, oxazolone, isoxazole, thiazole, pyridyl, pyrazine, furan or pyrimidyl.

3. The compound of claim 2, wherein C, which is substituted with (R$^3$)n3, is selected from

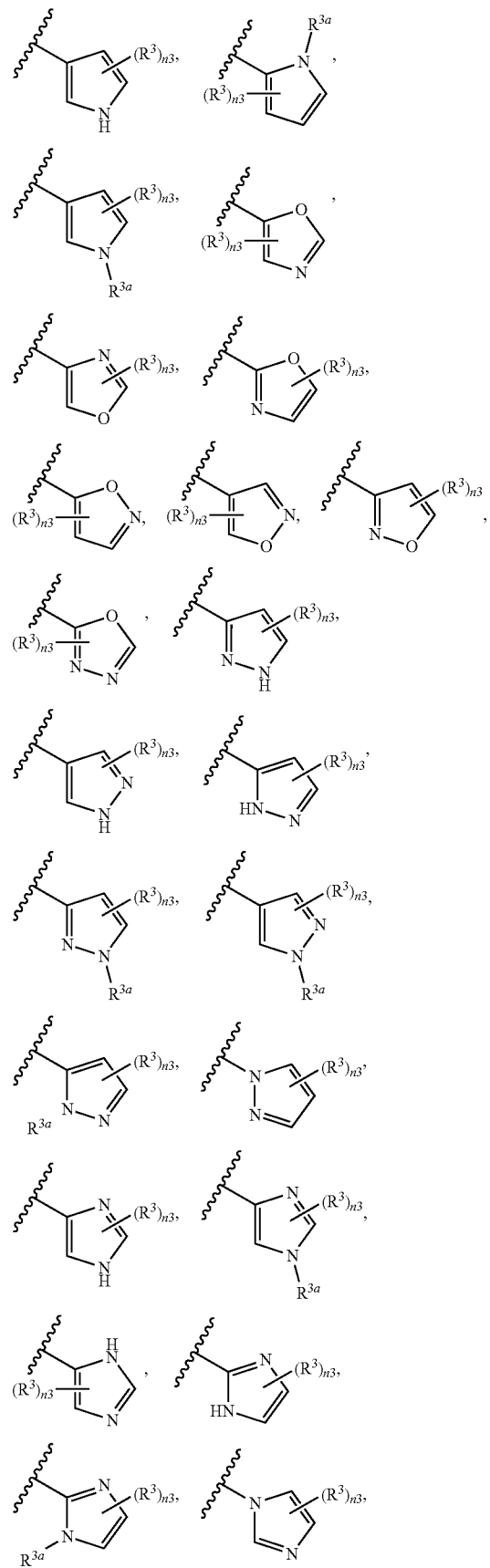

-continued

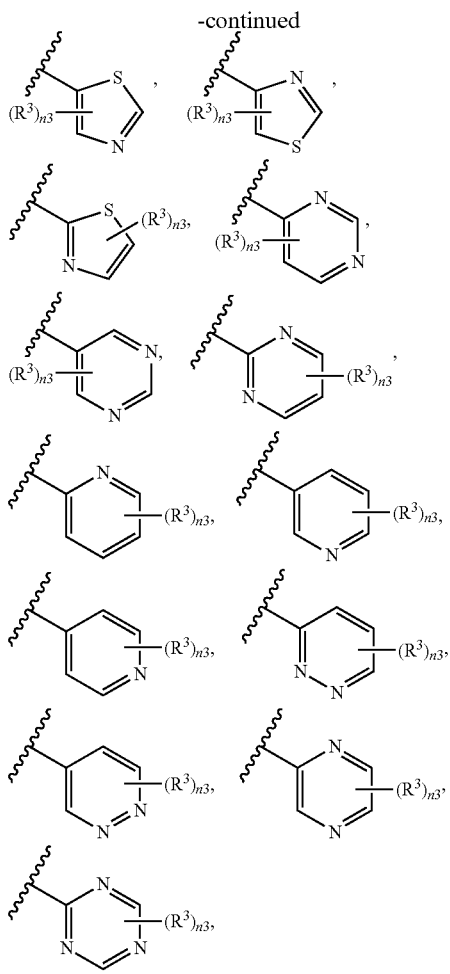

wherein R³ᵃ is C₁-C₃ alkyl.

4. The compound of claim 1, wherein:
   X is —(CR⁵R⁶)$_t$—;
   Y and Z are each —O—;
   V is —CH₂— or —CH₂CH₂—; and
   L is halogen.

5. The compound of claim 4, wherein:
   R⁵ and R⁶ are each independently hydrogen, or C₁-C₃ alkyl;
   W is —CH₂— or —C(CH₃)H—;
   V is —CH₂CH₂—; and
   R¹ and R² are each independently hydrogen, halogen, or —CN.

6. The compound of claim 1, wherein:
   at least one R³ is selected from —CN, C₁-C₃ alkoxy, —CONH₂, —NHSO₂CH₃, —N(CH₃)SO₂CH₃, —NHSO₂CH₂CH₃, —N(CH₃)SO₂CH₂CH₃, or —SO₂CH₃ and the other R³, if present, is selected from —CN, —CF₃, C₁-C₃ alkyl, C₂-C₃ alkenyl, C₂-C₃ alkynyl, C₁-C₃ alkoxy, —S(C₁-C₃ alkyl), —SO₂(C₁- C₃ alkyl), —NH₂, —(C₁-C₃ alkyl)NH₂, —NHSO₂CH₃, —NHSO₂CF₃, —N(CH₃)SO₂CH₃, SO₂CH₂CH₃, —N(CH₃)SO₂CH₂CH₃, —CH₂NHSO₂CH₃, —CH₂N(CH₃)SO₂CH₃, —SO₂NH₂, —CONH₂, —CON(C₁-C₃ alkyl)₂, —CONH(C₁-C₃ alkyl), —NHCO(C₁-C₃ alkyl), —N(CH₃)COO(C₁-C₃ alkyl), —NHCO(C₁-C₃ alkyl), or —N(CH₃)COO(C₁-C₃ alkyl).

7. The compound of claim 1, wherein:
   X is a bond or —(CR⁵R⁶)$_t$;
   W is a bond, —CH₂—, or —C(CH₃)H—;
   Y is —O—;
   Z is —O—;
   V is —CH₂— or —CH₂CH₂—; and
   L is halogen.

8. The compound of claim 1, wherein the compound has the structure of formula (G-II)

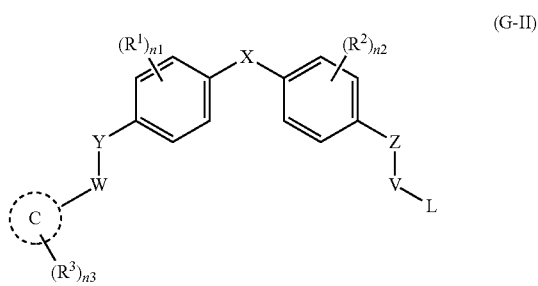

or a pharmaceutically acceptable salt, tautomer, or stereoisomer thereof, wherein:
   C is

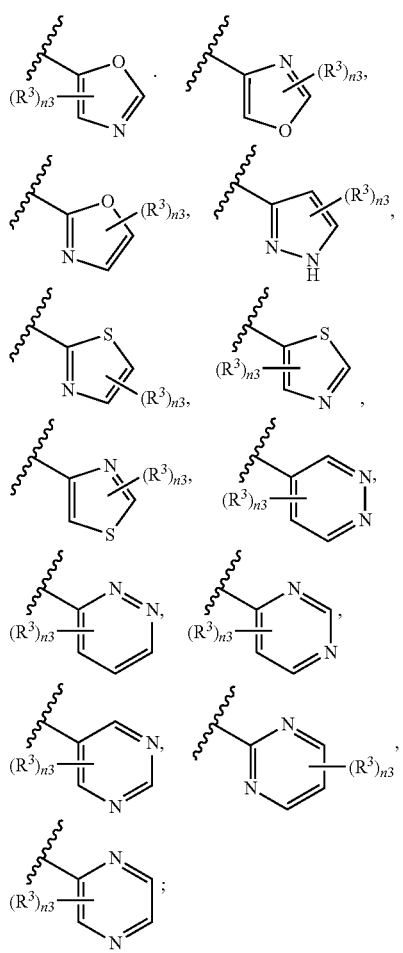

X is —(CR⁵R⁶)$_t$—;
Y is —O—;

Z is —O—;
W is —CH$_2$— or —C(CH$_3$)H—;
V is —CH$_2$CH$_2$—;
L is halogen;
R$^1$ and R$^2$ are each independently Cl or —CN;
at least one R$^3$ is selected from —CN, C$_1$-C$_3$ alkoxy, —CONH$_2$, —NHSO$_2$CH$_3$, —N(CH$_3$)SO$_2$CH$_3$, —NHSO$_2$CH$_2$CH$_3$, —N(CH$_3$)SO$_2$CH$_2$CH$_3$, or —SO$_2$CH$_3$ and the other R$^3$, if present, is selected from —CN, —CF$_3$, C$_1$-C$_3$ alkyl, C$_2$-C$_3$ alkenyl, C$_2$-C$_3$ alkynyl, C$_1$-C$_3$ alkoxy, —S(C$_1$-C$_3$ alkyl), —SO$_2$(C$_1$-C$_3$ alkyl), —NH$_2$, —(C$_1$-C$_3$ alkyl)NH$_2$, —NHSO$_2$CH$_3$, —NHSO$_2$CF$_3$, —N(CH$_3$)SO$_2$CH$_3$, —NHSO$_2$CH$_2$CH$_3$, —N(CH$_3$)SO$_2$CH$_2$CH$_3$, —CH$_2$NHSO$_2$CH$_3$, —CH$_2$N(CH$_3$)SO$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), —N(CH$_3$)COO(C$_1$-C$_3$ alkyl), —NHCO(C$_1$-C$_3$ alkyl), or —N(CH$_3$)COO(C$_1$-C$_3$ alkyl);
R$^5$ and R$^6$ are each independently hydrogen or methyl;
n1 and n2 are each independently 0, 1, or 2;
n3 is 1 or 2; and
t is 1.

9. The compound of claim 8, wherein:
at least one R$^3$ is selected from —NHSO$_2$CH$_3$, —NHSO$_2$CH$_2$CH$_3$, or —SO$_2$CH$_3$ and the other R$^3$, if present, is selected from —CN, C$_1$-C$_3$ alkyl, C$_1$-C$_3$ alkoxy, —SO$_2$(C$_1$-C$_3$ alkyl), —NH$_2$, —(C$_1$-C$_3$ alkyl)NH$_2$, —NHSO$_2$CH$_3$, —N(CH$_3$)SO$_2$CH$_3$, —NHSO$_2$CH$_2$CH$_3$, —N(CH$_3$)SO$_2$CH$_2$CH$_3$, —SO$_2$NH$_2$, —CONH$_2$, —CON(C$_1$-C$_3$ alkyl)$_2$, —CONH(C$_1$-C$_3$ alkyl), —NHCO(C$_1$-C$_3$ alkyl), —N(CH$_3$)COO(C$_1$-C$_3$ alkyl), —NHCO(C$_1$-C$_3$ alkyl), or —N(CH$_3$)COO(C$_1$-C$_3$ alkyl).

10. A compound selected from the group consisting of:

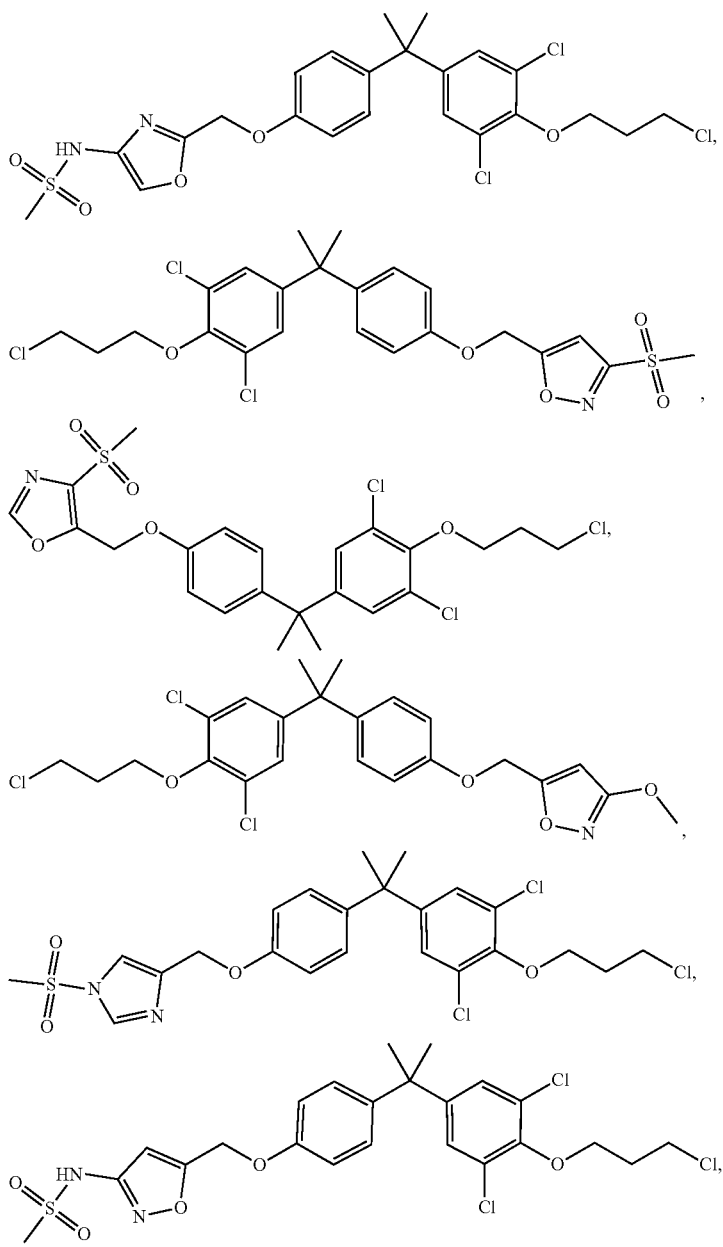

-continued
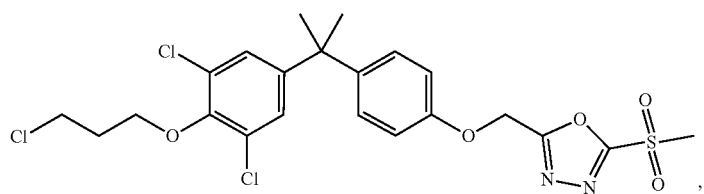
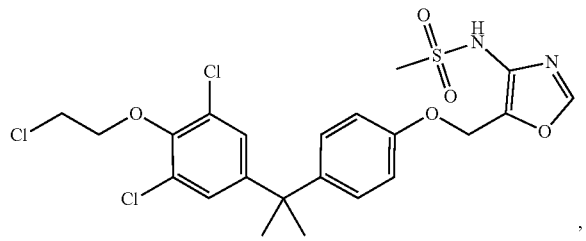
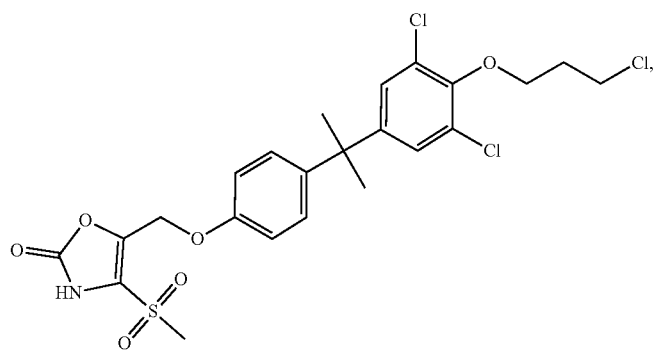
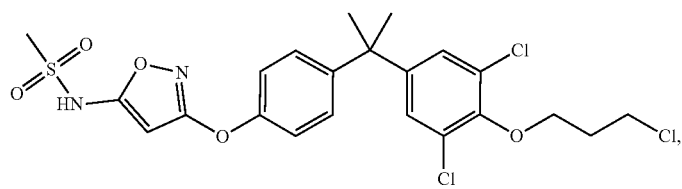
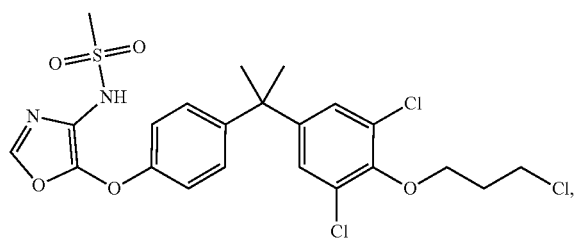
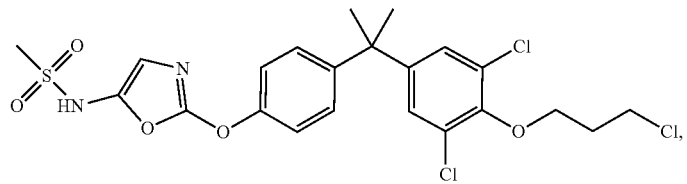
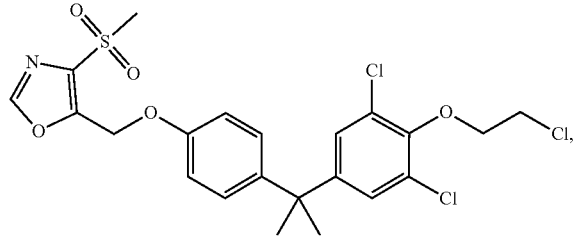

-continued
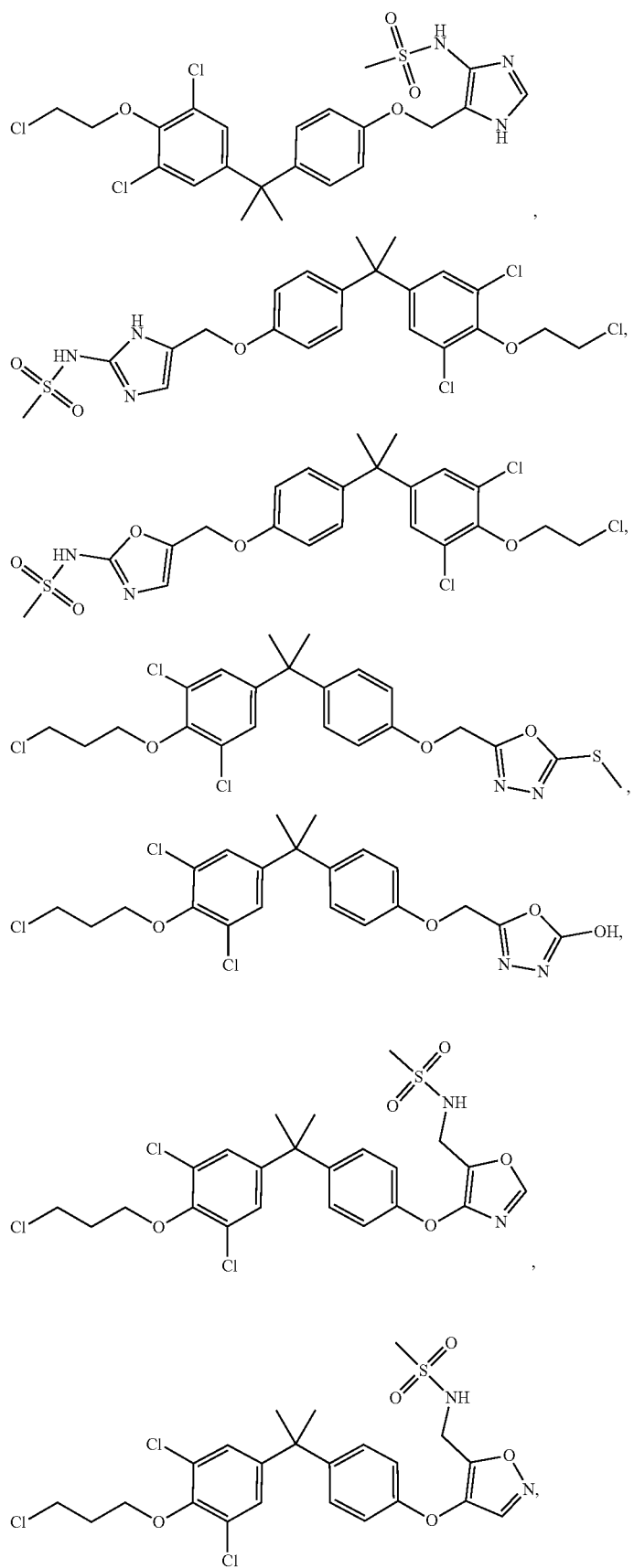

-continued
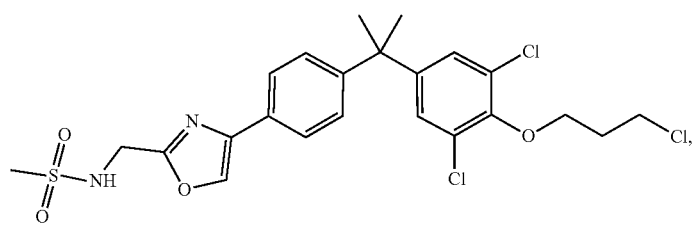
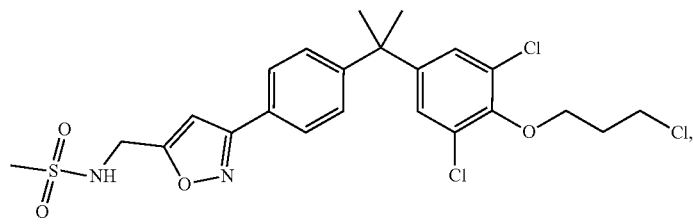
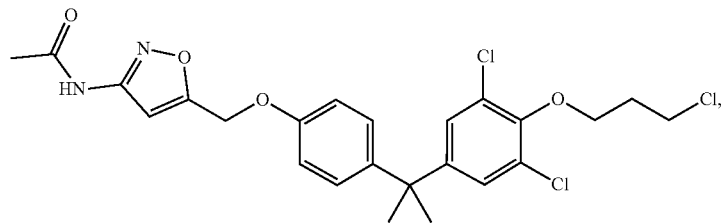
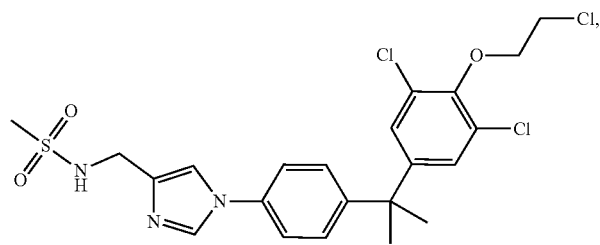
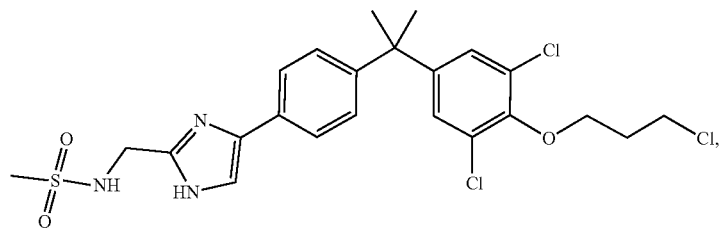
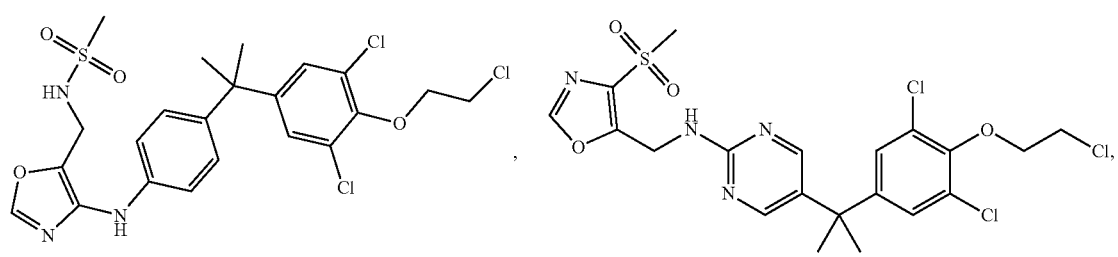
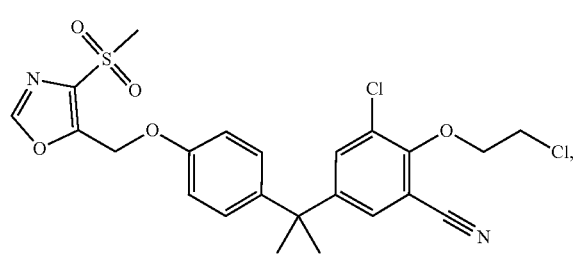

-continued
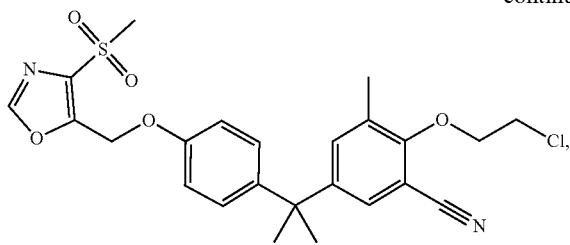
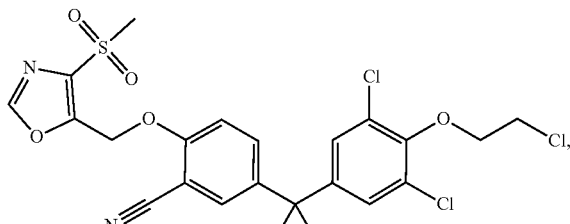
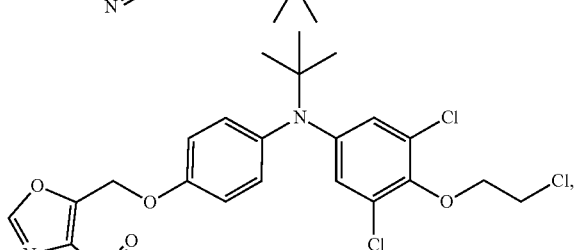
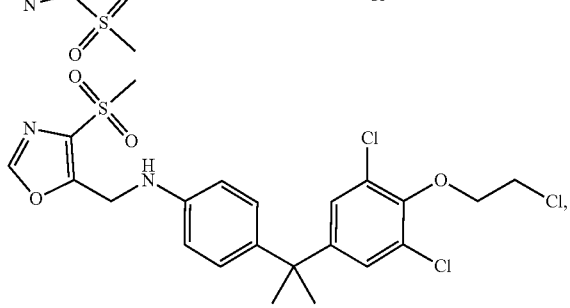
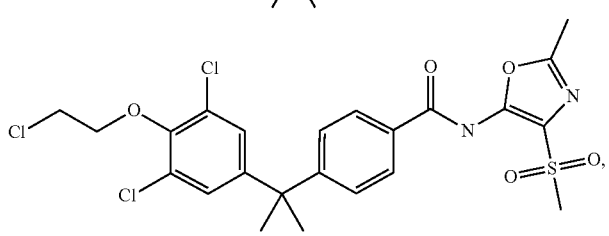
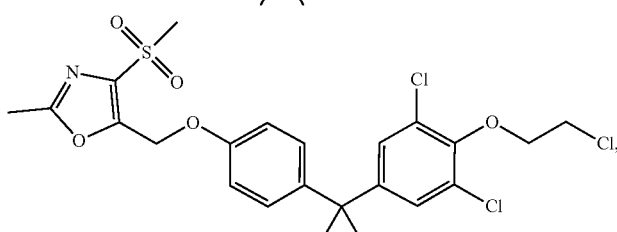
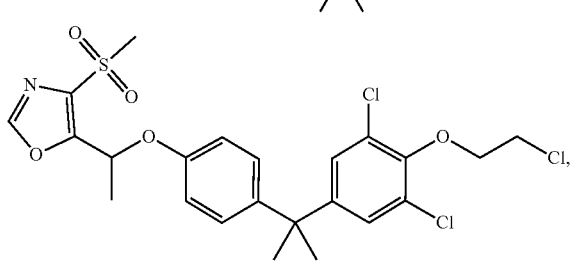

-continued
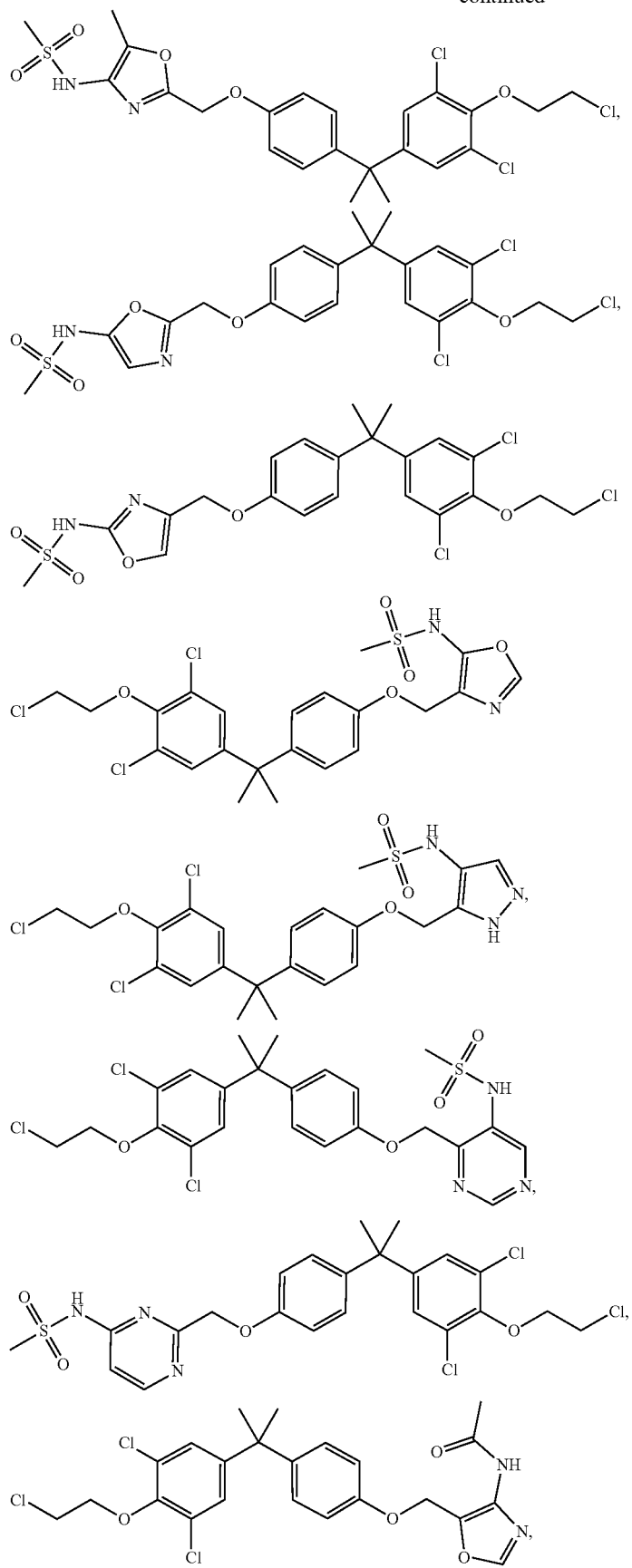

-continued
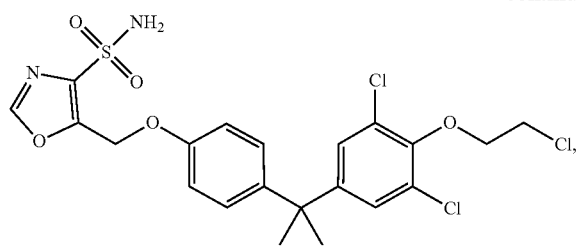
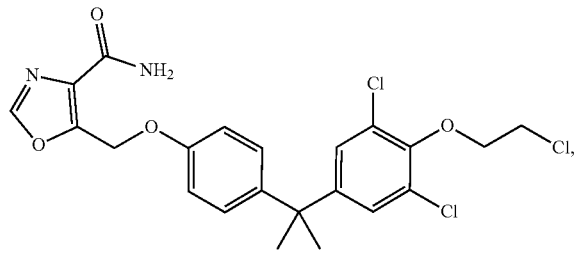
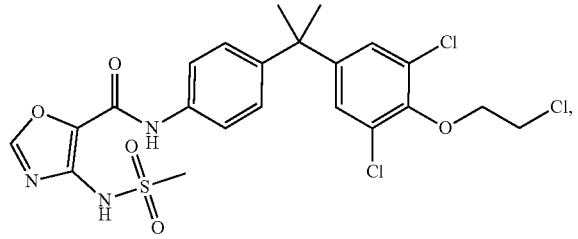
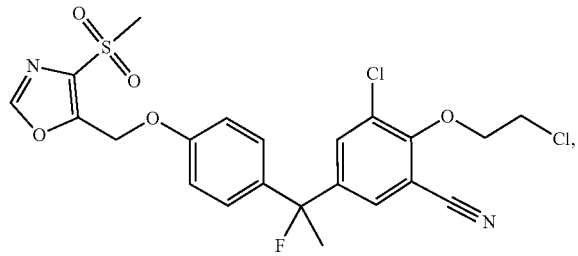
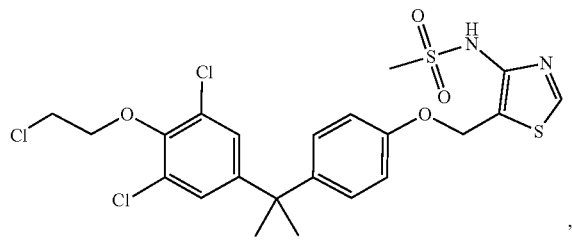
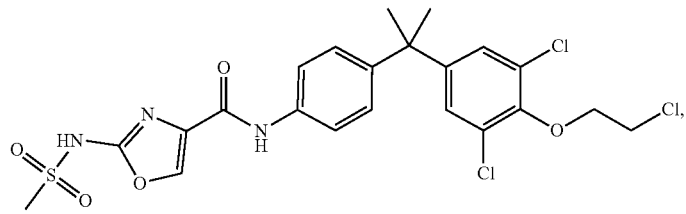
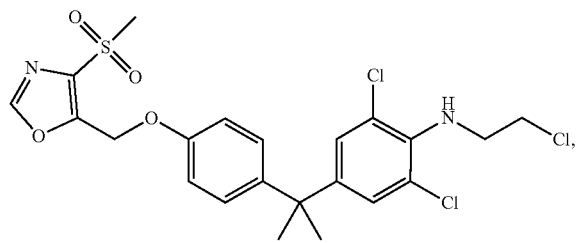

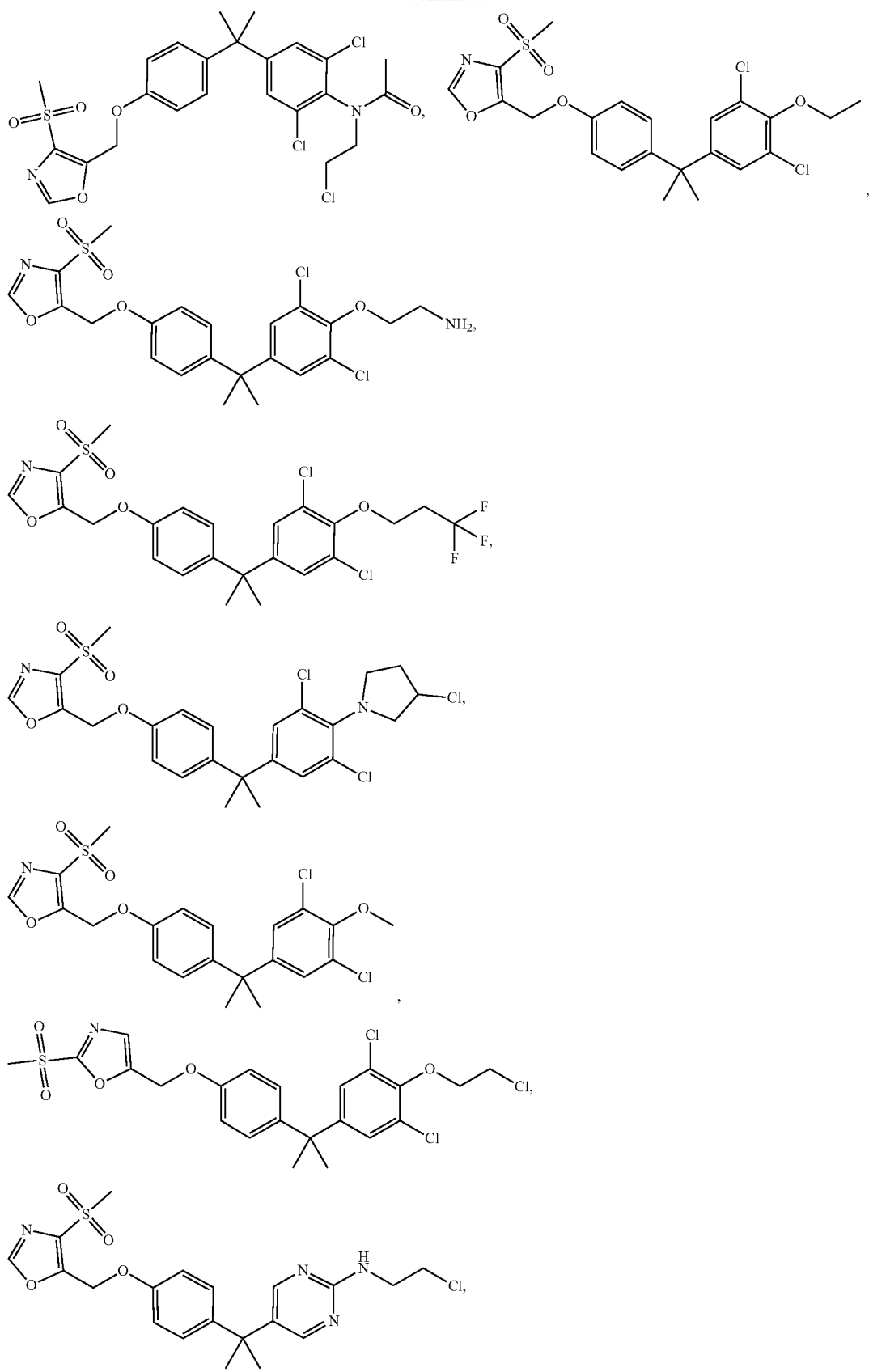

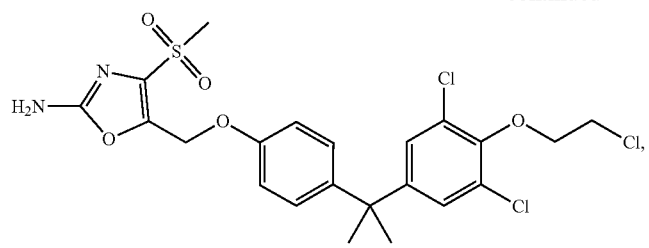
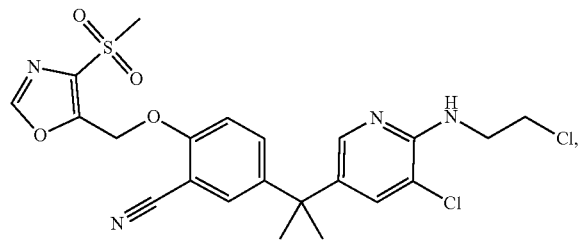
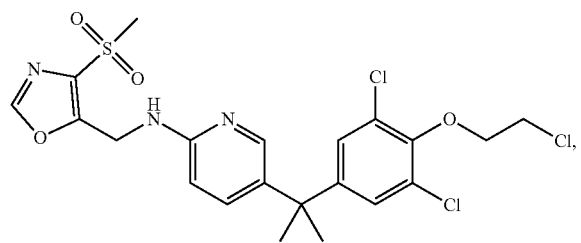
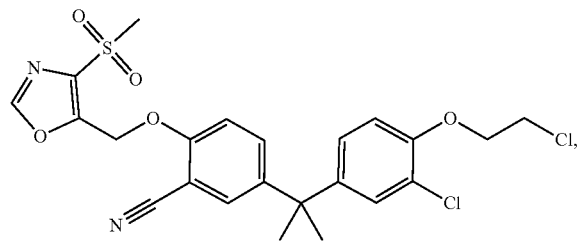
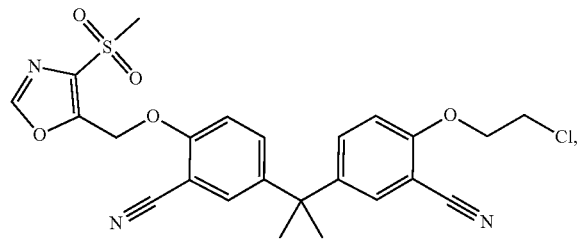
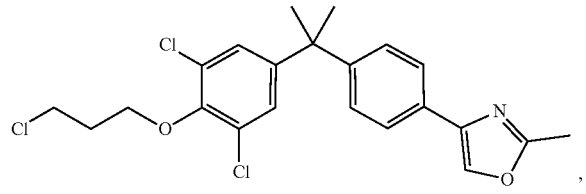
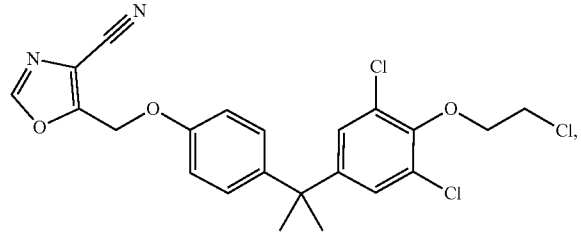

-continued
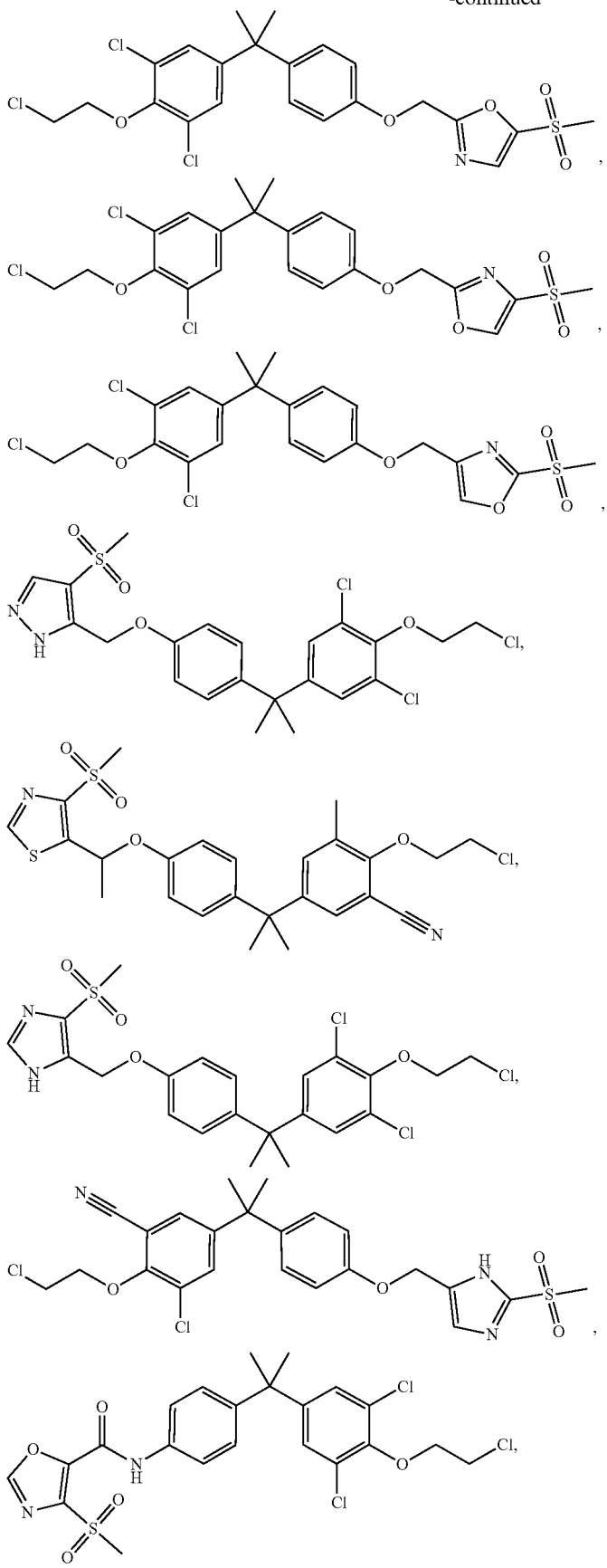

-continued
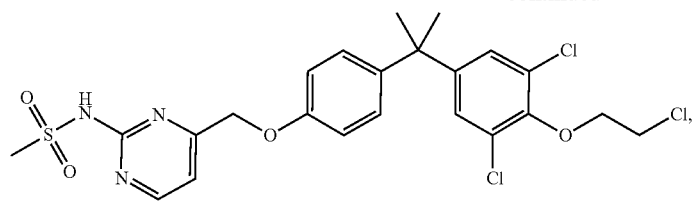
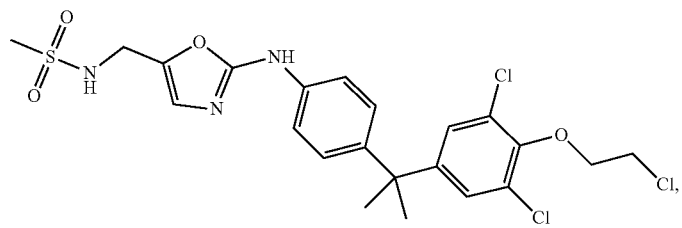
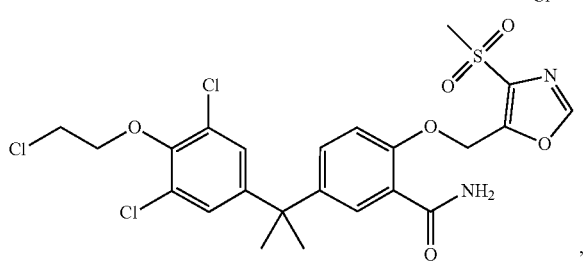
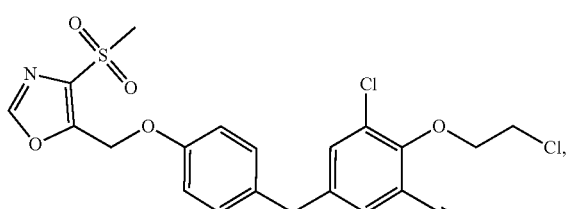
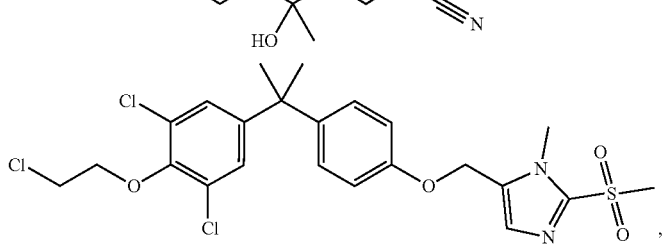
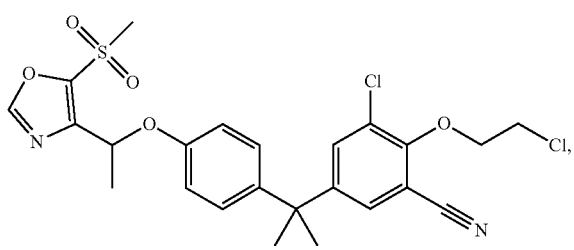
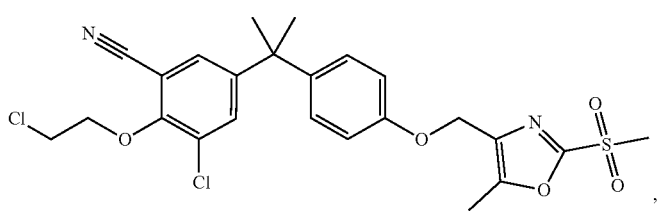

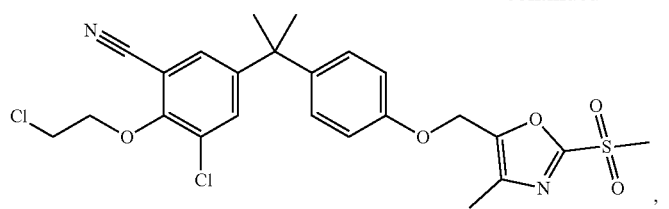
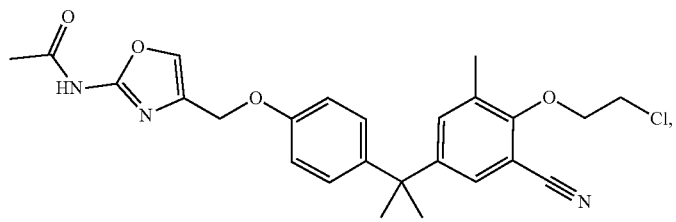
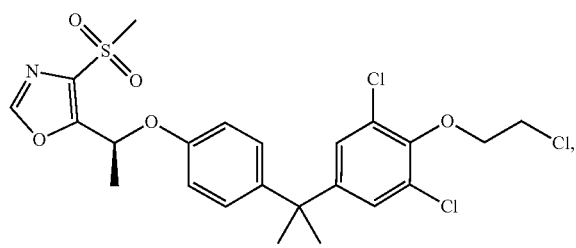
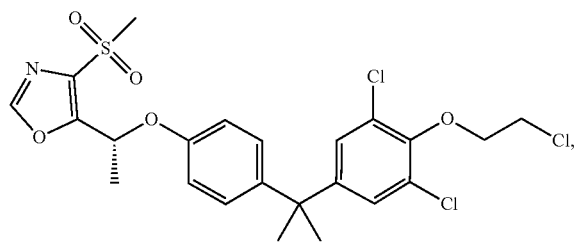
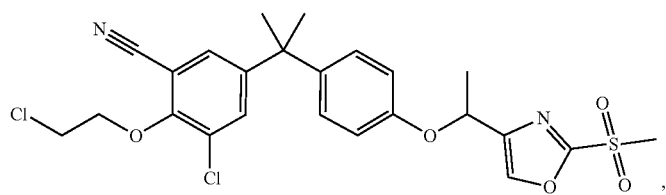
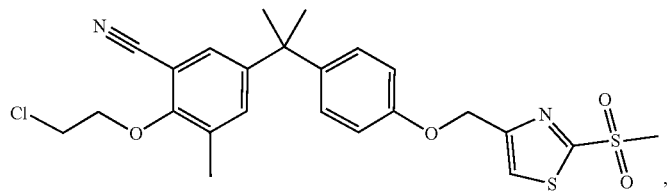
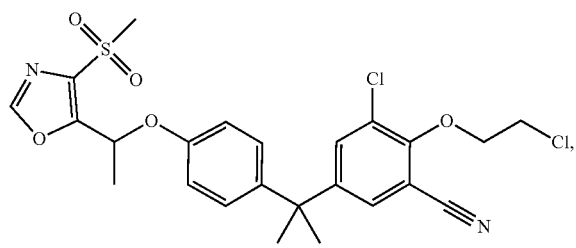

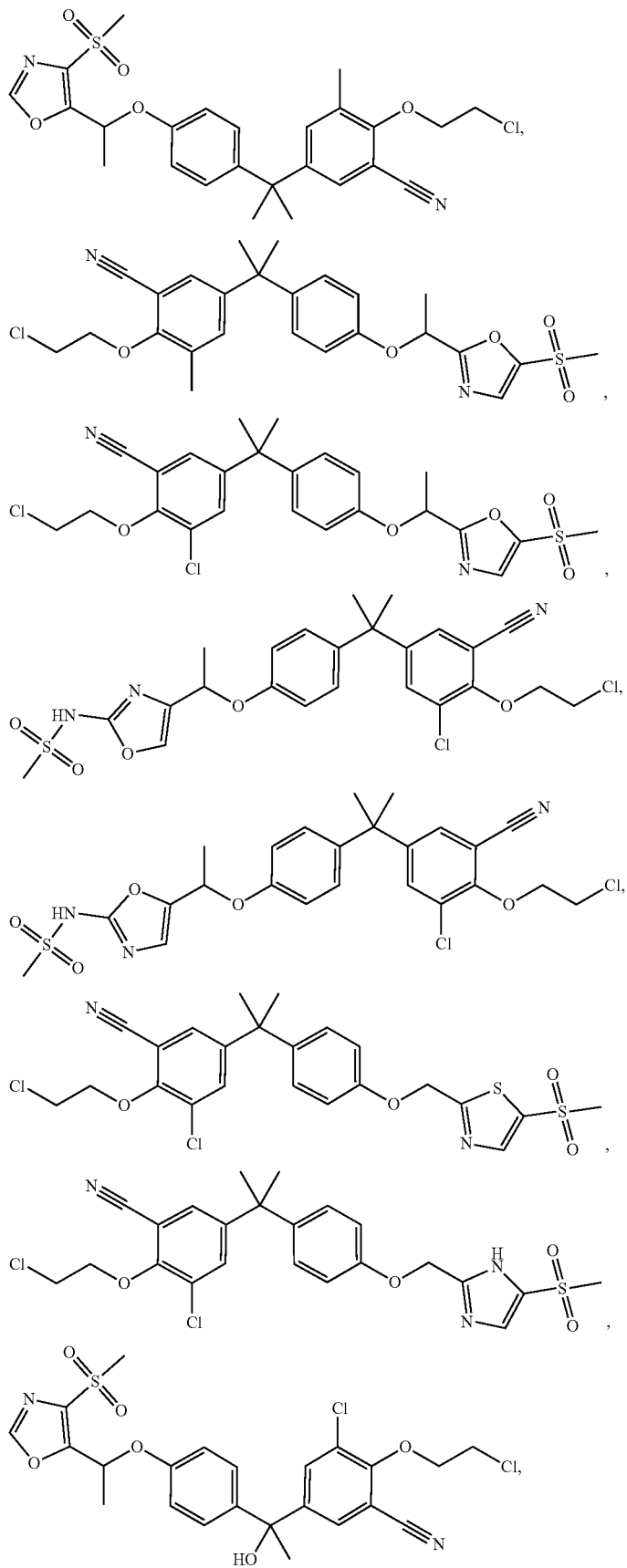

-continued
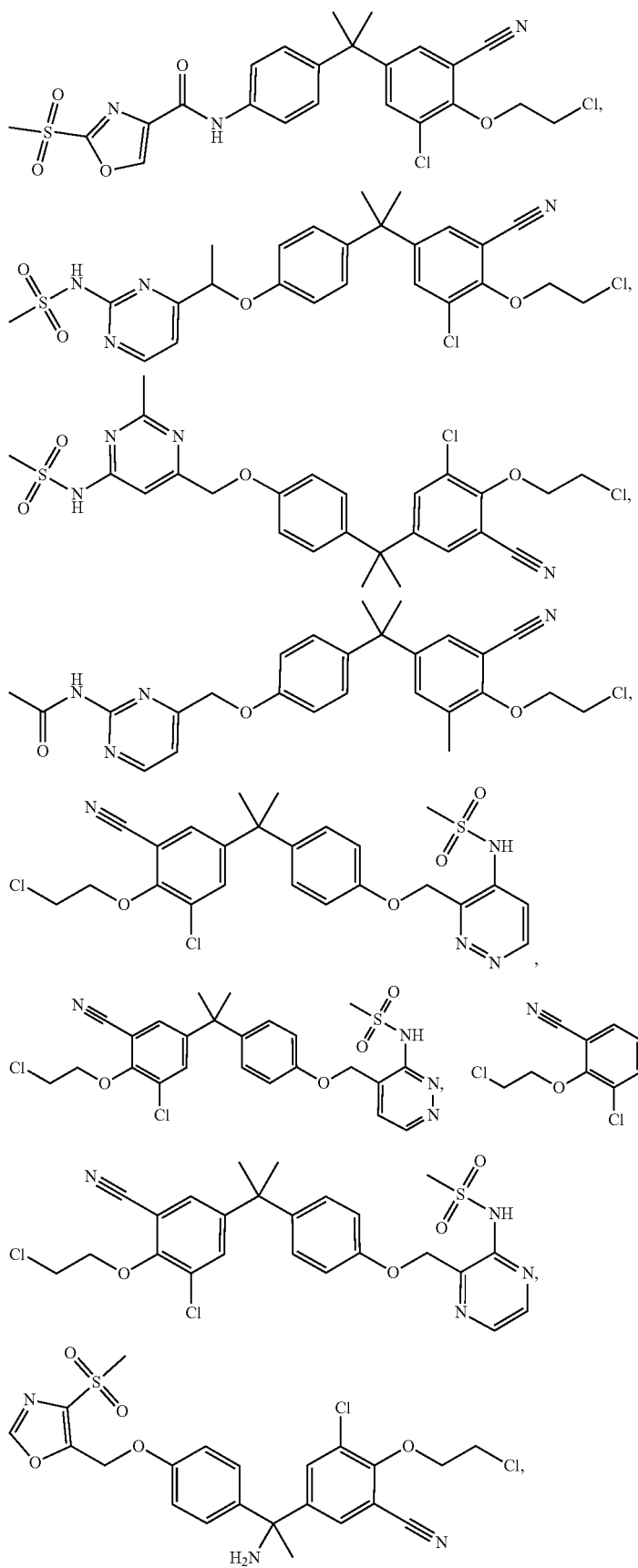

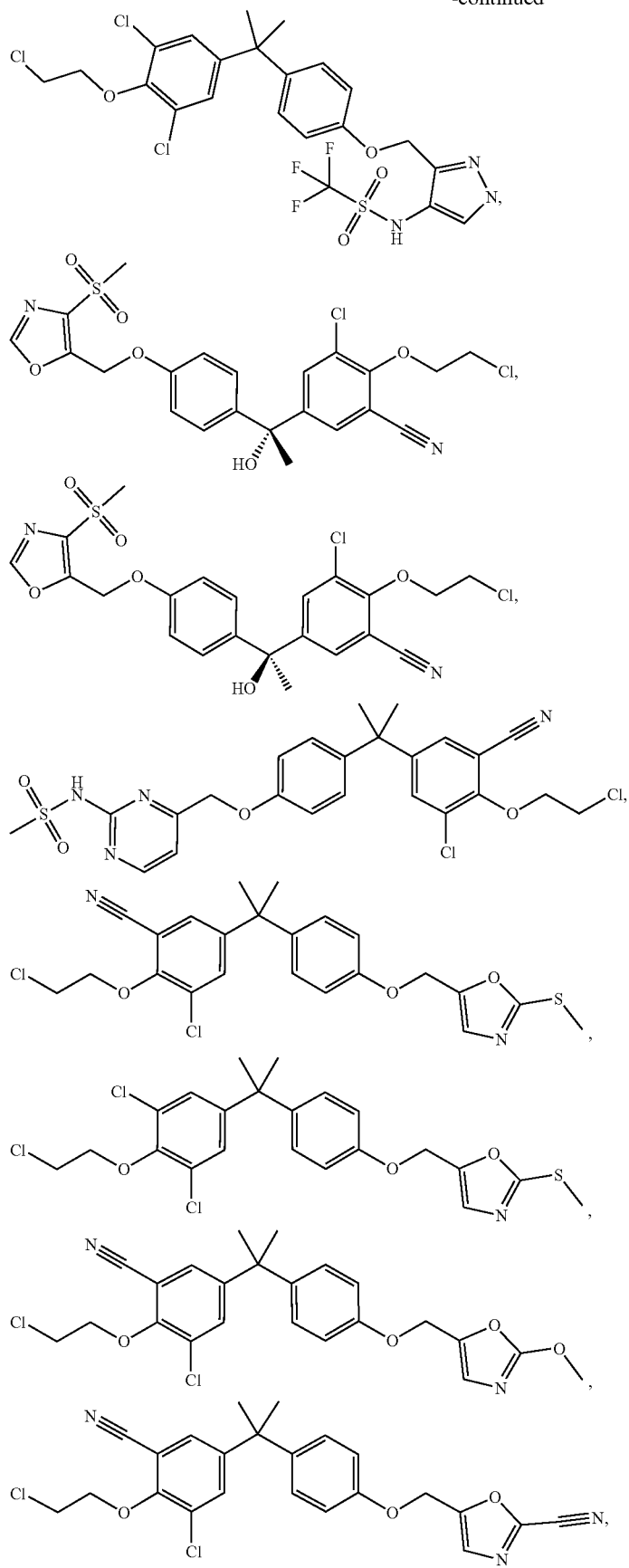

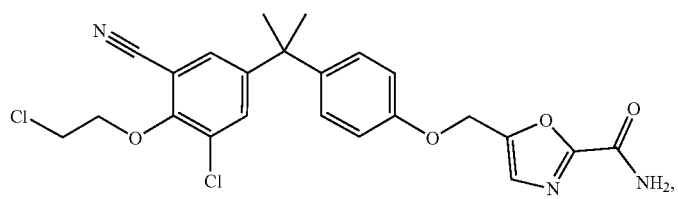
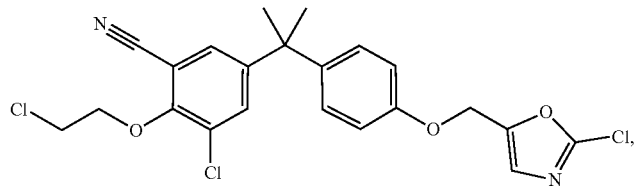
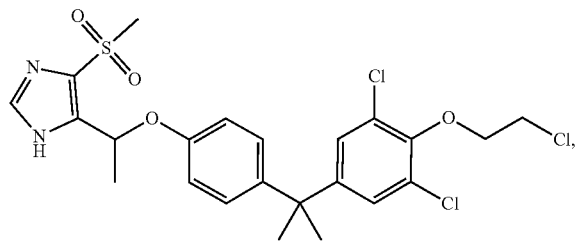
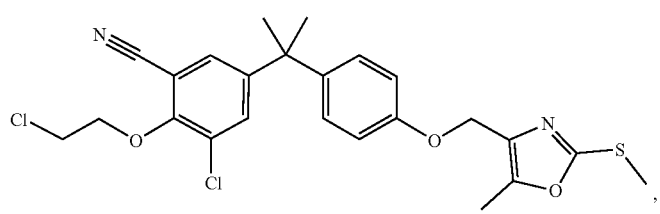
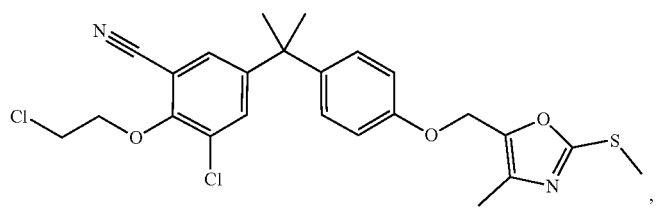
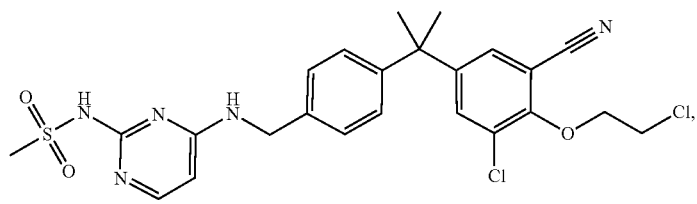
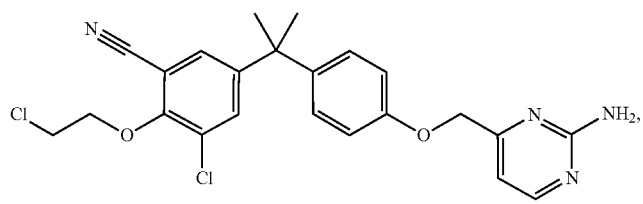
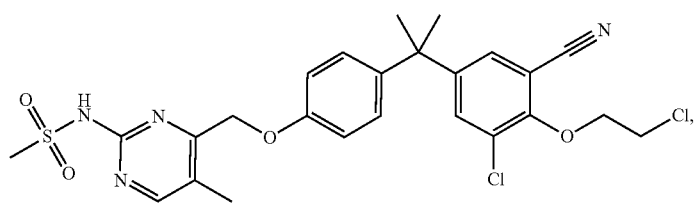

-continued
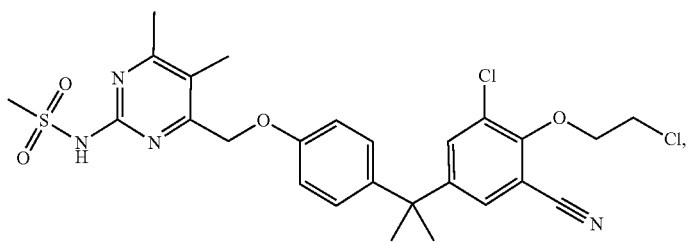
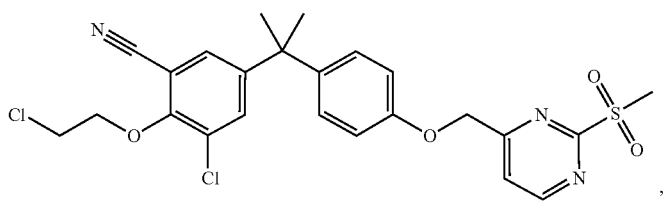
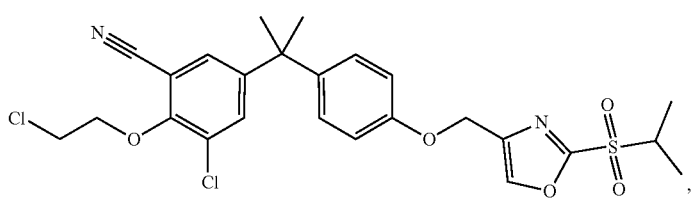
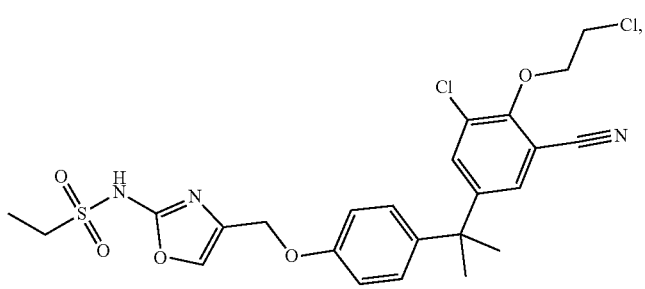
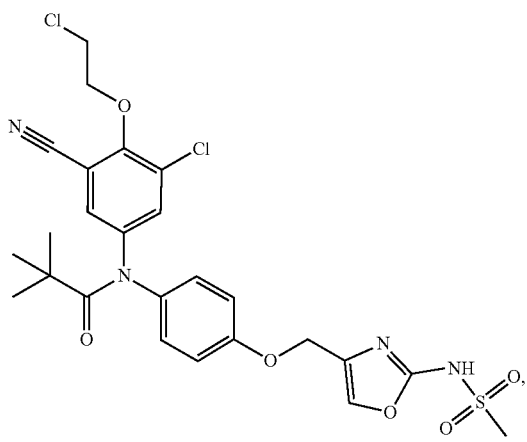
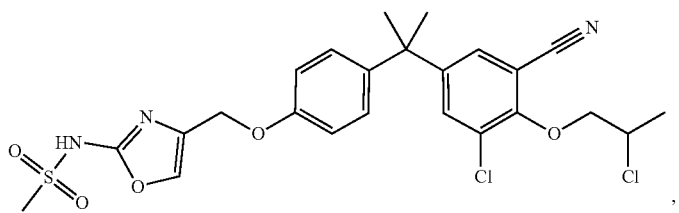

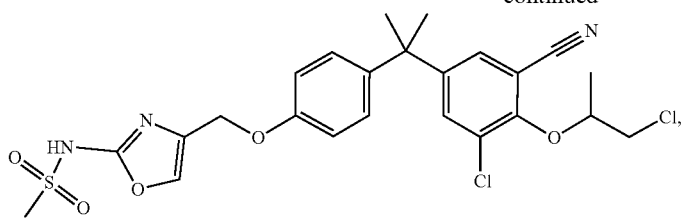
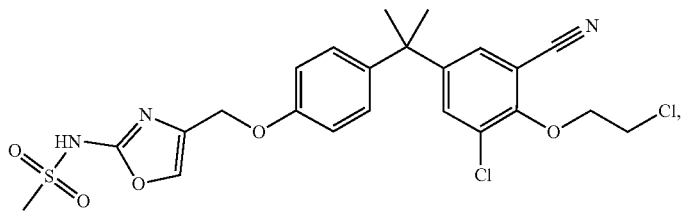
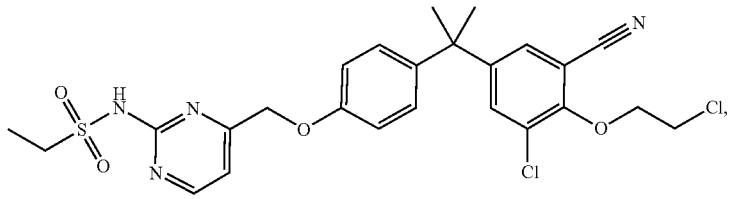
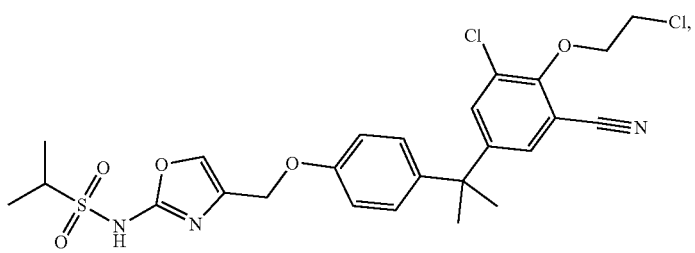
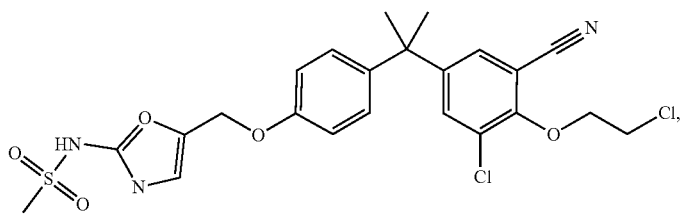
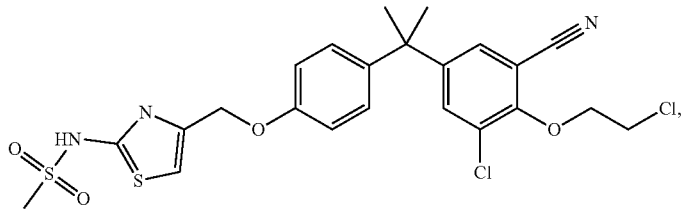
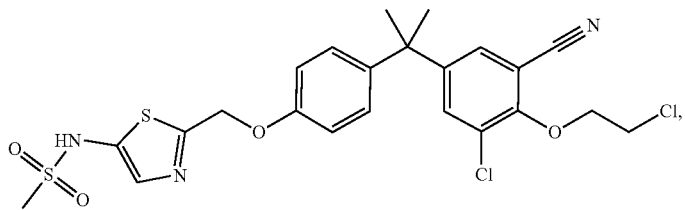
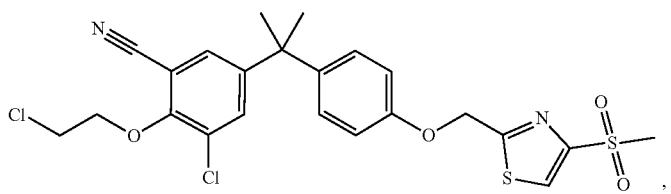

401
-continued
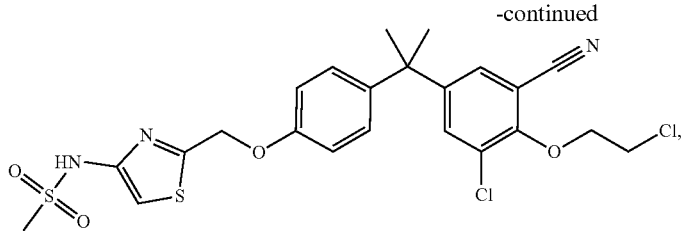
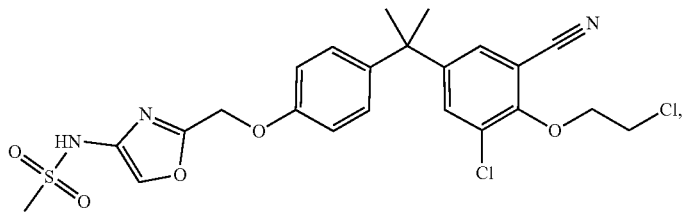
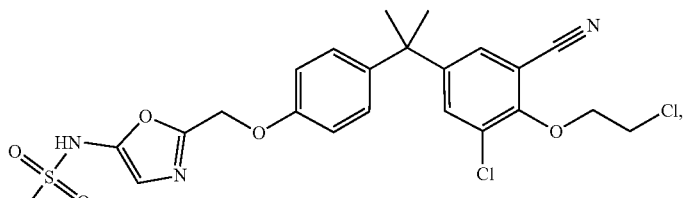
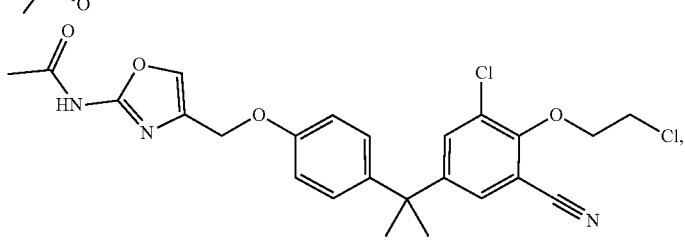
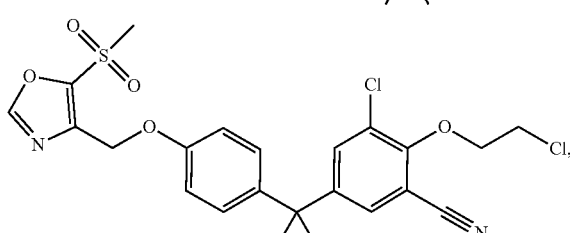
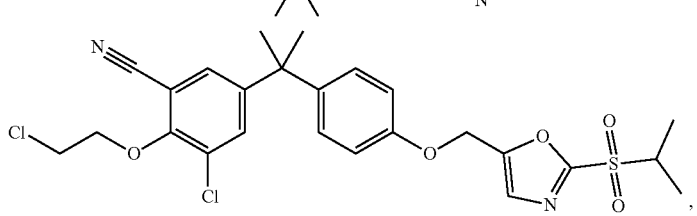
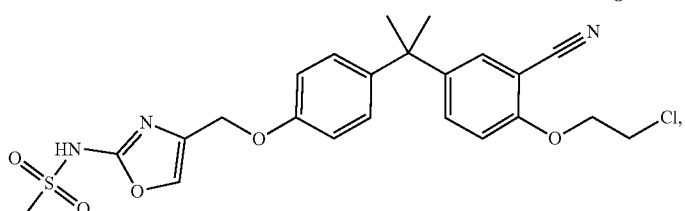
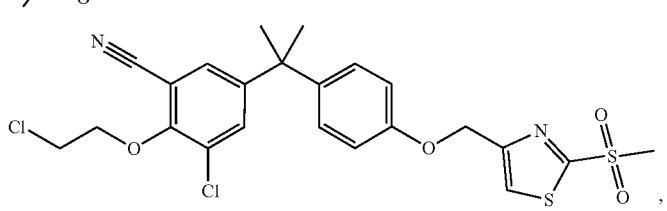
402

-continued
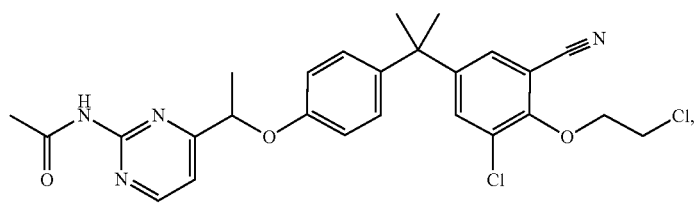
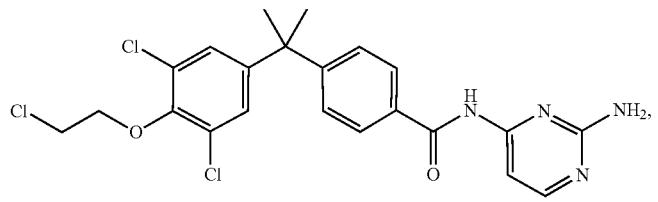
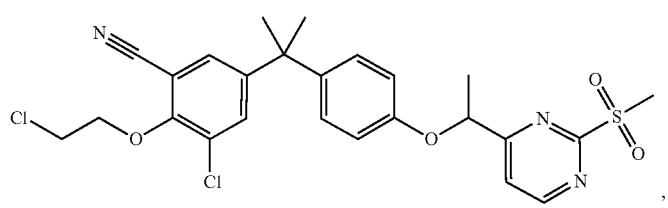
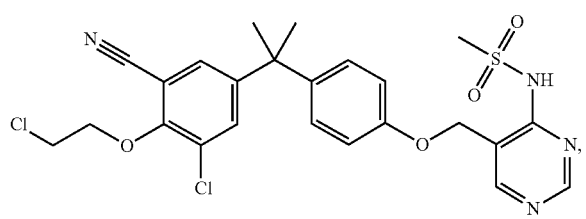
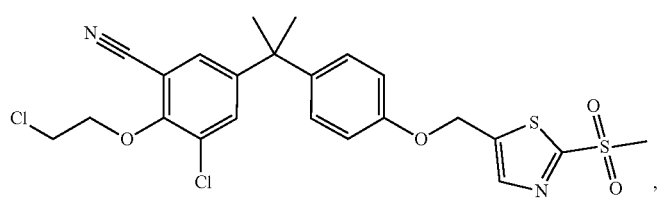
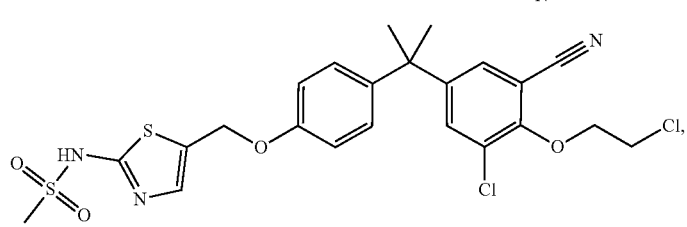
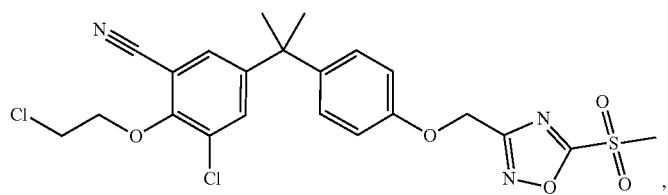
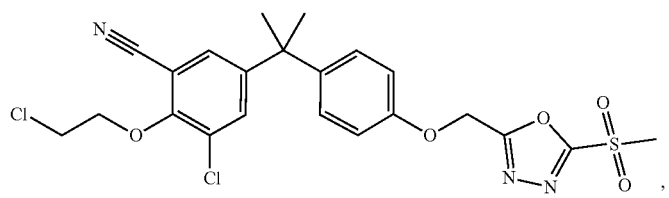

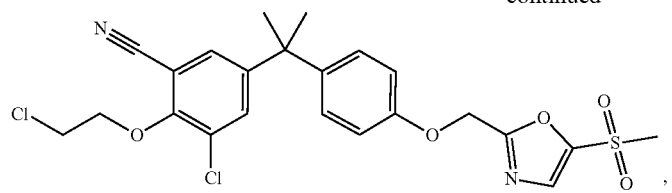
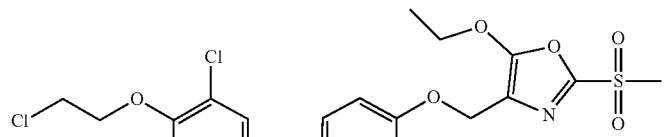
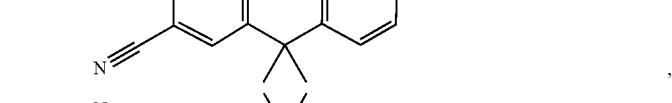
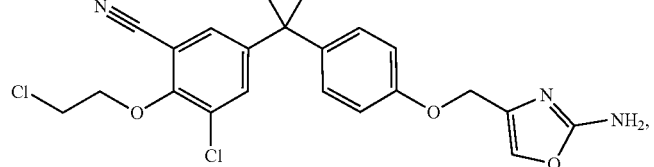
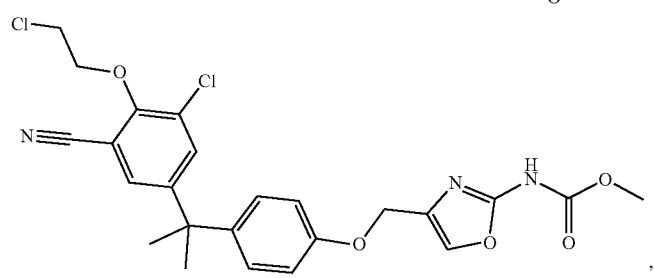
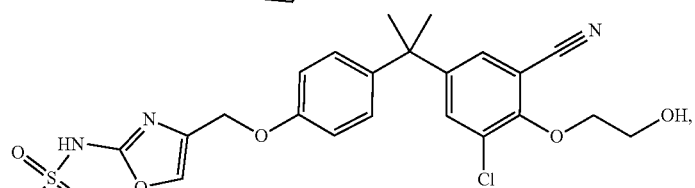
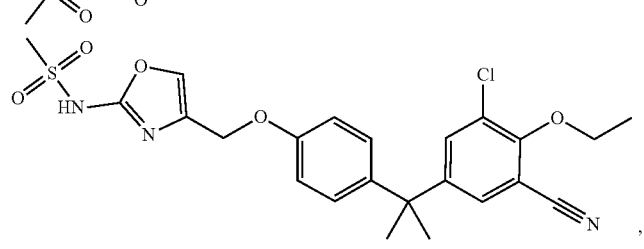
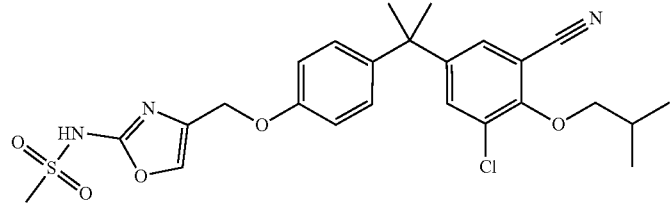
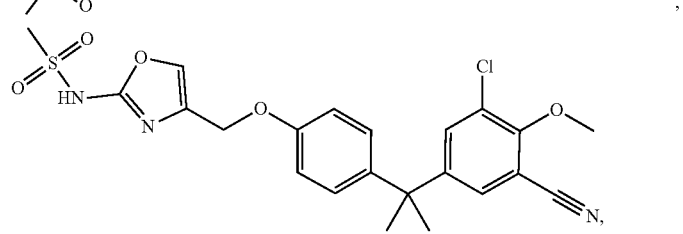

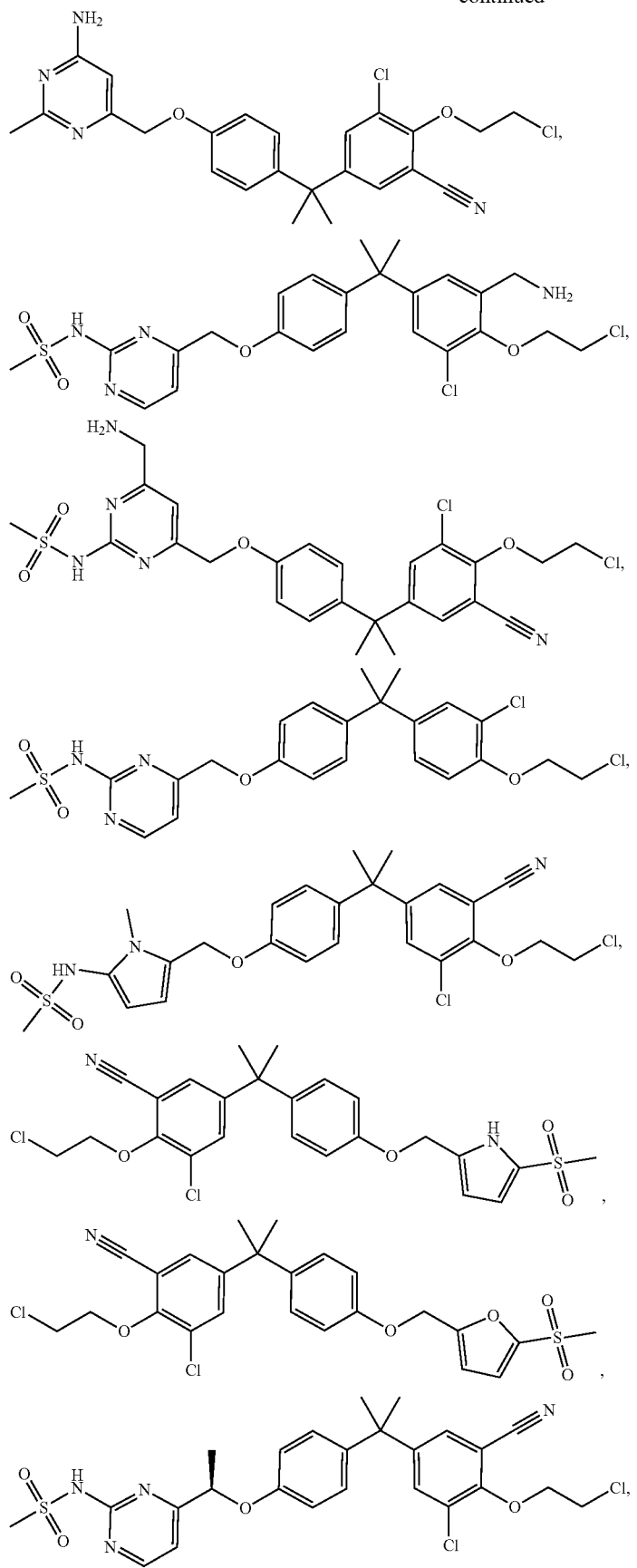

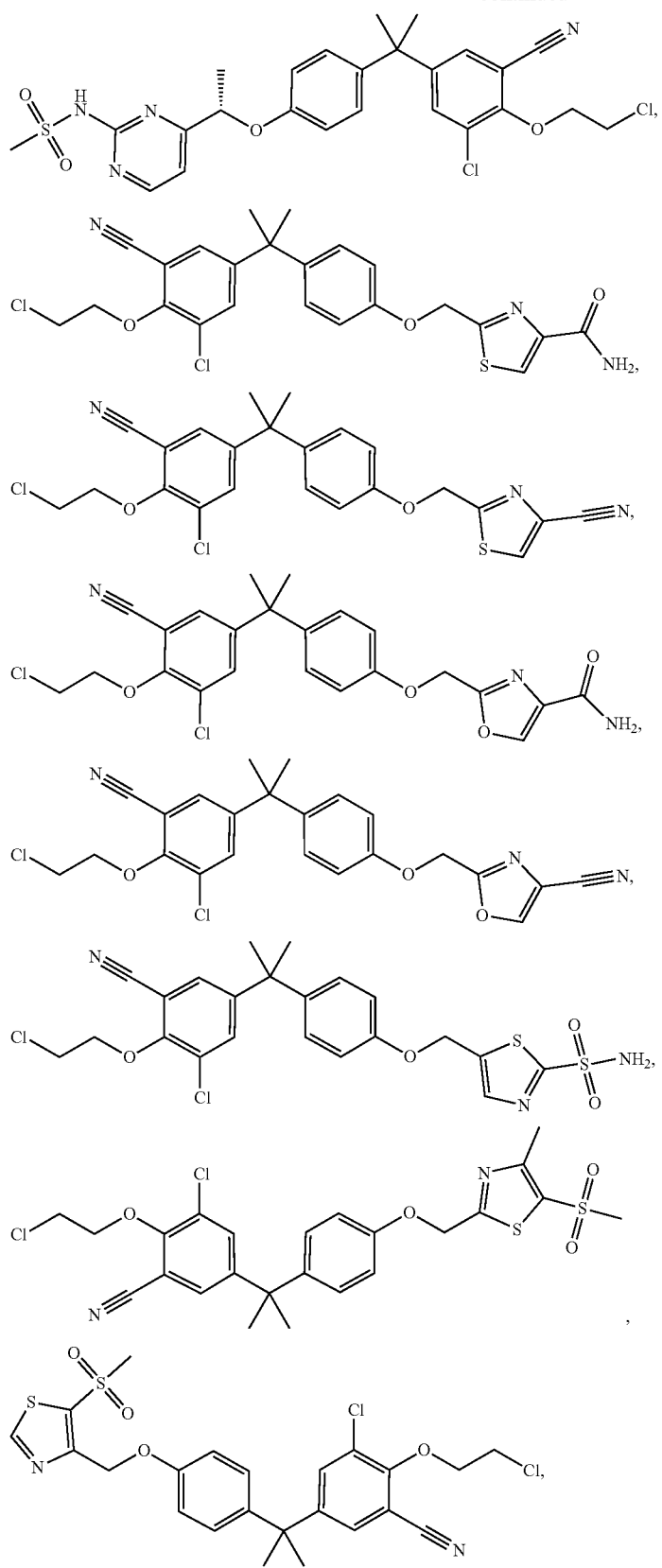

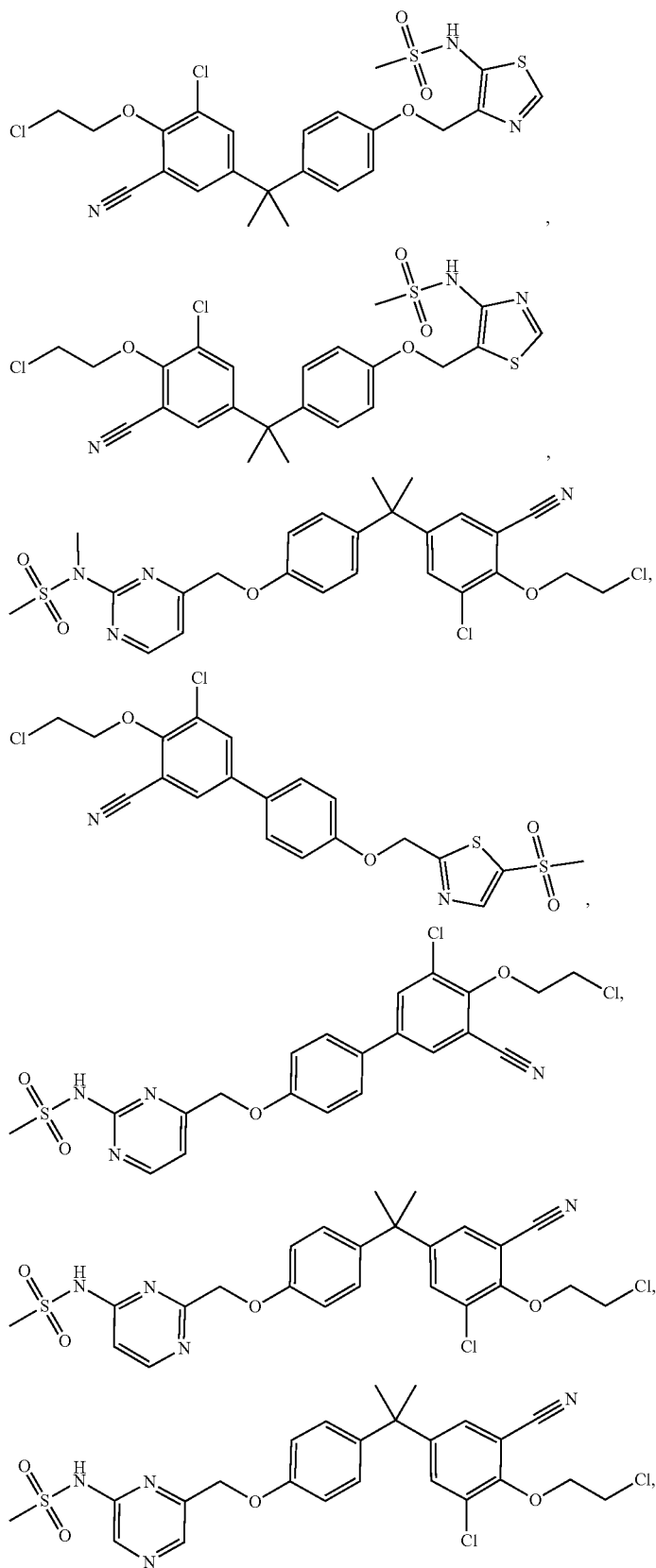

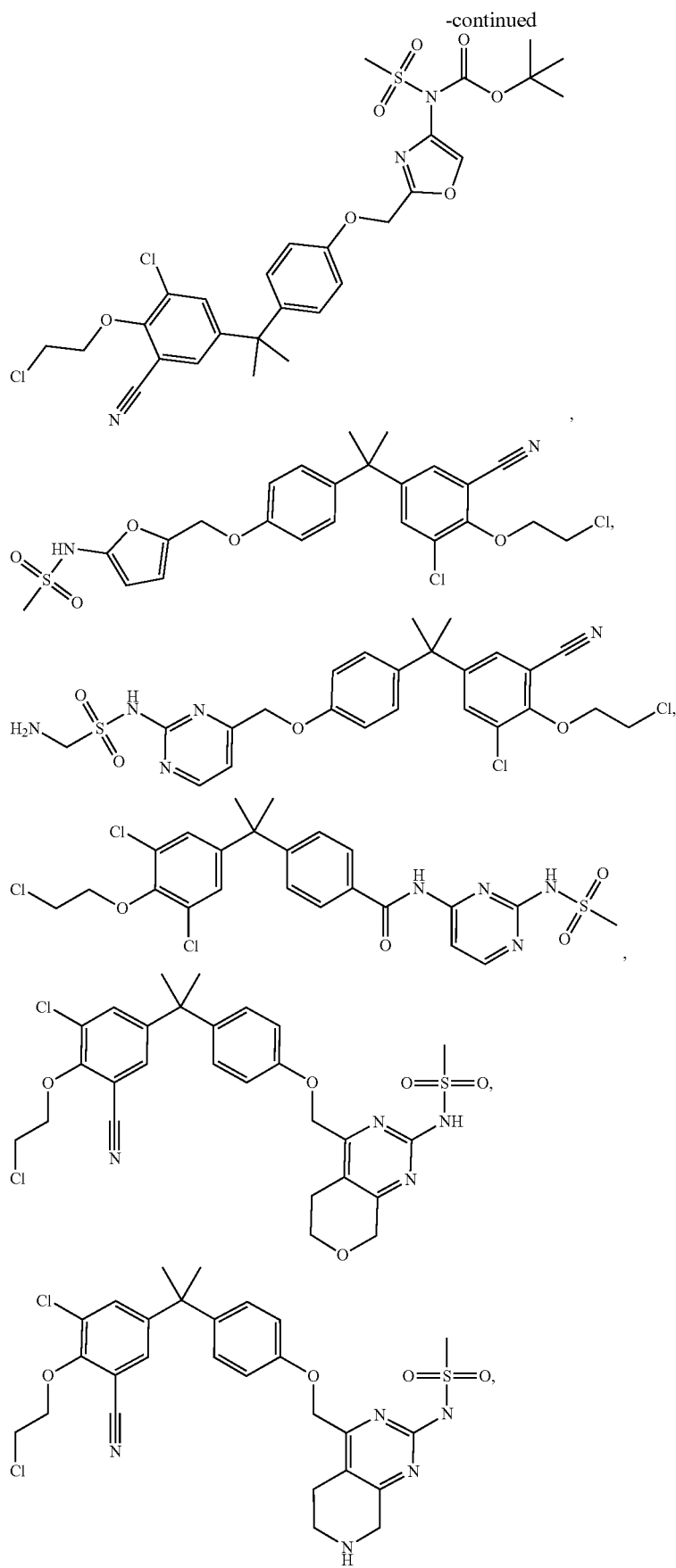

-continued
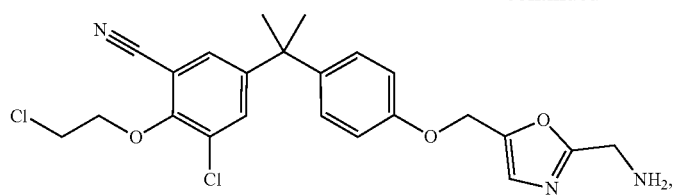
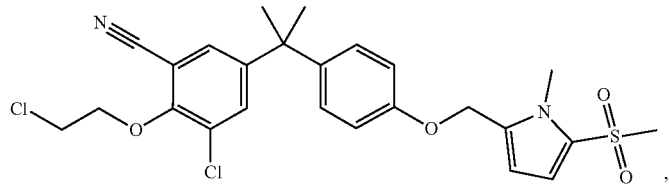
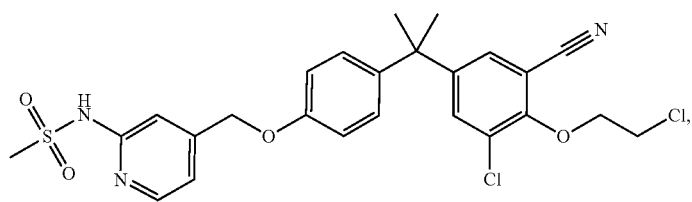
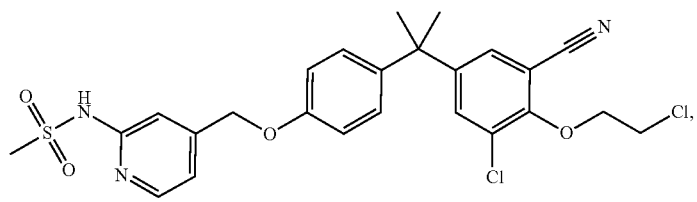
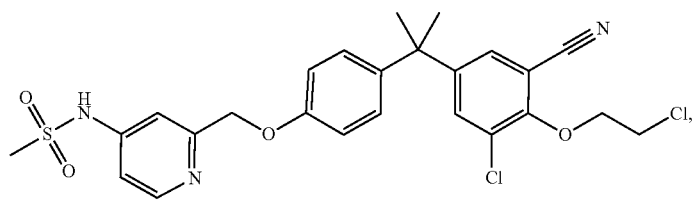
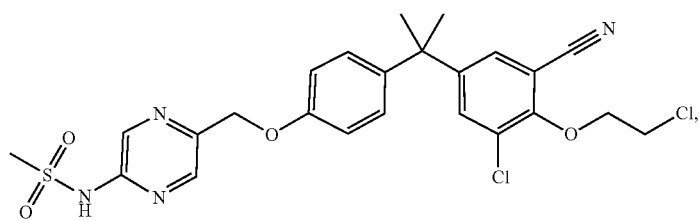
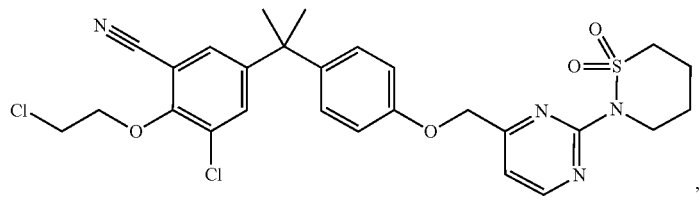
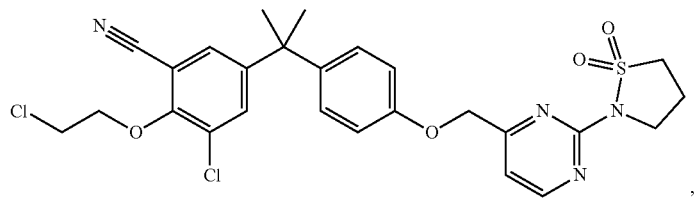

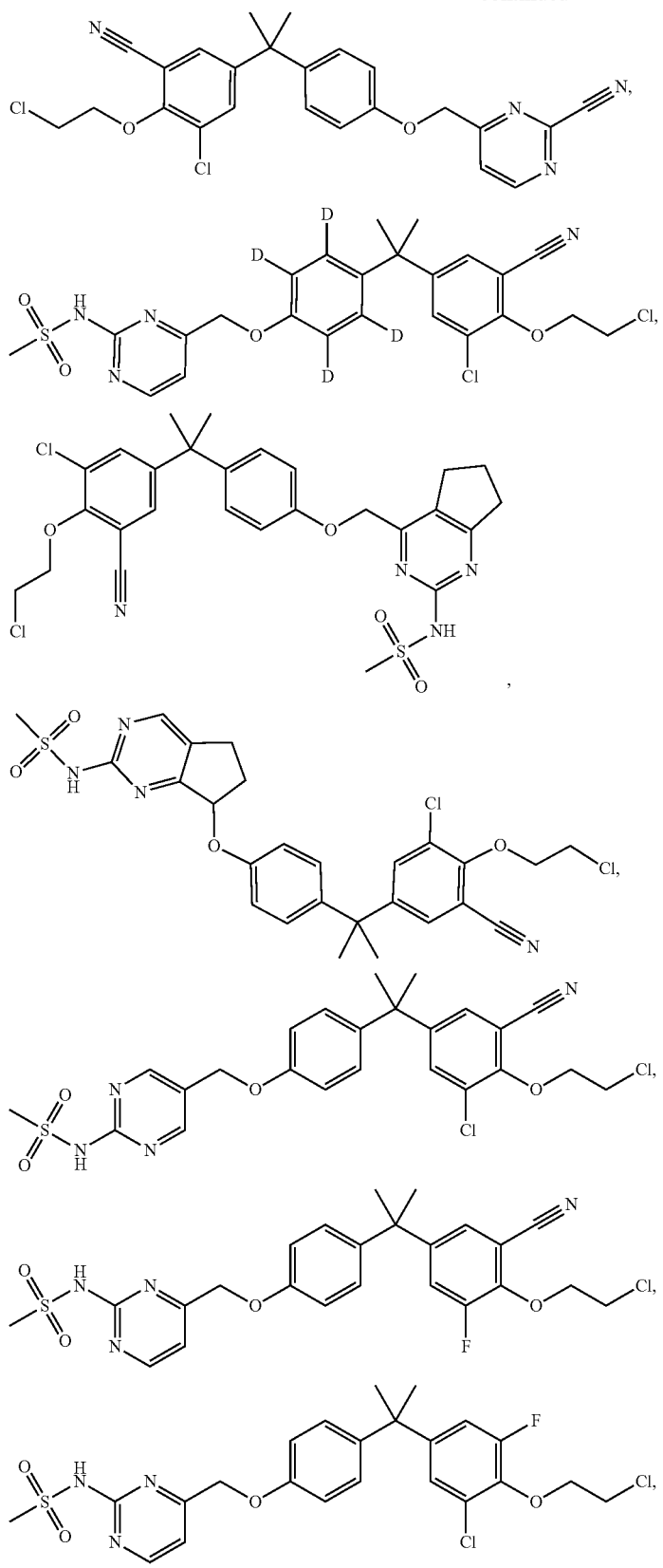

-continued
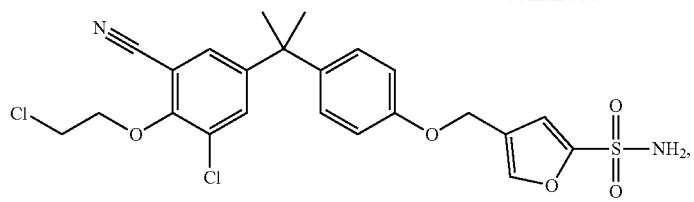
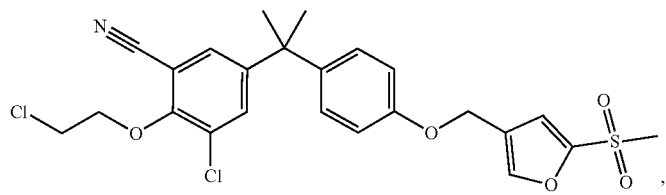
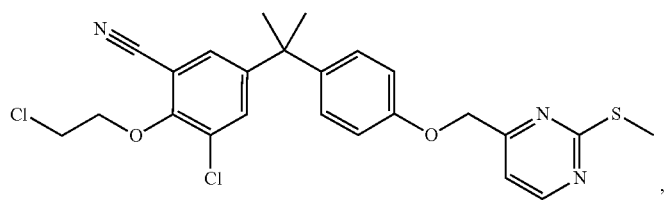
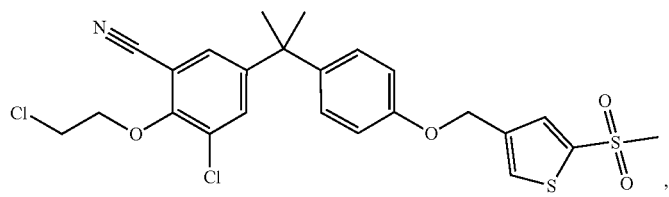
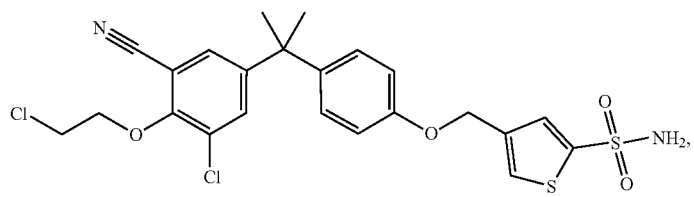
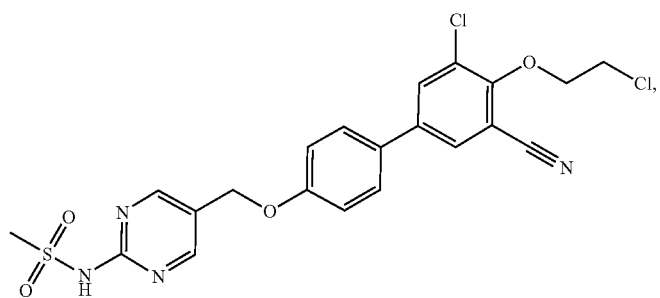
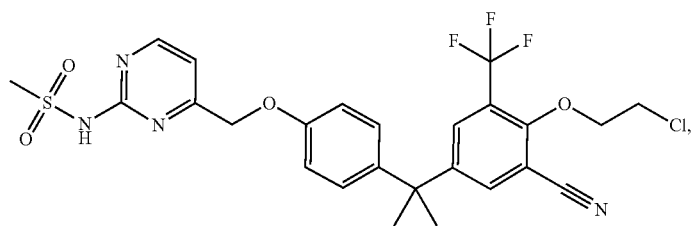
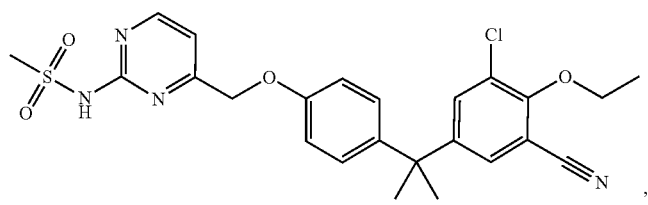

-continued
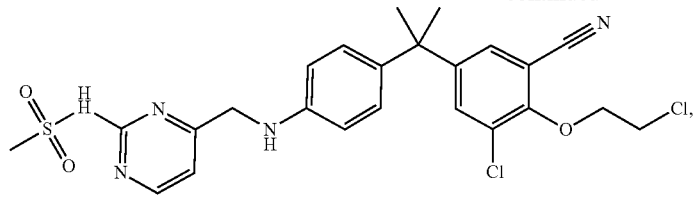
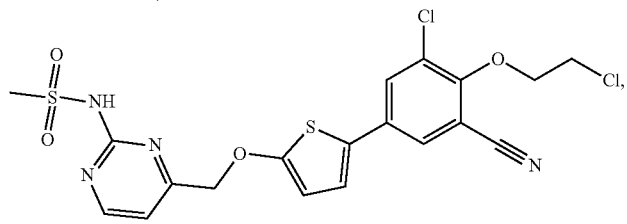
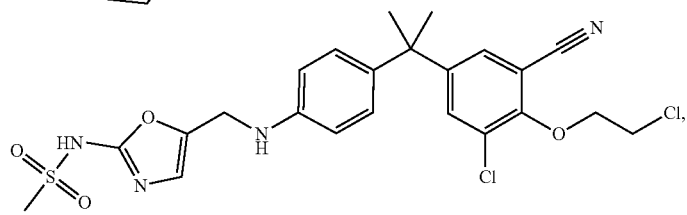
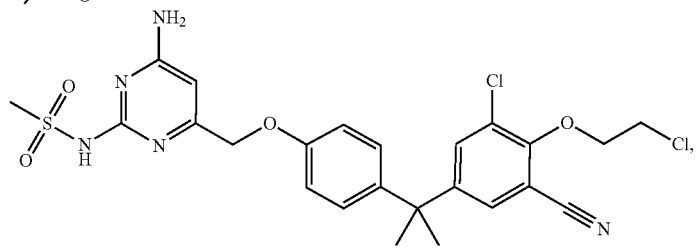
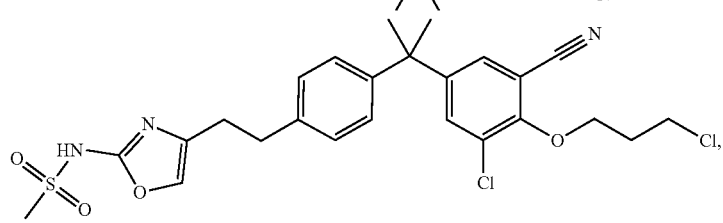
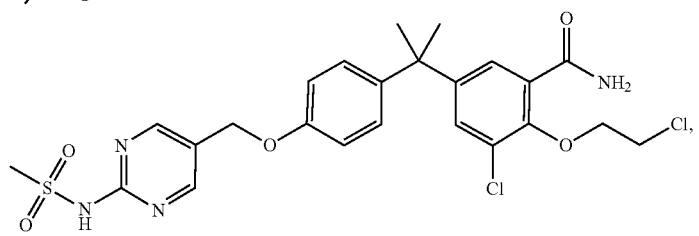
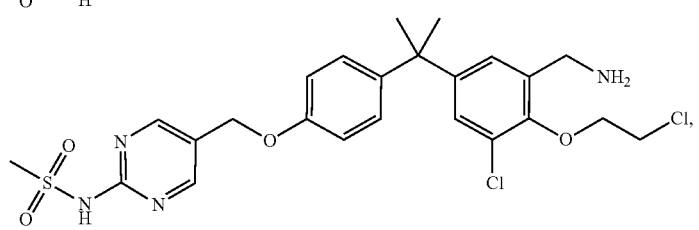
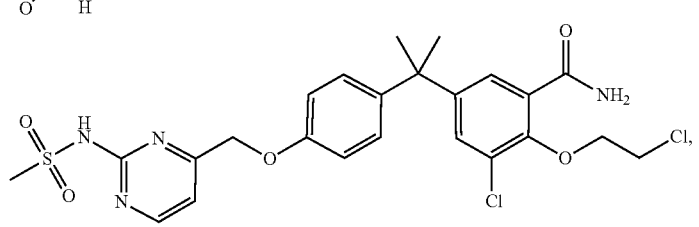

-continued
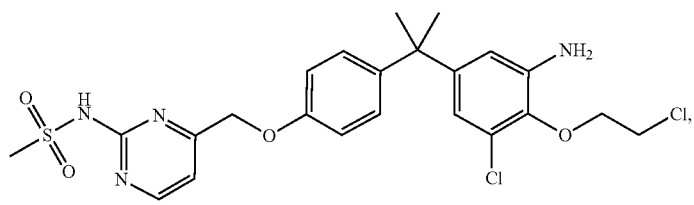
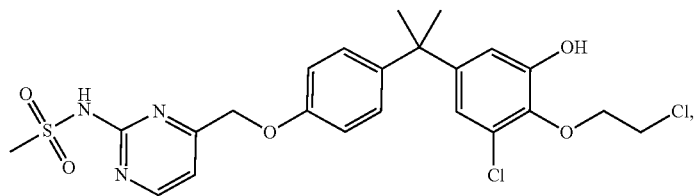
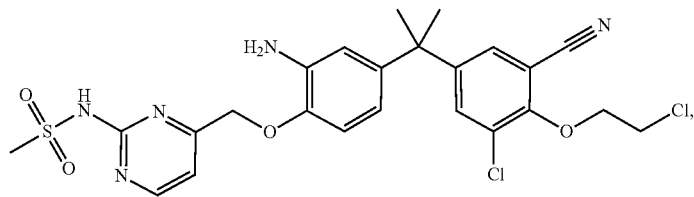
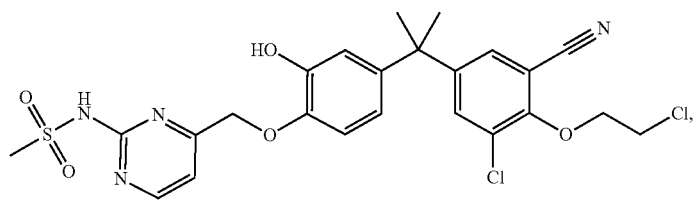
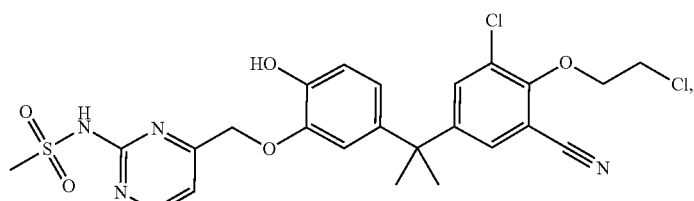
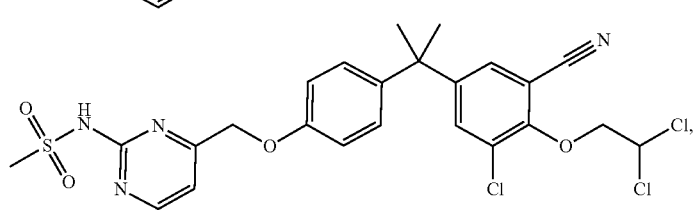
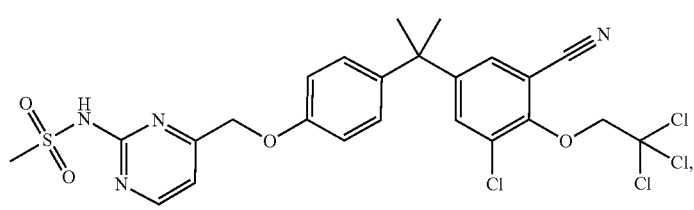
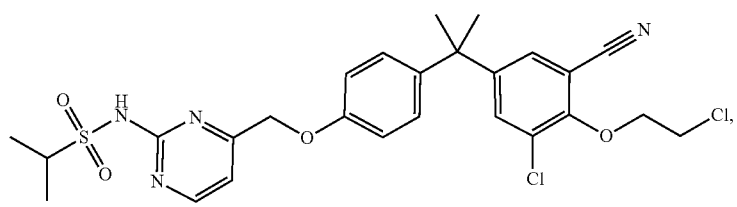

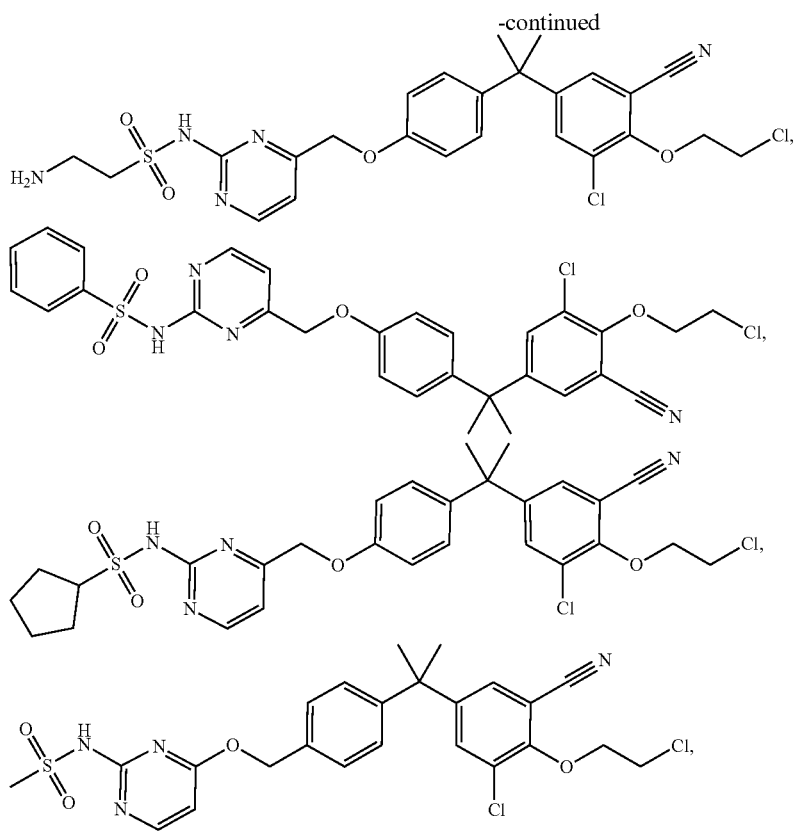
or a pharmaceutically acceptable salt, tautomer, or stereoisomer thereof.
11. The compound of claim 10, wherein the compound is selected from
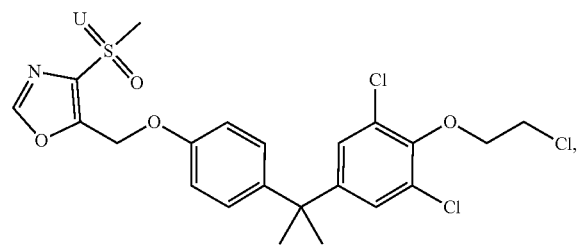
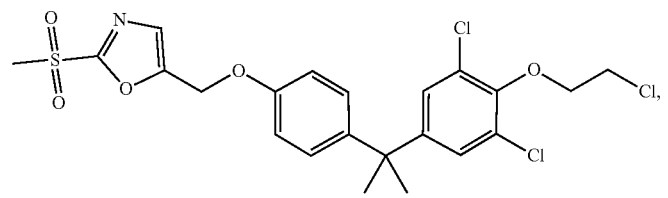
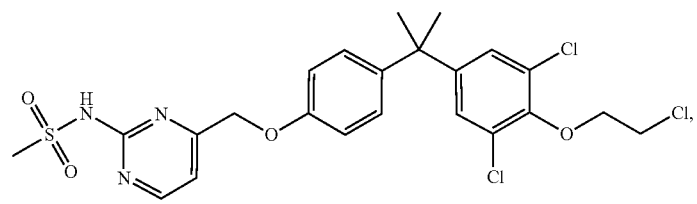

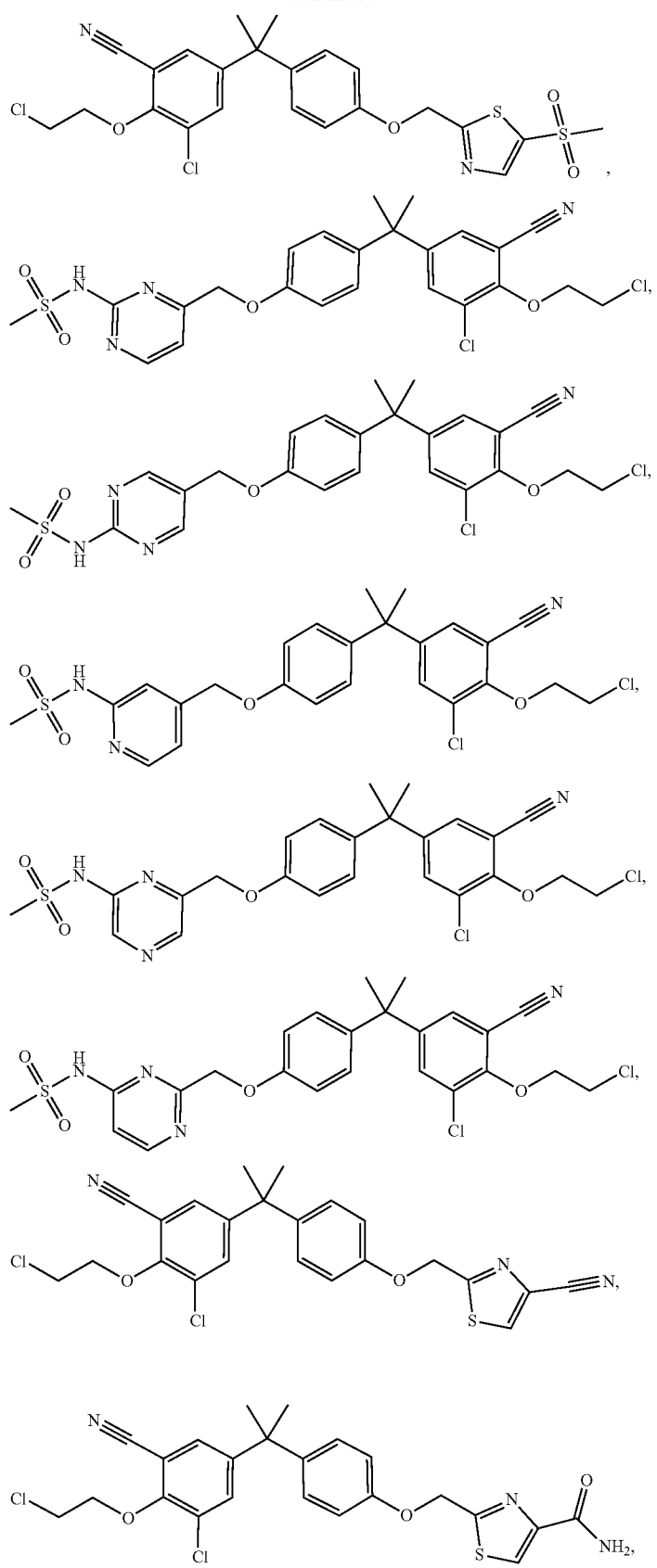

-continued
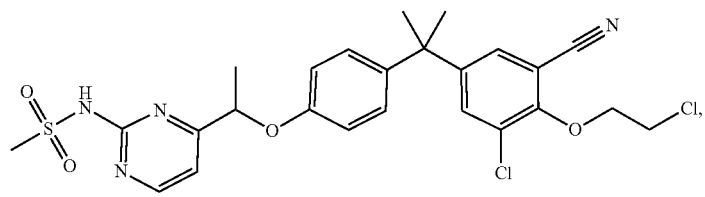
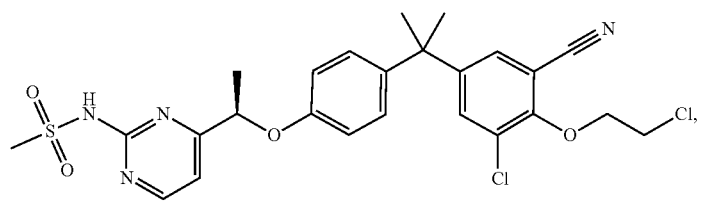
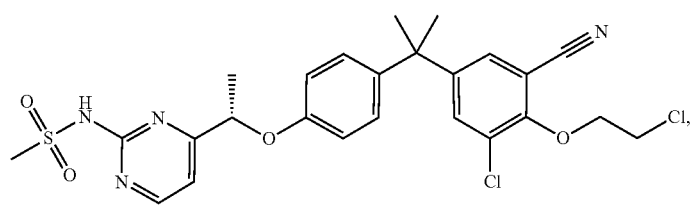
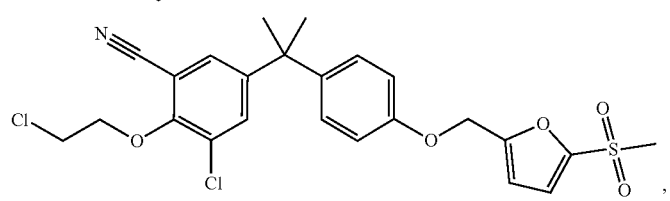
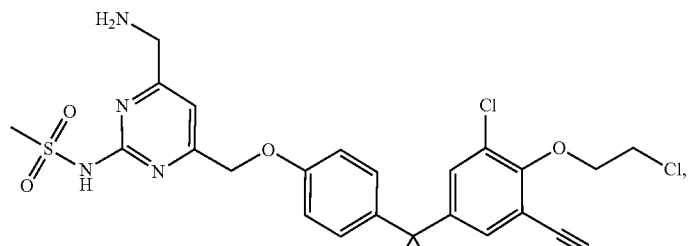
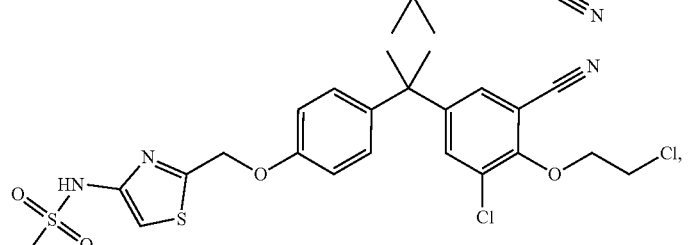
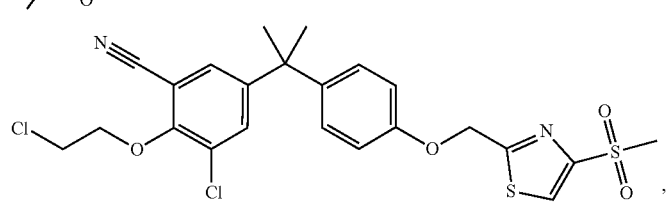
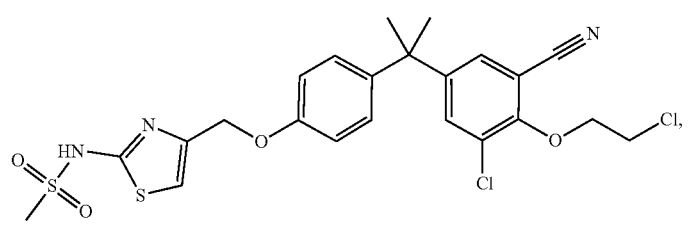

-continued

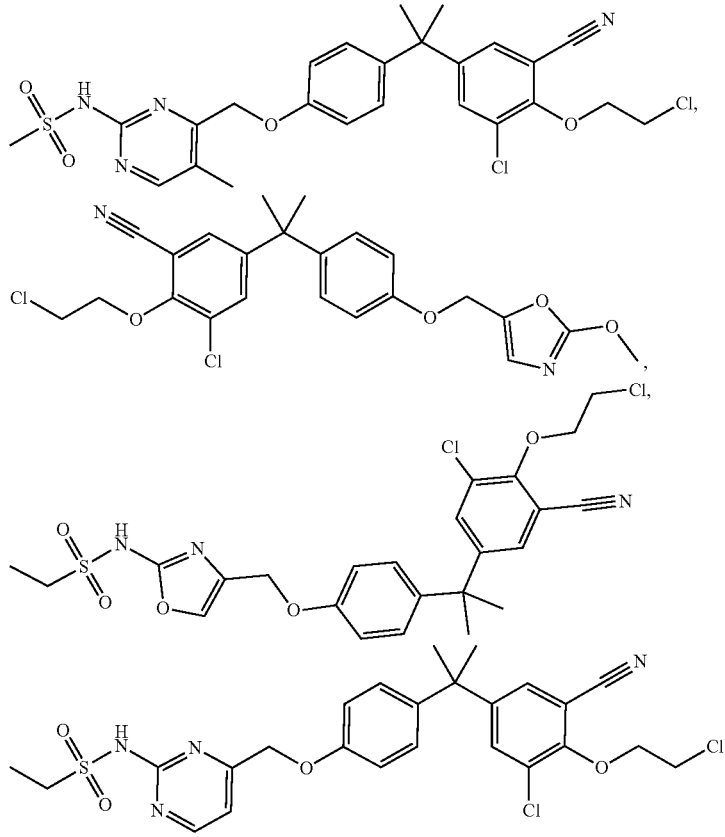

or a pharmaceutically acceptable salt, tautomer, or stereoisomer thereof.

12. A pharmaceutical composition comprising a compound of claim 1 and a pharmaceutically acceptable carrier.

13. A pharmaceutical composition comprising a compound of claim 8 and a pharmaceutically acceptable carrier.

14. A pharmaceutical composition comprising a compound of claim 10 and a pharmaceutically acceptable carrier.

15. A pharmaceutical composition comprising a compound of claim 11 and a pharmaceutically acceptable carrier.

16. A method for treating cancer, comprising administering the compound, pharmaceutically acceptable salt, tautomer, or stereoisomer of the compound of claim 1, to a subject in need thereof.

17. The method of claim 16, wherein the cancer is prostate cancer.

18. The method of claim 17, wherein the prostate cancer is metastatic castration-resistant prostate cancer.

19. The method of claim 18, wherein the prostate cancer expresses full-length androgen receptor or truncated androgen receptor splice variant.

20. The method of claim 17, wherein the compound is selected from

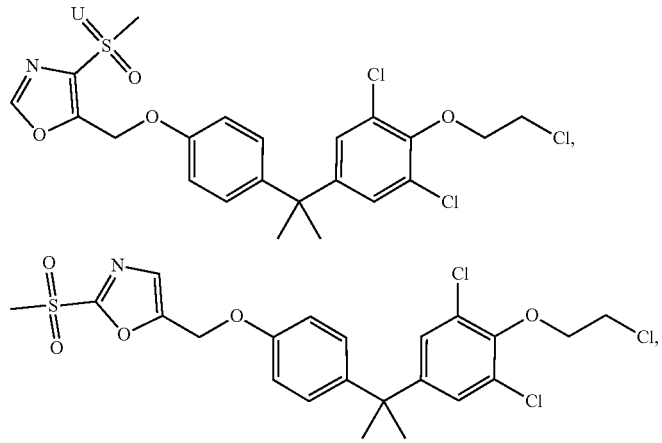

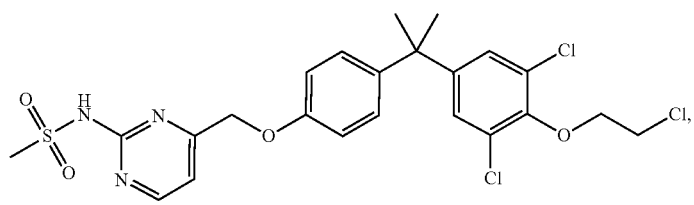
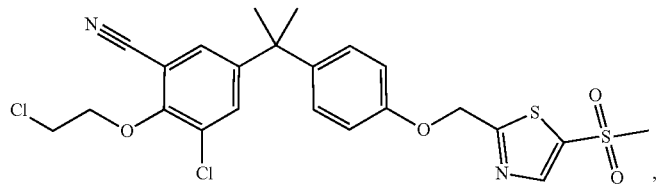
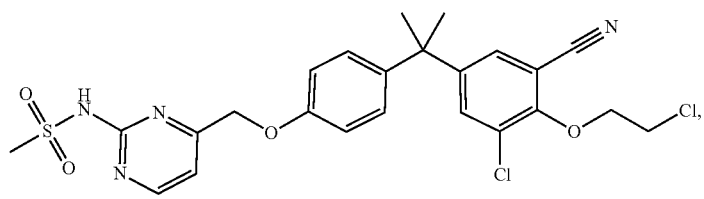
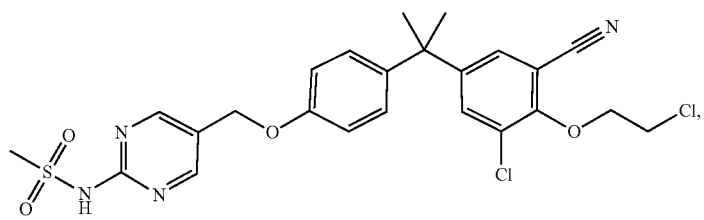
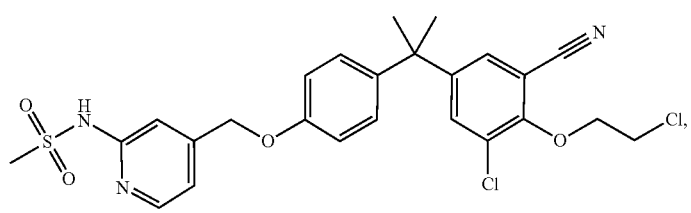
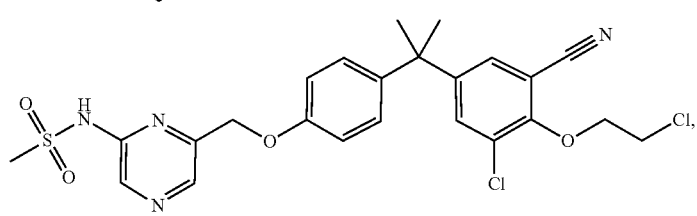
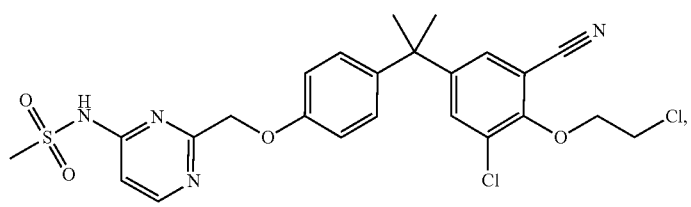
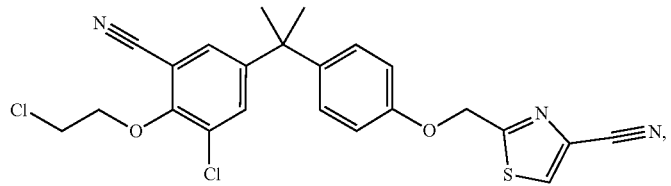

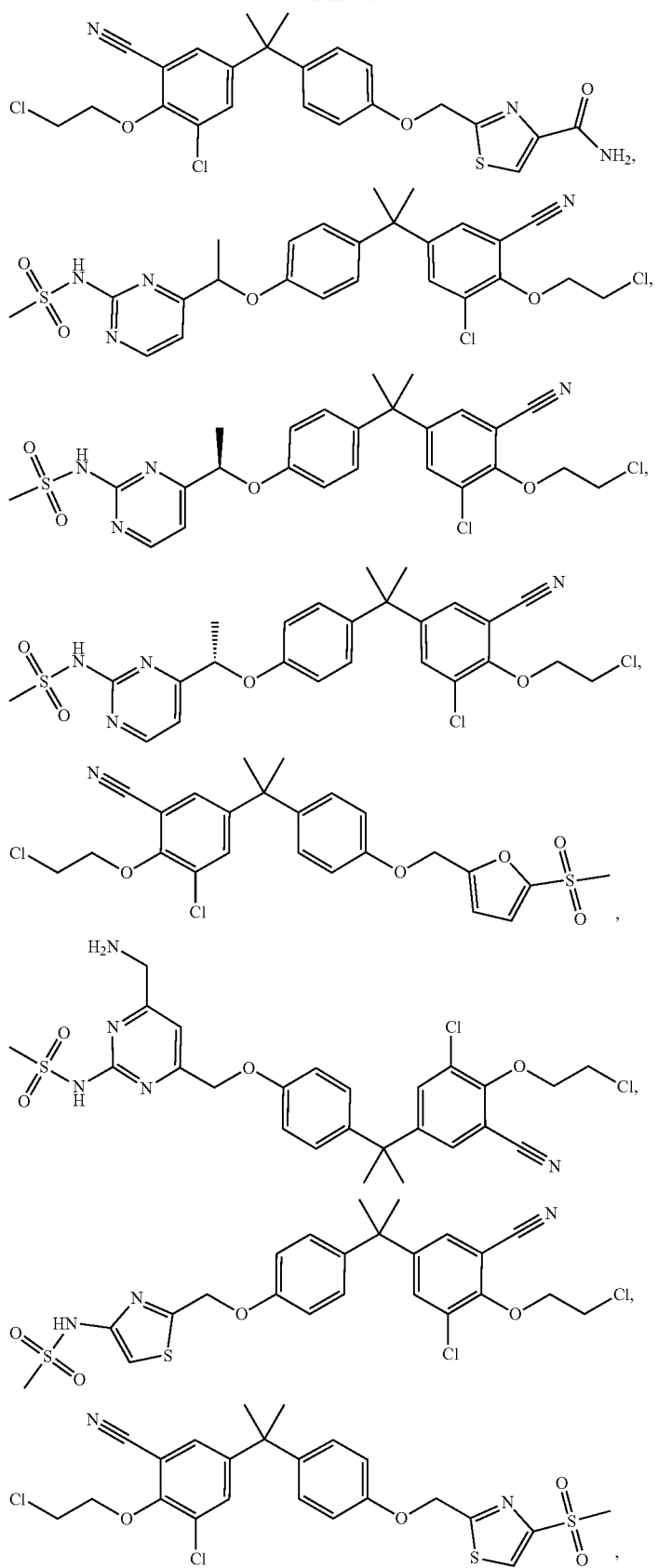

-continued

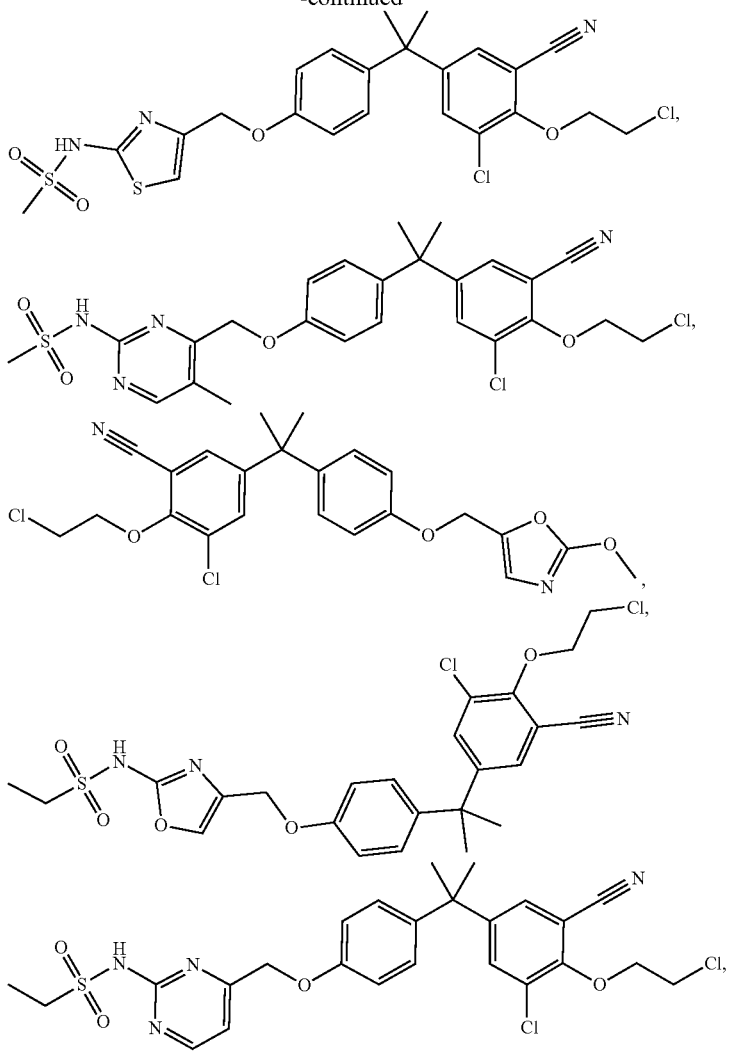

or a pharmaceutically acceptable salt, tautomer, or stereoisomer thereof.

21. A compound having the structure:

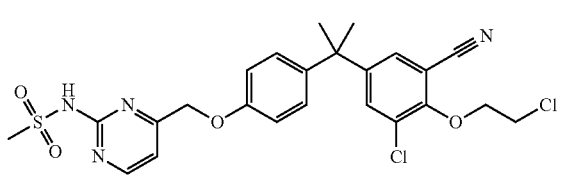 [SMILES: CC(C)(c1ccc(OCc2ccnc(NS(C)(=O)=O)n2)cc1)c1cc(Cl)c(OCCCl)c(C#N)c1]

or a pharmaceutically acceptable salt thereof.

22. A pharmaceutical composition comprising a compound or a pharmaceutically acceptable salt of the compound of claim 21, and a pharmaceutically acceptable carrier.

23. A method for treating prostate cancer, comprising administering a compound or a pharmaceutically acceptable salt of the compound of claim 21, to a subject in need thereof.

24. The method of claim 23, wherein the prostate cancer is metastatic castration-resistant prostate cancer.

25. The method of claim 24, wherein the prostate cancer expresses full-length androgen receptor or truncated androgen receptor splice variant.

* * * * *